(12) United States Patent
Lee et al.

(10) Patent No.: US 12,122,763 B2
(45) Date of Patent: Oct. 22, 2024

(54) SUBSTITUTED PIPERIDINES FOR ANDROGEN RECEPTOR DEGRADATION

(71) Applicant: UBIX THERAPEUTICS, INC., Seoul (KR)

(72) Inventors: Song Hee Lee, Seoul (KR); Je Ho Ryu, Seongnam-si (KR); Jung Min Ahn, Incheon (KR); Yu Ri Choi, Incheon (KR); Ho Hyun Lee, Siheung-si (KR); Mi Young Jang, Ansan-si (KR); Yae Jin Woo, Seongnam-si (KR); Hanwool Kim, Ansan-si (KR); Ji Young Kim, Seongnam-si (KR); Ji Youn Park, Seongnam-si (KR)

(73) Assignee: UBIX THERAPEUTICS, INC., Seoul (KR)

( * ) Notice: Subject to any disclaimer, the term of this patent is extended or adjusted under 35 U.S.C. 154(b) by 0 days.

(21) Appl. No.: 18/006,265

(22) PCT Filed: Jul. 19, 2021

(86) PCT No.: PCT/KR2021/009287
§ 371 (c)(1),
(2) Date: Jan. 20, 2023

(87) PCT Pub. No.: WO2022/019597
PCT Pub. Date: Jan. 27, 2022

(65) Prior Publication Data
US 2023/0348427 A1    Nov. 2, 2023

(30) Foreign Application Priority Data

Jul. 21, 2020   (KR) .................. 10-2020-0089940

(51) Int. Cl.
| | | |
|---|---|---|
| A61K 31/4545 | (2006.01) | |
| C07D 211/06 | (2006.01) | |
| C07D 401/14 | (2006.01) | |
| C07D 471/04 | (2006.01) | |
| C07D 471/10 | (2006.01) | |
| C07D 487/04 | (2006.01) | |
| C07D 487/10 | (2006.01) | |
| C07D 519/00 | (2006.01) | |

(52) U.S. Cl.
CPC ......... *C07D 401/14* (2013.01); *C07D 471/04* (2013.01); *C07D 471/10* (2013.01); *C07D 487/04* (2013.01); *C07D 487/10* (2013.01); *C07D 519/00* (2013.01)

(58) Field of Classification Search
CPC .................. A61K 31/4545; C07D 211/06
USPC .......................... 514/318; 546/194
See application file for complete search history.

(56) References Cited

U.S. PATENT DOCUMENTS

| | | | |
|---|---|---|---|
| 11,420,956 B2* | 8/2022 | Fan | .............. C07D 401/14 |
| 2014/0066425 A1 | 3/2014 | Tong | |
| 2018/0179183 A1 | 6/2018 | Crew et al. | |
| 2020/0216450 A1 | 7/2020 | Shu | |
| 2021/0087170 A1 | 3/2021 | Fan et al. | |

FOREIGN PATENT DOCUMENTS

| | | |
|---|---|---|
| CN | 109928956 A | 6/2019 |
| CN | 111285851 A | 6/2020 |
| RU | 2598854 C2 | 9/2016 |
| WO | 2018106870 A1 | 6/2018 |

(Continued)

OTHER PUBLICATIONS

Heinlein, C. et al., "Androgen Receptor in Prostate Cancer," Endocrine Reviews, 2004, vol. 25, No. 2, pp. 276-308.
Trewartha, D. et al., "Advances in prostate cancer treatment," Nature Reviews, Drug Discovery, Nov. 2013, vol. 12, pp. 823-824.
Lai, J. et al., "The Role of Androgen and Androgen Receptor in the Skin-Related Disorders," National Institute of Health, Arch Dermatol Res., Sep. 2012, vol. 304, No. 7, pp. 499-510.
Fu, D. et al., "Dihydrotestosterone-induced hair regrowth inhibition by activating androgen receptor in C57BL6 mice simulates androgenetic alopecia," ScienceDirect, Biomedicine & Pharmacotherapy, 2021, vol. 37, 12 pages.

(Continued)

*Primary Examiner* — Douglas M Willis
(74) *Attorney, Agent, or Firm* — MH2 TECHNOLOGY LAW GROUP, LLP

(57) ABSTRACT

The present disclosure provides a substituted piperidine compound of Chemical Formula 1, wherein X is $CR_3$, or a pharmaceutically acceptable salt thereof having activity of degrading androgen receptor (AR).

Chemical Formula 1

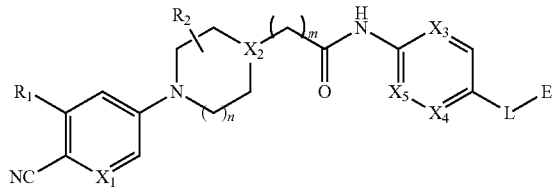

The present disclosure also provides a composition comprising such a substituted piperidine compound or a pharmaceutically acceptable salt thereof. The present disclosure also provides a medical use of a substituted piperidine compound according to the present disclosure, a salt thereof, and a composition comprising the same for the treatment or prophylaxis of AR-related diseases. The present disclosure also provides a method for treating or preventing an AR-related disease comprising administering to a subject in need thereof an effective amount of a substituted piperidine compound according to the present disclosure, a salt thereof, or a composition comprising the same.

8 Claims, No Drawings

(56) References Cited

FOREIGN PATENT DOCUMENTS

WO 2021061642 A1 4/2021

OTHER PUBLICATIONS

Michmerhuizen, A. et al., "ARe we there yet? Understanding androgen receptor signaling in breast cancer," npj Breast Cancer, 2020, vol. 6, No. 47, 19 pages.

* cited by examiner

SUBSTITUTED PIPERIDINES FOR ANDROGEN RECEPTOR DEGRADATION

CROSS-REFERENCE TO RELATED APPLICATIONS

This application is a national stage application of PCT/KR2021/009287 filed 19 Jul. 2021, which claims priority to Korean Patent Application No. 10-2020-0089940 filed 21 Jul. 2020. The entire disclosures of each application are herein incorporated by reference.

TECHNICAL FIELD

This application claims priority to Korean Patent Application No. 10-2020-0089940 filed on Jul. 21, 2020, and all contents disclosed in the specification and drawings of the application are incorporated into this application.

The present disclosure relates to a group of compounds that have the activity of degrading the androgen receptor. The present disclosure also relates to pharmaceutical compositions comprising such compounds. The present disclosure also relates to useful methods of treating androgen receptor related diseases using such compounds. That is, the present disclosure relates to the medical use of the compounds according to the present disclosure for treating or preventing androgen receptor related diseases.

BACKGROUND ART

Androgen hormone receptor (AR) is a transcription factor belonging to nuclear hormone receptor (NR). In the absence of androgens, AR binds to Heat Shock Protein 90 (Hsp90) in the cytosol. Hsp90 and AR are dissociated and androgen binds to AR. When AR binds to the hormone dihydrotestosterone (DHT), these complexes are translocated to the nucleus and, through a series of processes, activate the transcription of target genes.

AR contributes to the development of masculinity, but it is also a well-known oncogene in certain forms of cancer, including prostate cancer (Endocr. Rev. 2004, 25(2), 276-308). Current treatment regimens for androgen-related prostate cancer can be divided into two main categories. The first approach is to control androgen levels by removing androgens or preventing their translocation into the nucleus by interfering with the binding of its ligand, DHT. The second strategy aims to inhibit AR function by targeting AR (Nature Reviews Drug Discovery, 2013, 12, 823-824). That is, an alternative approach to treatment of prostate cancer involves deleting the AR protein. AR is an important driver of tumorigenesis in many forms of prostate cancer.

This AR can also be a major target for the treatment of acne, alopecia (especially androgenetic alopecia), cutaneous wounds, hirsutism, etc. (*Arch Dermatol Res.* 2012 September; 304(7): 499-510, Biomedicine & Pharmacotherapy 137 (2021) 111247), and it has been found that the expression and activation of AR also play an important role in breast cancer (especially androgen receptor-positive triple-negative breast cancer (AR+TNBC)) (npj Breast Cancer (2020) 6:47).

Representative anti-androgen receptor drugs include enzalutamide and bicalutamide, and apalutamide has recently been approved. However, about 15-25% of prostate cancer patients do not respond to anti-androgen drugs, and the approved drug shows excellent anticancer effects in the initial stage of administration, but drug resistance develops due to continuous use, making it difficult to use them any longer. Therefore, there is an urgent need to develop new therapeutic agents.

DISCLOSURE

Technical Problem

Accordingly, the problem to be solved by the present invention is to provide a compound having androgen receptor (AR)-degrading activity, pharmaceutical compositions comprising the same as an active ingredient, and medical uses for treating or preventing AR-related diseases.

Another problem to be solved by the present invention is to provide a method for treating or alleviating AR-related diseases, characterized in that it degrades AR and consequently lowers AR activity, and it comprises administering to a patient in need of treatment, improvement or prevention of AR related diseases the compound according to the present invention.

Technical Solution

Compounds of the Present Invention

In order to solve the above problem, one embodiment of the present invention provides a compound represented by the following Chemical Formula 1 or a pharmaceutically acceptable salt thereof.

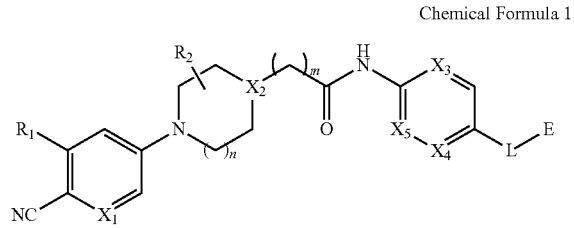

Chemical Formula 1

In the Chemical Formula 1,
$R_1$ is H, $C_{1-6}$alkyl, halogen, halo$C_{1-6}$alkyl, $C_{1-6}$alkoxy, or halo$C_{1-6}$alkoxy,
$R_2$ is H, $C_{1-4}$alkyl, halogen, or halo$C_{1-4}$alkyl,
$X_1$, $X_3$, $X_4$ and $X_5$ are each independently CH or N,
$X_2$ is $CR_3$ or N, wherein $R_3$ is H, $C_{1-6}$alkyl, halogen, halo$C_{1-6}$alkyl, $C_{1-6}$alkoxy, or —OH,
n is 0, 1, or 2,
m is 0 or 1,
L is the following Chemical Formula 2,

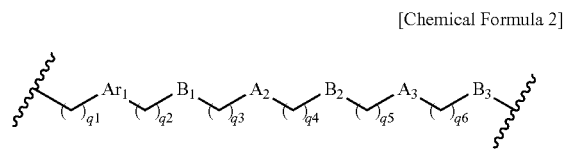

[Chemical Formula 2]

in the Chemical Formula 2,
$A_1$, $A_2$ and $A_3$ are each independently direct bond, —O—, —N($R_4$)—, —C(O)—, —CC—, —C(O)NH—, —NHC(O)—, —C(O)$CH_2$NH—, or —C(O)$CH_2$O—, wherein $R_4$ is H, $C_{1-6}$alkyl, or halo$C_{1-6}$alkyl,
$B_1$, $B_2$ and $B_3$ are each independently direct bond, $C_{3-12}$cycloalkyl, heterocycle, aryl, or heteroaryl, wherein these optionally have one or more hydrogens replaced by $C_{1-6}$alkyl, halogen, halo$C_{1-6}$alkyl, or —OH, q1 to q6 are each independently an integer of from 0 to 6, E is the following Chemical Formula 3 or 4.

[Chemical Formula 3]

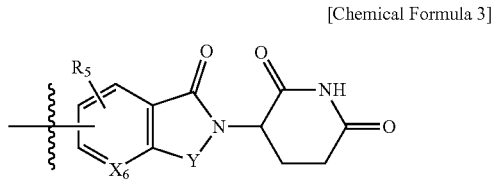

[Chemical Formula 4]

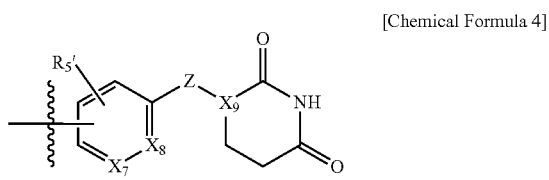

In the Chemical Formula 3 and 4, $X_6$, $X_7$, $X_5$ and $X_9$ are each independently CH or N, Y is —$C(R_6)_2$—, —C(O)—, —$C(R_6)_2$—$C(R_6')_2$—, —$C(R_6)$=$C(R_6')$—, —$C(R_6)$=N—, —N=$C(R_6)$—, or —N=N—, Z is direct bond, —$C(R_6)_2$—, —$N(R_6)$—, —O—, or —C(O)NH—, $R_5$ and $R_5'$ are each independently H, $C_{1-4}$alkyl, halogen, halo$C_{1-4}$alkyl, $C_{1-4}$alkoxy, or halo$C_{1-4}$alkoxy, $R_6$ and $R_6'$ are each independently H, $C_{1-4}$alkyl, halogen, halo$C_{1-4}$alkyl, $C_{1-4}$alkoxy, or halo$C_{1-4}$alkoxy.

The present inventors tried to develop a new compound with excellent AR degradation activity, (metabolism) stability, etc., and excellent physicochemical properties (cLogP value, water solubility, cell membrane permeability) as an active ingredient by combining a CRBN ligand (E in Chemical Formula 1) with a specific structure that binds to E3 ubiquitin ligase and a moiety that binds to AR (the left moiety relative to the linker). To this end, various reported AR-binding moieties such as enzalutamide were used, but contrary to expectations, the desired degree of activity or physical properties could not be achieved. When the novel AR binding moiety only used in the present invention was used, compounds having better activity and physical properties could be derived.

In addition, these compounds more fully met the various objects of the present invention in specific combinations. For example, in the case of a moiety (AR binder) that binds to AR, when the pyridine ring is converted to a pyrimidine or benzene ring, the AR degradation activity is relatively reduced. When the left benzene ring of Chemical Formula 1 was converted into a pyridine ring and F was introduced into the piperidine ring, the AR degradation activity tended to decrease. In addition, in the case of the linker (L in Formula 1), the linear linker was less preferred in terms of AR degrading activity and metabolic stability, and when the linker length was too short, the AR degrading activity tended to decrease. Some linker moieties were less desirable than others in terms of AR degradation activity or metabolic stability. In addition, in the case of CRBN binders (E in Chemical Formula 1), some CRBN binders were less preferred in terms of AR degradation activity, pharmacokinetics (oral absorption rate, etc.) or physicochemical properties (solubility, etc.).

On the other hand, the compounds of the present invention have excellent degradation activity against AR mutants (T877A, M896V, F876L, H874Y, L702H, W741C, etc.). Since resistance to existing anti-androgen receptor drugs can be caused by AR mutation, the excellent AR mutant-degrading activity of the compounds of the present invention can help overcome resistance to existing drugs. For example, the compounds of Examples 6 and 49 of the present disclosure showed degradation activity of 73% and 46%, respectively, for the T877A AR mutant at a concentration of 100 nM.

In addition, another mechanism by which resistance to existing treatments occurs is the expression of AR splicing variants (eg, AR-V7). The compounds of the present invention are excellent in reducing the expression of these variants (eg, AR-V7), and thus have a better anti-proliferative effect in AR-V7 positive prostate cancer cells. For example, the compounds of Examples 6 and 169 of the present disclosure inhibited the expression of AR-V7 by 87% and 48%, respectively, at a concentration of 100 nM.

As used herein, the terms "substituent", "radical", "group", "moiety", and "fragment" may be used interchangeably.

If a substituent is described as "optionally substituted", the substituent may be (1) unsubstituted or (2) substituted with one or more of the defined substituents. If the substitutable position is unsubstituted, the default substituent is hydride radical.

As used herein, the term "alkyl" means a saturated straight chain or branched non-cyclic hydrocarbon, unless the context clearly dictates otherwise, having from 1 to 10 carbon atoms. "Lower alkyl" means alkyl having from 1 to 4 carbon atoms. Representative saturated straight chain alkyls include -methyl, -ethyl, -n-propyl, -n-butyl, -n-pentyl, -n-hexyl, -n-heptyl, -n-octyl, -n-nonyl and -n-decyl, while saturated branched alkyls include -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like.

As used herein, the term "alkoxy" means —O-(alkyl) including —$OCH_3$, —$OCH_2CH_3$, —$O(CH_2)_2CH_3$, —$O(CH_2)_3CH_3$, —$O(CH_2)_4CH_3$, —$O(CH_2)_5CH_3$, and the like, wherein alkyl is as defined above.

As used herein, if the term "$C_{1-6}$", "C1-6", or "C1-C6" is used, it means the number of carbon atoms is from 1 to 6. For example, $C_{1-6}$alkyl means an alkyl which carbon number is any integer of from 1 to 6.

As used herein, the terms "halogen" and "halo" mean fluorine, chlorine, bromine or iodine. In a preferred embodiment of the present invention, the halogen is chlorine or fluorine.

As used herein, the term "haloalkyl", "haloalkoxy", "haloalkenyl" or "haloalkynyl" means an alkyl, alkoxy, alkenyl, or alkynyl group, respectively, wherein one or more hydrogen atoms are substituted with halogen atoms. For example, the haloalkyl includes —$CF_3$, —$CHF_2$, —$CH_2F$, —$CBr_3$, —$CHBr_2$, —$CH_2Br$, —$CCl_3$, —$CHCl_2$, —$CH_2Cl$, —$CI_3$, —$CHI_2$, —$CH_2I$, —$CH_2$—$CF_3$, —$CH_2$—$CHF_2$, —$CH_2$—$CH_2F$, —$CH_2$—$CBr_3$, —$CH_2$—$CHBr_2$, —$CH_2$—$CH_2Br$, —$CH_2$—$CCl_3$, —$CH_2$—$CHCl_2$, —$CH_2$—$CH_2Cl$, —$CH_2$—$CI_3$, —$CH_2$—$CHI_2$, —$CH_2$—$CH_2I$, and the like, wherein alkyl and halogen are as described above. In a preferred embodiment of the present invention, haloalkyl is —$CF_3$.

As used herein, the term "cycloalkyl" means a monocyclic or polycyclic saturated ring having carbon and hydrogen atoms and having no carbon-carbon multiple bonds. Examples of monocyclic rings include, but are not limited to, ($C_3$-$C_7$)cycloalkyl groups, including cyclopropyl, cyclobutyl, cyclopentyl, cyclohexyl, and cycloheptyl. Examples of polycyclic rings include, but are not limited to, fused bicyclic rings such as octahydropentalene and decahydronaphthalene; spiro rings such as spiro[3.3]heptane, spiro[3.4]octane, spiro[3.5]nonane, spiro[4.4]nonane, spiro[4.5]decane, and spiro[5.5]undecane; and bridged bicycle rings such as bicyclo[2.1.1]hexane, bicyclo[2.2.1]heptane, and bicyclo[2.2.2]octane. A cycloalkyl group can be unsubstituted or optionally substituted.

The term "heterocycle" or "heterocycloalkyl" means a 5- to 7-membered monocyclic, or 7- to 12-membered bicyclic, saturated heterocyclic ring which contains from 1 to 4 heteroatoms independently selected from nitrogen, oxygen and sulfur, and wherein the nitrogen and sulfur heteroatoms can be optionally oxidized, and the nitrogen heteroatom can be optionally quaternized. Heterocycles include heteroaryls as defined above. Representative heterocycles include oxirane, oxetane, tetrahydrofuran, tetrahydropyran, 1,4-dioxane, aziridine, azetidine, pyrrolidine, piperidine, piperazine, pyrrolidinone, hydantoin, valerolactam, thiirane, thietane, tetrahydrothiophene, tetrahydrothiopyran, morpholine, tetrahydropyridine, and tetrahydropyrimidine. Heterocycles include a bicyclic ring in which part of the heterocycle is fused to a benzene or cyclopenta-1,3-diene ring. The heterocycle can be attached via any heteroatom or carbon atom. In addition, heterocycles include fused bicyclic rings, spiro rings and bridged bicyclic rings in which one or more carbon atoms of the aforementioned polycyclic rings are replaced with nitrogen, oxygen or sulfur atoms. For example, when the heteroatom is nitrogen, these include, but are limited to, fused heterobicyclic rings such as octahydrocyclopenta[c]pyrrole, octahydropyrrolo[3,4-c]pyrrole, decahydroisoquinoline, and decahydro-2,6-naphthyridine; spiro rings such as 2-azaspiro[3.3]heptane, 2,6-diazaspiro[3.3]heptane, 2-azaspiro[3.4]octane, 2,6-diazaspiro[3.4]octane, 2-azaspiro[3.5]nonane, 2,7-diazaspiro[3.5]nonane, 2-azaspiro[4.4]nonane, 2,7-diazaspiro[4.4]nonane, 8-azaspiro[4.5]decane, 2,8-diazaspiro[4.5]decane, 3-azaspiro[5.5]undecane, and 3,9-diazaspiro[5.5]undecane; and bridged heterobicyclic rings such as 2-azabicyclo[2.1.1]hexane, 2-azabicyclo[2.2.1]heptane, 2,5-diazabicyclo[2.2.1]heptane, 2-azabicyclo[2.2.2]octane, and 2,5-diazabicyclo[2.2.2]octane.

As used herein, the term "aryl" means a carbocyclic aromatic group containing from 5 to 10 ring atoms. Representative examples include, but are not limited to, phenyl, tolyl, xylyl, naphthyl, tetrahydronaphthyl, anthracenyl, fluorenyl, indenyl, and azulenyl. A carbocyclic aromatic group can be unsubstituted or optionally substituted.

As used herein, the term "heteroaryl" means an aromatic heterocycle ring of 5- to 10- members and having at least one heteroatom selected from nitrogen, oxygen and sulfur, and containing at least 1 carbon atom, including both mono- and bicyclic ring systems. Representative heteroaryls are furan, 4H-pyran, pyrrole, imidazole, pyrazole, triazole, tetrazole, pyridine, pyrimidine, pyridazine, pyrazine, triazine, thiophene, oxazole, isoxazole, thiazole, isothiazole, oxadiazole, benzofuran, benzothiophene, quinoline, indole, benzoxazole, benzimidazole, benzothiazole, cinnoline, phthalazine, quinazoline, 1H-azepine, etc.

In various aspects such as AR degradation activity, (metabolism) stability, physicochemical properties, and the like, a preferred embodiment of the present invention provides a compound represented by the Chemical Formula 1 or a pharmaceutically acceptable salt thereof, wherein $R_1$ is H, $C_{1-6}$alkyl, halogen, or halo$C_{1-6}$alkyl,
$R_2$ is H or $C_{1-2}$alkyl,
$X_1$, $X_3$, $X_4$ and $X_5$ are each independently CH or N,
$X_2$ is $CR_3$ or N, wherein $R_3$ is H, $C_{1-6}$alkyl, halogen, or —OH,
n is 0, 1, or 2,
m is 0 or 1,
L is the following Chemical Formula 2,

[Chemical Formula 2]

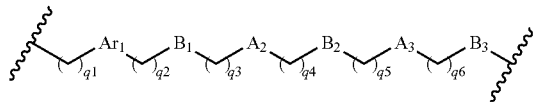

in the Chemical Formula 2,
$A_1$, $A_2$ and $A_3$ are each independently direct bond, —O—, —N($R_4$)—, —C(O)—, —CC—, —C(O)NH—, —NHC(O)—, —C(O)$CH_2$NH—, or —C(O)$CH_2$O— (preferably, direct bond, —O—, —N($R_4$)—, —C(O)—, —CC—, —C(O)NH—, or —C(O)$CH_2$NH—), wherein $R_4$ is H or $C_{1-6}$alkyl,
$B_1$, $B_2$ and $B_3$ are each independently direct bond, or any one of the following substituents,

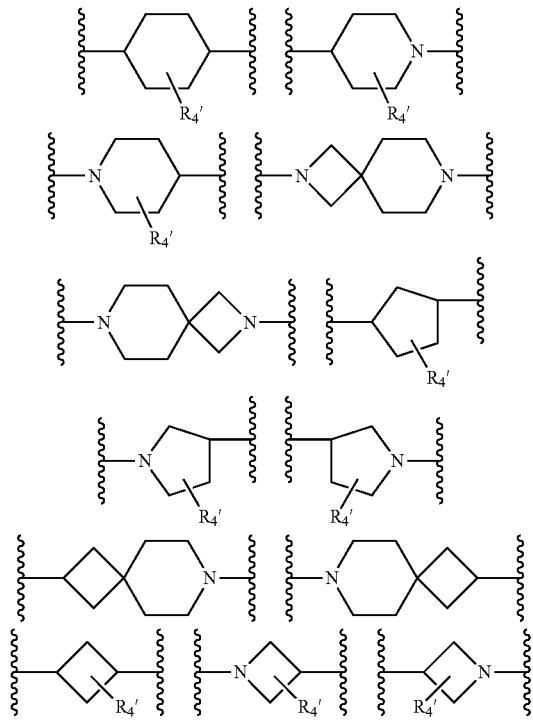

-continued

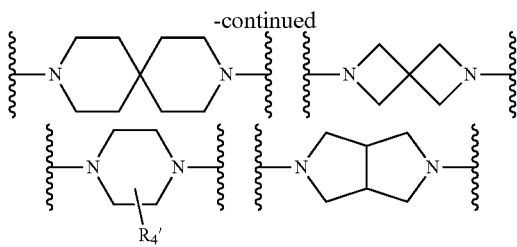

wherein, $R_4'$ are each independently H, $C_{1-4}$alkyl, halo$C_{1-4}$alkyl, halogen or —OH,
q1 to q6 are each independently an integer of from 0 to 4,
E is the following Chemical Formula 3 or 4.

[Chemical Formula 3]

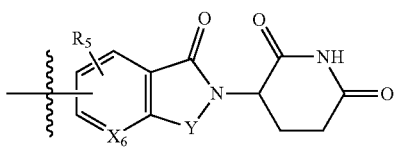

[Chemical Formula 4]

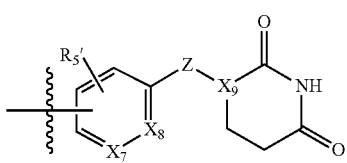

In the Chemical Formula 3 and 4,
$X_6$, $X_7$, $X_8$ and $X_9$ are each independently CH or N,
Y is —C($R_6$)$_2$—, —C(O)—, or —N=N—,
Z is direct bond, —N($R_6$)—, or —C(O)NH—,
$R_5$ and $R_5'$ are each independently H, $C_{1-4}$alkyl, halogen, halo$C_{1-4}$alkyl, or $C_{1-4}$alkoxy,
$R_6$ are each independently H, $C_{1-4}$alkyl, or halo$C_{1-4}$alkyl.
A preferred embodiment of the present invention provides a compound represented by the Chemical Formula 1 or a pharmaceutically salt thereof, wherein
$R_1$ is halogen or halo$C_{1-6}$alkyl (preferably, $R_1$ is Cl or $CF_3$),
$R_2$ is H,
$X_1$ is N or CH (preferably, CH),
$X_3$, $X_4$ and $X_5$ are each independently the combination of N, CH and CH; N, N and CH; or CH, N and N (preferably, N, CH and CH; or CH, N and N),
$X_2$ is $CR_2$, wherein $R_2$ is H, F or $CH_3$ (preferably, H),
n is 1,
m is 0,
L is the following Chemical Formula 2,

[Chemical Formula 2]

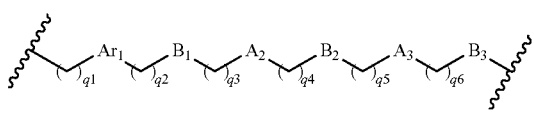

in the Chemical Formula 2,
$A_2$ is direct bond, $A_1$ and $A_3$ are each independently direct bond or —O— (preferably, when $A_3$ is —O—, $B_3$ is direct bond and $q_6$ is 0, and when $A_1$ is —O—, q1 is 0.),
$B_1$, $B_2$ and $B_3$ are each independently direct bond, or any one of the following substituents,

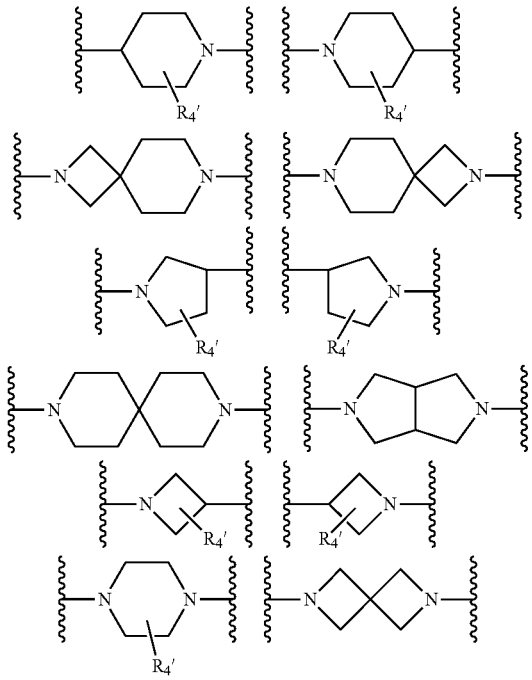

wherein, $R_4'$ is each independently H, or $C_{1-4}$alkyl (preferably, H or $CH_3$),
q1 to q6 are each independently an integer of from 0 to 2, (preferably,

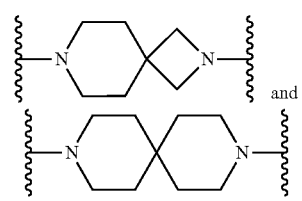

are not directly linked to the ring comprising $X_3$, $X_4$ and $X_5$.),
E is the following Chemical Formula 3.

[Chemical Formula 3]

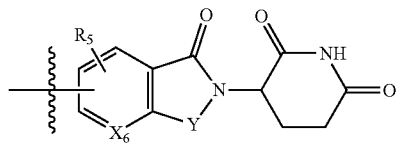

In the Chemical Formula 3,
$X_6$ is CH or N (preferably, CH),
Y is —C(O)— or —CH$_2$— (preferably, —C(O)—),
$R_5$ is H, or halogen (preferably, H or F).

In one embodiment of the present invention, Chemical Formula 1 excluding -L-E (linked to *-L-E) may be any one of the following structures:
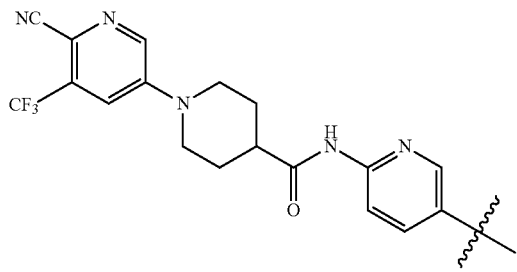
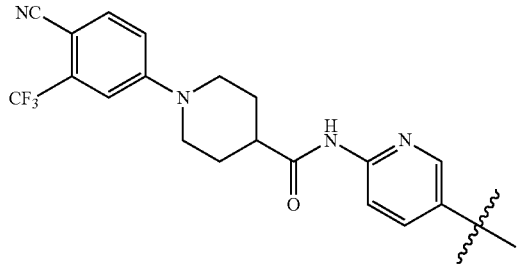
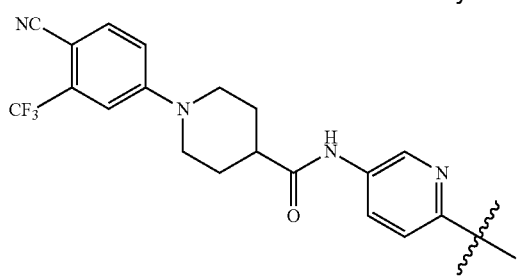
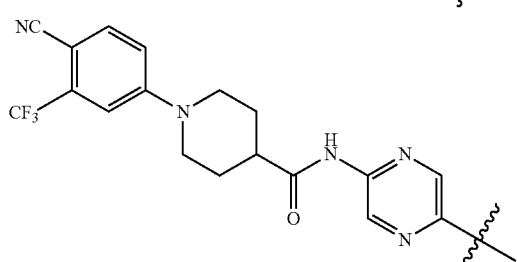
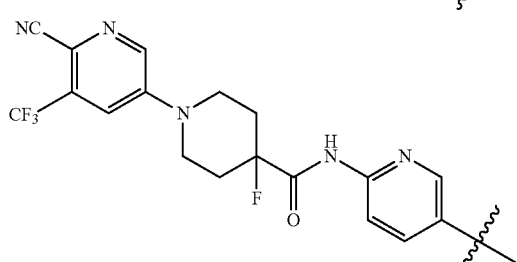
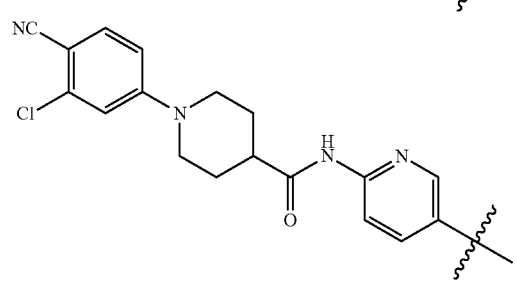
-continued
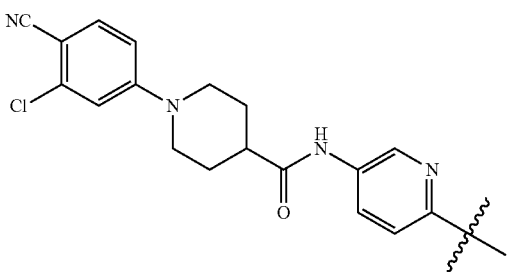
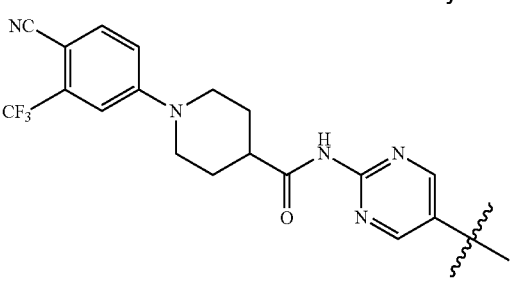
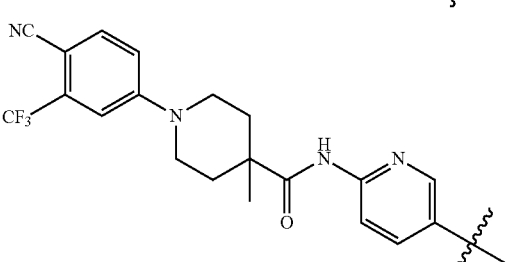
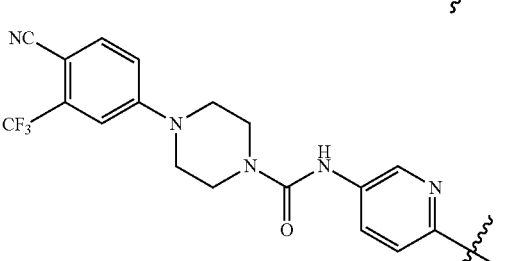
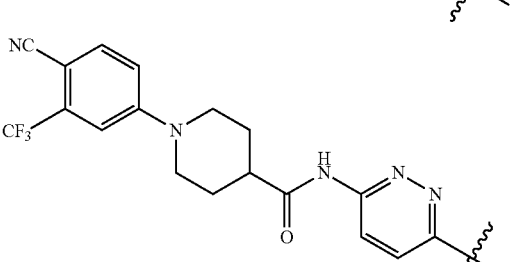
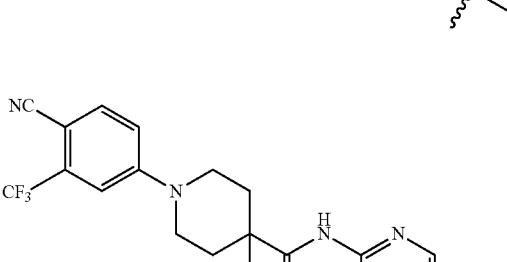
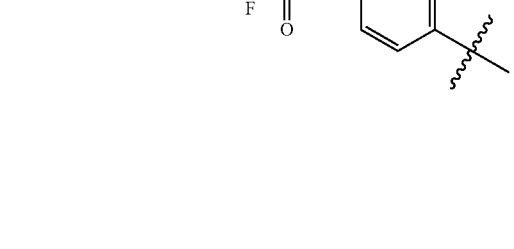

-continued
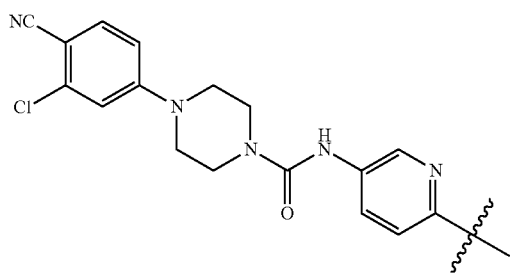
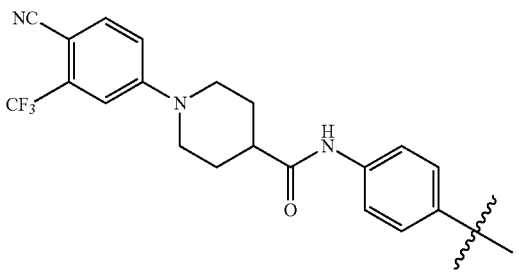
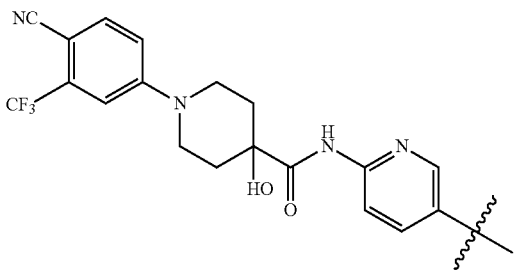
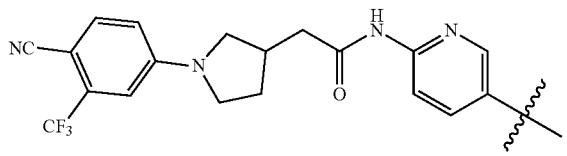
In a preferred embodiment of the present invention, Chemical Formula 1 excluding -L-E (linked to *-L-E) may be any one of the following structures:
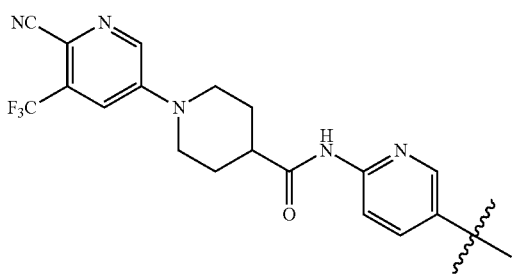
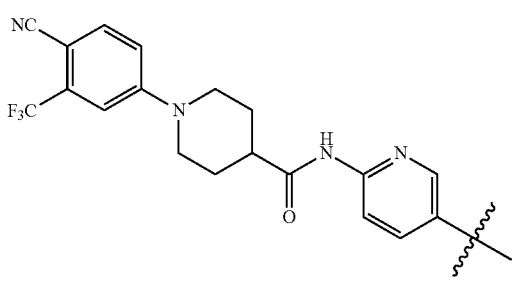
-continued
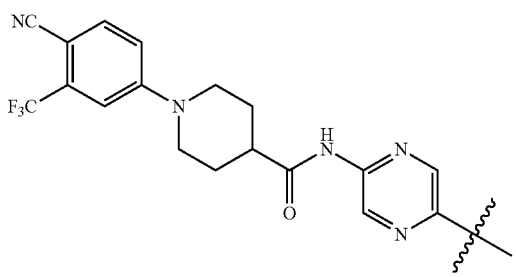
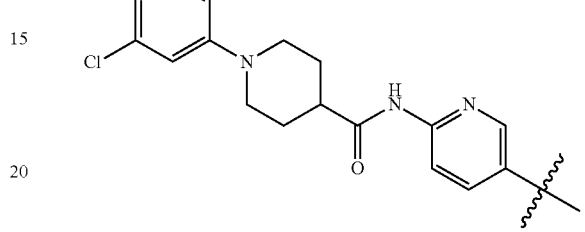
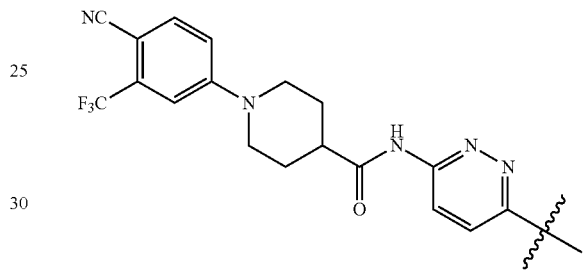
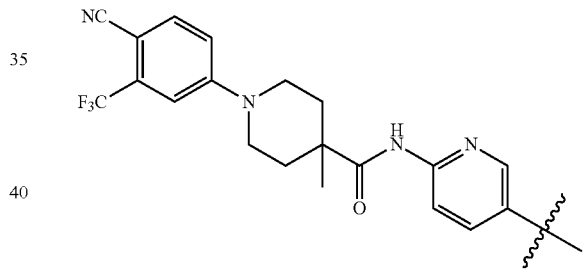
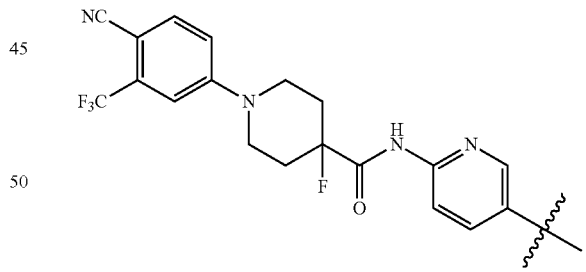
In one embodiment of the present invention, E in Chemical Formula 1 may be any one of the following structures:
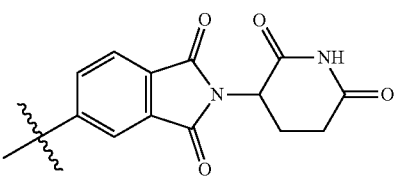

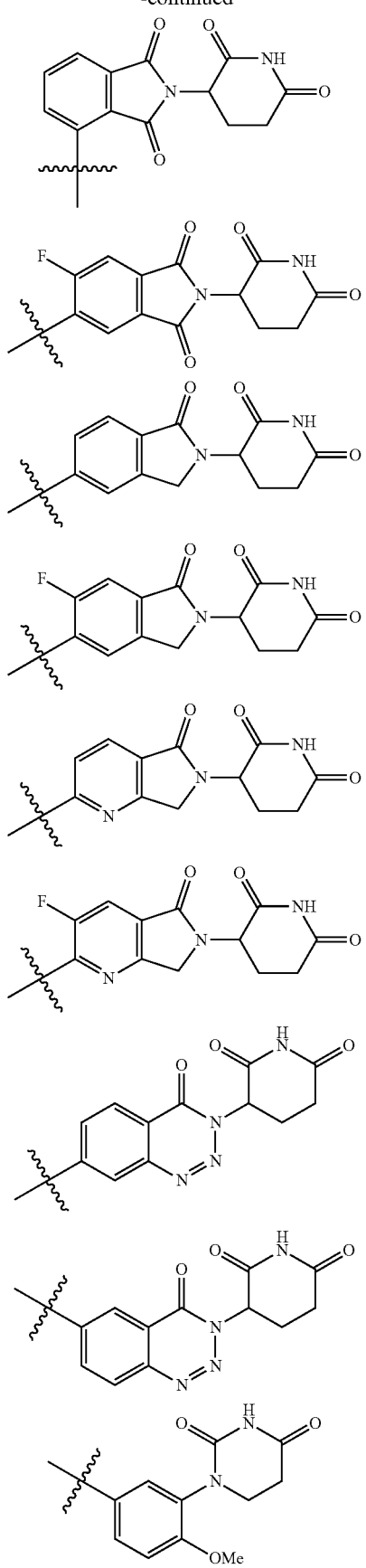
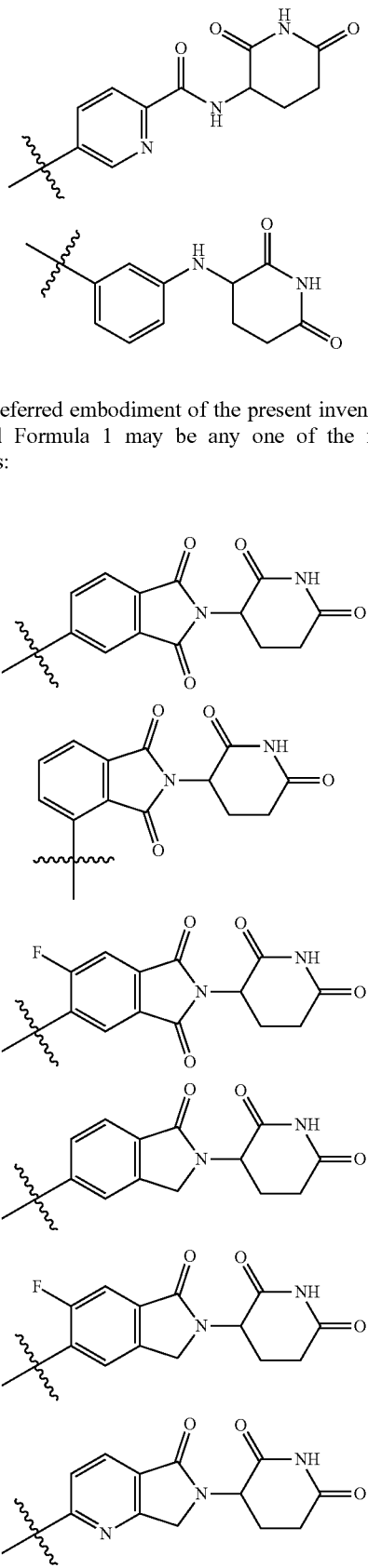
In a preferred embodiment of the present invention, E in Chemical Formula 1 may be any one of the following structures:

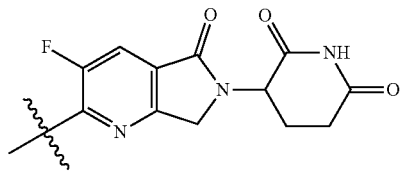
In an embodiment of the present invention, L in Chemical Formula 1 may be any one of the following structures:
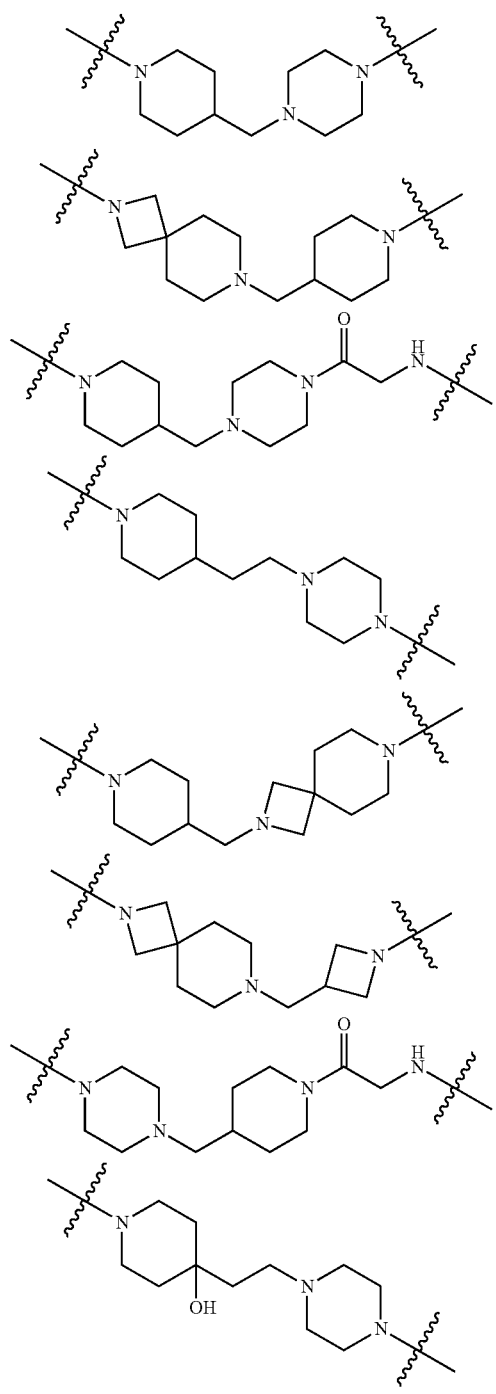
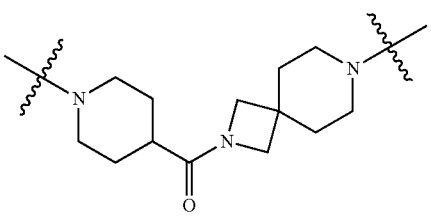
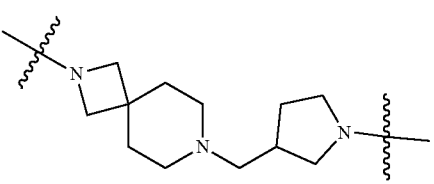
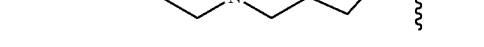
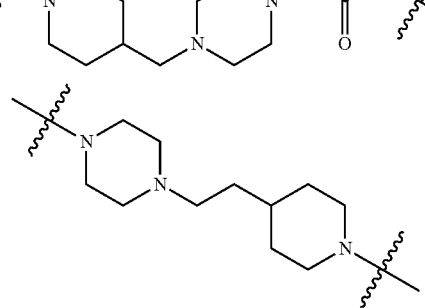
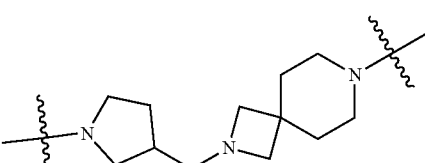
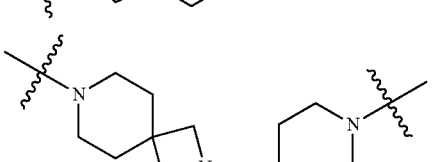
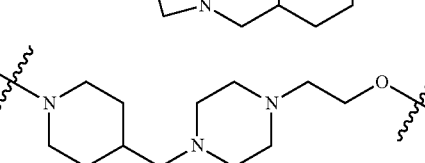
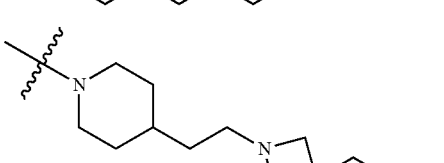
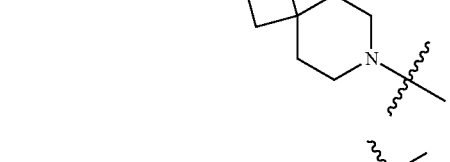
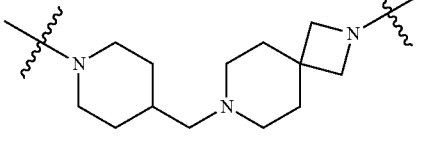

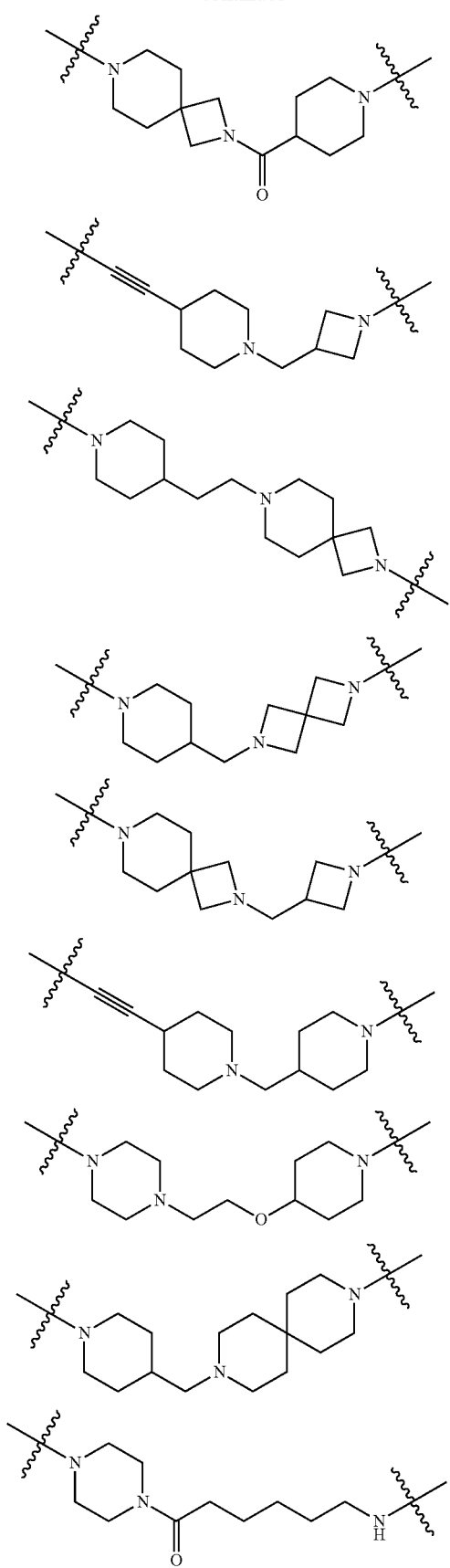
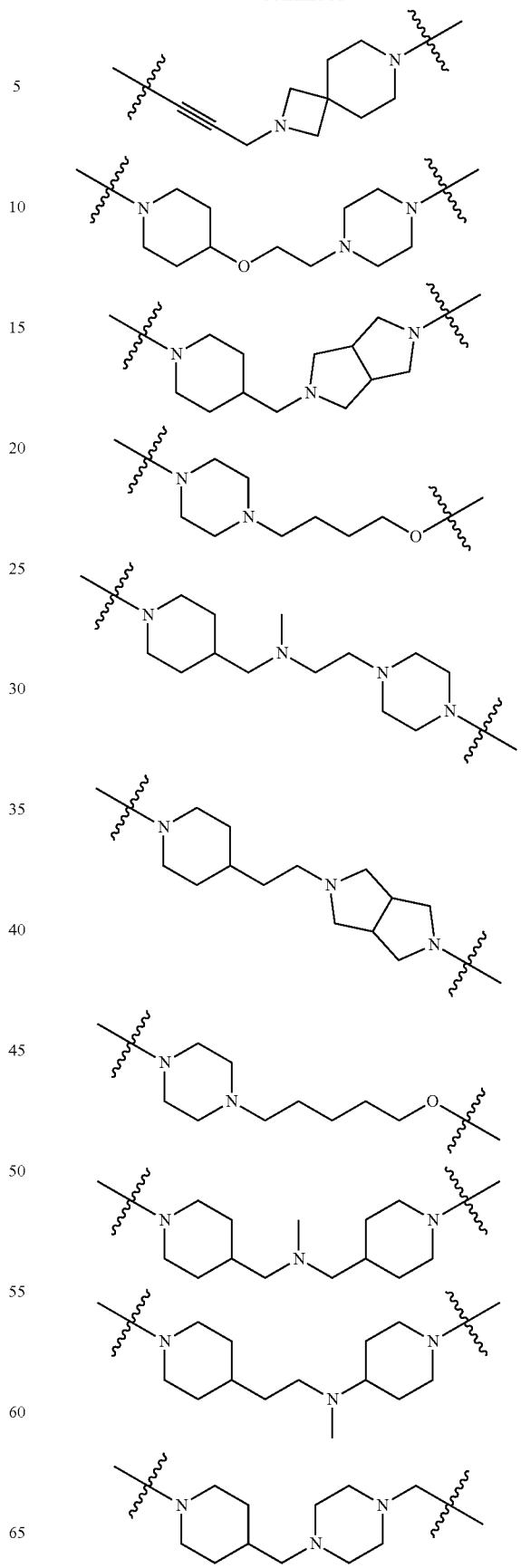

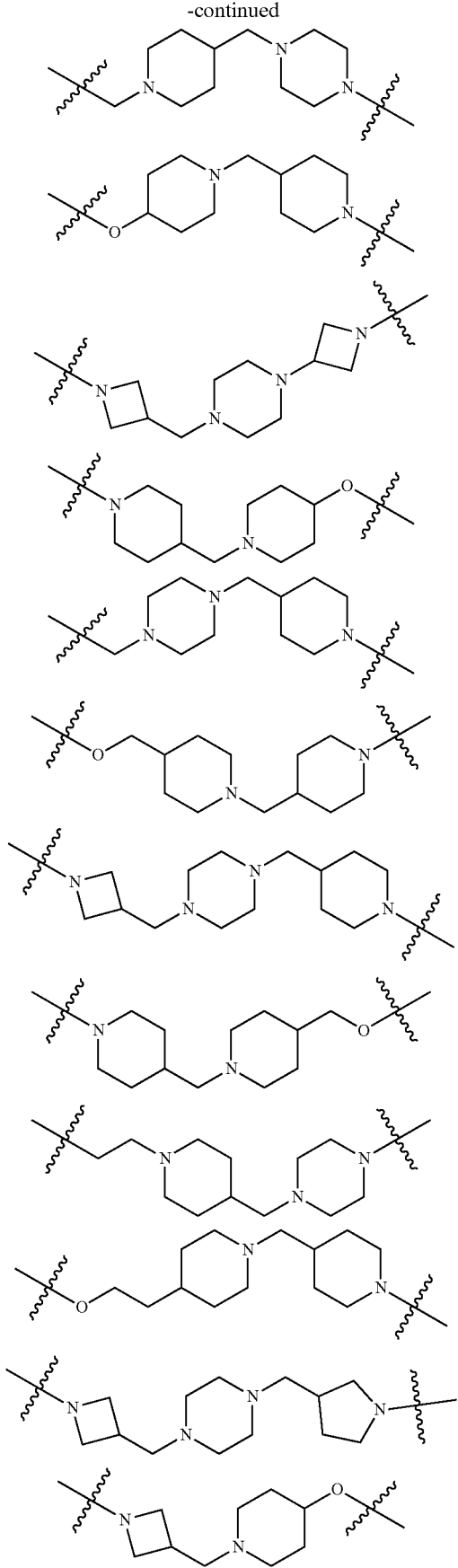
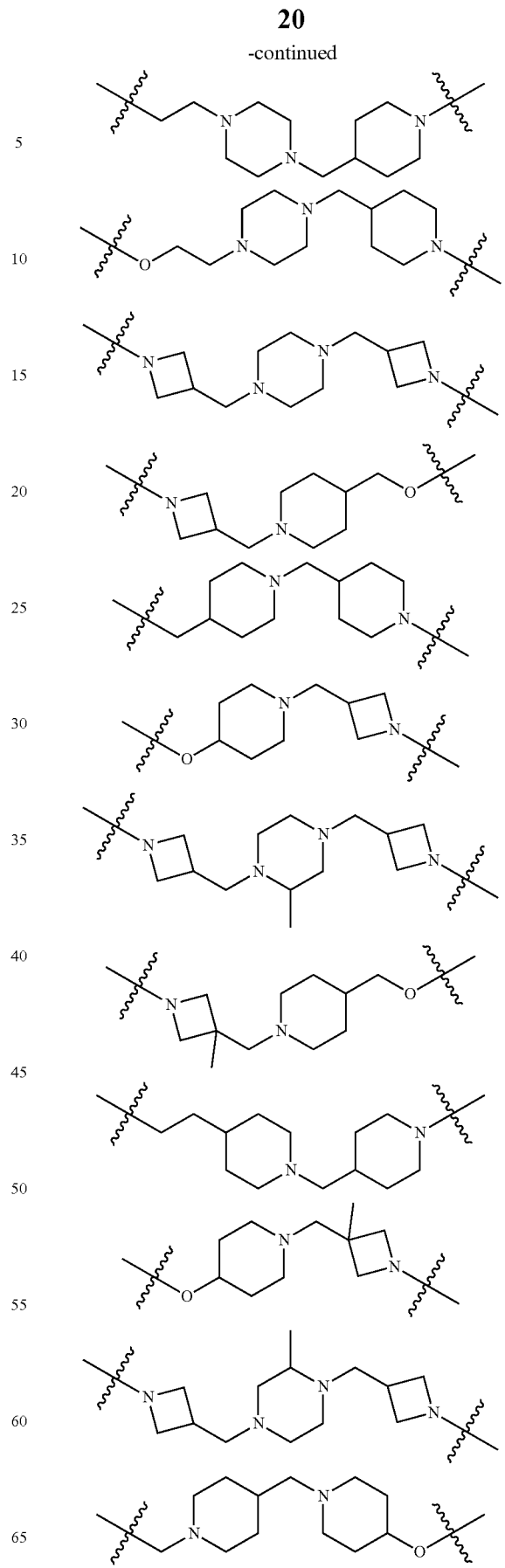

21
-continued
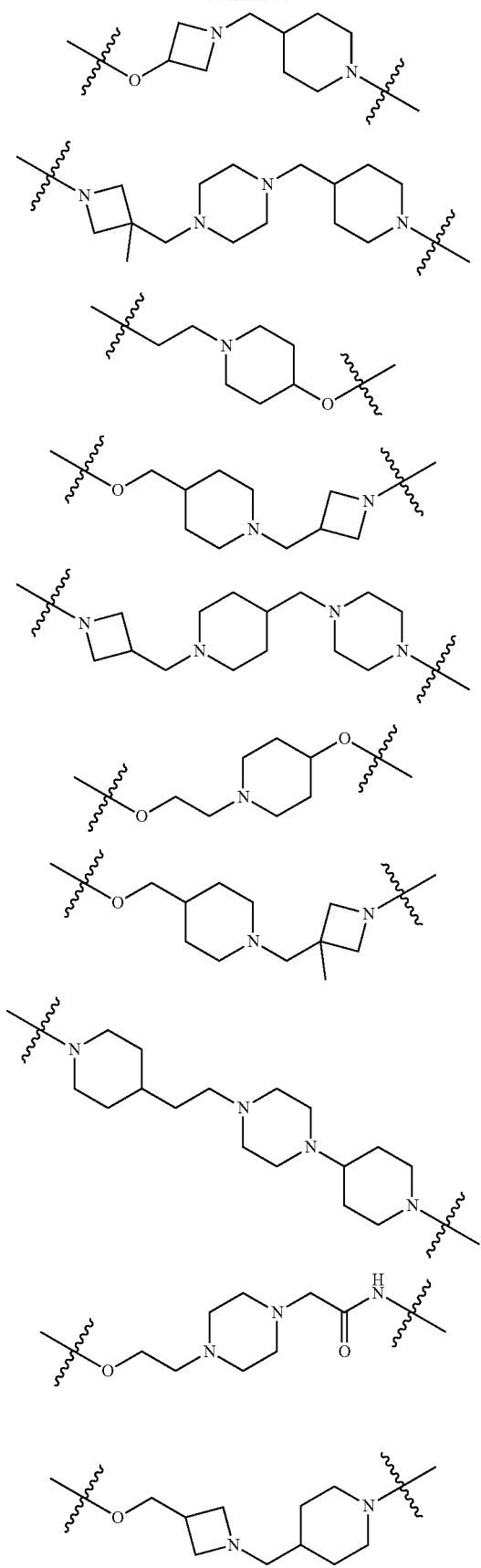
22
-continued
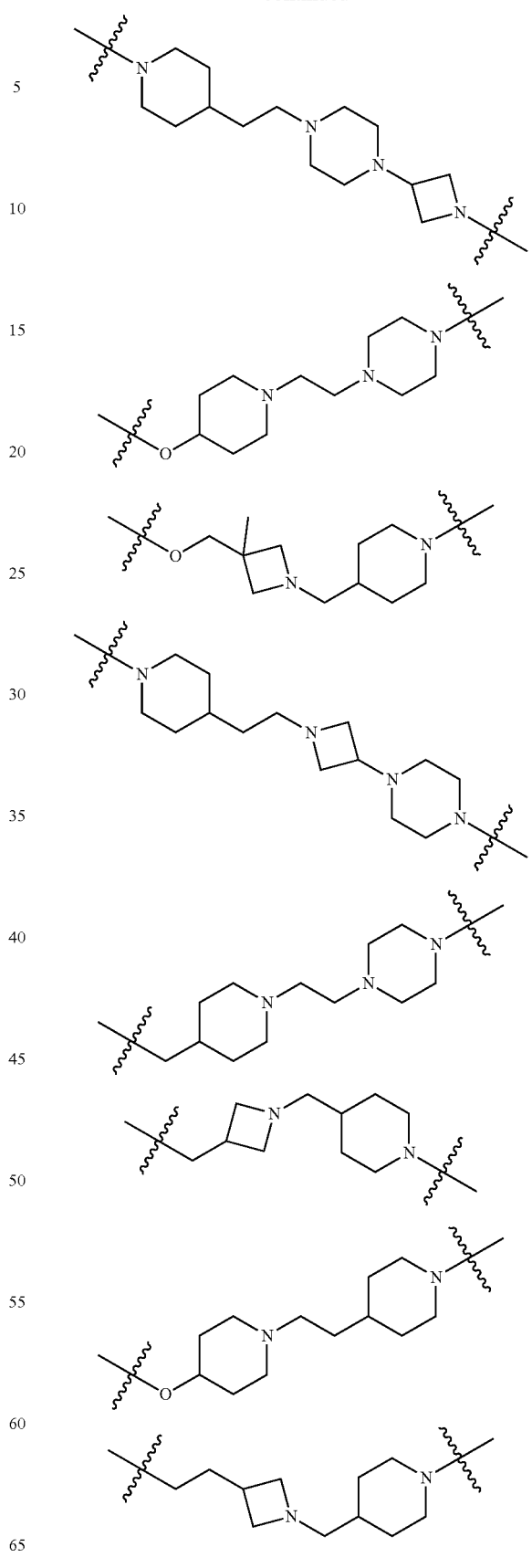

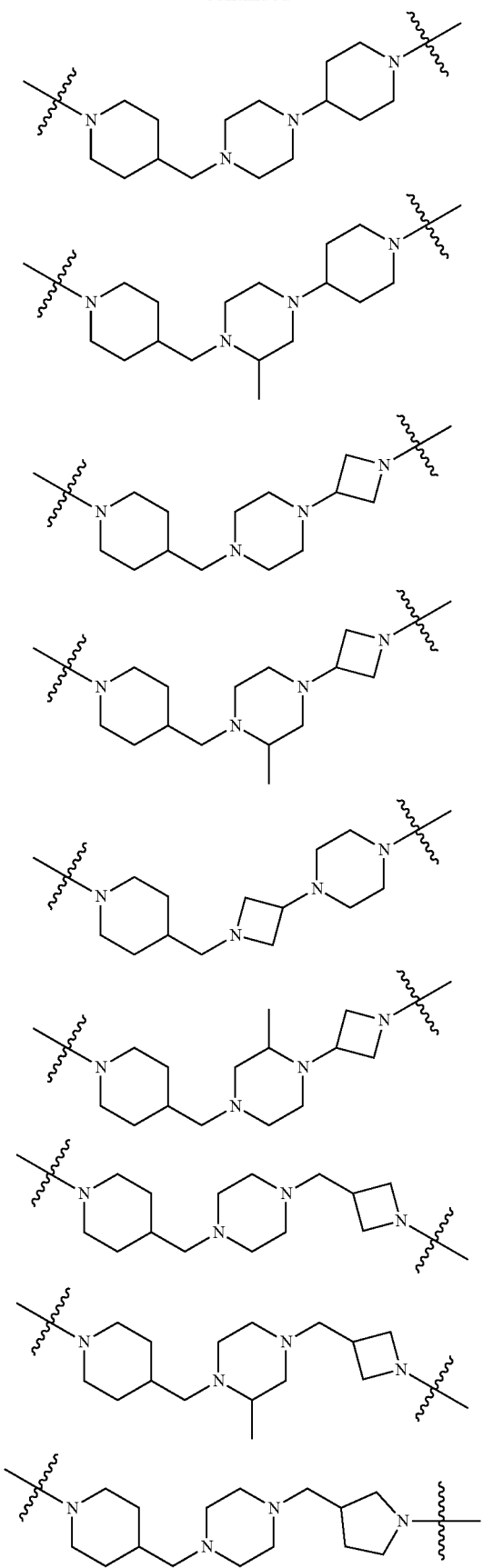
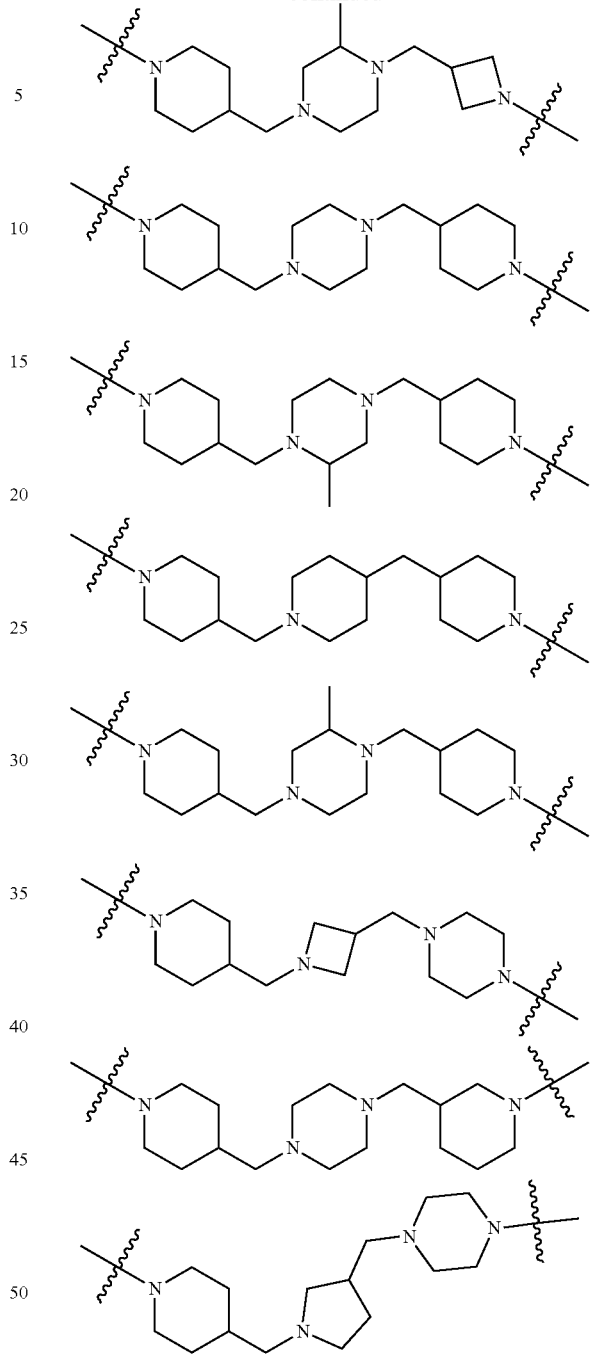

In this specification, * or ～～ means connected to another moiety.

Non-limiting examples of the compound of Chemical Formula 1 according to the present disclosure are the compounds prepared in the Examples described below. Each example number corresponds to each compound number. For example, the number of the final compound prepared in Example 150 is Compound 150.

Among the compounds, the compounds of Table 1 below were particularly preferable in terms of various aspects such as AR degradation activity, cancer cell line cytotoxicity, (metabolic) stability, physicochemical properties, etc.

TABLE 1

| Compound no. | IUPAC Name |
|---|---|
| 6 | 1-(4-cyano-3-(trifluoromethyl)phenyl)-N-(5-(4-((4-((1-(2-(2,6-dioxopiperidin-3-yl)-1,3-dioxoisoindolin-5-yl)piperidin-4-yl)methyl)piperazin-1-yl)methyl)piperidin-1-yl)pyridin-2-yl)piperidine-4-carboxamide |
| 11 | 1-(4-cyano-3-(trifluoromethyl)phenyl)-N-(5-(4-((4-((1-(2-(2,6-dioxopiperidin-3-yl)-1,3-dioxoisoindolin-5-yl)azetidin-3-yl)methyl)piperazin-1-yl)methyl)piperidin-1-yl)pyridin-2-yl)piperidine-4-carboxamide |
| 14 | 1-(4-cyano-3-(trifluoromethyl)phenyl)-N-(5-(4-((4-(((3R)-1-(2-(2,6-dioxopiperidin-3-yl)-1,3-dioxoisoindolin-5-yl)pyrrolidin-3-yl)methyl)piperazin-1-yl)methyl)piperidin-1-yl)pyridin-2-yl)piperidine-4-carboxamide |
| 15 | 1-(4-cyano-3-(trifluoromethyl)phenyl)-N-(5-(4-((4-(((3S)-1-(2-(2,6-dioxopiperidin-3-yl)-1,3-dioxoisoindolin-5-yl)pyrrolidin-3-yl)methyl)piperazin-1-yl)methyl)piperidin-1-yl)pyridin-2-yl)piperidine-4-carboxamide |
| 18 | 1-(4-cyano-3-(trifluoromethyl)phenyl)-N-(5-(4-((4-((1-(2-(2,6-dioxopiperidin-3-yl)-6-fluoro-1,3-dioxoisoindolin-5-yl)piperidin-4-yl)methyl)piperazin-1-yl)methyl)piperidin-1-yl)pyridin-2-yl)piperidine-4-carboxamide |
| 19 | 1-(4-cyano-3-(trifluoromethyl)phenyl)-N-(5-(4-((4-(((3R)-1-(2-(2,6-dioxopiperidin-3-yl)-6-fluoro-1,3-dioxoisoindolin-5-yl)pyrrolidin-3-yl)methyl)piperazin-1-yl)methyl)piperidin-1-yl)pyridin-2-yl)piperidine-4-carboxamide |
| 20 | 1-(4-cyano-3-(trifluoromethyl)phenyl)-N-(5-(4-((4-((1-(2-(2,6-dioxopiperidin-3-yl)-6-fluoro-1,3-dioxoisoindolin-5-yl)azetidin-3-yl)methyl)piperazin-1-yl)methyl)piperidin-1-yl)pyridin-2-yl)piperidine-4-carboxamide |
| 34 | 1-(4-cyano-3-(trifluoromethyl)phenyl)-N-(5-(4-((4-((1-(6-(2,6-dioxopiperidin-3-yl)-5-oxo-6,7-dihydro-5H-pyrrolo[3,4-b]pyridin-2-yl)piperidin-4-yl)methyl)piperazin-1-yl)methyl)piperidin-1-yl)pyridin-2-yl)piperidine-4-carboxamide |
| 35 | 1-(4-cyano-3-(trifluoromethyl)phenyl)-N-(5-(4-((4-(1-(2-(2,6-dioxopiperidin-3-yl)-1,3-dioxoisoindolin-5-yl)azetidin-3-yl)piperazin-1-yl)methyl)piperidin-1-yl)pyridin-2-yl)piperidine-4-carboxamide |
| 38 | 1-(4-cyano-3-(trifluoromethyl)phenyl)-N-(5-(4-((4-(((3S)-1-(2-(2,6-dioxopiperidin-3-yl)-6-fluoro-1,3-dioxoisoindolin-5-yl)pyrrolidin-3-yl)methyl)piperazin-1-yl)methyl)piperidin-1-yl)pyridin-2-yl)piperidine-4-carboxamide |
| 43 | 1-(4-cyano-3-(trifluoromethyl)phenyl)-N-(5-(4-(((2R)-4-(1-(6-(2,6-dioxopiperidin-3-yl)-5-oxo-6,7-dihydro-5H-pyrrolo[3,4-b]pyridin-2-yl)piperidin-4-yl)-2-methylpiperazin-1-yl) methyl)piperidin-1-yl)pyridin-2-yl)piperidine-4-carboxamide |
| 44 | 1-(4-cyano-3-(trifluoromethyl)phenyl)-N-(5-(4-(((2R)-4-((1-(6-(2,6-dioxopiperidin-3-yl)-5-oxo-6,7-dihydro-5H-pyrrolo[3,4-b]pyridin-2-yl)piperidin-4-yl)methyl)-2-methylpiperazin-1-yl)methyl)piperidin-1-yl)pyridin-2-yl)piperidine-4-carboxamide |
| 49 | 1-(4-cyano-3-(trifluoromethyl)phenyl)-N-(5-(4-((7-(2-(2,6-dioxopiperidin-3-yl)-1,3-dioxoisoindolin-5-yl)-2,7-diazaspiro[3.5]nonan-2-yl)methyl)piperidin-1-yl)pyridin-2-yl)piperidine-4-carboxamide |
| 66 | 1-(4-cyano-3-(trifluoromethyl)phenyl)-N-(5-(4-((6-(2-(2,6-dioxopiperidin-3-yl)-1,3-dioxoisoindolin-5-yl)-2,6-diazaspiro[3.3]heptan-2-yl)methyl)piperidin-1-yl)pyridin-2-yl)piperidine-4-carboxamide |
| 70 | 1-(4-cyano-3-(trifluoromethyl)phenyl)-N-(5-(4-((4-(1-(2-(2,6-dioxopiperidin-3-yl)-1,3-dioxoisoindolin-5-yl)piperidin-4-yl)piperazin-1-yl)methyl)piperidin-1-yl)pyridin-2-yl)piperidine-4-carboxamide |
| 75 | 1-(4-cyano-3-(trifluoromethyl)phenyl)-N-(5-(4-((4-(1-(6-(2,6-dioxopiperidin-3-yl)-5-oxo-6,7-dihydro-5H-pyrrolo[3,4-b]pyridin-2-yl)piperidin-4-yl)piperazin-1-yl)methyl)piperidin-1-yl)pyridin-2-yl)piperidine-4-carboxamide |
| 86 | 1-(4-cyano-3-(trifluoromethyl)phenyl)-N-(5-(4-(2-(4-(2-(2,6-dioxopiperidin-3-yl)-1,3-dioxoisoindolin-5-yl)piperazin-1-yl)ethyl)piperidin-1-yl)pyridin-2-yl)piperidine-4-carboxamide |
| 121 | 1-(4-cyano-3-(trifluoromethyl)phenyl)-N-(5-(7-((1-(2-(2,6-dioxopiperidin-3-yl)-1,3-dioxoisoindolin-5-yl)piperidin-4-yl)methyl)-2,7-diazaspiro[3.5]nonan-2-yl)pyridin-2-yl)piperidine-4-carboxamide |
| 133 | 1-(4-cyano-3-(trifluoromethyl)phenyl)-N-(5-(2-(1-((1-(2-(2,6-dioxopiperidin-3-yl)-1,3-dioxoisoindolin-5-yl)piperidin-4-yl)methyl)piperidin-4-yl)ethyl)pyridin-2-yl)piperidine-4-carboxamide |
| 140 | 1-(4-cyano-3-(trifluoromethyl)phenyl)-N-(5-(4-((4-(1-(2-(2,6-dioxopiperidin-3-yl)-1-oxoisoindolin-5-yl)piperidin-4-yl)piperazin-1-yl)methyl)piperidin-1-yl)pyridin-2-yl)piperidine-4-carboxamide |
| 143 | 1-(4-cyano-3-(trifluoromethyl)phenyl)-N-(5-(4-((4-((1-(2-(2,6-dioxopiperidin-3-yl)-1-oxoisoindolin-5-yl)piperidin-4-yl)methyl)piperazin-1-yl)methyl)piperidin-1-yl)pyridin-2-yl)piperidine-4-carboxamide |
| 146 | 1-(4-cyano-3-(trifluoromethyl)phenyl)-N-(5-(4-((4-((2-(2,6-dioxopiperidin-3-yl)-1,3-dioxoisoindolin-5-yl)oxy)piperidin-1-yl)methyl)piperidin-1-yl)pyridin-2-yl)piperidine-4-carboxamide |
| 147 | 1-(4-cyano-3-(trifluoromethyl)phenyl)-N-(5-(4-((4-(((2-(2,6-dioxopiperidin-3-yl)-1,3-dioxoisoindolin-5-yl)oxy)methyl)piperidin-1-yl)methyl)piperidin-1-yl)pyridin-2-yl)piperidine-4-carboxamide |
| 164 | 1-(4-cyano-3-(trifluoromethyl)phenyl)-N-(5-((1-((1-(2-(2,6-dioxopiperidin-3-yl)-1,3-dioxoisoindolin-5-yl)piperidin-4-yl)methyl)piperidin-4-yl)methyl)pyridin-2-yl)piperidine-4-carboxamide |
| 169 | 1-(4-cyano-3-(trifluoromethyl)phenyl)-N-(5-((1-((1-(2-(2,6-dioxopiperidin-3-yl)-1,3-dioxoisoindolin-5-yl)piperidin-4-yl)methyl)piperidin-4-yl)oxy)pyridin-2-yl)piperidine-4-carboxamide |
| 170 | 1-(4-cyano-3-(trifluoromethyl)phenyl)-N-(5-((1-((1-(2-(2,6-dioxopiperidin-3-yl)-6-fluoro-1,3-dioxoisoindolin-5-yl)piperidin-4-yl)methyl)piperidin-4-yl)oxy)pyridin-2-yl)piperidine-4-carboxamide |
| 173 | 1-(4-cyano-3-(trifluoromethyl)phenyl)-N-(5-((1-((1-(2-(2,6-dioxopiperidin-3-yl)-1,3-dioxoisoindolin-5-yl)piperidin-4-yl)methyl)azetidin-3-yl)oxy)pyridin-2-yl)piperidine-4-carboxamide |
| 174 | 1-(4-cyano-3-(trifluoromethyl)phenyl)-N-(5-((1-((1-(2-(2,6-dioxopiperidin-3-yl)-1,3-dioxoisoindolin-5-yl)piperidin-4-yl)methyl)piperidin-4-yl)methoxy)pyridin-2-yl)piperidine-4-carboxamide |
| 175 | 1-(4-cyano-3-(trifluoromethyl)phenyl)-N-(5-(2-(1-((1-(2-(2,6-dioxopiperidin-3-yl)-1,3-dioxoisoindolin-5-yl)piperidin-4-yl)methyl)piperidin-4-yl)ethoxy)pyridin-2-yl)piperidine-4-carboxamide |
| 181 | 1-(4-cyano-3-(trifluoromethyl)phenyl)-N-(5-((1-((1-(2-(2,6-dioxopiperidin-3-yl)-6-fluoro-1,3-dioxoisoindolin-5-yl)piperidin-4-yl)methyl)piperidin-4-yl)methoxy)pyridin-2-yl)piperidine-4-carboxamide |
| 182 | 1-(4-cyano-3-(trifluoromethyl)phenyl)-N-(5-((1-((1-(2-(2,6-dioxopiperidin-3-yl)-6-fluoro-1,3-dioxoisoindolin-5-yl)piperidin-4-yl)methyl)piperidin-4-yl)methyl)pyridin-2-yl)piperidine-4-carboxamide |
| 185 | 1-(4-cyano-3-(trifluoromethyl)phenyl)-N-(5-((1-((1-(2-(2,6-dioxopiperidin-3-yl)-1,3-dioxoisoindolin-5-yl)piperidin-4-yl)methyl)azetidin-3-yl)methoxy)pyridin-2-yl)piperidine-4-carboxamide |
| 187 | 1-(4-cyano-3-(trifluoromethyl)phenyl)-N-(6-((1-((1-(2-(2,6-dioxopiperidin-3-yl)-1,3-dioxoisoindolin-5-yl)piperidin-4-yl)methyl)piperidin-4-yl)oxy)pyridazin-3-yl)piperidine-4-carboxamide |
| 197 | 1-(4-cyano-3-(trifluoromethyl)phenyl)-N-(5-((1-((1-(2-(2,6-dioxopiperidin-3-yl)-6-fluoro-1,3-dioxoisoindolin-5-yl)piperidin-4-yl)methyl)azetidin-3-yl)methoxy)pyridin-2-yl)piperidine-4-carboxamide |

More specifically, the present inventors confirmed the following through various experiments.

An AR binder of a specific structure was more desirable for the purposes of the present invention. For example, in Chemical Formula 1, when the ring containing $X_3$ is a pyridine ring, it was preferred in many combinations, and when it is a pyrimidine or benzene ring, it was less preferred. In addition, when the pyridine ring was used, AR degradation activity was reduced when the N of pyridine was moved to position 3 instead of position 2 based on the amide.

Although linkers with specific structures, including 4-ethynylpiperidine, piperazinylethanol, and 1-methylpiperidine, exhibit some efficacy, they are less desirable for the purpose of the present invention, such as metabolic stability and AR degradation activity. The 2,7-diazaspiro[3.5]nonane linker, in which the 6-membered ring is first connected to the AR binder, was also less preferred in terms of AR degradation activity. In addition, when the linker length was short, when the linking position of the E moiety was switched from position 5 to position 4, the AR degradation activity was relatively reduced.

As the E structure of Chemical Formula 1, the structure of Chemical Formula 3 was more suitable for the AR binder structure of the present disclosure than the structure of Chemical Formula 4. In addition, even in the E structure of Chemical Formula 3, a specific structure was more preferable in terms of oral absorption rate, solubility, AR degradation activity, and the like.

As used herein, the term "pharmaceutically acceptable salt(s)" refers to a salt prepared from active compounds according to the present disclosure with relatively non-toxic acids or bases, depending on the particular substituents of those compounds. When the compounds have a relatively acidic group, base-added salts can be obtained by contacting the neutral compounds with a sufficient amount of the desired base and a pure or inert solvent. Suitable pharmaceutically acceptable base addition salts include, but are not limited to sodium, potassium, calcium, aluminum, organic amino, magnesium salts and the like. When the compounds have a relatively basic group, acid-added salts can be obtained by contacting the neutral compounds with a sufficient amount of the desired acid and pure or inert solvent. Suitable pharmaceutically acceptable acid addition salts include salts derived from non-toxic organic acids including, but are not limited to, acetic acid, propionic acid, isobutyl acid, oxalic acid, maleic acid, malonic acid, benzoic acid, succinic acid, suberic acid, fumaric acid, mandelic acid, phthalic acid, benzenesulfonic acid, p-tolylsulfonic acid, citric acid, tartaric acid, methanesulfonic acid, and the like, and non-toxic inorganic acids including, but are not limited to, hydrochloric acid, hydrobromic acid, nitric acid, carbonic acid, monohydrogencarbonic acid, phosphoric acid, monohydrogenphosphoric acid, dihydrogenphosphoric acid, sulfuric acid, monohydrogensulfuric acid, hydrogen iodide, phosphorous acid and the like. Also it includes a salt of amino acid such as arginate or its analogues, and it also includes analogues of organic acid such as glucuronic or galacturonic acid. Some specific compounds of this disclosure have both basic and acidic functionality for the conversion of compounds with a basic or acidic portion (addition) salts. Other examples of salts are well known through literature known in the art to which the present invention pertains.

As used herein, the phrase "compound(s) of this/the invention" includes any compound(s) of Chemical Formula 1, as well as clathrates, hydrates, solvates, or polymorphs thereof. And, even if the term "compound(s) of the invention" does not mention its pharmaceutically acceptable sat, the term includes salts thereof. In one embodiment, the compounds of this disclosure include stereo-chemically pure compounds, e.g., those substantially free (e.g., greater than 85% ee, greater than 90% ee, greater than 95% ee, greater than 97% ee, or greater than 99% ee) of other stereoisomers. That is, if the compounds of Chemical Formula 1 according to the present disclosure or salts thereof are tautomeric isomers and/or stereoisomers (e.g., geometrical isomers and conformational isomers), such isolated isomers and their mixtures also are included in the scope of this disclosure. If the compounds of the present disclosure or salts thereof have an asymmetric carbon in their structures, their active optical isomers and their racemic mixtures also are included in the scope of this disclosure.

As used herein, the term "polymorph" refers to solid crystalline forms of a compound of this disclosure or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

As used herein, the term "solvate" means a compound or its salt according to this disclosure that further includes a stoichiometric or non-stoichiometric amount of a solvent bound by non-covalent intermolecular forces. Preferred solvents are volatile, non-toxic, and acceptable for administration to humans in trace amounts.

As used herein, the term "hydrate" means a compound or its salt according to this disclosure that further includes a stoichiometric or non-stoichiometric amount of water bound by non-covalent intermolecular forces.

As used herein, the term "clathrate" means a compound or its salt in the form of a crystal lattice that contains spaces (e.g., channels) that have a guest molecule (e.g., a solvent or water) trapped within.

As used herein, the term "purified" means that when isolated, the isolate is greater than 90% pure, in one embodiment greater than 95% pure, in another embodiment greater than 99% pure and in another embodiment greater than 99.9% pure.

Medical Uses and Methods of Treatment of the Compounds According to the Present Invention The present invention further provides methods for treating a disease or condition in a subject having or susceptible to having such a disease or condition, by administering to the subject a therapeutically-effective amount of one or more compounds as described above. In one embodiment, the treatment is preventative treatment. In another embodiment, the treatment is palliative treatment. In another embodiment, the treatment is restorative treatment.

1. Diseases or Conditions

The compounds of the present invention for degrading AR are useful for various therapeutic or prophylactic uses (e.g., cancer, prostate cancer, Kennedy disease). These compounds can be used to degrade AR to lower AR activity, and can also be used to treat AR-related diseases or to prevent exacerbation of these diseases. Accordingly, the present invention provides a method for degrading AR in a cell. In this method the cells are contacted with an effective amount of a compound of the invention. In one embodiment, the cell is present in a subject. The method of the present invention comprises administering to a subject in need of treatment or prevention a pharmaceutical composition comprising a therapeutically or prophylactically effective amount of a compound according to the present invention.

In one embodiment, the present invention provides a method of degrading AR in a cell of an AR-associated disease. For example, the present invention can be used to degrade AR in cells of a subject having an AR-related disease, which will be described later, and consequently lower AR activity. In another embodiment of the present invention, the present invention can be used to degrade AR in cells of cancer, in particular prostate cancer.

In another embodiment, the present invention provides a method of treating an AR-related disease, comprising administering to a subject a therapeutically effective amount of a compound of Chemical Formula 1 or a pharmaceutically acceptable salt thereof. Such a method comprises administering to a subject in need of treatment an amount of a compound of the invention sufficient to degrade AR, i.e., a therapeutically effective amount. In such a method, a compound of the present invention may be administered to the subject in the form of a pharmaceutical composition described herein.

In the present invention, AR-related diseases include, but are not limited to, asthma (multiple sclerosis, cancer (especially prostate cancer, breast cancer (especially androgen receptor positive triple negative breast cancer (AR+ TNBC))), Kennedy's disease, acne, alopecia (especially androgenetic alopecia), cutaneous wound, Hirsutism, ciliopathy, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, cystic fibrosis, Duchenne muscular dystrophy, haemochromatosis, haemophilia, Klinefelter's syndrome, neurofibromatosis, phenylketonuria, polycystic kidney disease, Prader-Willi syndrome, sickle-cell disease, Tay-Sachs disease, Turner syndrome. In a preferred embodiment of the present invention, the AR-related disease is cancer, more preferably prostate cancer.

That is, the present invention provides a medical use of the compound of Chemical Formula 1 or a pharmaceutically acceptable salt thereof for treating or preventing the above diseases.

2. Subjects

Suitable subjects to be treated according to the present invention include mammalian subjects. Mammals according to the present disclosure include, but are not limited to, human, canine, feline, bovine, caprine, equine, ovine, porcine, rodents, lagomorphs, primates, and the like, and encompass mammals in utero.

In one embodiment, the suitable subject to be treated according to the present invention is human.

3. Administration and Dosing

The compounds of the present invention are generally administered in a therapeutically effective amount.

As used herein, "effective amount" refers to an amount of a compound of the invention sufficient to slow or minimize the progression of a AR-related disease or to provide a therapeutic benefit in the treatment or management of a AR-related disease. "Effective amount" also refers to an amount sufficient to inhibit or reduce AR activity, either in vitro or in vivo.

The compounds of the present invention can be administered by any suitable route in the form of a pharmaceutical composition adapted to such a route, and in a dose effective for the treatment intended. An effective dosage is typically in the range of about 0.001 to about 100 mg per kg body weight per day, preferably about 0.01 to about 50 mg/kg/day, in single or divided doses. Depending on age, species and disease or condition being treated, dosage levels below the lower limit of this range may be suitable. In other cases, still larger doses may be used without harmful side effects. Larger doses may also be divided into several smaller doses, for administration throughout the day.

Pharmaceutical Compositions of the Compounds of the Present Invention

In another embodiment, the present invention provides a pharmaceutical composition comprising the compound of Chemical Formula 1 or a pharmaceutically acceptable salt thereof, and a pharmaceutically acceptable carrier or excipient. In one embodiment of the present invention, the pharmaceutical composition is used for the treatment or prevention of AR-related diseases, preferably prostate cancer, which is described above.

The term "pharmaceutically acceptable" means suitable for use as a pharmaceutical preparation, and generally considered safe for such use. The term also means that it has been officially approved by the governing body of a country for this use, or is listed in the Korean Pharmacopoeia or the United States Pharmacopoeia.

Pharmaceutical Compositions, Dosage Forms and Administration Routes

For the treatment of the diseases or conditions referred to above, the compounds described herein or pharmaceutically acceptable salts thereof can be administered as follows:

Oral Administration

The compounds of the present invention may be administered orally, including by swallowing, so that the compound enters the gastrointestinal tract, or absorbed into the blood stream directly from the mouth (e.g., buccal or sublingual administration).

Suitable compositions for oral administration include solid, liquid, gel or powder formulations, and have a dosage form such as tablet, lozenge, capsule, granule or powder.

Compositions for oral administration may optionally be enteric coated and may exhibit delayed or sustained release through the enteric coating. That is, the composition for oral administration according to the present invention may be a formulation having an immediate or modified release pattern.

Liquid formulations can include solutions, syrups and suspensions, which can be used in soft or hard capsules. Such formulations may include a pharmaceutically acceptable carrier, for example, water, ethanol, polyethylene glycol, cellulose, or an oil. The formulation may also include one or more emulsifying agents and/or suspending agents.

In a tablet dosage form the amount of drug, active ingredient, present may be from about 0.05% to about 95% by weight, more typically from about 2% to about 50% by weight of the dosage form. In addition, tablets may contain a disintegrant, comprising from about 0.5% to about 35% by weight, more typically from about 2% to about 25% of the dosage form. Examples of disintegrants include, but are not limited to, lactose, starch, sodium starch glycolate, crospovidone, croscarmellose sodium, maltodextrin, or mixtures thereof.

Suitable lubricants, for use in a tablet, may be present in amounts from about 0.1% to about 5% by weight, and include, but are not limited to, talc, silicon dioxide, stearic acid, calcium, zinc or magnesium stearate, sodium stearyl fumarate and the like.

Suitable binders, for use in a tablet, include, but are not limited to, gelatin, polyethylene glycol, sugars, gums, starch, polyvinyl pyrrolidone, hydroxypropyl cellulose, hydroxypropylmethyl cellulose and the like. Suitable diluents, for use in a tablet, include, but are not limited to, mannitol, xylitol, lactose, dextrose, sucrose, sorbitol, microcrystalline cellulose and starch.

Suitable solubilizers, for use in a tablet, may be present in amounts from about 0.1% to about 3% by weight, and include, but are not limited to, polysorbates, sodium lauryl sulfate, sodium dodecyl sulfate, propylene carbonate, diethyleneglycol monoethyl ether, dimethyl isosorbide, polyethylene glycol (natural or hydrogenated) castor oil, HCOR™ (Nikkol), oleyl ester, Gelucire™, caprylic/caprylic acid mono/diglyceride, sorbitan fatty acid esters, and Solutol HS™

Parenteral Administration

Compounds of the present disclosure may be administered directly into the blood stream, muscle, or internal organs. Suitable means for parenteral administration include intravenous, intra-muscular, subcutaneous intraarterial, intraperitoneal, intrathecal, intracranial, and the like. Suitable devices for parenteral administration include injectors (including needle and needle-free injectors) and infusion methods.

Compositions for parenteral administration may be formulated as immediate or modified release, including delayed or sustained release.

Most parenteral formulations are liquid compositions, and the liquid composition is an aqueous solution containing the active ingredient according to the present invention, a salt, a buffering agent, an isotonic agent, and the like.

Parenteral formulations may also be prepared in a dehydrated form (e.g., by lyophilization) or as sterile non-aqueous solutions. These formulations can be used with a suitable vehicle, such as sterile water. Solubility-enhancing agents may also be used in preparation of parenteral solutions.

Topical Administration

Compounds of the present invention may be administered topically to the skin or transdermally. Formulations for this topical administration can include lotions, solutions, creams, gels, hydrogels, ointments, foams, implants, patches and the like. Pharmaceutically acceptable carriers for topical administration formulations can include water, alcohol, mineral oil, glycerin, polyethylene glycol and the like. Topical administration can also be performed by electroporation, iontophoresis, phonophoresis and the like.

Compositions for topical administration may be formulated as immediate or modified release, including delayed or sustained release.

ADVANTAGEOUS EFFECTS

The present disclosure provides compounds capable of exhibiting various pharmacological activities by degrading AR, pharmaceutical compositions comprising the compound as an active ingredient, their medical uses (especially prostate cancer), and methods of treatment or prevention comprising administering the compound to a subject in need of such treatment or prevention. The compound according to the present invention or a pharmaceutically acceptable salt thereof is excellent in various aspects such as efficacy, (metabolism) stability, physicochemical properties, etc.

MODE FOR INVENTION

Hereinafter, the present invention is described in considerable detail with examples to help those skilled in the art understand the present invention. However, the following examples are offered by way of illustration and are not intended to limit the scope of the invention. It is apparent that various changes may be made without departing from the spirit and scope of the invention or sacrificing all of its material advantages.

Preparation of Compounds of the Present Invention

Hereinafter, the synthesis process of some compounds of the present invention will be described, and the other compounds not mentioned below can be prepared by substituting starting materials, intermediates and/or reactants in a similar manner.

Intermediate 1-1: 1-(4-cyano-3-(trifluoromethyl)phenyl)piperidine-4-carboxylic acid

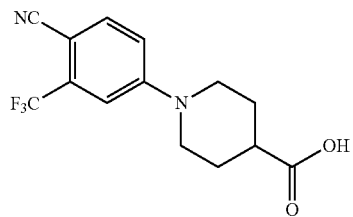 [SMILES: N#Cc1ccc(N2CCC(C(=O)O)CC2)cc1Cl]

4-fluoro-2-(trifluoromethyl)benzonitrile (5.00 g, 26.4 mmol), piperidine-4-carboxylic acid (3.41 g, 15.9 mmol), and DIPEA (11.0 mL, 79.2 mmol) were suspended in DMSO (20.0 ml) and then stirred at 90° C. for 16 hours. After distilled water (30 ml) was added to the reaction solution, the solution was extracted with EtOAc (25 ml×3). The organic layer was dried over anhydrous sodium sulfate, filtered, and concentrated under reduced pressure. The obtained residue was recrystallized (EtOAc) to give 5.98 g (76%) of an off-white solid. m/z 299.06 [M+H]$^+$.

Intermediate 1-2:
1-(3-chloro-4-cyanophenyl)piperidine-4-carboxylic acid

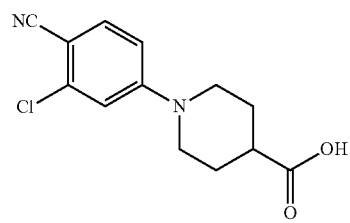

Intermediate 1-2 was synthesized in a similar manner to the synthesis method of Intermediate 1-1.

Intermediate 1-3: 1-(4-cyano-3-(trifluoromethyl)phenyl)-4-methylpiperidine-4-carboxylic acid

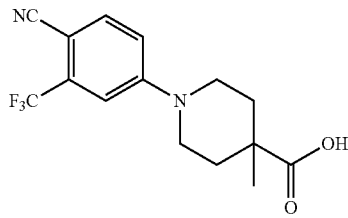

Intermediate 1-3 was synthesized in a similar manner to the synthesis method of Intermediate 1-1.

Intermediate 1-4: 1-(4-cyano-3-(trifluoromethyl)phenyl)-4-hydroxypiperidine-4-carboxylic acid

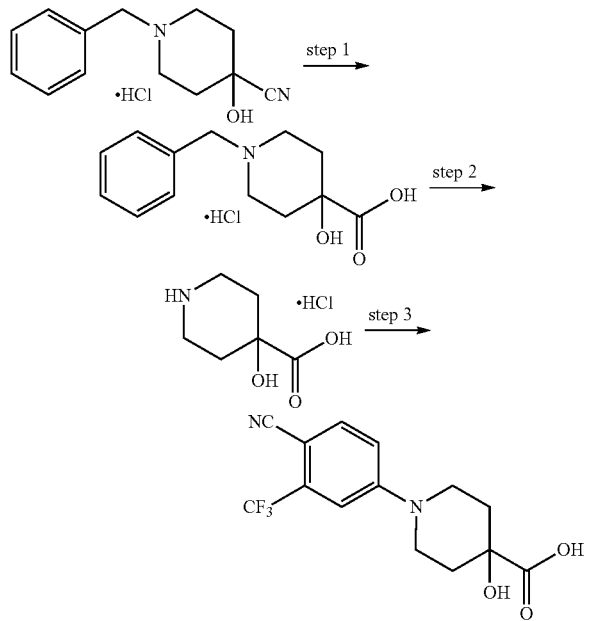

Step 1: Synthesis of 1-benzyl-4-hydroxypiperidine-4-carboxylic acid hydrochloride 1-benzyl-4-hydroxypiperidine-4-carbonitrile hydrochloride (500 mg, 1.97 mmol) was suspended in 6 N HCl aqueous solution (2.0 mL) and stirred in a microwave at 120° C. for 1 hour. The reaction solution was filtered and concentrated under reduced pressure to give 542 mg of a white solid.

Step 2: Synthesis of 4-hydroxypiperidine-4-carboxylic acid hydrochloride

After dissolving 1-benzyl-4-hydroxypiperidine-4-carboxylic acid hydrochloride (542 mg, 1.66 mmol) in EtOH (20 mL), Pd/C (10 wt % Pd, 180 mg) was added and stirred for 3 hours at room temperature under a hydrogen stream. The reaction solution was filtered and concentrated to give 237 mg of a white solid.

Step 3: Synthesis of 1-(4-cyano-3-(trifluoromethyl)phenyl)-4-hydroxypiperidine-4-carboxylic acid 4-hydroxypiperidine-4-carboxylic acid hydrochloride (77 mg, 0.43 mmol), 4-fluoro-2-(trifluoromethyl)benzonitrile (100 mg, 0.529 mmol), and DIPEA (0.18 mL, 1.06 mmol) were suspended in DMSO (3.0 ml) and stirred 90° C. for 16 hours. After adding distilled water (3.0 ml) to the reaction solution, extraction was performed with EtOAc (2.5 ml×3), and the organic layer was dried over anhydrous sodium sulfate, filtered, and concentrated under reduced pressure. The obtained residue was recrystallized (EtOAc) to give 35 mg (26%) of a white solid. m/z 496.10 [M+H]$^+$.

Intermediate 1-5: 1-(4-cyano-3-(trifluoromethyl)phenyl)-4-fluoropiperidine-4-carboxylic acid

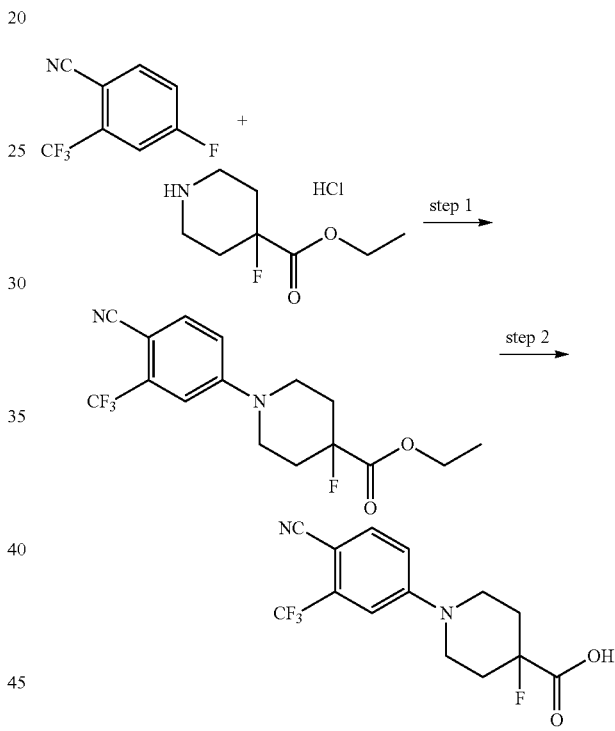

Step 1: Synthesis of ethyl 1-(4-cyano-3-(trifluoromethyl)phenyl)-4-fluoropiperidine-4-carboxylate 4-fluoro-2-(trifluoromethyl)benzonitrile (100 mg, 0.529 mmol), ethyl 4-fluoropiperidine-4-carboxylate hydrochloride (123 mg, 0.582 mmol), and K$_2$CO$_3$ (146 mg, 1.06 mmol) were suspended in DMSO (5.0 ml) and stirred 100° C. for 16 hours. After adding distilled water (3.0 ml) to the reaction solution, extraction was performed with EtOAc (2.5 ml×3), and the organic layer was dried over anhydrous sodium sulfate, filtered, and concentrated under reduced pressure. The resulting residue was subjected to MPLC (30% EtOAc/Hexane) to give 191 mg of a white solid. m/z 345.40 [M+H]$^+$

Step 2: Synthesis of 1-(4-cyano-3-(trifluoromethyl)phenyl)-4-fluoropiperidine-4-carboxylic acid After suspending ethyl 1-(4-cyano-3-(trifluoromethyl)phenyl)-4-fluoropiperidine-4-carboxylate (255 mg) in THF (3.0 mL) and distilled water (1.0 mL), LiOH·H₂O (89 mg, 2.12 mmol) was added and stirred at room temperature for 1 hour. The solvent was evaporated and extracted with distilled water. Again, 1 N HCl was added to the aqueous layer and extracted with EtOAc (20 ml×2). The organic layer was dried over anhydrous sodium sulfate, filtered, and concentrated under reduced pressure to give 112 mg (2Step 67%) of a white solid. m/z 317.03 [M+H]⁺.

Intermediate 1-6: 2-(1-(4-cyano-3-(trifluoromethyl)phenyl)pyrrolidin-3-yl)acetic acid

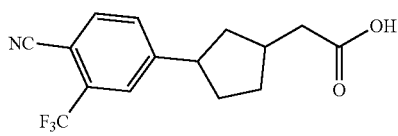 [SMILES: N#Cc1ccc(C2CCC(CC(=O)O)C2)cc1C(F)(F)F]

Intermediate 1-6 was synthesized in a similar way to the synthesis method of Intermediate 1-5.

Intermediate 1-7: 1-(6-cyano-5-(trifluoromethyl)pyridin-3-yl)piperidine-4-carboxylic acid

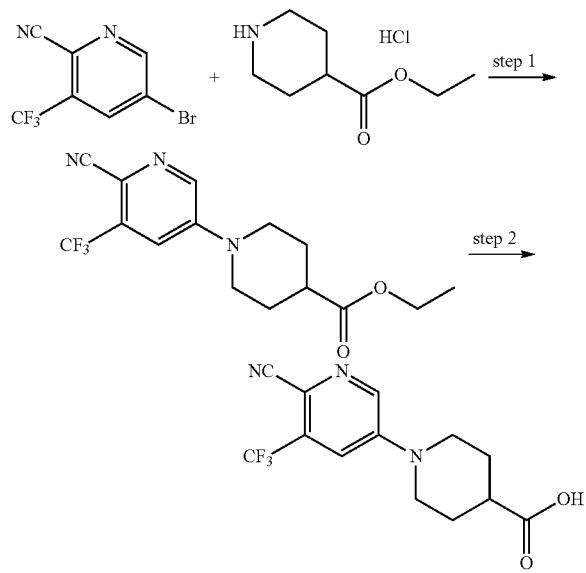

Step 1: Synthesis of ethyl 1-(6-cyano-5-(trifluoromethyl)pyridin-3-yl)piperidine-4-carboxylate 5-bromo-3-(trifluoromethyl)-2-pyridinecarbonitrile (500 mg, 1.99 mmol), ethyl piperidine-4-carboxylate (344 mg, 2.19 mmol), CuI (38 mg, 0.199 mmol), and K₂CO₃ (550 mg, 3.98 mmol) were suspended in DMF (3.0 ml) and stirred in a microwave at 150° C. for 1 hour. After adding distilled water (10 ml) to the reaction solution, the mixture was extracted with EtOAc (10 ml×2), dried over anhydrous sodium sulfate, filtered, and concentrated under reduced pressure. The resulting residue was subjected to MPLC (30% EtOAc/Hexane) to give 449 mg (69%) of a white solid. m/z 328.09 [M+H]⁺.

Step 2: Synthesis of 1-(6-cyano-5-(trifluoromethyl)pyridin-3-yl)piperidine-4-carboxylic acid After suspending ethyl 1-(6-cyano-5-(trifluoromethyl)pyridin-3-yl)piperidine-4-carboxylate (449 mg, 1.37 mmol) in THF (10.0 mL) and distilled water (5.0 mL), LiOH·H₂O (230 mg, 5.49 mmol) was added and stirred at room temperature for 1 hour. After evaporating the solvent and extracting with distilled water, 1 N HCl was added to the aqueous layer and extracted with EtOAc (20 ml×2). The organic layer was dried over anhydrous sodium sulfate, filtered, and concentrated under reduced pressure to give 327 mg (81%) of a white liquid. m/z 300.05 [M+H]⁺.

Intermediate 1-8: 1-(6-cyano-5-(trifluoromethyl)pyridin-3-yl)-4-fluoropiperidine-4-carboxylic acid

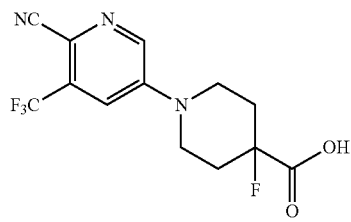 [SMILES: N#Cc1ncc(N2CCC(F)(C(=O)O)CC2)cc1C(F)(F)F]

Intermediates 1-8 were synthesized in a similar manner to the synthesis method of Intermediates 1-7.

Intermediate 2-1: 2-(2,6-dioxopiperidin-3-yl)-5-fluoroisoindoline-1,3-dione

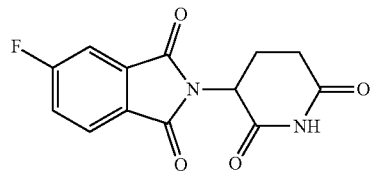 [SMILES: O=C1CCC(N2C(=O)c3ccc(F)cc3C2=O)C(=O)N1]

5-fluoroisobenzofuran-1,3-dione (5.00 g, 30.1 mmol), 3-aminopiperidine-2,6-dione hydrochloride (4.95 g, 30.1 mmol), and sodium acetate (4.94 mg, 60.2 mmol) were suspended in AcOH (50 ml) and stirred at 120° C. for 24 hours. After concentrating the solvent under reduced pressure, distilled water (30 ml) was added to the reaction solution, and the resulting solid was filtered to give 7.55 g (90%) of a purple solid.

Intermediate 2-2: 2-(2,6-dioxopiperidin-3-yl)-4-fluoroisoindoline-1,3-dione

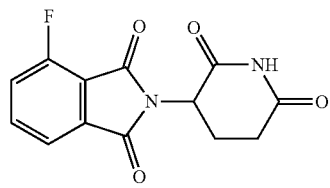 [SMILES: O=C1CCC(N2C(=O)c3cccc(F)c3C2=O)C(=O)N1]

Intermediate 2-2 was synthesized in a similar manner to the synthesis method of Intermediate 2-1.

Intermediate 2-3: 2-(2,6-dioxopiperidin-3-yl)-5,6-difluoroisoindoline-1,3-dione

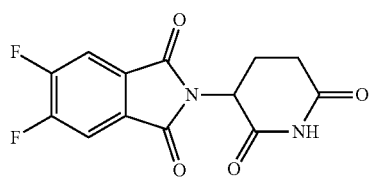 [SMILES: O=C1CCC(N2C(=O)c3cc(F)c(F)cc3C2=O)C(=O)N1]

Intermediate 2-3 was synthesized in a similar manner to the synthesis method of Intermediate 2-1.

Intermediate 2-4: 3-(6-fluoro-4-oxobenzo[d][1,2,3]triazin-3(4H)-yl)piperidine-2,6-dione

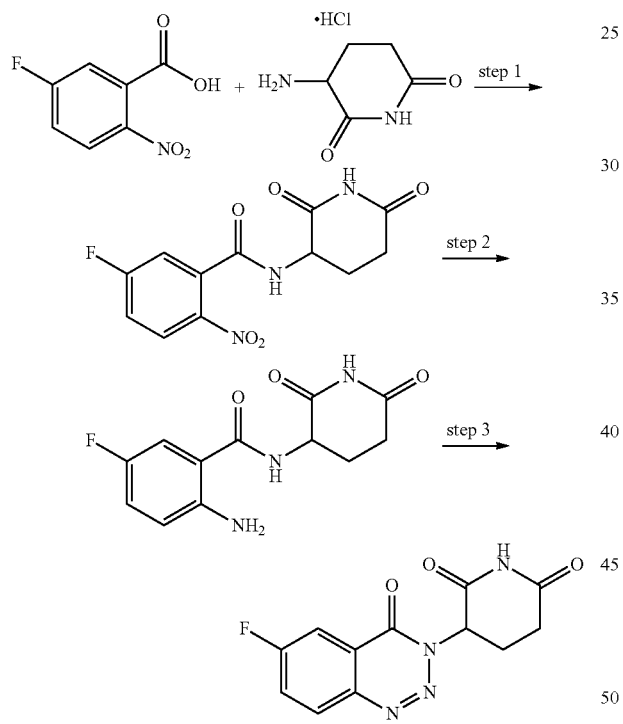

Step 1: Synthesis of N-(2,6-dioxopiperidin-3-yl)-5-fluoro-2-nitrobenzamide 5-fluoro-2-nitrobenzoic acid (2.00 g, 10.8 mmol), 3-aminopiperidine-2,6-dione hydrochloride (2.14 g, 13.0 mmol), EDCI (2.48 g, 13.0 mmol), HOBt (1.75 g, 13.0 mmol), and DIPEA (3.76 mL, 21.6 mmol) were suspended in DMF (10.0 ml) and stirred at room temperature for 16 hours. After adding distilled water (20 ml) to the reaction solution, extraction was performed with EtOAc (25 ml×2), and the organic layer was dried over anhydrous sodium sulfate, filtered, and concentrated under reduced pressure. The obtained residue was recrystallized (EtOAc) to give 2.28 g (72%) of an off-white solid.

Step 2: Synthesis of 2-amino-N-(2,6-dioxopiperidin-3-yl)-5-fluorobenzamide

After dissolving N-(2,6-dioxopiperidin-3-yl)-5-fluoro-2-nitrobenzamide (2.28 mg, 7.72 mmol) in a mixture of DMF (10 mL) and MeOH (10 mL), Pd/C (10 wt % Pd, 228 mg) was added and stirred for 3 hours at room temperature under a hydrogen stream. The reaction solution was filtered and concentrated to give a brown solid (1.62 g, 79%).

Step 3: Synthesis of 3-(6-fluoro-4-oxobenzo[d][1,2,3]triazin-3(4H)-yl)piperidine-2,6-dione After suspending 2-amino-N-(2,6-dioxopiperidin-3-yl)-5-fluorobenzamide (1.60 g, 6.04 mmol) in AcOH (10.0 mL), sodium nitrite (631 mg, 9.16 mmol) was added and the mixture was stirred at room temperature for 2 hours. After adding distilled water (30 ml) to the reaction solution, extraction was performed with EtOAc (25 ml×3), and the organic layer was dried over anhydrous sodium sulfate, filtered, and concentrated under reduced pressure. The obtained residue was recrystallized (EtOAc) to give 756 mg (45%) of an off-white solid.

Intermediate 2-5: 3-(7-fluoro-4-oxobenzo[d][1,2,3]triazin-3(4H)-yl)piperidine-2,6-dione

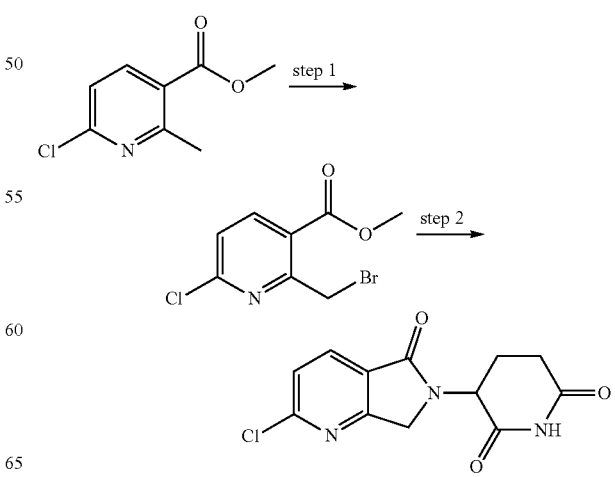

Intermediate 2-5 was synthesized in a similar manner to the synthesis method of Intermediate 2-4.

Intermediate 2-6: 3-(2-chloro-5-oxo-5,7-dihydro-6H-pyrrolo[3,4-b]pyridin-6-yl)piperidine-2,6-dione Step 1: Synthesis of methyl 2-(bromomethyl)-6-chloronicotinate Methyl 6-chloro-2-methylnicotinate (1.00 g, 5.38 mmol), N-bromosuccinimide (1.44 g, 8.08 mmol), and AHCN (130 mg, 0.0538 mmol) were suspended in ACN (10.0 mL) and stirred in a microwave at 110° C. for 4 hours. After adding distilled water (10 ml) to the reaction mixture, extraction was performed with EtOAC (10 ml×2). The organic layer was washed with brine (10 ml×2), dried over anhydrous sodium sulfate, filtered, and concentrated under reduced pressure. The resulting residue was subjected to MPLC (10% EtOAc/Hexane) to give 980 mg of a white solid. m/z 263.99 [M+H]$^+$.

Step 2: Synthesis of 3-(2-chloro-5-oxo-5,7-dihydro-6H-pyrrolo[3,4-b]pyridin-6-yl)piperidine-2,6-dione Methyl 2-(bromomethyl)-6-chloronicotinate (980 mg), 3-aminopiperidine-2,6-dione hydrochloride (686 mg, 4.17 mmol), and DIPEA (1.05 mL, 10.4 mmol) were suspended in ACN (10.0 mL) and stirred at 110° C. for 2 hours. After adding distilled water (30 ml) to the reaction solution, extraction was performed with EtOAc (25 ml×3), and the organic layer was dried over anhydrous sodium sulfate, filtered, and concentrated under reduced pressure. The obtained residue was recrystallized (MeOH) to give 244 mg (2Step 16%) of an off-white solid. m/z 280.09 [M+H]$^+$.

Intermediate 2-7: 3-((3-aminophenyl)amino)piperidine-2,6-dione

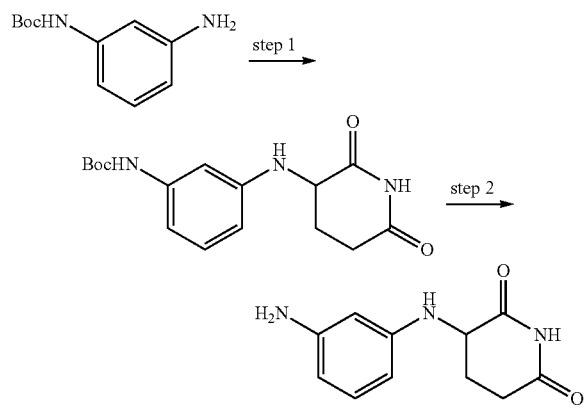

Step 1: Synthesis of tert-butyl (3-((2,6-dioxopiperidin-3-yl)amino)phenyl)carbamate After tert-butyl (3-aminophenyl)carbamate (300 mg, 1.44 mmol) and 3-bromopiperidine-2,6-dione (331 mg, 1.73 mmol) were suspended in DMF (5.0 mL), NaHCO$_3$ (241 mg, 2.88 mmol) was added and stirred at 50° C. for 16 hours. After adding distilled water (30 ml) to the reaction solution, the resulting solid was filtered to give 323 mg (70%) of a green solid. m/z 342.20 [M+Na]$^+$.

Step 2: Synthesis of 3-((3-aminophenyl)amino)piperidine-2,6-dione

After tert-butyl (3-((2,6-dioxopiperidin-3-yl)amino)phenyl)carbamate (100 mg, 0.313 mmol) was suspended in DCM (1.00 ml), 4M HCl in dioxane (0.39 mL, 1.57 mmol) was added and stirred at room temperature for 1 hour. The reaction solution was concentrated, an aqueous NaHCO$_3$ solution (15 ml) was added, extracted with DCM (20 ml×2), and the organic layer was dried over anhydrous sodium sulfate, filtered, and concentrated under reduced pressure to give 34 mg (51%) of a brown solid. m/z 220.20 [M+H]$^+$ Intermediate 2-8: 5-(bromomethyl)-2-(2,6-dioxopiperidin-3-yl)isoindoline-1,3-dione

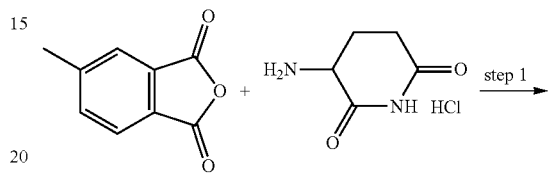

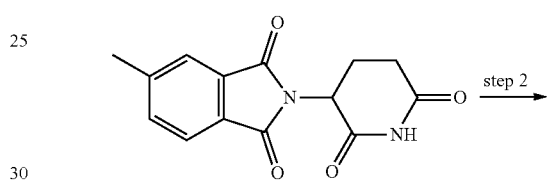

Step 1: Synthesis of 2-(2,6-dioxopiperidin-3-yl)-5-methylisoindoline-1,3-dione 5-methylisobenzofuran-1,3-dione (2.18 g, 13.44 mmol), 3-aminopiperidine-2,6-dione hydrochloride (2.21 g, 13.44 mmol), and NaOAc (2.20 g, 26.89 mmol) were suspended in AcOH (22 mL) and then stirred under reflux at 120° C. for 16 hours. After concentrating the reaction solution under reduced pressure, distilled water (100 mL) was added, and the precipitated solid was filtered to give 3.2 g (87%) of a purple solid.

Step 2: Synthesis of 5-(bromomethyl)-2-(2,6-dioxopiperidin-3-yl)isoindoline-1,3-dione 2-(2,6-dioxopiperidin-3-yl)-5-methylisoindoline-1,3-dione (541.8 mg, 1.99 mmol), N-bromosuccinimide (390.0 mg, 2.19 mmol), and ACHN (97.7 mg, 0.4 mmol) were suspended in ACN (10 mL) and then stirred under reflux at 80° C. for 11 hours. After concentrating the reaction solution under reduced pressure, the obtained residue was subjected to MPLC (40% EtOAc/Hexane) to give 420 mg (60%) of a white solid.

Intermediate 3-1: 1-(2-(2,6-dioxopiperidin-3-yl)-1,3-dioxoisoindolin-5-yl)piperidine-4-carbaldehyde

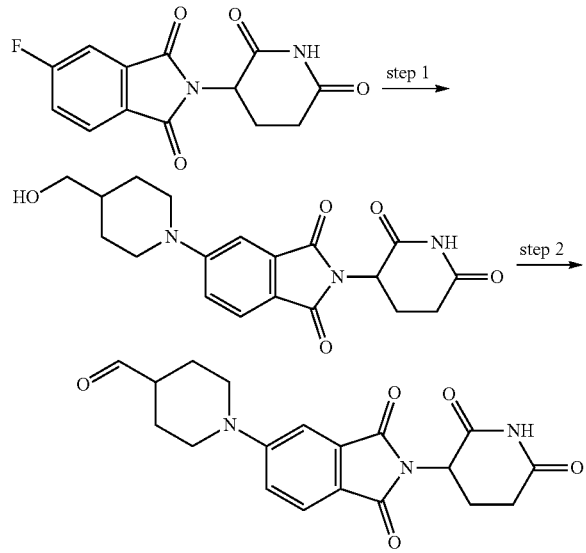

Step 1: Synthesis of 2-(2,6-dioxopiperidin-3-yl)-5-(4-(hydroxymethyl)piperidin-1-yl)isoindoline-1,3-dione 2-(2,6-dioxopiperidin-3-yl)-5-fluoroisoindoline-1,3-dione (Intermediate 2-1, 300 mg, 1.09 mmol), piperidin-4-ylmethanol (149 mg, 1.30 mmol), and DIPEA (0.29 mL, 1.64 mmol) were suspended in DMSO (5.0 ml) and stirred at 100° C. for 16 hours. After adding distilled water (30 ml) to the reaction solution, extraction was performed with EtOAc (25 ml×3), and the organic layer was dried over anhydrous sodium sulfate, filtered, and concentrated under reduced pressure. The obtained residue was subjected to MPLC (50% EtOAc/Hexane) to give 332 mg (82%) of a yellow solid.

Step 2: Synthesis of 1-(2-(2,6-dioxopiperidin-3-yl)-1,3-dioxoisoindolin-5-yl)piperidine-4-carbaldehyde 2-(2,6-dioxopiperidin-3-yl)-5-(4-(hydroxymethyl)piperidin-1-yl)isoindoline-1,3-dione (332 mg, 0.894 mmol) was suspended in DCM (5.0 ml). After that, DMP (569 mg, 1.34 mmol) was added and the mixture was stirred at room temperature for 2 hours. After adding $Na_2S_2O_3$ aqueous solution (10 ml) to the reaction solution, extraction was performed with DCM (25 ml×2), and the organic layer was dried over anhydrous sodium sulfate, filtered, and concentrated under reduced pressure. The resulting residue was subjected to MPLC (50% EtOAc/DCM) to give 303 mg (92%) of a yellow solid.

Intermediate 3-2 to Intermediate 3-13

Intermediate 3-2 to 3-13 were synthesized in a similar manner to the synthesis method of Intermediate 3-1.

TABLE 2

| | |
|---|---|
| Intermediate 3-2: 1-(2-(2,6-dioxopiperidin-3-yl)-1,3-dioxoisoindolin-4-yl)piperidine-4-carbaldehyde | 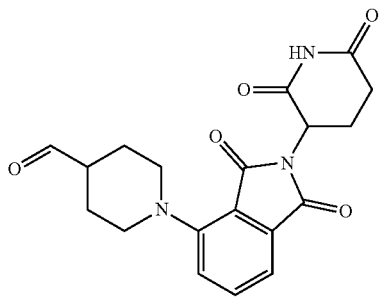 [SMILES: O=CC1CCN(c2cccc3c2C(=O)N(C2CCC(=O)NC2=O)C3=O)CC1] |
| Intermediate 3-3: 1-(2-(2,6-dioxopiperidin-3-yl)-1,3-dioxoisoindolin-5-yl)azetidine-3-carbaldehyde | 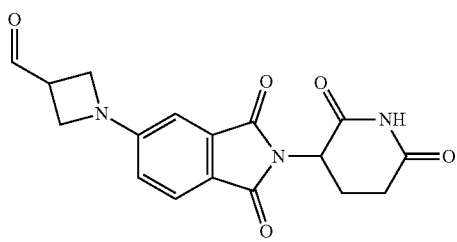 [SMILES: O=CC1CN(c2ccc3c(c2)C(=O)N(C2CCC(=O)NC2=O)C3=O)C1] |
| Intermediate 3-4: (3S)-1-(2-(2,6-dioxopiperidin-3-yl)-1,3-dioxoisoindolin-5-yl)pyrrolidine-3-carbaldehyde | 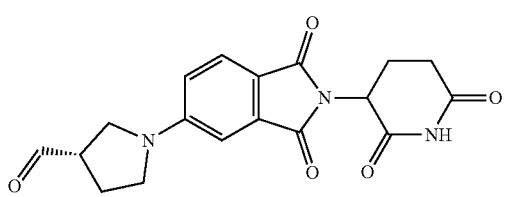 [SMILES: O=C[C@H]1CCN(c2ccc3c(c2)C(=O)N(C2CCC(=O)NC2=O)C3=O)C1] |

TABLE 2-continued

Intermediate 3-5: (3R)-1-(2-(2,6-dioxopiperidin-3-yl)-1,3-dioxoisoindolin-5-yl)pyrrolidine-3-carbaldehyde

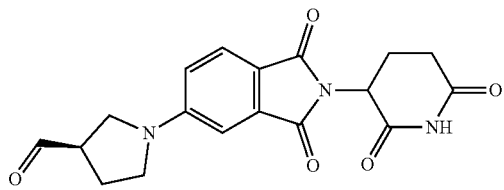 [SMILES: O=C[C@@H]1CCN(c2ccc3c(c2)C(=O)N(C2CCC(=O)NC2=O)C3=O)C1]

Intermediate 3-6: (3S)-1-(2-(2,6-dioxopiperidin-3-yl)-1,3-dioxoisoindolin-5-yl)piperidine-3-carbaldehyde

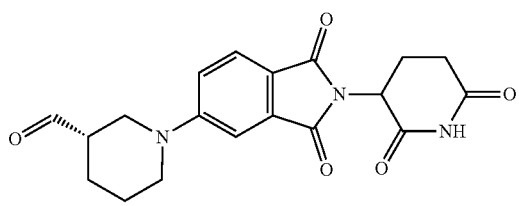 [SMILES: O=C[C@H]1CCCN(c2ccc3c(c2)C(=O)N(C2CCC(=O)NC2=O)C3=O)C1]

Intermediate 3-7: (3R)-1-(2-(2,6-dioxopiperidin-3-yl)-1,3-dioxoisoindolin-5-yl)piperidine-3-carbaldehyde

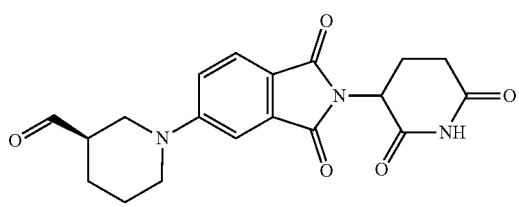 [SMILES: O=C[C@@H]1CCCN(c2ccc3c(c2)C(=O)N(C2CCC(=O)NC2=O)C3=O)C1]

Intermediate 3-8: 1-(2-(2,6-dioxopiperidin-3-yl)-6-fluoro-1,3-dioxoisoindolin-5-yl)piperidine-4-carbaldehyde

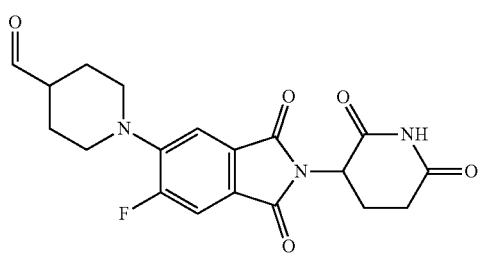 [SMILES: O=CC1CCN(c2cc3c(cc2F)C(=O)N(C2CCC(=O)NC2=O)C3=O)CC1]

Intermediate 3-9: 1-(2-(2,6-dioxopiperidin-3-yl)-6-fluoro-1,3-dioxoisoindolin-5-yl)azetidine-3-carbaldehyde

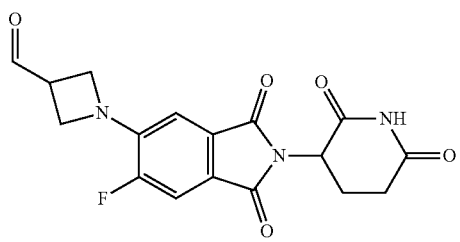 [SMILES: O=CC1CN(c2cc3c(cc2F)C(=O)N(C2CCC(=O)NC2=O)C3=O)C1]

Intermediate 3-10: (3S)-1-(2-(2,6-dioxopiperidin-3-yl)-6-fluoro-1,3-dioxoisoindolin-5-yl)pyrrolidine-3-carbaldehyde

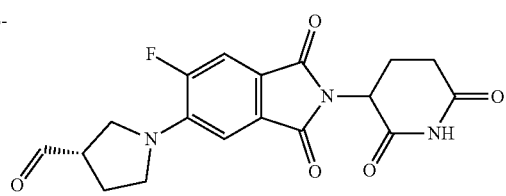

Intermediate 3-11: (3R)-1-(2-(2,6-dioxopiperidin-3-yl)-6-fluoro-1,3-dioxoisoindolin-5-yl)pyrrolidine-3-carbaldehyde

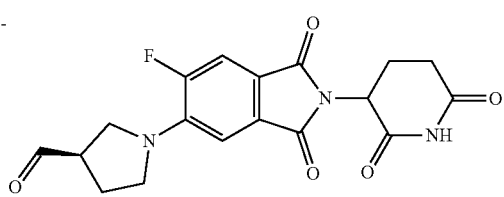

TABLE 2-continued

Intermediate 3-12: 1-(2-(2,6-dioxopiperidin-3-yl)-1,3-dioxoisoindolin-5-yl)-3-methylazetidine-3-carbaldehyde

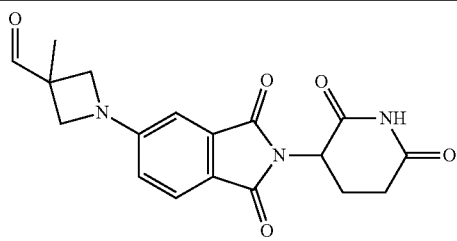

Intermediate 3-13: 2-(1-(2-(2,6-dioxopiperidin-3-yl)-1,3-dioxoisoindolin-5-yl)piperidin-4-yl)acetaldehyde

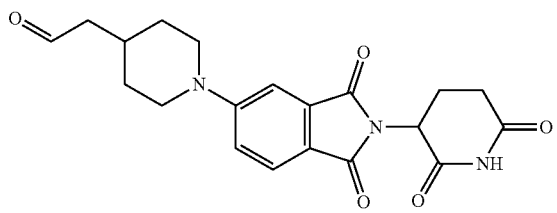 [SMILES: O=CCC1CCN(c2ccc3c(c2)C(=O)N(C2CCC(=O)NC2=O)C3=O)CC1]

Intermediate 3-14: 2-(2,6-dioxopiperidin-3-yl)-5-(2,7-diazaspiro[3.5]nonan-7-yl)isoindoline-1,3-dione

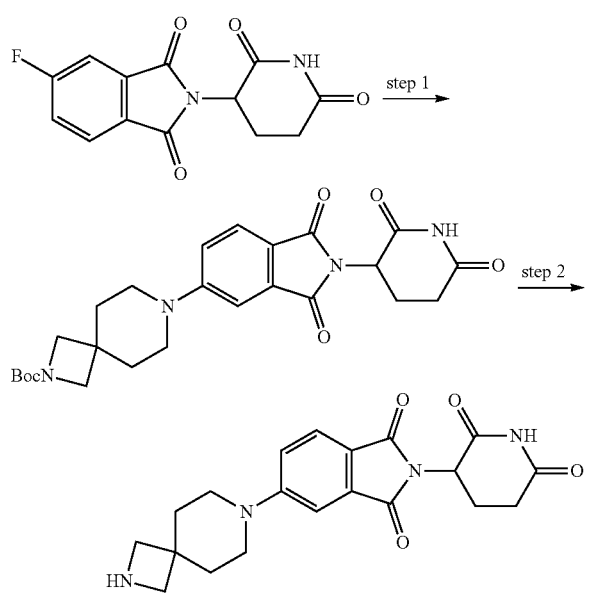

Step 1: Synthesis of tert-butyl 7-(2-(2,6-dioxopiperidin-3-yl)-1,3-dioxoisoindolin-5-yl)-2,7-diazaspiro[3.5]nonane-2-carboxylate 2-(2,6-dioxopiperidin-3-yl)-5-fluoroisoindoline-1,3-dione (Intermediate 2-1, 500 mg, 1.81 mmol), tert-butyl 2,7-diazaspiro[3.5]nonane-2-carboxylate (473 mg, 2.09 mmol), and DIPEA (0.63 mL, 3.62 mmol) were suspended in DMSO (4.0 ml) and stirred at 100° C. for 16 hours. After adding distilled water (20 ml) to the reaction solution, extraction was performed with EtOAc (25 ml×3), and the organic layer was dried over anhydrous sodium sulfate, filtered, and concentrated under reduced pressure. The obtained residue was subjected to MPLC (50% EtOAc/Hexane) to give 748 mg (86%) of a yellow solid.

Step 2: Synthesis of 2-(2,6-dioxopiperidin-3-yl)-5-(2,7-diazaspiro[3.5]nonan-7-yl)isoindoline-1,3-dione Tert-butyl 7-(2-(2,6-dioxopiperidin-3-yl)-1,3-dioxoisoindolin-5-yl)-2,7-diazaspiro[3.5]nonane-2-carboxylate (100 mg, 0.21 mmol) was suspended in DCM (1.0 mL). Then, 4M HCl in dioxane (0.5 mL, 2.1 mmol) was added, and the mixture was stirred at room temperature for 2 hours. The reaction solution was filtered and concentrated under reduced pressure to give 84 mg (96%) of an off-white solid.

Intermediate 3-15: 2-(2,6-dioxopiperidin-3-yl)-1,3-dioxoisoindolin-5-yl)glycine

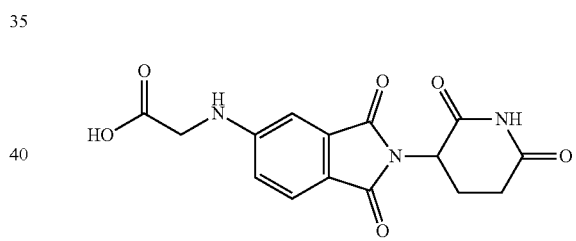

Intermediate 3-15 was synthesized in a similar manner to the synthesis method of Intermediate 3-14.

Intermediate 4-1: tert-butyl (S)-4-(pyrrolidin-3-ylmethyl)piperazine-1-carboxylate

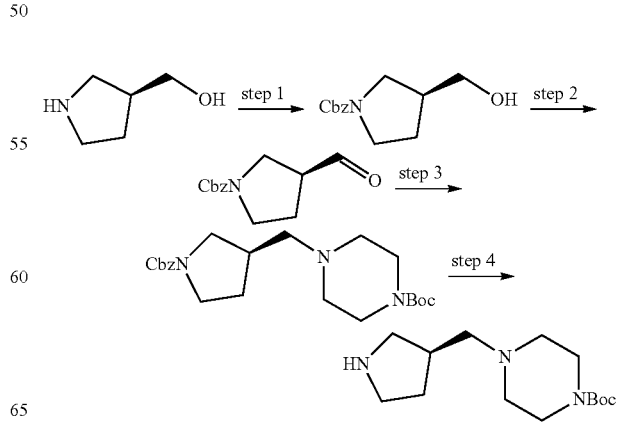

Step 1: Synthesis of benzyl (S)-3-(hydroxymethyl)pyrrolidine-1-carboxylate

After (S)-pyrrolidin-3-ylmethanol (1.00 g, 9.87 mmol) was suspended in ACN (10.0 ml), benzyl chloroformate (1.55 mL, 10.9 mmol) and TEA (1.52 mL, 10.9 mmol) were added at 0° C. and stirred at room temperature for 16 hours. After adding distilled water (15 ml) to the reaction mixture, extraction was performed with EtOAc (20 ml×2), and the organic layer was dried over anhydrous sodium sulfate, filtered, and concentrated under reduced pressure. The resulting residue was subjected to MPLC (50% EtOAc/DCM) to give 2.07 g (89%) of a colorless liquid.

Step 2: Synthesis of benzyl (S)-3-formylpyrrolidine-1-carboxylate

After benzyl (S)-3-(hydroxymethyl) pyrrolidine-1-carboxylate (2.07 g, 8.79 mmol) was suspended in DCM (20.0 ml), DMP (4.48 mg, 10.6 mmol) was added and stirred at room temperature for 2 hours. After adding Na₂S₂O₃ aqueous solution (20 ml) to the reaction mixture, extraction was performed with DCM (25 ml×2), and the organic layer was dried over anhydrous sodium sulfate, filtered, and concentrated under reduced pressure. The obtained residue was subjected to MPLC (50% EtOAc/DCM) to give 1.62 g (79%) of a colorless liquid.

Step 3: Synthesis of tert-butyl (R)-4-((1-((benzyloxy)carbonyl)pyrrolidin-3-yl)methyl)piperazine-1-carboxylate After suspending benzyl (S)-3-formylpyrrolidine-1-carboxylate (1.12 g, 4.80 mmol) and tert-butyl piperazine-1-carboxylate (1.07 g, 5.76 mmol) in ACN (20.0 ml), sodium triacetoxyborohydride (3.05 g, 14.4 mmol) was added and stirred at room temperature for 16 hours. NaHCO₃ aqueous solution (20 ml) was added to the reaction solution, followed by extraction with EtOAc (25 ml×2), and the organic layer was dried over anhydrous sodium sulfate, filtered, and concentrated under reduced pressure. The resulting residue was subjected to MPLC (50% EtOAc/Hexane) to give 1.32 g (68%) of a colorless liquid.

Step 4: Synthesis of tert-butyl (S)-4-(pyrrolidin-3-ylmethyl)piperazine-1-carboxylate After dissolving tert-butyl (R)-4-((1-((benzyloxy)carbonyl)pyrrolidin-3-yl)methyl)piperazine-1-carboxylate (1.39 g, 3.27 mmol) in MeOH (10 mL), Pd/C (10 wt % Pd, 132 mg) was added and stirred for 3 hours at room temperature under a hydrogen stream. The reaction solution was filtered and concentrated to give a white solid (874 mg, 99%).

Intermediate 4-2 to Intermediate 4-8

Intermediates 4-2 to 4-8 were synthesized in a similar manner to the synthesis method of Intermediate 4-1.

TABLE 3

| | |
|---|---|
| Intermediate 4-2: tert-butyl (R)-4-(pyrrolidin-3-ylmethyl)piperazine-1-carboxylate | 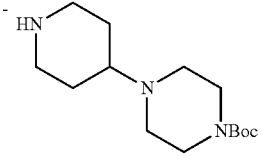 |
| Intermediate 4-3: tert-butyl 4-(piperidin-4-ylmethyl)piperazine-1-carboxylate | 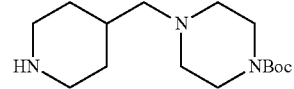 |
| Intermediate 4-4: tert-butyl 4-(piperidin-4-yl)piperazine-1-carboxylate | 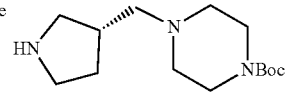 |
| Intermediate 4-5: tert-butyl 4-(azetidin-3-ylmethyl)piperazine-1-carboxylate | 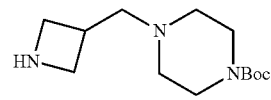 [SMILES: CC(C)(C)OC(=O)N1CCN(CC2CNC2)CC1] |
| Intermediate 4-6: tert-butyl 4-(azetidin-3-yl)piperazine-1-carboxylate | 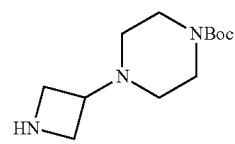 [SMILES: CC(C)(C)OC(=O)N1CCN(C2CNC2)CC1] |
| Intermediate 4-7: tert-butyl 2-(piperidin-4-ylmethyl)-2,7-diazaspiro[3.5]nonane-7-carboxylate | 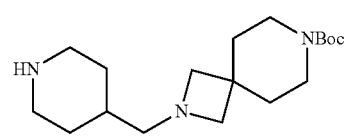 [SMILES: CC(C)(C)OC(=O)N1CCC2(CC1)CN(CC1CCNCC1)C2] |

| | |
|---|---|
| Intermediate 4-8: tert-butyl 4-(2-(piperidin-4-yl)ethyl)piperazine-1-carboxylate | 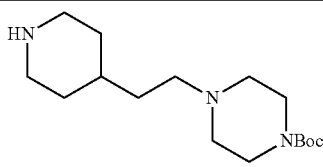 |

Intermediate 4-9: tert-butyl 4-(piperazin-1-yl)piperidine-1-carboxylate

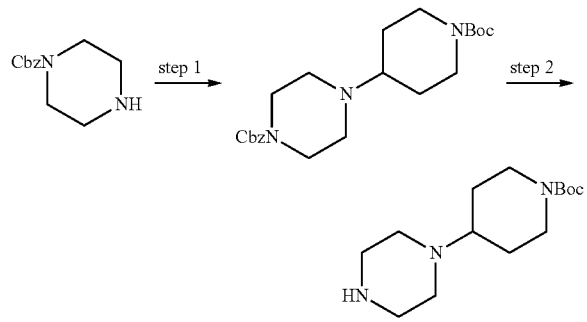

Step 1: Synthesis of benzyl 4-(1-(tert-butoxycarbonyl)piperidin-4-yl)piperazine-1-carboxylate After suspending benzyl piperazine-1-carboxylate (1.03 g, 4.54 mmol) and tert-butyl 4-oxopiperidine-1-carboxylate (905 mg, 4.45 mmol) in MeOH (20.0 ml), sodium triacetoxyborohydride (1.92 g, 9.08 mmol) was added and stirred at room temperature for 16 hours. NaHCO$_3$ aqueous solution (20 ml) was added to the reaction solution, followed by extraction with EtOAc (25 ml×2), and the organic layer was dried over anhydrous sodium sulfate, filtered, and concentrated under reduced pressure. The resulting residue was subjected to MPLC (50% EtOAc/Hexane) to give 880 mg (48%) of a colorless liquid.

Step 2: Synthesis of tert-butyl 4-(piperazin-1-yl)piperidine-1-carboxylate

After dissolving benzyl 4-(1-(tert-butoxycarbonyl)piperidin-4-yl)piperazine-1-carboxylate (880 mg, 2.39 mmol) in MeOH (20 mL), Pd/C (10 wt % Pd, 88 mg) was added and stirred for 6 hours at room temperature under a hydrogen stream. The reaction solution was filtered and concentrated. A white solid (600 mg, 93%) was obtained.

Intermediate 4-10: tert-butyl 4-(piperazin-1-ylmethyl)piperidine-1-carboxylate

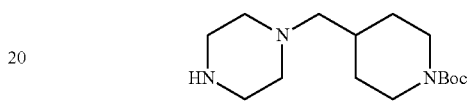

Intermediate 4-10 was synthesized in a similar way to the synthesis method of Intermediate 4-9.

Intermediate 4-11: tert-butyl 4-(2-hydroxyethyl)piperazine-1-carboxylate

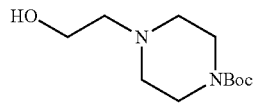

After suspending 2-(piperazin-1-yl)ethan-1-ol (300 mg, 2.30 mmol) in THF (15.0 ml), di-tert-butyl dicarbonate (0.90 mL, 3.92 mmol) and TEA (0.96 mL, 6.90 mmol) was added at 0° C. and stirred at room temperature for 3 hours. After adding distilled water (15 ml) to the reaction mixture, extraction was performed with EtOAc (20 ml×2), and the organic layer was dried over anhydrous sodium sulfate, filtered, and concentrated under reduced pressure. The resulting residue was subjected to MPLC (50% EtOAc/Hexane) to give 205 mg (39%) of a colorless liquid.

Example 1: 1-(4-cyano-3-(trifluoromethyl)phenyl)-N-(5-(4-((7-(2-(2,6-dioxopiperidin-3-yl)-1,3-dioxoisoindolin-5-yl)-2,7-diazaspiro[3.5]nonan-2-yl)methyl)piperidin-1-yl)pyridin-2-yl)piperidine-4-carboxamide

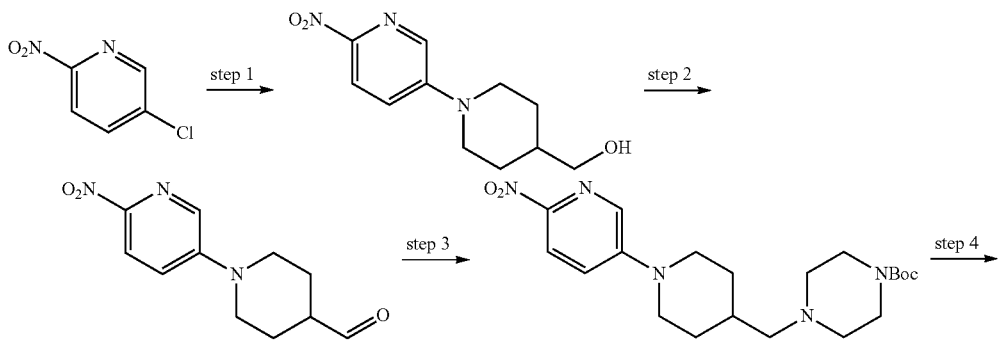

-continued

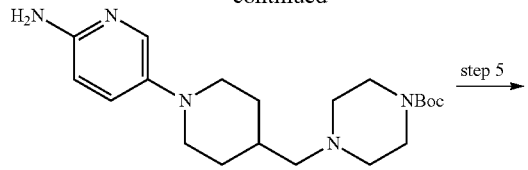

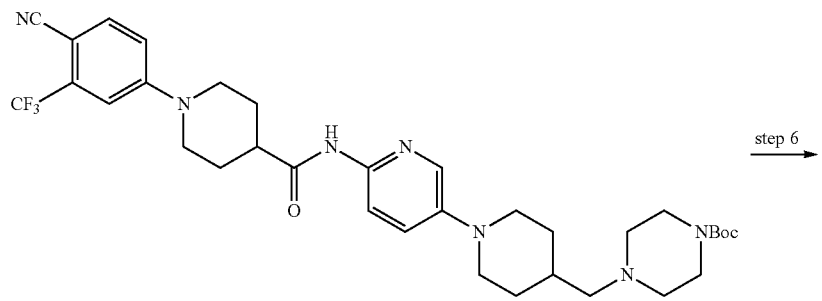

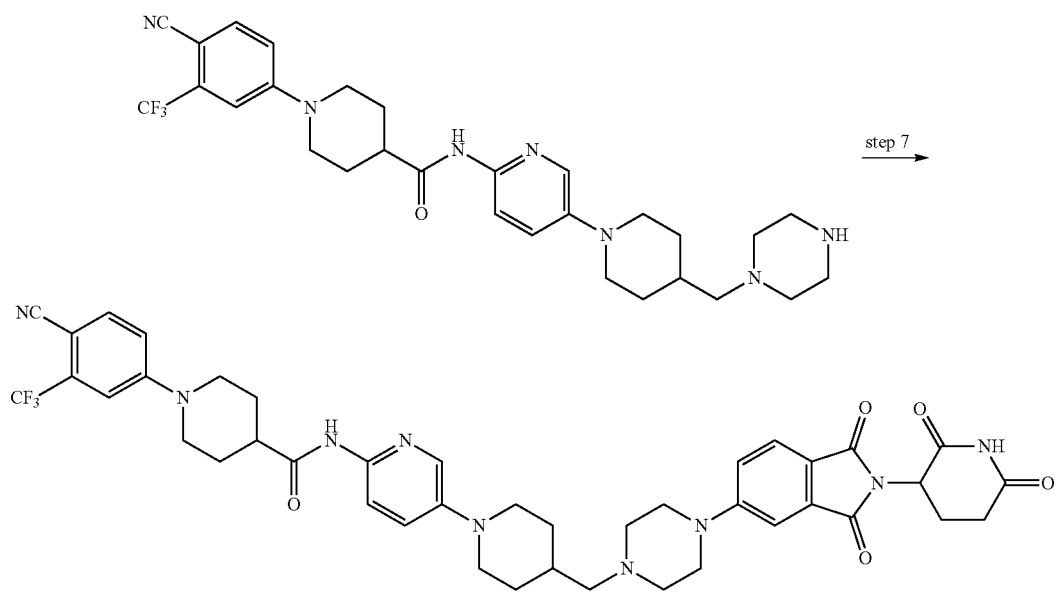

Step 1: Synthesis of (1-(6-nitropyridin-3-yl)piperidin-4-yl)methanol 5-chloro-2-nitropyridine (5.00 g, 31.5 mmol), piperidin-4-ylmethanol (5.45 g, 47.3 mmol), and DIPEA (11.1 ml, 63.0 mmol) were suspended in DMSO (20.0 ml) and then stirred at 90° C. for 16 hours. After adding distilled water (15 ml) to the reaction solution, extraction was performed with EtOAc (25 ml×2), and the organic layer was dried over anhydrous sodium sulfate, filtered, and concentrated under reduced pressure. The resulting residue was subjected to MPLC (50% EtOAc/Hexane) to give 5.66 g (76%) of a yellow solid.

Step 2: Synthesis of 1-(6-nitropyridin-3-yl)piperidine-4-carbaldehyde

After suspending (1-(6-nitropyridin-3-yl)piperidin-4-yl)methanol (2.00 g, 8.43 mmol) in DCM (3.0 ml), DMP (5.36 g, 12.6 mmol) was added and stirred at room temperature for 4 hours. After adding $Na_2S_2O_3$ aqueous solution (15 ml) to the reaction mixture, extraction was performed with DCM (25 ml×2), and the organic layer was dried over anhydrous sodium sulfate, filtered, and concentrated under reduced pressure. The resulting residue was subjected to MPLC (50% EtOAc/Hexane) to give 1.90 g (96%) of a yellow solid.

Step 3: Synthesis of tert-butyl 4-((1-(6-nitropyridin-3-yl)piperidin-4-yl)methyl)piperazine-1-carboxylate After suspending 1-(6-nitropyridin-3-yl)piperidine-4-carbaldehyde (300 mg, 1.28 mmol), and tert-butyl piperazine-1-carboxylate (285 mg, 1.53 mmol) in MeOH (20.0 ml), sodium triacetoxyborohydride (814 mg, 3.84 mmol) was added and stirred at room temperature for 16 hours. NaHCO$_3$ aqueous solution (15 ml) was added to the reaction mixture, followed by extraction with EtOAc (25 ml×2), and the organic layer was dried over anhydrous sodium sulfate, filtered, and concentrated under reduced pressure. The obtained residue was subjected to MPLC (50% EtOAc/Hexane) to give 419 mg (81%) of a yellow solid. m/z 406.38 [M+H]$^+$.

Step 4: Synthesis of tert-butyl 4-((1-(6-aminopyridin-3-yl)piperidin-4-yl)methyl)piperazine-1-carboxylate After dissolving tert-butyl 4-((1-(6-nitropyridin-3-yl)piperidin-4-yl)methyl)piperazine-1-carboxylate (419 mg, 1.03 mmol) in the mixed solution of DCM (20 ml) and MeOH (10 ml), Pd/C (10 wt % Pd, 84 mg) was added and stirred at room temperature for 6 hours under a hydrogen stream.

The reaction solution was filtered and concentrated to give a brown solid (374 mg, 97%). m/z 376.42 [M+H]$^+$.

Step 5: Synthesis of tert-butyl 4-((1-(6-(1-(4-cyano-3-(trifluoromethyl)phenyl)piperidine-4-carboxamido)pyridin-3-yl)piperidin-4-yl)methyl)piperazine-1-carboxylate Tert-butyl 4-((1-(6-aminopyridin-3-yl)piperidin-4-yl)methyl)piperazine-1-carboxylate (374 mg, 0.996 mmol), 1-(4-cyano-3-(trifluoromethyl)phenyl)piperidine-4-carboxylic acid (Intermediate 1-1, 356 mg, 1.20 mmol), HATU (456 mg, 1.20 mmol), and DIPEA (0.35 mL, 1.99 mmol) were suspended in DMF (3.0 ml), and then stirred for 16 hours at room temperature. After adding distilled water (15 ml) to the reaction solution, extraction was performed with EtOAc (25 ml×2), and the organic layer was dried over anhydrous sodium sulfate, filtered, and concentrated under reduced pressure. The resulting residue was subjected to MPLC (50% EtOAc/Hexane) to give 453 mg (69%) of a brown solid.

Step 6: Synthesis of 1-(4-cyano-3-(trifluoromethyl)phenyl)-N-(5-(4-(piperazin-1-ylmethyl)piperidin-1-yl)pyridin-2-yl)piperidine-4-carboxamide After suspending tert-butyl 4-((1-(6-(1-(4-cyano-3-(trifluoromethyl)phenyl)piperidine-4-carboxamido)pyridin-3-yl)piperidin-4-yl)methyl)piperazine-1-carboxylate (453 mg, 0.680 mmol) in DCM (3.00 ml), 4 M HCl in dioxane (1.31 mL, 3.40 mmol) was added and stirred at room temperature for 1 hour. The reaction solution was concentrated, and then NaHCO$_3$ aqueous solution (15 ml) was added, followed by extraction with DCM (25 ml×2). The organic layer was dried over anhydrous sodium sulfate, filtered, and concentrated under reduced pressure. 305 mg (76%) of a white solid was obtained.

Step 7: Synthesis of 1-(4-cyano-3-(trifluoromethyl)phenyl)-N-(5-(4-((4-(2-(2,6-dioxopiperidin-3-yl)-1,3-dioxoisoindolin-5-yl)piperazin-1-yl)methyl)piperidin-1-yl)pyridin-2-yl)piperidine-4-carboxamide 1-(4-cyano-3-(trifluoromethyl)phenyl)-N-(5-(4-(piperazin-1-ylmethyl)piperidin-1-yl)pyridin-2-yl)piperidine-4-carboxamide (50 mg, 0.094 mmol), 2-(2,6-dioxopiperidin-3-yl)-5-fluoroisoindoline-1,3-dione (Intermediate 2-1, 39 mg, 0.14 mmol), and DIPEA (0.033 mL, 0.19 mmol) were suspended in DMSO (3.0 ml) and stirred at 90° C. for 16 hours. After adding distilled water (15 ml) to the reaction solution, extraction was performed with EtOAc (25 ml×2), and the organic layer was dried over anhydrous sodium sulfate, filtered, and concentrated under reduced pressure. The obtained residue was subjected to MPLC (10% MeOH/DCM) to give 24 mg (31%) of a yellow solid.

Example 2: 1-(3-chloro-4-cyanophenyl)-N-(5-(4-((4-(2-(2,6-dioxopiperidin-3-yl)-1,3-dioxoisoindolin-5-yl)piperazin-1-yl)methyl)piperidin-1-yl)pyridin-2-yl)piperidine-4-carboxamide

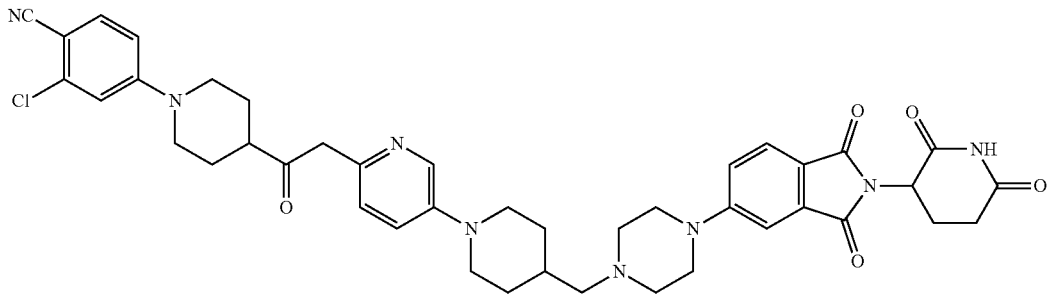 [SMILES: N#Cc1ccc(N2CCC(C(=O)Cc3ccc(N4CCC(CN5CCN(c6ccc7c(c6)C(=O)N(C6CCC(=O)NC6=O)C7=O)CC5)CC4)cn3)CC2)cc1Cl]

Example 2 was synthesized in a similar way to the synthesis method of Example 1, using 1-(3-chloro-4-cyanophenyl)piperidine-4-carboxylic acid (Intermediate 1-2) instead of 1-(4-cyano-3-(trifluoromethyl)phenyl)piperidine-4-carboxylic acid (Intermediate 1-1).

Example 3: 1-(4-cyano-3-(trifluoromethyl)phenyl)-N-(5-(4-((4-(2-((2-(2,6-dioxopiperidin-3-yl)-1,3-dioxoisoindolin-5-yl)oxy)ethyl)piperazin-1-yl)methyl)piperidin-1-yl)pyridin-2-yl)piperidine-4-carboxamide

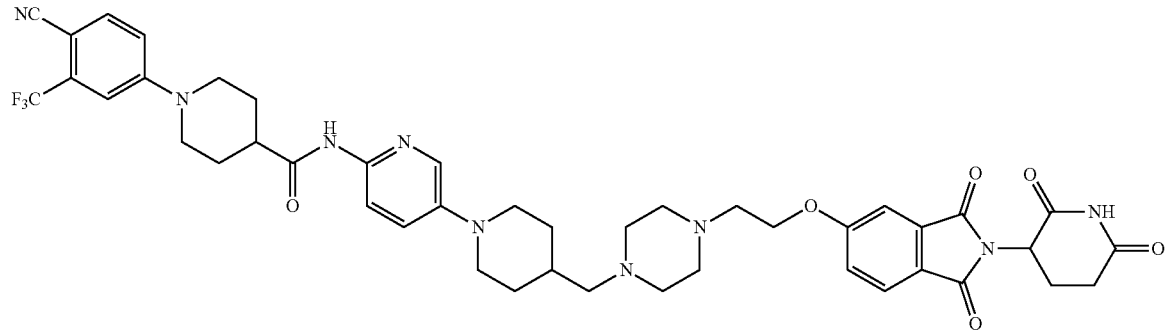 [SMILES: N#Cc1ccc(N2CCC(C(=O)Nc3ccc(N4CCC(CN5CCN(CCOc6ccc7c(c6)C(=O)N(C6CCC(=O)NC6=O)C7=O)CC5)CC4)cn3)CC2)cc1C(F)(F)F]

1-(4-cyano-3-(trifluoromethyl)phenyl)-N-(5-(4-(piperazin-1-ylmethyl)piperidin-1-yl)pyridin-2-yl)piperidine-4-carboxamide (11 mg, 0.020 mmol), 2-(2,6-dioxopiperidin-3-yl)-5-(2-iodoethoxy)isoindoline-1,3-dione (WO2018/119448 A1, 8.6 mg, 0.020 mmol), and $K_2CO_3$ (5.52 mg, 0.04 mmol) were suspended in DMF (2.0 ml) and stirred at 70° C. for 16 hours. After adding distilled water (15 ml) to the reaction solution, extraction was performed with EtOAc (25 ml×2), and the organic layer was dried over anhydrous sodium sulfate, filtered, and concentrated under reduced pressure. The resulting residue was subjected to MPLC (10% MeOH/DCM) to give 2.3 mg (13%) of a yellow solid.

Example 4: 1-(4-cyano-3-(trifluoromethyl)phenyl)-N-(5-(4-((4-((2-(2,6-dioxopiperidin-3-yl)-1,3-dioxoisoindolin-5-yl)methyl)piperazin-1-yl)methyl)piperidin-1-yl)pyridin-2-yl)piperidine-4-carboxamide

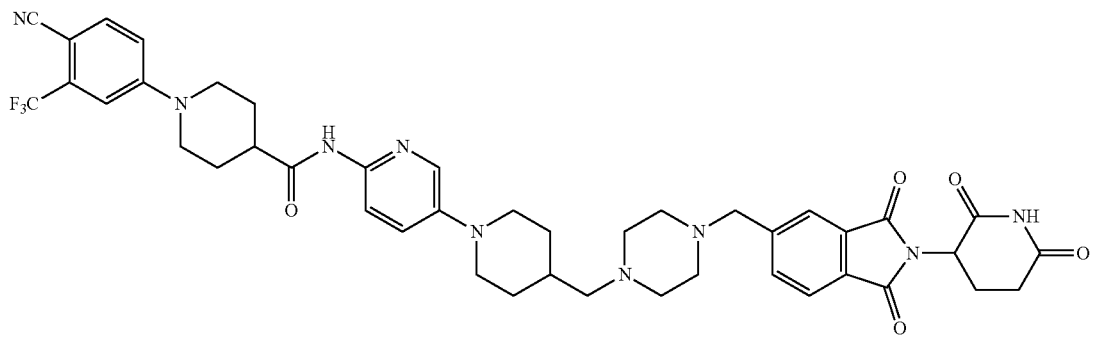 [SMILES: N#Cc1ccc(N2CCC(C(=O)Nc3ccc(N4CCC(CN5CCN(Cc6ccc7c(c6)C(=O)N(C6CCC(=O)NC6=O)C7=O)CC5)CC4)cn3)CC2)cc1C(F)(F)F]

Example 4 was synthesized in a similar way to the synthesis method of Example 3, using 5-(bromomethyl)-2-(2,6-dioxopiperidin-3-yl)isoindoline-1,3-dione (Intermediate 2-8) instead of 2-(2,6-dioxopiperidin-3-yl)-5-(2-iodoethoxy)isoindoline-1,3-dione (WO2018/119448 A1).

Example 5: 1-(4-cyano-3-(trifluoromethyl)phenyl)-N-(5-(4-((4-((2-(2,6-dioxopiperidin-3-yl)-1,3-dioxoisoindolin-5-yl)glycyl)piperazin-1-yl)methyl)piperidin-1-yl)pyridin-2-yl)piperidine-4-carboxamide

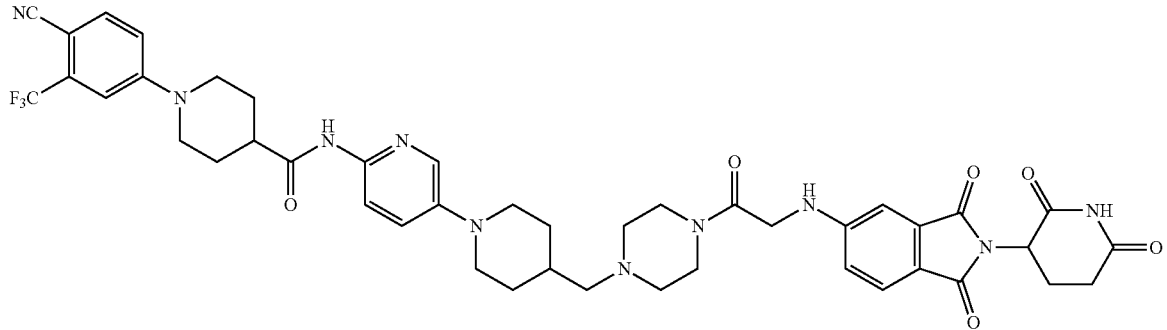

1-(4-cyano-3-(trifluoromethyl)phenyl)-N-(5-(4-(piperazin-1-ylmethyl)piperidin-1-yl)pyridin-2-yl)piperidine-4-carboxamide (35 mg, 0.059 mmol), (2-(2,6-dioxopiperidin-3-yl)-1,3-dioxoisoindolin-5-yl)glycine (Intermediate 3-15, 30 mg, 0.071 mmol), HATU (27 mg, 0.071 mmol), and DIPEA (0.04 mL, 0.24 mmol) were suspended in DMF (1.0 ml) and stirred at room temperature for 16 hours. After adding distilled water (15 ml) to the reaction solution, extraction was performed with EtOAc (25 ml×2), and the organic layer was dried over anhydrous sodium sulfate, filtered, and concentrated under reduced pressure. The obtained residue was subjected to MPLC (10% MeOH/DCM) to give 6 mg (12%) of a yellow solid.

Example 6: 1-(4-cyano-3-(trifluoromethyl)phenyl)-N-(5-(4-((4-((1-(2-(2,6-dioxopiperidin-3-yl)-1,3-dioxoisoindolin-5-yl)piperidin-4-yl)methyl)piperazin-1-yl)methyl)piperidin-1-yl)pyridin-2-yl)piperidine-4-carboxamide

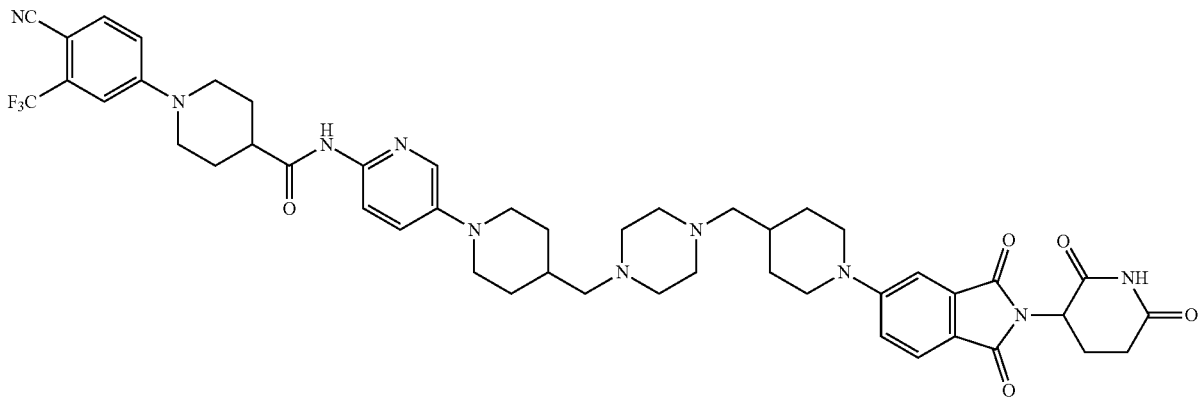

1-(4-cyano-3-(trifluoromethyl)phenyl)-N-(5-(4-(piperazin-1-ylmethyl)piperidin-1-yl)pyridin-2-yl)piperidine-4-carboxamide (35 mg, 0.063 mmol), and 1-(2-(2,6-dioxopiperidin-3-yl)-1,3-dioxoisoindolin-5-yl)piperidine-4-carbaldehyde (Intermediate 3-1, 28 mg, 0.076 mmol) were suspended in ACN (20.0 ml), to which sodium triacetoxyborohydride (40 mg, 0.19 mmol) was added and then stirred at room temperature for 16 hours. NaHCO$_3$ aqueous solution (15 ml) was added to the reaction mixture, followed by extraction with EtOAc (25 ml×2), and the organic layer was dried over anhydrous sodium sulfate, filtered, and concentrated under reduced pressure. The resulting residue was subjected to MPLC (10% MeOH/DCM) to give 7 mg (12%) of a yellow solid.

Example 7: 1-(3-chloro-4-cyanophenyl)-N-(5-(4-((4-((1-(2-(2,6-dioxopiperidin-3-yl)-1,3-dioxoisoindolin-5-yl)piperidin-4-yl)methyl)piperazin-1-yl)methyl)piperidin-1-yl)pyridin-2-yl)piperidine-4-carboxamide

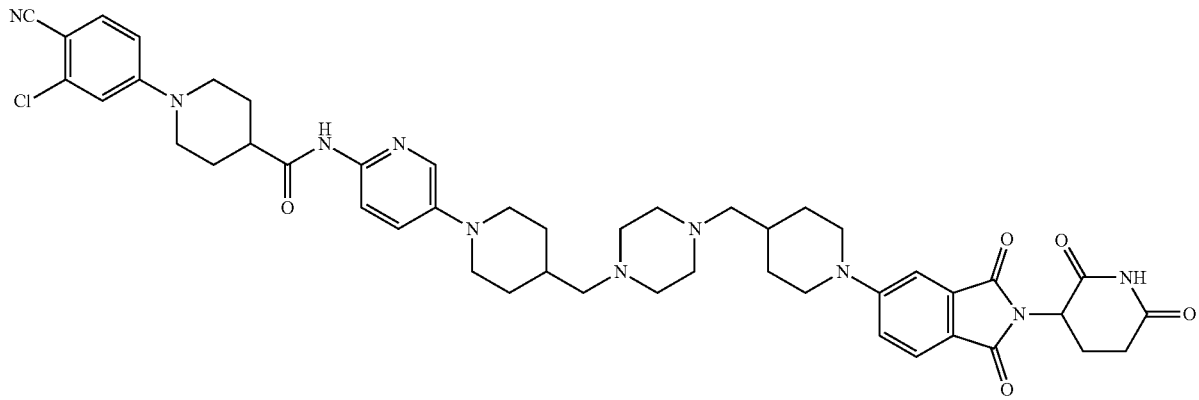 [SMILES: N#Cc1ccc(N2CCC(C(=O)Nc3ccc(N4CCC(CN5CCN(CC6CCN(c7ccc8c(c7)C(=O)N(C7CCC(=O)NC7=O)C8=O)CC6)CC5)CC4)cn3)CC2)cc1Cl]

Example 7 was synthesized in a similar way to the synthesis methods of Examples 1 and 6, using 1-(3-chloro-4-cyanophenyl)piperidine-4-carboxylic acid (Intermediate 1-2) instead of 1-(4-cyano-3-(trifluoromethyl)phenyl)piperidine-4-carboxylic acid (Intermediate 1-1).

Example 8: 1-(4-cyano-3-(trifluoromethyl)phenyl)-N-(5-(4-((4-((1-(2-(2,6-dioxopiperidin-3-yl)-1,3-dioxoisoindolin-5-yl)piperidin-4-yl)methyl)piperazin-1-yl)methyl)piperidin-1-yl)pyridin-2-yl)-4-fluoropiperidine-4-carboxamide

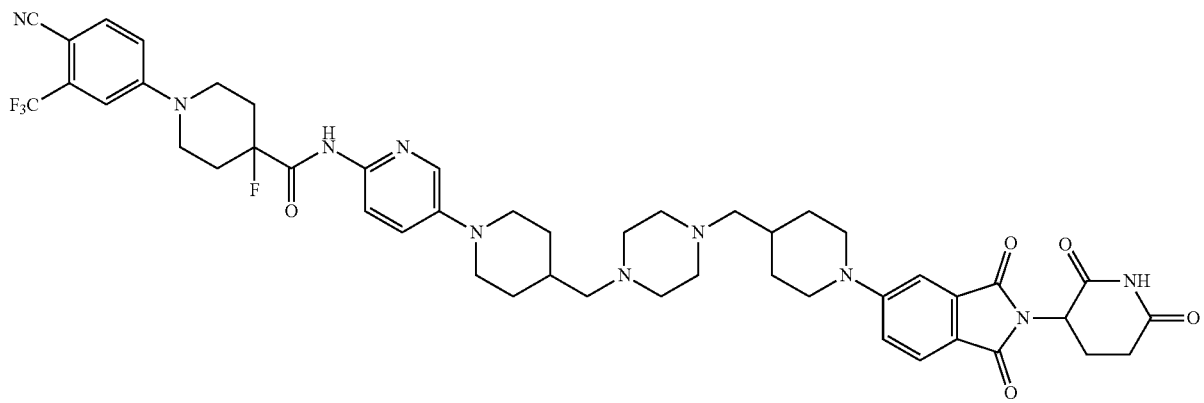

Example 8 was synthesized in a similar way to the synthesis methods of Examples 1 and 6, using 1-(4-cyano-3-(trifluoromethyl)phenyl)-4-fluoropiperidine-4-carboxylic acid (Intermediate 1-5) instead of 1-(4-cyano-3-(trifluoromethyl)phenyl)piperidine-4-carboxylic acid (Intermediate 1-1).

Example 9: 1-(6-cyano-5-(trifluoromethyl)pyridin-3-yl)-N-(5-(4-((4-((1-(2-(2,6-dioxopiperidin-3-yl)-1,3-dioxoisoindolin-5-yl)piperidin-4-yl)methyl)piperazin-1-yl)methyl)piperidin-1-yl)pyridin-2-yl)piperidine-4-carboxamide

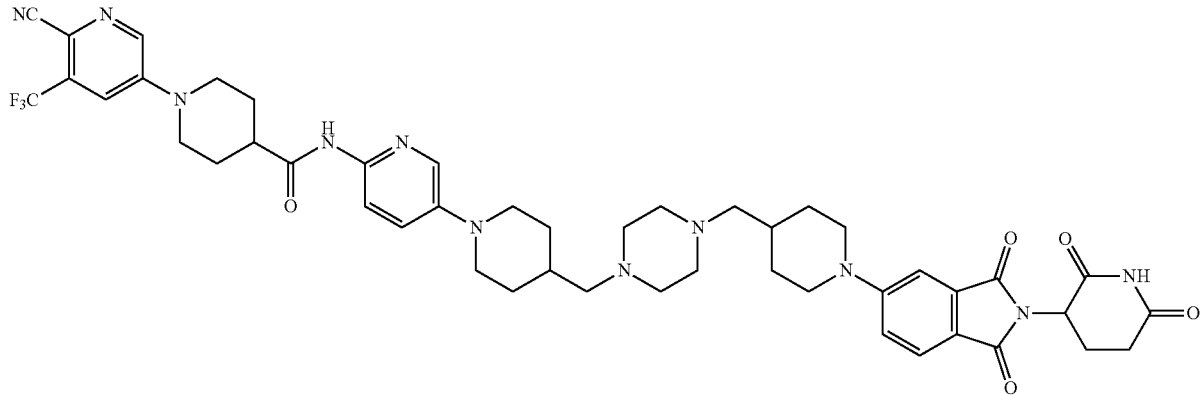

Example 9 was synthesized in a similar way to the synthesis methods of Examples 1 and 6, using 1-(6-cyano-5-(trifluoromethyl)pyridin-3-yl)piperidine-4-carboxylic acid (Intermediate 1-7) instead of 1-(4-cyano-3-(trifluoromethyl)phenyl)piperidine-4-carboxylic acid (Intermediate 1-1).

Example 10: 1-(6-cyano-5-(trifluoromethyl)pyridin-3-yl)-N-(5-(4-((4-((1-(2-(2,6-dioxopiperidin-3-yl)-1,3-dioxoisoindolin-5-yl)piperidin-4-yl)methyl)piperazin-1-yl)methyl)piperidin-1-yl)pyridin-2-yl)-4-fluoropiperidine-4-carboxamide

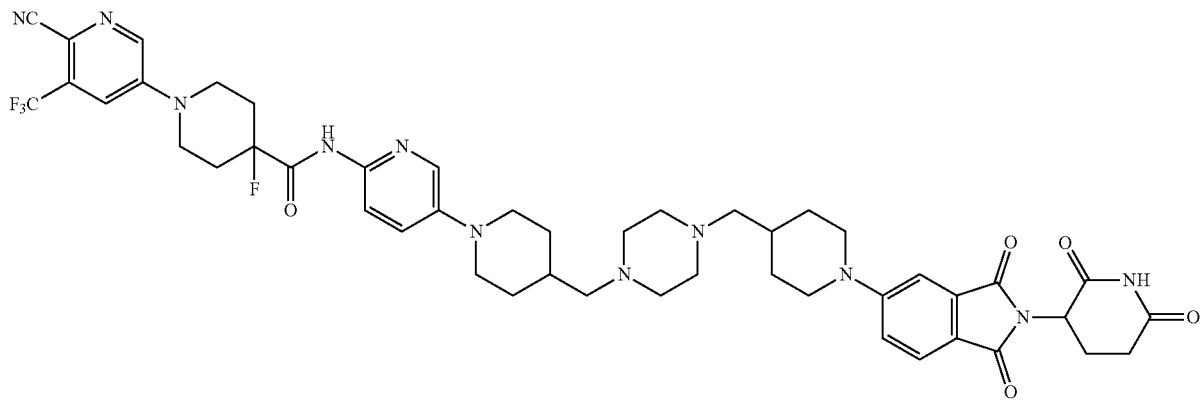 [SMILES: N#Cc1ccc(N2CCC(F)(C(=O)Nc3ccc(N4CCC(CN5CCN(CC6CCN(c7ccc8c(c7)C(=O)N(C7CCC(=O)NC7=O)C8=O)CC6)CC5)CC4)cn3)CC2)cc1C(F)(F)F]

Example 10 was synthesized in a similar way to the synthesis methods of Examples 1 and 6, using 1-(6-cyano-5-(trifluoromethyl)pyridin-3-yl)-4-fluoropiperidine-4-carboxylic acid (Intermediate 1-8) instead of 1-(4-cyano-3-(trifluoromethyl)phenyl)piperidine-4-carboxylic acid (Intermediate 1-1).

Example 11: 1-(4-cyano-3-(trifluoromethyl)phenyl)-N-(5-(4-((4-((1-(2-(2,6-dioxopiperidin-3-yl)-1,3-dioxoisoindolin-5-yl)azetidin-3-yl)methyl)piperazin-1-yl)methyl)piperidin-1-yl)pyridin-2-yl)piperidine-4-carboxamide

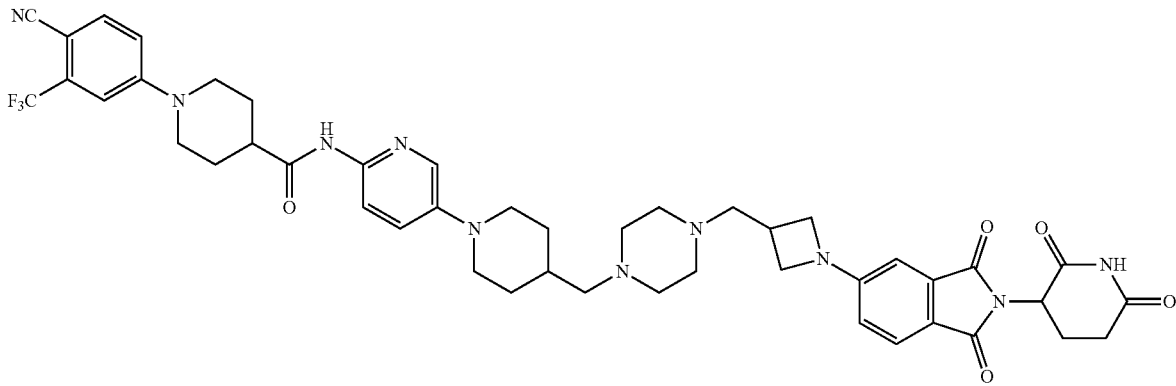 [SMILES: N#Cc1ccc(N2CCC(C(=O)Nc3ccc(N4CCC(CN5CCN(CC6CN(c7ccc8c(c7)C(=O)N(C7CCC(=O)NC7=O)C8=O)C6)CC5)CC4)cn3)CC2)cc1C(F)(F)F]

Example 11 was synthesized in a similar way to the synthesis method of Example 6, using 1-(2-(2,6-dioxopiperidin-3-yl)-1,3-dioxoisoindolin-5-yl)azetidine-3-carbaldehyde (Intermediate 3-3) instead of 1-(2-(2,6-dioxopiperidin-3-yl)-1,3-dioxoisoindolin-5-yl)piperidine-4-carbaldehyde (Intermediate 3-1).

Example 12: 1-(3-chloro-4-cyanophenyl)-N-(5-(4-((4-((1-(2-(2,6-dioxopiperidin-3-yl)-1,3-dioxoisoindolin-5-yl)azetidin-3-yl)methyl)piperazin-1-yl)methyl)piperidin-1-yl)pyridin-2-yl)piperidine-4-carboxamide

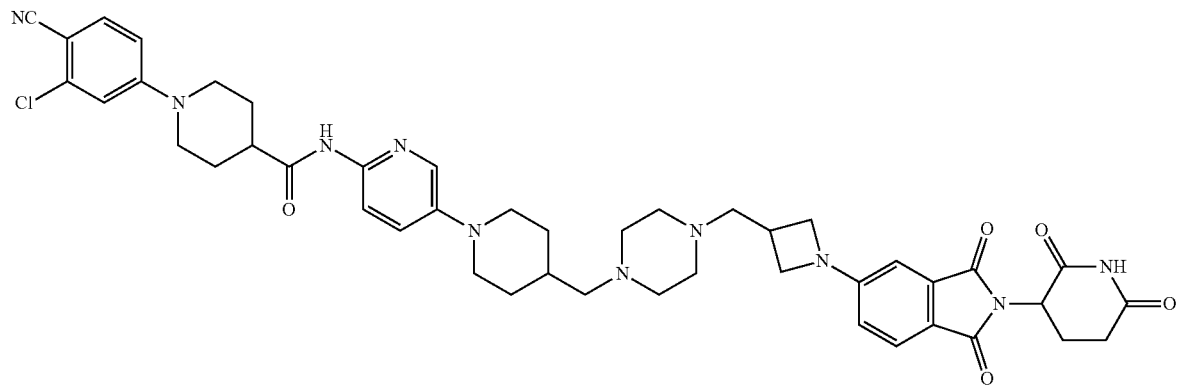 [SMILES: N#Cc1ccc(N2CCC(C(=O)Nc3ccc(N4CCC(CN5CCN(CC6CN(c7ccc8c(c7)C(=O)N(C7CCC(=O)NC7=O)C8=O)C6)CC5)CC4)cn3)CC2)cc1Cl]

Example 12 was synthesized in a similar way to the synthesis methods of Examples 1 and 6, using 1-(3-chloro-4-cyanophenyl)piperidine-4-carboxylic acid (Intermediate 1-2) and 1-(2-(2,6-dioxopiperidin-3-yl)-1,3-dioxoisoindolin-5-yl)azetidine-3-carbaldehyde (Intermediate 3-3), respectively, instead of 1-(4-cyano-3-(trifluoromethyl)phenyl)piperidine-4-carboxylic acid (Intermediate 1-1) and 1-(2-(2,6-dioxopiperidin-3-yl)-1,3-dioxoisoindolin-5-yl)piperidine-4-carbaldehyde (Intermediate 3-1).

Example 13: 1-(4-cyano-3-(trifluoromethyl)phenyl)-N-(5-(4-((4-(((1-(2-(2,6-dioxopiperidin-3-yl)-1,3-dioxoisoindolin-4-yl)piperidin-4-yl)methyl)piperazin-1-yl)methyl)piperidin-1-yl)pyridin-2-yl)piperidine-4-carboxamide

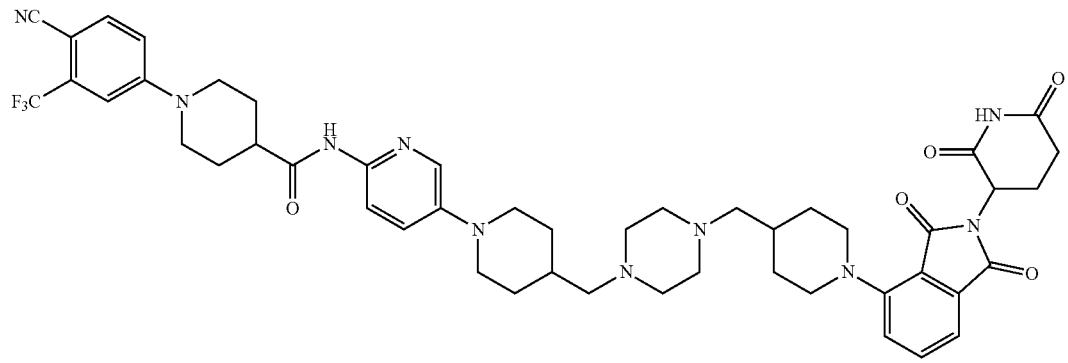 [SMILES: N#Cc1ccc(N2CCC(C(=O)Nc3ccc(N4CCC(CN5CCN(CC6CCN(c7cccc8c7C(=O)N(C7CCC(=O)NC7=O)C8=O)CC6)CC5)CC4)cn3)CC2)cc1C(F)(F)F]

Example 13 was synthesized in a similar way to the synthesis method of Example 6, using 1-(2-(2,6-dioxopiperidin-3-yl)-1,3-dioxoisoindolin-4-yl)piperidine-4-carbaldehyde (Intermediate 3-2) instead of 1-(2-(2,6-dioxopiperidin-3-yl)-1,3-dioxoisoindolin-5-yl)piperidine-4-carbaldehyde (Intermediate 3-1).

Example 14: 1-(4-cyano-3-(trifluoromethyl)phenyl)-N-(5-(4-((4-(((3R)-1-(2-(2,6-dioxopiperidin-3-yl)-1,3-dioxoisoindolin-5-yl)pyrrolidin-3-yl)methyl)piperazin-1-yl)methyl)piperidin-1-yl)pyridin-2-yl)piperidine-4-carboxamide

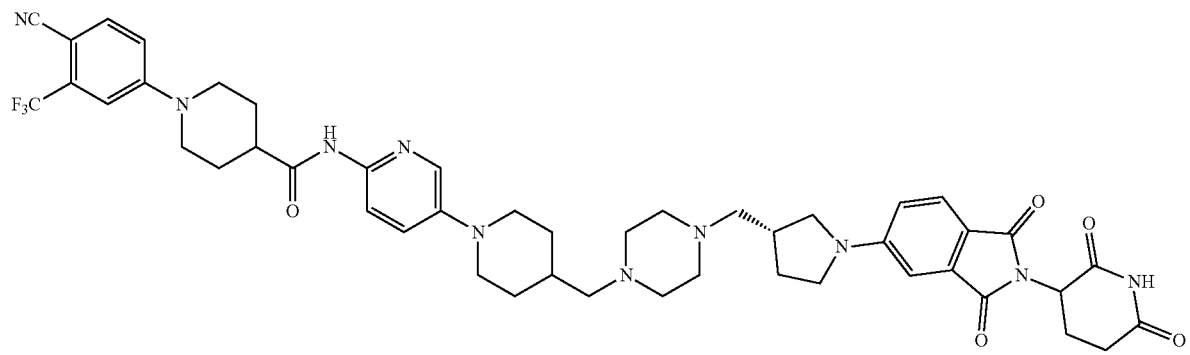 [SMILES: N#Cc1ccc(N2CCC(C(=O)Nc3ccc(N4CCC(CN5CCN(C[C@H]6CCN(c7ccc8c(c7)C(=O)N(C7CCC(=O)NC7=O)C8=O)C6)CC5)CC4)cn3)CC2)cc1C(F)(F)F]

Example 14 was synthesized in a similar way to the synthesis method of Example 6, using (3S)-1-(2-(2,6-dioxopiperidin-3-yl)-1,3-dioxoisoindolin-5-yl)pyrrolidine-3-carbaldehyde (Intermediate 3-4) instead of 1-(2-(2,6-dioxopiperidin-3-yl)-1,3-dioxoisoindolin-5-yl)piperidine-4-carbaldehyde (Intermediate 3-1).

Example 15: 1-(4-cyano-3-(trifluoromethyl)phenyl)-N-(5-(4-((4-(((3S)-1-(2-(2,6-dioxopiperidin-3-yl)-1,3-dioxoisoindolin-5-yl)pyrrolidin-3-yl)methyl)piperazin-1-yl)methyl)piperidin-1-yl)pyridin-2-yl)piperidine-4-carboxamide

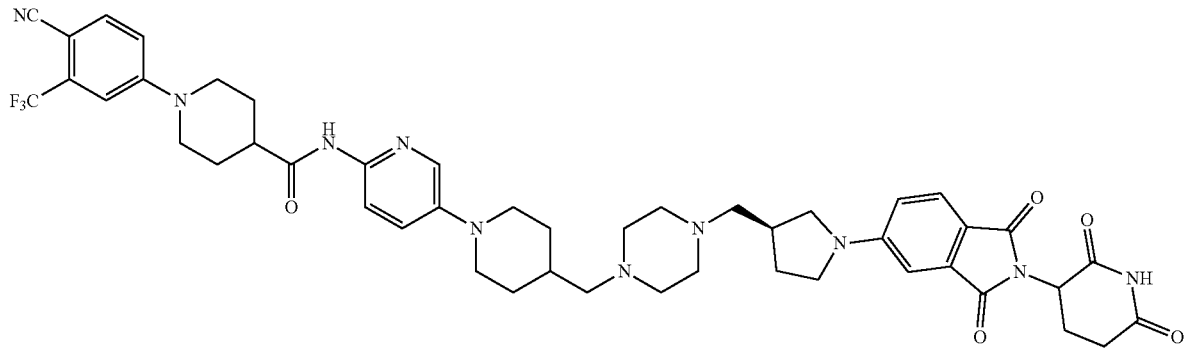 [SMILES: N#Cc1ccc(N2CCC(C(=O)Nc3ccc(N4CCC(CN5CCN(C[C@@H]6CCN(c7ccc8c(c7)C(=O)N(C7CCC(=O)NC7=O)C8=O)C6)CC5)CC4)cn3)CC2)cc1C(F)(F)F]

Example 15 was synthesized in a similar way to the synthesis method of Example 6, using (3R)-1-(2-(2,6-dioxopiperidin-3-yl)-1,3-dioxoisoindolin-5-yl)pyrrolidine-3-carbaldehyde (Intermediate 3-5) instead of 1-(2-(2,6-dioxopiperidin-3-yl)-1,3-dioxoisoindolin-5-yl)piperidine-4-carbaldehyde (Intermediate 3-1).

Example 16: 1-(4-cyano-3-(trifluoromethyl)phenyl)-N-(5-(4-((4-(((3R)-1-(2-(2,6-dioxopiperidin-3-yl)-1,3-dioxoisoindolin-5-yl)piperidin-3-yl)methyl)piperazin-1-yl)methyl)piperidin-1-yl)pyridin-2-yl)piperidine-4-carboxamide

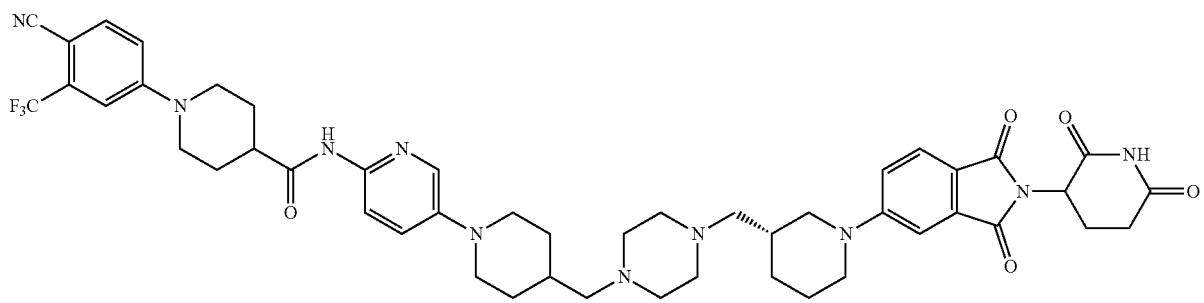 [SMILES: N#Cc1ccc(N2CCC(C(=O)Nc3ccc(N4CCC(CN5CCN(C[C@H]6CCCN(c7ccc8c(c7)C(=O)N(C7CCC(=O)NC7=O)C8=O)C6)CC5)CC4)cn3)CC2)cc1C(F)(F)F]

Example 16 was synthesized in a similar way to the synthesis method of Example 6, using (3S)-1-(2-(2,6-dioxopiperidin-3-yl)-1,3-dioxoisoindolin-5-yl)piperidine-3-carbaldehyde (Intermediate 3-6) instead of 1-(2-(2,6-dioxopiperidin-3-yl)-1,3-dioxoisoindolin-5-yl)piperidine-4-carbaldehyde (Intermediate 3-1).

Example 17: 1-(4-cyano-3-(trifluoromethyl)phenyl)-N-(5-(4-((4-(((3S)-1-(2-(2,6-dioxopiperidin-3-yl)-1,3-dioxoisoindolin-5-yl)piperidin-3-yl)methyl)piperazin-1-yl)methyl)piperidin-1-yl)pyridin-2-yl)piperidine-4-carboxamide

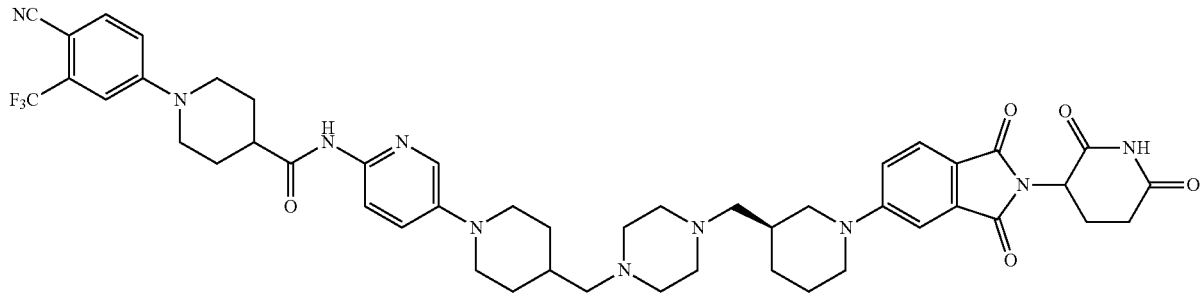 [SMILES: N#Cc1ccc(N2CCC(C(=O)Nc3ccc(N4CCC(CN5CCN(C[C@@H]6CCCN(c7ccc8c(c7)C(=O)N(C7CCC(=O)NC7=O)C8=O)C6)CC5)CC4)cn3)CC2)cc1C(F)(F)F]

Example 17 was synthesized in a similar way to the synthesis method of Example 6, using (3R)-1-(2-(2,6-dioxopiperidin-3-yl)-1,3-dioxoisoindolin-5-yl)piperidine-3-carbaldehyde (Intermediate 3-7) instead of 1-(2-(2,6-dioxopiperidin-3-yl)-1,3-dioxoisoindolin-5-yl)piperidine-4-carbaldehyde (Intermediate 3-1).

Example 18: 1-(4-cyano-3-(trifluoromethyl)phenyl)-N-(5-(4-((4-((1-(2-(2,6-dioxopiperidin-3-yl)-6-fluoro-1,3-dioxoisoindolin-5-yl)piperidin-4-yl)methyl)piperazin-1-yl)methyl)piperidin-1-yl)pyridin-2-yl)piperidine-4-carboxamide

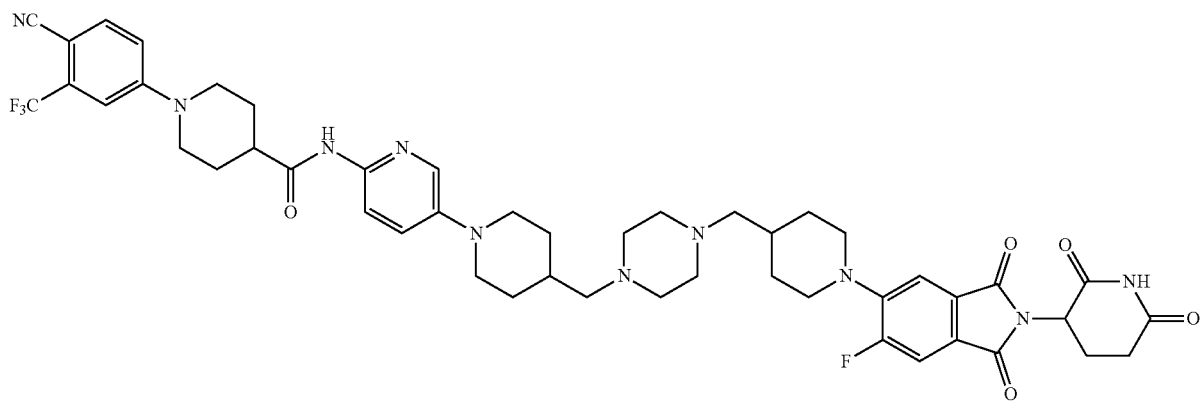 [SMILES: N#Cc1ccc(N2CCC(C(=O)Nc3ccc(N4CCC(CN5CCN(CC6CCN(c7cc8c(cc7F)C(=O)N(C7CCC(=O)NC7=O)C8=O)CC6)CC5)CC4)cn3)CC2)cc1C(F)(F)F]

Example 18 was synthesized in a similar way to the synthesis method of Example 6, using 1-(2-(2,6-dioxopiperidin-3-yl)-6-fluoro-1,3-dioxoisoindolin-5-yl)piperidine-4-carbaldehyde (Intermediate 3-8) instead of 1-(2-(2,6-dioxopiperidin-3-yl)-1,3-dioxoisoindolin-5-yl)piperidine-4-carbaldehyde (Intermediate 3-1).

Example 19: 1-(4-cyano-3-(trifluoromethyl)phenyl)-
N-(5-(4-((4-(((3R)-1-(2-(2,6-dioxopiperidin-3-yl)-6-
fluoro-1,3-dioxoisoindolin-5-yl)pyrrolidin-3-yl)
methyl)piperazin-1-yl)methyl)piperidin-1-yl)pyridin-
2-yl)piperidine-4-carboxamide

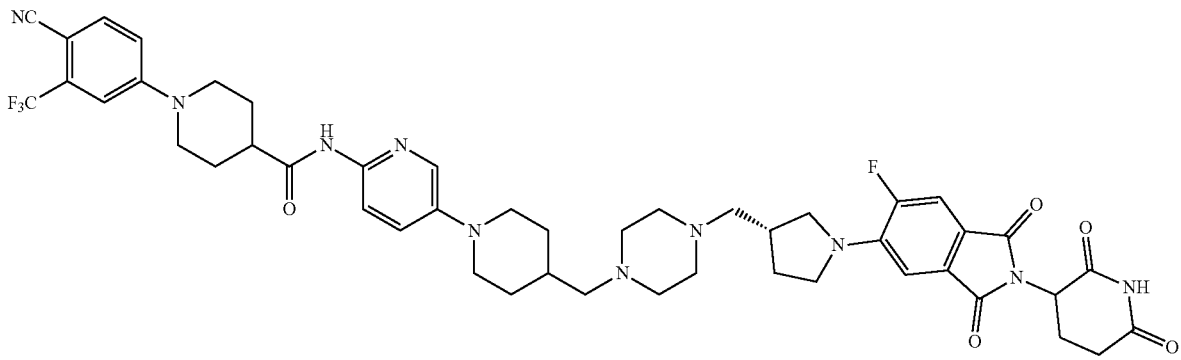

Example 19 was synthesized in a similar way to the synthesis method of Example 6, using (3S)-1-(2-(2,6-dioxopiperidin-3-yl)-6-fluoro-1,3-dioxoisoindolin-5-yl)pyrrolidine-3-carbaldehyde (Intermediate 3-10) instead of 1-(2-(2,6-dioxopiperidin-3-yl)-1,3-dioxoisoindolin-5-yl)piperidine-4-carbaldehyde (Intermediate 3-1).

Example 20: 1-(4-cyano-3-(trifluoromethyl)phenyl)-
N-(5-(4-((4-((1-(2-(2,6-dioxopiperidin-3-yl)-6-
fluoro-1,3-dioxoisoindolin-5-yl)azetidin-3-yl)
methyl)piperazin-1-yl)methyl)piperidin-1-yl)pyridin-
2-yl)piperidine-4-carboxamide

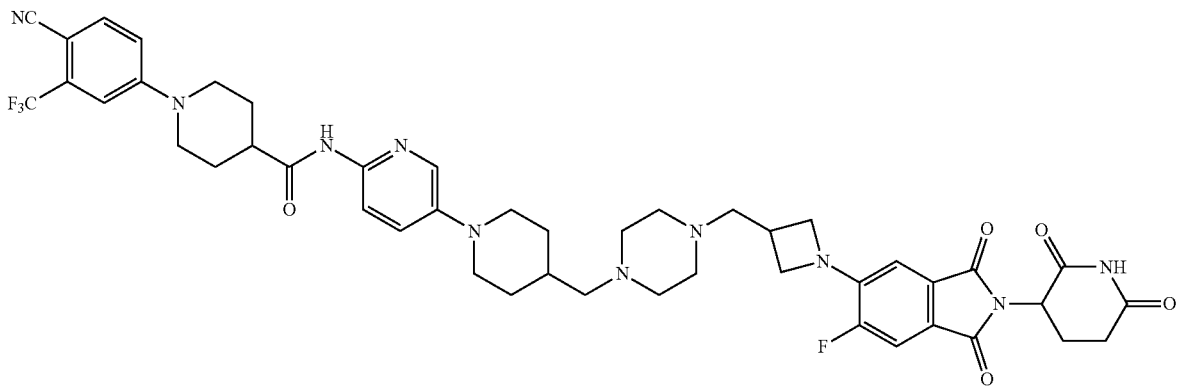 [SMILES: N#Cc1ccc(N2CCC(C(=O)Nc3ccc(N4CCC(CN5CCN(CC6CN(c7cc8c(cc7F)C(=O)N(C7CCC(=O)NC7=O)C8=O)C6)CC5)CC4)cn3)CC2)cc1C(F)(F)F]

Example 20 was synthesized in a similar way to the synthesis method of Example 6, using 1-(2-(2,6-dioxopiperidin-3-yl)-6-fluoro-1,3-dioxoisoindolin-5-yl)azetidine-3-carbaldehyde (Intermediate 3-9) instead of 1-(2-(2,6-dioxopiperidin-3-yl)-1,3-dioxoisoindolin-5-yl)piperidine-4-carbaldehyde (Intermediate 3-1).

Example 21: 1-(4-cyano-3-(trifluoromethyl)phenyl)-N-(4-(4-((4-(((1-(2-(2,6-dioxopiperidin-3-yl)-1,3-dioxoisoindolin-5-yl)piperidin-4-yl)methyl)piperazin-1-yl)methyl)piperidin-1-yl)phenyl)piperidine-4-carboxamide

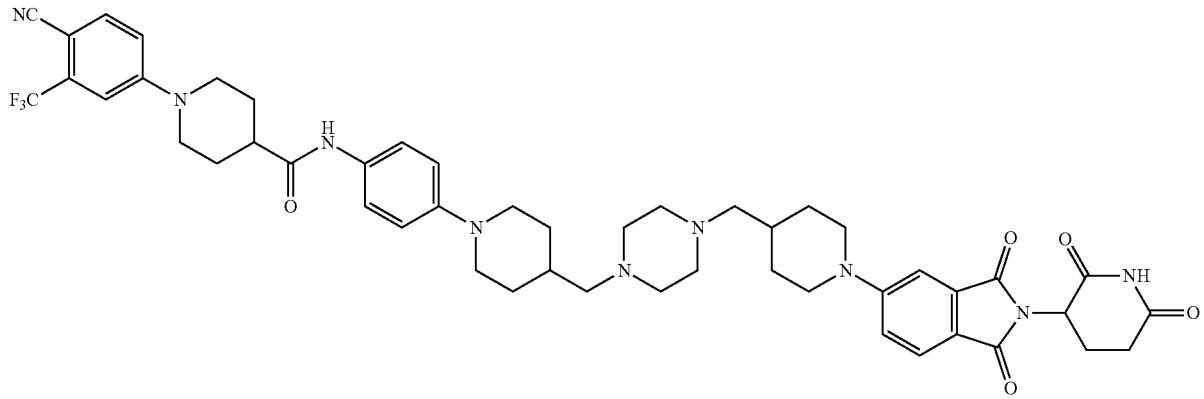

Example 21 was synthesized in a similar way to the synthesis methods of Examples 1 and 6, using 4-fluoronitrobenzene instead of 5-chloro-2-nitropyridine.

Example 22: 1-(4-cyano-3-(trifluoromethyl)phenyl)-N-(4-(4-((4-(((3R)-1-(2-(2,6-dioxopiperidin-3-yl)-1,3-dioxoisoindolin-5-yl)pyrrolidin-3-yl)methyl)piperazin-1-yl)methyl)piperidin-1-yl)phenyl)piperidine-4-carboxamide

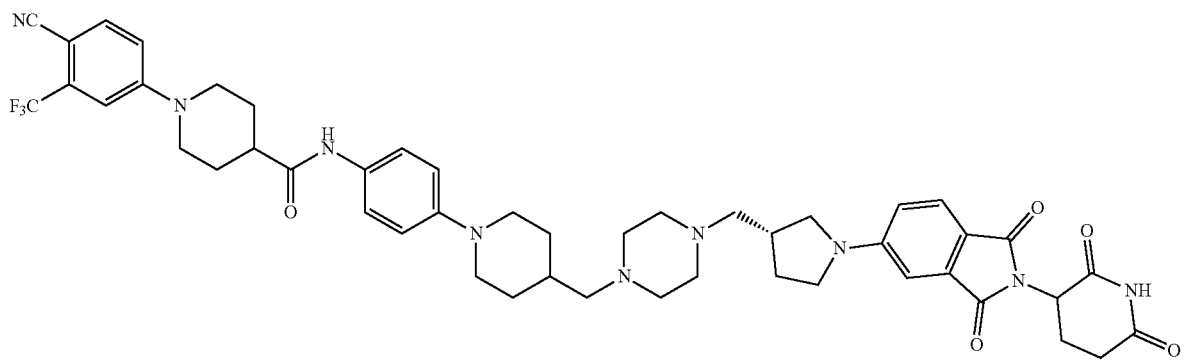 [SMILES: N#Cc1ccc(N2CCC(C(=O)Nc3ccc(N4CCC(CN5CCN(C[C@H]6CCN(c7ccc8c(c7)C(=O)N(C7CCC(=O)NC7=O)C8=O)C6)CC5)CC4)cc3)CC2)cc1C(F)(F)F]

Example 22 was synthesized in a similar way to the synthesis methods of Examples 1 and 6, using 4-fluoronitrobenzene and (3S)-1-(2-(2,6-dioxopiperidin-3-yl)-1,3-dioxoisoindolin-5-yl)pyrrolidine-3-carbaldehyde (Intermediate 3-4), respectively, instead of 5-chloro-2-nitropyridine and 1-(2-(2,6-dioxopiperidin-3-yl)-1,3-dioxoisoindolin-5-yl)piperidine-4-carbaldehyde (Intermediate 3-1).

Example 23: 1-(4-cyano-3-(trifluoromethyl)phenyl)-N-(5-(4-(((2R)-4-((1-(2-(2,6-dioxopiperidin-3-yl)-1,3-dioxoisoindolin-5-yl)piperidin-4-yl)methyl)-2-methylpiperazin-1-yl)methyl)piperidin-1-yl)pyridin-2-yl)piperidine-4-carboxamide

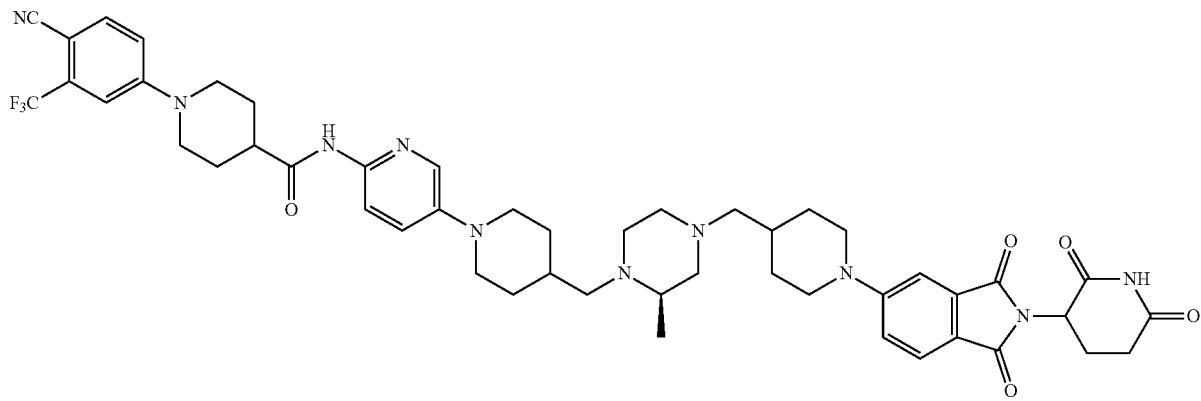 [SMILES: C[C@@H]1CN(CC2CCN(c3ccc4c(c3)C(=O)N(C3CCC(=O)NC3=O)C4=O)CC2)CCN1CC1CCN(c2ccc(NC(=O)C3CCN(c4ccc(C#N)c(C(F)(F)F)c4)CC3)nc2)CC1]

Example 23 was synthesized in a similar way to the synthesis methods of Examples 1 and 6, using tert-butyl (R)-3-methylpiperazine-1-carboxylate instead of tert-butyl piperazine-1-carboxylate.

Example 24: 1-(4-cyano-3-(trifluoromethyl)phenyl)-N-(5-(4-(((2R)-4-((1-(2-(2,6-dioxopiperidin-3-yl)-1,3-dioxoisoindolin-5-yl)azetidin-3-yl)methyl)-2-methylpiperazin-1-yl)methyl)piperidin-1-yl)pyridin-2-yl)piperidine-4-carboxamide

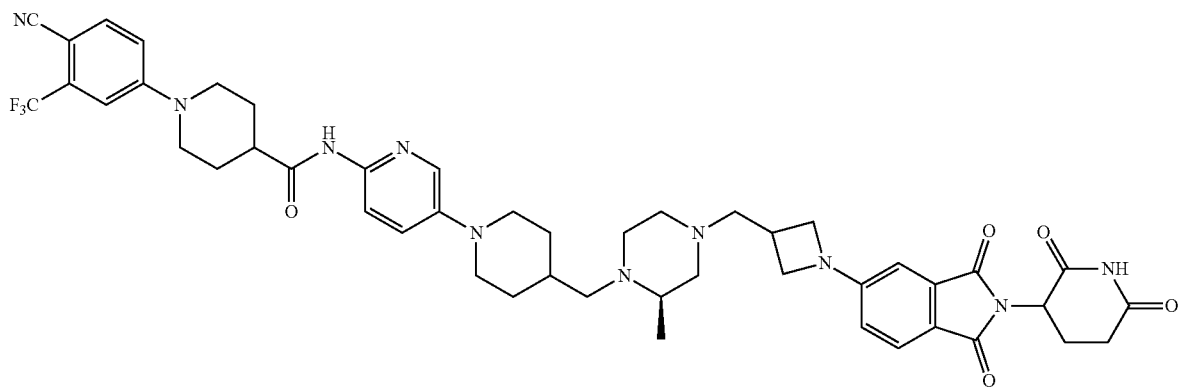 [SMILES: C[C@@H]1CN(CC2CN(c3ccc4c(c3)C(=O)N(C3CCC(=O)NC3=O)C4=O)C2)CCN1CC1CCN(c2ccc(NC(=O)C3CCN(c4ccc(C#N)c(C(F)(F)F)c4)CC3)nc2)CC1]

Example 24 was synthesized in a similar way to the synthesis methods of Examples 1and 6, using tert-butyl (R)-3-methylpiperazine-1-carboxylate and 1-(2-(2,6-dioxopiperidin-3-yl)-1,3-dioxoisoindolin-5-yl)azetidine-3-carbaldehyde (Intermediate 3-3), respectively, instead of tert-butyl piperazine-1-carboxylate and 1-(2-(2,6-dioxopiperidin-3-yl)-1,3-dioxoisoindolin-5-yl)piperidine-4-carbaldehyde (Intermediate 3-1).

Example 25: 1-(4-cyano-3-(trifluoromethyl)phenyl)-N-(5-(4-(((3R)-4-((1-(2-(2,6-dioxopiperidin-3-yl)-1,3-dioxoisoindolin-5-yl)piperidin-4-yl)methyl)-3-methylpiperazin-1-yl)methyl)piperidin-1-yl)pyridin-2-yl)piperidine-4-carboxamide

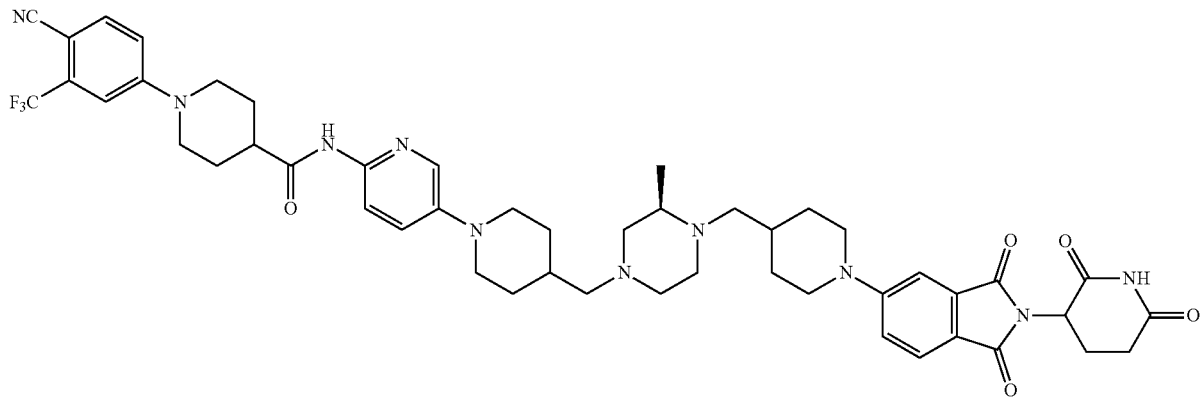 [SMILES: C[C@@H]1CN(CC2CCN(c3ccc(NC(=O)C4CCN(c5ccc(C#N)c(C(F)(F)F)c5)CC4)nc3)CC2)CCN1CC1CCN(c2ccc3c(c2)C(=O)N(C2CCC(=O)NC2=O)C3=O)CC1]

Example 25 was synthesized in a similar way to the synthesis methods of Examples 1 and 6, using tert-butyl (R)-2-methylpiperazine-1-carboxylate instead of tert-butyl piperazine-1-carboxylate.

Example 26: 1-(4-cyano-3-(trifluoromethyl)phenyl)-N-(5-(4-(((3R)-4-((1-(2-(2,6-dioxopiperidin-3-yl)-1,3-dioxoisoindolin-5-yl)azetidin-3-yl)methyl)-3-methylpiperazin-1-yl)methyl)piperidin-1-yl)pyridin-2-yl)piperidine-4-carboxamide

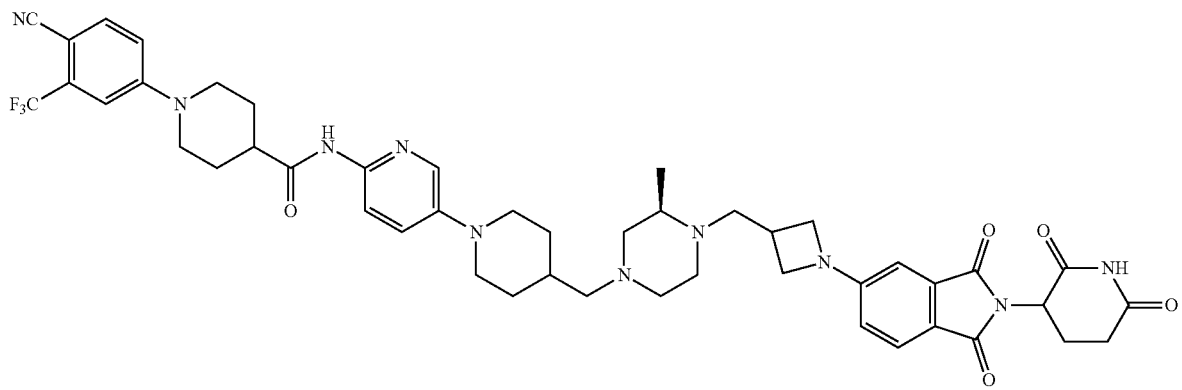 [SMILES: C[C@@H]1CN(CC2CCN(c3ccc(NC(=O)C4CCN(c5ccc(C#N)c(C(F)(F)F)c5)CC4)nc3)CC2)CCN1CC1CN(c2ccc3c(c2)C(=O)N(C2CCC(=O)NC2=O)C3=O)C1]

Example 26 was synthesized in a similar way to the synthesis methods of Examples 1 and 6, using tert-butyl (R)-2-methylpiperazine-1-carboxylate and 1-(2-(2,6-dioxopiperidin-3-yl)-1,3-dioxoisoindolin-5-yl)azetidine-3-carbaldehyde (Intermediate 3-3), respectively, instead of tert-butyl piperazine-1-carboxylate and 1-(2-(2,6-dioxopiperidin-3-yl)-1,3-dioxoisoindolin-5-yl)piperidine-4-carbaldehyde (Intermediate 3-1).

Example 27: 1-(4-cyano-3-(trifluoromethyl)phenyl)-N-(5-(3-((4-((1-(2-(2,6-dioxopiperidin-3-yl)-1,3-dioxoisoindolin-5-yl)piperidin-4-yl)methyl)piperazin-1-yl)methyl)azetidin-1-yl)pyridin-2-yl)piperidine-4-carboxamide

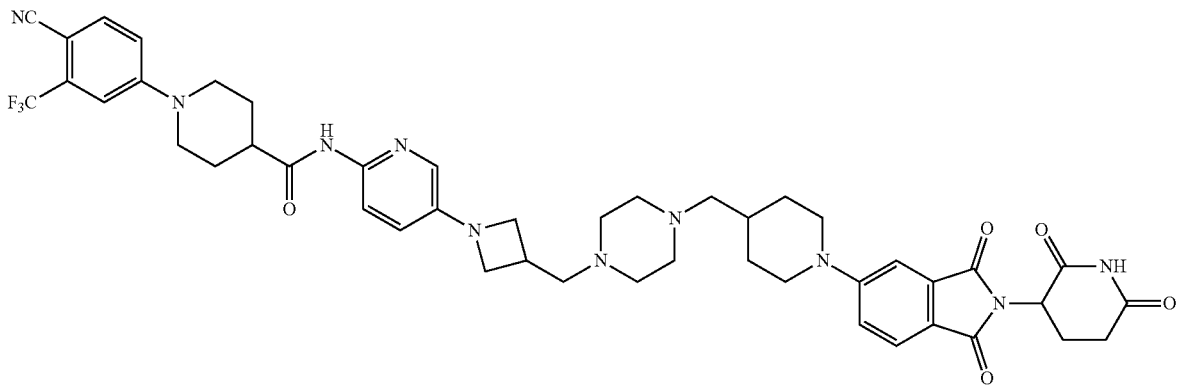 [SMILES: N#Cc1ccc(N2CCC(C(=O)Nc3ccc(N4CC(CN5CCN(CC6CCN(c7ccc8c(c7)C(=O)N(C7CCC(=O)NC7=O)C8=O)CC6)CC5)C4)cn3)CC2)cc1C(F)(F)F]

Example 27 was synthesized in a similar way to the synthesis methods of Examples 1 and 6, using azetidin-3-ylmethanol instead of piperidin-4-ylmethanol.

Example 28: 1-(4-cyano-3-(trifluoromethyl)phenyl)-N-(5-(3-((4-(((3R)-1-(2-(2,6-dioxopiperidin-3-yl)-1,3-dioxoisoindolin-5-yl)pyrrolidin-3-yl)methyl)piperazin-1-yl)methyl)azetidin-1-yl)pyridin-2-yl)piperidine-4-carboxamide

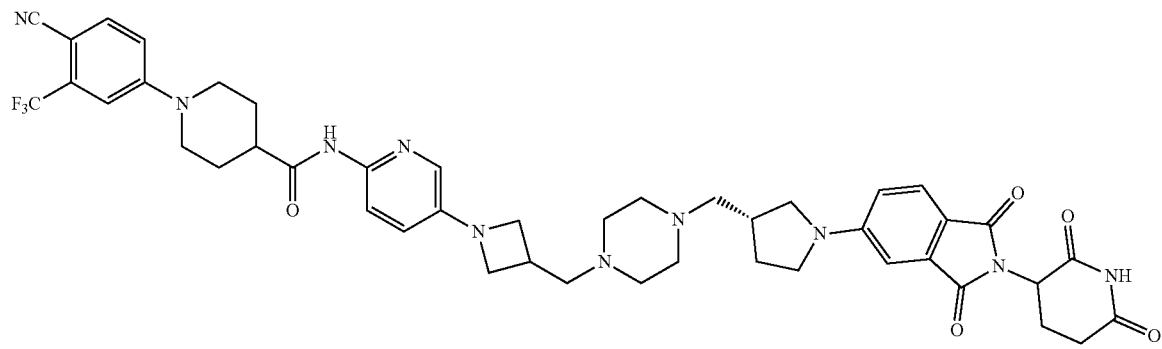 [SMILES: N#Cc1ccc(N2CCC(C(=O)Nc3ccc(N4CC(CN5CCN(C[C@H]6CCN(c7ccc8c(c7)C(=O)N(C7CCC(=O)NC7=O)C8=O)C6)CC5)C4)cn3)CC2)cc1C(F)(F)F]

Example 28 was synthesized in a similar way to the synthesis methods of Examples 1 and 6, using azetidin-3-ylmethanol and (3S)-1-(2-(2,6-dioxopiperidin-3-yl)-1,3-dioxoisoindolin-5-yl)pyrrolidine-3-carbaldehyde (Intermediate 3-4), respectively, instead of piperidin-4-ylmethanol and 1-(2-(2,6-dioxopiperidin-3-yl)-1,3-dioxoisoindolin-5-yl)piperidine-4-carbaldehyde (Intermediate 3-1).

Example 29: 1-(4-cyano-3-(trifluoromethyl)phenyl)-
N-(5-(3-((4-(((3S)-1-(2-(2,6-dioxopiperidin-3-yl)-1,
3-dioxoisoindolin-5-yl)pyrrolidin-3-yl)methyl)piper-
azin-1-yl)methyl)azetidin-1-yl)pyridin-2-yl)
piperidine-4-carboxamide

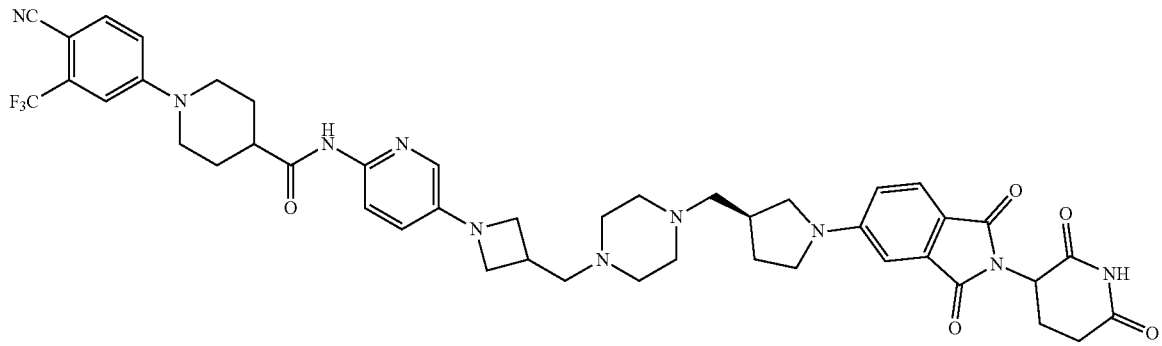 [SMILES: N#Cc1ccc(N2CCC(C(=O)Nc3ccc(N4CC(CN5CCN(C[C@@H]6CCN(c7ccc8c(c7)C(=O)N(C7CCC(=O)NC7=O)C8=O)C6)CC5)C4)cn3)CC2)cc1C(F)(F)F]

Example 29 was synthesized in a similar way to the synthesis methods of Examples 1and 6, using azetidin-3-ylmethanol and (3R)-1-(2-(2,6-dioxopiperidin-3-yl)-1,3-dioxoisoindolin-5-yl)pyrrolidine-3-carbaldehyde (Intermediate 3-5), respectively, instead of piperidin-4-ylmethanol and 1-(2-(2,6-dioxopiperidin-3-yl)-1,3-dioxoisoindolin-5-yl)piperidine-4-carbaldehyde (Intermediate 3-1).

Example 30: 1-(4-cyano-3-(trifluoromethyl)phenyl)-
N-(5-(3-((4-((1-(2-(2,6-dioxopiperidin-3-yl)-1,3-
dioxoisoindolin-5-yl)azetidin-3-yl)methyl)piperazin-
1-yl)methyl)azetidin-1-yl)pyridin-2-yl)piperidine-4-
carboxamide

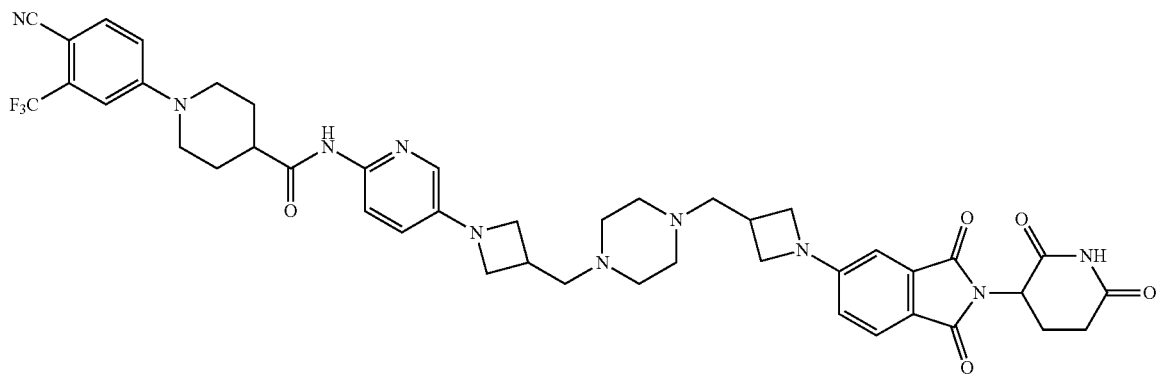 [SMILES: N#Cc1ccc(N2CCC(C(=O)Nc3ccc(N4CC(CN5CCN(CC6CN(c7ccc8c(c7)C(=O)N(C7CCC(=O)NC7=O)C8=O)C6)CC5)C4)cn3)CC2)cc1C(F)(F)F]

Example 30 was synthesized in a similar way to the synthesis methods of Examples 1and 6, using azetidin-3-ylmethanol and 1-(2-(2,6-dioxopiperidin-3-yl)-1,3-dioxoisoindolin-5-yl)azetidine-3-carbaldehyde (Intermediate 3-3), respectively, instead of piperidin-4-ylmethanol and 1-(2-(2,6-dioxopiperidin-3-yl)-1,3-dioxoisoindolin-5-yl)piperidine-4-carbaldehyde (Intermediate 3-1).

Example 31: 1-(4-cyano-3-(trifluoromethyl)phenyl)-
N-(5-(3-(((2R)-4-((1-(2-(2,6-dioxopiperidin-3-yl)-1,
3-dioxoisoindolin-5-yl)azetidin-3-yl)methyl)-2-
methylpiperazin-1-yl)methyl)azetidin-1-yl)pyridin-
2-yl)piperidine-4-carboxamide

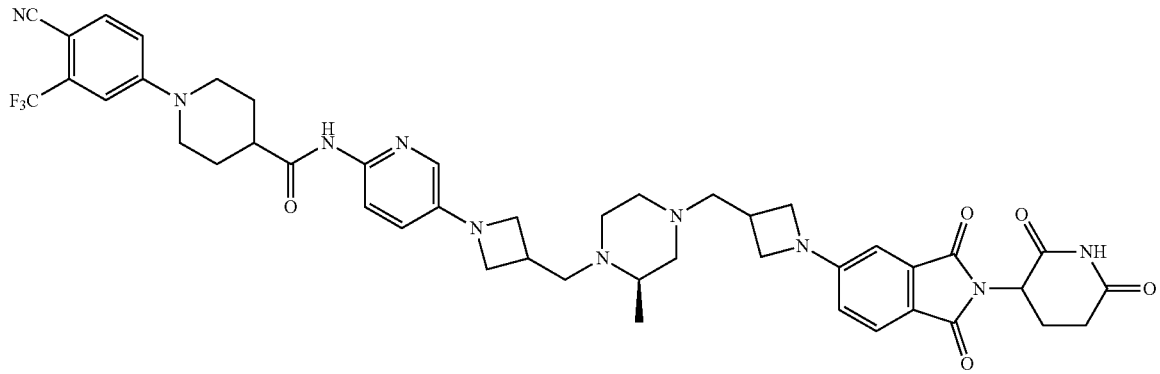 [SMILES: C[C@@H]1CN(CC2CN(c3ccc4c(c3)C(=O)N(C3CCC(=O)NC3=O)C4=O)C2)CCN1CC1CN(c2ccc(NC(=O)C3CCN(c4ccc(C#N)c(C(F)(F)F)c4)CC3)nc2)C1]

Example 31 was synthesized in a similar way to the synthesis methods of Examples 1 and 6, using azetidin-3-ylmethanol, tert-butyl (R)-3-methylpiperazine-1-carboxylate, and 1-(2-(2,6-dioxopiperidin-3-yl)-1,3-dioxoisoindolin-5-yl)azetidine-3-carbaldehyde (Intermediate 3-3), respectively, instead of piperidin-4-ylmethanol, tert-butyl piperazine-1-carboxylate, and 1-(2-(2,6-dioxopiperidin-3-yl)-1,3-dioxoisoindolin-5-yl)piperidine-4-carbaldehyde (Intermediate 3-1).

Example 32: 1-(4-cyano-3-(trifluoromethyl)phenyl)-
N-(5-(3-(((3R)-4-((1-(2-(2,6-dioxopiperidin-3-yl)-1,
3-dioxoisoindolin-5-yl)azetidin-3-yl)methyl)-3-
methylpiperazin-1-yl)methyl)azetidin-1-yl)pyridin-
2-yl)piperidine-4-carboxamide

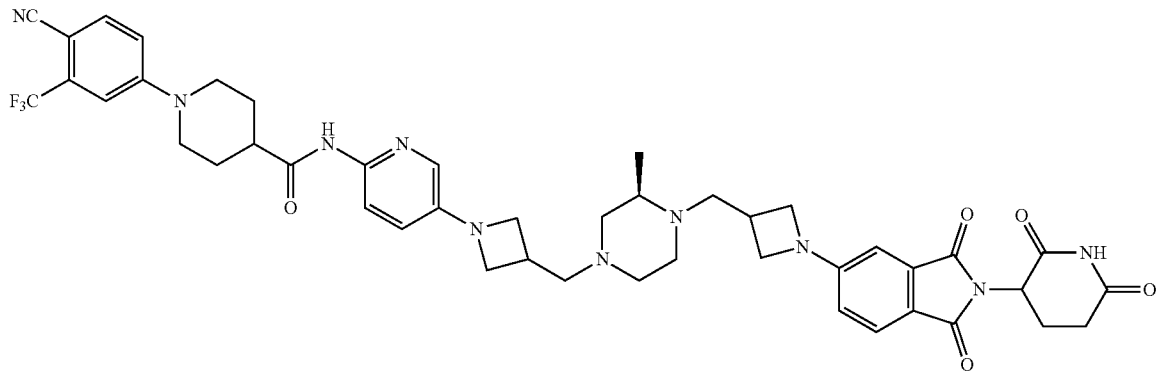 [SMILES: C[C@@H]1CN(CC2CN(c3ccc(NC(=O)C4CCN(c5ccc(C#N)c(C(F)(F)F)c5)CC4)nc3)C2)CCN1CC1CN(c2ccc3c(c2)C(=O)N(C2CCC(=O)NC2=O)C3=O)C1]

Example 32 was synthesized in a similar way to the synthesis methods of Examples 1 and 6, using azetidin-3-ylmethanol, tert-butyl (R)-2-methylpiperazine-1-carboxylate, and 1-(2-(2,6-dioxopiperidin-3-yl)-1,3-dioxoisoindolin-5-yl)azetidine-3-carbaldehyde (Intermediate 3-3), respectively, instead of piperidin-4-ylmethanol, tert-butyl piperazine-1-carboxylate, and 1-(2-(2,6-dioxopiperidin-3-yl)-1,3-dioxoisoindolin-5-yl)piperidine-4-carbaldehyde (Intermediate 3-1).

Example 33: 1-(4-cyano-3-(trifluoromethyl)phenyl)-N-(5-(4-((4-(1-(6-(2,6-dioxopiperidin-3-yl)-5-oxo-6,7-dihydro-5H-pyrrolo[3,4-b]pyridin-2-yl)azetidin-3-yl)piperazin-1-yl)methyl)piperidin-1-yl)pyridin-2-yl)piperidine-4-carboxamide

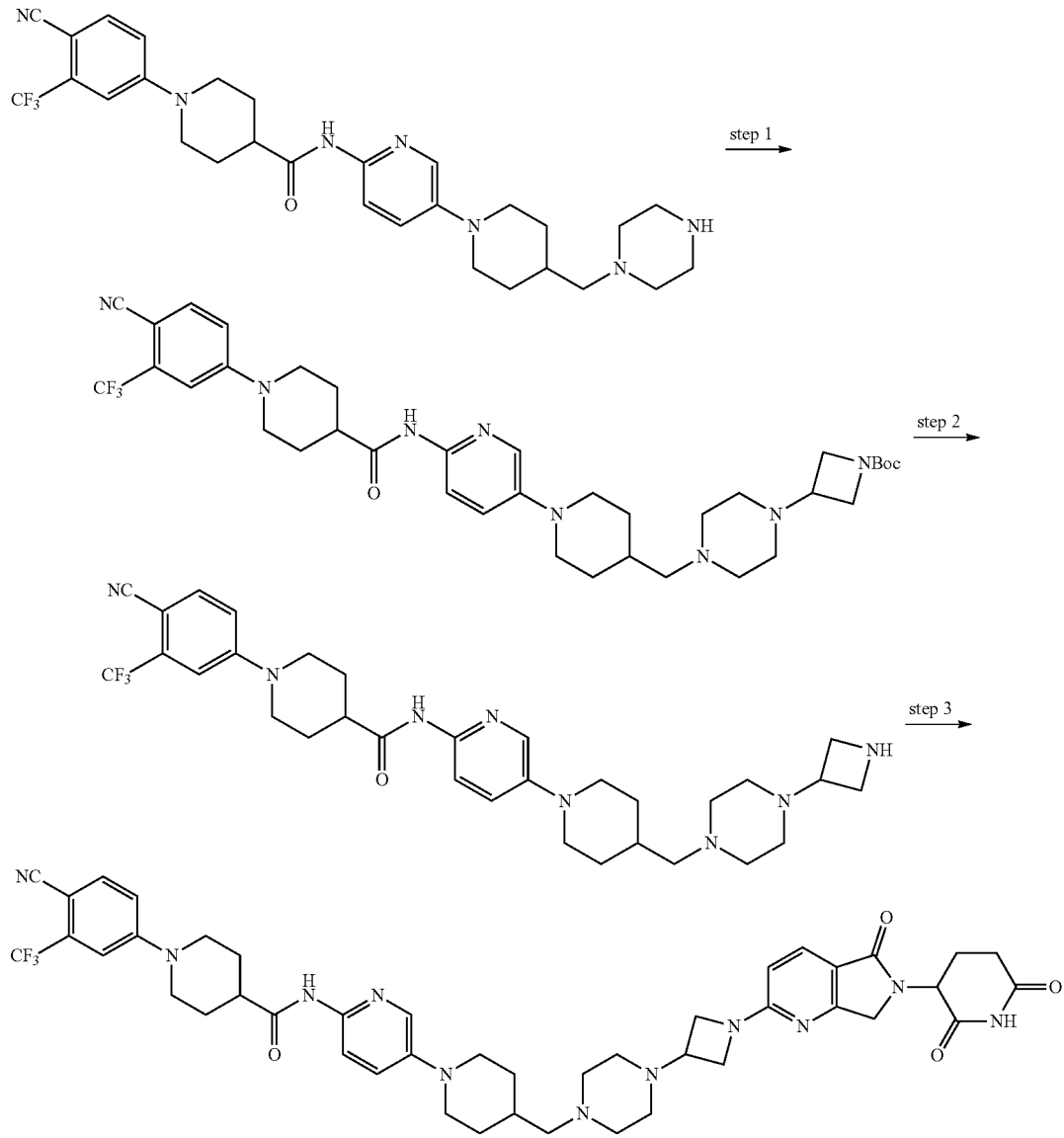 [SMILES: N#Cc1ccc(N2CCC(C(=O)Nc3ccc(N4CCC(CN5CCNCC5)CC4)cn3)CC2)cc1C(F)(F)F ; CC(C)(C)OC(=O)N1CC(N2CCN(CC3CCN(c4ccc(NC(=O)C5CCN(c6ccc(C#N)c(C(F)(F)F)c6)CC5)nc4)CC3)CC2)C1 ; N#Cc1ccc(N2CCC(C(=O)Nc3ccc(N4CCC(CN5CCN(C6CNC6)CC5)CC4)cn3)CC2)cc1C(F)(F)F ; N#Cc1ccc(N2CCC(C(=O)Nc3ccc(N4CCC(CN5CCN(C6CN(c7ccc8c(n7)CN(C7CCC(=O)NC7=O)C8=O)C6)CC5)CC4)cn3)CC2)cc1C(F)(F)F]

Step 1: Synthesis of tert-butyl 3-(4-((1-(6-(1-(4-cyano-3-(trifluoromethyl)phenyl)piperidine-4-carboxamido)pyridin-3-yl)piperidin-4-yl)methyl)piperazin-1-yl)azetidine-1-carboxylate 1-(4-cyano-3-(trifluoromethyl)phenyl)-N-(5-(4-(piperazin-1-ylmethyl)piperidin-1-yl)pyridin-2-yl)piperidine-4-carboxamide (200 mg, 0.360 mmol), and tert-butyl 3-oxoazetidine-1-carboxylate (74 mg, 0.432 mmol) were suspended in ACN (20.0 ml), to which sodium triacetoxyborohydride (229 mg, 1.08 mmol) was added, and the mixture was stirred at room temperature for 16 hours. NaHCO$_3$ aqueous solution (15 ml) was added to the reaction mixture, followed by extraction with EtOAc (25 ml×2), and the organic layer was dried over anhydrous sodium sulfate, filtered, and concentrated under reduced pressure. The resulting residue was subjected to MPLC (10% MeOH/DCM) to give 129 mg (50%) of a white solid. m/z 711.35 [M+H]$^+$.

Step 2: Synthesis of N-(5-(4-((4-(azetidin-3-yl)piperazin-1-yl)methyl)piperidin-1-yl)pyridin-2-yl)-1-(4-cyano-3-(trifluoromethyl)phenyl)piperidine-4-carboxamide After suspending tert-butyl 3-(4-((1-(6-(1-(4-cyano-3-(trifluoromethyl)phenyl)piperidine-4-carboxamido)pyridin-3-yl)piperidin-4-yl)methyl)piperazin-1-yl)azetidine-1-carboxylate (129 mg, 0.181 mmol) in DCM (1.00 ml), 4 M HCl in dioxane (0.23 mL, 0.905 mmol) was added and stirred at room temperature for 1 hour. The reaction solution was concentrated, NaHCO$_3$ aqueous solution (15 ml) was added, extracted with DCM (25 ml×2), and the organic layer was dried over anhydrous sodium sulfate, filtered, and concentrated under reduced pressure. 109 mg (99%) of a white solid was obtained. m/z 611.44 [M+H]$^+$.

Step 3: Synthesis of 1-(4-cyano-3-(trifluoromethyl) phenyl)-N-(5-(4-((4-(1-(6-(2,6-dioxopiperidin-3-yl)-5-oxo-6,7-dihydro-5H-pyrrolo[3,4-b]pyridin-2-yl) azetidin-3-yl)piperazin-1-yl)methyl)piperidin-1-yl) pyridin-2-yl)piperidine-4-carboxamide N-(5-(4-((4-(azetidin-3-yl)piperazin-1-yl)methyl)piperidin-1-yl)pyridin-2-yl)-1-(4-cyano-3-(trifluoromethyl)phenyl)piperidine-4-carboxamide (30 mg, 0.046 mmol), 3-(2-chloro-5-oxo-5,7-dihydro-6H-pyrrolo[3,4-b]pyridin-6-yl) piperidine-2,6-dione (Intermediate 2-6, 16 mg, 0.056 mmol), DIPEA (0.02 mL, 0.092 mmol) were suspended in DMSO (1.0 ml) and stirred at 90° C. for 16 hours. After adding distilled water (15 ml) to the reaction solution, extraction was performed with EtOAc (25 ml×2), and the organic layer was dried over anhydrous sodium sulfate, filtered, and concentrated under reduced pressure. The obtained residue was subjected to MPLC (10% MeOH/DCM) to give 18 mg (45%) of an off-white solid.

Example 34: 1-(4-cyano-3-(trifluoromethyl)phenyl)-N-(5-(4-((4-((1-(6-(2,6-dioxopiperidin-3-yl)-5-oxo-6,7-dihydro-5H-pyrrolo[3,4-b]pyridin-2-yl)piperidin-4-yl)methyl)piperazin-1-yl)methyl)piperidin-1-yl)pyridin-2-yl)piperidine-4-carboxamide

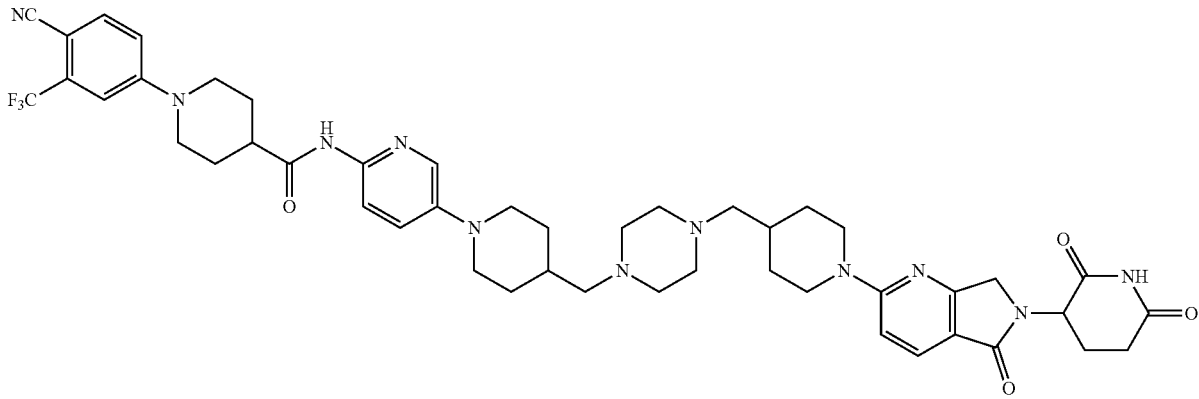 [SMILES: N#Cc1ccc(N2CCC(C(=O)Nc3ccc(N4CCC(CN5CCN(CC6CCN(c7ccc8c(n7)CN(C7CCC(=O)NC7=O)C8=O)CC6)CC5)CC4)cn3)CC2)cc1C(F)(F)F]

Example 34 was synthesized in a similar way to the synthesis method of Example 33, using tert-butyl 4-formylpiperidine-1-carboxylate instead of tert-butyl 3-oxoazetidine-1-carboxylate.

Example 35: 1-(4-cyano-3-(trifluoromethyl)phenyl)-N-(5-(4-((4-(1-(2-(2,6-dioxopiperidin-3-yl)-1,3-dioxoisoindolin-5-yl)azetidin-3-yl)piperazin-1-yl) methyl)piperidin-1-yl)pyridin-2-yl)piperidine-4-carboxamide

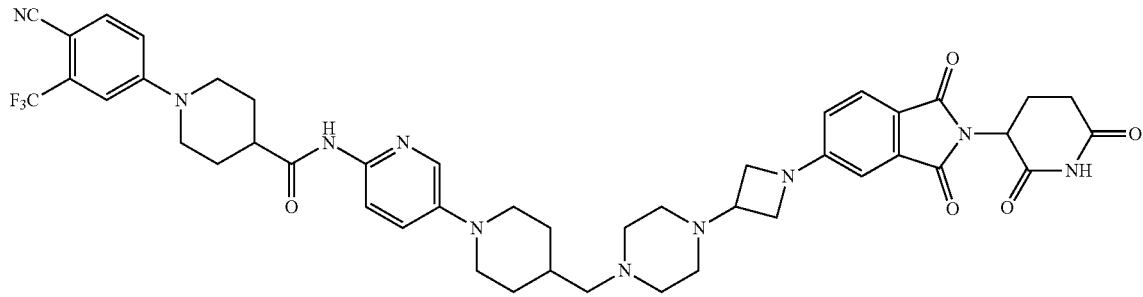 [SMILES: N#Cc1ccc(N2CCC(C(=O)Nc3ccc(N4CCC(CN5CCN(C6CN(c7ccc8c(c7)C(=O)N(C7CCC(=O)NC7=O)C8=O)C6)CC5)CC4)cn3)CC2)cc1C(F)(F)F]

Example 35 was synthesized in a similar way to the synthesis method of Example 33, using 2-(2,6-dioxopiperidin-3-yl)-5-fluoroisoindoline-1,3-dione (Intermediate 2-1) instead of 3-(2-chloro-5-oxo-5,7-dihydro-6H-pyrrolo[3,4-b]pyridin-6-yl)piperidine-2,6-dione (Intermediate 2-6).

Example 36: 1-(4-cyano-3-(trifluoromethyl)phenyl)-N-(5-(3-((4-(1-(2-(2,6-dioxopiperidin-3-yl)-1,3-dioxoisoindolin-5-yl)azetidin-3-yl)piperazin-1-yl)methyl)azetidin-1-yl)pyridin-2-yl)piperidine-4-carboxamide

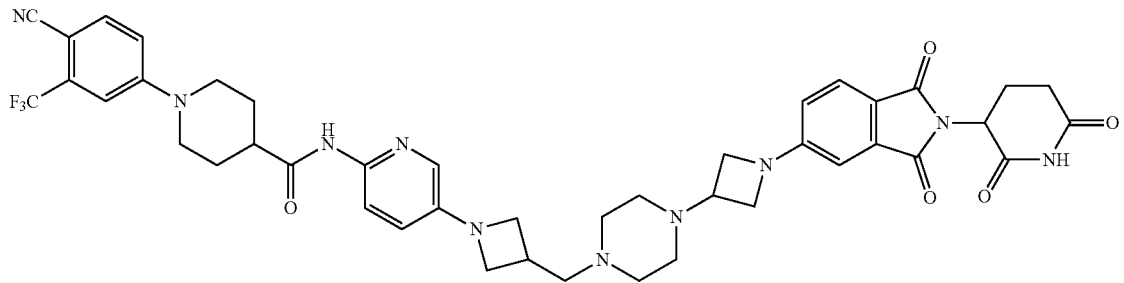 [SMILES: N#Cc1ccc(N2CCC(C(=O)Nc3ccc(N4CC(CN5CCN(C6CN(c7ccc8c(c7)C(=O)N(C7CCC(=O)NC7=O)C8=O)C6)CC5)C4)cn3)CC2)cc1C(F)(F)F]

Example 36 was synthesized in a similar way to the synthesis methods of Examples 1 and 33, using azetidin-3-ylmethanol and 2-(2,6-dioxopiperidin-3-yl)-5-fluoroisoindoline-1,3-dione (Intermediate 2-1), respectively, instead of piperidin-4-ylmethanol and 3-(2-chloro-5-oxo-5,7-dihydro-6H-pyrrolo[3,4-b]pyridin-6-yl)piperidine-2,6-dione (Intermediate 2-6).

Example 37: 1-(4-cyano-3-(trifluoromethyl)phenyl)-N-(5-(4-((4-(((3S)-1-(6-(2,6-dioxopiperidin-3-yl)-5-oxo-6,7-dihydro-5H-pyrrolo[3,4-b]pyridin-2-yl)pyrrolidin-3-yl)methyl)piperazin-1-yl)methyl)piperidin-1-yl)pyridin-2-yl)piperidine-4-carboxamide

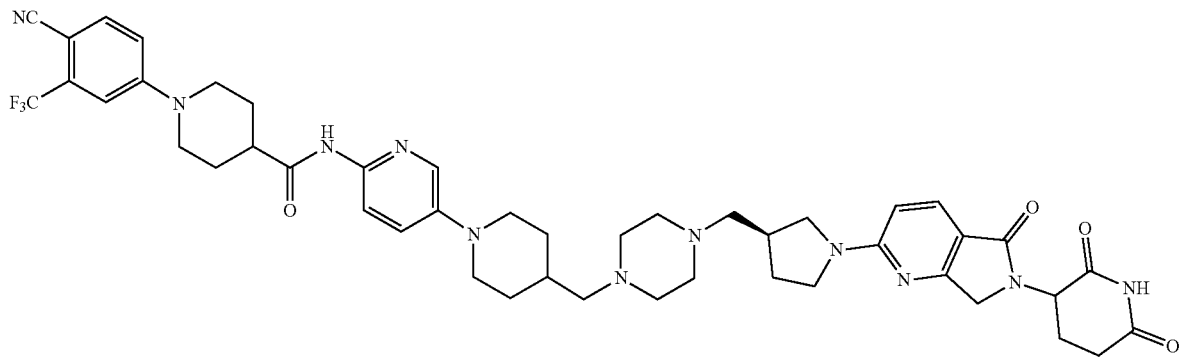 [SMILES: N#Cc1ccc(N2CCC(C(=O)Nc3ccc(N4CCC(CN5CCN(C[C@@H]6CCN(c7ccc8c(n7)CN(C7CCC(=O)NC7=O)C8=O)C6)CC5)CC4)cn3)CC2)cc1C(F)(F)F]

Example 37 was synthesized in a similar way to the synthesis method of Example 33, using tert-butyl (R)-3-formylpyrrolidine-1-carboxylate instead of tert-butyl 3-oxoazetidine-1-carboxylate.

Example 38: 1-(4-cyano-3-(trifluoromethyl)phenyl)-N-(5-(4-((4-(((3S)-1-(2-(2,6-dioxopiperidin-3-yl)-6-fluoro-1,3-dioxoisoindolin-5-yl)pyrrolidin-3-yl)methyl)piperazin-1-yl)methyl)piperidin-1-yl)pyridin-2-yl)piperidine-4-carboxamide

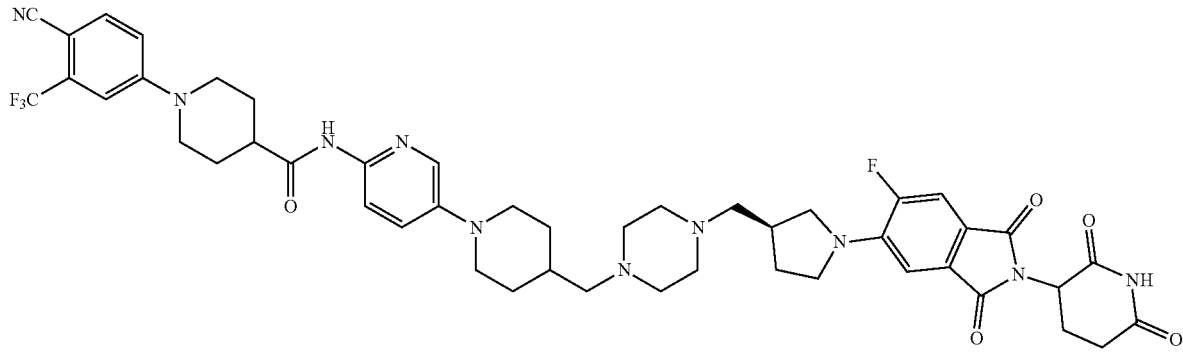 [SMILES: N#Cc1ccc(N2CCC(C(=O)Nc3ccc(N4CCC(CN5CCN(C[C@@H]6CCN(c7cc8c(cc7F)C(=O)N(C7CCC(=O)NC7=O)C8=O)C6)CC5)CC4)cn3)CC2)cc1C(F)(F)F]

Example 38 was synthesized in a similar way to the synthesis method of Example 33, using tert-butyl (R)-3-formylpyrrolidine-1-carboxylate and 2-(2,6-dioxopiperidin-3-yl)-5,6-difluoroisoindoline-1,3-dione (Intermediate 2-3), respectively, instead of tert-butyl 3-oxoazetidine-1-carboxylate and 3-(2-chloro-5-oxo-5,7-dihydro-6H-pyrrolo[3,4-b]pyridin-6-yl)piperidine-2,6-dione (Intermediate 2-6).

Example 39: 1-(4-cyano-3-(trifluoromethyl)phenyl)-N-(5-(4-((4-(((3R)-1-(6-(2,6-dioxopiperidin-3-yl)-5-oxo-6,7-dihydro-5H-pyrrolo[3,4-b]pyridin-2-yl)pyrrolidin-3-yl)methyl)piperazin-1-yl)methyl)piperidin-1-yl)pyridin-2-yl)piperidine-4-carboxamide

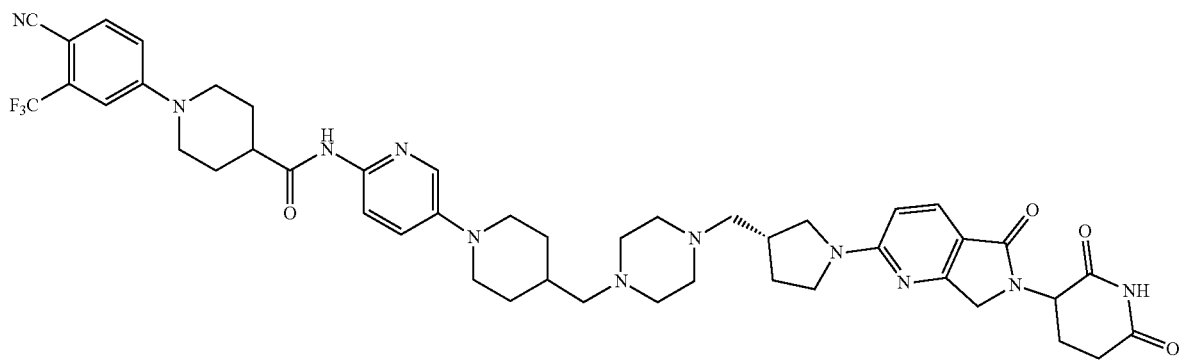 [SMILES: N#Cc1ccc(N2CCC(C(=O)Nc3ccc(N4CCC(CN5CCN(C[C@H]6CCN(c7ccc8c(n7)CN(C7CCC(=O)NC7=O)C8=O)C6)CC5)CC4)cn3)CC2)cc1C(F)(F)F]

Example 39 was synthesized in a similar way to the synthesis method of Example 33, using tert-butyl (S)-3-formylpyrrolidine-1-carboxylate instead of tert-butyl 3-oxoazetidine-1-carboxylate.

Example 40: 1-(4-cyano-3-(trifluoromethyl)phenyl)-N-(5-(4-(((3R)-4-(1-(2-(2,6-dioxopiperidin-3-yl)-1,3-dioxoisoindolin-5-yl)azetidin-3-yl)-3-methylpiperazin-1-yl)methyl)piperidin-1-yl)pyridin-2-yl)piperidine-4-carboxamide

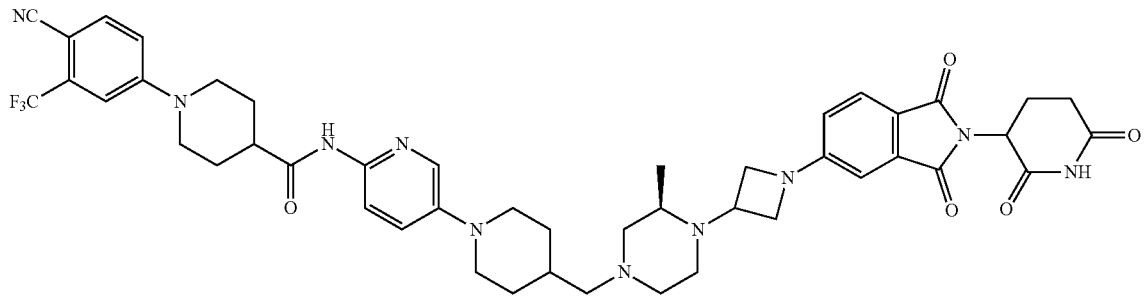 [SMILES: C[C@@H]1CN(CC2CCN(c3ccc(NC(=O)C4CCN(c5ccc(C#N)c(C(F)(F)F)c5)CC4)nc3)CC2)CCN1C1CN(c2ccc3c(c2)C(=O)N(C2CCC(=O)NC2=O)C3=O)C1]

Example 40 was synthesized in a similar way to the synthesis methods of Examples 1 and 33, using tert-butyl (R)-2-methylpiperazine-1-carboxylate and 2-(2,6-dioxopiperidin-3-yl)-5-fluoroisoindoline-1,3-dione (Intermediate 2-1), respectively, instead of tert-butyl piperazine-1-carboxylate and 3-(2-chloro-5-oxo-5,7-dihydro-6H-pyrrolo[3,4-b]pyridin-6-yl)piperidine-2,6-dione (Intermediate 2-6).

Example 41: 1-(4-cyano-3-(trifluoromethyl)phenyl)-N-(5-(4-(((2R)-4-(1-(2-(2,6-dioxopiperidin-3-yl)-1,3-dioxoisoindolin-5-yl)azetidin-3-yl)-2-methylpiperazin-1-yl)methyl)piperidin-1-yl)pyridin-2-yl)piperidine-4-carboxamide

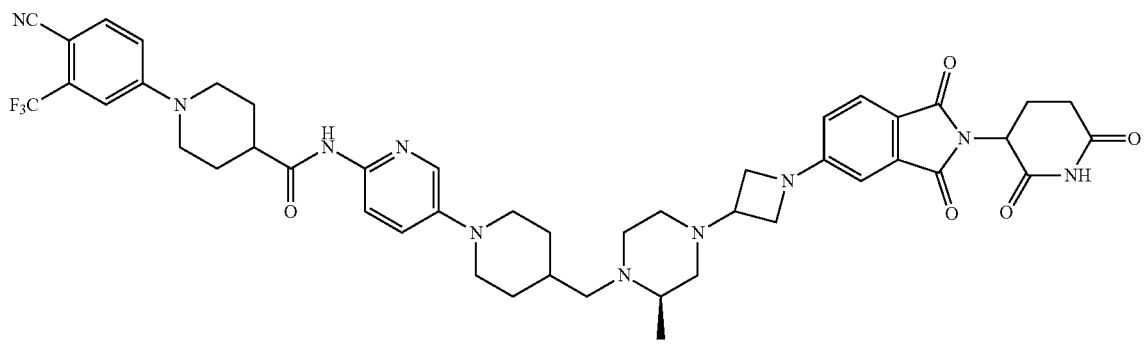 [SMILES: C[C@@H]1CN(C2CN(c3ccc4c(c3)C(=O)N(C3CCC(=O)NC3=O)C4=O)C2)CCN1CC1CCN(c2ccc(NC(=O)C3CCN(c4ccc(C#N)c(C(F)(F)F)c4)CC3)nc2)CC1]

Example 41 was synthesized in a similar way to the synthesis methods of Examples 1 and 33, using tert-butyl (R)-3-methylpiperazine-1-carboxylate and 2-(2,6-dioxopiperidin-3-yl)-5-fluoroisoindoline-1,3-dione (Intermediate 2-1), respectively, instead of tert-butyl piperazine-1-carboxylate and 3-(2-chloro-5-oxo-5,7-dihydro-6H-pyrrolo[3,4-b]pyridin-6-yl)piperidine-2,6-dione (Intermediate 2-6).

Example 42: 1-(4-cyano-3-(trifluoromethyl)phenyl)-N-(5-(4-(((2R)-4-(1-(2-(2,6-dioxopiperidin-3-yl)-1,3-dioxoisoindolin-5-yl)piperidin-4-yl)-2-methylpiperazin-1-yl)methyl)piperidin-1-yl)pyridin-2-yl)piperidine-4-carboxamide

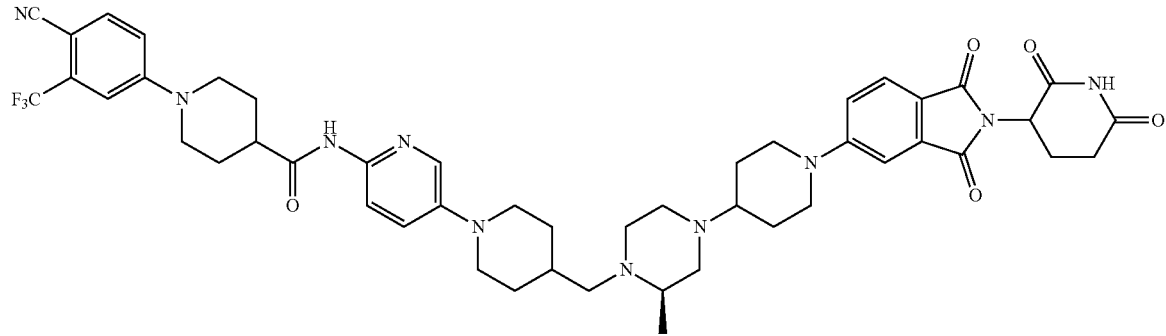 [SMILES: C[C@@H]1CN(C2CCN(c3ccc4c(c3)C(=O)N(C3CCC(=O)NC3=O)C4=O)CC2)CCN1CC1CCN(c2ccc(NC(=O)C3CCN(c4ccc(C#N)c(C(F)(F)F)c4)CC3)nc2)CC1]

Example 42 was synthesized in a similar way to the synthesis methods of Examples 1 and 33, using tert-butyl (R)-3-methylpiperazine-1-carboxylate, tert-butyl 4-oxopiperidine-1-carboxylate, and 2-(2,6-dioxopiperidin-3-yl)-5-fluoroisoindoline-1,3-dione (Intermediate 2-1), respectively, instead of tert-butyl piperazine-1-carboxylate, tert-butyl 3-oxoazetidine-1-carboxylate, and 3-(2-chloro-5-oxo-5,7-dihydro-6H-pyrrolo[3,4-b]pyridin-6-yl)piperidine-2,6-dione (Intermediate 2-6).

Example 43: 1-(4-cyano-3-(trifluoromethyl)phenyl)-N-(5-(4-(((2R)-4-(1-(6-(2,6-dioxopiperidin-3-yl)-5-oxo-6,7-dihydro-5H-pyrrolo[3,4-b]pyridin-2-yl)piperidin-4-yl)-2-methylpiperazin-1-yl)methyl)piperidin-1-yl)pyridin-2-yl)piperidine-4-carboxamide

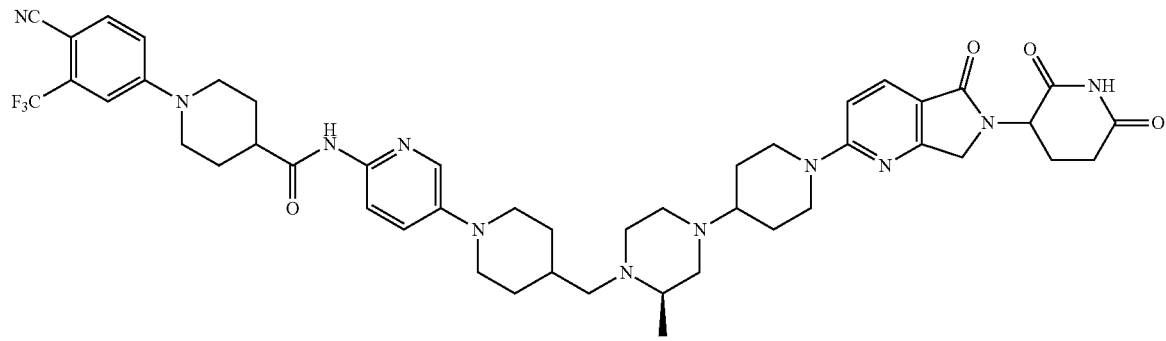 [SMILES: C[C@@H]1CN(C2CCN(c3ccc4c(n3)CN(C3CCC(=O)NC3=O)C4=O)CC2)CCN1CC1CCN(c2ccc(NC(=O)C3CCN(c4ccc(C#N)c(C(F)(F)F)c4)CC3)nc2)CC1]

Example 43 was synthesized in a similar way to the synthesis methods of Examples 1 and 33, using tert-butyl (R)-3-methylpiperazine-1-carboxylate and tert-butyl 4-oxopiperidine-1-carboxylate, respectively, instead of tert-butyl piperazine-1-carboxylate and tert-butyl 3-oxoazetidine-1-carboxylate.

Example 44: 1-(4-cyano-3-(trifluoromethyl)phenyl)-N-(5-(4-(((2R)-4-((1-(6-(2,6-dioxopiperidin-3-yl)-5-oxo-6,7-dihydro-5H-pyrrolo[3,4-b]pyridin-2-yl)piperidin-4-yl)methyl)-2-methylpiperazin-1-yl)methyl)piperidin-1-yl)pyridin-2-yl)piperidine-4-carboxamide

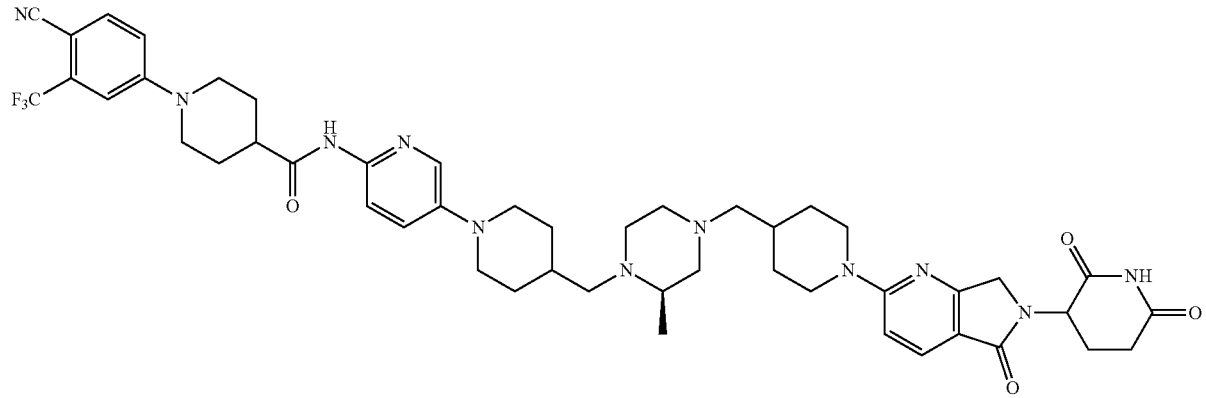 [SMILES: C[C@@H]1CN(CC2CCN(c3ccc4c(n3)CN(C3CCC(=O)NC3=O)C4=O)CC2)CCN1CC1CCN(c2ccc(NC(=O)C3CCN(c4ccc(C#N)c(C(F)(F)F)c4)CC3)nc2)CC1]

Example 44 was synthesized in a similar way to the synthesis methods of Examples 1 and 33, using tert-butyl (R)-3-methylpiperazine-1-carboxylate and tert-butyl 4-formylpiperidine-1-carboxylate, respectively, instead of tert-butyl piperazine-1-carboxylate and tert-butyl 4-oxopiperidine-1-carboxylate.

Example 45: 1-(4-cyano-3-(trifluoromethyl)phenyl)-N-(5-(4-(((2S)-4-(1-(6-(2,6-dioxopiperidin-3-yl)-5-oxo-6,7-dihydro-5H-pyrrolo[3,4-b]pyridin-2-yl)piperidin-4-yl)-2-methylpiperazin-1-yl)methyl)piperidin-1-yl)pyridin-2-yl)piperidine-4-carboxamide

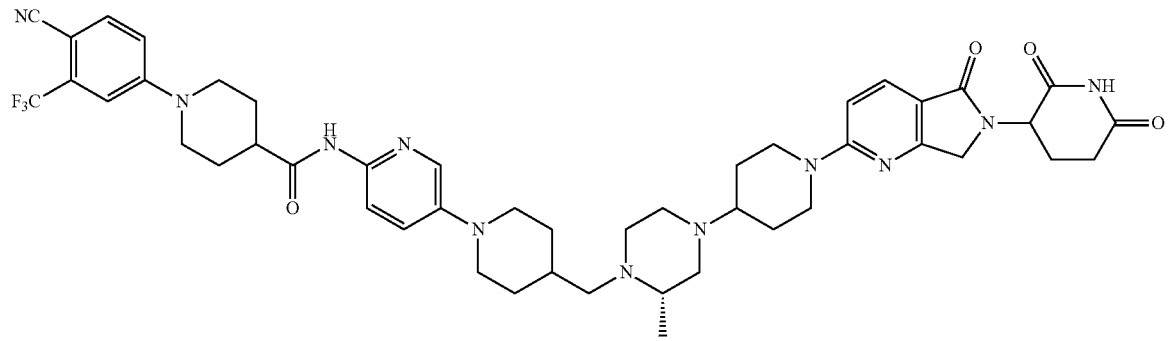 [SMILES: C[C@H]1CN(C2CCN(c3ccc4c(n3)CN(C3CCC(=O)NC3=O)C4=O)CC2)CCN1CC1CCN(c2ccc(NC(=O)C3CCN(c4ccc(C#N)c(C(F)(F)F)c4)CC3)nc2)CC1]

Example 45 was synthesized in a similar way to the synthesis methods of Examples 1 and 33, using tert-butyl (S)-3-methylpiperazine-1-carboxylate and tert-butyl 4-oxopiperidine-1-carboxylate, respectively, instead of tert-butyl piperazine-1-carboxylate and tert-butyl 3-oxoazetidine-1-carboxylate.

Example 46: 1-(4-cyano-3-(trifluoromethyl)phenyl)-N-(5-(4-(((2S)-4-((1-(6-(2,6-dioxopiperidin-3-yl)-5-oxo-6,7-dihydro-5H-pyrrolo[3,4-b]pyridin-2-yl)piperidin-4-yl)methyl)-2-methylpiperazin-1-yl)methyl)piperidin-1-yl)pyridin-2-yl)piperidine-4-carboxamide

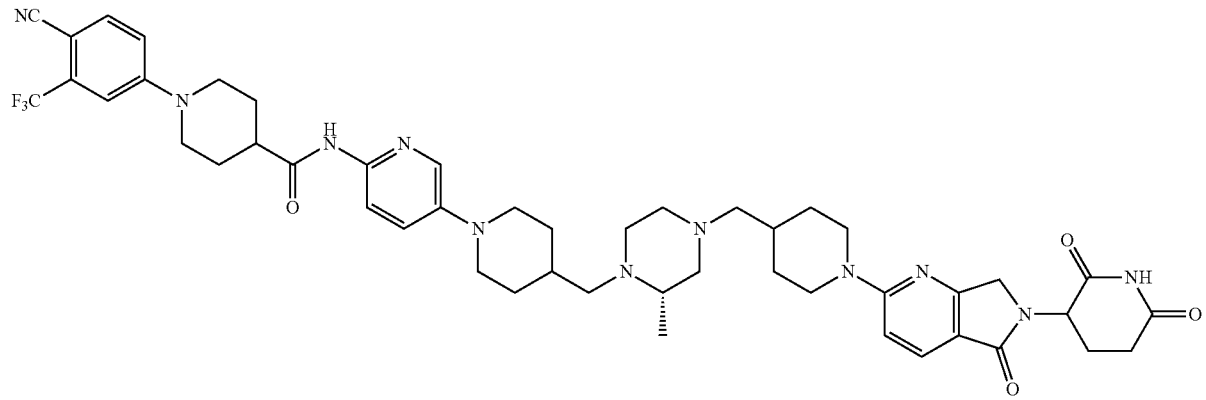 [SMILES: C[C@H]1CN(CC2CCN(c3ccc4c(n3)CN(C3CCC(=O)NC3=O)C4=O)CC2)CCN1CC1CCN(c2ccc(NC(=O)C3CCN(c4ccc(C#N)c(C(F)(F)F)c4)CC3)nc2)CC1]

Example 46 was synthesized in a similar way to the synthesis methods of Examples 1 and 33, using tert-butyl (S)-3-methylpiperazine-1-carboxylate and tert-butyl 4-formylpiperidine-1-carboxylate, respectively, instead of tert-butyl piperazine-1-carboxylate and tert-butyl 3-oxoazetidine-1-carboxylate.

Example 47: 1-(4-cyano-3-(trifluoromethyl)phenyl)-N-(5-(4-(((3R)-4-((1-(6-(2,6-dioxopiperidin-3-yl)-5-oxo-6,7-dihydro-5H-pyrrolo[3,4-b]pyridin-2-yl)piperidin-4-yl)methyl)-3-methylpiperazin-1-yl)methyl)piperidin-1-yl)pyridin-2-yl)piperidine-4-carboxamide

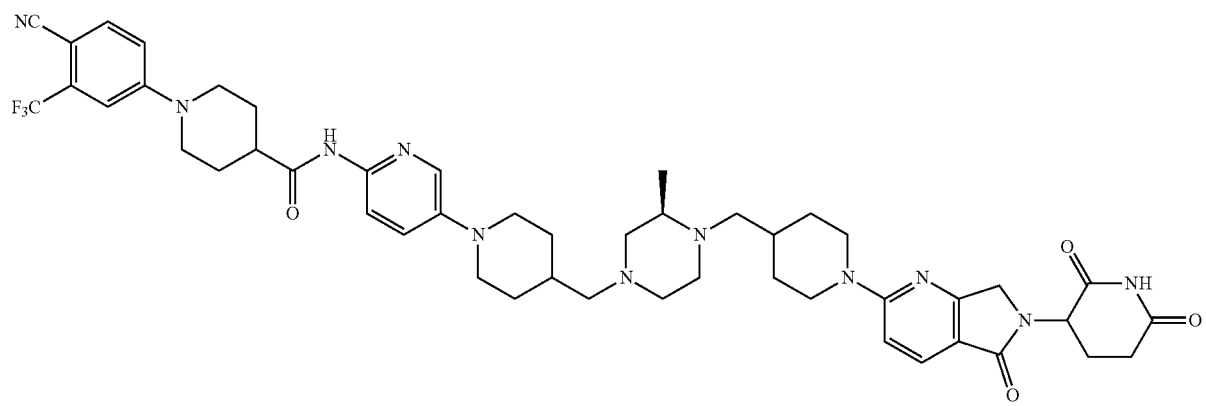 [SMILES: C[C@@H]1CN(CC2CCN(c3ccc(NC(=O)C4CCN(c5ccc(C#N)c(C(F)(F)F)c5)CC4)nc3)CC2)CCN1CC1CCN(c2ccc3c(n2)CN(C2CCC(=O)NC2=O)C3=O)CC1]

Example 47 was synthesized in a similar way to the synthesis methods of Examples 1 and 33, using tert-butyl (R)-2-methylpiperazine-1-carboxylate and tert-butyl 4-formylpiperidine-1-carboxylate, respectively, instead of tert-butyl piperazine-1-carboxylate and tert-butyl 3-oxoazetidine-1-carboxylate.

Example 48: 1-(4-cyano-3-(trifluoromethyl)phenyl)-N-(5-(4-(((3S)-4-((1-(6-(2,6-dioxopiperidin-3-yl)-5-oxo-6,7-dihydro-5H-pyrrolo[3,4-b]pyridin-2-yl)piperidin-4-yl)methyl)-3-methylpiperazin-1-yl)methyl)piperidin-1-yl)pyridin-2-yl)piperidine-4-carboxamide

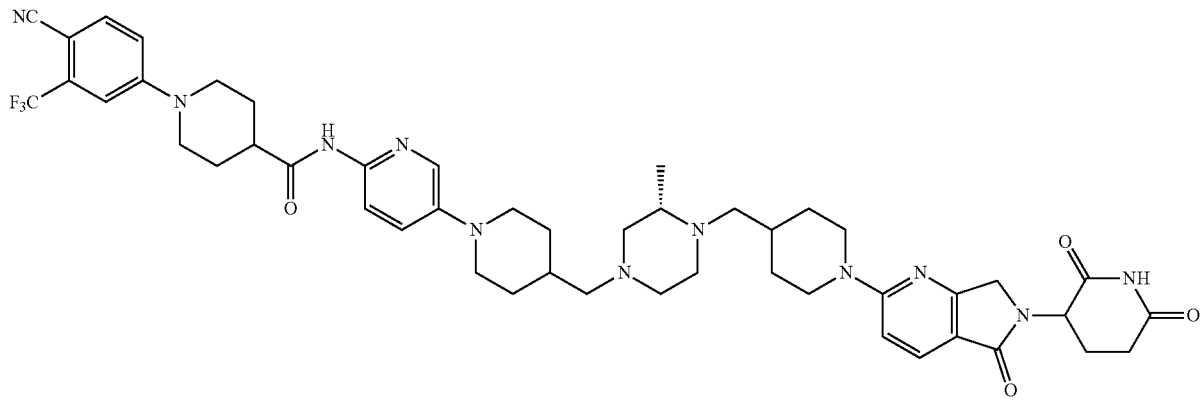 [SMILES: C[C@H]1CN(CC2CCN(c3ccc(NC(=O)C4CCN(c5ccc(C#N)c(C(F)(F)F)c5)CC4)nc3)CC2)CCN1CC1CCN(c2ccc3c(n2)CN(C2CCC(=O)NC2=O)C3=O)CC1]

Example 48 was synthesized in a similar way to the synthesis methods of Examples 1 and 33, using tert-butyl (S)-2-methylpiperazine-1-carboxylate and tert-butyl 4-formylpiperidine-1-carboxylate, respectively, instead of tert-butyl piperazine-1-carboxylate and tert-butyl 3-oxoazetidine-1-carboxylate.

Example 49: 1-(4-cyano-3-(trifluoromethyl)phenyl)-N-(5-(4-((7-(2-(2,6-dioxopiperidin-3-yl)-1,3-dioxoisoindolin-5-yl)-2,7-diazaspiro[3.5]nonan-2-yl)methyl)piperidin-1-yl)pyridin-2-yl)piperidine-4-carboxamide

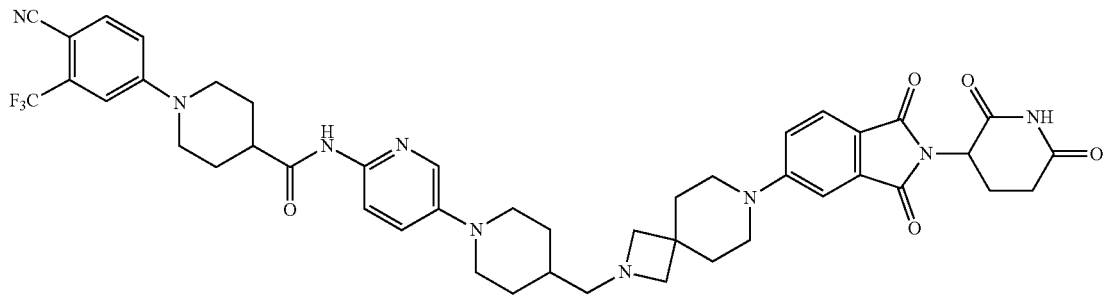 [SMILES: N#Cc1ccc(N2CCC(C(=O)Nc3ccc(N4CCC(CN5CC6(CCN(c7ccc8c(c7)C(=O)N(C7CCC(=O)NC7=O)C8=O)CC6)C5)CC4)cn3)CC2)cc1Cl]

Example 49 was synthesized in a similar way to the synthesis method of Example 1, using tert-butyl 2,7-diazaspiro[3.5]nonane-7-carboxylate instead of tert-butyl piperazine-1-carboxylate.

Example 50: 1-(3-chloro-4-cyanophenyl)-N-(5-(4-((7-(2-(2,6-dioxopiperidin-3-yl)-1,3-dioxoisoindolin-5-yl)-2,7-diazaspiro[3.5]nonan-2-yl)methyl)piperidin-1-yl)pyridin-2-yl)piperidine-4-carboxamide

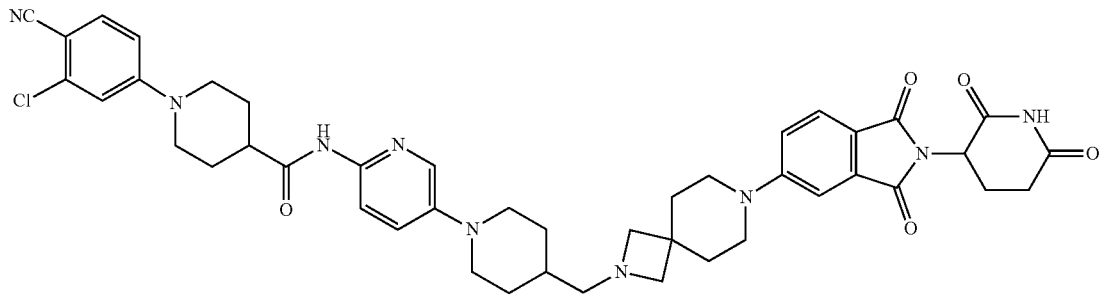

Example 50 was synthesized in a similar way to the synthesis method of Example 1, using 1-(3-chloro-4-cyanophenyl)piperidine-4-carboxylic acid (Intermediate 1-2) and tert-butyl 2,7-diazaspiro[3.5]nonane-7-carboxylate, respectively, instead of 1-(4-cyano-3-(trifluoromethyl)phenyl)piperidine-4-carboxylic acid (Intermediate 1-1) and tert-butyl piperazine-1-carboxylate.

Example 51: 1-(4-cyano-3-(trifluoromethyl)phenyl)-N-(5-(4-((7-(2-(2,6-dioxopiperidin-3-yl)-1,3-dioxoisoindolin-5-yl)-2,7-diazaspiro[3.5]nonan-2-yl)methyl)piperidin-1-yl)pyridin-2-yl)-4-methylpiperidine-4-carboxamide

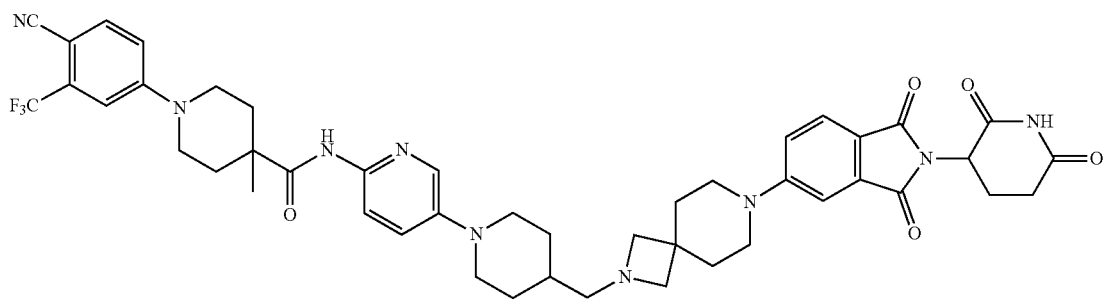 [SMILES: CC1(C(=O)Nc2ccc(N3CCC(CN4CC5(CCN(c6ccc7c(c6)C(=O)N(C6CCC(=O)NC6=O)C7=O)CC5)C4)CC3)cn2)CCN(c2ccc(C#N)c(C(F)(F)F)c2)CC1]

Example 51 was synthesized in a similar way to the synthesis method of Example 1, using 1-(4-cyano-3-(trifluoromethyl)phenyl)-4-methylpiperidine-4-carboxylic acid (Intermediate 1-3) and tert-butyl 2,7-diazaspiro[3.5]nonane-7-carboxylate, respectively, instead of 1-(4-cyano-3-(trifluoromethyl)phenyl)piperidine-4-carboxylic acid (Intermediate 1-1) and tert-butyl piperazine-1-carboxylate.

Example 52: 1-(4-cyano-3-(trifluoromethyl)phenyl)-
N-(5-(4-((7-(3-(2,6-dioxopiperidin-3-yl)-4-oxo-3,4-
dihydrobenzo[d][1,2,3]triazin-7-yl)-2,7-diazaspiro
[3.5]nonan-2-yl)methyl)piperidin-1-yl)pyridin-2-yl)
piperidine-4-carboxamide

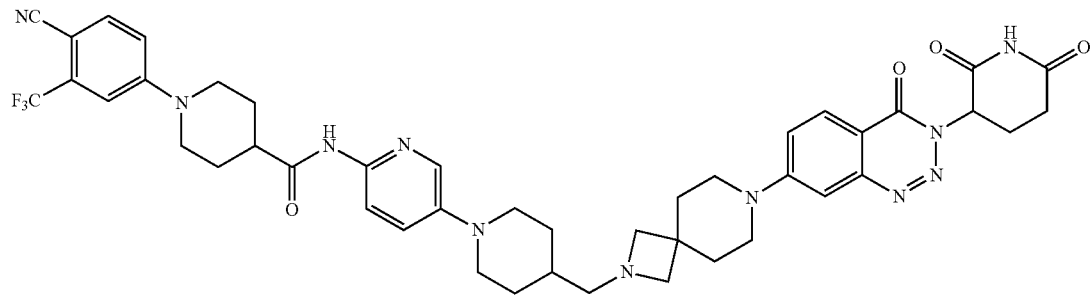 [SMILES: N#Cc1ccc(N2CCC(C(=O)Nc3ccc(N4CCC(CN5CC6(CCN(c7ccc8c(=O)n(C9CCC(=O)NC9=O)nnc8c7)CC6)C5)CC4)cn3)CC2)cc1C(F)(F)F]

Example 52 was synthesized in a similar way to the synthesis method of Example 1, using tert-butyl 2,7-diazaspiro[3.5]nonane-7-carboxylate and 3-(7-fluoro-4-oxobenzo[d][1,2,3]triazin-3(4H)-yl)piperidine-2,6-dione (Intermediate 2-5), respectively, instead of tert-butyl piperazine-1-carboxylate and 2-(2,6-dioxopiperidin-3-yl)-5-fluoroisoindoline-1,3-dione (Intermediate 2-1).

Example 53: 1-(4-cyano-3-(trifluoromethyl)phenyl)-
N-(5-(4-((7-(3-(2,6-dioxopiperidin-3-yl)-4-oxo-3,4-
dihydrobenzo[d][1,2,3]triazin-6-yl)-2,7-diazaspiro
[3.5]nonan-2-yl)methyl)piperidin-1-yl)pyridin-2-yl)
piperidine-4-carboxamide

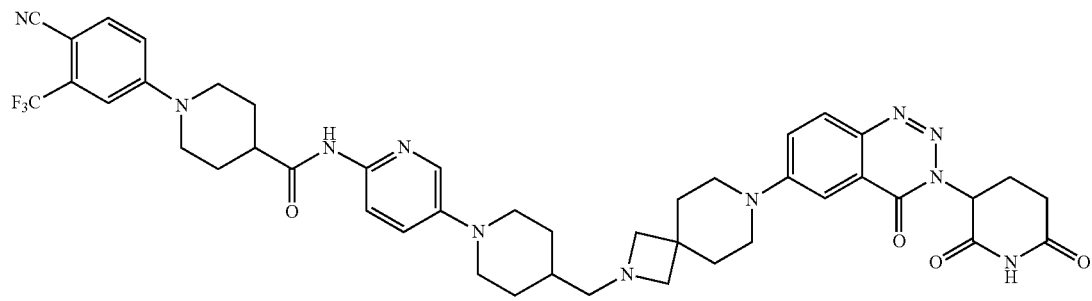 [SMILES: N#Cc1ccc(N2CCC(C(=O)Nc3ccc(N4CCC(CN5CC6(CCN(c7ccc8nnn(C9CCC(=O)NC9=O)c(=O)c8c7)CC6)C5)CC4)cn3)CC2)cc1C(F)(F)F]

Example 53 was synthesized in a similar way to the synthesis method of Example 1, using tert-butyl 2,7-diazaspiro[3.5]nonane-7-carboxylate and 3-(6-fluoro-4-oxobenzo[d][1,2,3]triazin-3(4H)-yl)piperidine-2,6-dione (Intermediate 2-4), respectively, instead of tert-butyl piperazine-1-carboxylate and 2-(2,6-dioxopiperidin-3-yl)-5-fluoroisoindoline-1,3-dione (Intermediate 2-1).

Example 54: 1-(4-cyano-3-(trifluoromethyl)phenyl)-N-(5-(4-((7-(2-(2,6-dioxopiperidin-3-yl)-1,3-dioxoisoindolin-5-yl)-2,7-diazaspiro[3.5]nonan-2-yl)methyl)piperidin-1-yl)pyridin-2-yl)-4-fluoropiperidine-4-carboxamide

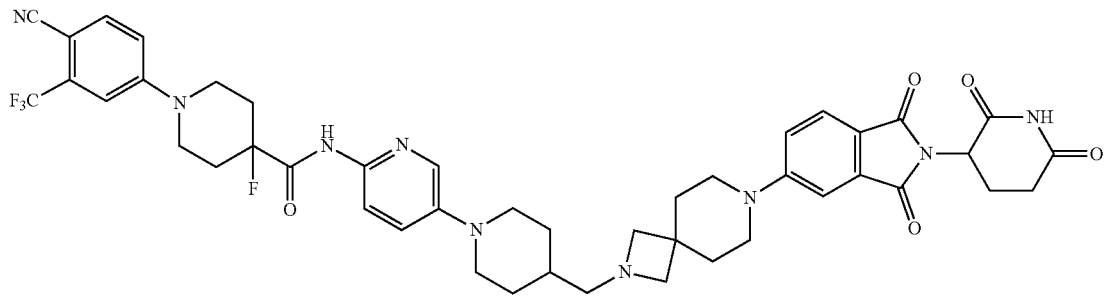

Example 54 was synthesized in a similar way to the synthesis method of Example 1, using 1-(4-cyano-3-(trifluoromethyl)phenyl)-4-fluoropiperidine-4-carboxylic acid (Intermediate 1-5) and tert-butyl 2,7-diazaspiro[3.5]nonane-7-carboxylate, respectively, instead of 1-(4-cyano-3-(trifluoromethyl)phenyl)piperidine-4-carboxylic acid (Intermediate 1-1) and tert-butyl piperazine-1-carboxylate.

Example 55: 1-(4-cyano-3-(trifluoromethyl)phenyl)-N-(5-(4-((7-(2-(2,6-dioxopiperidin-3-yl)-1,3-dioxoisoindolin-5-yl)-2,7-diazaspiro[3.5]nonan-2-yl)methyl)piperidin-1-yl)pyridin-2-yl)-4-hydroxypiperidine-4-carboxamide

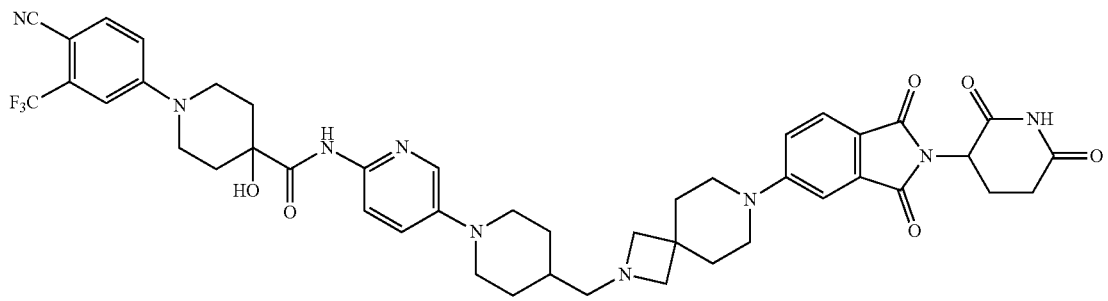 [SMILES: N#Cc1ccc(N2CCC(O)(C(=O)Nc3ccc(N4CCC(CN5CC6(CCN(c7ccc8c(c7)C(=O)N(C7CCC(=O)NC7=O)C8=O)CC6)C5)CC4)cn3)CC2)cc1C(F)(F)F]

Example 55 was synthesized in a similar way to the synthesis method of Example 1, using 1-(4-cyano-3-(trifluoromethyl)phenyl)-4-hydroxypiperidine-4-carboxylic acid (Intermediate 1-4) and tert-butyl 2,7-diazaspiro[3.5]nonane-7-carboxylate, respectively, instead of 1-(4-cyano-3-(trifluoromethyl)phenyl)piperidine-4-carboxylic acid (Intermediate 1-1) and tert-butyl piperazine-1-carboxylate.

Example 56: 2-(1-(4-cyano-3-(trifluoromethyl)phenyl)pyrrolidin-3-yl)-N-(5-(4-((7-(2-(2,6-dioxopiperidin-3-yl)-1,3-dioxoisoindolin-5-yl)-2,7-diazaspiro[3.5]nonan-2-yl)methyl)piperidin-1-yl)pyridin-2-yl)acetamide

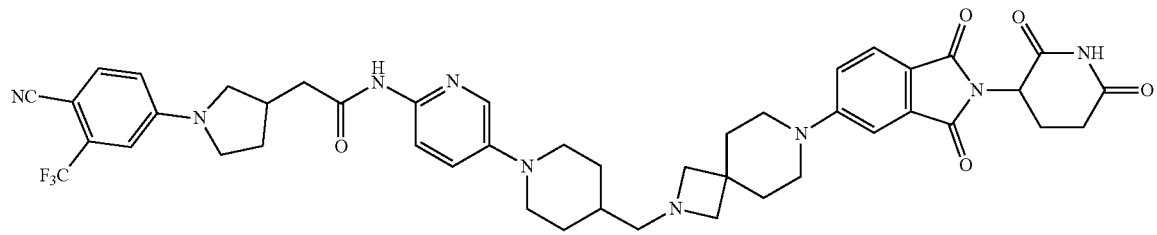 [SMILES: N#Cc1ccc(N2CCC(CC(=O)Nc3ccc(N4CCC(CN5CC6(CCN(c7ccc8c(c7)C(=O)N(C7CCC(=O)NC7=O)C8=O)CC6)C5)CC4)cn3)C2)cc1C(F)(F)F]

Example 56 was synthesized in a similar way to the synthesis method of Example 1, using 2-(1-(4-cyano-3-(trifluoromethyl)phenyl)pyrrolidin-3-yl)acetic acid (Intermediate 1-6) and tert-butyl 2,7-diazaspiro[3.5]nonane-7-carboxylate, respectively, instead of 1-(4-cyano-3-(trifluoromethyl)phenyl)piperidine-4-carboxylic acid (Intermediate 1-1) and tert-butyl piperazine-1-carboxylate.

Example 57: 1-(6-cyano-5-(trifluoromethyl)pyridin-3-yl)-N-(5-(4-((7-(2-(2,6-dioxopiperidin-3-yl)-1,3-dioxoisoindolin-5-yl)-2,7-diazaspiro[3.5]nonan-2-yl)methyl)piperidin-1-yl)pyridin-2-yl)piperidine-4-carboxamide

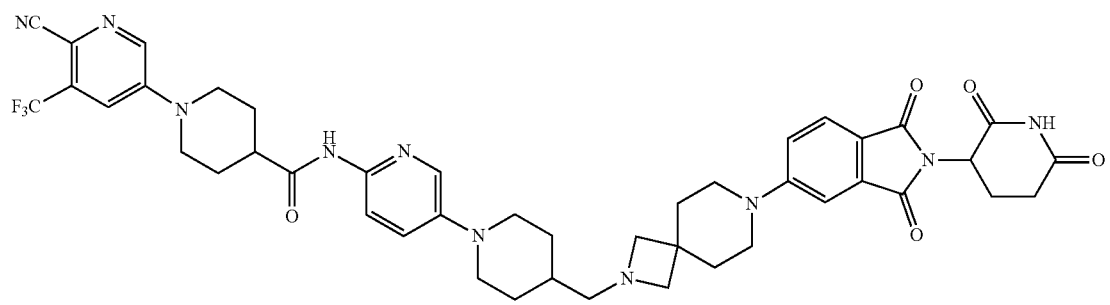

Example 57 was synthesized in a similar way to the synthesis method of Example 1, using 1-(6-cyano-5-(trifluoromethyl)pyridin-3-yl)piperidine-4-carboxylic acid (Intermediate 1-7) and tert-butyl 2,7-diazaspiro[3.5]nonane-7-carboxylate, respectively, instead of 1-(4-cyano-3-(trifluoromethyl)phenyl)piperidine-4-carboxylic acid (Intermediate 1-1) and tert-butyl piperazine-1-carboxylate.

Example 58: 1-(6-cyano-5-(trifluoromethyl)pyridin-3-yl)-N-(5-(4-((7-(2-(2,6-dioxopiperidin-3-yl)-1,3-dioxoisoindolin-5-yl)-2,7-diazaspiro[3.5]nonan-2-yl)methyl)piperidin-1-yl)pyridin-2-yl)-4-fluoropiperidine-4-carboxamide

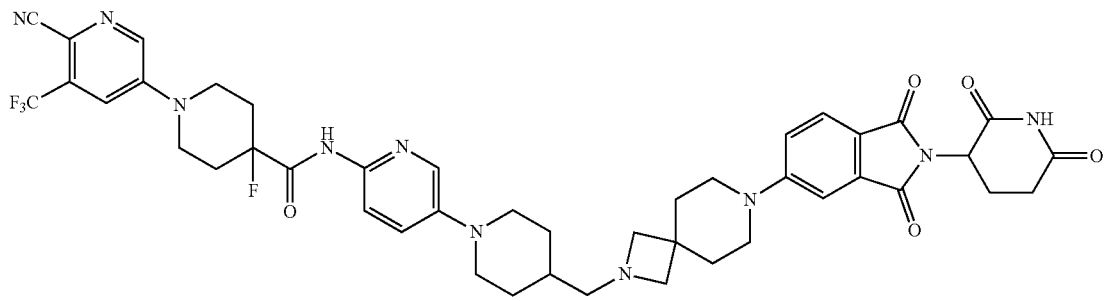 [SMILES: N#Cc1ncc(N2CCC(F)(C(=O)Nc3ccc(N4CCC(CN5CC6(CCN(c7ccc8c(c7)C(=O)N(C7CCC(=O)NC7=O)C8=O)CC6)C5)CC4)cn3)CC2)cc1C(F)(F)F]

Example 58 was synthesized in a similar way to the synthesis method of Example 1, using 1-(6-cyano-5-(trifluoromethyl)pyridin-3-yl)-4-fluoropiperidine-4-carboxylic acid (Intermediate 1-8) and tert-butyl 2,7-diazaspiro[3.5]nonane-7-carboxylate, respectively, instead of 1-(4-cyano-3-(trifluoromethyl)phenyl)piperidine-4-carboxylic acid (Intermediate 1-1) and tert-butyl piperazine-1-carboxylate.

Example 59: 1-(4-cyano-3-(trifluoromethyl)phenyl)-N-(6-(4-((7-(2-(2,6-dioxopiperidin-3-yl)-1,3-dioxoisoindolin-5-yl)-2,7-diazaspiro[3.5]nonan-2-yl)methyl)piperidin-1-yl)pyridin-3-yl)piperidine-4-carboxamide

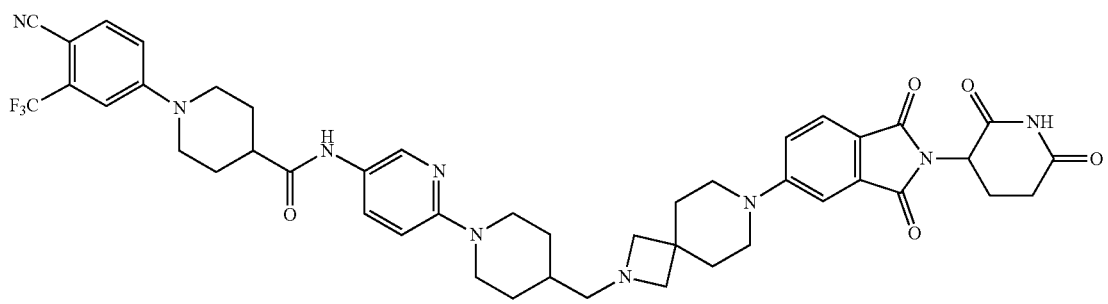

Example 59 was synthesized in a similar way to the synthesis method of Example 1, using 2-chloro-5-nitropyridine and tert-butyl 2,7-diazaspiro[3.5]nonane-7-carboxylate, respectively, instead of 5-chloro-2-nitropyridine and tert-butyl piperazine-1-carboxylate.

Example 60: 1-(3-chloro-4-cyanophenyl)-N-(6-(4-((7-(2-(2,6-dioxopiperidin-3-yl)-1,3-dioxoisoindolin-5-yl)-2,7-diazaspiro[3.5]nonan-2-yl)methyl)piperidin-1-yl)pyridin-3-yl)piperidine-4-carboxamide

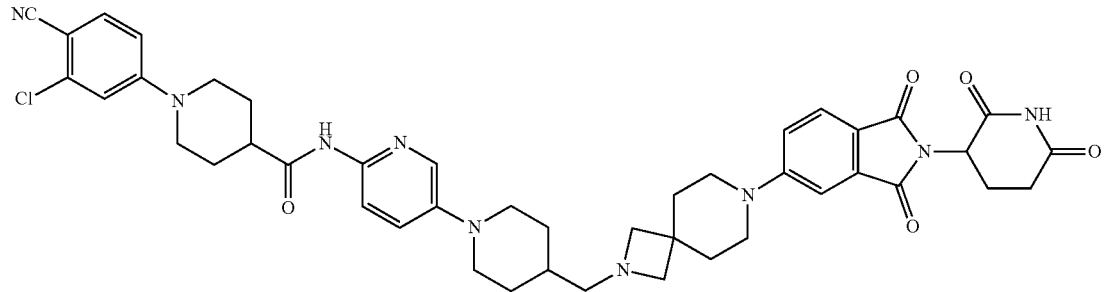 [SMILES: N#Cc1ccc(N2CCC(C(=O)Nc3ccc(N4CCC(CN5CC6(CCN(c7ccc8c(c7)C(=O)N(C7CCC(=O)NC7=O)C8=O)CC6)C5)CC4)cn3)CC2)cc1Cl]

Example 60 was synthesized in a similar way to the synthesis method of Example 1, using 1-(3-chloro-4-cyanophenyl)piperidine-4-carboxylic acid (Intermediate 1-2), 2-chloro-5-nitropyridine, and tert-butyl 2,7-diazaspiro[3.5]nonane-7-carboxylate, respectively, instead of 1-(4-cyano-3-(trifluoromethyl)phenyl)piperidine-4-carboxylic acid (Intermediate 1-1), 5-chloro-2-nitropyridine, and tert-butyl piperazine-1-carboxylate.

Example 61: 1-(4-cyano-3-(trifluoromethyl)phenyl)-N-(5-((3S)-3-((7-(2-(2,6-dioxopiperidin-3-yl)-1,3-dioxoisoindolin-5-yl)-2,7-diazaspiro[3.5]nonan-2-yl)methyl)pyrrolidin-1-yl)pyridin-2-yl)piperidine-4-carboxamide

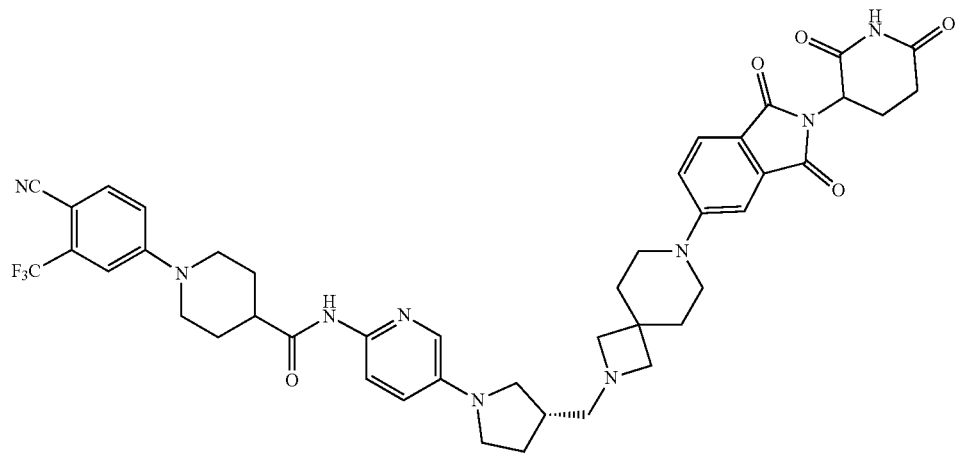 [SMILES: N#Cc1ccc(N2CCC(C(=O)Nc3ccc(N4CC[C@@H](CN5CC6(CCN(c7ccc8c(c7)C(=O)N(C7CCC(=O)NC7=O)C8=O)CC6)C5)C4)cn3)CC2)cc1C(F)(F)F]

Example 61 was synthesized in a similar way to the synthesis method of Example 1, using (R)-pyrrolidin-3-ylmethanol and tert-butyl 2,7-diazaspiro[3.5]nonane-7-carboxylate, respectively, instead of piperidin-4-ylmethanol and tert-butyl piperazine-1-carboxylate.

Example 62: 1-(4-cyano-3-(trifluoromethyl)phenyl)-N-(5-((3R)-3-((7-(2-(2,6-dioxopiperidin-3-yl)-1,3-dioxoisoindolin-5-yl)-2,7-diazaspiro[3.5]nonan-2-yl)methyl)pyrrolidin-1-yl)pyridin-2-yl)piperidine-4-carboxamide

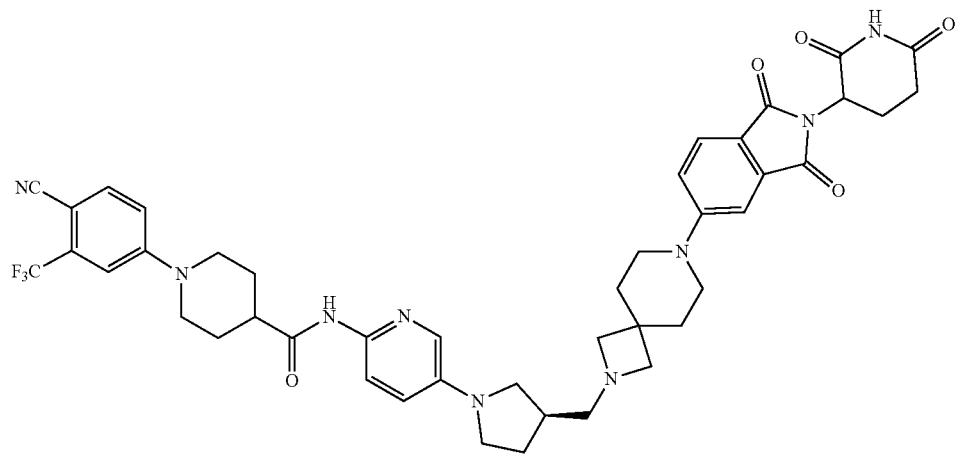 [SMILES: N#Cc1ccc(N2CCC(C(=O)Nc3ccc(N4CC[C@H](CN5CC6(CCN(c7ccc8c(c7)C(=O)N(C7CCC(=O)NC7=O)C8=O)CC6)C5)C4)cn3)CC2)cc1C(F)(F)F]

Example 62 was synthesized in a similar way to the synthesis method of Example 1, using (S)-pyrrolidin-3-ylmethanol and tert-butyl 2,7-diazaspiro[3.5]nonane-7-carboxylate, respectively, instead of piperidin-4-ylmethanol and tert-butyl piperazine-1-carboxylate.

Example 63: 1-(4-cyano-3-(trifluoromethyl)phenyl)-N-(5-(4-((2-(2-(2,6-dioxopiperidin-3-yl)-1,3-dioxoisoindolin-5-yl)-2,7-diazaspiro[3.5]nonan-7-yl)methyl)piperidin-1-yl)pyridin-2-yl)piperidine-4-carboxamide

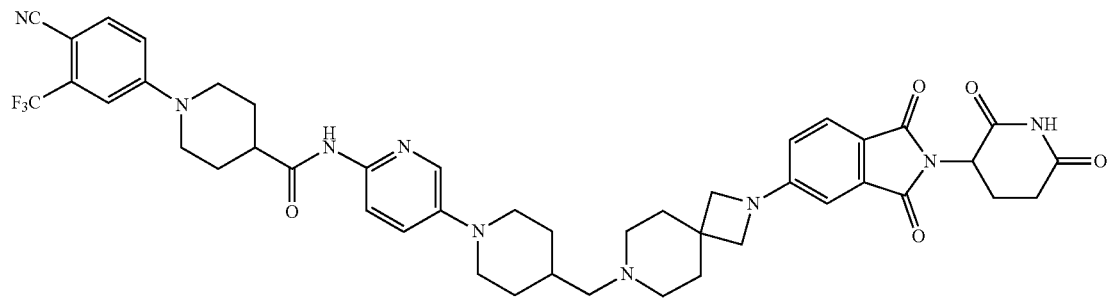 [SMILES: N#Cc1ccc(N2CCC(C(=O)Nc3ccc(N4CCC(CN5CCC6(CC5)CN(c5ccc7c(c5)C(=O)N(C5CCC(=O)NC5=O)C7=O)C6)CC4)cn3)CC2)cc1C(F)(F)F]

Example 63 was synthesized in a similar way to the synthesis method of Example 1, using tert-butyl 2,7-diazaspiro[3.5]nonane-2-carboxylate instead of tert-butyl piperazine-1-carboxylate.

Example 64: 1-(3-chloro-4-cyanophenyl)-N-(5-(4-((2-(2-(2,6-dioxopiperidin-3-yl)-1,3-dioxoisoindolin-5-yl)-2,7-diazaspiro[3.5]nonan-7-yl)methyl)piperidin-1-yl)pyridin-2-yl)piperidine-4-carboxamide

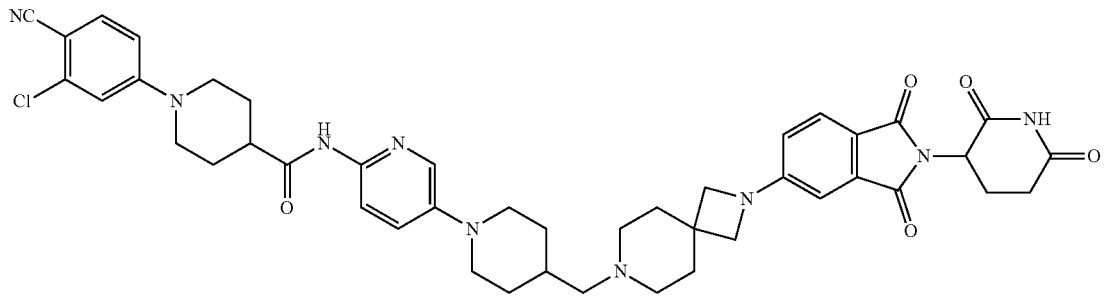 [SMILES: N#Cc1ccc(N2CCC(C(=O)Nc3ccc(N4CCC(CN5CCC6(CC5)CN(c5ccc7c(c5)C(=O)N(C5CCC(=O)NC5=O)C7=O)C6)CC4)cn3)CC2)cc1Cl]

Example 64 was synthesized in a similar way to the synthesis method of Example 1, using 1-(3-chloro-4-cyanophenyl)piperidine-4-carboxylic acid (Intermediate 1-2) and tert-butyl 2,7-diazaspiro[3.5]nonane-2-carboxylate, respectively, instead of 1-(4-cyano-3-(trifluoromethyl)phenyl)piperidine-4-carboxylic acid (Intermediate 1-1) and tert-butyl piperazine-1-carboxylate.

Example 65: 1-(4-cyano-3-(trifluoromethyl)phenyl)-N-(5-(4-((2-(3-(2,4-dioxotetrahydropyrimidin-1(2H)-yl)-4-methoxybenzoyl)-2,7-diazaspiro[3.5]nonan-7-yl)methyl)piperidin-1-yl)pyridin-2-yl)piperidine-4-carboxamide

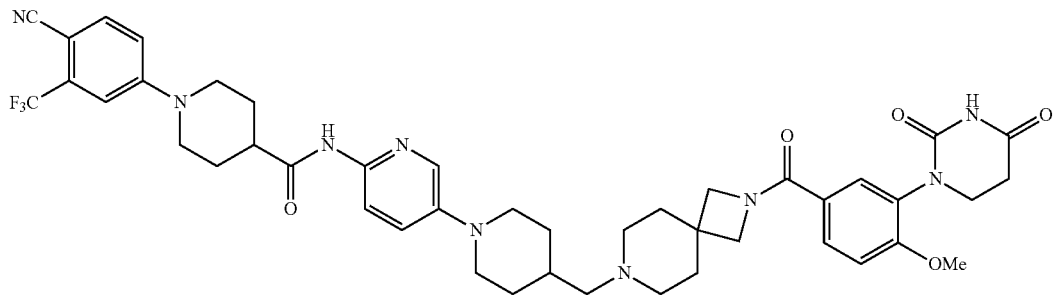 [SMILES: COc1ccc(C(=O)N2CC3(CCN(CC4CCN(c5ccc(NC(=O)C6CCN(c7ccc(C#N)c(C(F)(F)F)c7)CC6)nc5)CC4)CC3)C2)cc1N1CCC(=O)NC1=O]

N-(5-(4-((2,7-diazaspiro[3.5]nonan-7-yl)methyl)piperidin-1-yl)pyridin-2-yl)-1-(4-cyano-3-(trifluoromethyl)phenyl)piperidine-4-carboxamide hydrochloride (50 mg, 0.079 mmol), 3-(2,4-dioxotetrahydropyrimidin-1(2H)-yl)-4-methoxybenzoic acid (WO2019/186343, 25 mg, 0.095 mmol), HATU (36 mg, 0.095 mmol), and DIPEA (0.03 mL, 0.16 mmol) were suspended in DMF (1.0 ml) and stirred at room temperature for 16 hours. After adding distilled water (15 ml) to the reaction solution, extraction was performed with EtOAc (25 ml×2), and the organic layer was dried over anhydrous sodium sulfate, filtered, and concentrated under reduced pressure. The resulting residue was subjected to MPLC (10% MeOH/DCM) to give 18 mg (27%) of a white solid.

Example 66: 1-(4-cyano-3-(trifluoromethyl)phenyl)-N-(5-(4-((6-(2-(2,6-dioxopiperidin-3-yl)-1,3-dioxoisoindolin-5-yl)-2,6-diazaspiro[3.3]heptan-2-yl)methyl)piperidin-1-yl)pyridin-2-yl)piperidine-4-carboxamide

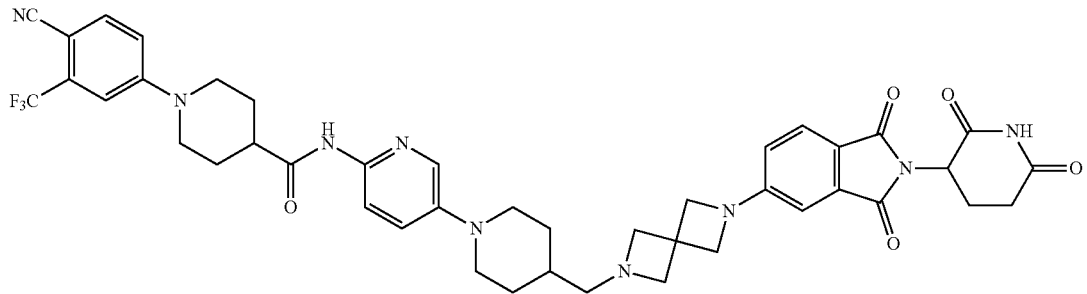

Example 66 was synthesized in a similar way to the synthesis method of Example 1, using tert-butyl 2,6-diazaspiro[3.3]heptane-2-carboxylate instead of tert-butyl piperazine-1-carboxylate.

Example 67: 1-(3-chloro-4-cyanophenyl)-N-(5-(4-((6-(2-(2,6-dioxopiperidin-3-yl)-1,3-dioxoisoindolin-5-yl)-2,6-diazaspiro[3.3]heptan-2-yl)methyl)piperidin-1-yl)pyridin-2-yl)piperidine-4-carboxamide

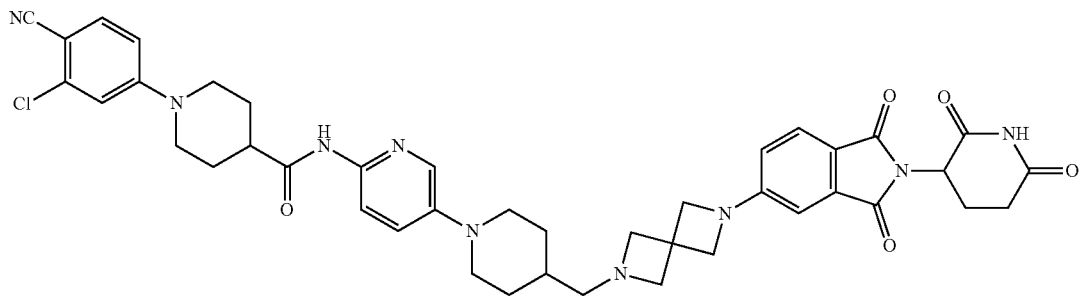 [SMILES: N#Cc1ccc(N2CCC(C(=O)Nc3ccc(N4CCC(CN5CC6(C5)CN(c5ccc7c(c5)C(=O)N(C5CCC(=O)NC5=O)C7=O)C6)CC4)cn3)CC2)cc1Cl]

Example 67 was synthesized in a similar way to the synthesis method of Example 1, using 1-(3-chloro-4-cyanophenyl)piperidine-4-carboxylic acid (Intermediate 1-2) and tert-butyl 2,6-diazaspiro[3.3]heptane-2-carboxylate, respectively, instead of 1-(4-cyano-3-(trifluoromethyl)phenyl)piperidine-4-carboxylic acid (Intermediate 1-1) and tert-butyl piperazine-1-carboxylate.

Example 68: 1-(4-cyano-3-(trifluoromethyl)phenyl)-N-(5-(4-((9-(2-(2,6-dioxopiperidin-3-yl)-1,3-dioxoisoindolin-5-yl)-3,9-diazaspiro[5.5]undecan-3-yl)methyl)piperidin-1-yl)pyridin-2-yl)piperidine-4-carboxamide

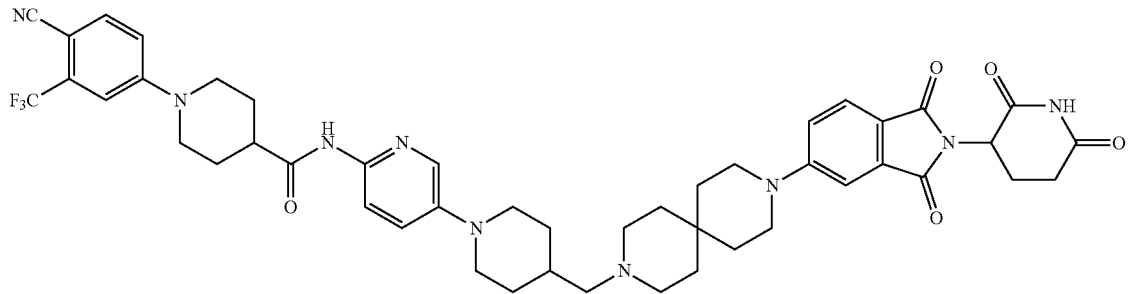 [SMILES: N#Cc1ccc(N2CCC(C(=O)Nc3ccc(N4CCC(CN5CCC6(CC5)CCN(c5ccc7c(c5)C(=O)N(C5CCC(=O)NC5=O)C7=O)CC6)CC4)cn3)CC2)cc1C(F)(F)F]

Example 68 was synthesized in a similar way to the synthesis method of Example 1, using tert-butyl 3,9-diazaspiro[5.5]undecane-3-carboxylate instead of tert-butyl piperazine-1-carboxylate.

Example 69: 1-(3-chloro-4-cyanophenyl)-N-(5-(4-((9-(2-(2,6-dioxopiperidin-3-yl)-1,3-dioxoisoindolin-5-yl)-3,9-diazaspiro[5.5]undecan-3-yl)methyl)piperidin-1-yl)pyridin-2-yl)piperidine-4-carboxamide

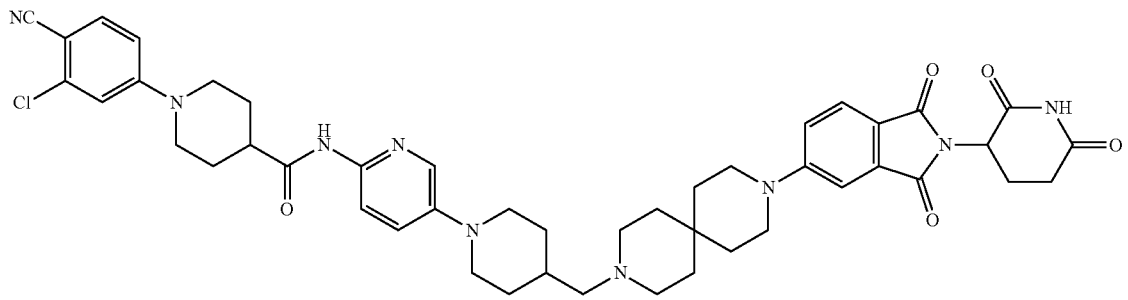 [SMILES: N#Cc1ccc(N2CCC(C(=O)Nc3ccc(N4CCC(CN5CCC6(CC5)CCN(c5ccc7c(c5)C(=O)N(C5CCC(=O)NC5=O)C7=O)CC6)CC4)cn3)CC2)cc1Cl]

Example 69 was synthesized in a similar way to the synthesis method of Example 1, using 1-(3-chloro-4-cyanophenyl)piperidine-4-carboxylic acid (Intermediate 1-2) and tert-butyl 3,9-diazaspiro[5.5]undecane-3-carboxylate, respectively, instead of 1-(4-cyano-3-(trifluoromethyl)phenyl)piperidine-4-carboxylic acid (Intermediate 1-1) and tert-butyl piperazine-1-carboxylate.

Example 70: 1-(4-cyano-3-(trifluoromethyl)phenyl)-N-(5-(4-((4-(1-(2-(2,6-dioxopiperidin-3-yl)-1,3-di-oxoisoindolin-5-yl)piperidin-4-yl)piperazin-1-yl)methyl)piperidin-1-yl)pyridin-2-yl)piperidine-4-carboxamide

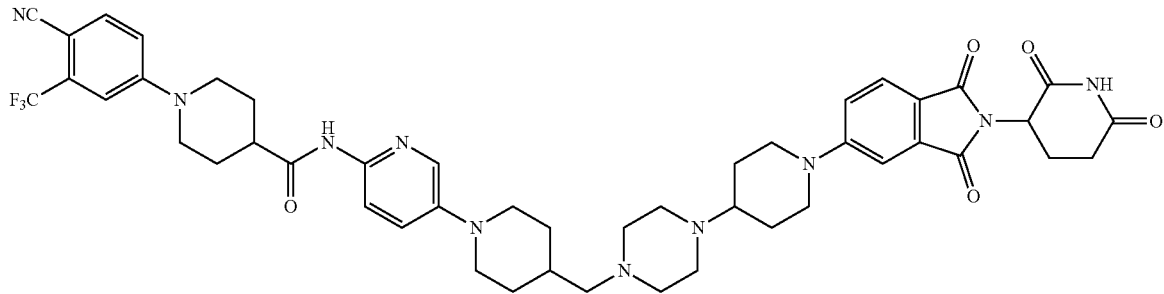

Example 70 was synthesized in a similar way to the synthesis method of Example 1, using tert-butyl 4-(piperazin-1-yl)piperidine-1-carboxylate (Intermediate 4-9) instead of tert-butyl piperazine-1-carboxylate.

Example 71: 1-(3-chloro-4-cyanophenyl)-N-(5-(4-((4-(1-(2-(2,6-dioxopiperidin-3-yl)-1,3-dioxoisoindolin-5-yl)piperidin-4-yl)piperazin-1-yl)methyl)piperidin-1-yl)pyridin-2-yl)piperidine-4-carboxamide

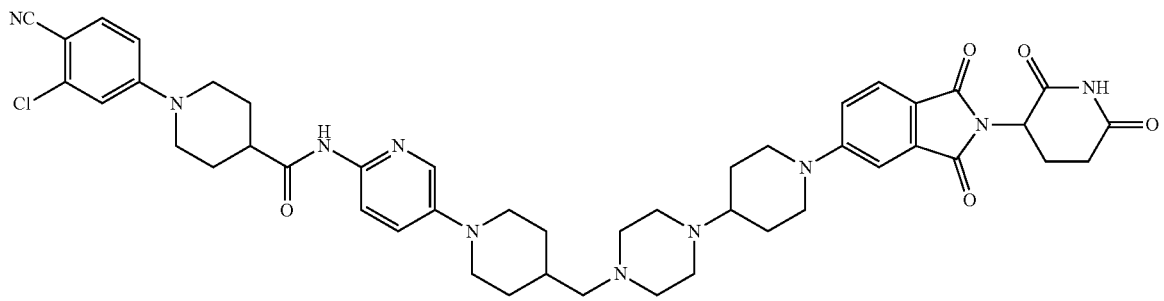 [SMILES: N#Cc1ccc(N2CCC(C(=O)Nc3ccc(N4CCC(CN5CCN(C6CCN(c7ccc8c(c7)C(=O)N(C7CCC(=O)NC7=O)C8=O)CC6)CC5)CC4)cn3)CC2)cc1Cl]

Example 71 was synthesized in a similar way to the synthesis method of Example 1, using 1-(3-chloro-4-cyanophenyl)piperidine-4-carboxylic acid (Intermediate 1-2) and tert-butyl 4-(piperazin-1-yl)piperidine-1-carboxylate (Intermediate 4-9), respectively, instead of 1-(4-cyano-3-(trifluoromethyl)phenyl)piperidine-4-carboxylic acid (Intermediate 1-1) and tert-butyl piperazine-1-carboxylate.

Example 72: 1-(4-cyano-3-(trifluoromethyl)phenyl)-N-(5-(4-((4-(1-(2-(2,6-dioxopiperidin-3-yl)-1,3-dioxoisoindolin-5-yl)piperidin-4-yl)piperazin-1-yl)methyl)piperidin-1-yl)pyridin-2-yl)-4-fluoropiperidine-4-carboxamide

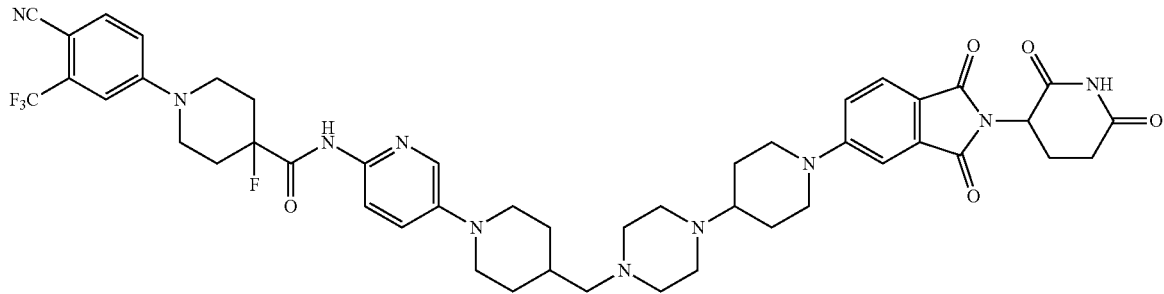

Example 72 was synthesized in a similar way to the synthesis method of Example 1, using 1-(4-cyano-3-(trifluoromethyl)phenyl)-4-fluoropiperidine-4-carboxylic acid (Intermediate 1-5) and tert-butyl 4-(piperazin-1-yl)piperidine-1-carboxylate (Intermediate 4-9), respectively, instead of 1-(4-cyano-3-(trifluoromethyl)phenyl)piperidine-4-carboxylic acid (Intermediate 1-1) and tert-butyl piperazine-1-carboxylate.

Example 73: 1-(6-cyano-5-(trifluoromethyl)pyridin-3-yl)-N-(5-(4-((4-(1-(2-(2,6-dioxopiperidin-3-yl)-1,3-dioxoisoindolin-5-yl)piperidin-4-yl)piperazin-1-yl)methyl)piperidin-1-yl)pyridin-2-yl)piperidine-4-carboxamide

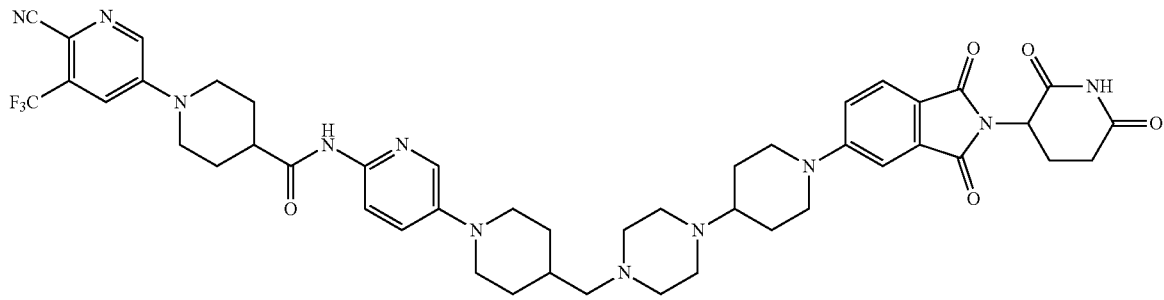

Example 73 was synthesized in a similar way to the synthesis method of Example 1, using 1-(6-cyano-5-(trifluoromethyl)pyridin-3-yl)piperidine-4-carboxylic acid (Intermediate 1-7) and tert-butyl 4-(piperazin-1-yl)piperidine-1-carboxylate (Intermediate 4-9), respectively, instead of 1-(4-cyano-3-(trifluoromethyl)phenyl)piperidine-4-carboxylic acid (Intermediate 1-1) and tert-butyl piperazine-1-carboxylate.

Example 74: 1-(6-cyano-5-(trifluoromethyl)pyridin-3-yl)-N-(5-(4-((4-(1-(2-(2,6-dioxopiperidin-3-yl)-1,3-dioxoisoindolin-5-yl)piperidin-4-yl)piperazin-1-yl)methyl)piperidin-1-yl)pyridin-2-yl)-4-fluoropiperidine-4-carboxamide

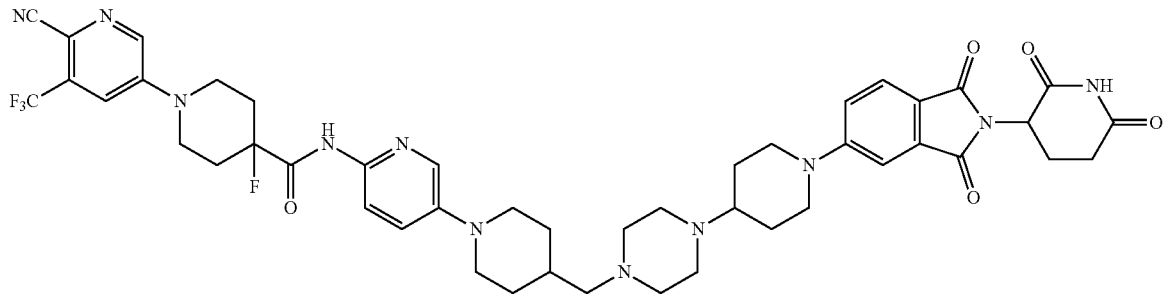 [SMILES: N#Cc1ncc(N2CCC(F)(C(=O)Nc3ccc(N4CCC(CN5CCN(C6CCN(c7ccc8c(c7)C(=O)N(C7CCC(=O)NC7=O)C8=O)CC6)CC5)CC4)cn3)CC2)cc1C(F)(F)F]

Example 74 was synthesized in a similar way to the synthesis method of Example 1, using 1-(6-cyano-5-(trifluoromethyl)pyridin-3-yl)-4-fluoropiperidine-4-carboxylic acid (Intermediate 1-8) and tert-butyl 4-(piperazin-1-yl)piperidine-1-carboxylate (Intermediate 4-9), respectively, instead of 1-(4-cyano-3-(trifluoromethyl)phenyl)piperidine-4-carboxylic acid (Intermediate 1-1) and tert-butyl piperazine-1-carboxylate.

Example 75: 1-(4-cyano-3-(trifluoromethyl)phenyl)-N-(5-(4-((4-(1-(6-(2,6-dioxopiperidin-3-yl)-5-oxo-6,7-dihydro-5H-pyrrolo[3,4-b]pyridin-2-yl)piperidin-4-yl)piperazin-1-yl)methyl)piperidin-1-yl)pyridin-2-yl)piperidine-4-carboxamide

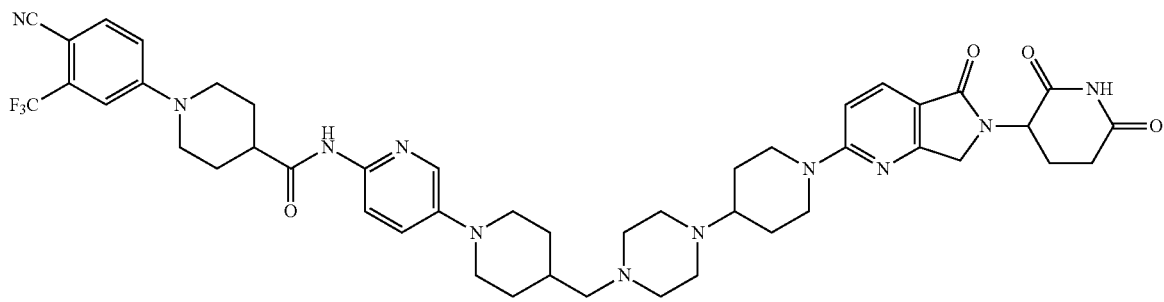 [SMILES: N#Cc1ccc(N2CCC(C(=O)Nc3ccc(N4CCC(CN5CCN(C6CCN(c7ccc8c(n7)CN(C7CCC(=O)NC7=O)C8=O)CC6)CC5)CC4)cn3)CC2)cc1C(F)(F)F]

Example 75 was synthesized in a similar way to the synthesis method of Example 1, using tert-butyl 4-(piperazin-1-yl)piperidine-1-carboxylate (Intermediate 4-9) and 3-(2-chloro-5-oxo-5,7-dihydro-6H-pyrrolo[3,4-b]pyridin-6-yl)piperidine-2,6-dione (Intermediate 2-6), respectively, instead of tert-butyl piperazine-1-carboxylate and 2-(2,6-dioxopiperidin-3-yl)-5-fluoroisoindoline-1,3-dione (Intermediate 2-1).

Example 76: 1-(4-cyano-3-(trifluoromethyl)phenyl)-N-(5-(4-((4-(1-(2-(2,6-dioxopiperidin-3-yl)-1,3-dioxoisoindolin-4-yl)piperidin-4-yl)piperazin-1-yl)methyl)piperidin-1-yl)pyridin-2-yl)piperidine-4-carboxamide

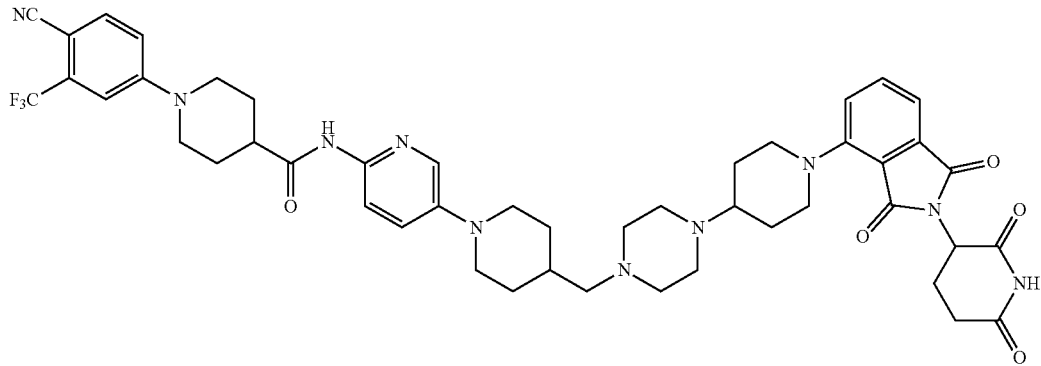 [SMILES: N#Cc1ccc(N2CCC(C(=O)Nc3ccc(N4CCC(CN5CCN(C6CCN(c7cccc8c7C(=O)N(C7CCC(=O)NC7=O)C8=O)CC6)CC5)CC4)cn3)CC2)cc1C(F)(F)F]

Example 76 was synthesized in a similar way to the synthesis method of Example 1, using tert-butyl 4-(piperazin-1-yl)piperidine-1-carboxylate (Intermediate 4-9) and 2-(2,6-dioxopiperidin-3-yl)-4-fluoroisoindoline-1,3-dione (Intermediate 2-2), respectively, instead of tert-butyl piperazine-1-carboxylate and 2-(2,6-dioxopiperidin-3-yl)-5-fluoroisoindoline-1,3-dione (Intermediate 2-1).

Example 77: 1-(4-cyano-3-(trifluoromethyl)phenyl)-N-(5-(4-((3-(4-(2-(2,6-dioxopiperidin-3-yl)-1,3-dioxoisoindolin-5-yl)piperazin-1-yl)azetidin-1-yl)methyl)piperidin-1-yl)pyridin-2-yl)piperidine-4-carboxamide

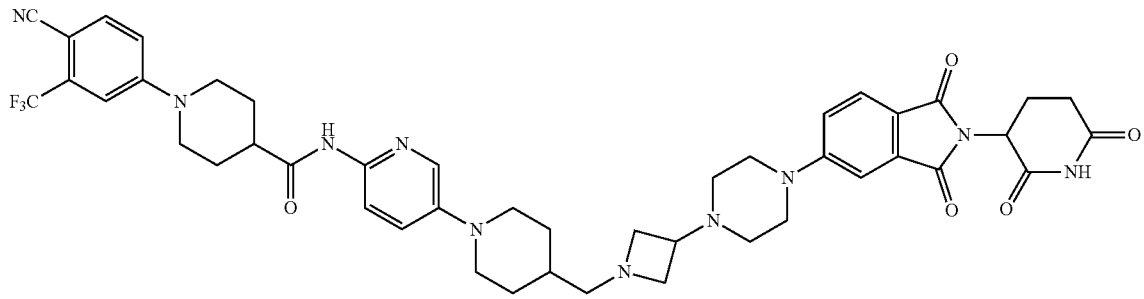 [SMILES: N#Cc1ccc(N2CCC(C(=O)Nc3ccc(N4CCC(CN5CC(N6CCN(c7ccc8c(c7)C(=O)N(C7CCC(=O)NC7=O)C8=O)CC6)C5)CC4)cn3)CC2)cc1C(F)(F)F]

Example 77 was synthesized in a similar way to the synthesis method of Example 1, using tert-butyl 4-(azetidin-3-yl)piperazine-1-carboxylate (Intermediate 4-6) instead of tert-butyl piperazine-1-carboxylate.

Example 78: 1-(4-cyano-3-(trifluoromethyl)phenyl)-N-(5-(4-((3-(4-(6-(2,6-dioxopiperidin-3-yl)-5-oxo-6,7-dihydro-5H-pyrrolo[3,4-b]pyridin-2-yl)piperazin-1-yl)azetidin-1-yl)methyl)piperidin-1-yl)pyridin-2-yl)piperidine-4-carboxamide

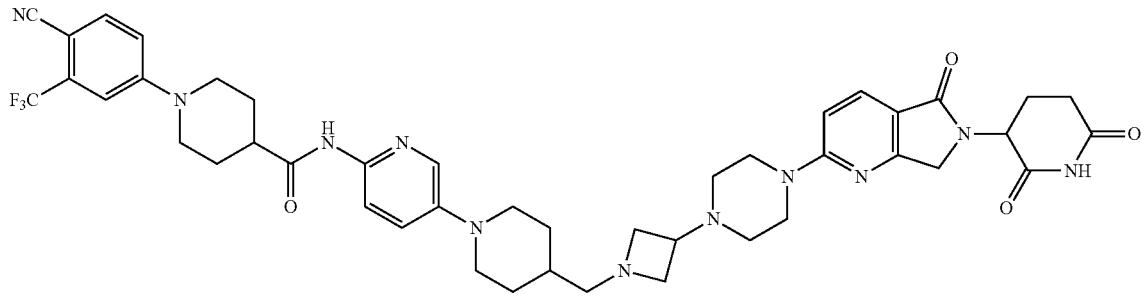 [SMILES: N#Cc1ccc(N2CCC(C(=O)Nc3ccc(N4CCC(CN5CC(N6CCN(c7ccc8c(n7)CN(C7CCC(=O)NC7=O)C8=O)CC6)C5)CC4)cn3)CC2)cc1C(F)(F)F]

Example 78 was synthesized in a similar way to the synthesis method of Example 1, using tert-butyl 4-(azetidin-3-yl)piperazine-1-carboxylate (Intermediate 4-6) and 3-(2-chloro-5-oxo-5,7-dihydro-6H-pyrrolo[3,4-b]pyridin-6-yl)piperidine-2,6-dione (Intermediate 2-6), respectively, instead of tert-butyl piperazine-1-carboxylate and 2-(2,6-dioxopiperidin-3-yl)-5-fluoroisoindoline-1,3-dione (Intermediate 2-1).

Example 79: 1-(4-cyano-3-(trifluoromethyl)phenyl)-N-(5-(4-((3-((4-(2-(2,6-dioxopiperidin-3-yl)-1,3-dioxoisoindolin-5-yl)piperazin-1-yl)methyl)azetidin-1-yl)methyl)piperidin-1-yl)pyridin-2-yl)piperidine-4-carboxamide

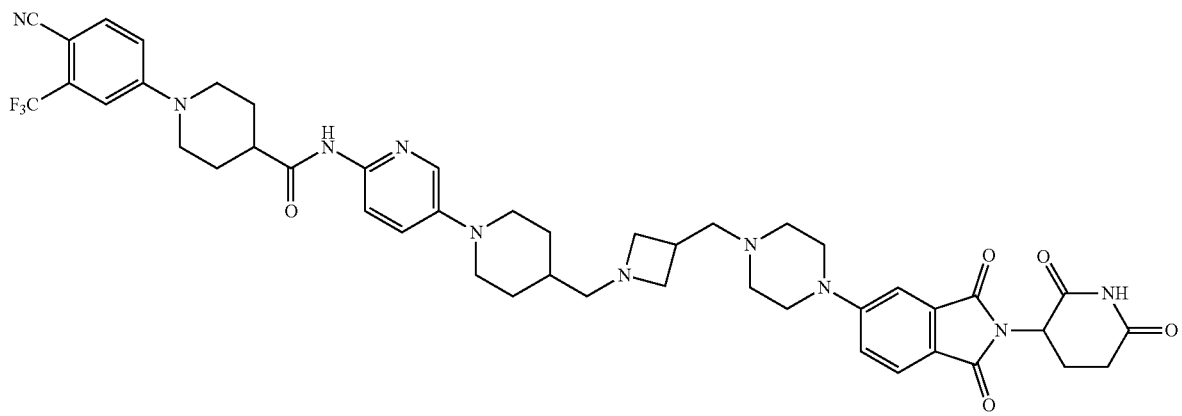 [SMILES: N#Cc1ccc(N2CCC(C(=O)Nc3ccc(N4CCC(CN5CC(CN6CCN(c7ccc8c(c7)C(=O)N(C7CCC(=O)NC7=O)C8=O)CC6)C5)CC4)cn3)CC2)cc1C(F)(F)F]

Example 79 was synthesized in a similar way to the synthesis method of Example 1, using tert-butyl 4-(azetidin-3-ylmethyl)piperazine-1-carboxylate (Example 4-5) instead of tert-butyl piperazine-1-carboxylate.

Example 80: 1-(4-cyano-3-(trifluoromethyl)phenyl)-
N-(5-(4-((3-((4-(6-(2,6-dioxopiperidin-3-yl)-5-oxo-
6,7-dihydro-5H-pyrrolo[3,4-b]pyridin-2-yl)piper-
azin-1-yl)methyl)azetidin-1-yl)methyl)piperidin-1-
yl)pyridin-2-yl)piperidine-4-carboxamide

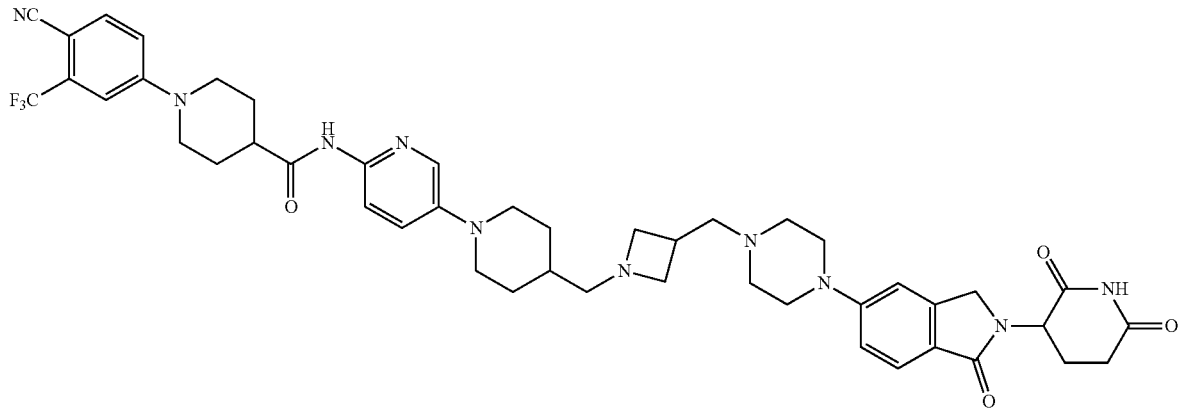 [SMILES: N#Cc1ccc(N2CCC(C(=O)Nc3ccc(N4CCC(CN5CC(CN6CCN(c7ccc8c(c7)CN(C7CCC(=O)NC7=O)C8=O)CC6)C5)CC4)cn3)CC2)cc1C(F)(F)F]

Example 80 was synthesized in a similar way to the synthesis method of Example 1, using tert-butyl 4-(azetidin-3-ylmethyl)piperazine-1-carboxylate (Example 4-5) and 3-(2-chloro-5-oxo-5,7-dihydro-6H-pyrrolo[3,4-b]pyridin-6-yl)piperidine-2,6-dione (Intermediate 2-6), respectively, instead of tert-butyl piperazine-1-carboxylate and 2-(2,6-dioxopiperidin-3-yl)-5-fluoroisoindoline-1,3-dione (Intermediate 2-1).

Example 81: 1-(4-cyano-3-(trifluoromethyl)phenyl)-
N-(5-(4-((4-((4-(2-(2,6-dioxopiperidin-3-yl)-1,3-
dioxoisoindolin-5-yl)piperazin-1-yl)methyl)piperi-
din-1-yl)methyl)piperidin-1-yl)pyridin-2-yl)
piperidine-4-carboxamide

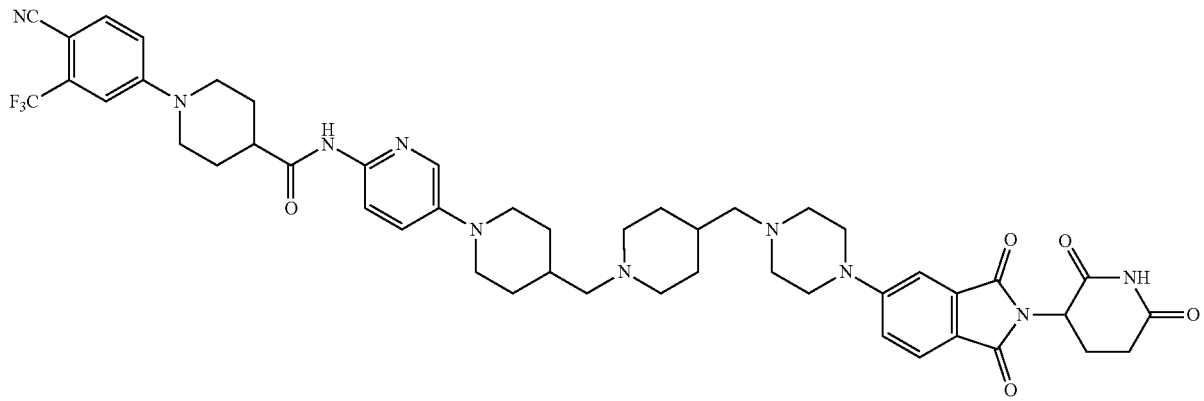 [SMILES: N#Cc1ccc(N2CCC(C(=O)Nc3ccc(N4CCC(CN5CCC(CN6CCN(c7ccc8c(c7)C(=O)N(C7CCC(=O)NC7=O)C8=O)CC6)CC5)CC4)cn3)CC2)cc1C(F)(F)F]

Example 81 was synthesized in a similar way to the synthesis method of Example 1, using tert-butyl 4-(piperidin-4-ylmethyl)piperazine-1-carboxylate (Intermediate 4-3) instead of tert-butyl piperazine-1-carboxylate.

Example 82: 1-(4-cyano-3-(trifluoromethyl)phenyl)-N-(5-(4-(((3S)-3-((4-(2-(2,6-dioxopiperidin-3-yl)-1,3-dioxoisoindolin-5-yl)piperazin-1-yl)methyl)pyrrolidin-1-yl)methyl)piperidin-1-yl)pyridin-2-yl)piperidine-4-carboxamide

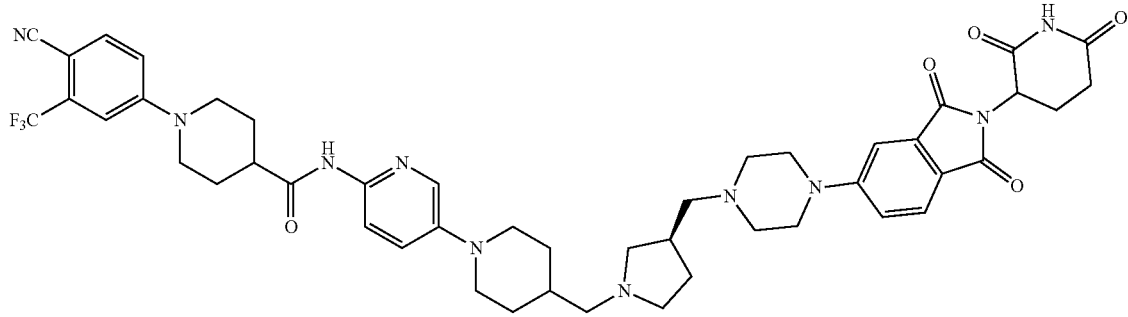 [SMILES: N#Cc1ccc(N2CCC(C(=O)Nc3ccc(N4CCC(CN5CC[C@H](CN6CCN(c7ccc8c(c7)C(=O)N(C7CCC(=O)NC7=O)C8=O)CC6)C5)CC4)cn3)CC2)cc1C(F)(F)F]

Example 82 was synthesized in a similar way to the synthesis method of Example 1, using tert-butyl (S)-4-(pyrrolidin-3-ylmethyl)piperazine-1-carboxylate (Intermediate 4-1) instead of tert-butyl piperazine-1-carboxylate.

Example 83: 1-(4-cyano-3-(trifluoromethyl)phenyl)-N-(5-(4-(((3R)-3-((4-(2-(2,6-dioxopiperidin-3-yl)-1,3-dioxoisoindolin-5-yl)piperazin-1-yl)methyl)pyrrolidin-1-yl)methyl)piperidin-1-yl)pyridin-2-yl)piperidine-4-carboxamide

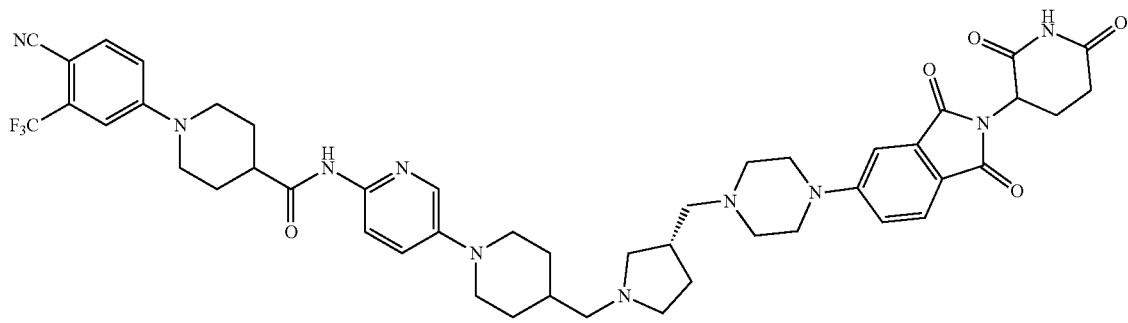 [SMILES: N#Cc1ccc(N2CCC(C(=O)Nc3ccc(N4CCC(CN5CC[C@@H](CN6CCN(c7ccc8c(c7)C(=O)N(C7CCC(=O)NC7=O)C8=O)CC6)C5)CC4)cn3)CC2)cc1C(F)(F)F]

Example 83 was synthesized in a similar way to the synthesis method of Example 1, using tert-butyl (R)-4-(pyrrolidin-3-ylmethyl)piperazine-1-carboxylate (Intermediate 4-2) instead of tert-butyl piperazine-1-carboxylate.

Example 84: 1-(4-cyano-3-(trifluoromethyl)phenyl)-N-(5-(4-((((1-(2-(2,6-dioxopiperidin-3-yl)-1,3-dioxoisoindolin-5-yl)piperidin-4-yl)methyl)(methyl)amino)methyl)piperidin-1-yl)pyridin-2-yl)piperidine-4-carboxamide

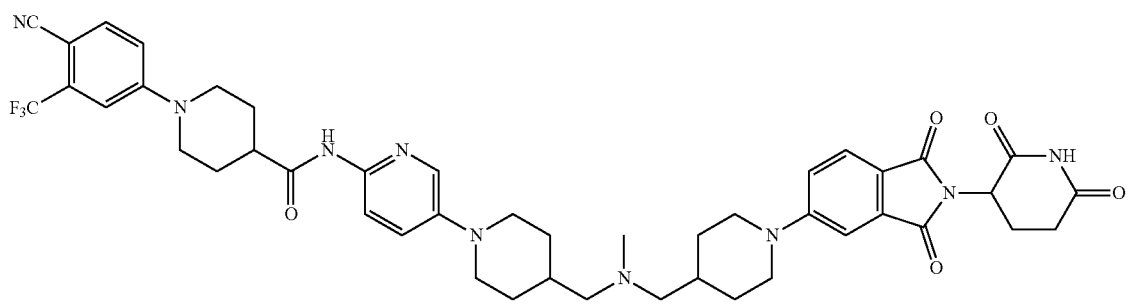 [SMILES: CN(CC1CCN(c2ccc(NC(=O)C3CCN(c4ccc(C#N)c(C(F)(F)F)c4)CC3)nc2)CC1)CC1CCN(c2ccc3c(c2)C(=O)N(C2CCC(=O)NC2=O)C3=O)CC1]

Example 84 was synthesized in a similar way to the synthesis method of Example 1, using tert-butyl 4-((methylamino)methyl)piperidine-1-carboxylate instead of tert-butyl piperazine-1-carboxylate.

Example 85: 1-(4-cyano-3-(trifluoromethyl)phenyl)-N-(5-(4-((5-(2-(2,6-dioxopiperidin-3-yl)-1,3-dioxoisoindolin-5-yl)hexahydropyrrolo[3,4-c]pyrrol-2(1H)-yl)methyl)piperidin-1-yl)pyridin-2-yl)piperidine-4-carboxamide

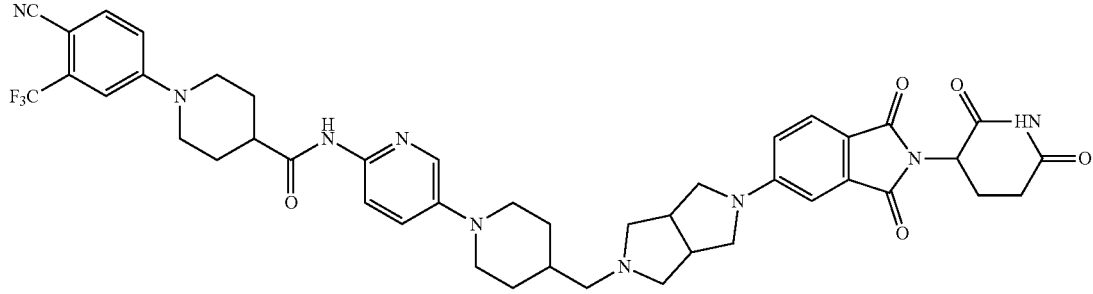 [SMILES: N#Cc1ccc(N2CCC(C(=O)Nc3ccc(N4CCC(CN5CC6CN(c7ccc8c(c7)C(=O)N(C7CCC(=O)NC7=O)C8=O)CC6C5)CC4)cn3)CC2)cc1C(F)(F)F]

Example 85 was synthesized in a similar way to the synthesis method of Example 1, using tert-butyl hexahydropyrrolo[3,4-c]pyrrole-2(1H)-carboxylate instead of tert-butyl piperazine-1-carboxylate.

Example 86: 1-(4-cyano-3-(trifluoromethyl)phenyl)-N-(5-(4-(2-(4-(2-(2,6-dioxopiperidin-3-yl)-1,3-dioxoisoindolin-5-yl)piperazin-1-yl)ethyl)piperidin-1-yl)pyridin-2-yl)piperidine-4-carboxamide

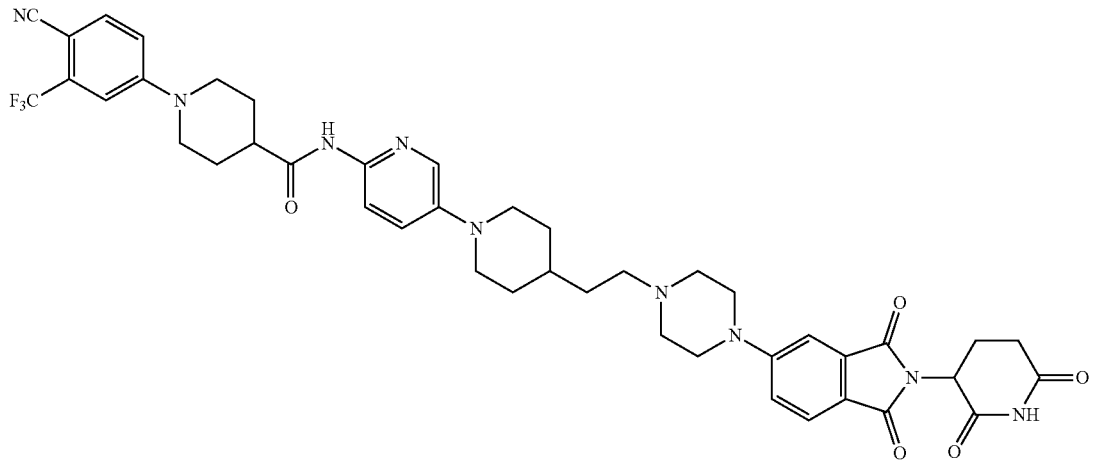 [SMILES: N#Cc1ccc(N2CCC(C(=O)Nc3ccc(N4CCC(CCN5CCN(c6ccc7c(c6)C(=O)N(C6CCC(=O)NC6=O)C7=O)CC5)CC4)cn3)CC2)cc1Cl]

Example 86 was synthesized in a similar way to the synthesis method of Example 1, using 2-(piperidin-4-yl)ethan-1-ol instead of piperidin-4-ylmethanol.

Example 87: 1-(3-chloro-4-cyanophenyl)-N-(5-(4-(2-(4-(2-(2,6-dioxopiperidin-3-yl)-1,3-dioxoisoindolin-5-yl)piperazin-1-yl)ethyl)piperidin-1-yl)pyridin-2-yl)piperidine-4-carboxamide

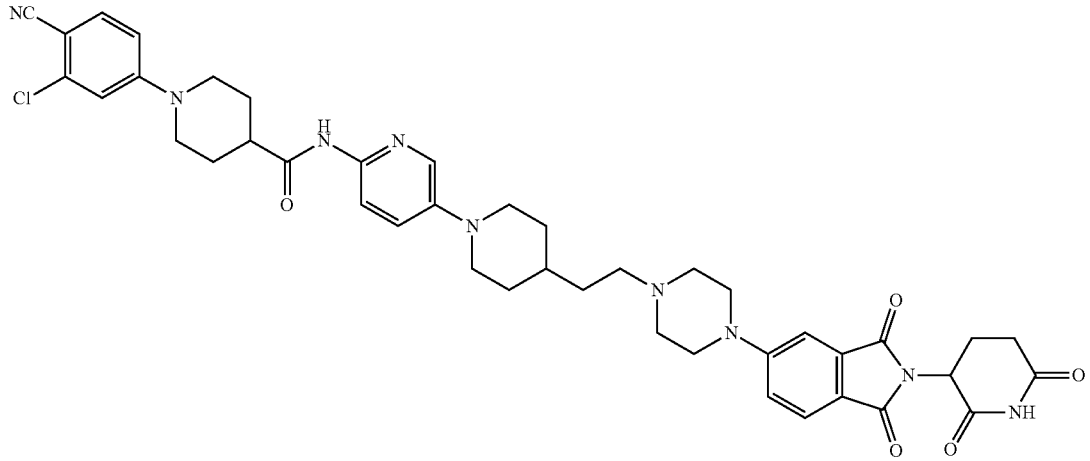

Example 87 was synthesized in a similar way to the synthesis method of Example 1, using 1-(3-chloro-4-cyanophenyl)piperidine-4-carboxylic acid (Intermediate 1-2) and 2-(piperidin-4-yl)ethan-1-ol, respectively, instead of 1-(4-cyano-3-(trifluoromethyl)phenyl)piperidine-4-carboxylic acid (Intermediate 1-1) and piperidin-4-ylmethanol.

Example 88: 1-(4-cyano-3-(trifluoromethyl)phenyl)-N-(5-(4-(2-(4-(2-(2,6-dioxopiperidin-3-yl)-1,3-dioxoisoindolin-5-yl)piperazin-1-yl)ethyl)piperidin-1-yl)pyridin-2-yl)-4-fluoropiperidine-4-carboxamide

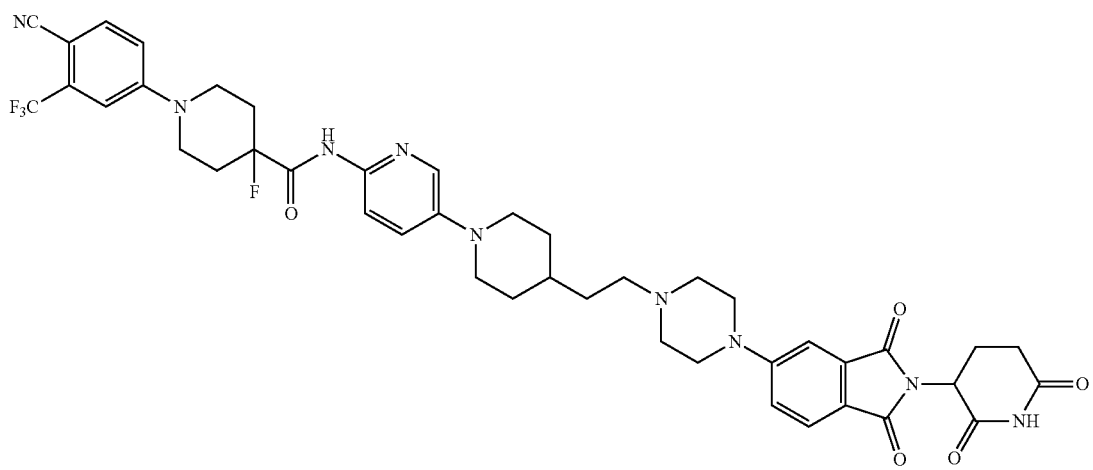

Example 88 was synthesized in a similar way to the synthesis method of Example 1, using 1-(4-cyano-3-(trifluoromethyl)phenyl)-4-fluoropiperidine-4-carboxylic acid (Intermediate 1-5) and 2-(piperidin-4-yl)ethan-1-ol, respectively, instead of 1-(4-cyano-3-(trifluoromethyl)phenyl)piperidine-4-carboxylic acid (Intermediate 1-1) and piperidin-4-ylmethanol.

Example 89: 1-(6-cyano-5-(trifluoromethyl)pyridin-3-yl)-N-(5-(4-(2-(4-(2-(2,6-dioxopiperidin-3-yl)-1,3-dioxoisoindolin-5-yl)piperazin-1-yl)ethyl)piperidin-1-yl)pyridin-2-yl)piperidine-4-carboxamide

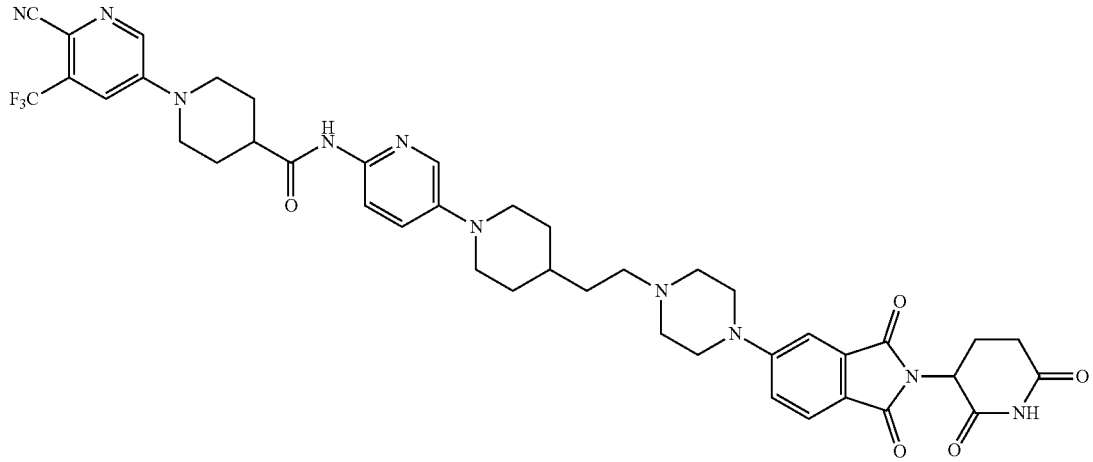

Example 89 was synthesized in a similar way to the synthesis method of Example 1, using 1-(6-cyano-5-(trifluoromethyl)pyridin-3-yl)piperidine-4-carboxylic acid (Intermediate 1-7) and 2-(piperidin-4-yl)ethan-1-ol, respectively, instead of 1-(4-cyano-3-(trifluoromethyl)phenyl)piperidine-4-carboxylic acid (Intermediate 1-1) and piperidin-4-ylmethanol.

Example 90: 1-(6-cyano-5-(trifluoromethyl)pyridin-3-yl)-N-(5-(4-(2-(4-(2-(2,6-dioxopiperidin-3-yl)-1,3-dioxoisoindolin-5-yl)piperazin-1-yl)ethyl)piperidin-1-yl)pyridin-2-yl)-4-fluoropiperidine-4-carboxamide

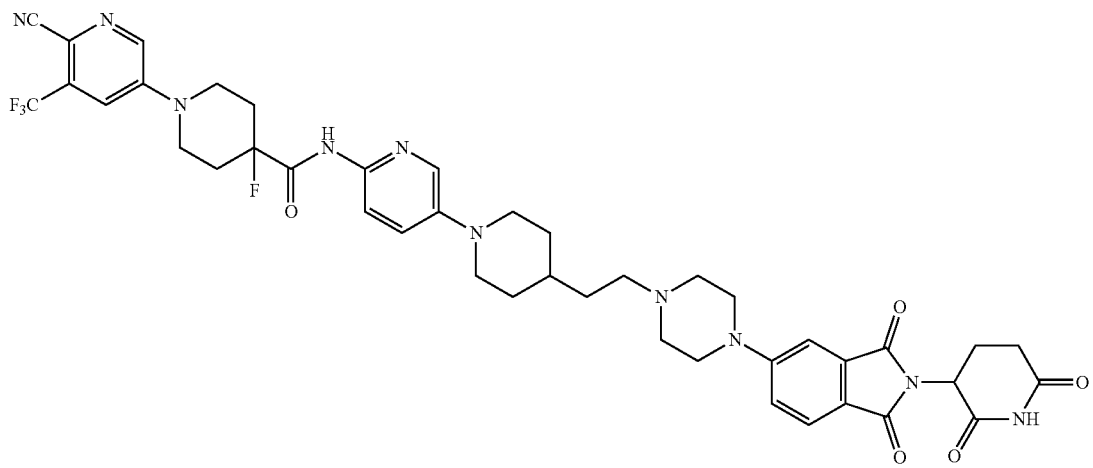

Example 90 was synthesized in a similar way to the synthesis method of Example 1, using 1-(6-cyano-5-(trifluoromethyl)pyridin-3-yl)-4-fluoropiperidine-4-carboxylic acid (Intermediate 1-8) and 2-(piperidin-4-yl)ethan-1-ol, respectively, instead of 1-(4-cyano-3-(trifluoromethyl)phenyl)piperidine-4-carboxylic acid (Intermediate 1-1) and piperidin-4-ylmethanol.

Example 91: 1-(4-cyano-3-(trifluoromethyl)phenyl)-N-(5-(4-(2-(4-(1-(2-(2,6-dioxopiperidin-3-yl)-1,3-dioxoisoindolin-5-yl)piperidin-4-yl)piperazin-1-yl)ethyl)piperidin-1-yl)pyridin-2-yl)piperidine-4-carboxamide

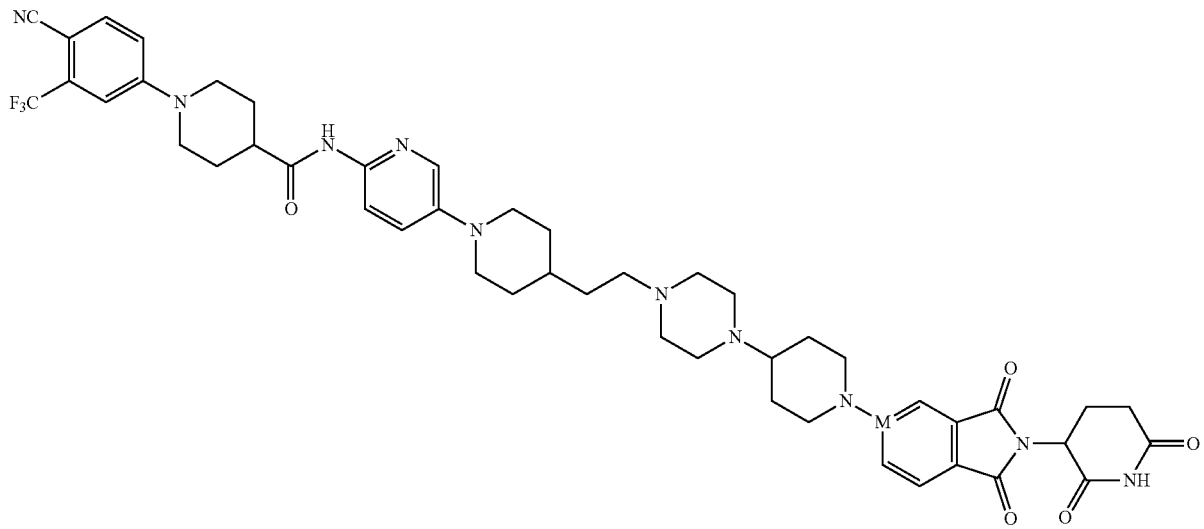

Example 91 was synthesized in a similar way to the synthesis method of Example 1, using 2-(piperidin-4-yl)ethan-1-ol and tert-butyl 4-(piperazin-1-yl)piperidine-1-carboxylate (Intermediate 4-9), respectively, instead of piperidin-4-ylmethanol and tert-butyl piperazine-1-carboxylate.

Example 92: 1-(4-cyano-3-(trifluoromethyl)phenyl)-N-(5-(4-(2-(4-(6-(2,6-dioxopiperidin-3-yl)-5-oxo-6,7-dihydro-5H-pyrrolo[3,4-b]pyridin-2-yl)piperazin-1-yl)ethyl)piperidin-1-yl)pyridin-2-yl)piperidine-4-carboxamide

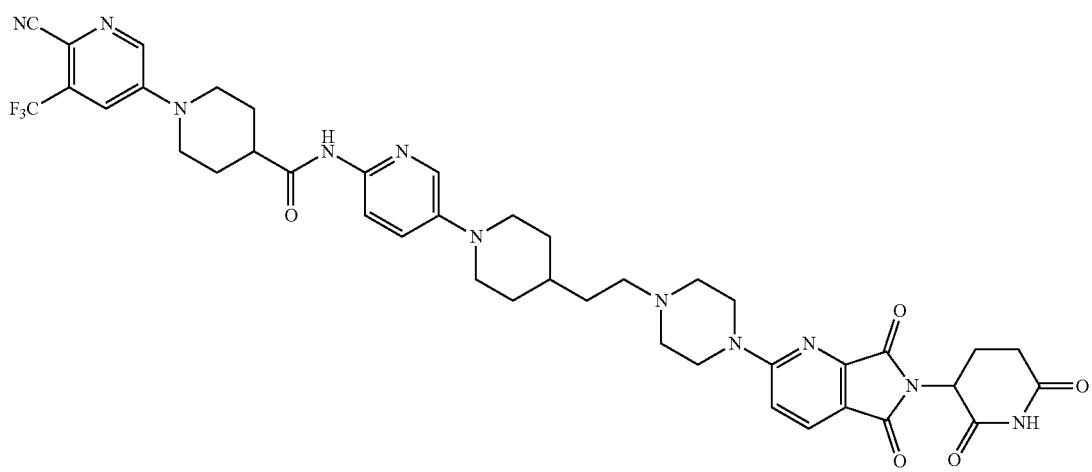

Example 92 was synthesized in a similar way to the synthesis method of Example 1, using 2-(piperidin-4-yl)ethan-1-ol and 3-(2-chloro-5-oxo-5,7-dihydro-6H-pyrrolo[3,4-b]pyridin-6-yl)piperidine-2,6-dione (Intermediate 2-6), respectively, instead of piperidin-4-ylmethanol and 2-(2,6-dioxopiperidin-3-yl)-5-fluoroisoindoline-1,3-dione (Intermediate 2-1).

Example 93: 1-(4-cyano-3-(trifluoromethyl)phenyl)-N-(5-(4-(2-(4-(2-(2,6-dioxopiperidin-3-yl)-1,3-dioxoisoindolin-4-yl)piperazin-1-yl)ethyl)piperidin-1-yl)pyridin-2-yl)piperidine-4-carboxamide

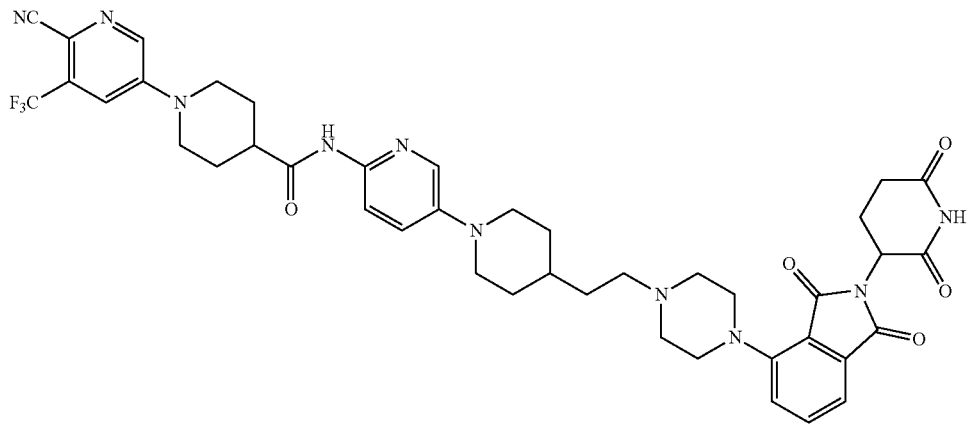 [SMILES: N#Cc1ncc(N2CCC(C(=O)Nc3ccc(N4CCC(CCN5CCN(c6cccc7c6C(=O)N(C6CCC(=O)NC6=O)C7=O)CC5)CC4)cn3)CC2)cc1C(F)(F)F]

Example 93 was synthesized in a similar way to the synthesis method of Example 1, using 2-(piperidin-4-yl)ethan-1-ol and 2-(2,6-dioxopiperidin-3-yl)-4-fluoroisoindoline-1,3-dione (Intermediate 2-2), respectively, instead of piperidin-4-ylmethanol and 2-(2,6-dioxopiperidin-3-yl)-5-fluoroisoindoline-1,3-dione (Intermediate 2-1).

Example 94: 1-(4-cyano-3-(trifluoromethyl)phenyl)-N-(5-(4-(2-(7-(2-(2,6-dioxopiperidin-3-yl)-1,3-dioxoisoindolin-5-yl)-2,7-diazaspiro[3.5]nonan-2-yl)ethyl)piperidin-1-yl)pyridin-2-yl)piperidine-4-carboxamide

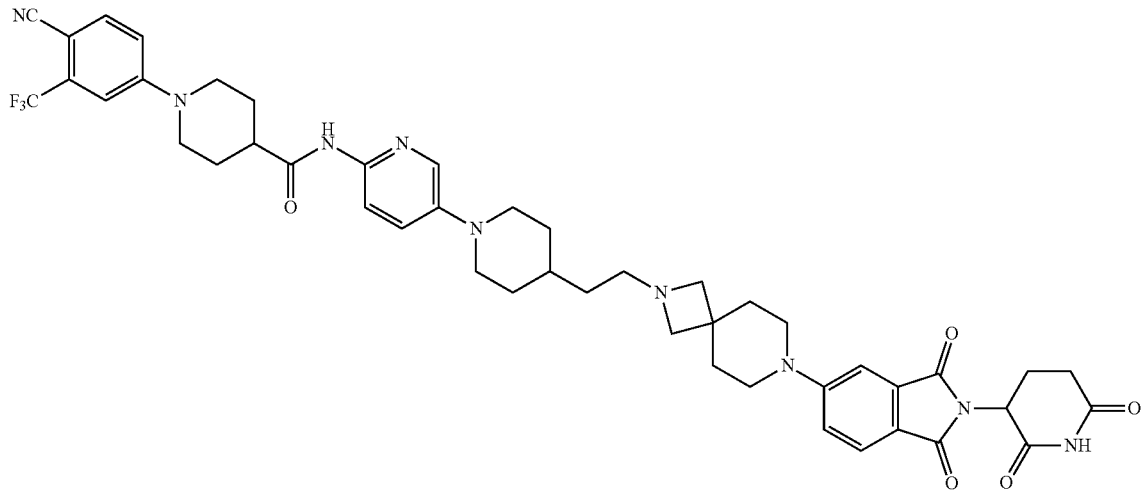 [SMILES: N#Cc1ccc(N2CCC(C(=O)Nc3ccc(N4CCC(CCN5CC6(CCN(c7ccc8c(c7)C(=O)N(C7CCC(=O)NC7=O)C8=O)CC6)C5)CC4)cn3)CC2)cc1C(F)(F)F]

Example 94 was synthesized in a similar way to the synthesis method of Example 1, using 2-(piperidin-4-yl)ethan-1-ol and tert-butyl 2,7-diazaspiro[3.5]nonane-7-carboxylate, respectively, instead of piperidin-4-ylmethanol and tert-butyl piperazine-1-carboxylate.

Example 95: 1-(4-cyano-3-(trifluoromethyl)phenyl)-N-(5-(4-(2-(2-(2-(2,6-dioxopiperidin-3-yl)-1,3-dioxoisoindolin-5-yl)-2,7-diazaspiro[3.5]nonan-7-yl)ethyl)piperidin-1-yl)pyridin-2-yl)piperidine-4-carboxamide

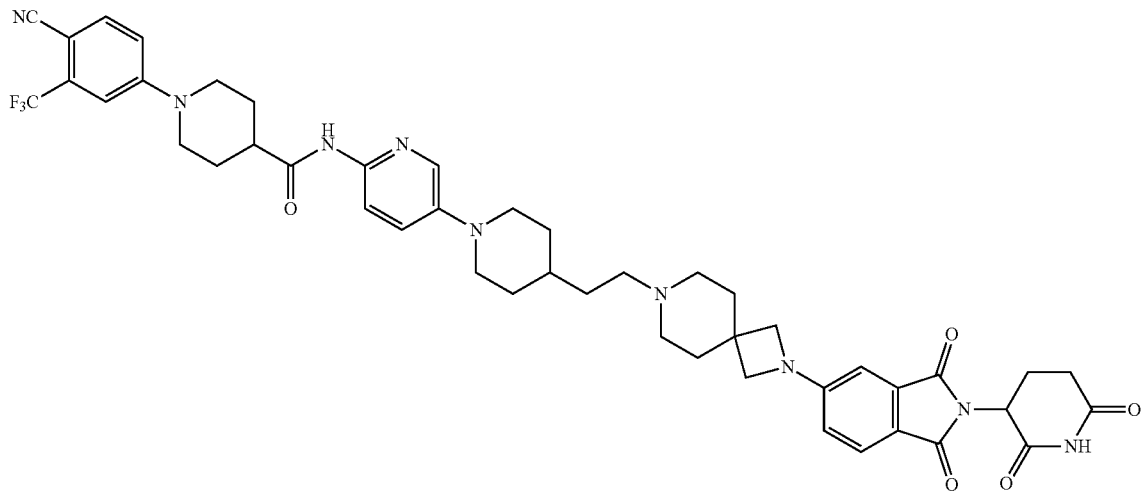 [SMILES: N#Cc1ccc(N2CCC(C(=O)Nc3ccc(N4CCC(CCN5CCC6(CC5)CN(c5ccc7c(c5)C(=O)N(C5CCC(=O)NC5=O)C7=O)C6)CC4)cn3)CC2)cc1C(F)(F)F]

Example 95 was synthesized in a similar way to the synthesis method of Example 1, using 2-(piperidin-4-yl)ethan-1-ol and tert-butyl 2,7-diazaspiro[3.5]nonane-2-carboxylate, respectively, instead of piperidin-4-ylmethanol and tert-butyl piperazine-1-carboxylate.

Example 96: 1-(4-cyano-3-(trifluoromethyl)phenyl)-N-(5-(4-(2-(2-(6-(2,6-dioxopiperidin-3-yl)-5-oxo-6,7-dihydro-5H-pyrrolo[3,4-b]pyridin-2-yl)-2,7-diazaspiro[3.5]nonan-7-yl)ethyl)piperidin-1-yl)pyridin-2-yl)piperidine-4-carboxamide

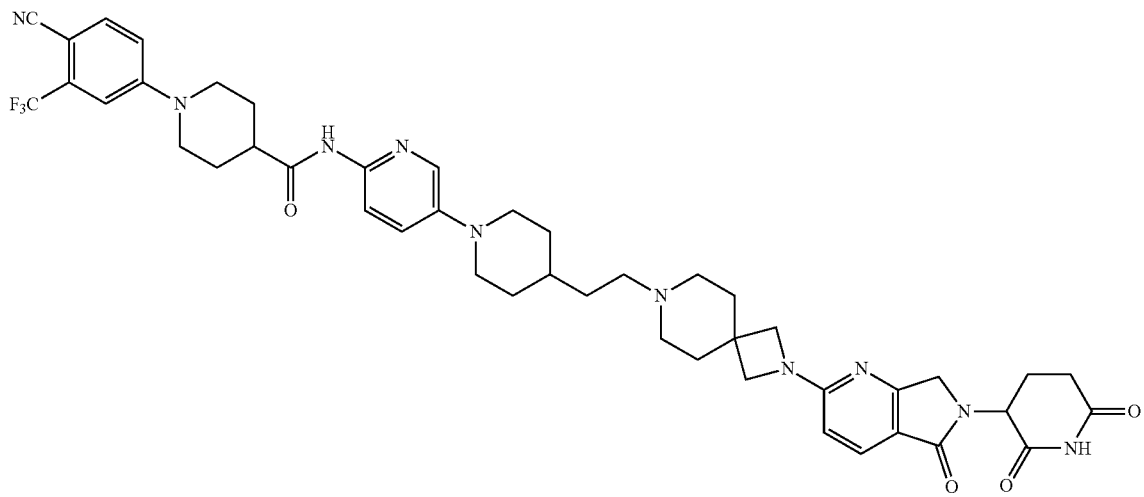 [SMILES: N#Cc1ccc(N2CCC(C(=O)Nc3ccc(N4CCC(CCN5CCC6(CC5)CN(c5ccc7c(n5)CN(C5CCC(=O)NC5=O)C7=O)C6)CC4)cn3)CC2)cc1C(F)(F)F]

Example 96 was synthesized in a similar way to the synthesis method of Example 1, using 2-(piperidin-4-yl)ethan-1-ol, tert-butyl 2,7-diazaspiro[3.5]nonane-2-carboxylate, and 3-(2-chloro-5-oxo-5,7-dihydro-6H-pyrrolo[3,4-b]pyridin-6-yl)piperidine-2,6-dione (Intermediate 2-6), respectively, instead of piperidin-4-ylmethanol, tert-butyl piperazine-1-carboxylate, and 2-(2,6-dioxopiperidin-3-yl)-5-fluoroisoindoline-1,3-dione (Intermediate 2-1).

Example 97: 1-(4-cyano-3-(trifluoromethyl)phenyl)-
N-(5-(4-(2-(3-(4-(2-(2,6-dioxopiperidin-3-yl)-1,3-
dioxoisoindolin-5-yl)piperazin-1-yl)azetidin-1-yl)
ethyl)piperidin-1-yl)pyridin-2-yl)piperidine-4-
carboxamide

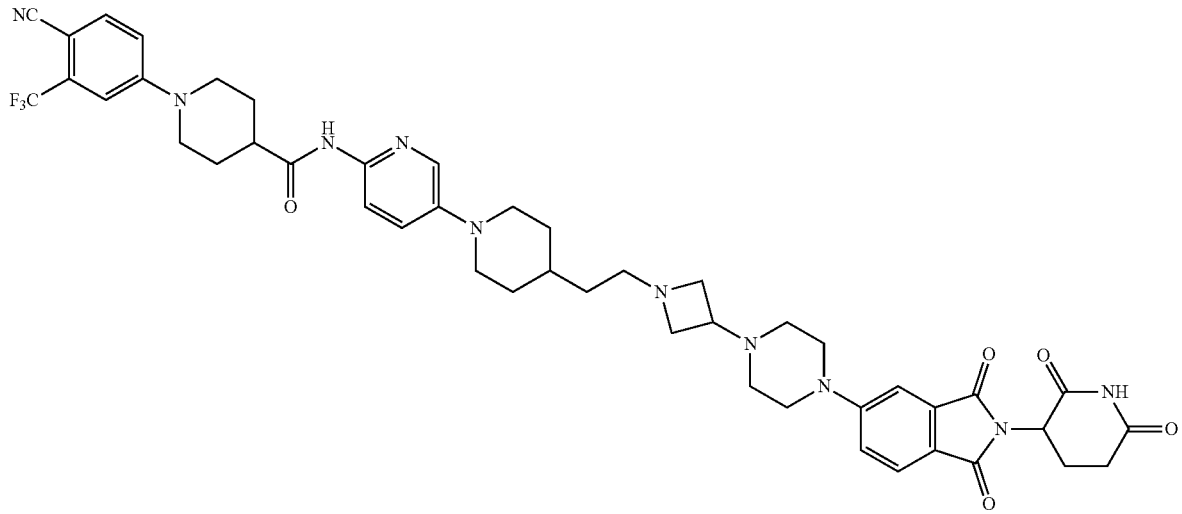 [SMILES: N#Cc1ccc(N2CCC(C(=O)Nc3ccc(N4CCC(CCN5CC(N6CCN(c7ccc8c(c7)C(=O)N(C7CCC(=O)NC7=O)C8=O)CC6)C5)CC4)cn3)CC2)cc1C(F)(F)F]

Example 97 was synthesized in a similar way to the synthesis method of Example 1, using 2-(piperidin-4-yl)ethan-1-ol and tert-butyl 4-(azetidin-3-yl)piperazine-1-carboxylate (Intermediate 4-6), respectively, instead of piperidin-4-ylmethanol and tert-butyl piperazine-1-carboxylate.

Example 98: 1-(4-cyano-3-(trifluoromethyl)phenyl)-
N-(5-(4-(2-(3-(4-(6-(2,6-dioxopiperidin-3-yl)-5-oxo-
6,7-dihydro-5H-pyrrolo[3,4-b]pyridin-2-yl)piper-
azin-1-yl)azetidin-1-yl)ethyl)piperidin-1-yl)pyridin-
2-yl)piperidine-4-carboxamide

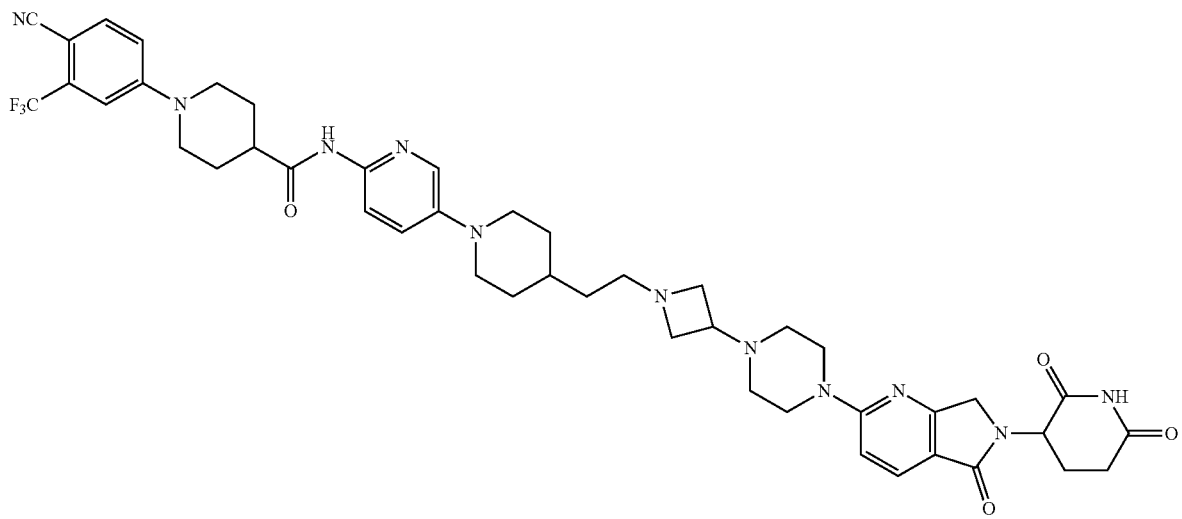 [SMILES: N#Cc1ccc(N2CCC(C(=O)Nc3ccc(N4CCC(CCN5CC(N6CCN(c7ccc8c(n7)CN(C7CCC(=O)NC7=O)C8=O)CC6)C5)CC4)cn3)CC2)cc1C(F)(F)F]

Example 98 was synthesized in a similar way to the synthesis method of Example 1, using 2-(piperidin-4-yl)ethan-1-ol, tert-butyl 4-(azetidin-3-yl)piperazine-1-carboxylate (Intermediate 4-6), and 3-(2-chloro-5-oxo-5,7-dihydro-6H-pyrrolo[3,4-b]pyridin-6-yl)piperidine-2,6-dione (Intermediate 2-6), respectively, instead of piperidin-4-ylmethanol, tert-butyl piperazine-1-carboxylate, and 2-(2,6-dioxopiperidin-3-yl)-5-fluoroisoindoline-1,3-dione (Intermediate 2-1).

Example 99: 1-(4-cyano-3-(trifluoromethyl)phenyl)-N-(5-(4-(2-(4-(1-(2-(2,6-dioxopiperidin-3-yl)-1,3-dioxoisoindolin-5-yl)azetidin-3-yl)piperazin-1-yl)ethyl)piperidin-1-yl)pyridin-2-yl)piperidine-4-carboxamide

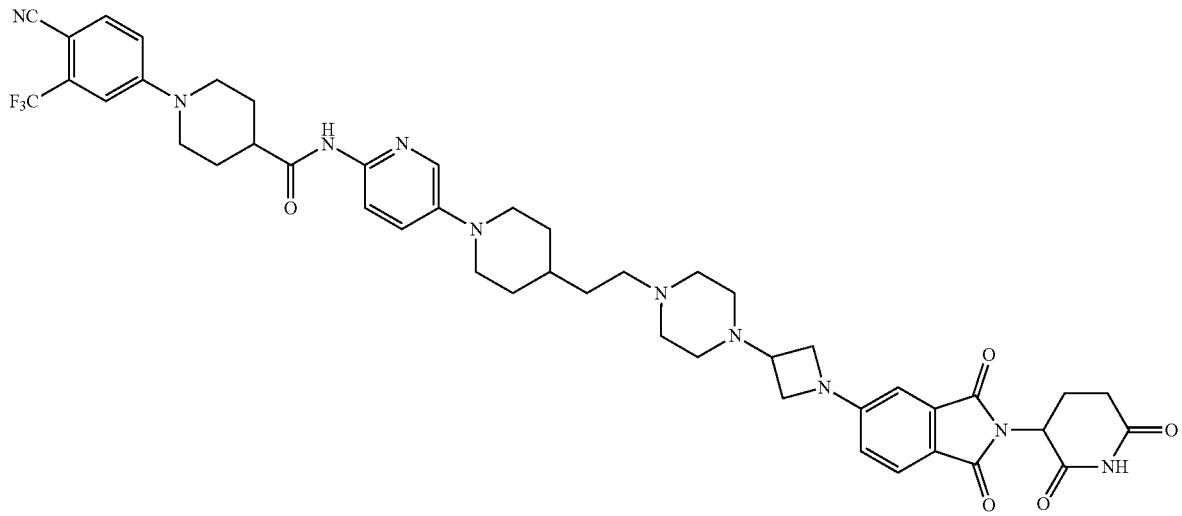 [SMILES: N#Cc1ccc(N2CCC(C(=O)Nc3ccc(N4CCC(CCN5CCN(C6CN(c7ccc8c(c7)C(=O)N(C7CCC(=O)NC7=O)C8=O)C6)CC5)CC4)cn3)CC2)cc1C(F)(F)F]

Example 99 was synthesized in a similar way to the synthesis methods of Examples 1 and 33, using 2-(piperidin-4-yl)ethan-1-ol and 2-(2,6-dioxopiperidin-3-yl)-5-fluoroisoindoline-1,3-dione (Intermediate 2-1), respectively, instead of piperidin-4-ylmethanol and 3-(2-chloro-5-oxo-5,7-dihydro-6H-pyrrolo[3,4-b]pyridin-6-yl)piperidine-2,6-dione (Intermediate 2-6).

Example 100: 1-(4-cyano-3-(trifluoromethyl)phenyl)-N-(5-(4-(2-(4-(1-(6-(2,6-dioxopiperidin-3-yl)-5-oxo-6,7-dihydro-5H-pyrrolo[3,4-b]pyridin-2-yl)azetidin-3-yl)piperazin-1-yl)ethyl)piperidin-1-yl)pyridin-2-yl)piperidine-4-carboxamide

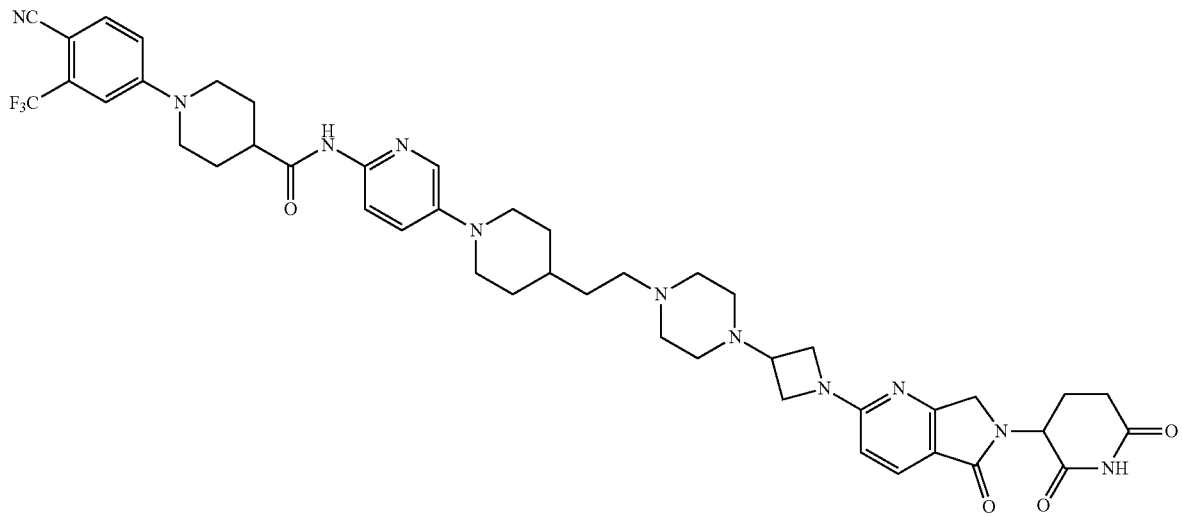 [SMILES: N#Cc1ccc(N2CCC(C(=O)Nc3ccc(N4CCC(CCN5CCN(C6CN(c7ccc8c(n7)CN(C7CCC(=O)NC7=O)C8=O)C6)CC5)CC4)cn3)CC2)cc1C(F)(F)F]

Example 100 was synthesized in a similar way to the synthesis methods of Examples 1 and 33, using 2-(piperidin-4-yl)ethan-1-ol instead of piperidin-4-ylmethanol.

Example 101: 1-(4-cyano-3-(trifluoromethyl)phenyl)-N-(5-(4-(2-(5-(2-(2,6-dioxopiperidin-3-yl)-1,3-dioxoisoindolin-5-yl)hexahydropyrrolo[3,4-c]pyrrol-2(1H)-yl)ethyl)piperidin-1-yl)pyridin-2-yl)piperidine-4-carboxamide

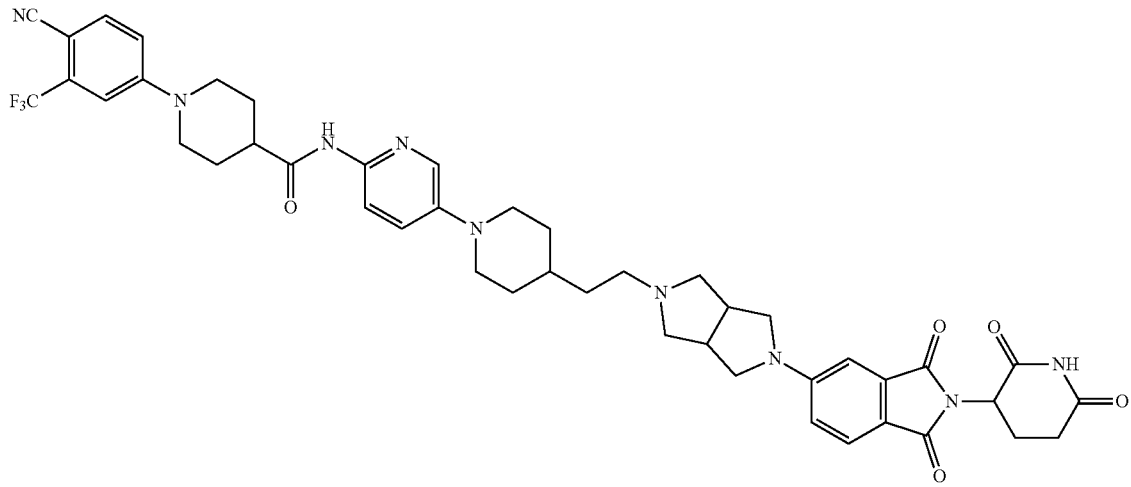 [SMILES: N#Cc1ccc(N2CCC(C(=O)Nc3ccc(N4CCC(CCN5CC6CN(c7ccc8c(c7)C(=O)N(C7CCC(=O)NC7=O)C8=O)CC6C5)CC4)cn3)CC2)cc1C(F)(F)F]

Example 101 was synthesized in a similar way to the synthesis method of Example 1, using 2-(piperidin-4-yl)ethan-1-ol and tert-butyl hexahydropyrrolo[3,4-c]pyrrole-2(1H)-carboxylate, respectively, instead of piperidin-4-ylmethanol and tert-butyl piperazine-1-carboxylate.

Example 102: 1-(4-cyano-3-(trifluoromethyl)phenyl)-N-(5-(4-(2-((1-(2-(2,6-dioxopiperidin-3-yl)-1,3-dioxoisoindolin-5-yl)piperidin-4-yl)(methyl)amino)ethyl)piperidin-1-yl)pyridin-2-yl)piperidine-4-carboxamide

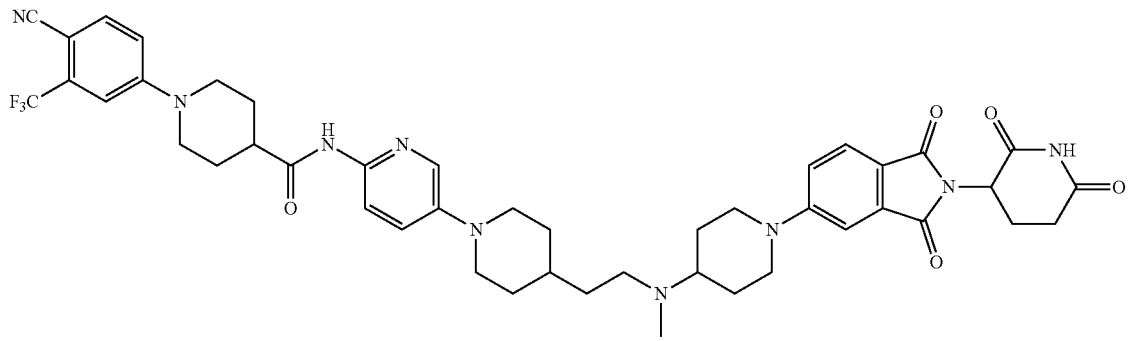 [SMILES: CN(CCC1CCN(c2ccc(NC(=O)C3CCN(c4ccc(C#N)c(C(F)(F)F)c4)CC3)nc2)CC1)C1CCN(c2ccc3c(c2)C(=O)N(C2CCC(=O)NC2=O)C3=O)CC1]

Example 102 was synthesized in a similar way to the synthesis method of Example 1, using 2-(piperidin-4-yl)ethan-1-ol and tert-butyl 4-(methylamino)piperidine-1-carboxylate, respectively, instead of piperidin-4-ylmethanol and tert-butyl piperazine-1-carboxylate.

Example 103: 4-(4-cyano-3-(trifluoromethyl)phenyl)-N-(6-(4-((7-(2-(2,6-dioxopiperidin-3-yl)-1,3-dioxoisoindolin-5-yl)-2,7-diazaspiro[3.5]nonan-2-yl)methyl)piperidin-1-yl)pyridin-3-yl)piperazine-1-carboxamide

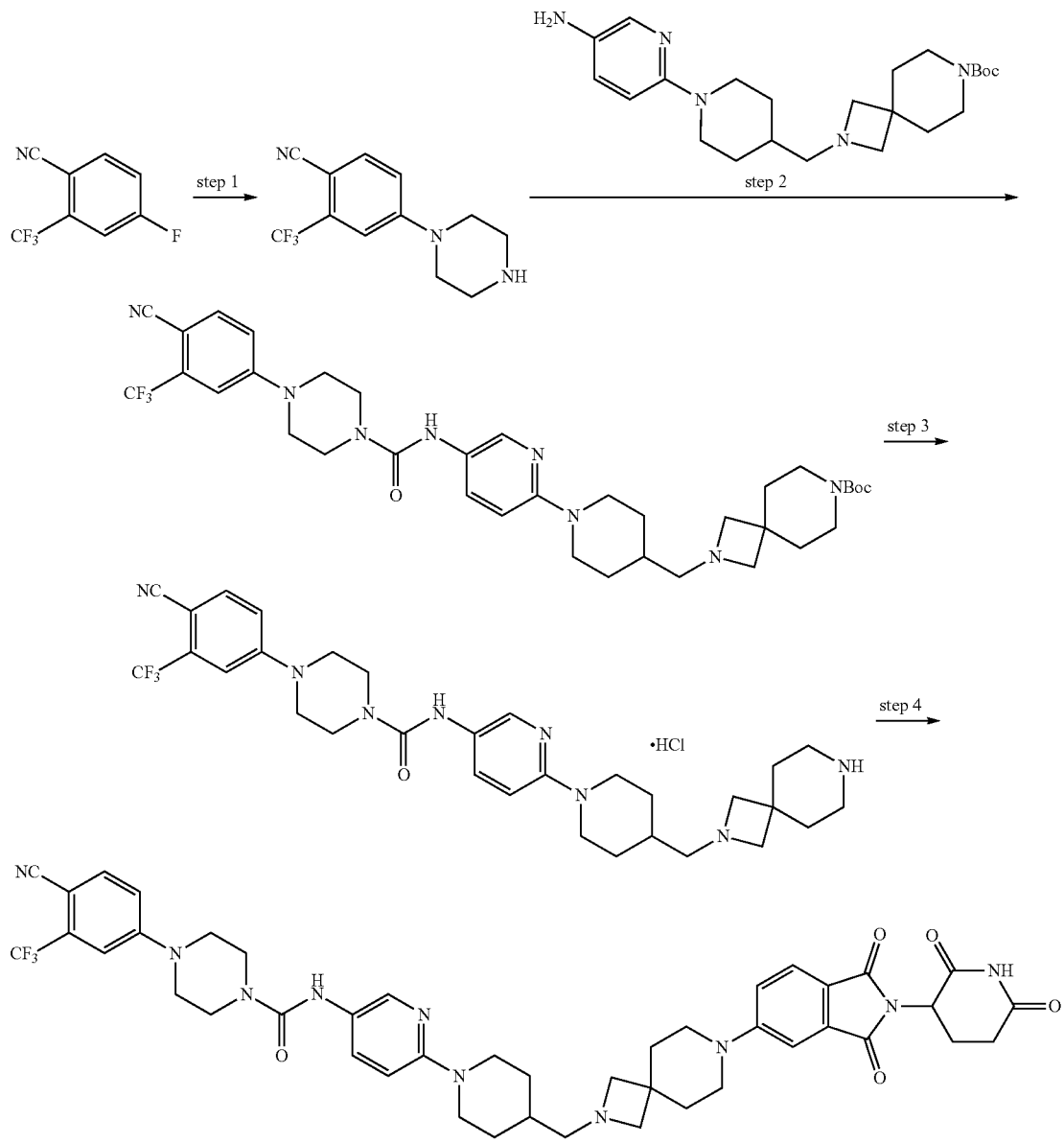

Step 1: Synthesis of 4-(piperazin-1-yl)-2-(trifluoromethyl)benzonitrile 4-fluoro-2-(trifluoromethyl)benzonitrile (1.00 g, 5.29 mmol), and piperazine (683 mg, 7.93 mmol) were suspended in DMF (5.0 mL) and stirred at 85° C. for 1 hour. After adding distilled water (20 mL) to the reaction solution, extraction was performed with EtOAc (20 mL×2), and the organic layer was dried over anhydrous sodium sulfate, filtered, and concentrated under reduced pressure. The resulting residue was subjected to MPLC (10% DCM/MeOH) to give 968 mg (72%) of a white solid. m/z 256.13 [M+H]+.

Step 2: Synthesis of tert-butyl 2-((1-(5-(4-(4-cyano-3-(trifluoromethyl)phenyl)piperazine-1-carboxamido)pyridin-2-yl)piperidin-4-yl)methyl)-2,7-diazaspiro[3.5]nonane-7-carboxylate After suspending tert-butyl 2-((1-(5-aminopyridin-2-yl)piperidin-4-yl)methyl)-2,7-diazaspiro[3.5]nonane-7-carboxylate (100 mg, 0.24 mmol) in ACN (5.0 mL), phenyl chloroformate (0.04 mL, 0.26 mmol), triethylamine (0.04 mL, 0.26 mmol), and DMAP (30 mg, 0.24 mmol) were added at 0° C. and stirred at room temperature for 3 hours. After adding distilled water (20 mL) to the reaction solution, extraction was performed with EtOAc (20 mL×2), and the organic layer was dried over anhydrous sodium sulfate, filtered, and concentrated under reduced pressure. After suspending the obtained residue in ACN (5.0 mL), 4-(piperazin-1-yl)-2-(trifluoromethyl)benzonitrile (91 mg, 0.36 mmol) and pyridine (0.02 mL, 0.26 mmol) were added and stirred at 90° C. for 16 hours. After adding distilled water (20 mL) to the reaction solution, extraction was performed with EtOAc (20 mL×2), and the organic layer was dried over anhydrous magnesium sulfate, filtered, and concentrated under reduced pressure. The obtained residue was subjected to MPLC (10% MeOH/DCM) to give 33 mg (19%) of a purple solid. m/z 697.47 [M+H]$^+$.

Step 3: Synthesis of N-(6-(4-((2,7-diazaspiro[3.5]nonan-2-yl)methyl)piperidin-1-yl)pyridin-3-yl)-4-(4-cyano-3-(trifluoromethyl)phenyl)piperazine-1-carboxamide hydrochloride After suspending tert-butyl 2-((1-(5-(4-(4-cyano-3-(trifluoromethyl)phenyl)piperazine-1-carboxamido)pyridin-2-yl)piperidin-4-yl)methyl)-2,7-diazaspiro[3.5]nonane-7-carboxylate (33 mg, 0.47 mmol) in DCM (0.5 mL), 4M HCl in dioxane (0.2 mL, 0.47 mmol) was added and stirred at room temperature for 2 hours. The reaction solution was filtered and concentrated under reduced pressure. 29 mg (99%) of a purple solid was obtained.

Step 4: Synthesis of 4-(4-cyano-3-(trifluoromethyl)phenyl)-N-(6-(4-((7-(2-(2,6-dioxopiperidin-3-yl)-1,3-dioxoisoindolin-5-yl)-2,7-diazaspiro[3.5]nonan-2-yl)methyl)piperidin-1-yl)pyridin-3-yl)piperazine-1-carboxamide N-(6-(4-((2,7-diazaspiro[3.5]nonan-2-yl)methyl)piperidin-1-yl)pyridin-3-yl)-4-(4-cyano-3-(trifluoromethyl)phenyl)piperazine-1-carboxamide hydrochloride (29 mg, 0.050 mmol), 2-(2,6-dioxopiperidin-3-yl)-5-fluoroisoindoline-1,3-dione (Intermediate 2-1, 21 mg, 0.075 mmol), and DIPEA (0.013 mL, 0.075 mmol) were suspended in DMSO (1.0 ml) and stirred at 90° C. for 16 hours. After adding water (15 ml) to the reaction solution, extraction was performed with EtOAc (25 ml×2), and the organic layer was dried over anhydrous sodium sulfate, filtered, and concentrated under reduced pressure. The obtained residue was subjected to MPLC (10% MeOH/DCM) to give 3 mg (7%) of a yellow solid.

Example 104: 4-(3-chloro-4-cyanophenyl)-N-(6-(4-((7-(2-(2,6-dioxopiperidin-3-yl)-1,3-dioxoisoindolin-5-yl)-2,7-diazaspiro[3.5]nonan-2-yl)methyl)piperidin-1-yl)pyridin-3-yl)piperazine-1-carboxamide

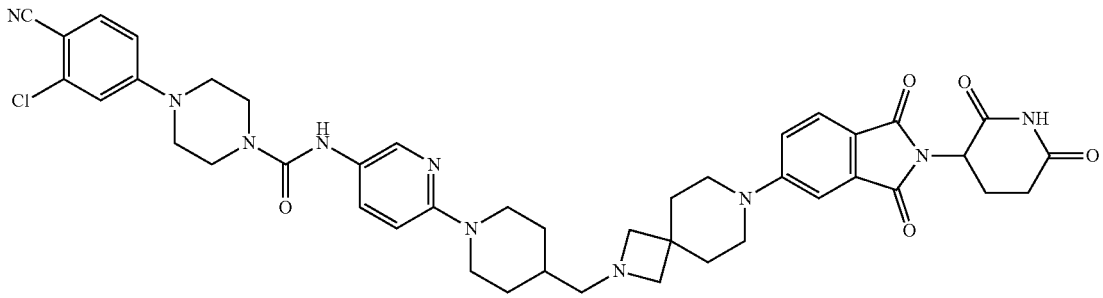 [SMILES: N#Cc1ccc(N2CCN(C(=O)Nc3ccc(N4CCC(CN5CC6(CCN(c7ccc8c(c7)C(=O)N(C7CCC(=O)NC7=O)C8=O)CC6)C5)CC4)nc3)CC2)cc1Cl]

Example 104 was synthesized in a similar way to the synthesis method of Example 103, using 2-chloro-4-fluorobenzonitrile instead of 4-fluoro-2-(trifluoromethyl)benzonitrile.

Example 105: 5-(4-(4-((1-(6-(1-(4-cyano-3-(trifluoromethyl)phenyl)piperidine-4-carboxamido)pyridin-3-yl)piperidin-4-yl)methyl)piperazin-1-yl)piperidin-1-yl)-N-(2,6-dioxopiperidin-3-yl)picolinamide

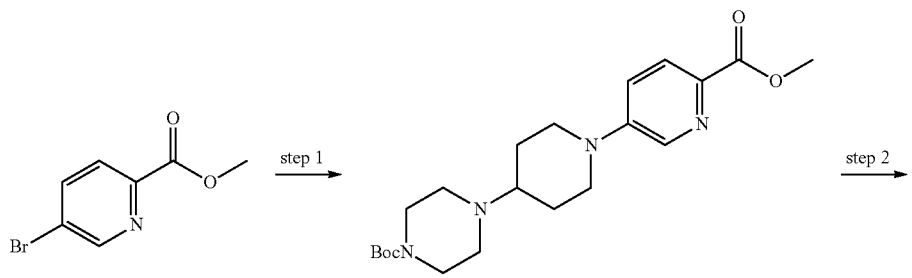

-continued
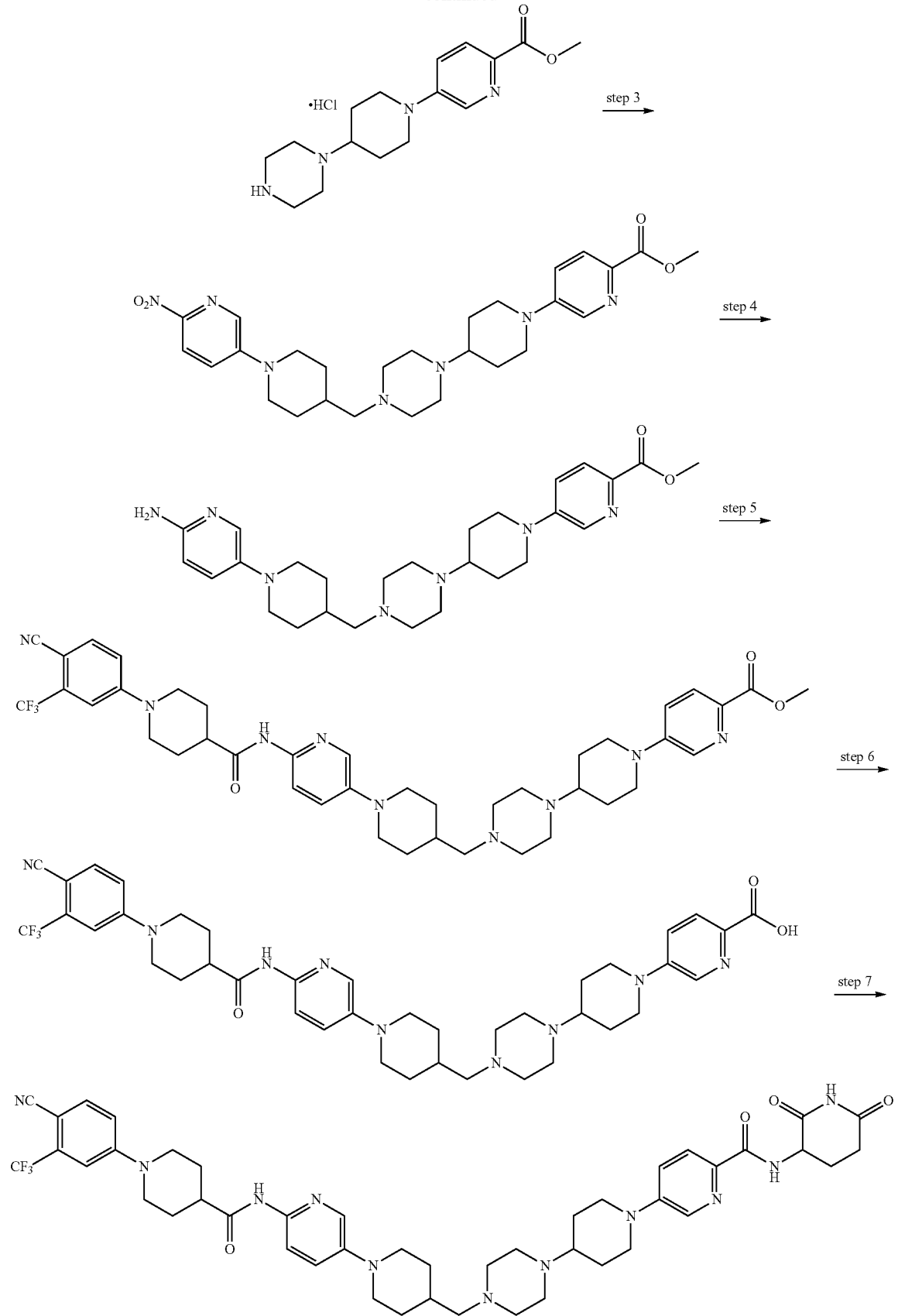

Step 1: Synthesis of tert-butyl 4-(1-(6-(methoxycarbonyl)pyridin-3-yl)piperidin-4-yl)piperazine-1-carboxylate Methyl 5-bromopicolinate (100 mg, 0.463 mmol), tert-butyl 4-(piperidin-4-yl)piperazine-1-carboxylate (Intermediate 4-4, 125 mg, 0.463 mmol), $Pd_2(dba)_3$ (12 mg, 0.0139 mmol), Ruphos (21 mg, 0.0463 mmol), and $Cs_2CO_3$ (452 mg, 1.39 mmol) were suspended in toluene (10.0 mL) and stirred at room temperature for 2 hours. After adding distilled water (15 ml) to the reaction solution, extraction was performed with EtOAc (25 ml×2), and the organic layer was dried over anhydrous sodium sulfate, filtered, and concentrated under reduced pressure. The obtained residue was subjected to MPLC (10% MeOH/DCM) to give 66 mg (35%) of a white solid. m/z 405.41 [M+Na]$^+$.

Step 2: Synthesis of methyl 5-(4-(piperazin-1-yl)piperidin-1-yl)picolinate hydrochloride After suspending tert-butyl 4-(1-(6-(methoxycarbonyl) pyridin-3-yl)piperidin-4-yl)piperazine-1-carboxylate (66 mg, 0.16 mmol) in DCM (1.0 mL), 4M HCl in dioxane (0.20 mL, 0.82 mmol) was added and stirred at room temperature for 2 hours. The reaction solution was concentrated under reduced pressure. 54 mg (100%) of a white solid was obtained.

Step 3: Synthesis of methyl 5-(4-(4-((1-(6-nitropyridin-3-yl)piperidin-4-yl)methyl)piperazin-1-yl)piperidin-1-yl)picolinate After suspending methyl 5-(4-(piperazin-1-yl)piperidin-1-yl)picolinate hydrochloride (54 mg, 0.16 mmol) and 1-(6-nitropyridin-3-yl)piperidine-4-carbaldehyde (37 mg, 0.16 mmol) in ACN (5.0 ml), sodium triacetoxyborohydride (101 mg, 0.48 mmol) were added and stirred at room temperature for 16 hours. $NaHCO_3$ aqueous solution (15 ml) was added to the reaction mixture, followed by extraction with EtOAc (25 ml×2), and the organic layer was dried over anhydrous sodium sulfate, filtered, and concentrated under reduced pressure. The resulting residue was subjected to MPLC (10% MeOH/DCM) to give 34 mg (41%) of a yellow solid. m/z 524.28 [M+H]$^+$.

Step 4: Synthesis of methyl 5-(4-(4-((1-(6-amino-pyridin-3-yl)piperidin-4-yl)methyl)piperazin-1-yl) piperidin-1-yl)picolinate After dissolving methyl 5-(4-(4-((1-(6-nitropyridin-3-yl) piperidin-4-yl)methyl)piperazin-1-yl)piperidin-1-yl)picolinate (34 mg, 0.065 mmol) in a mixture of DCM (3 mL) and MeOH (1 mL), Pd/C (10 wt % Pd, 3 mg) was added and stirred for 6 hours at room temperature under a hydrogen stream. The reaction solution was filtered and concentrated. 31 mg (97%) of a purple solid was obtained. m/z 494.38 [M+H]$^+$.

Step 5: Synthesis of methyl 5-(4-(4-((1-(6-(1-(4-cyano-3-(trifluoromethyl)phenyl)piperidine-4-carboxamido)pyridin-3-yl)piperidin-4-yl)methyl)piperazin-1-yl)piperidin-1-yl)picolinate Methyl 5-(4-(4-((1-(6-aminopyridin-3-yl)piperidin-4-yl) methyl)piperazin-1-yl)piperidin-1-yl)picolinate (31 mg, 0.063 mmol), 1-(4-cyano-3-(trifluoromethyl)phenyl)piperidine-4-carboxylic acid (Intermediate 1-1, 22 mg, 0.076 mmol), HATU (28 mg, 0.076 mmol), and DIPEA (0.02 mL, 0.13 mmol) were suspended in DMF (1.0 ml) and stirred at room temperature for 16 hours. After adding distilled water (15 ml) to the reaction solution, extraction was performed with EtOAc (20 ml×2), and the organic layer was dried over anhydrous sodium sulfate, filtered, and concentrated under reduced pressure. The obtained residue was subjected to MPLC (10% MeOH/DCM) to give 20 mg (41%) of a gray solid. m/z 796.49 [M+Na]$^+$.

Step 6: Synthesis of 5-(4-(4-((1-(6-(1-(4-cyano-3-(trifluoromethyl)phenyl)piperidine-4-carboxamido) pyridin-3-yl)piperidin-4-yl)methyl)piperazin-1-yl) piperidin-1-yl)picolinic acid After suspending methyl 5-(4-(4-((1-(6-(1-(4-cyano-3-(trifluoromethyl)phenyl)piperidine-4-carboxamido)pyridin-3-yl)piperidin-4-yl)methyl)piperazin-1-yl)piperidin-1-yl)picolinate (20 mg, 0.026 mmol) in THF (3.0 mL) and distilled water (1.0 mL), LiOH·$H_2O$ (4 mg, 0.11 mmol) was added and stirred at room temperature for 3 hours. After evaporation of the solvent and extraction with distilled water, 1N HCl was added to the aqueous layer and extraction was performed with EtOAc (20 ml×2). The organic layer was dried over anhydrous sodium sulfate, filtered, and concentrated under reduced pressure to give 18 mg (91%) of a white solid. m/z 760.51 [M+H]$^+$.

Step 7: Synthesis of 5-(4-(4-((1-(6-(1-(4-cyano-3-(trifluoromethyl)phenyl)piperidine-4-carboxamido) pyridin-3-yl)piperidin-4-yl)methyl)piperazin-1-yl) piperidin-1-yl)-N-(2,6-dioxopiperidin-3-yl) picolinamide 5-(4-(4-((1-(6-(1-(4-cyano-3-(trifluoromethyl)phenyl)piperidine-4-carboxamido)pyridin-3-yl)piperidin-4-yl) methyl)piperazin-1-yl)piperidin-1-yl)picolinic acid (18 mg, 0.024 mmol), 3-aminopiperidine-2,6-dione Hydrochloride (5 mg, 0.028 mmol), HATU (11 mg, 0.028 mmol), and DIPEA (0.01 mL, 0.048 mmol) were suspended in DMF (1.0 ml) and stirred at room temperature for 16 hours. After adding distilled water (15 ml) to the reaction solution, extraction was performed with EtOAc (25 ml×2), and the organic layer was dried over anhydrous sodium sulfate, filtered, and concentrated under reduced pressure. The resulting residue was subjected to MPLC (10% MeOH/DCM) to give 10 mg (48%) of a yellow solid.

Example 106: 5-(4-((4-((1-(6-(1-(4-cyano-3-(trifluoromethyl)phenyl)piperidine-4-carboxamido)pyridin-3-yl)piperidin-4-yl)methyl)piperazin-1-yl)methyl)piperidin-1-yl)-N-(2,6-dioxopiperidin-3-yl)picolinamide

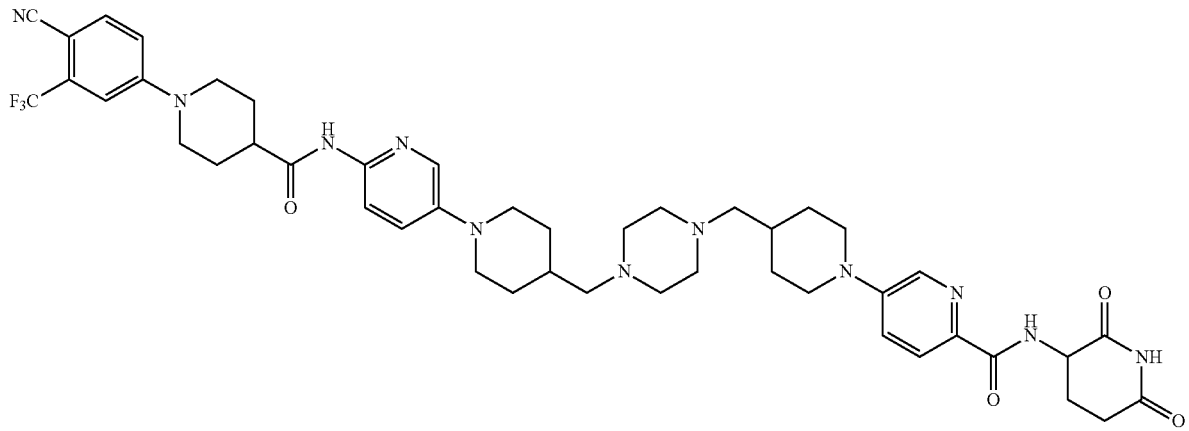 [SMILES: N#Cc1ccc(N2CCC(C(=O)Nc3ccc(N4CCC(CN5CCN(CC6CCN(c7ccc(C(=O)NC8CCC(=O)NC8=O)nc7)CC6)CC5)CC4)cn3)CC2)cc1C(F)(F)F]

Example 106 was synthesized in a similar way to the synthesis method of Example 105, using tert-butyl 4-(piperidin-4-ylmethyl)piperazine-1-carboxylate (Intermediate 4-3) instead of III tert-butyl 4-(piperidin-4-yl)piperazine-1-carboxylate (Intermediate 4-4).

Example 107: 5-(4-(2-(1-(6-(1-(4-cyano-3-(trifluoromethyl)phenyl)piperidine-4-carboxamido)pyridin-3-yl)piperidin-4-yl)ethyl)piperazin-1-yl)-N-(2,6-dioxopiperidin-3-yl)picolinamide

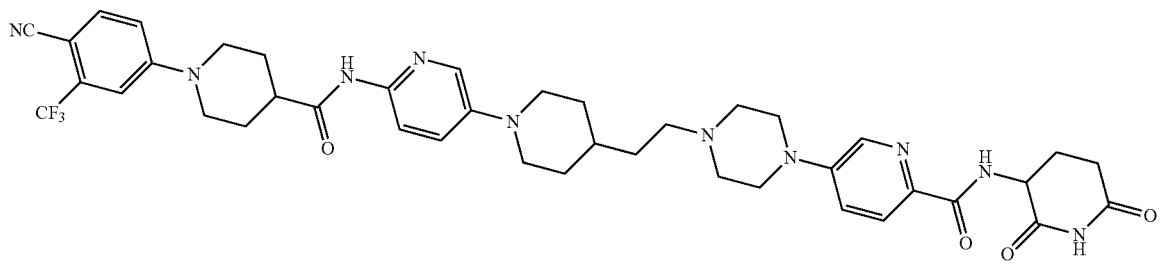 [SMILES: N#Cc1ccc(N2CCC(C(=O)Nc3ccc(N4CCC(CCN5CCN(c6ccc(C(=O)NC7CCC(=O)NC7=O)nc6)CC5)CC4)cn3)CC2)cc1C(F)(F)F]

Example 107 was synthesized in a similar way to the synthesis method of Example 105, using 2-(1-(6-nitropyridin-3-yl)piperidin-4-yl)acetaldehyde and tert-butyl piperazine-1-carboxylate, respectively, instead of 1-(6-nitropyridin-3-yl)piperidine-4-carbaldehyde and tert-butyl 4-(piperidin-4-yl)piperazine-1-carboxylate (Intermediate 4-4).

Example 108: 5-(4-(((R)-4-((1-(6-(1-(4-cyano-3-(trifluoromethyl)phenyl)piperidine-4-carboxamido)pyridin-3-yl)piperidin-4-yl)methyl)-3-methylpiperazin-1-yl)methyl)piperidin-1-yl)-N-(2,6-dioxopiperidin-3-yl)picolinamide
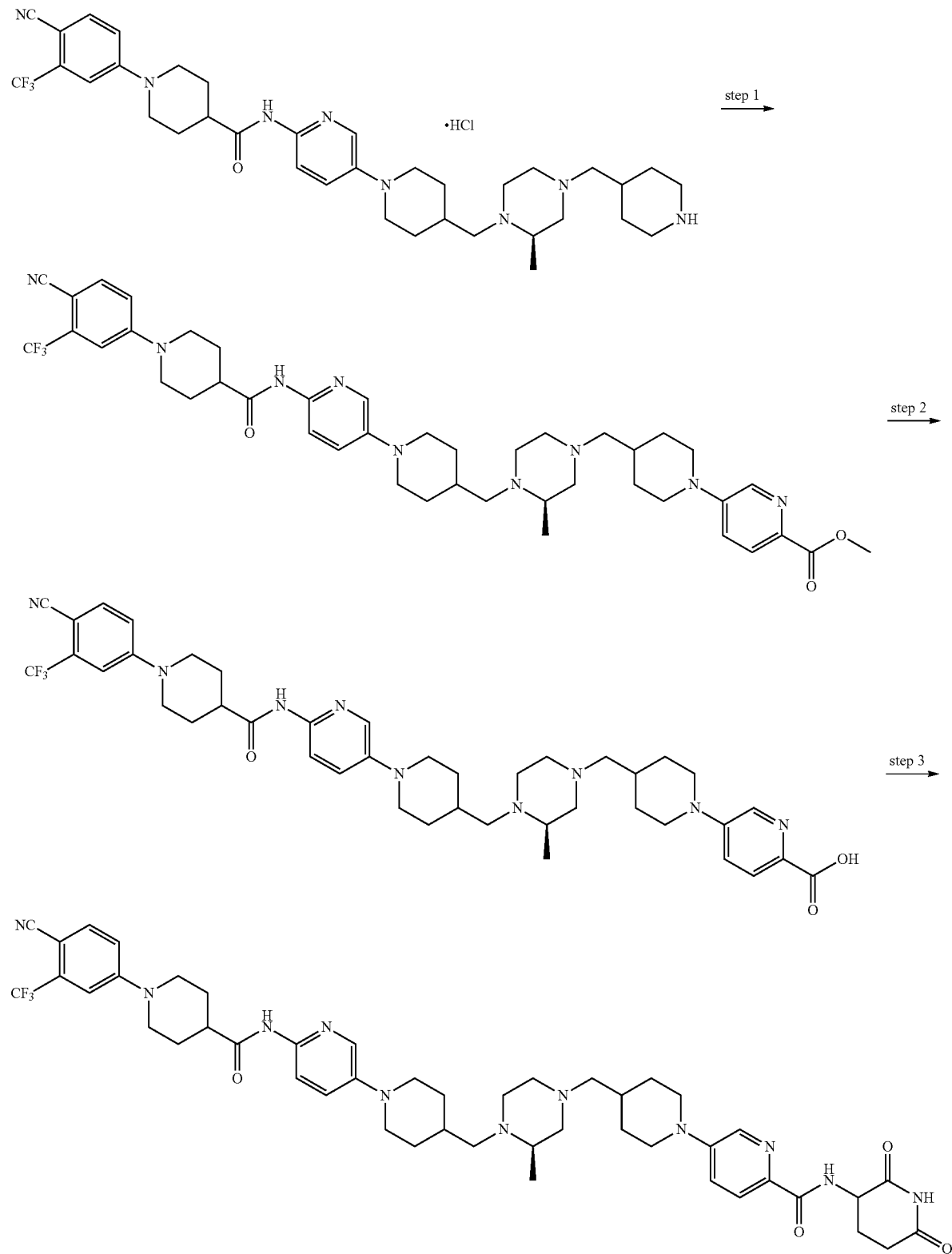 [SMILES: C[C@@H]1CN(CC2CCNCC2)CCN1CC1CCN(c2ccc(NC(=O)C3CCN(c4ccc(C#N)c(C(F)(F)F)c4)CC3)nc2)CC1 ; Cl ; COC(=O)c1ccc(N2CCC(CN3CCN(CC4CCN(c5ccc(NC(=O)C6CCN(c7ccc(C#N)c(C(F)(F)F)c7)CC6)nc5)CC4)[C@H](C)C3)CC2)cn1 ; C[C@@H]1CN(CC2CCN(c3ccc(C(=O)O)nc3)CC2)CCN1CC1CCN(c2ccc(NC(=O)C3CCN(c4ccc(C#N)c(C(F)(F)F)c4)CC3)nc2)CC1 ; C[C@@H]1CN(CC2CCN(c3ccc(C(=O)NC4CCC(=O)NC4=O)nc3)CC2)CCN1CC1CCN(c2ccc(NC(=O)C3CCN(c4ccc(C#N)c(C(F)(F)F)c4)CC3)nc2)CC1]

Step 1: Synthesis of methyl (R)-5-(4-((4-((1-(6-(1-(4-cyano-3-(trifluoromethyl)phenyl)piperidine-4-carboxamido)pyridin-3-yl)piperidin-4-yl)methyl)-3-methylpiperazin-1-yl)methyl)piperidin-1-yl) picolinate (R)-1-(4-cyano-3-(trifluoromethyl)phenyl)-N-(5-(4-((2-methyl-4-(piperidin-4-ylmethyl)piperazin-1-yl)methyl)piperidin-1-yl)pyridin-2-yl)piperidine-4-carboxamide hydrochloride (70 mg, 0.010 mmol), methyl 5-fluoropicolinate (23 mg, 0.15 mmol), and DIPEA (0.03 mL, 0.20 mmol) were suspended in DMSO (1.0 ml) and stirred at 70° C. for 16 hours. After adding distilled water (15 ml) to the reaction solution, extraction was performed with EtOAc (20 ml×2), and the organic layer was dried over anhydrous sodium sulfate, filtered, and concentrated under reduced pressure. The resulting residue was subjected to MPLC (10% MeOH/DCM) to give 26 mg (33%) of an off-white solid.

Step 2: Synthesis of (R)-5-(4-((4-((1-(6-(1-(4-cyano-3-(trifluoromethyl)phenyl)piperidine-4-carboxamido)pyridin-3-yl)piperidin-4-yl)methyl)-3-methylpiperazin-1-yl)methyl)piperidin-1-yl)picolinic acid After suspending methyl (R)-5-(4-((4-((1-(6-(1-(4-cyano-3-(trifluoromethyl)phenyl)piperidine-4-carboxamido)pyridin-3-yl)piperidin-4-yl)methyl)-3-methylpiperazin-1-yl)methyl)piperidin-1-yl)picolinate (26 mg, 0.040 mmol) in THF (3.0 mL) and distilled water (1.0 mL), LiOH·H₂O (7 mg, 0.16 mmol) was added and stirred at room temperature for 3 hours. After evaporation of the solvent and extraction with distilled water, 1N HCl was added to the aqueous layer and extraction was performed with EtOAc (20 ml×2). The organic layer was dried over anhydrous sodium sulfate, filtered, and concentrated under reduced pressure. 25 mg (98%) of a white solid was obtained. m/z 788.51 [M+H]⁺.

Step 3: Synthesis of 5-(4-(((R)-4-((1-(6-(1-(4-cyano-3-(trifluoromethyl)phenyl)piperidine-4-carboxamido)pyridin-3-yl)piperidin-4-yl)methyl)-3-methylpiperazin-1-yl)methyl)piperidin-1-yl)-N-(2,6-dioxopiperidin-3-yl)picolinamide (R)-5-(4-((4-((1-(6-(1-(4-cyano-3-(trifluoromethyl)phenyl)piperidine-4-carboxamido)pyridin-3-yl)piperidin-4-yl)methyl)-3-methylpiperazin-1-yl)methyl)piperidin-1-yl)picolinic acid (27 mg, 0.034 mmol), 3-aminopiperidine-2,6-dione hydrochloride (6.8 mg, 0.0.041 mmol), HATU (16 mg, 0.041 mmol), and DIPEA (0.01 mL, 0.068 mmol) were suspended in DMF (1.0 ml) and stirred at room temperature for 16 hours. After adding distilled water (15 ml) to the reaction solution, extraction was performed with EtOAc (20 ml×2), and the organic layer was dried over anhydrous sodium sulfate, filtered, and concentrated under reduced pressure. The resulting residue was subjected to MPLC (10% MeOH/DCM) to give 10 mg (32%) of a white solid.

Example 109: 5-(4-(((S)-4-((1-(6-(1-(4-cyano-3-(trifluoromethyl)phenyl)piperidine-4-carboxamido)pyridin-3-yl)piperidin-4-yl)methyl)-3-methylpiperazin-1-yl)methyl)piperidin-1-yl)-N-(2,6-dioxopiperidin-3-yl)picolinamide

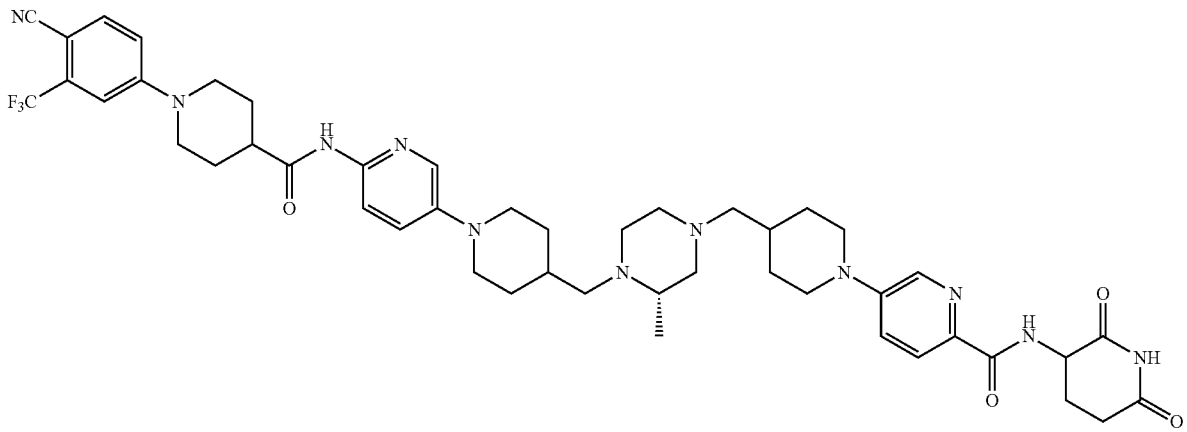 [SMILES: C[C@H]1CN(CC2CCN(c3ccc(C(=O)NC4CCC(=O)NC4=O)nc3)CC2)CCN1CC1CCN(c2ccc(NC(=O)C3CCN(c4ccc(C#N)c(C(F)(F)F)c4)CC3)nc2)CC1]

Example 109 was synthesized in a similar way to the synthesis method of Example 108, using (S)-1-(4-cyano-3-(trifluoromethyl)phenyl)-N-(5-(4-((2-methylpiperazin-1-yl)methyl)piperidin-1-yl)pyridin-2-yl)piperidine-4-carboxamide hydrochloride instead of (R)-1-(4-cyano-3-(trifluoromethyl)phenyl)-N-(5-(4-((2-methylpiperazin-1-yl)methyl)piperidin-1-yl)pyridin-2-yl)piperidine-4-carboxamide hydrochloride.

Example 110: 1-(4-cyano-3-(trifluoromethyl)phenyl)-N-(5-(4-(((2-(4-(2-(2,6-dioxopiperidin-3-yl)-1,3-dioxoisoindolin-5-yl)piperazin-1-yl)ethyl)(methyl)amino)methyl)piperidin-1-yl)pyridin-2-yl)piperidine-4-carboxamide
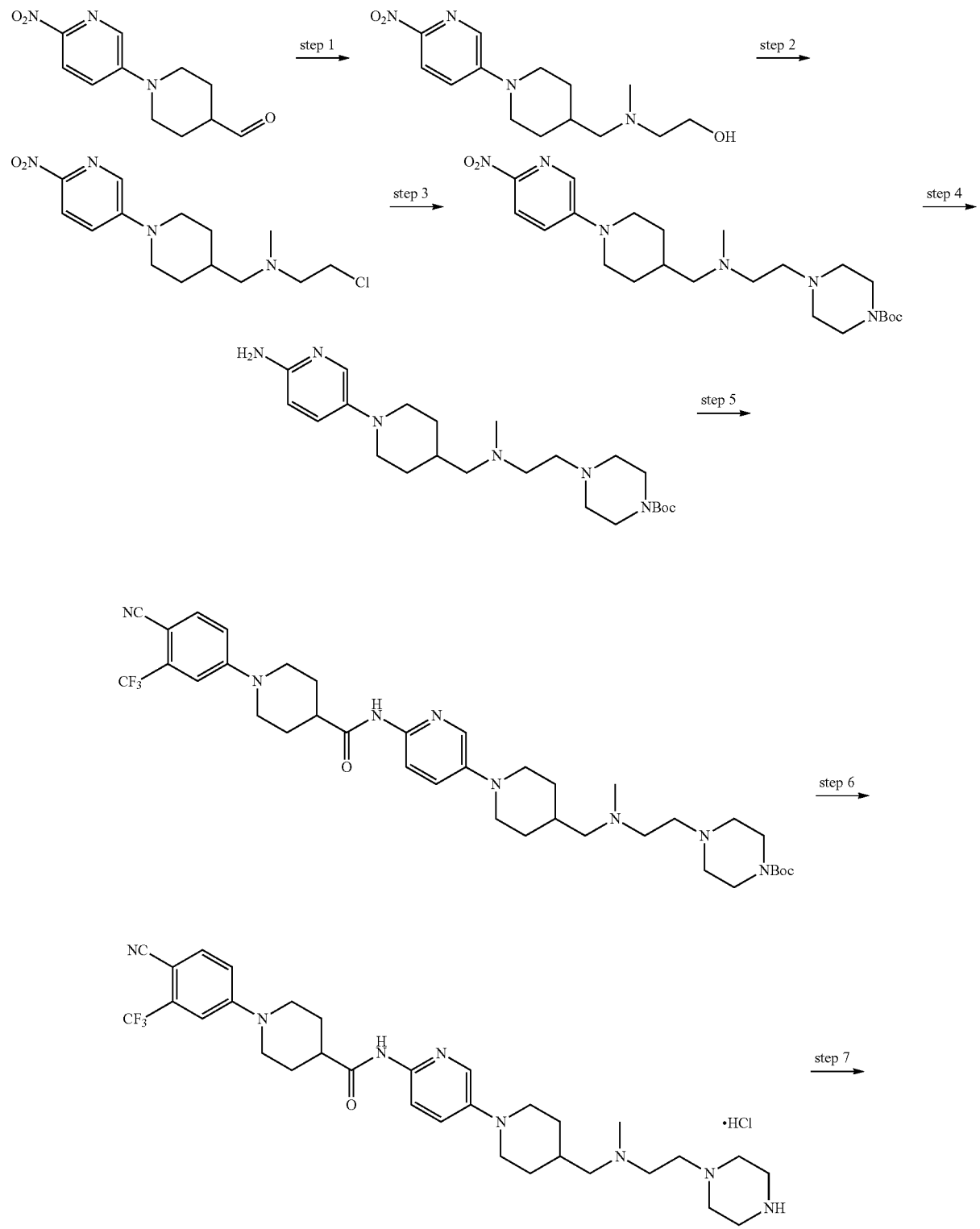

-continued

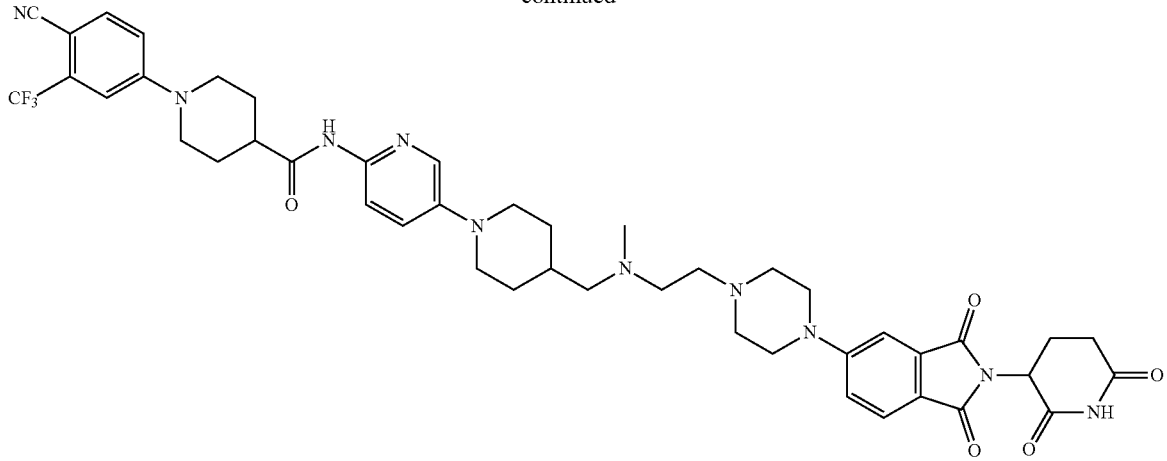

Step 1: Synthesis of 2-(methyl((1-(6-nitropyridin-3-yl)piperidin-4-yl)methyl)amino)ethan-1-ol After suspending 1-(6-nitropyridin-3-yl)piperidine-4-carbaldehyde (200 mg, 0.850 mmol), and 2-(methylamino)ethan-1-ol (77 mg, 1.02 mmol) in MeOH (10.0 ml), sodium triacetoxyborohydride (540 mg, 2.55 mmol) was added and stirred at room temperature for 16 hours. NaHCO$_3$ aqueous solution (15 ml) was added to the reaction mixture, followed by extraction with EtOAc (20 ml×2), and the organic layer was dried over anhydrous sodium sulfate, filtered, and concentrated under reduced pressure. The resulting residue was subjected to MPLC (10% MeOH/DCM) to give 149 mg (60%) of a yellow solid. m/z 295.06 [M+H]$^+$.

Step 2: Synthesis of 2-chloro-N-methyl-N-((1-(6-nitropyridin-3-yl)piperidin-4-yl)methyl)ethan-1-amine After suspending 2-(methyl((1-(6-nitropyridin-3-yl)piperidin-4-yl)methyl)amino)ethan-1-ol (49 mg, 0.17 mmol), tosyl chloride (63 mg, 0.33 mmol), and DMAP (11 mg, 0.09 mmol) in DCM (10.0 ml), TEA (0.05 ml, 0.33 mmol) was added and stirred at room temperature for 12 hours. After adding distilled water (15 ml) to the reaction solution, extraction was performed with DCM (20 ml×2), and the organic layer was dried over anhydrous sodium sulfate, filtered, and concentrated under reduced pressure. The obtained residue was subjected to MPLC (50% EtOAc/Hexane) to give 39 mg (73%) of a yellow solid. m/z 313.18 [M+H]$^+$.

Step 3: Synthesis of tert-butyl 4-(2-(methyl((1-(6-nitropyridin-3-yl)piperidin-4-yl)methyl)amino)ethyl)piperazine-1-carboxylate 2-chloro-N-methyl-N-((1-(6-nitropyridin-3-yl)piperidin-4-yl)methyl)ethan-1-amine (39 mg, 0.12 mmol), tert-butyl piperazine-1-carboxylate (835 mg, 0.19 mmol), K$_2$CO$_3$ (33 mg, 0.24 mmol), and KI (10 mg, 0.088 mmol) were suspended in DMF (1.0 ml) and stirred at 70° C. for 16 hours. After adding distilled water (15 ml) to the reaction solution, extraction was performed with EtOAc (20 ml×2), and the organic layer was dried over anhydrous sodium sulfate, filtered, and concentrated under reduced pressure. The resulting residue was subjected to MPLC (10% MeOH/DCM) to give 53 mg (95%) of a yellow solid. m/z 463.37 [M+H]$^+$.

Step 4: Synthesis of tert-butyl 4-(2-(((1-(6-aminopyridin-3-yl)piperidin-4-yl)methyl)(methyl)amino)ethyl)piperazine-1-carboxylate After suspending tert-butyl 4-(2-(methyl((1-(6-nitropyridin-3-yl)piperidin-4-yl)methyl)amino)ethyl)piperazine-1-carboxylate (53 mg, 0.11 mmol) in a mixture of DCM (3 mL) and MeOH (9 mL), Pd/C (10 wt % Pd, 11 mg) was added and stirred for 6 hours at room temperature under a hydrogen stream. The reaction solution was filtered and concentrated. A gray solid (43 mg, 91%) was obtained. m/z 433.38 [M+H]$^+$.

Step 5: Synthesis of tert-butyl 4-(2-(((1-(6-(1-(4-cyano-3-(trifluoromethyl)phenyl)piperidine-4-carboxamido)pyridin-3-yl)piperidin-4-yl)methyl)(methyl)amino)ethyl)piperazine-1-carboxylate Tert-butyl 4-(2-(((1-(6-aminopyridin-3-yl)piperidin-4-yl)methyl)(methyl)amino)ethyl)piperazine-1-carboxylate (43 mg, 0.10 mmol), 1-(4-cyano-3-(trifluoromethyl)phenyl)piperidine-4-carboxylic acid (Intermediate 1-1, 36 mg, 0.12 mmol), HATU (46 mg, 0.12 mmol), and DIPEA (0.03 mL, 0.03 mmol) were suspended in DMF (1.0 ml) and stirred at room temperature for 16 hours. After adding distilled water (15 ml) to the reaction solution, extraction was performed with EtOAc (20 ml×2), and the organic layer was dried over anhydrous sodium sulfate, filtered, and concentrated under reduced pressure. The obtained residue was subjected to MPLC (10% MeOH/DCM) to give 57 mg (80%) of an off-white solid. m/z 713.48 [M+H]$^+$.

Step 6: Synthesis of 1-(4-cyano-3-(trifluoromethyl)phenyl)-N-(5-(4-((methyl(2-(piperazin-1-yl)ethyl)amino)methyl)piperidin-1-yl)pyridin-2-yl)piperidine-4-carboxamide hydrochloride After suspending tert-butyl 4-(2-(((1-(6-(1-(4-cyano-3-(trifluoromethyl)phenyl)piperidine-4-carboxamido)pyridin-3-yl)piperidin-4-yl)methyl)(methyl)amino)ethyl)piperazine-1-carboxylate (57 mg, 0.080 mmol) in DCM (1.00 ml), 4 M HCl in dioxane (0.1 mL, 0.40 mmol) was added and stirred at room temperature for 1 hour. The reaction solution was concentrated under reduced pressure. 51 mg (98%) of a white solid was obtained.

Step 7: Synthesis of 1-(4-cyano-3-(trifluoromethyl)phenyl)-N-(5-(4-(((2-(4-(2-(2,6-dioxopiperidin-3-yl)-1,3-dioxoisoindolin-5-yl)piperazin-1-yl)ethyl)(methyl)amino)methyl)piperidin-1-yl)pyridin-2-yl)piperidine-4-carboxamide 1-(4-cyano-3-(trifluoromethyl)phenyl)-N-(5-(4-((methyl(2-(piperazin-1-yl)ethyl)amino)methyl)piperidin-1-yl)pyridin-2-yl)piperidine-4-carboxamide hydrochloride (51 mg, 0.079 mmol), 2-(2,6-dioxopiperidin-3-yl)-5-fluoroisoindoline-1,3-dione (Intermediate 2-1, 32 mg, 0.12 mmol), and DIPEA (0.02 mL, 0.12 mmol) were suspended in DMSO (3.0 ml) and stirred at 90° C. for 16 hours. After adding distilled water (15 ml) to the reaction solution, extraction was performed with EtOAc (20 ml×2), and the organic layer was dried over anhydrous sodium sulfate, filtered, and concentrated under reduced pressure. The resulting residue was subjected to MPLC (10% MeOH/DCM) to give 34 mg (50%) of a yellow solid.

Example 111: 1-(4-cyano-3-(trifluoromethyl)phenyl)-N-(5-(4-(6-((2-(2,6-dioxopiperidin-3-yl)-1,3-dioxoisoindolin-5-yl)amino)hexanoyl)piperazin-1-yl)pyridin-2-yl)piperidine-4-carboxamide

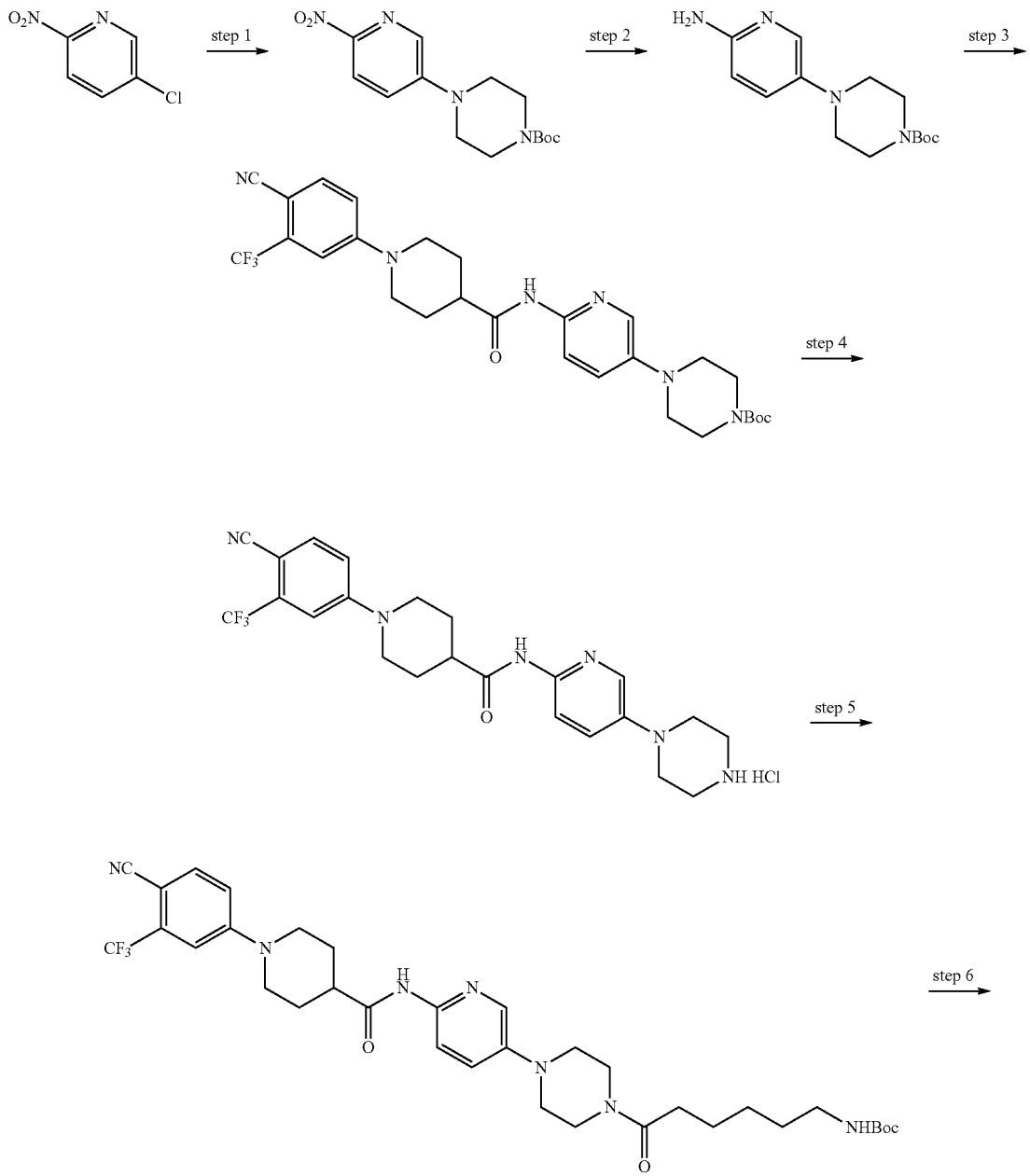

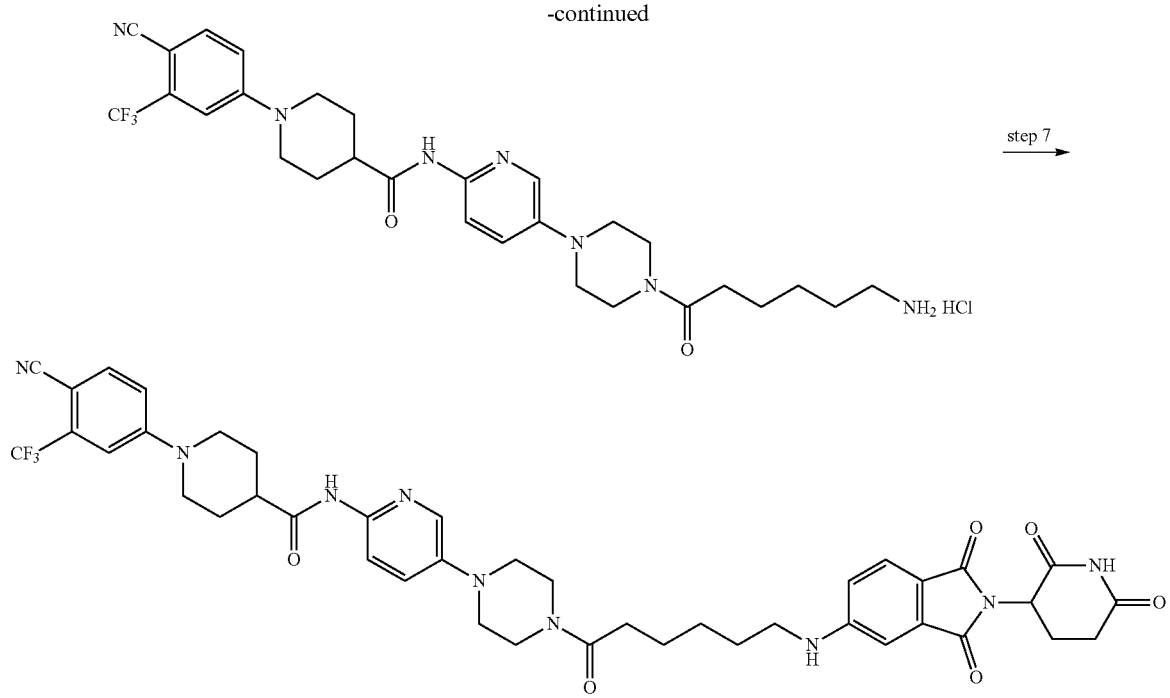

Step 1: Synthesis of tert-butyl 4-(6-nitropyridin-3-yl)piperazine-1-carboxylate 5-chloro-2-nitropyridine (1 g, 6.31 mmol), N-Boc-piperazine (1.41 g, 7.57 mmol), and DIPEA (3.3 mL, 3.3 mmol) were suspended in DMSO (10.0 mL) and stirred at 110° C. for 16 hours. After adding distilled water (5 mL) and 1N HCl aqueous solution (5 mL) to the reaction mixture, extraction was performed with EtOAc (5 mL×2), and the organic layer was dried over anhydrous magnesium sulfate, filtered, and concentrated under reduced pressure. The resulting residue was subjected to MPLC (50% EA/Hexane) to give 1.88 g (97%) of a yellow solid.

Step 2: Synthesis of tert-butyl 4-(6-aminopyridin-3-yl)piperazine-1-carboxylate tert-butyl 4-(6-nitropyridin-3-yl)piperazine-1-carboxylate (830 mg, 2.69 mmol), and 10% Pd/C (287 mg, 0.27 mmol) was suspended in EtOH (8.0 mL) and stirred at room temperature for 6 hours under a hydrogen stream. After filtering the reaction solution, it was concentrated under reduced pressure. The resulting residue was subjected to MPLC (10% MeOH/DCM) to give 686 mg (92%) of a brown solid.

Step 3: Synthesis of tert-butyl 4-(6-(1-(4-cyano-3-(trifluoromethyl)phenyl)piperidine-4-carboxamido)pyridin-3-yl)piperazine-1-carboxylate 1-(4-cyano-3-(trifluoromethyl)phenyl)piperidine-4-carboxylic acid (Intermediate 1-1, 167 mg, 1.68 mmol), tert-butyl 4-(6-aminopyridin-3-yl)piperazine-1-carboxylate (500 mg, 1.68 mmol), HATU (957 mg, 2.52 mmol), and DIPEA (0.58 mL, 3.36 mmol) were suspended in DMF (5 mL) and stirred at room temperature for 16 hours. After adding distilled water (2 mL) and 1N HCl aqueous solution (2 mL) to the reaction solution, extraction was performed with EtOAc (5 mL×2), and the organic layer was dried over anhydrous magnesium sulfate, filtered, and concentrated under reduced pressure. The resulting residue was subjected to MPLC (10% MeOH/DCM) to give 810 mg (87%) of a yellow solid.

Step 4: Synthesis of 1-(4-cyano-3-(trifluoromethyl)phenyl)-N-(5-(piperazin-1-yl)pyridin-2-yl)piperidine-4-carboxamide hydrochloride After suspending tert-butyl 4-(6-(1-(4-cyano-3-(trifluoromethyl)phenyl)piperidine-4-carboxamido)pyridin-3-yl)piperazine-1-carboxylate (810 mg, 1.45 mmol) in DCM (5 mL), 4N HCl in dioxane (0.7 mL, 2.90 mmol) was added and stirred at room temperature for 16 hours. The reaction solution was concentrated under reduced pressure. 717 mg (99%) of a yellow solid was obtained.

Step 5: Synthesis of tert-butyl (6-(4-(6-(1-(4-cyano-3-(trifluoromethyl)phenyl)piperidine-4-carboxamido)pyridin-3-yl)piperazin-1-yl)-6-oxohexyl)carbamate 1-(4-cyano-3-(trifluoromethyl)phenyl)-N-(5-(piperazin-1-yl)pyridin-2-yl)piperidine-4-carboxamide hydrochloride (100 mg, 0.22 mmol), 6-((tert-butoxycarbonyl)amino)hexanoic acid (50 mg, 0.22 mmol), HATU (124 mg, 0.33 mmol), and DIPEA (0.12 mL, 0.73 mmol) were suspended in DMF (1 mL) and stirred at room temperature for 16 hours. After adding distilled water (1 mL) and 1N HCl aqueous solution (1 mL) to the reaction mixture, extraction was performed with EtOAc (1 mL×2), and the organic layer was dried over anhydrous magnesium sulfate, filtered, and concentrated under reduced pressure. The resulting residue was subjected to MPLC (10% MeOH/DCM) to give 105 mg (71%) of a yellow solid.

Step 6: Synthesis of N-(5-(4-(6-aminohexanoyl) piperazin-1-yl)pyridin-2-yl)-1-(4-cyano-3-(trifluoromethyl)phenyl)piperidine-4-carboxamide hydrochloride After suspending tert-butyl (6-(4-(6-(1-(4-cyano-3-(trifluoromethyl)phenyl)piperidine-4-carboxamido)pyridin-3-yl)piperazin-1-yl)-6-oxohexyl)carbamate (85 mg, 0.14 mmol) in DCM (1 mL), 4N HCl in dioxane (0.07 mL, 0.28 mmol) was added and stirred at room temperature for 16 hours. The reaction solution was concentrated under reduced pressure. 82 mg (99%) of a yellow solid was obtained.

Step 7: Synthesis of 1-(4-cyano-3-(trifluoromethyl) phenyl)-N-(5-(4-(6-((2-(2,6-dioxopiperidin-3-yl)-1,3-dioxoisoindolin-5-yl)amino)hexanoyl)piperazin-1-yl)pyridin-2-yl)piperidine-4-carboxamide N-(5-(4-(6-aminohexanoyl)piperazin-1-yl)pyridin-2-yl)-1-(4-cyano-3-(trifluoromethyl)phenyl)piperidine-4-carboxamide hydrochloride (82 mg, 0.14 mmol), 2-(2,6-dioxopiperidin-3-yl)-5-fluoroisoindoline-1,3-dione (Intermediate 2-1, 38 mg, 0.14 mmol), and DIPEA (0.07 mL, 0.41 mmol) were suspended in DMSO (1 mL) and stirred at 90° C. for 16 hours. After adding distilled water (1 mL) to the reaction solution, extraction was performed with EtOAc (1 mL×2), and the organic layer was dried over anhydrous magnesium sulfate, filtered, and concentrated under reduced pressure. The resulting residue was subjected to MPLC (10% MeOH/DCM) to give 10 mg (9%) of a yellow solid.

Example 112: 1-(3-chloro-4-cyanophenyl)-N-(5-(4-(6-((2-(2,6-dioxopiperidin-3-yl)-1,3-dioxoisoindolin-5-yl)amino)hexanoyl)piperazin-1-yl)pyridin-2-yl)piperidine-4-carboxamide

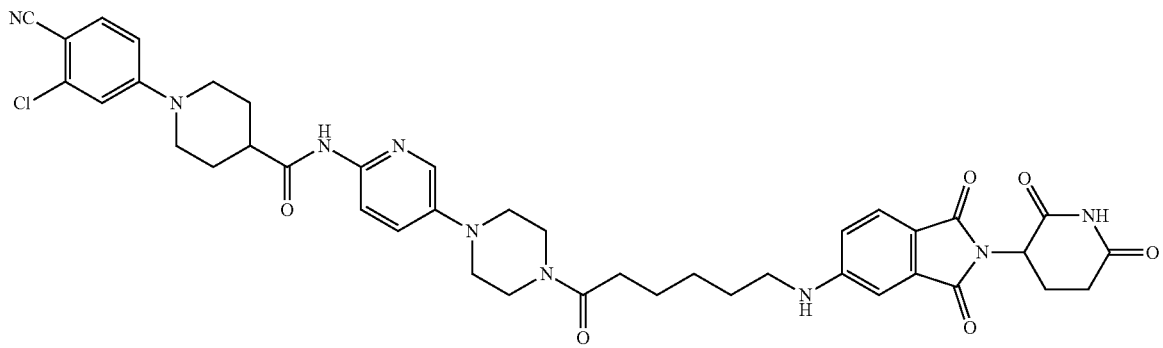 [SMILES: N#Cc1ccc(N2CCC(C(=O)Nc3ccc(N4CCN(C(=O)CCCCCNc5ccc6c(c5)C(=O)N(C5CCC(=O)NC5=O)C6=O)CC4)cn3)CC2)cc1Cl]

Example 112 was synthesized in a similar way to the synthesis method of Example 111, using 1-(3-chloro-4-cyanophenyl)piperidine-4-carboxylic acid (Intermediate 1-2) instead of 1-(4-cyano-3-(trifluoromethyl)phenyl)piperidine-4-carboxylic acid (Intermediate 1-1).

Example 113: 1-(4-cyano-3-(trifluoromethyl)phenyl)-N-(5-(4-(5-((2-(2,6-dioxopiperidin-3-yl)-1,3-dioxoisoindolin-5-yl)oxy)pentyl)piperazin-1-yl)pyridin-2-yl)piperidine-4-carboxamide

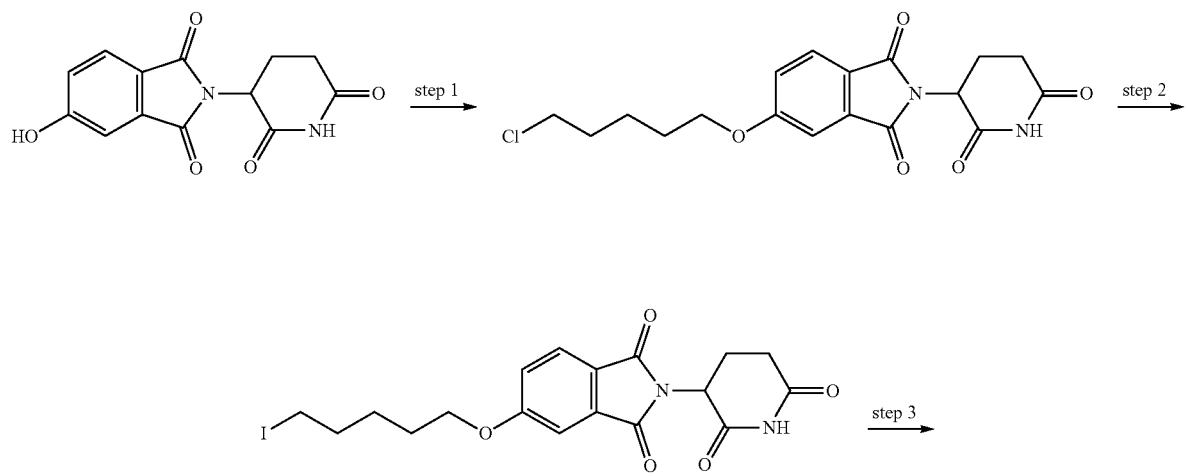

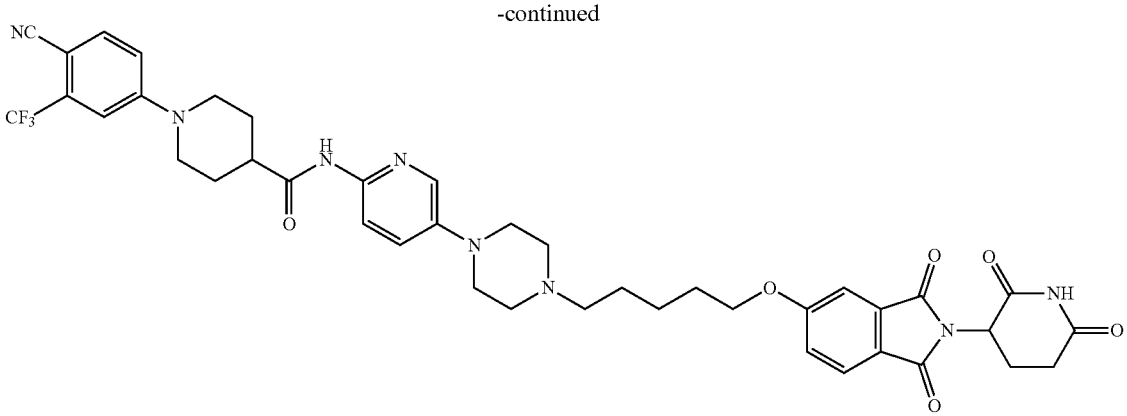

Step 1: Synthesis of 5-((5-chloropentyl)oxy)-2-(2,6-dioxopiperidin-3-yl)isoindoline-1,3-dione 2-(2,6-dioxopiperidin-3-yl)-5-hydroxyisoindoline-1,3-dione (1.0 g, 3.65 mmol), 1-bromo-5-chloropentane (0.48 mL, 3.64 mmol), and K$_2$CO$_3$ (756 mg, 5.47 mmol) were suspended in DMF (10 mL) and stirred at 70° C. for 16 hours. After adding distilled water (50 mL) to the reaction solution, the mixture was extracted with EtOAc (25 mL×2). The organic layer was washed with brine (30 mL×2), dried over anhydrous sodium sulfate, filtered, and concentrated under reduced pressure. The obtained residue was subjected to MPLC (60% EA/Hex) to give 100 mg (8%) of a white solid.

Step 2: Synthesis of 2-(2,6-dioxopiperidin-3-yl)-5-((5-iodopentyl)oxy)isoindoline-1,3-dione After suspending 5-((5-chloropentyl)oxy)-2-(2,6-dioxopiperidin-3-yl)isoindoline-1,3-dione (96.5 mg, 0.26 mmol) in acetone (5 mL), NaI (153.8 mg, 1.0 mmol) was added and stirred under reflux at 80° C. for 16 hours. After adding sodium thiosulfate solution (15 mL) to the reaction solution, extraction was performed with DCM (20 mL×2), and the organic layer was dried over anhydrous sodium sulfate, filtered, and concentrated under reduced pressure. 90 mg (75%) of a white solid was obtained.

Step 3: Synthesis of 1-(4-cyano-3-(trifluoromethyl)phenyl)-N-(5-(4-(5-((2-(2,6-dioxopiperidin-3-yl)-1,3-dioxoisoindolin-5-yl)oxy)pentyl)piperazin-1-yl)pyridin-2-yl)piperidine-4-carboxamide 1-(4-cyano-3-(trifluoromethyl)phenyl)-N-(5-(piperazin-1-yl)pyridin-2-yl)piperidine-4-carboxamide hydrochloride (23.3 mg, 0.05 mmol), 2-(2,6-dioxopiperidin-3-yl)-5-((5-iodopentyl)oxy)isoindoline-1,3-dione (23.8 mg, 0.05 mmol), and DIPEA (0.02 mL, 0.1 mmol) were suspended in DMSO (1 mL) and stirred at 70° C. for 6 hours. After adding distilled water (15 mL) to the reaction solution, the mixture was extracted with EtOAc (10 mL×2). The organic layer was washed with brine (10 mL×2), dried over anhydrous sodium sulfate, filtered, and concentrated under reduced pressure. The resulting residue was subjected to MPLC (3% MeOH/DCM) to give 12.1 mg (30%) of a white solid.

Example 114: 1-(3-chloro-4-cyanophenyl)-N-(5-(4-(5-((2-(2,6-dioxopiperidin-3-yl)-1,3-dioxoisoindolin-5-yl)oxy)pentyl)piperazin-1-yl)pyridin-2-yl)piperidine-4-carboxamide

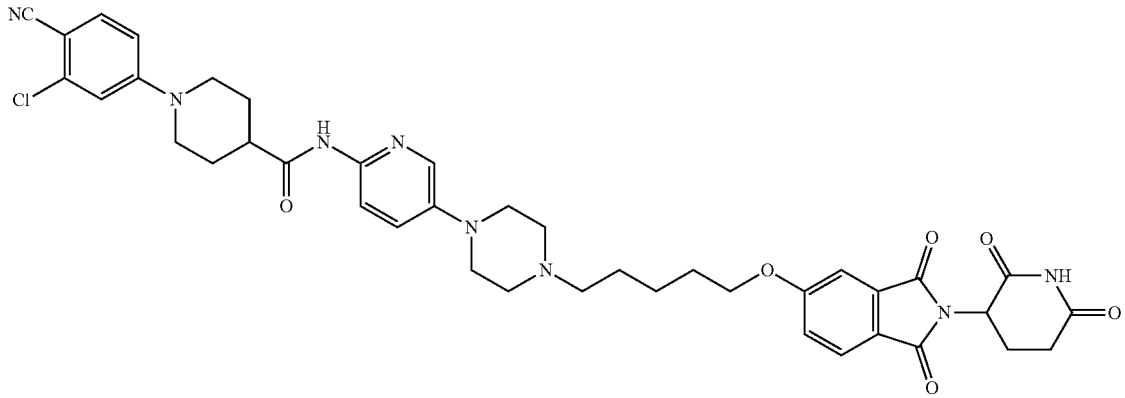 [SMILES: N#Cc1ccc(N2CCC(C(=O)Nc3ccc(N4CCN(CCCCCOc5ccc6c(c5)C(=O)N(C5CCC(=O)NC5=O)C6=O)CC4)cn3)CC2)cc1Cl]

Example 114 was synthesized in a similar way to the synthesis methods of Examples 111 and 113, using 1-(3-chloro-4-cyanophenyl)piperidine-4-carboxylic acid (Intermediate 1-2) instead of 1-(4-cyano-3-(trifluoromethyl)phenyl)piperidine-4-carboxylic acid (Intermediate 1-1).

Example 115: 1-(4-cyano-3-(trifluoromethyl)phenyl)-N-(5-(4-(4-((2-(2,6-dioxopiperidin-3-yl)-1,3-dioxoisoindolin-5-yl)oxy)butyl)piperazin-1-yl)pyridin-2-yl)piperidine-4-carboxamide

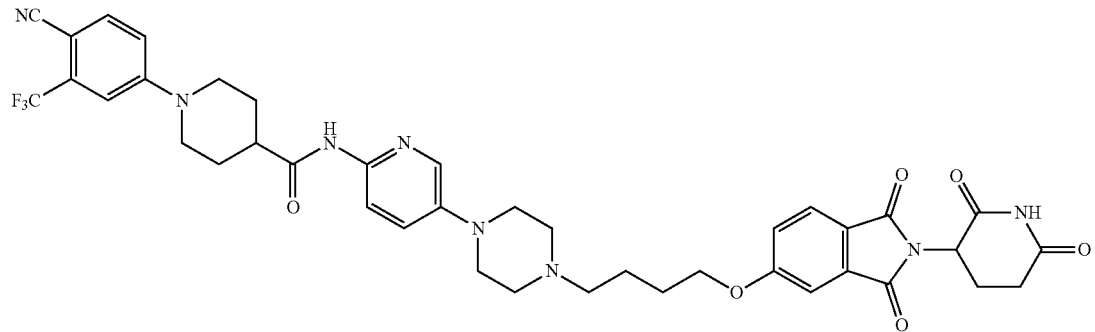 [SMILES: N#Cc1ccc(N2CCC(C(=O)Nc3ccc(N4CCN(CCCCOc5ccc6c(c5)C(=O)N(C5CCC(=O)NC5=O)C6=O)CC4)cn3)CC2)cc1Cl]

Example 115 was synthesized in a similar way to the synthesis method of Example 113, using 1-bromo-4-chlorobutane instead of 1-bromo-5-chloropentane.

Example 116: 1-(3-chloro-4-cyanophenyl)-N-(5-(4-(4-((2-(2,6-dioxopiperidin-3-yl)-1,3-dioxoisoindolin-5-yl)oxy)butyl)piperazin-1-yl)pyridin-2-yl)piperidine-4-carboxamide

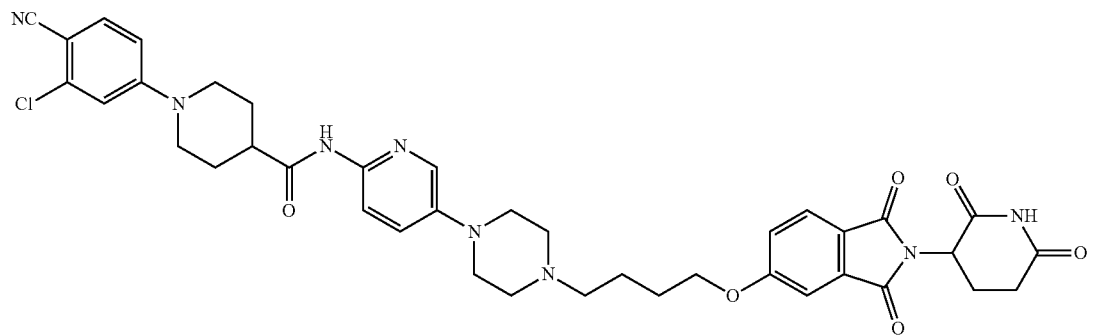

Example 116 was synthesized in a similar way to the synthesis methods of Examples 111 and 113, using 1-(3-chloro-4-cyanophenyl)piperidine-4-carboxylic acid (Intermediate 1-2) and 1-bromo-4-chlorobutane, respectively, instead of 1-(4-cyano-3-(trifluoromethyl)phenyl)piperidine-4-carboxylic acid (Intermediate 1-1) and 1-bromo-5-chloropentane.

Example 117: 1-(4-cyano-3-(trifluoromethyl)phenyl)-N-(5-(4-(2-((1-(2-(2,6-dioxopiperidin-3-yl)-1,3-dioxoisoindolin-5-yl)piperidin-4-yl)oxy)ethyl)piperazin-1-yl)pyridin-2-yl)piperidine-4-carboxamide

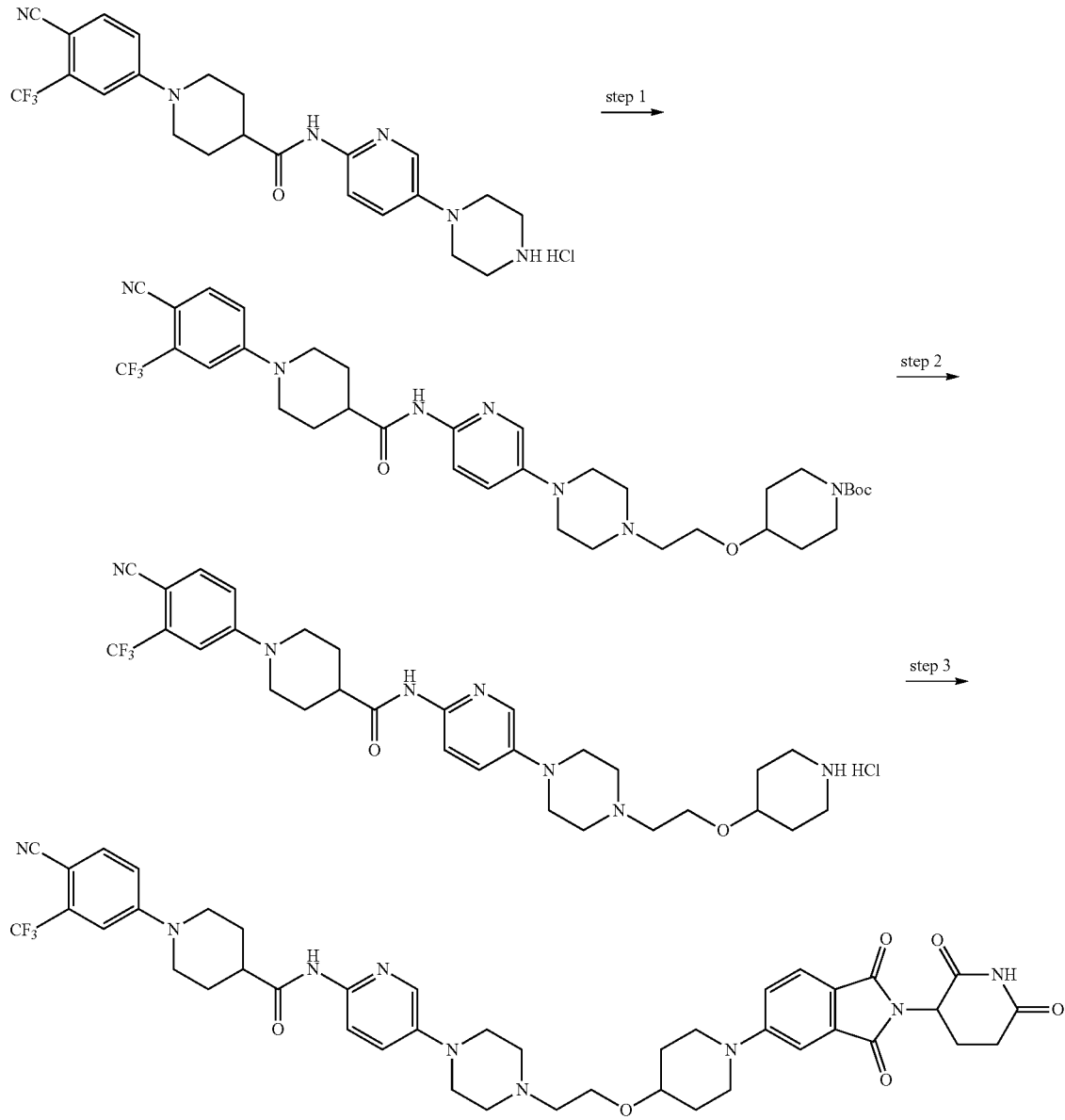

Step 1: Synthesis of tert-butyl 4-(2-(4-(6-(1-(4-cyano-3-(trifluoromethyl)phenyl)piperidine-4-carboxamido)pyridin-3-yl)piperazin-1-yl)ethoxy)piperidine-1-carboxylate After suspending 1-(4-cyano-3-(trifluoromethyl)phenyl)-N-(5-(piperazin-1-yl)pyridin-2-yl)piperidine-4-carboxamide hydrochloride (31.6 mg, 0.063 mmol), and tert-butyl 4-(2-(tosyloxy)ethoxy)piperidine-1-carboxylate (25.2 mg, 0.063 mmol) in DMF (1 ml), DIPEA (0.03 ml, 0.19 mmol) was added and stirred at 70° C. for 4 hours. After adding distilled water (5 ml) to the reaction solution, extraction was performed with EtOAc (5 ml×2). The organic layer was washed with brine (3 ml), dried over anhydrous magnesium sulfate, filtered, and concentrated under reduced pressure. The resulting residue was subjected to MPLC (5% MeOH/DCM) to give 22.4 mg (52%) of a white solid.

Step 2: Synthesis of 1-(4-cyano-3-(trifluoromethyl) phenyl)-N-(5-(4-(2-(piperidin-4-yloxy)ethyl)piperazin-1-yl)pyridin-2-yl)piperidine-4-carboxamide hydrochloride After suspending tert-butyl 4-(2-(4-(6-(1-(4-cyano-3-(trifluoromethyl)phenyl)piperidine-4-carboxamido)pyridin-3-yl)piperazin-1-yl)ethoxy)piperidine-1-carboxylate (13 mg, 0.019 mmol) in DCM (0.5 ml), 4N HCl in dioxane (0.005 ml, 0.16 mmol) was added and stirred at room temperature for 30 minutes. The reaction solution was concentrated. 10 mg (90%) of a white solid was obtained.

Step 3: Synthesis of 1-(4-cyano-3-(trifluoromethyl) phenyl)-N-(5-(4-(2-((1-(2-(2,6-dioxopiperidin-3-yl)- 1,3-dioxoisoindolin-5-yl)piperidin-4-yl)oxy)ethyl) piperazin-1-yl)pyridin-2-yl)piperidine-4- carboxamide After suspending 1-(4-cyano-3-(trifluoromethyl)phenyl)- N-(5-(4-(2-(piperidin-4-yloxy)ethyl)piperazin-1-yl)pyridin- 2-yl)piperidine-4-carboxamide hydrochloride (18 mg, 0.03 mmol), and 2-(2,6-dioxopiperidin-3-yl)-5-fluoroisoindo- line-1,3-dione (Intermediate 2-1, 8 mg, 0.03 mmol) in DMSO (1 ml), DIPEA (0.02 ml, 0.09 mmol) was added and stirred in a microwave at 120° C. for 1 hour. After adding distilled water (10 ml) to the reaction mixture, extraction was performed with EtOAc (10 ml×2). The organic layer was washed with brine (10 ml×2), dried over anhydrous magnesium sulfate, filtered, and concentrated under reduced pressure. The resulting residue was subjected to PTLC (5% MeOH/DCM) to give 3.2 mg (13%) of a yellow solid.

Example 118: 1-(3-chloro-4-cyanophenyl)-N-(5-(4- (2-((1-(2-(2,6-dioxopiperidin-3-yl)-1,3-dioxoisoin- dolin-5-yl)piperidin-4-yl)oxy)ethyl)piperazin-1-yl) pyridin-2-yl)piperidine-4-carboxamide

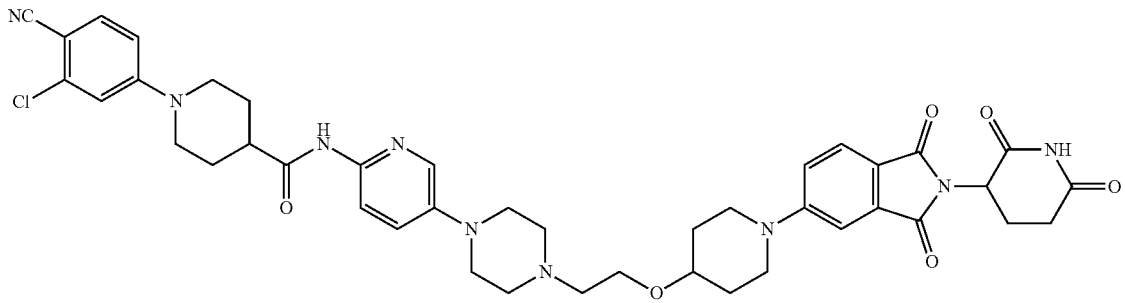 [SMILES: N#Cc1ccc(N2CCC(C(=O)Nc3ccc(N4CCN(CCOC5CCN(c6ccc7c(c6)C(=O)N(C6CCC(=O)NC6=O)C7=O)CC5)CC4)cn3)CC2)cc1Cl]

Example 118 was synthesized in a similar way to the synthesis methods of Examples 111 and 117, using 1-(3- chloro-4-cyanophenyl)piperidine-4-carboxylic acid (Inter- mediate 1-2) instead of 1-(4-cyano-3-(trifluoromethyl)phe- nyl)piperidine-4-carboxylic acid (Intermediate 1-1).

Example 119: 1-(4-cyano-3-(trifluoromethyl)phe- nyl)-N-(5-(4-(2-(1-(2-(2,6-dioxopiperidin-3-yl)-1,3- dioxoisoindolin-5-yl)piperidin-4-yl)ethyl)piperazin- 1-yl)pyridin-2-yl)piperidine-4-carboxamide

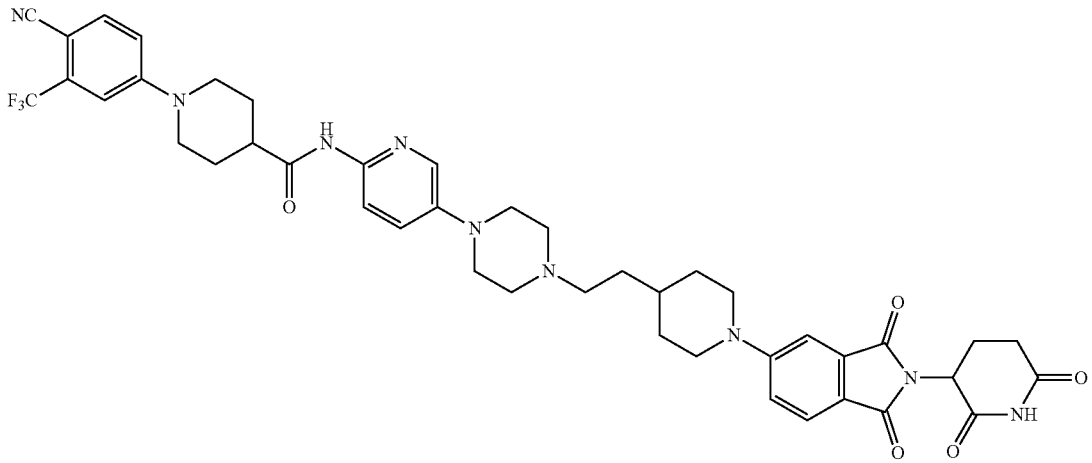 [SMILES: N#Cc1ccc(N2CCC(C(=O)Nc3ccc(N4CCN(CCC5CCN(c6ccc7c(c6)C(=O)N(C6CCC(=O)NC6=O)C7=O)CC5)CC4)cn3)CC2)cc1Cl]

After suspending 1-(4-cyano-3-(trifluoromethyl)phenyl)- N-(5-(piperazin-1-yl)pyridin-2-yl)piperidine-4-carboxam- ide hydrochloride (60 mg, 0.12 mmol), and 2-(1-(2-(2,6- dioxopiperidin-3-yl)-1,3-dioxoisoindolin-5-yl)piperidin-4- yl)acetaldehyde (Intermediate 3-13, 55 mg, 0.14 mmol) in ACN (20.0 ml), sodium triacetoxyborohydride (76 mg, 0.36 mmol) was added and stirred at room temperature for 16 hours. NaHCO₃ aqueous solution (15 ml) was added to the reaction mixture, followed by extraction with EtOAc (25 ml×2), and the organic layer was dried over anhydrous sodium sulfate, filtered, and concentrated under reduced pressure. The resulting residue was subjected to MPLC (10% MeOH/DCM) to give 11 mg (11%) of a white solid.

Example 120: 1-(3-chloro-4-cyanophenyl)-N-(5-(4-(2-(1-(2-(2,6-dioxopiperidin-3-yl)-1,3-dioxoisoindolin-5-yl)piperidin-4-yl)ethyl)piperazin-1-yl)pyridin-2-yl)piperidine-4-carboxamide

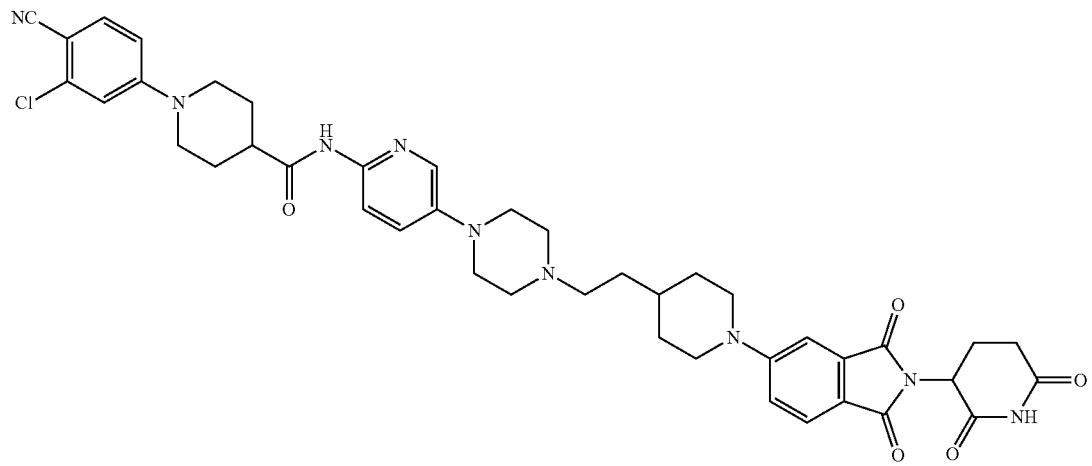

Example 120 was synthesized in a similar way to the synthesis methods of Examples 111 and 119, using 1-(3-chloro-4-cyanophenyl)piperidine-4-carboxylic acid (Intermediate 1-2) instead of 1-(4-cyano-3-(trifluoromethyl)phenyl)piperidine-4-carboxylic acid (Intermediate 1-1).

Example 121: 1-(4-cyano-3-(trifluoromethyl)phenyl)-N-(5-(7-((1-(2-(2,6-dioxopiperidin-3-yl)-1,3-dioxoisoindolin-5-yl)piperidin-4-yl)methyl)-2,7-diazaspiro[3.5]nonan-2-yl)pyridin-2-yl)piperidine-4-carboxamide

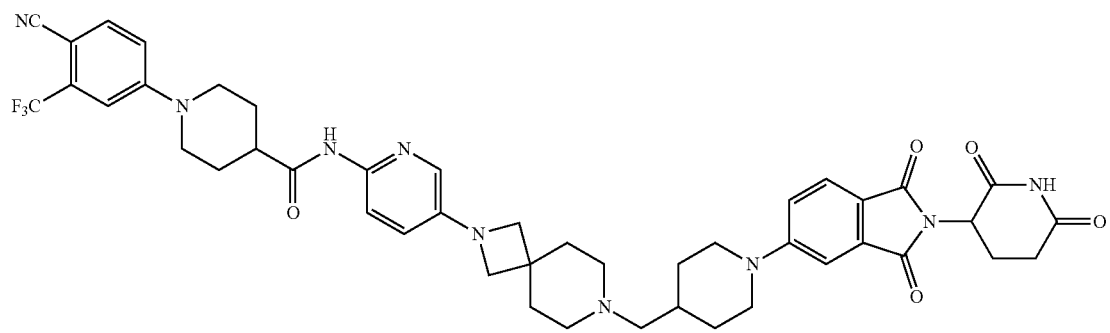 [SMILES: N#Cc1ccc(N2CCC(C(=O)Nc3ccc(N4CC5(CCN(CC6CCN(c7ccc8c(c7)C(=O)N(C7CCC(=O)NC7=O)C8=O)CC6)CC5)C4)cn3)CC2)cc1Cl]

Example 121 was synthesized in a similar way to the synthesis methods of Examples 111 and 119, using tert-butyl 2,7-diazaspiro[3.5]nonane-7-carboxylate and 1-(2-(2,6-dioxopiperidin-3-yl)-1,3-dioxoisoindolin-5-yl)piperidine-4-carbaldehyde (Intermediate 3-1), respectively, instead of tert-butyl piperazine-1-carboxylate and 2-(1-(2-(2,6-dioxopiperidin-3-yl)-1,3-dioxoisoindolin-5-yl)piperidin-4-yl)acetaldehyde (Intermediate 3-13).

Example 122: 1-(3-chloro-4-cyanophenyl)-N-(5-(7-((1-(2-(2,6-dioxopiperidin-3-yl)-1,3-dioxoisoindolin-5-yl)piperidin-4-yl)methyl)-2,7-diazaspiro[3.5]nonan-2-yl)pyridin-2-yl)piperidine-4-carboxamide

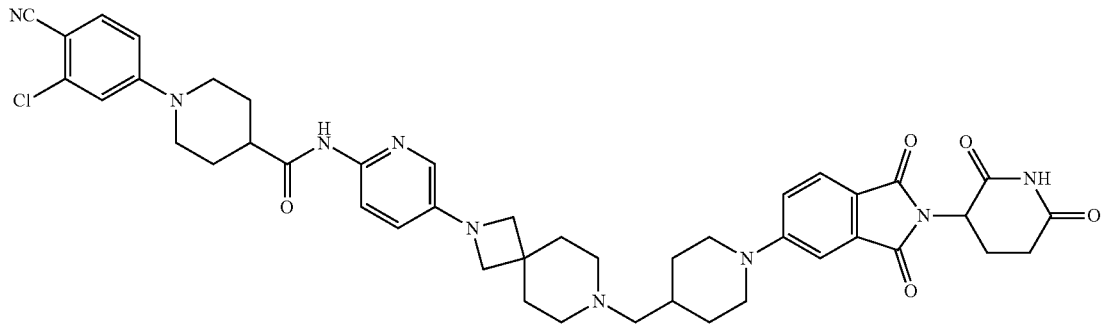

Example 122 was synthesized in a similar way to the synthesis methods of Examples 111 and 119, using 1-(3-chloro-4-cyanophenyl)piperidine-4-carboxylic acid (Intermediate 1-2), tert-butyl 2,7-diazaspiro[3.5]nonane-7-carboxylate, and 1-(2-(2,6-dioxopiperidin-3-yl)-1,3-dioxoisoindolin-5-yl)piperidine-4-carbaldehyde (Intermediate 3-1), respectively, instead of 1-(4-cyano-3-(trifluoromethyl)phenyl)piperidine-4-carboxylic acid (Intermediate 1-1), tert-butyl piperazine-1-carboxylate, and 2-(1-(2-(2,6-dioxopiperidin-3-yl)-1,3-dioxoisoindolin-5-yl)piperidin-4-yl)acetaldehyde (Intermediate 3-13).

Example 123: 1-(4-cyano-3-(trifluoromethyl)phenyl)-N-(5-(7-((1-(2-(2,6-dioxopiperidin-3-yl)-1,3-dioxoisoindolin-5-yl)azetidin-3-yl)methyl)-2,7-diazaspiro[3.5]nonan-2-yl)pyridin-2-yl)piperidine-4-carboxamide

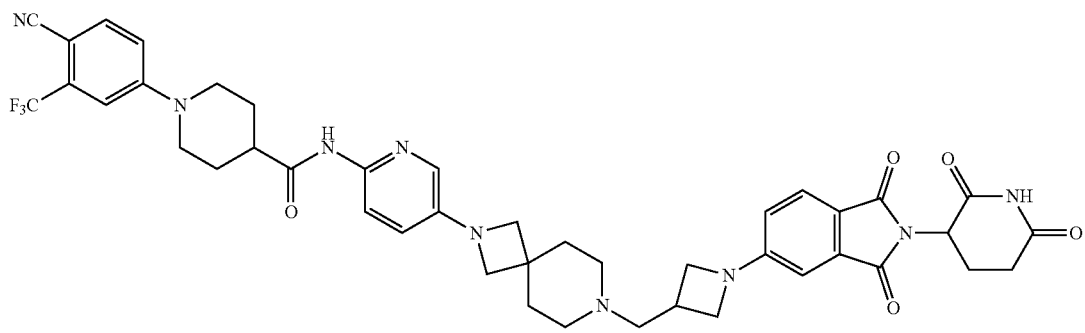 [SMILES: N#Cc1ccc(N2CCC(C(=O)Nc3ccc(N4CC5(CCN(CC6CN(c7ccc8c(c7)C(=O)N(C7CCC(=O)NC7=O)C8=O)C6)CC5)C4)cn3)CC2)cc1Cl]

Example 123 was synthesized in a similar way to the synthesis methods of Examples 111 and 119, using tert-butyl 2,7-diazaspiro[3.5]nonane-7-carboxylate and 1-(2-(2,6-dioxopiperidin-3-yl)-1,3-dioxoisoindolin-5-yl)azetidine-3-carbaldehyde (Intermediate 3-3), respectively, instead of tert-butyl piperazine-1-carboxylate and 2-(1-(2-(2,6-dioxopiperidin-3-yl)-1,3-dioxoisoindolin-5-yl)piperidin-4-yl)acetaldehyde (Intermediate 3-13).

Example 124: 1-(3-chloro-4-cyanophenyl)-N-(5-(7-((1-(2-(2,6-dioxopiperidin-3-yl)-1,3-dioxoisoindolin-5-yl)azetidin-3-yl)methyl)-2,7-diazaspiro[3.5]nonan-2-yl)pyridin-2-yl)piperidine-4-carboxamide

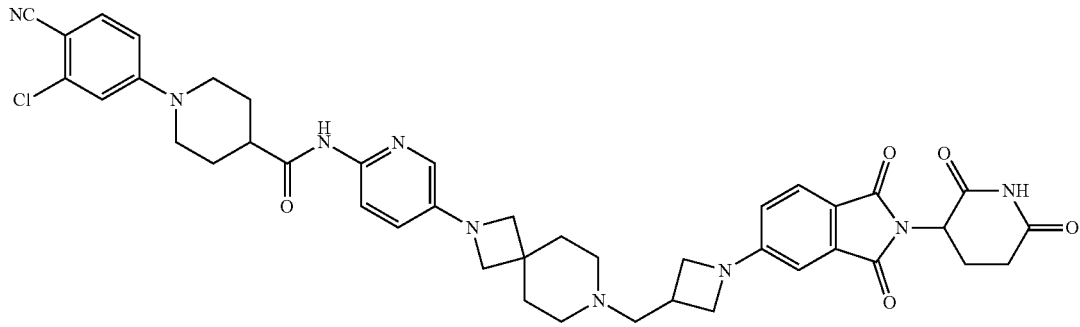

Example 124 was synthesized in a similar way to the synthesis methods of Examples 111 and 119, using 1-(3-chloro-4-cyanophenyl)piperidine-4-carboxylic acid (Intermediate 1-2), tert-butyl 2,7-diazaspiro[3.5]nonane-7-carboxylate, and 1-(2-(2,6-dioxopiperidin-3-yl)-1,3-dioxoisoindolin-5-yl)azetidine-3-carbaldehyde (Intermediate 3-3), respectively, instead of 1-(4-cyano-3-(trifluoromethyl)phenyl)piperidine-4-carboxylic acid (Intermediate 1-1), tert-butyl piperazine-1-carboxylate, and 2-(1-(2-(2,6-dioxopiperidin-3-yl)-1,3-dioxoisoindolin-5-yl)piperidin-4-yl)acetaldehyde (Intermediate 3-13).

Example 125: 1-(4-cyano-3-(trifluoromethyl)phenyl)-N-(5-(7-(((3R)-1-(2-(2,6-dioxopiperidin-3-yl)-1,3-dioxoisoindolin-5-yl)pyrrolidin-3-yl)methyl)-2,7-diazaspiro[3.5]nonan-2-yl)pyridin-2-yl)piperidine-4-carboxamide

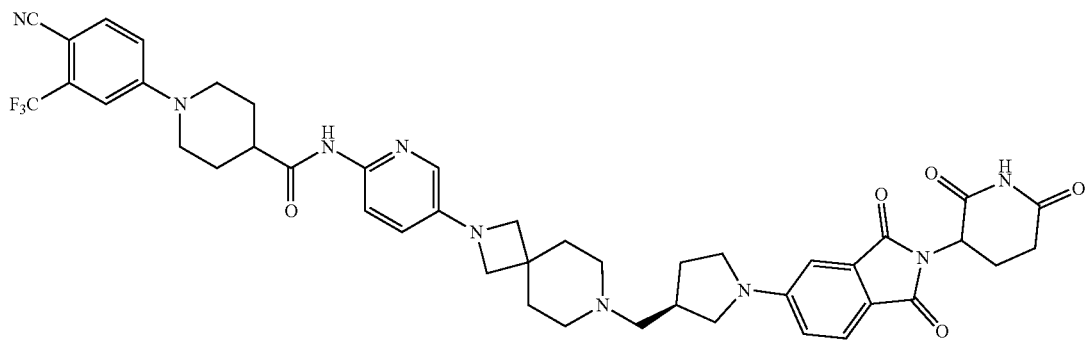 [SMILES: N#Cc1ccc(N2CCC(C(=O)Nc3ccc(N4CC5(CCN(C[C@H]6CCN(c7ccc8c(c7)C(=O)N(C7CCC(=O)NC7=O)C8=O)C6)CC5)C4)cn3)CC2)cc1C(F)(F)F]

Example 125 was synthesized in a similar way to the synthesis methods of Examples 111 and 119, using tert-butyl 2,7-diazaspiro[3.5]nonane-7-carboxylate and (3S)-1-(2-(2,6-dioxopiperidin-3-yl)-1,3-dioxoisoindolin-5-yl)pyrrolidine-3-carbaldehyde (Intermediate 3-4), respectively, instead of tert-butyl piperazine-1-carboxylate and 2-(1-(2-(2,6-dioxopiperidin-3-yl)-1,3-dioxoisoindolin-5-yl)piperidin-4-yl)acetaldehyde (Intermediate 3-13).

Example 126: 1-(4-cyano-3-(trifluoromethyl)phenyl)-N-(5-(7-(((3S)-1-(2-(2,6-dioxopiperidin-3-yl)-1,3-dioxoisoindolin-5-yl)pyrrolidin-3-yl)methyl)-2,7-diazaspiro[3.5]nonan-2-yl)pyridin-2-yl)piperidine-4-carboxamide

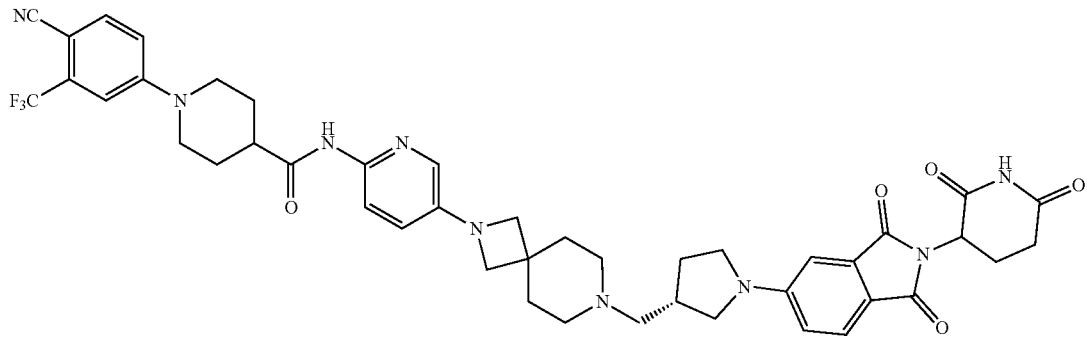 [SMILES: N#Cc1ccc(N2CCC(C(=O)Nc3ccc(N4CC5(CCN(C[C@@H]6CCN(c7ccc8c(c7)C(=O)N(C7CCC(=O)NC7=O)C8=O)C6)CC5)C4)cn3)CC2)cc1C(F)(F)F]

Example 126 was synthesized in a similar way to the synthesis methods of Examples 111 and 119, using tert-butyl 2,7-diazaspiro[3.5]nonane-7-carboxylate and (3R)-1-(2-(2,6-dioxopiperidin-3-yl)-1,3-dioxoisoindolin-5-yl)pyrrolidine-3-carbaldehyde (Intermediate 3-5), respectively, instead of tert-butyl piperazine-1-carboxylate and 2-(1-(2-(2,6-dioxopiperidin-3-yl)-1,3-dioxoisoindolin-5-yl)piperidin-4-yl)acetaldehyde (Intermediate 3-13).

Example 127: 1-(4-cyano-3-(trifluoromethyl)phenyl)-N-(5-(2-((1-(2-(2,6-dioxopiperidin-3-yl)-1,3-dioxoisoindolin-5-yl)piperidin-4-yl)methyl)-2,7-diazaspiro[3.5]nonan-7-yl)pyridin-2-yl)piperidine-4-carboxamide

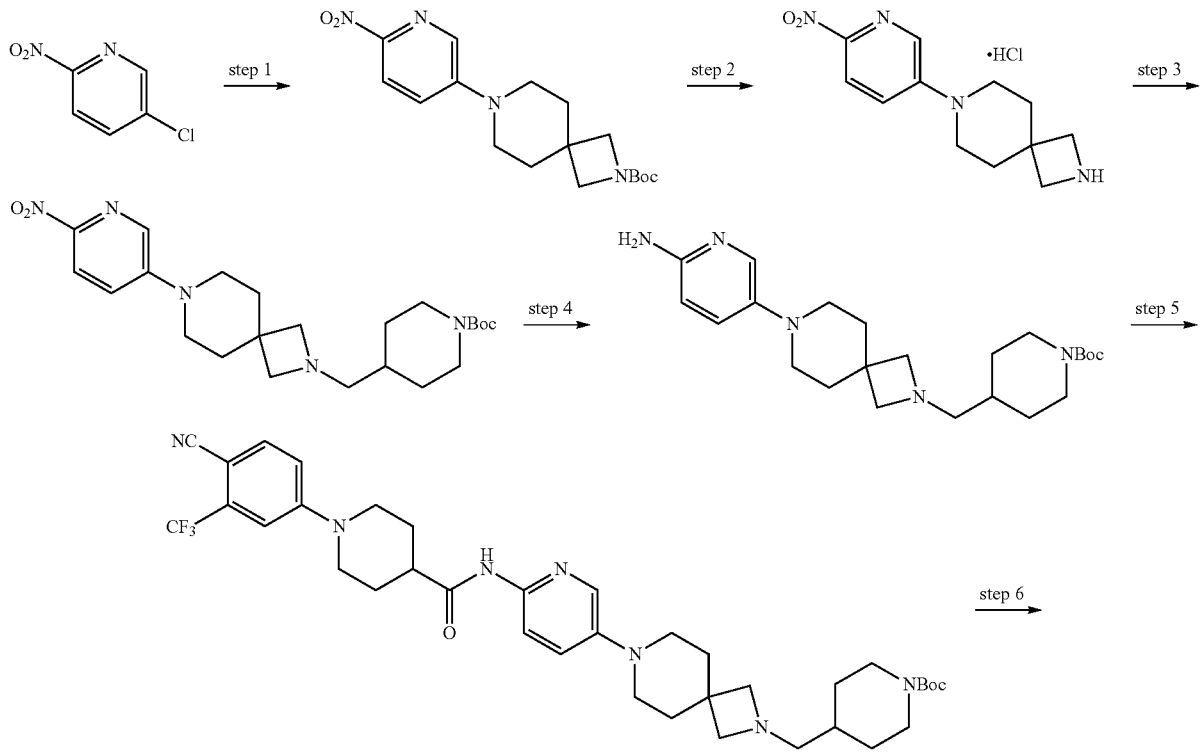

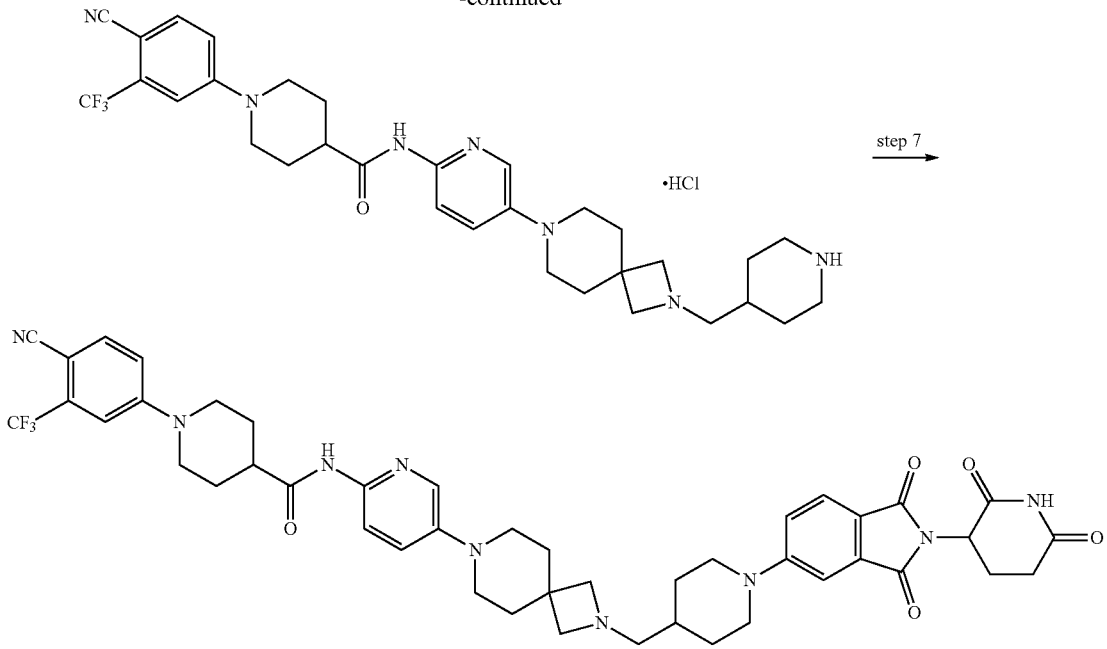

Step 1: Synthesis of tert-butyl 7-(6-nitropyridin-3-yl)-2,7-diazaspiro[3.5]nonane-2-carboxylate 5-chloro-2-nitropyridine (1.0 g, 6.31 mmol), tert-butyl 2,7-diazaspiro[3.5]nonane-2-carboxylate (1.43 g, 6.31 mmol), and TEA (2.6 mL, 18.93 mmol) were suspended in DMSO (10.0 ml) and stirred in a microwave reactor at 90° C. for 1 hour. After adding distilled water (10 ml) to the reaction mixture, extraction was performed with EtOAc (10 ml×2). The organic layer was washed with brine (10 mL×2), dried over anhydrous magnesium sulfate, filtered, and concentrated under reduced pressure. The obtained residue was recrystallized (MeOH/hexane) to give 2.12 g (97%) of a yellow solid.

Step 2: Synthesis of 7-(6-nitropyridin-3-yl)-2,7-diazaspiro[3.5]nonane hydrochloride After suspending tert-butyl 7-(6-nitropyridin-3-yl)-2,7-diazaspiro[3.5]nonane-2-carboxylate (750 mg, 2.15 mmol) in MeOH (5 mL), 4N HCl in dioxane (1 mL, 4.3 mmol) was added and stirred at room temperature for 16 hours. The reaction solution was concentrated under reduced pressure and recrystallized (MeOH/hexane) to give 391 mg (73%) of a yellow solid.

Step 3: Synthesis of tert-butyl 4-((7-(6-nitropyridin-3-yl)-2,7-diazaspiro[3.5]nonan-2-yl)methyl)piperidine-1-carboxylate After suspending 7-(6-nitropyridin-3-yl)-2,7-diazaspiro[3.5]nonane hydrochloride (152 mg, 0.612 mmol), and 1-Boc-4-piperidinecarboxaldehyde (157 mg, 0.735 mmol) in MeOH (10.0 ml), sodium triacetoxyborohydride (259 mg, 1.22 mmol) was added and stirred at room temperature for 16 hours. NaHCO$_3$ aqueous solution (15 ml) was added to the reaction solution, followed by extraction with EtOAc (25 ml×2), and the organic layer was dried over anhydrous sodium sulfate, filtered, and concentrated under reduced pressure. The obtained residue was subjected to MPLC (10% MeOH/DCM) to give 196 mg (72%) of a yellow solid. m/z 446.31 [M+H]$^+$.

Step 4: Synthesis of tert-butyl 4-((7-(6-aminopyridin-3-yl)-2,7-diazaspiro[3.5]nonan-2-yl)methyl)piperidine-1-carboxylate After dissolving tert-butyl 4-((7-(6-nitropyridin-3-yl)-2,7-diazaspiro[3.5]nonan-2-yl)methyl)piperidine-1-carboxylate (196 mg, 0.440 mmol) in a mixture of DCM (10 mL) and MeOH (5 mL), Pd/C (10 wt % Pd, 39 mg) was added and stirred under a hydrogen stream at room temperature for 3 hours. The reaction solution was filtered and concentrated. 156 mg (85%) of a brown solid was obtained. m/z 416.26 [M+H]$^+$.

Step 5: Synthesis of tert-butyl 4-((7-(6-(1-(4-cyano-3-(trifluoromethyl)phenyl)piperidine-4-carboxamido)pyridin-3-yl)-2,7-diazaspiro[3.5]nonan-2-yl)methyl)piperidine-1-carboxylate Tert-butyl 4-((7-(6-aminopyridin-3-yl)-2,7-diazaspiro[3.5]nonan-2-yl)methyl)piperidine-1-carboxylate (80 mg, 0.19 mmol), 1-(4-cyano-3-(trifluoromethyl)phenyl)piperidine-4-carboxylic acid (Intermediate 1-1, 69 mg, 0.23 mmol), HATU (87 mg, 0.23 mmol), and DIPEA (0.066 mL, 0.38 mmol) were suspended in DMF (1.0 ml) and stirred at room temperature for 16 hours. After adding distilled water (15 ml) to the reaction solution, extraction was performed with EtOAc (25 ml×2), and the organic layer was dried over anhydrous sodium sulfate, filtered, and concentrated under reduced pressure. The obtained residue was subjected to MPLC (10% MeOH/DCM) to give 100 mg (76%) of a brown solid. m/z 696.45 [M+H]$^+$.

Step 6: Synthesis of 1-(4-cyano-3-(trifluoromethyl)phenyl)-N-(5-(2-(piperidin-4-ylmethyl)-2,7-diazaspiro[3.5]nonan-7-yl)pyridin-2-yl)piperidine-4-carboxamide hydrochloride After suspending tert-butyl 4-((7-(6-(1-(4-cyano-3-(trifluoromethyl)phenyl)piperidine-4-carboxamido)pyridin-3- yl)-2,7-diazaspiro[3.5]nonan-2-yl)methyl)piperidine-1-carboxylate (100 mg, 0.144 mmol) in DCM (1.00 ml), 4 M HCl in dioxane (0.36 mL, 1.44 mmol) was added and stirred at room temperature for 1 hour. The reaction solution was concentrated. 89 mg (98%) of a white solid was obtained. m/z 596.36 [M+H]$^+$.

Step 7: Synthesis of 1-(4-cyano-3-(trifluoromethyl)phenyl)-N-(5-(2-((1-(2-(2,6-dioxopiperidin-3-yl)-1,3-dioxoisoindolin-5-yl)piperidin-4-yl)methyl)-2,7-diazaspiro[3.5]nonan-7-yl)pyridin-2-yl)piperidine-4-carboxamide 1-(4-cyano-3-(trifluoromethyl)phenyl)-N-(5-(2-(piperidin-4-ylmethyl)-2,7-diazaspiro[3.5]nonan-7-yl)pyridin-2-yl)piperidine-4-carboxamide hydrochloride (30 mg, 0.047 mmol), 2-(2,6-dioxopiperidin-3-yl)-5-fluoroisoindoline-1,3-dione (Intermediate 2-1, 20 mg, 0.071 mmol), and DIPEA (0.02 mL, 0.094 mmol) were suspended in DMSO (1.0 ml) and stirred at 90° C. for 16 hours. After adding distilled water (15 ml) to the reaction solution, extraction was performed with EtOAc (25 ml×2), and the organic layer was dried over anhydrous sodium sulfate, filtered, and concentrated under reduced pressure. The resulting residue was subjected to MPLC (10% MeOH/DCM) to give 12 mg (30%) of a yellow solid.

Example 128: 1-(4-cyano-3-(trifluoromethyl)phenyl)-N-(5-(2-((1-(2-(2,6-dioxopiperidin-3-yl)-1,3-dioxoisoindolin-5-yl)azetidin-3-yl)methyl)-2,7-diazaspiro[3.5]nonan-7-yl)pyridin-2-yl)piperidine-4-carboxamide

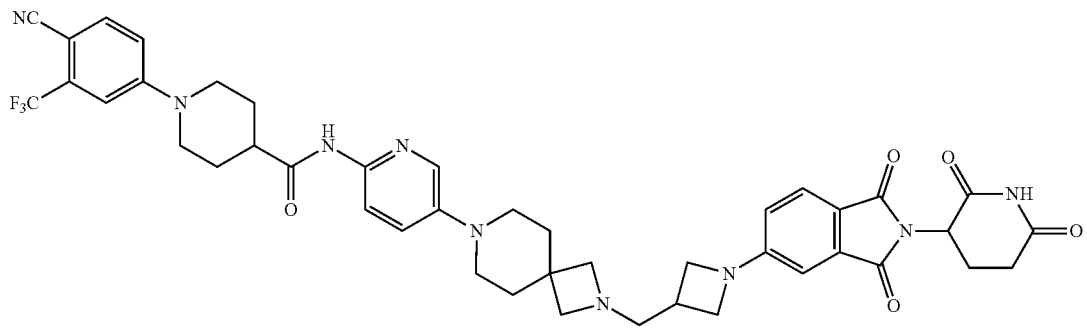 [SMILES: N#Cc1ccc(N2CCC(C(=O)Nc3ccc(N4CCC5(CC4)CN(CC4CN(c6ccc7c(c6)C(=O)N(C6CCC(=O)NC6=O)C7=O)C4)C5)cn3)CC2)cc1C(F)(F)F]

Example 128 was synthesized in a similar way to the synthesis method of Example 127, using tert-butyl 3-formylazetidine-1-carboxylate instead of 1-Boc-4-piperidinecarboxaldehyde.

Example 129: 1-(4-cyano-3-(trifluoromethyl)phenyl)-N-(5-(2-(1-(2-(2,6-dioxopiperidin-3-yl)-1,3-dioxoisoindolin-5-yl)piperidine-4-carbonyl)-2,7-diazaspiro[3.5]nonan-7-yl)pyridin-2-yl)piperidine-4-carboxamide

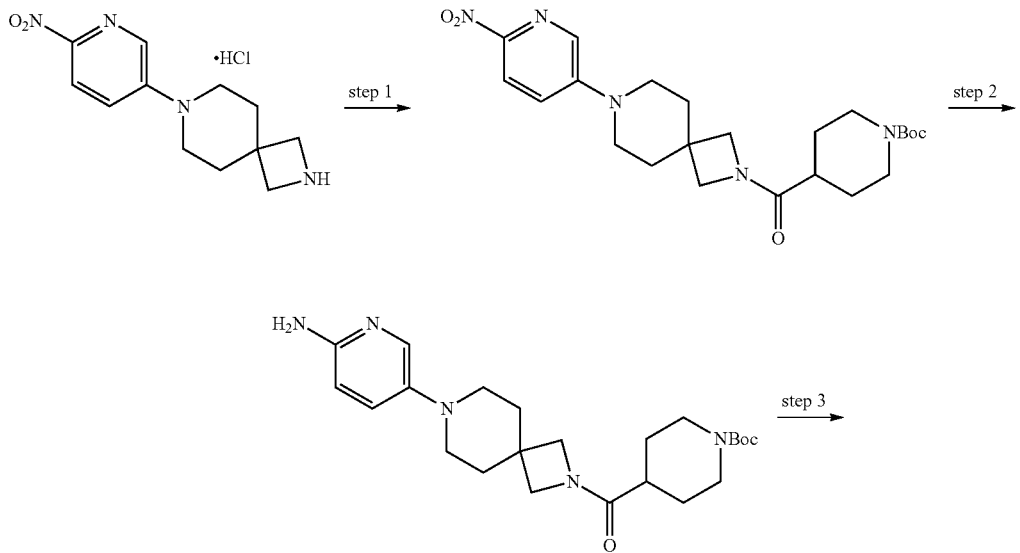

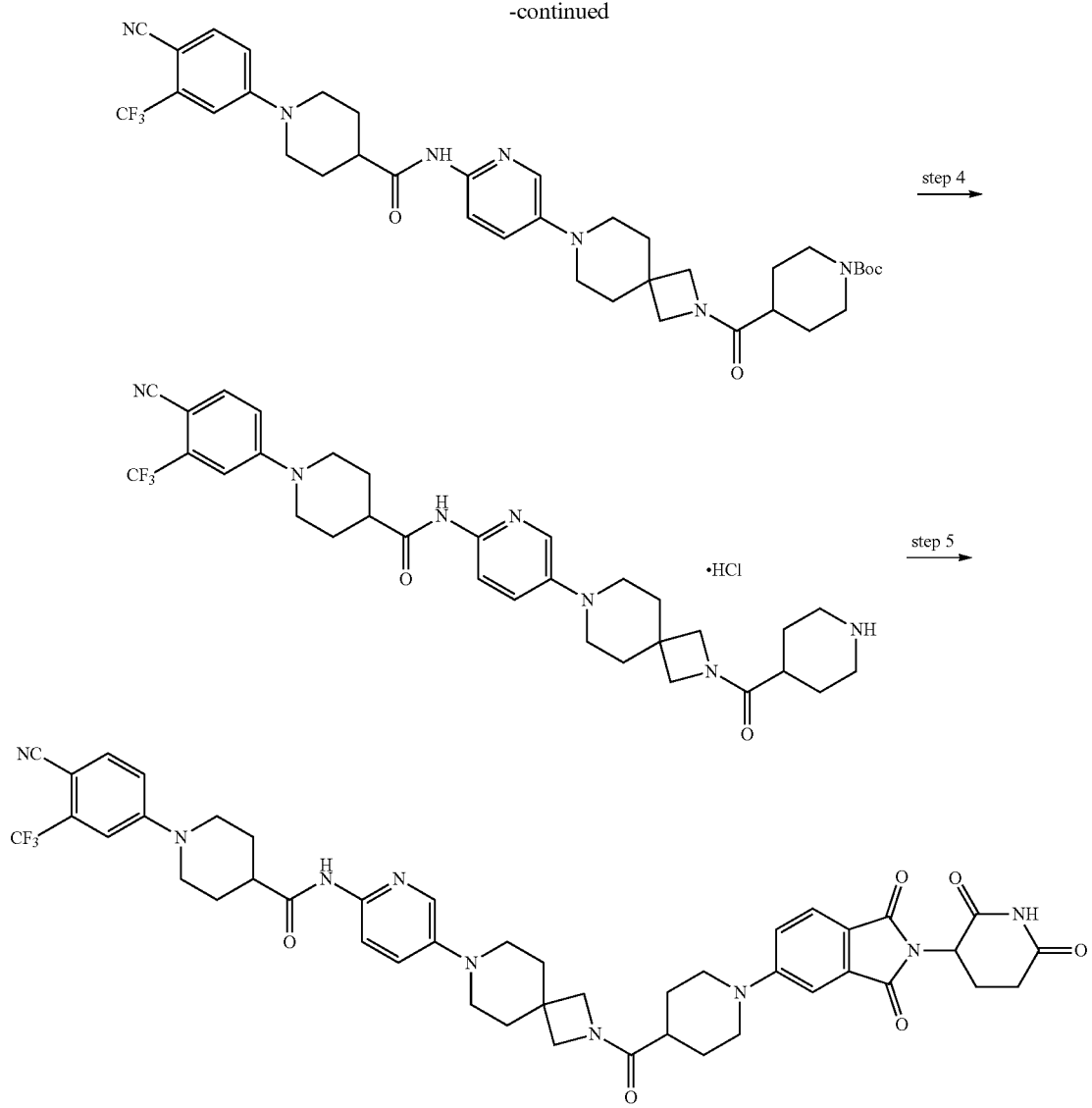

Step 1: Synthesis of tert-butyl 4-(7-(6-nitropyridin-3-yl)-2,7-diazaspiro[3.5]nonane-2-carbonyl)piperidine-1-carboxylate 7-(6-nitropyridin-3-yl)-2,7-diazaspiro[3.5]nonane hydrochloride (90 mg, 0.36 mmol), N-Boc-piperidine-4-carboxylic acid (100 mg, 0.43 mmol), HATU (163 mg, 0.43 mmol), and DIPEA (0.13 mL, 0.72 mmol) were suspended in DMF (3.0 ml) and stirred at room temperature for 16 hours. After adding distilled water (15 ml) to the reaction solution, extraction was performed with EtOAc (25 ml×2), and the organic layer was dried over anhydrous sodium sulfate, filtered, and concentrated under reduced pressure. The resulting residue was subjected to MPLC (10% MeOH/DCM) to give 116 mg (70%) of a yellow solid. m/z 482.20 [M+Na]$^+$.

Step 2: Synthesis of tert-butyl 4-(7-(6-aminopyridin-3-yl)-2,7-diazaspiro[3.5]nonane-2-carbonyl)piperidine-1-carboxylate After suspending tert-butyl 4-(7-(6-nitropyridin-3-yl)-2,7-diazaspiro[3.5]nonane-2-carbonyl)piperidine-1-carboxylate (116 mg, 0.252 mmol) in a mixture of DCM (10 mL) and MeOH (5 mL), Pd/C (10 wt % Pd, 23 mg) was added and stirred under a hydrogen stream at room temperature for 3 hours. The reaction solution was filtered and concentrated. A brown solid (105 mg, 96%) was obtained. m/z 430.22 [M+H]$^+$.

Step 3: Synthesis of tert-butyl 4-(7-(6-(1-(4-cyano-3-(trifluoromethyl)phenyl)piperidine-4-carboxamido)pyridin-3-yl)-2,7-diazaspiro[3.5]nonane-2-carbonyl)piperidine-1-carboxylate Tert-butyl 4-(7-(6-aminopyridin-3-yl)-2,7-diazaspiro[3.5]nonane-2-carbonyl)piperidine-1-carboxylate (105 mg, 0.244 mmol), 1-(4-cyano-3-(trifluoromethyl)phenyl)piperidine-4-carboxylic acid (Intermediate 1-1, 57 mg, 0.293 mmol), HATU (111 mg, 0.293 mmol), and DIPEA (0.085 mL, 0.488 mmol) were suspended in DMF (1.0 ml) and stirred at room temperature for 16 hours. After adding distilled water (15 ml) to the reaction solution, extraction was performed with EtOAc (25 ml×2), and the organic layer was dried over anhydrous sodium sulfate, filtered, and concentrated under reduced pressure. The obtained residue was subjected to MPLC (10% MeOH/DCM) to give 116 mg (67%) of a purple solid. m/z 710.35 [M+H]⁺.

Step 4: Synthesis of 1-(4-cyano-3-(trifluoromethyl)phenyl)-N-(5-(2-(piperidine-4-carbonyl)-2,7-diazaspiro[3.5]nonan-7-yl)pyridin-2-yl)piperidine-4-carboxamide hydrochloride After suspending tert-butyl 4-(7-(6-(1-(4-cyano-3-(trifluoromethyl)phenyl)piperidine-4-carboxamido)pyridin-3-yl)-2,7-diazaspiro[3.5]nonane-2-carbonyl)piperidine-1-carboxylate (116 mg, 0.163 mmol) in DCM (1.00 ml), 4 M HCl in dioxane (0.41 mL, 1.63 mmol) was added and stirred at room temperature for 1 hour. The reaction solution was concentrated. 102 mg (97%) of a pink solid was obtained. m/z 610.28 [M+H]⁺.

Step 5: Synthesis of 1-(4-cyano-3-(trifluoromethyl)phenyl)-N-(5-(2-(1-(2-(2,6-dioxopiperidin-3-yl)-1,3-dioxoisoindolin-5-yl)piperidine-4-carbonyl)-2,7-diazaspiro[3.5]nonan-7-yl)pyridin-2-yl)piperidine-4-carboxamide 1-(4-cyano-3-(trifluoromethyl)phenyl)-N-(5-(2-(piperidine-4-carbonyl)-2,7-diazaspiro[3.5]nonan-7-yl)pyridin-2-yl)piperidine-4-carboxamide hydrochloride (40 mg, 0.065 mmol), 2-(2,6-dioxopiperidin-3-yl)-5-fluoroisoindoline-1,3-dione (Intermediate 2-1, 27 mg, 0.097 mmol), and DIPEA (0.02 mL, 0.13 mmol) were suspended in DMSO (1.0 ml) and stirred at 90° C. for 16 hours. After adding distilled water (15 ml) to the reaction solution, extraction was performed with EtOAc (25 ml×2), and the organic layer was dried over anhydrous sodium sulfate, filtered, and concentrated under reduced pressure. The resulting residue was subjected to MPLC (10% MeOH/DCM) to give 15 mg (27%) of a yellow solid.

Example 130: 1-(4-cyano-3-(trifluoromethyl)phenyl)-N-(5-(4-((1-((2-(2,6-dioxopiperidin-3-yl)-1,3-dioxoisoindolin-5-yl)glycyl)piperidin-4-yl)methyl)piperazin-1-yl)pyridin-2-yl)piperidine-4-carboxamide

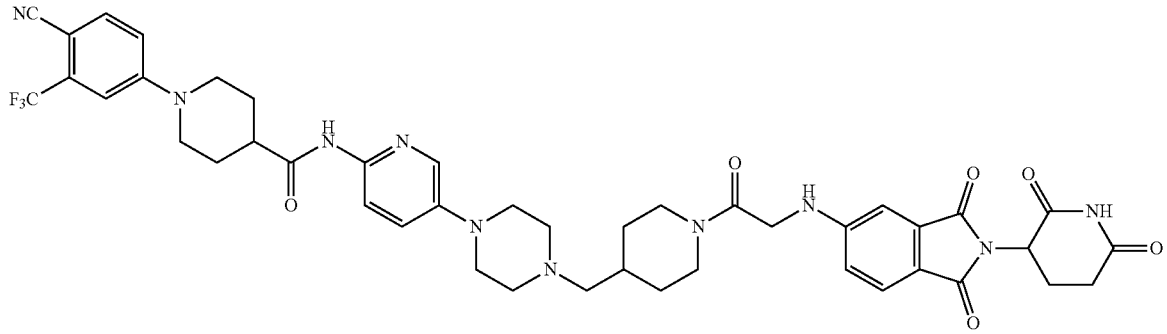 [SMILES: N#Cc1ccc(N2CCC(C(=O)Nc3ccc(N4CCN(CC5CCN(C(=O)CNc6ccc7c(c6)C(=O)N(C6CCC(=O)NC6=O)C7=O)CC5)CC4)cn3)CC2)cc1C(F)(F)F]

Example 130 was synthesized in a similar way to the synthesis methods of Examples 127 and 5, using tert-butyl piperazine-1-carboxylate instead of tert-butyl 2,7-diazaspiro[3.5]nonane-2-carboxylate.

Example 131: 1-(4-cyano-3-(trifluoromethyl)phenyl)-N-(5-((1-((1-(2-(2,6-dioxopiperidin-3-yl)-1,3-dioxoisoindolin-5-yl)piperidin-4-yl)methyl)piperidin-4-yl)ethynyl)pyridin-2-yl)piperidine-4-carboxamide

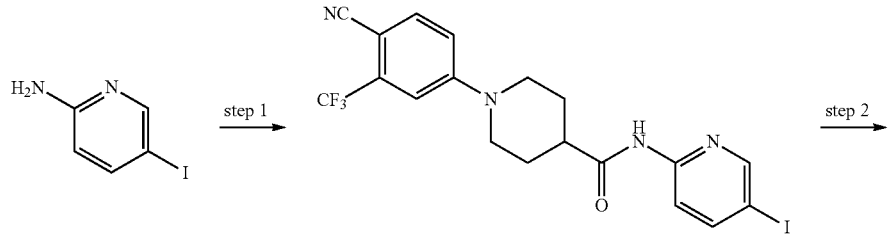

-continued
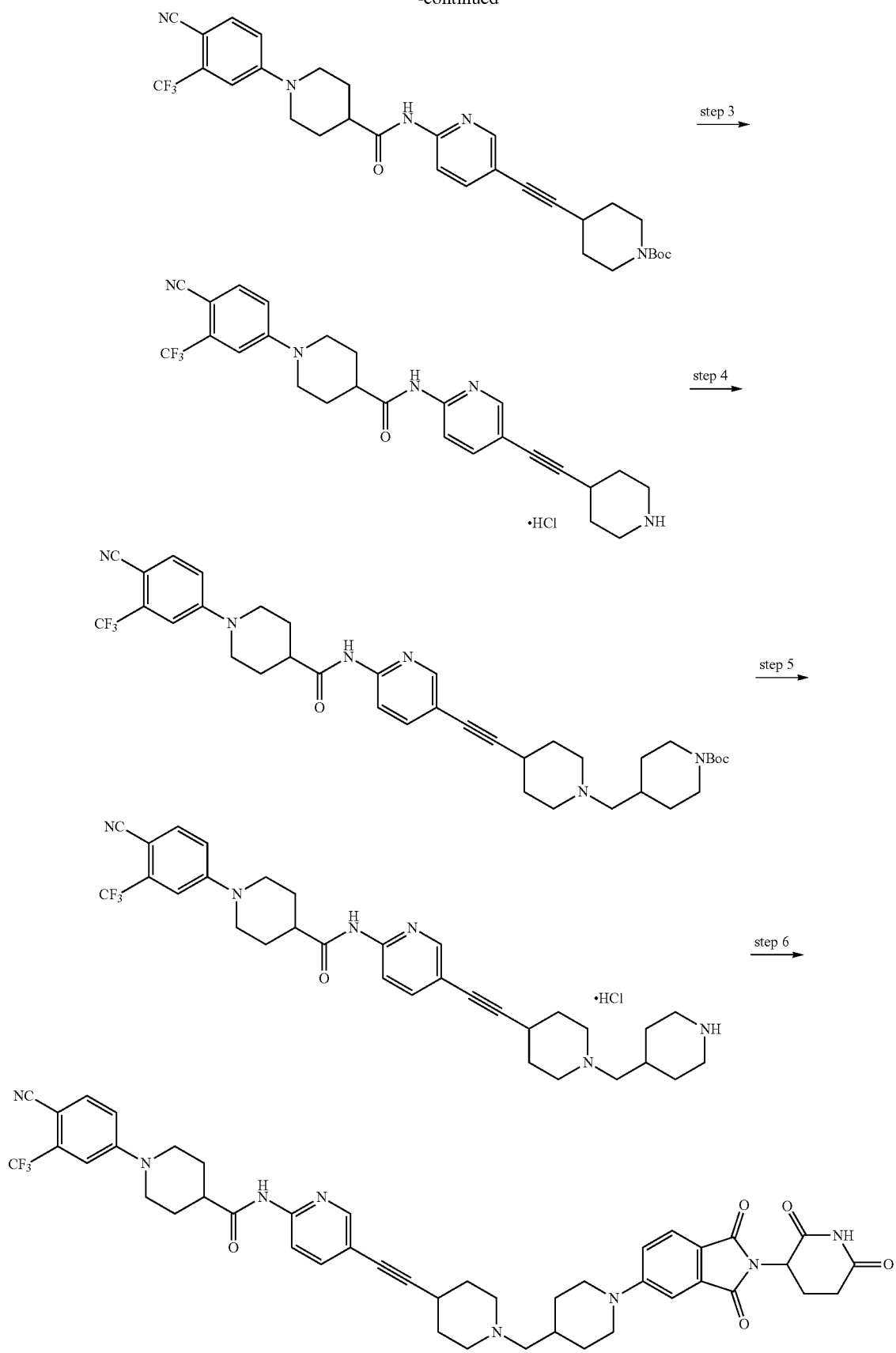

Step 1: Synthesis of 1-(4-cyano-3-(trifluoromethyl)phenyl)-N-(5-iodopyridin-2-yl)piperidine-4-carboxamide 5-iodopyridin-2-amine (300 mg, 1.36 mmol), 1-(4-cyano-3-(trifluoromethyl)phenyl)piperidine-4-carboxylic acid (Intermediate 1-1, 406 mg, 1.36 mmol), HATU (620 mg, 1.63 mmol), and DIPEA (0.47 mL, 2.72 mmol) were suspended in DMF (2.0 ml) and stirred at room temperature for 16 hours. After adding distilled water (15 ml) to the reaction solution, extraction was performed with EtOAc (25 ml×2), and the organic layer was dried over anhydrous sodium sulfate, filtered, and concentrated under reduced pressure. The resulting residue was subjected to MPLC (10% EtOAc/Hexane) to give 207 mg (30%) of a white solid. m/z 501.03 [M+H]$^+$.

Step 2: Synthesis of tert-butyl 4-((6-(1-(4-cyano-3-(trifluoromethyl)phenyl)piperidine-4-carboxamido)pyridin-3-yl)ethynyl)piperidine-1-carboxylate 1-(4-cyano-3-(trifluoromethyl)phenyl)-N-(5-iodopyridin-2-yl)piperidine-4-carboxamide (300 mg, 0.60 mmol), tert-butyl 4-ethynylpiperidine-1-carboxylate (190 mg, 0.90 mmol), Pd(PPh$_3$)$_2$Cl$_2$ (20 mg, 0.03 mmol), CuI (6 mg, 0.03 mmol), and TEA (0.17 mL, 1.2 mmol) were suspended in DMF (2.0 mL) and stirred at room temperature for 2 hours. After adding distilled water (15 ml) to the reaction solution, extraction was performed with EtOAc (25 ml×2), and the organic layer was dried over anhydrous sodium sulfate, filtered, and concentrated under reduced pressure. The resulting residue was subjected to MPLC (25% EtOAc/Hexane) to give 302 mg (87%) of a brown solid. m/z 604.29 [M+Na]$^+$.

Step 3: Synthesis of 1-(4-cyano-3-(trifluoromethyl)phenyl)-N-(5-(piperidin-4-ylethynyl)pyridin-2-yl)piperidine-4-carboxamide hydrochloride After suspending tert-butyl 4-((6-(1-(4-cyano-3-(trifluoromethyl)phenyl)piperidine-4-carboxamido)pyridin-3-yl)ethynyl)piperidine-1-carboxylate (302 mg, 0.437 mmol) in DCM (2.00 ml), 4 M HCl in dioxane (1.0 mL, 4.37 mmol) was added and stirred at room temperature for 1 hour. The reaction solution was concentrated. 221 mg (89%) of a light tan solid was obtained. m/z 482.24 [M+H]$^+$.

Step 4: Synthesis of tert-butyl 4-((4-((6-(1-(4-cyano-3-(trifluoromethyl)phenyl)piperidine-4-carboxamido)pyridin-3-yl)ethynyl)piperidin-1-yl)methyl)piperidine-1-carboxylate After suspending 1-(4-cyano-3-(trifluoromethyl)phenyl)-N-(5-(piperidin-4-ylethynyl)pyridin-2-yl)piperidine-4-carboxamide hydrochloride (100 mg, 0.21 mmol), and 1-Boc-4-piperidinecarboxaldehyde (81 mg, 0.386 mmol) in MeOH (10.0 ml), sodium triacetoxyborohydride (123 mg, 0.579 mmol) was added and stirred at room temperature for 16 hours. NaHCO$_3$ aqueous solution (15 ml) was added to the reaction mixture, followed by extraction with EtOAc (25 ml×2), and the organic layer was dried over anhydrous sodium sulfate, filtered, and concentrated under reduced pressure. The resulting residue was subjected to MPLC (10% MeOH/DCM) to give 30 mg (21%) of a pale tan solid. m/z 679.35 [M+H]$^+$.

Step 5: Synthesis of 1-(4-cyano-3-(trifluoromethyl)phenyl)-N-(5-((1-(piperidin-4-ylmethyl)piperidin-4-yl)ethynyl)pyridin-2-yl)piperidine-4-carboxamide hydrochloride After suspending tert-butyl 4-((4-((6-(1-(4-cyano-3-(trifluoromethyl)phenyl)piperidine-4-carboxamido)pyridin-3-yl)ethynyl)piperidin-1-yl)methyl)piperidine-1-carboxylate (30 mg, 0.044 mmol) in DCM (1.00 ml), 4 M HCl in dioxane (0.1 mL, 0.44 mmol) was added and stirred at room temperature for 1 hour. The reaction solution was concentrated. 27 mg (98%) of a brown solid was obtained. m/z 579.26 [M+H]$^+$.

Step 6: Synthesis of 1-(4-cyano-3-(trifluoromethyl)phenyl)-N-(5-((1-((1-(2-(2,6-dioxopiperidin-3-yl)-1,3-dioxoisoindolin-5-yl)piperidin-4-yl)methyl)piperidin-4-yl)ethynyl)pyridin-2-yl)piperidine-4-carboxamide 1-(4-cyano-3-(trifluoromethyl)phenyl)-N-(5-((1-(piperidin-4-ylmethyl)piperidin-4-yl)ethynyl)pyridin-2-yl)piperidine-4-carboxamide hydrochloride (27 mg, 0.043 mmol), 2-(2,6-dioxopiperidin-3-yl)-5-fluoroisoindoline-1,3-dione (Intermediate 2-1, 18 mg, 0.065 mmol), and DIPEA (0.01 mL, 0.065 mmol) were suspended in DMSO (1.0 ml) and stirred at 90° C. for 16 hours. After adding distilled water (15 ml) to the reaction solution, extraction was performed with EtOAc (25 ml×2), and the organic layer was dried over anhydrous sodium sulfate, filtered, and concentrated under reduced pressure. The resulting residue was subjected to MPLC (10% MeOH/DCM) to give 7 mg (19%) of a yellow solid.

Example 132: 1-(4-cyano-3-(trifluoromethyl)phenyl)-N-(5-((1-((1-(2-(2,6-dioxopiperidin-3-yl)-1,3-dioxoisoindolin-5-yl)azetidin-3-yl)methyl)piperidin-4-yl)ethynyl)pyridin-2-yl)piperidine-4-carboxamide

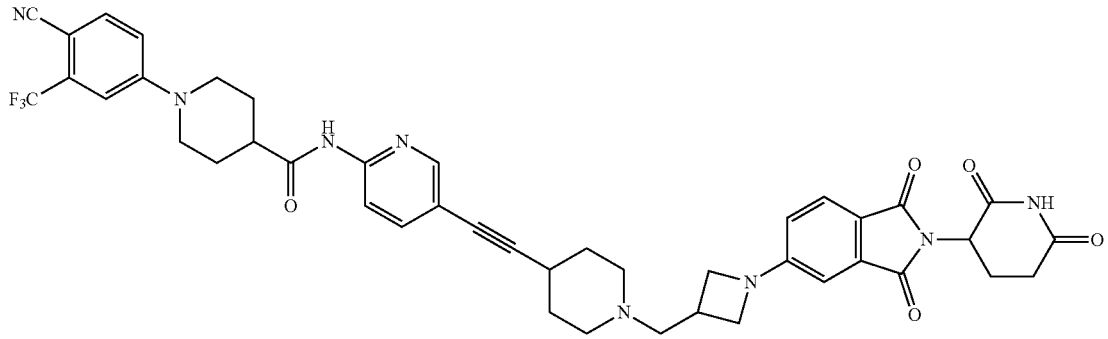 [SMILES: N#Cc1ccc(N2CCC(C(=O)Nc3ccc(C#CC4CCN(CC5CN(c6ccc7c(c6)C(=O)N(C6CCC(=O)NC6=O)C7=O)C5)CC4)cn3)CC2)cc1C(F)(F)F]

Example 132 was synthesized in a similar way to the synthesis method of Example 131, using tert-butyl 3-formylazetidine-1-carboxylate instead of tert-butyl 4-formylpiperidine-1-carboxylate.

Example 133: 1-(4-cyano-3-(trifluoromethyl)phenyl)-N-(5-(2-(1-((1-(2-(2,6-dioxopiperidin-3-yl)-1,3-dioxoisoindolin-5-yl)piperidin-4-yl)methyl)piperidin-4-yl)ethyl)pyridin-2-yl)piperidine-4-carboxamide

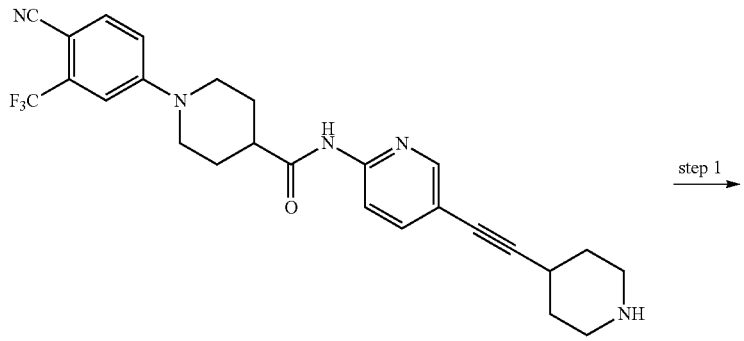

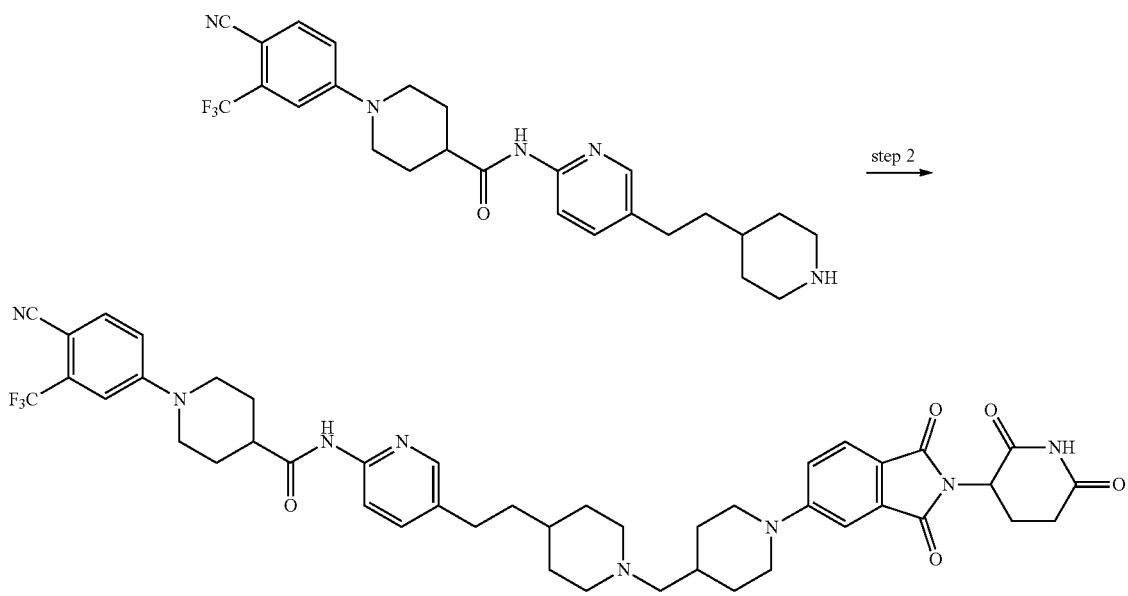

Step 1: Synthesis of 1-(4-cyano-3-(trifluoromethyl) phenyl)-N-(5-(2-(piperidin-4-yl)ethyl)pyridin-2-yl) piperidine-4-carboxamide After dissolving 1-(4-cyano-3-(trifluoromethyl)phenyl)-N-(5-(piperidin-4-ylethynyl)pyridin-2-yl)piperidine-4-carboxamide (58 mg, 0.12 mmol) in MeOH (10 mL), Pd/C (10 wt % Pd, 12 mg) was added and stirred under a hydrogen stream at room temperature for 6 hours. The reaction solution was filtered and concentrated. 56 mg (96%) of a white solid was obtained. m/z 486.26 [M+H]$^+$.

Step 2: Synthesis of 1-(4-cyano-3-(trifluoromethyl) phenyl)-N-(5-(2-(1-((1-(2-(2,6-dioxopiperidin-3-yl)-1,3-dioxoisoindolin-5-yl)piperidin-4-yl)methyl)piperidin-4-yl)ethyl)pyridin-2-yl)piperidine-4-carboxamide After suspending 1-(4-cyano-3-(trifluoromethyl)phenyl)-N-(5-(2-(piperidin-4-yl)ethyl)pyridin-2-yl)piperidine-4-carboxamide (56 mg, 0.12 mmol), and 1-(2-(2,6-dioxopiperidin-3-yl)-1,3-dioxoisoindolin-5-yl)piperidine-4-carbaldehyde (Intermediate 3-1, 53 mg, 0.14 mmol) in ACN (5.0 ml), sodium triacetoxyborohydride (76 mg, 0.36 mmol) was added and stirred at room temperature for 16 hours.

Example 134: 1-(4-cyano-3-(trifluoromethyl)phenyl)-N-(5-(3-(7-(2-(2,6-dioxopiperidin-3-yl)-1,3-dioxoisoindolin-5-yl)-2,7-diazaspiro[3.5]nonan-2-yl)prop-1-yn-1-yl)pyridin-2-yl)piperidine-4-carboxamide

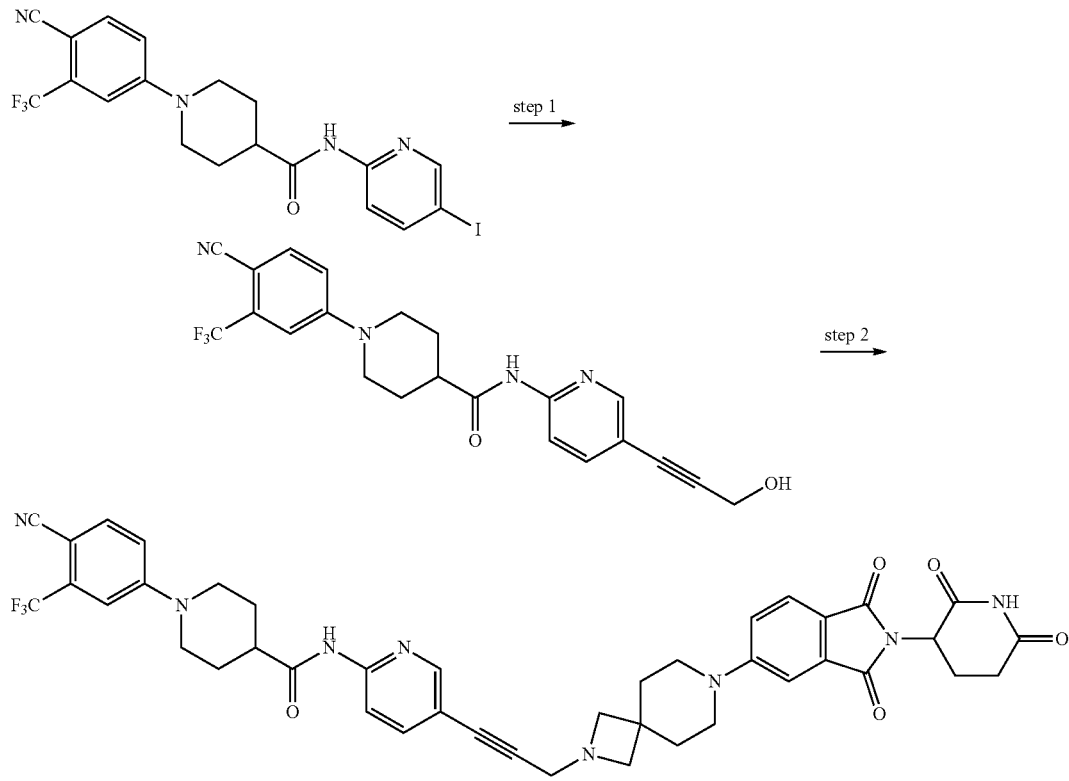

Step 1: Synthesis of 1-(4-cyano-3-(trifluoromethyl)phenyl)-N-(5-(3-hydroxyprop-1-yn-1-yl)pyridin-2-yl)piperidine-4-carboxamide 1-(4-cyano-3-(trifluoromethyl)phenyl)-N-(5-iodopyridin-2-yl)piperidine-4-carboxamide (1.00 g, 1.99 mmol), prop-2-yn-1-ol (0.17 ml, 2.99 mmol), Pd(PPh$_3$)$_2$Cl$_2$ (28 mg, 0.04 mmol), CuI (7.6 mg, 0.04 mmol), and TEA (0.55 ml, 4.0 mmol) were suspended in DMF (2.0 mL) and stirred in a microwave at 120° C. for 30 minutes. After adding distilled water (2 ml) to the reaction solution, extraction was performed with EtOAc (2 ml×2), and the organic layer was dried over anhydrous sodium sulfate, filtered, and concentrated under reduced pressure. The resulting residue was subjected to MPLC (25% EtOAc/Hexane) to give 434 mg (51%) of a yellow solid.

Step 2: Synthesis of 1-(4-cyano-3-(trifluoromethyl)phenyl)-N-(5-(3-(7-(2-(2,6-dioxopiperidin-3-yl)-1,3-dioxoisoindolin-5-yl)-2,7-diazaspiro[3.5]nonan-2-yl)prop-1-yn-1-yl)pyridin-2-yl)piperidine-4-carboxamide 1-(4-cyano-3-(trifluoromethyl)phenyl)-N-(5-(3-hydroxyprop-1-yn-1-yl)pyridin-2-yl)piperidine-4-carboxamide (9.2 mg, 0.02 mmol), TEA (0.04 ml, 0.04 mmol), and mesyl chloride (0.02 ml, 0.03 mmol) were suspended in DCM (0.3 ml) and stirred at room temperature for 5 minutes. The reaction solution was concentrated. The obtained residue was suspended in DMF (0.3 ml), and Cs$_2$CO$_3$ (7 mg, 0.02 mmol) and 2-(2,6-dioxopiperidin-3-yl)-5-(2,7-diazaspiro[3.5]nonan-2-yl)isoindoline-1,3-dione (Intermediate 3-14, 13.5 mg, 0.03 mmol) were added thereto. Then, the mixture was stirred at room temperature for 16 hours. After adding distilled water (0.5 ml) to the reaction solution, extraction was performed with EtOAc (1 ml×2), and the organic layer was dried over anhydrous sodium sulfate, filtered, and concentrated under reduced pressure. The obtained residue was subjected to MPLC (10% MeOH/DCM) to give 3.2 mg (19%) of a yellow solid.

Example 135: 1-(4-cyano-3-(trifluoromethyl)phenyl)-N-(5-(4-((7-(2-(2,6-dioxopiperidin-3-yl)-1-oxoisoindolin-5-yl)-2,7-diazaspiro[3.5]nonan-2-yl)methyl)piperidin-1-yl)pyridin-2-yl)piperidine-4-carboxamide
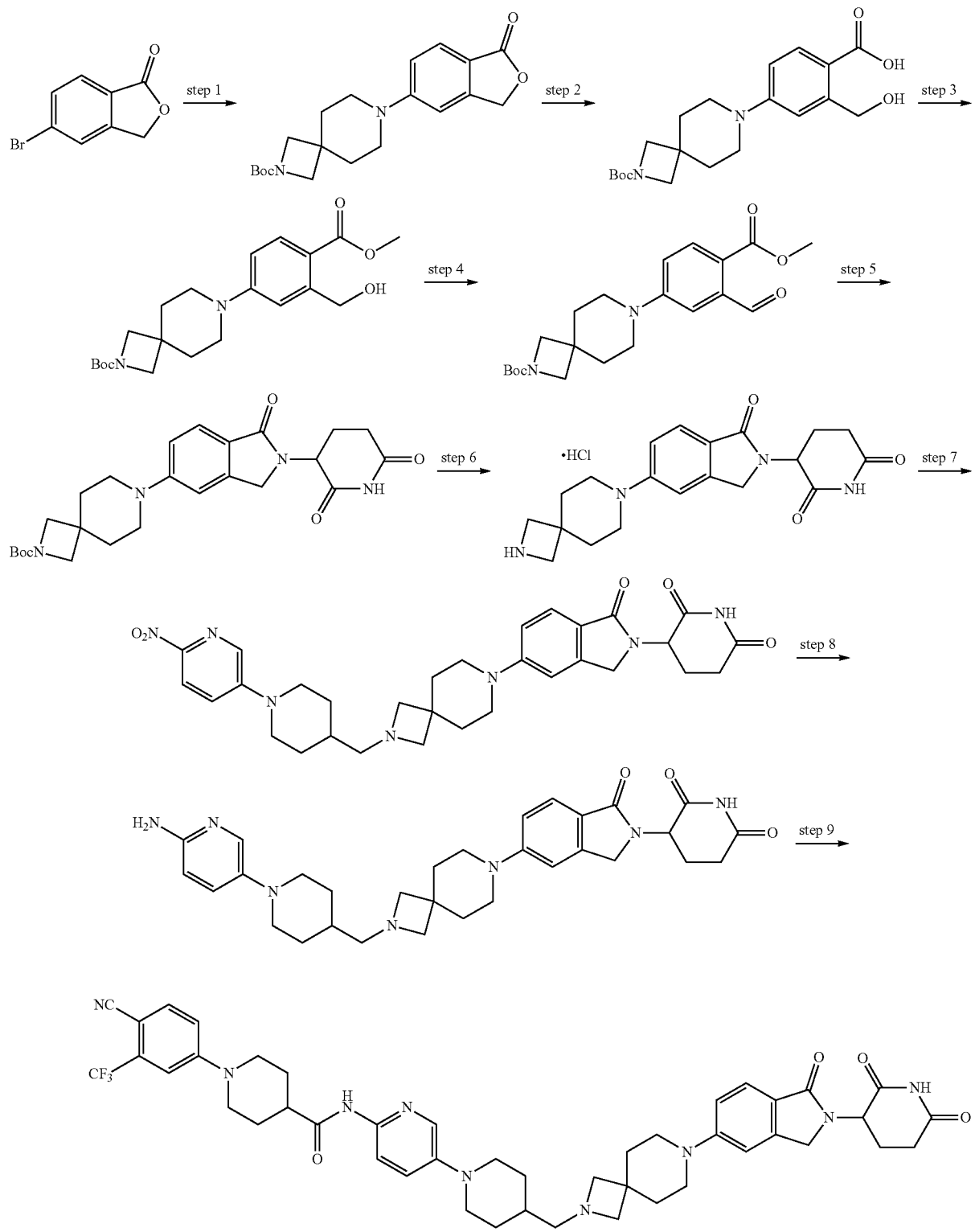

Step 1: Synthesis of tert-butyl 7-(1-oxo-1,3-dihydroisobenzofuran-5-yl)-2,7-diazaspiro[3.5]nonane-2-carboxylate After suspending 5-bromophthalide (3.00 g, 14.1 mmol), 2-Boc-2,7-diazaspiro[3,5]nonane (3.19 g, 14.1 mmol), and K₃PO₄ (5.99 g, 28.2 mmol) in DMF (20.0 mL), Pd₂(dba)₃ (1.29 g, 1.41 mmol) and Xantphos (815 mg, 1.41 mmol) were added and stirred at 100° C. for 16 hours. After adding distilled water (15 ml) to the reaction solution, extraction was performed with EtOAc (25 ml×2), and the organic layer was dried over anhydrous sodium sulfate, filtered, and concentrated under reduced pressure. The resulting residue was subjected to MPLC (50% EtOAc/Hexane) to give 2.53 g (50%) of a brown solid. m/z 359.23 [M+H]⁺.

Step 2: Synthesis of 4-(2-(tert-butoxycarbonyl)-2,7-diazaspiro[3.5]nonan-7-yl)-2-(hydroxymethyl)benzoic acid After suspending tert-butyl 7-(1-oxo-1,3-dihydroisobenzofuran-5-yl)-2,7-diazaspiro[3.5]nonane-2-carboxylate (2.53 g, 7.06 mmol) in a mixture of THF (5.0 mL), MeOH (5.0 mL), and distilled water (5.0 mL), NaOH (1.13 g, 28.2 mmol) was added and stirred at room temperature for 1 hour. After evaporating the solvent and extracting with distilled water, 1 N HCl was added to the aqueous layer and extracted with EtOAc (25 ml×2). The organic layer was dried over anhydrous sodium sulfate, filtered, and concentrated under reduced pressure. The obtained residue was recrystallized (EtOAc/Hexane) to give 1.75 g (66%) of a yellow solid. m/z 377.22 [M+H]⁺.

Step 3: Synthesis of tert-butyl 7-(3-(hydroxymethyl)-4-(methoxycarbonyl)phenyl)-2,7-diazaspiro[3.5]nonane-2-carboxylate After suspending 4-(2-(tert-butoxycarbonyl)-2,7-diazaspiro[3.5]nonan-7-yl)-2-(hydroxymethyl)benzoic acid (1.75 g, 4.65 mmol) in MeOH (10.0 mL) and EtOAc (10.0 mL), trimethylsilyldiazomethane (6.98 mmol, 14.0 mL) was added at −10° C. and stirred at −10° C. for 2 hours. After adding distilled water (15 ml) to the reaction solution, extraction was performed with EtOAc (25 ml×2), and the organic layer was dried over anhydrous sodium sulfate, filtered, and concentrated under reduced pressure. The resulting residue was subjected to MPLC (50% EtOAc/Hexane) to give 1.24 g (68%) of a yellow solid. m/z 391.28 [M+H]⁺.

Step 4: Synthesis of tert-butyl 7-(3-formyl-4-(methoxycarbonyl)phenyl)-2,7-diazaspiro[3.5]nonane-2-carboxylate After suspending tert-butyl 7-(3-(hydroxymethyl)-4-(methoxycarbonyl)phenyl)-2,7-diazaspiro[3.5]nonane-2-carboxylate (620 mg, 1.59 mmol) in DCM (20.0 ml), DMP (1.10 g, 2.59 mmol) was added and stirred at room temperature for 2 hours. After adding Na₂S₂O₃ aqueous solution (15 ml) to the reaction solution, extraction was performed with DCM (25 ml×2), and the organic layer was dried over anhydrous sodium sulfate, filtered, and concentrated under reduced pressure. The resulting residue was subjected to MPLC (30% EtOAc/Hexane) to give 523 mg (85%) of a yellow solid. m/z 389.22 [M+H]⁺.

Step 5: Synthesis of tert-butyl 7-(2-(2,6-dioxopiperidin-3-yl)-1-oxoisoindolin-5-yl)-2,7-diazaspiro[3.5]nonane-2-carboxylate After suspending tert-butyl 7-(3-formyl-4-(methoxycarbonyl)phenyl)-2,7-diazaspiro[3.5]nonane-2-carboxylate (523 mg, 1.35 mmol), and 3-aminopiperidine-2,6-dione hydrochloride (333 mg, 2.03 mmol) in MeOH (10.0 ml), sodium triacetoxyborohydride (858 mg, 4.05 mmol) was added and stirred at room temperature for 16 hours. NaHCO₃ aqueous solution (15 ml) was added to the reaction mixture, followed by extraction with EtOAc (25 ml×2), and the organic layer was dried over anhydrous sodium sulfate, filtered, and concentrated under reduced pressure. The obtained residue was subjected to MPLC (10% MeOH/DCM) to give 227 mg (36%) of a gray solid. m/z 469.29 [M+H]⁺.

Step 6: Synthesis of 3-(1-oxo-5-(2,7-diazaspiro[3.5]nonan-7-yl)isoindolin-2-yl)piperidine-2,6-dione hydrochloride After suspending tert-butyl 7-(2-(2,6-dioxopiperidin-3-yl)-1-oxoisoindolin-5-yl)-2,7-diazaspiro[3.5]nonane-2-carboxylate (227 mg, 0.484 mmol) in DCM (2.0 ml), 4 M HCl in dioxane (0.61 mL, 2.42 mmol) was added and stirred at room temperature for 1 hour. The reaction solution was concentrated. 194 mg (99%) of a brown solid was obtained.

Step 7: Synthesis of 3-(5-(2-((1-(6-nitropyridin-3-yl)piperidin-4-yl)methyl)-2,7-diazaspiro[3.5]nonan-7-yl)-1-oxoisoindolin-2-yl)piperidine-2,6-dione After suspending 3-(1-oxo-5-(2,7-diazaspiro[3.5]nonan-7-yl)isoindolin-2-yl)piperidine-2,6-dione hydrochloride (200 mg, 0.494 mmol), and 1-(6-nitropyridin-3-yl)piperidine-4-carbaldehyde (128 mg, 0.543 mmol) in MeOH (5.0 ml), sodium triacetoxyborohydride (419 mg, 1.98 mmol) was added and stirred at room temperature for 16 hours. NaHCO₃ aqueous solution (15 ml) was added to the reaction mixture, followed by extraction with EtOAc (25 ml×2), and the organic layer was dried over anhydrous sodium sulfate, filtered, and concentrated under reduced pressure. The resulting residue was subjected to MPLC (10% MeOH/DCM) to give 95 mg (33%) of a white solid. m/z 588.36 [M+H]⁺.

Step 8: Synthesis of 3-(5-(2-((1-(6-aminopyridin-3-yl)piperidin-4-yl)methyl)-2,7-diazaspiro[3.5]nonan-7-yl)-1-oxoisoindolin-2-yl)piperidine-2,6-dione After dissolving 3-(5-(2-((1-(6-nitropyridin-3-yl)piperidin-4-yl)methyl)-2,7-diazaspiro[3.5]nonan-7-yl)-1-oxoisoindolin-2-yl)piperidine-2,6-dione (95 mg, 0.17 mmol) in a mixture of DCM (10 mL) and MeOH (5 mL), Pd/C (10 wt % Pd, 19 mg) was added and stirred under a hydrogen stream at room temperature for 6 hours. The reaction solution was filtered and concentrated. 56 mg (59%) of a brown solid was obtained. m/z 558.33 [M+H]⁺.

Step 9: Synthesis of 1-(4-cyano-3-(trifluoromethyl)phenyl)-N-(5-(4-((7-(2-(2,6-dioxopiperidin-3-yl)-1-oxoisoindolin-5-yl)-2,7-diazaspiro[3.5]nonan-2-yl)methyl)piperidin-1-yl)pyridin-2-yl)piperidine-4-carboxamide 3-(5-(2-((1-(6-aminopyridin-3-yl)piperidin-4-yl)methyl)-2,7-diazaspiro[3.5]nonan-7-yl)-1-oxoisoindolin-2-yl)piperidine-2,6-dione (20 mg, 0.033 mmol), 1-(4-cyano-3-(trifluoromethyl)phenyl)piperidine-4-carboxylic acid (Intermediate 1-1, 12 mg, 0.039 mmol), HATU (15 mg, 0.039 mmol), and DIPEA (0.01 mL, 0.066 mmol) were suspended in DMF (1.0 ml) and stirred at room temperature for 16 hours. After adding distilled water (15 ml) to the reaction solution, extraction was performed with EtOAc (25 ml×2), and the organic layer was dried over anhydrous sodium sulfate, filtered, and concentrated under reduced pressure. The resulting residue was subjected to MPLC (10% MeOH/DCM) to give 5 mg (16%) of a yellow solid.

Example 136: 1-(4-cyano-3-(trifluoromethyl)phenyl)-N-(5-(4-((7-(2-(2,6-dioxopiperidin-3-yl)-1-oxoisoindolin-5-yl)-2,7-diazaspiro[3.5]nonan-2-yl)methyl)piperidin-1-yl)pyridin-2-yl)-4-fluoropiperidine-4-carboxamide

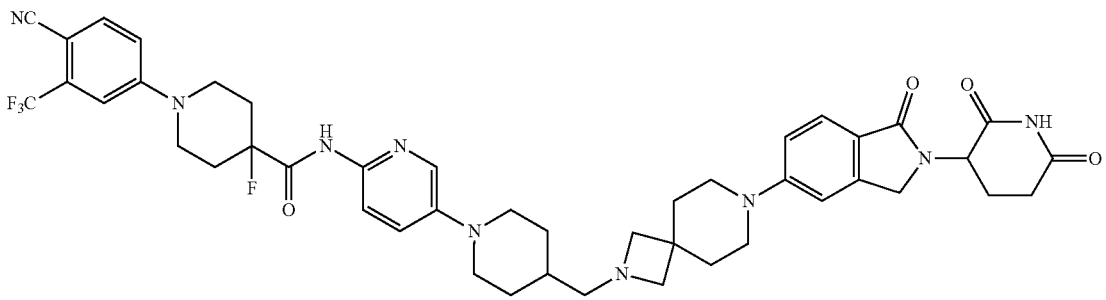 [SMILES: N#Cc1ccc(N2CCC(F)(C(=O)Nc3ccc(N4CCC(CN5CC6(CCN(c7ccc8c(c7)CN(C7CCC(=O)NC7=O)C8=O)CC6)C5)CC4)cn3)CC2)cc1C(F)(F)F]

Example 136 was synthesized in a similar way to the synthesis method of Example 135, using 1-(4-cyano-3-(trifluoromethyl)phenyl)-4-fluoropiperidine-4-carboxylic acid (Intermediate 1-5) instead of 1-(4-cyano-3-(trifluoromethyl)phenyl)piperidine-4-carboxylic acid (Intermediate 1-1).

Example 137: 1-(6-cyano-5-(trifluoromethyl)pyridin-3-yl)-N-(5-(4-((7-(2-(2,6-dioxopiperidin-3-yl)-1-oxoisoindolin-5-yl)-2,7-diazaspiro[3.5]nonan-2-yl)methyl)piperidin-1-yl)pyridin-2-yl)piperidine-4-carboxamide

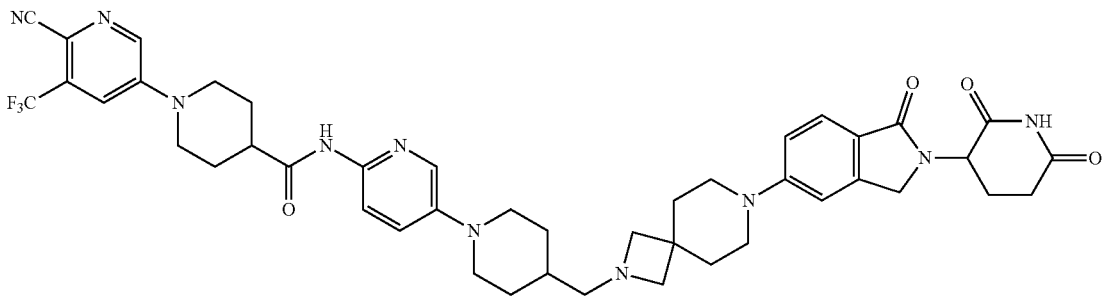 [SMILES: N#Cc1ncc(N2CCC(C(=O)Nc3ccc(N4CCC(CN5CC6(CCN(c7ccc8c(c7)CN(C7CCC(=O)NC7=O)C8=O)CC6)C5)CC4)cn3)CC2)cc1C(F)(F)F]

Example 137 was synthesized in a similar way to the synthesis method of Example 135, using 1-(6-cyano-5-(trifluoromethyl)pyridin-3-yl)piperidine-4-carboxylic acid (Intermediate 1-7) instead of 1-(4-cyano-3-(trifluoromethyl)phenyl)piperidine-4-carboxylic acid (Intermediate 1-1).

Example 138: 1-(4-cyano-3-(trifluoromethyl)phenyl)-N-(5-(4-(2-(7-(2-(2,6-dioxopiperidin-3-yl)-1-oxoisoindolin-5-yl)-2,7-diazaspiro[3.5]nonan-2-yl)ethyl)piperidin-1-yl)pyridin-2-yl)piperidine-4-carboxamide

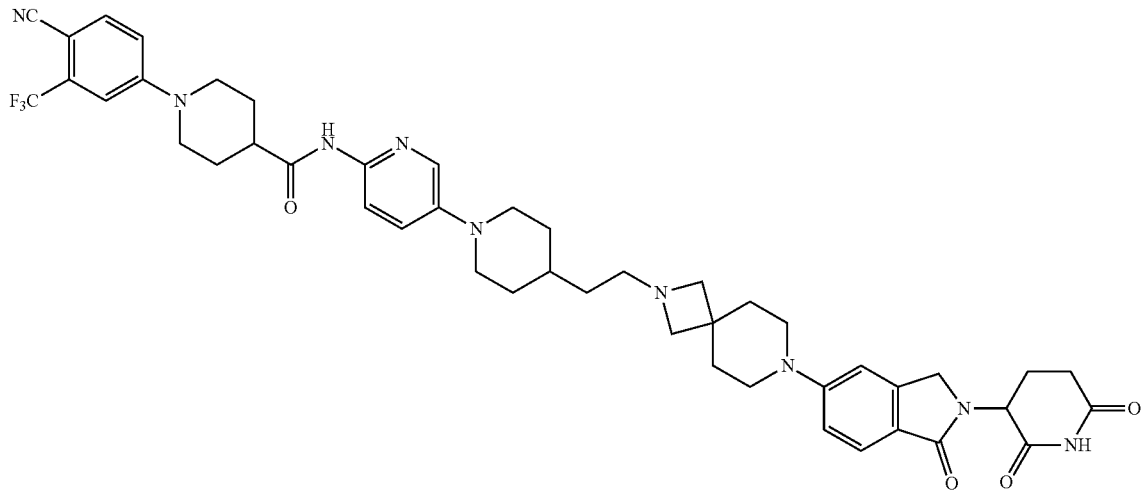 [SMILES: N#Cc1ccc(N2CCC(C(=O)Nc3ccc(N4CCC(CCN5CC6(CCN(c7ccc8c(c7)CN(C7CCC(=O)NC7=O)C8=O)CC6)C5)CC4)cn3)CC2)cc1C(F)(F)F]

Example 138 was synthesized in a similar way to the synthesis method of Example 135, using 2-(1-(6-nitropyridin-3-yl)piperidin-4-yl)acetaldehyde instead of 1-(6-nitropyridin-3-yl)piperidine-4-carbaldehyde.

Example 139: 1-(4-cyano-3-(trifluoromethyl)phenyl)-N-(5-(4-(2-(4-(2-(2,6-dioxopiperidin-3-yl)-1-oxoisoindolin-5-yl)piperazin-1-yl)ethyl)piperidin-1-yl)pyridin-2-yl)piperidine-4-carboxamide

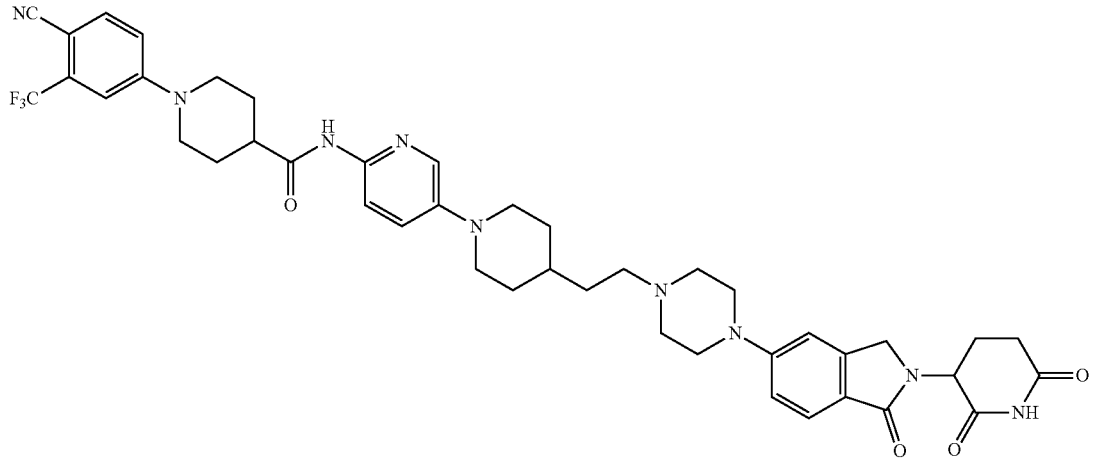 [SMILES: N#Cc1ccc(N2CCC(C(=O)Nc3ccc(N4CCC(CCN5CCN(c6ccc7c(c6)CN(C6CCC(=O)NC6=O)C7=O)CC5)CC4)cn3)CC2)cc1C(F)(F)F]

Example 139 was synthesized in a similar way to the synthesis method of Example 135, using tert-butyl piperazine-1-carboxylate and 2-(1-(6-nitropyridin-3-yl)piperidin-4-yl)acetaldehyde, respectively, instead of tert-butyl 2,7-diazaspiro[3.5]nonane-2-carboxylate and 1-(6-nitropyridin-3-yl)piperidine-4-carbaldehyde.

Example 140: 1-(4-cyano-3-(trifluoromethyl)phenyl)-N-(5-(4-((4-(1-(2-(2,6-dioxopiperidin-3-yl)-1-oxoisoindolin-5-yl)piperidin-4-yl)piperazin-1-yl)methyl)piperidin-1-yl)pyridin-2-yl)piperidine-4-carboxamide

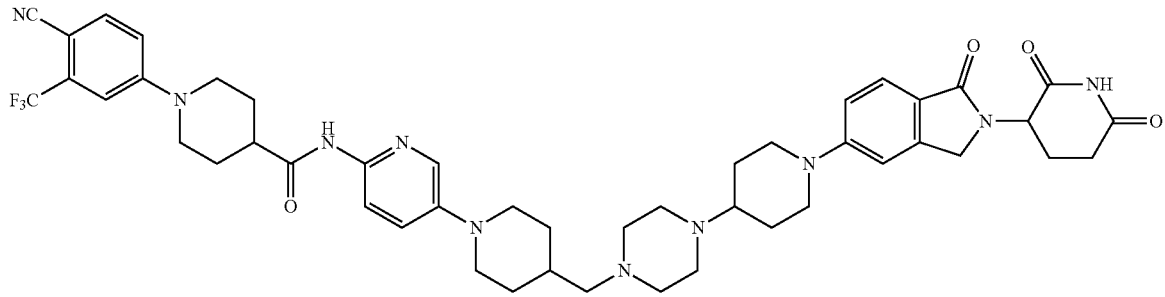

Example 140 was synthesized in a similar way to the synthesis method of Example 135, using tert-butyl 4-(piperidin-4-yl)piperazine-1-carboxylate (Intermediate 4-4) instead of tert-butyl 2,7-diazaspiro[3.5]nonane-2-carboxylate.

Example 141: 1-(4-cyano-3-(trifluoromethyl)phenyl)-N-(5-(4-((4-(1-(2-(2,6-dioxopiperidin-3-yl)-1-oxoisoindolin-5-yl)piperidin-4-yl)piperazin-1-yl)methyl)piperidin-1-yl)pyridin-2-yl)-4-fluoropiperidine-4-carboxamide

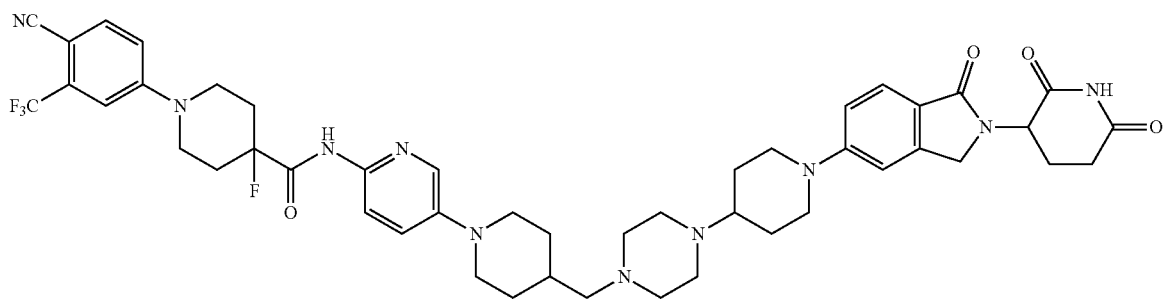 [SMILES: N#Cc1ccc(N2CCC(C(=O)Nc3ccc(N4CCC(CN5CCN(C6CCN(c7ccc8c(c7)CN(C7CCC(=O)NC7=O)C8=O)CC6)CC5)CC4)cn3)CC2)cc1C(F)(F)F]

Example 141 was synthesized in a similar way to the synthesis method of Example 135, using tert-butyl 4-(piperidin-4-yl)piperazine-1-carboxylate (Intermediate 4-4) and 1-(4-cyano-3-(trifluoromethyl)phenyl)-4-fluoropiperidine-4-carboxylic acid (Intermediate 1-5), respectively, instead of tert-butyl 2,7-diazaspiro[3.5]nonane-2-carboxylate and 1-(4-cyano-3-(trifluoromethyl)phenyl)piperidine-4-carboxylic acid (Intermediate 1-1).

Example 142: 1-(6-cyano-5-(trifluoromethyl)pyridin-3-yl)-N-(5-(4-((4-(1-(2-(2,6-dioxopiperidin-3-yl)-1-oxoisoindolin-5-yl)piperidin-4-yl)piperazin-1-yl)methyl)piperidin-1-yl)pyridin-2-yl)piperidine-4-carboxamide

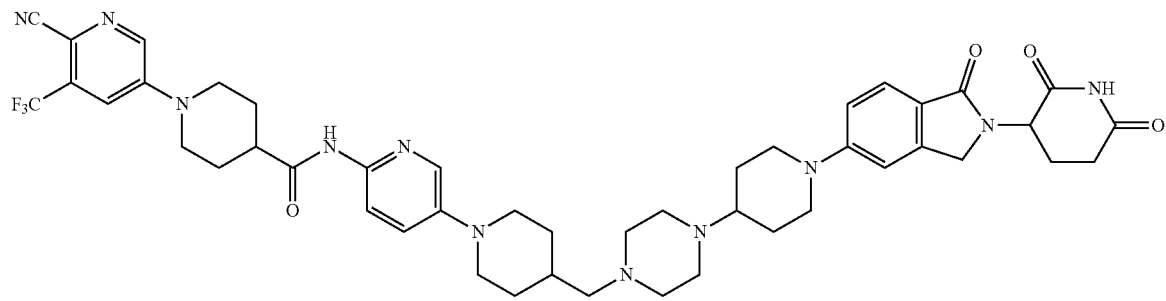 [SMILES: N#Cc1ncc(N2CCC(C(=O)Nc3ccc(N4CCC(CN5CCN(C6CCN(c7ccc8c(c7)CN(C7CCC(=O)NC7=O)C8=O)CC6)CC5)CC4)cn3)CC2)cc1C(F)(F)F]

Example 142 was synthesized in a similar way to the synthesis method of Example 135, using tert-butyl 4-(piperidin-4-yl)piperazine-1-carboxylate (Intermediate 4-4) and 1-(6-cyano-5-(trifluoromethyl)pyridin-3-yl)piperidine-4-carboxylic acid (Intermediate 1-7), respectively, instead of tert-butyl 2,7-diazaspiro[3.5]nonane-2-carboxylate and 1-(4-cyano-3-(trifluoromethyl)phenyl)piperidine-4-carboxylic acid (Intermediate 1-1).

Example 143: 1-(4-cyano-3-(trifluoromethyl)phenyl)-N-(5-(4-((4-((1-(2-(2,6-dioxopiperidin-3-yl)-1-oxoisoindolin-5-yl)piperidin-4-yl)methyl)piperazin-1-yl)methyl)piperidin-1-yl)pyridin-2-yl)piperidine-4-carboxamide

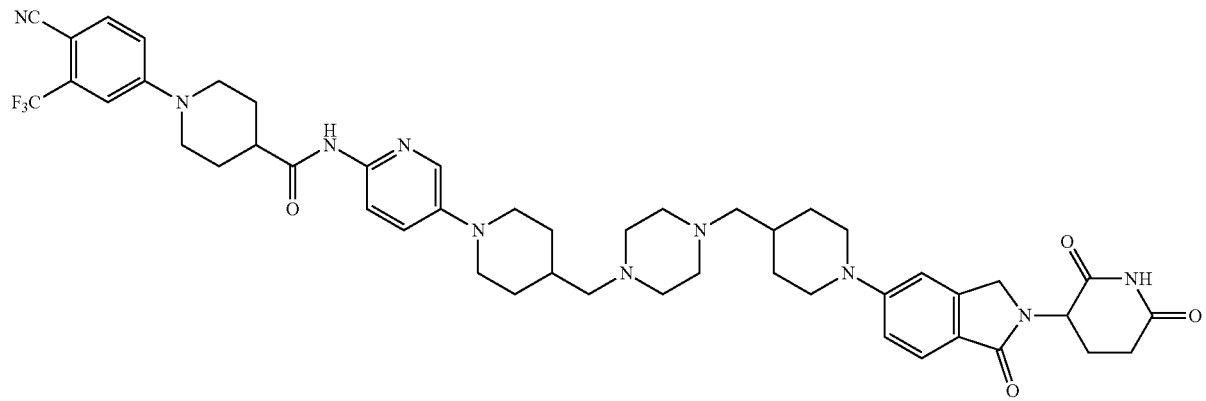 [SMILES: N#Cc1ccc(N2CCC(C(=O)Nc3ccc(N4CCC(CN5CCN(CC6CCN(c7ccc8c(c7)CN(C7CCC(=O)NC7=O)C8=O)CC6)CC5)CC4)cn3)CC2)cc1C(F)(F)F]

Example 143 was synthesized in a similar way to the synthesis method of Example 135, using tert-butyl 4-(piperidin-4-ylmethyl)piperazine-1-carboxylate (Intermediate 4-3) instead of tert-butyl 2,7-diazaspiro[3.5]nonane-2-carboxylate.

Example 144: 1-(4-cyano-3-(trifluoromethyl)phenyl)-N-(5-(4-((4-((1-(2-(2,6-dioxopiperidin-3-yl)-1-oxoisoindolin-5-yl)piperidin-4-yl)methyl)piperazin-1-yl)methyl)piperidin-1-yl)pyridin-2-yl)-4-fluoropiperidine-4-carboxamide

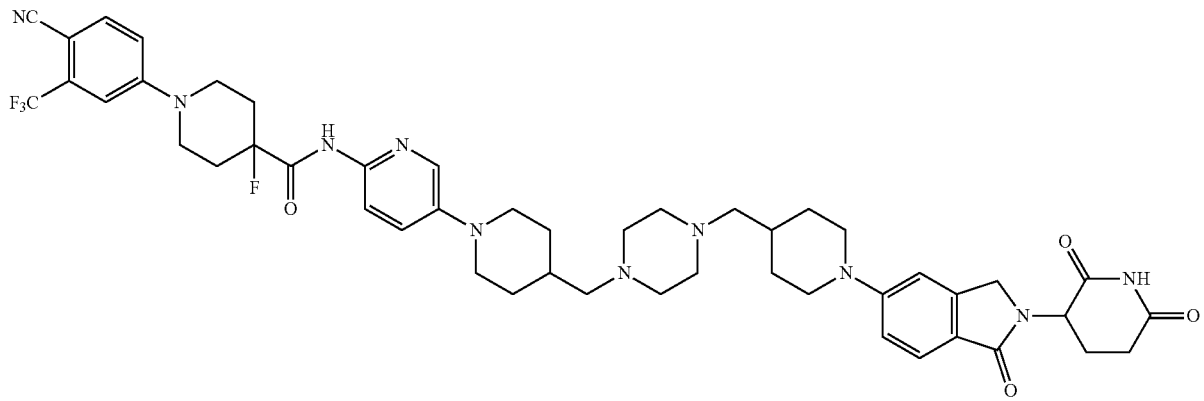 [SMILES: N#Cc1ccc(N2CCC(F)(C(=O)Nc3ccc(N4CCC(CN5CCN(CC6CCN(c7ccc8c(c7)CN(C7CCC(=O)NC7=O)C8=O)CC6)CC5)CC4)cn3)CC2)cc1C(F)(F)F]

Example 144 was synthesized in a similar way to the synthesis method of Example 135, using tert-butyl 4-(piperidin-4-ylmethyl)piperazine-1-carboxylate (Intermediate 4-3) and 1-(4-cyano-3-(trifluoromethyl)phenyl)-4-fluoropiperidine-4-carboxylic acid (Intermediate 1-5), respectively, instead of tert-butyl 2,7-diazaspiro[3.5]nonane-2-carboxylate and 1-(4-cyano-3-(trifluoromethyl)phenyl)piperidine-4-carboxylic acid (Intermediate 1-1).

Example 145: 1-(6-cyano-5-(trifluoromethyl)pyridin-3-yl)-N-(5-(4-((4-((1-(2-(2,6-dioxopiperidin-3-yl)-1-oxoisoindolin-5-yl)piperidin-4-yl)methyl)piperazin-1-yl)methyl)piperidin-1-yl)pyridin-2-yl)piperidine-4-carboxamide

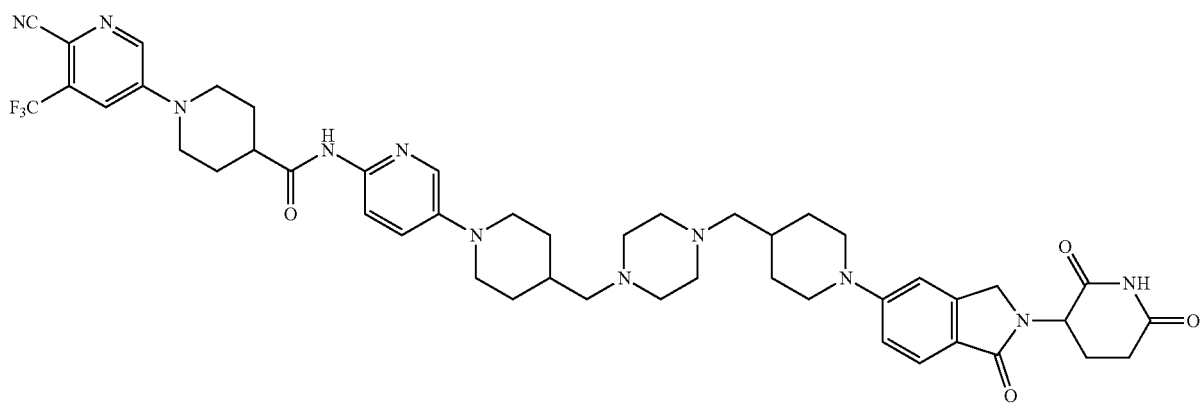 [SMILES: N#Cc1ncc(N2CCC(C(=O)Nc3ccc(N4CCC(CN5CCN(CC6CCN(c7ccc8c(c7)CN(C7CCC(=O)NC7=O)C8=O)CC6)CC5)CC4)cn3)CC2)cc1C(F)(F)F]

Example 145 was synthesized in a similar way to the synthesis method of Example 135, using tert-butyl 4-(piperidin-4-ylmethyl)piperazine-1-carboxylate (Intermediate 4-3) and 1-(6-cyano-5-(trifluoromethyl)pyridin-3-yl)piperidine-4-carboxylic acid (Intermediate 1-7), respectively, instead of tert-butyl 2,7-diazaspiro[3.5]nonane-2-carboxylate and 1-(4-cyano-3-(trifluoromethyl)phenyl)piperidine-4-carboxylic acid (Intermediate 1-1).

Example 146: 1-(4-cyano-3-(trifluoromethyl)phenyl)-N-(5-(4-((4-((2-(2,6-dioxopiperidin-3-yl)-1,3-dioxoisoindolin-5-yl)oxy)piperidin-1-yl)methyl)piperidin-1-yl)pyridin-2-yl)piperidine-4-carboxamide

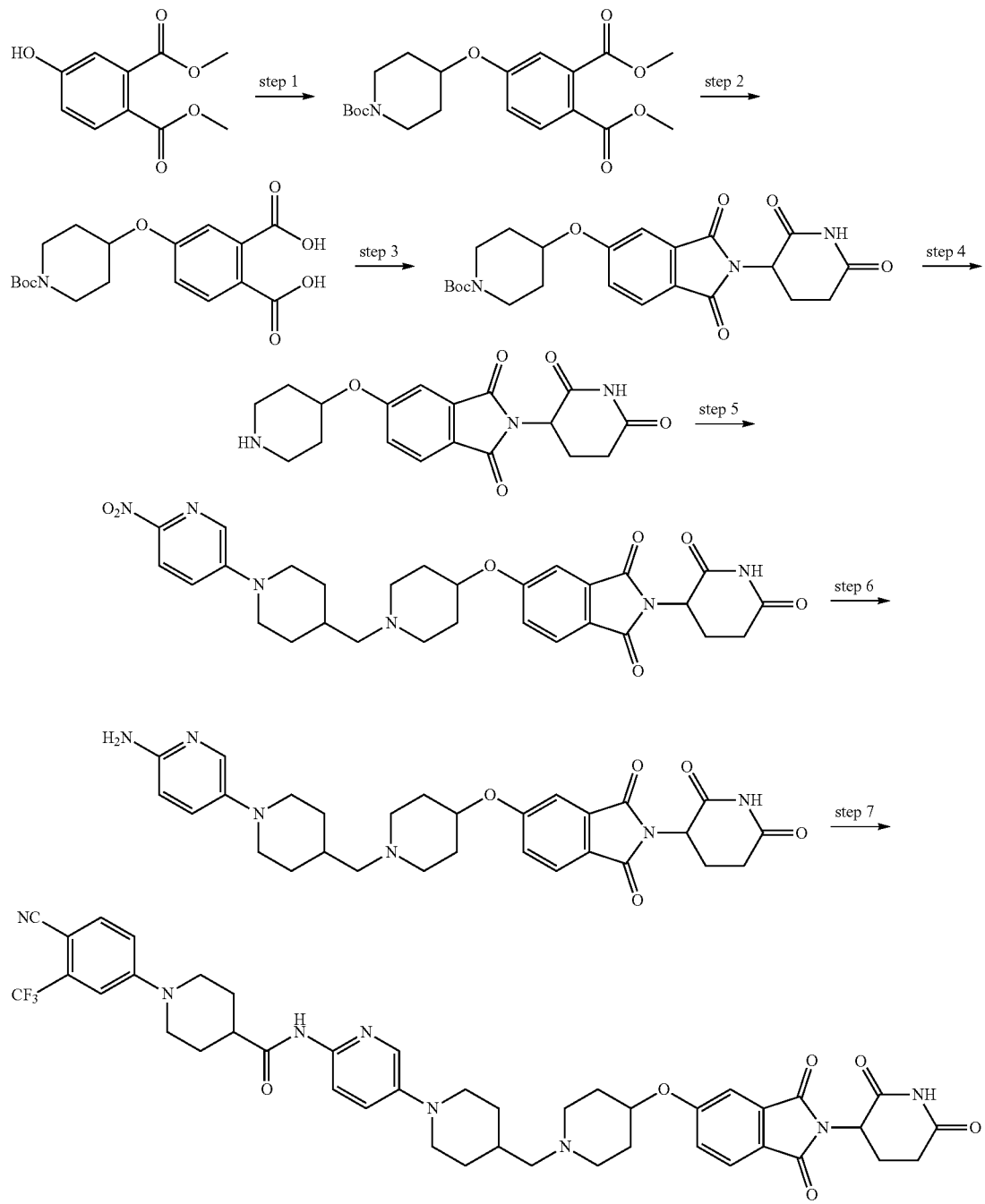

Step 1: Synthesis of dimethyl 4-((1-(tert-butoxycarbonyl)piperidin-4-yl)oxy)phthalate After suspending dimethyl 4-hydroxyphthalate (300 mg, 1.43 mmol), 1-(tert-butoxycarbonyl)-4-hydroxypiperidine (315 mg, 1.57 mmol), and triphenyl phosphine (1.13 g, 4.29 mmol) in THF (15.0 ml), DEAD (0.67 mL, 4.29 mmol) was added and stirred at 40° C. for 16 hours. After adding distilled water (15 ml) to the reaction solution, extraction was performed with EtOAc (25 ml×2), and the organic layer was dried over anhydrous sodium sulfate, filtered, and concentrated under reduced pressure. The resulting residue was subjected to MPLC (30% EtOAc/Hexane) to give 512 mg (91%) of a colorless liquid.

Step 2: Synthesis of 4-((1-(tert-butoxycarbonyl) piperidin-4-yl)oxy)phthalic acid After suspending dimethyl 4-((1-(tert-butoxycarbonyl)piperidin-4-yl)oxy)phthalate (512 mg, 1.30 mmol) in a mixture of THF (10.0 mL), MeOH (10.0 mL), and distilled water (10.0 mL), NaOH (311 g, 7.80 mmol) was added and stirred at room temperature for 4 hours. After evaporation of the solvent and extraction with distilled water, 1N HCl was added to the aqueous layer and extraction was performed with EtOAc (25 ml×2). The organic layer was dried over anhydrous sodium sulfate, filtered, and concentrated under reduced pressure. 416 mg (88%) of a white solid was obtained.

Step 3: Synthesis of tert-butyl 4-((2-(2,6-dioxopiperidin-3-yl)-1,3-dioxoisoindolin-5-yl)oxy)piperidine-1-carboxylate 4-((1-(tert-butoxycarbonyl)piperidin-4-yl)oxy)phthalic acid (416 mg, 1.14 mmol), and 3-aminopiperidine-2,6-dione hydrochloride (206 mg, 1.25 mmol) were suspended in pyridine (4.0 ml) and stirred at 110° C. for 16 hours. After adding distilled water (15 ml) to the reaction solution, extraction was performed with EtOAc (25 ml×2), and the organic layer was dried over anhydrous sodium sulfate, filtered, and concentrated under reduced pressure. The resulting residue was subjected to MPLC (30% EtOAc/Hexane) to give 396 mg (76%) of a blue solid.

Step 4: Synthesis of 2-(2,6-dioxopiperidin-3-yl)-5-(piperidin-4-yloxy)isoindoline-1,3-dione After suspending tert-butyl 4-((2-(2,6-dioxopiperidin-3-yl)-1,3-dioxoisoindolin-5-yl)oxy)piperidine-1-carboxylate (396 mg, 0.87 mmol) in DCM (3.00 ml), 4M HCl in dioxane (1.01 mL, 4.03 mmol) was added and stirred at room temperature for 1 hour. After concentrating the reaction mixture, aqueous NaHCO₃ solution (15 ml) was added, followed by extraction with DCM (25 ml×2). The organic layer was dried over anhydrous sodium sulfate, filtered, and concentrated under reduced pressure. 255 mg (88%) of a white solid was obtained.

Step 5: Synthesis of 2-(2,6-dioxopiperidin-3-yl)-5-((1-((1-(6-nitropyridin-3-yl)piperidin-4-yl)methyl)piperidin-4-yl)oxy)isoindoline-1,3-dione After suspending 2-(2,6-dioxopiperidin-3-yl)-5-(piperidin-4-yloxy)isoindoline-1,3-dione (100 mg, 0.279 mmol), and 1-(6-nitropyridin-3-yl)piperidine-4-carbaldehyde (66 mg, 0.279 mmol) in MeOH (20.0 ml), sodium triacetoxyborohydride (177 mg, 0.837 mmol) was added and stirred at room temperature for 16 hours. NaHCO₃ aqueous solution (15 ml) was added to the reaction mixture, followed by extraction with EtOAc (20 ml×2), and the organic layer was dried over anhydrous sodium sulfate, filtered, and concentrated under reduced pressure. The obtained residue was subjected to MPLC (10% MeOH/DCM) to give 123 mg (77%) of a yellow solid. m/z 577.15 [M+H]⁺.

Step 6: Synthesis of 5-((1-((1-(6-aminopyridin-3-yl)piperidin-4-yl)methyl)piperidin-4-yl)oxy)-2-(2,6-dioxopiperidin-3-yl)isoindoline-1,3-dione After dissolving 2-(2,6-dioxopiperidin-3-yl)-5-((1-((1-(6-nitropyridin-3-yl)piperidin-4-yl)methyl)piperidin-4-yl)oxy)isoindoline-1,3-dione (123 mg, 0.213 mmol) in a mixture of DCM (5 mL) and MeOH (10 mL), Pd/C (10 wt % Pd, 25 mg) was added and stirred under a hydrogen stream at room temperature for 4 hours. The reaction solution was filtered and concentrated. A yellow solid (100 mg, 86%) was obtained. m/z 547.42 [M+H]⁺.

Step 7: Synthesis of 1-(4-cyano-3-(trifluoromethyl) phenyl)-N-(5-(4-((4-((2-(2,6-dioxopiperidin-3-yl)-1,3-dioxoisoindolin-5-yl)oxy)piperidin-1-yl)methyl) piperidin-1-yl)pyridin-2-yl)piperidine-4-carboxamide 5-((1-((1-(6-aminopyridin-3-yl)piperidin-4-yl)methyl)piperidin-4-yl)oxy)-2-(2,6-dioxopiperidin-3-yl)isoindoline-1,3-dione (50 mg, 0.091 mmol), 1-(4-cyano-3-(trifluoromethyl)phenyl)piperidine-4-carboxylic acid (Intermediate 1-1, 32 mg, 0.11 mmol), HATU (42 mg, 0.11 mmol), and DIPEA (0.02 mL, 0.18 mmol) were suspended in DMF (2.0 ml) and stirred at room temperature for 16 hours. After adding distilled water (15 ml) to the reaction solution, extraction was performed with EtOAc (20 ml×2), and the organic layer was dried over anhydrous sodium sulfate, filtered, and concentrated under reduced pressure. The resulting residue was subjected to MPLC (10% MeOH/DCM) to give 29 mg (38%) of an off-white solid.

Example 147: 1-(4-cyano-3-(trifluoromethyl)phenyl)-N-(5-(4-((4-(((2-(2,6-dioxopiperidin-3-yl)-1,3-dioxoisoindolin-5-yl)oxy)methyl)piperidin-1-yl)methyl)piperidin-1-yl)pyridin-2-yl)piperidine-4-carboxamide

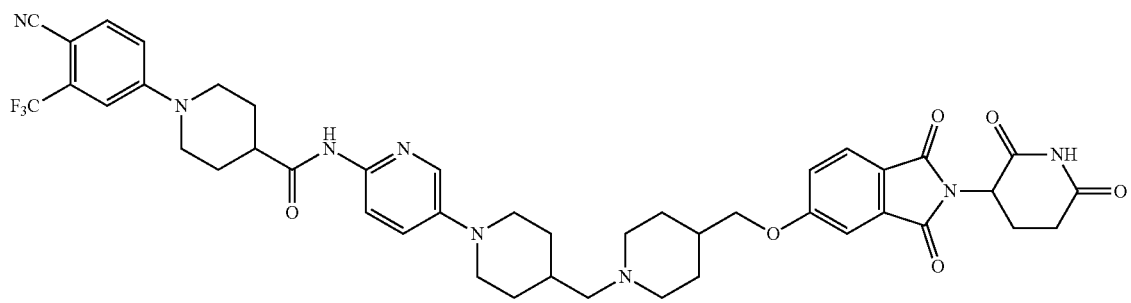 [SMILES: N#Cc1ccc(N2CCC(C(=O)Nc3ccc(N4CCC(CN5CCC(COc6ccc7c(c6)C(=O)N(C6CCC(=O)NC6=O)C7=O)CC5)CC4)cn3)CC2)cc1C(F)(F)F]

Example 147 was synthesized in a similar way to the synthesis method of Example 146, using tert-butyl 4-(hydroxymethyl)piperidine-1-carboxylate instead of tert-butyl 4-hydroxypiperidine-1-carboxylate.

Example 148: 1-(4-cyano-3-(trifluoromethyl)phenyl)-N-(5-(3-((4-((2-(2,6-dioxopiperidin-3-yl)-1,3-dioxoisoindolin-5-yl)oxy)piperidin-1-yl)methyl)azetidin-1-yl)pyridin-2-yl)piperidine-4-carboxamide

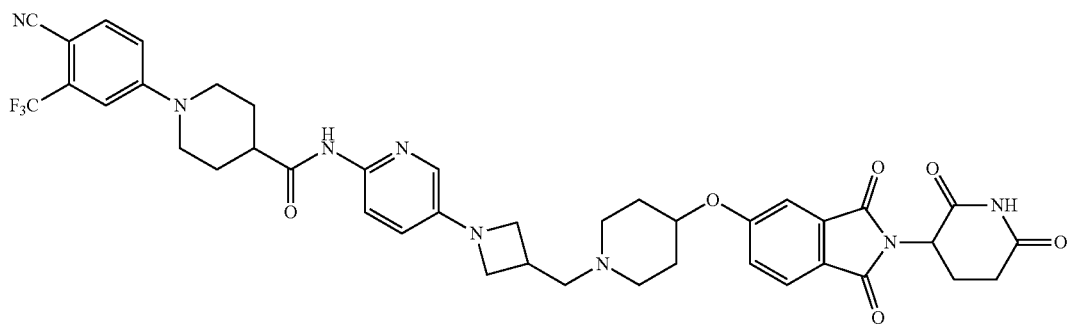 [SMILES: N#Cc1ccc(N2CCC(C(=O)Nc3ccc(N4CC(CN5CCC(Oc6ccc7c(c6)C(=O)N(C6CCC(=O)NC6=O)C7=O)CC5)C4)cn3)CC2)cc1C(F)(F)F]

Example 148 was synthesized in a similar way to the synthesis method of Example 146, using 1-(6-nitropyridin-3-yl)azetidine-3-carbaldehyde instead of 1-(6-nitropyridin-3-yl)piperidine-4-carbaldehyde.

Example 149: 1-(4-cyano-3-(trifluoromethyl)phenyl)-N-(5-(3-((4-(((2-(2,6-dioxopiperidin-3-yl)-1,3-dioxoisoindolin-5-yl)oxy)methyl)piperidin-1-yl)methyl)azetidin-1-yl)pyridin-2-yl)piperidine-4-carboxamide

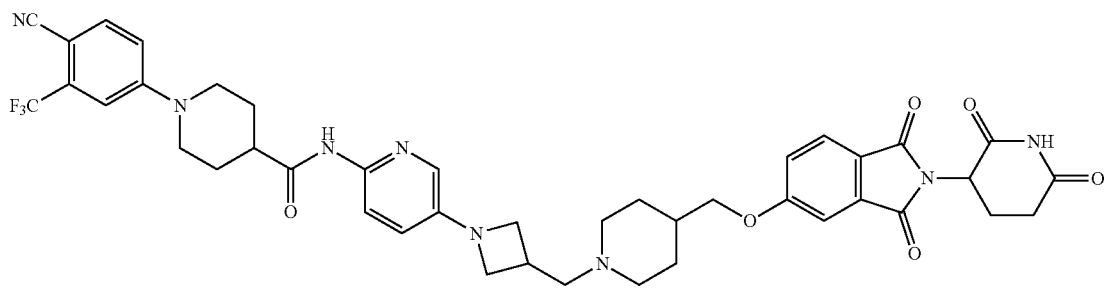 [SMILES: N#Cc1ccc(N2CCC(C(=O)Nc3ccc(N4CC(CN5CCC(COc6ccc7c(c6)C(=O)N(C6CCC(=O)NC6=O)C7=O)CC5)C4)cn3)CC2)cc1C(F)(F)F]

Example 149 was synthesized in a similar way to the synthesis method of Example 146, using tert-butyl 4-(hydroxymethyl)piperidine-1-carboxylate and 1-(6-nitropyridin-3-yl)azetidine-3-carbaldehyde, respectively, instead of tert-butyl 4-hydroxypiperidine-1-carboxylate and 1-(6-nitropyridin-3-yl)piperidine-4-carbaldehyde.

Example 150: 1-(4-cyano-3-(trifluoromethyl)phenyl)-N-(5-(4-(2-(4-(2-(2,6-dioxopiperidin-3-yl)-1,3-dioxoisoindolin-5-yl)piperazin-1-yl)ethoxy)piperidin-1-yl)pyridin-2-yl)piperidine-4-carboxamide

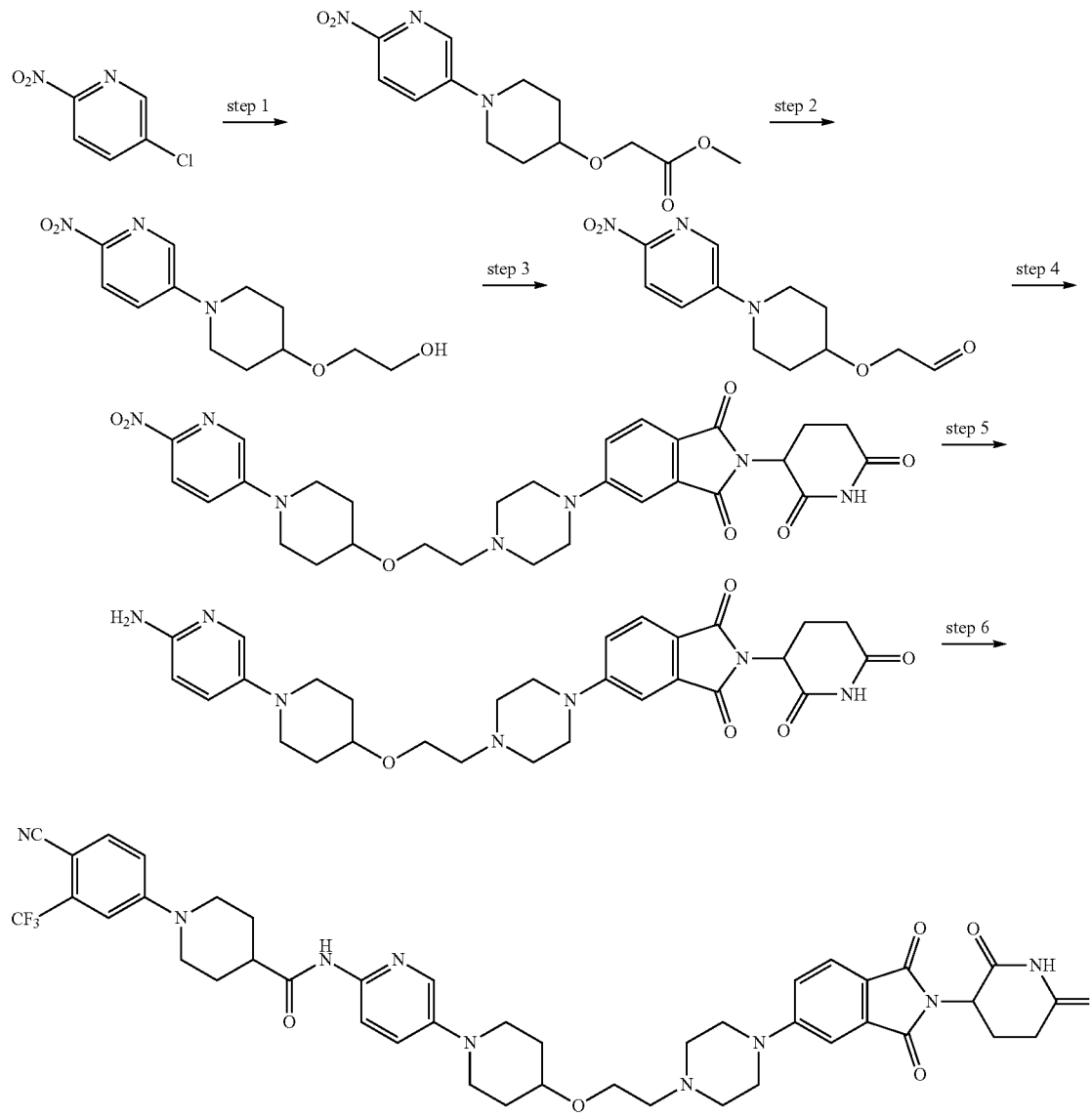

Step 1: Synthesis of methyl 2-((1-(6-nitropyridin-3-yl)piperidin-4-yl)oxy)acetate After suspending 5-chloro-2-nitropyridine (801.3 mg, 5.05 mmol), and methyl 2-(piperidin-4-yloxy)acetate hydrochloride (1.06 g, 5.05 mmol) in DMSO (8.5 ml), TEA (2.8 ml, 20.2 mmol) was added and stirred in a microwave at 120° C. for 1 hour. After adding distilled water (20 ml) to the reaction solution, extraction was performed with EtOAc (15 ml×2). The organic layer was washed with brine (15 ml×2), dried over anhydrous magnesium sulfate, filtered, and concentrated under reduced pressure. The resulting residue was subjected to MPLC (10% MeOH/DCM) to give 1.0 g (67%) of a yellow solid.

Step 2: Synthesis of 2-((1-(6-nitropyridin-3-yl)piperidin-4-yl)oxy)ethan-1-ol

After suspending methyl 2-((1-(6-nitropyridin-3-yl)piperidin-4-yl)oxy)acetate (430 mg, 1.46 mmol) in anhydrous THF (10 ml), 2 M LAH in THF (0.23 ml, 5.1 mmol) was slowly added and stirred at room temperature for 2 hours. Distilled water (10 ml) and 1 N HCl aqueous solution (0.5 ml) were added to the reaction solution, followed by extraction with EtOAc (15 ml×2). The organic layer was washed with brine (5 ml×2), dried over anhydrous magnesium sulfate, filtered, and concentrated under reduced pressure. The resulting residue was subjected to PTLC (0.5% MeOH/DCM) to give 82 mg (21%) of a yellow solid.

Step 3: Synthesis of 2-((1-(6-nitropyridin-3-yl)piperidin-4-yl)oxy)acetaldehyde

After suspending 2-((1-(6-nitropyridin-3-yl)piperidin-4-yl)oxy)ethan-1-ol (70.6 mg, 0.28 mmol) in DCM (13 ml), DMP (134.4 mg, 0.31 mmol) was added and stirred at room temperature for 2 hours. After adding $Na_2S_2O_3$ aqueous solution (10 ml) to the reaction mixture, extraction was performed with DCM (25 ml×2), and the organic layer was dried over anhydrous sodium sulfate, filtered, and concentrated under reduced pressure. The resulting residue was subjected to MPLC (5% MeOH/DCM) to give 41.3 mg (55%) of a yellow solid.

Step 4: Synthesis of 2-(2,6-dioxopiperidin-3-yl)-5-(4-(2-((1-(6-nitropyridin-3-yl)piperidin-4-yl)oxy)ethyl)piperazin-1-yl)isoindoline-1,3-dione After suspending 2-((1-(6-nitropyridin-3-yl)piperidin-4-yl)oxy)acetaldehyde (41.3 mg, 0.155 mmol), and 2-(2,6-dioxopiperidin-3-yl)-5-(piperazin-1-yl)isoindoline-1,3-dione (68.4 mg, 0.155 mmol) in MeOH (1.0 ml) and DCM (0.5 ml), sodium triacetoxyborohydride (66 mg, 0.311 mmol) was added and stirred at room temperature for 30 minutes. $NaHCO_3$ aqueous solution (3 ml) was added to the reaction solution, followed by extraction with EtOAc (3 ml×2), and the organic layer was dried over anhydrous sodium sulfate, filtered, and concentrated under reduced pressure. The resulting residue was subjected to MPLC (5% MeOH/DCM) to give 35 mg (38%) of a yellow solid.

Step 5: Synthesis of 5-(4-(2-((1-(6-aminopyridin-3-yl)piperidin-4-yl)oxy)ethyl)piperazin-1-yl)-2-(2,6-dioxopiperidin-3-yl)isoindoline-1,3-dione After dissolving 2-(2,6-dioxopiperidin-3-yl)-5-(4-(2-((1-(6-nitropyridin-3-yl)piperidin-4-yl)oxy)ethyl)piperazin-1-yl)isoindoline-1,3-dione (38 mg, 0.064 mmol) in MeOH (1.0 mL), Pd/C (10 wt % Pd, 3.8 mg) was added and stirred under a hydrogen stream at room temperature for 2 hours. The reaction solution was filtered and concentrated. A yellow solid (24 mg, 72%) was obtained.

Step 6: Synthesis of 1-(4-cyano-3-(trifluoromethyl)phenyl)-N-(5-(4-(2-(4-(2-(2,6-dioxopiperidin-3-yl)-1,3-dioxoisoindolin-5-yl)piperazin-1-yl)ethoxy)piperidin-1-yl)pyridin-2-yl)piperidine-4-carboxamide 5-(4-(2-((1-(6-aminopyridin-3-yl)piperidin-4-yl)oxy)ethyl)piperazin-1-yl)-2-(2,6-dioxopiperidin-3-yl)isoindoline-1,3-dione (12.5 mg, 0.02 mmol), 1-(4-cyano-3-(trifluoromethyl)phenyl)piperidine-4-carboxylic acid (Intermediate 1-1, 6.56 mg, 0.02 mmol), HATU (12.5 mg, 0.03 mmol), and DIPEA (0.01 ml, 0.03 mmol) were suspended in DMF (1.0 ml) and stirred at room temperature for 16 hours. After adding distilled water (1 ml) to the reaction solution, extraction was performed with EtOAc (1 ml×2), and the organic layer was dried over anhydrous sodium sulfate, filtered, and concentrated under reduced pressure. The resulting residue was subjected to MPLC (5% MeOH/DCM) to give 6 mg (32%) of a brown solid.

Example 151: 1-(3-chloro-4-cyanophenyl)-N-(5-(4-(2-(4-(2-(2,6-dioxopiperidin-3-yl)-1,3-dioxoisoindolin-5-yl)piperazin-1-yl)ethoxy)piperidin-1-yl)pyridin-2-yl)piperidine-4-carboxamide

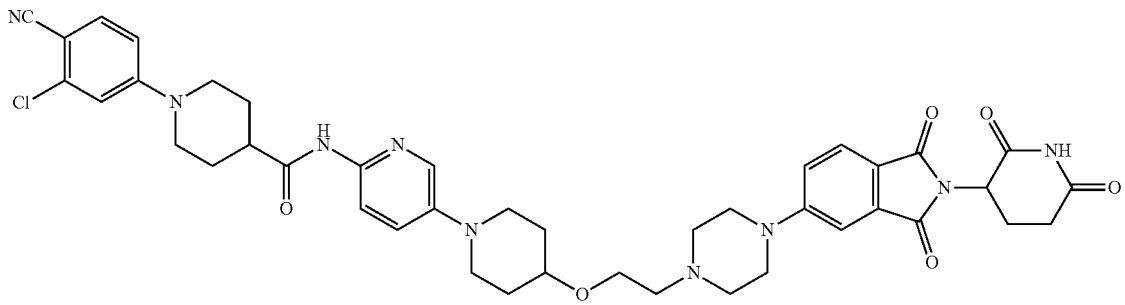 [SMILES: N#Cc1ccc(N2CCC(C(=O)Nc3ccc(N4CCC(OCCN5CCN(c6ccc7c(c6)C(=O)N(C6CCC(=O)NC6=O)C7=O)CC5)CC4)cn3)CC2)cc1Cl]

Example 150 was synthesized in a similar way to the synthesis method of Example 151, using 1-(3-chloro-4-cyanophenyl)piperidine-4-carboxylic acid (Intermediate 1-2) instead of 1-(4-cyano-3-(trifluoromethyl)phenyl)piperidine-4-carboxylic acid (Intermediate 1-1).

Example 152: 1-(4-cyano-3-(trifluoromethyl)phenyl)-N-(5-(4-(2-(4-(2-(2,6-dioxopiperidin-3-yl)-1,3-dioxoisoindolin-4-yl)piperazin-1-yl)ethoxy)piperidin-1-yl)pyridin-2-yl)piperidine-4-carboxamide

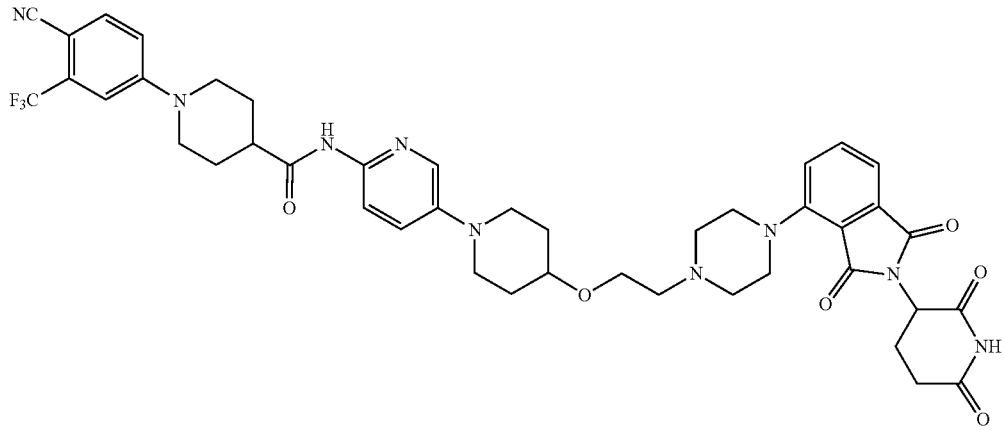 [SMILES: N#Cc1ccc(N2CCC(C(=O)Nc3ccc(N4CCC(OCCN5CCN(c6cccc7c6C(=O)N(C6CCC(=O)NC6=O)C7=O)CC5)CC4)cn3)CC2)cc1C(F)(F)F]

Example 152 was synthesized in a similar way to the synthesis method of Example 150, using 2-(2,6-dioxopiperidin-3-yl)-4-(piperazin-1-yl)isoindoline-1,3-dione instead of 2-(2,6-dioxopiperidin-3-yl)-5-(piperazin-1-yl)isoindoline-1,3-dione.

Example 153: 1-(4-cyano-3-(trifluoromethyl)phenyl)-N-(5-(4-(2-(4-(2-(2,6-dioxopiperidin-3-yl)-1,3-dioxoisoindolin-5-yl)piperazin-1-yl)ethyl)-4-hydroxypiperidin-1-yl)pyridin-2-yl)piperidine-4-carboxamide

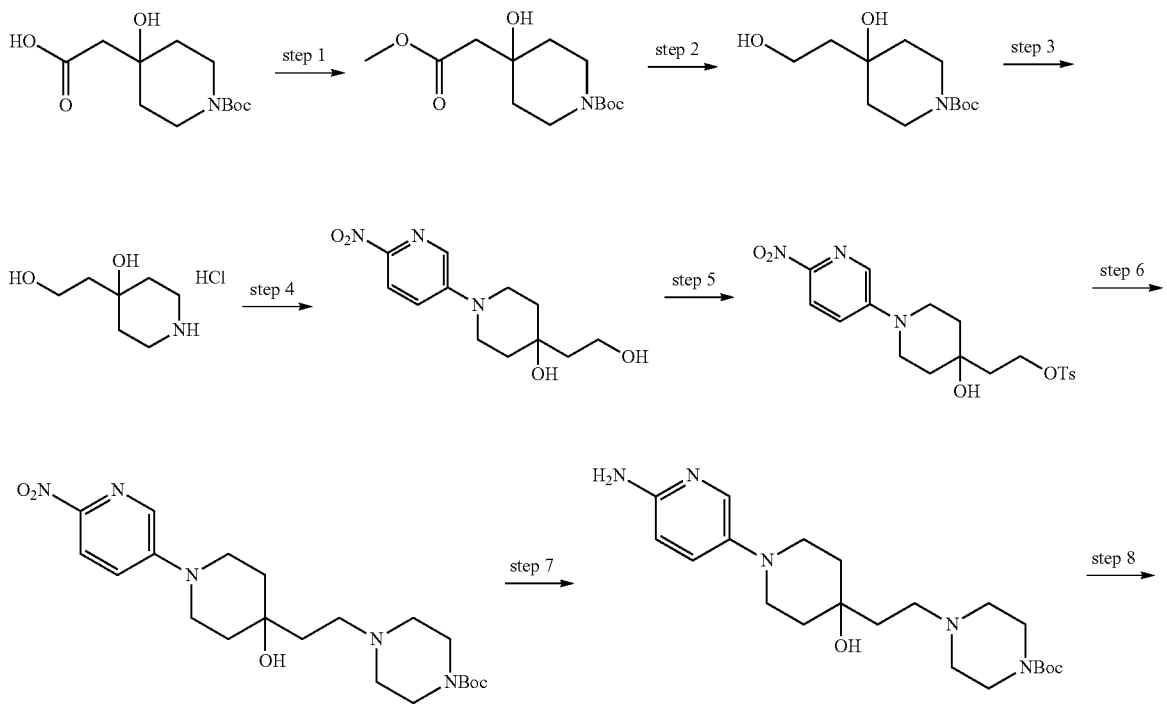

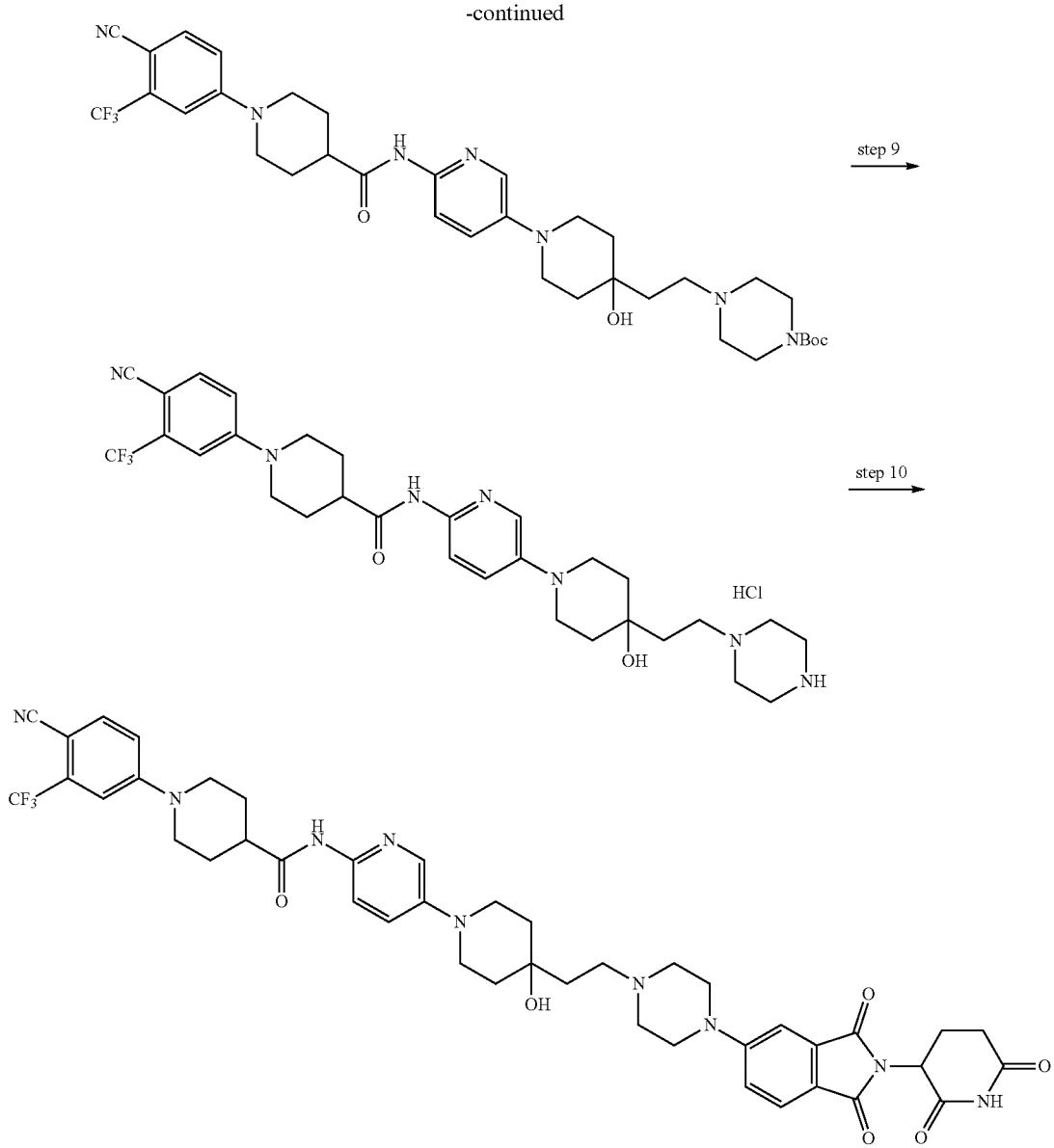

Step 1: Synthesis of tert-butyl 4-hydroxy-4-(2-methoxy-2-oxoethyl)piperidine-1-carboxylate 2-(1-(tert-butoxycarbonyl)-4-hydroxypiperidin-4-yl)acetic acid (100 mg, 0.38 mmol), and 2M trimethylsilyldiazomethane in hexane (0.82 ml, 1.17 mmol) were suspended in MeOH: EtOAc=1:1 (4 ml) and stirred at −10° C. for 1 hour. After adding distilled water (15 ml) to the reaction solution, extraction was performed with EtOAc (20 ml), and the organic layer was dried over anhydrous sodium sulfate, filtered, and concentrated under reduced pressure. The resulting residue was subjected to MPLC (5% MeOH/DCM) to give 96 mg (93%) of a clear oil.

Step 2: Synthesis of tert-butyl 4-hydroxy-4-(2-hydroxyethyl)piperidine-1-carboxylate After suspending tert-butyl 4-hydroxy-4-(2-methoxy-2-oxoethyl)piperidine-1-carboxylate (89 mg, 0.33 mmol) in THF (3.3 ml), 2M LAH in THF (0.4 ml, 0.81 mmol) was slowly added and stirred at room temperature for 1 hour. After slowly adding 1 N HCl to the reaction mixture, distilled water (20 ml) was added and extraction was performed with EtOAc (20 ml). The organic layer was dried over anhydrous sodium sulfate, filtered, and concentrated under reduced pressure. The obtained residue was subjected to MPLC (5% MeOH/DCM) to give 44 mg (55%) of a clear oil.

Step 3: Synthesis of 4-(2-hydroxyethyl)piperidin-4-ol hydrochloride

After suspending tert-butyl 4-hydroxy-4-(2-hydroxyethyl)piperidine-1-carboxylate (42 mg, 0.17 mmol) in DCM (1.7 ml), 4M HCl in dioxane (0.26 ml, 1.03 mmol) was added and stirred at room temperature for 4 hours. The reaction solution was concentrated. 30 mg (97%) of a white solid was obtained.

Step 4: Synthesis of 4-(2-hydroxyethyl)-1-(6-nitropyridin-3-yl)piperidin-4-ol 4-(2-hydroxyethyl)piperidin-4-ol hydrochloride (30 mg, 0.17 mmol), 5-chloro-2-nitropyridine (26 mg, 0.17 mmol), and DIPEA (0.09 ml, 0.5 mmol) were suspended in DMSO (1.65 ml) and stirred in a microwave at 120° C. for 1 hour. After adding distilled water (15 ml) to the reaction solution, extraction was performed with EtOAc (25 ml), and the organic layer was dried over anhydrous magnesium sulfate, filtered, and concentrated under reduced pressure. The resulting residue was subjected to MPLC (5% MeOH/DCM) to give 19 mg (34%) of a yellow solid.

Step 5: Synthesis of 2-(4-hydroxy-1-(6-nitropyridin-3-yl)piperidin-4-yl)ethyl 4-methylbenzenesulfonate 4-(2-hydroxyethyl)-1-(6-nitropyridin-3-yl)piperidin-4-ol (17 mg, 0.06 mmol), 4-toluenesulfonyl chloride (12.2 mg, 0.06 mmol), DMAP (1.56 mg, 0.013 mmol), and TEA (0.02 ml, 0.13 mmol) were suspended at 0° C. in DCM (0.64 ml) and stirred at room temperature for 5 hours. After adding distilled water (15 ml) to the reaction solution, extraction was performed with DCM (20 ml), and the organic layer was dried over anhydrous magnesium sulfate, filtered, and concentrated under reduced pressure. The obtained residue was subjected to MPLC (5% MeOH/DCM) to give 22 mg (82%) of a yellow solid.

Step 6: Synthesis of tert-butyl 4-(2-(4-hydroxy-1-(6-nitropyridin-3-yl)piperidin-4-yl)ethyl)piperazine-1-carboxylate 2-(4-hydroxy-1-(6-nitropyridin-3-yl)piperidin-4-yl)ethyl 4-methylbenzenesulfonate (40 mg, 0.09 mmol), tert-butyl piperazine-1-carboxylate (34 mg, 0.14 mmol), and K$_2$CO$_3$ (26 mg, 0.19 mmol) were suspended in DMF (1 ml) and stirred at 70° C. for 8 hours. After adding distilled water (20 ml) to the reaction solution, extraction was performed with EtOAc (20 ml), and the organic layer was dried over anhydrous sodium sulfate, filtered, and concentrated under reduced pressure. The resulting residue was subjected to MPLC (3% MeOH/DCM) to give 26 mg (63%) of a yellow solid.

Step 7: Synthesis of tert-butyl 4-(2-(1-(6-aminopyridin-3-yl)-4-hydroxypiperidin-4-yl)ethyl)piperazine-1-carboxylate After dissolving tert-butyl 4-(2-(4-hydroxy-1-(6-nitropyridin-3-yl)piperidin-4-yl)ethyl)piperazine-1-carboxylate (30 mg, 0.07 mmol) in MeOH (0.7 ml), palladium (10 wt. % on activated carbon, 15 mg) was added and stirred under a hydrogen stream at room temperature for 2 hours. The reaction solution was filtered and concentrated under reduced pressure. 28 mg (99%) of a brown solid was obtained.

Step 8: Synthesis of tert-butyl 4-(2-(1-(6-(1-(4-cyano-3-(trifluoromethyl)phenyl)piperidine-4-carboxamido)pyridin-3-yl)-4-hydroxypiperidin-4-yl)ethyl)piperazine-1-carboxylate 1-(4-cyano-3-(trifluoromethyl)phenyl)piperidine-4-carboxylic acid (Intermediate 1-1, 21 mg, 0.07 mmol), tert-butyl 4-(2-(1-(6-aminopyridin-3-yl)-4-hydroxypiperidin-4-yl)ethyl)piperazine-1-carboxylate (28 mg, 0.07 mmol), HATU (32 mg, 0.08 mmol), and DIPEA (0.03 ml, 0.14 mmol) were suspended in DMF (0.7 ml) and stirred at room temperature for 18 hours. After adding distilled water (15 ml) to the reaction solution, extraction was performed with EtOAc (20 ml), and the organic layer was dried over anhydrous sodium sulfate, filtered, and concentrated under reduced pressure. The obtained residue was subjected to MPLC (5% MeOH/DCM) to give 20 mg (43%) of a brown solid.

Step 9: Synthesis of 1-(4-cyano-3-(trifluoromethyl)phenyl)-N-(5-(4-hydroxy-4-(2-(piperazin-1-yl)ethyl)piperidin-1-yl)pyridin-2-yl)piperidine-4-carboxamide hydrochloride After suspending tert-butyl 4-(2-(1-(6-(1-(4-cyano-3-(trifluoromethyl)phenyl)piperidine-4-carboxamido)pyridin-3-yl)-4-hydroxypiperidin-4-yl)ethyl)piperazine-1-carboxylate (19 mg, 0.03 mmol) in DCM (0.3 ml), 4M HCl in dioxane (0.04 ml, 0.16 mmol) was added and stirred at room temperature for 2 hours. The reaction solution was concentrated. 18 mg (97%) of a white solid was obtained.

Step 10: Synthesis of 1-(4-cyano-3-(trifluoromethyl)phenyl)-N-(5-(4-(2-(4-(2-(2,6-dioxopiperidin-3-yl)-1,3-dioxoisoindolin-5-yl)piperazin-1-yl)ethyl)-4-hydroxypiperidin-1-yl)pyridin-2-yl)piperidine-4-carboxamide 1-(4-cyano-3-(trifluoromethyl)phenyl)-N-(5-(4-hydroxy-4-(2-(piperazin-1-yl)ethyl)piperidin-1-yl)pyridin-2-yl)piperidine-4-carboxamide hydrochloride (18 mg, 0.03 mmol), 2-(2,6-dioxopiperidin-3-yl)-5-fluoroisoindoline-1,3-dione (Intermediate 2-1, 8 mg, 0.03 mmol), and DIPEA (0.015 ml, 0.08 mmol) were suspended in DMSO (0.3 ml) and stirred at 90° C. for 18 hours. After adding distilled water (15 ml) to the reaction solution, extraction was performed with EtOAc (25 ml), and the organic layer was dried over anhydrous sodium sulfate, filtered, and concentrated under reduced pressure. The resulting residue was subjected to MPLC (10% MeOH/DCM) to give 5 mg (22%) of a yellow solid.

Example 154: 1-(4-cyano-3-(trifluoromethyl)phenyl)-N-(5-(4-(7-(2-(2,6-dioxopiperidin-3-yl)-1,3-dioxoisoindolin-5-yl)-2,7-diazaspiro[3.5]nonane-2-carbonyl)piperidin-1-yl)pyridin-2-yl)piperidine-4-carboxamide

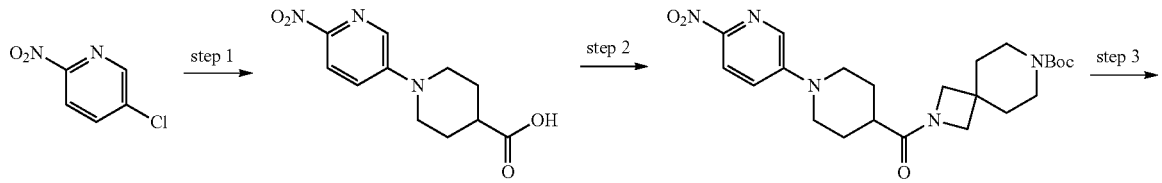

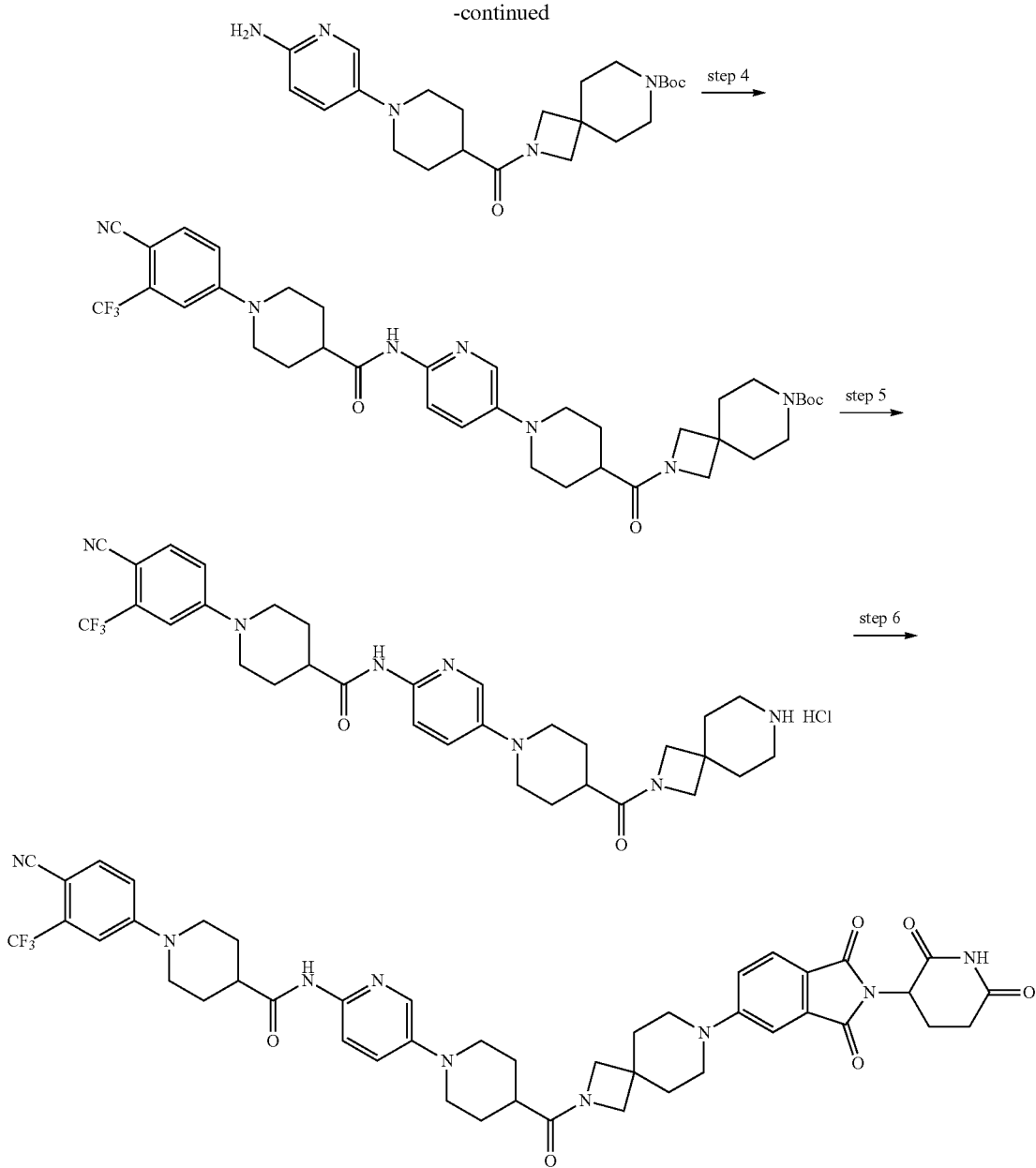

Step 1: Synthesis of 1-(6-nitropyridin-3-yl)piperidine-4-carboxylic acid 5-chloro-2-nitropyridine (1 g, 6.31 mmol), piperidine-4-carboxylic acid (896 mg, 6.91 mmol), and TEA (2.6 mL, 18.93 mmol) were suspended in DMSO (10 mL) and stirred in a microwave reactor at 120° C. for 2 hours. After adding distilled water (10 mL) to the reaction solution, by-products were removed by extraction with EtOAc (10 mL), and the aqueous layer was concentrated under reduced pressure. 650 mg (41%) of a yellow solid was obtained.

Step 2: Synthesis of tert-butyl 2-(1-(6-nitropyridin-3-yl)piperidine-4-carbonyl)-2,7-diazaspiro[3.5]nonane-7-carboxylate 1-(6-nitropyridin-3-yl)piperidine-4-carboxylic acid (232 mg, 0.93 mmol), tert-butyl 2,7-diazaspiro[3.5]nonane-7-carboxylate hydrochloride (242 mg, 0.93 mmol), HATU (527 mg, 0.39 mmol), and DIPEA (0.47 mL, 2.77 mmol) were suspended in DMF (3 mL) and stirred at room temperature for 16 hours. After adding distilled water (2 mL) to the reaction mixture, the mixture was extracted with EtOAc (3 mL×2). The organic layer was washed with brine (2 mL×2), dried over anhydrous magnesium sulfate, filtered, and concentrated under reduced pressure. The obtained residue was subjected to MPLC (10% MeOH/DCM) to give 199 mg (47%) of a yellow solid.

Step 3: Synthesis of tert-butyl 2-(1-(6-aminopyridin-3-yl)piperidine-4-carbonyl)-2,7-diazaspiro[3.5]nonane-7-carboxylate Tert-butyl 2-(1-(6-nitropyridin-3-yl)piperidine-4-carbonyl)-2,7-diazaspiro[3.5]nonane-7-carboxylate (199 mg, 0.43 mmol), 10% Pd/C (194 mg, 0.086 mmol) were suspended in MeOH (1 mL) and DCM (1 mL) and stirred under a hydrogen stream at room temperature for 16 hours. The reaction solution was filtered and concentrated under reduced pressure. 207 mg (100%) of a brown solid was obtained.

Step 4: Synthesis of tert-butyl 2-(1-(6-(1-(4-cyano-3-(trifluoromethyl)phenyl)piperidine-4-carboxamido)pyridin-3-yl)piperidine-4-carbonyl)-2,7-diazaspiro[3.5]nonane-7-carboxylate Tert-butyl 2-(1-(6-aminopyridin-3-yl)piperidine-4-carbonyl)-2,7-diazaspiro[3.5]nonane-7-carboxylate (207 mg, 0.48 mmol), 1-(4-cyano-3-(trifluoromethyl)phenyl)piperidine-4-carboxylic acid (Intermediate 1-1, 144 mg, 0.48 mmol), HATU (275 mg, 0.72 mmol), and DIPEA (0.25 mL, 1.45 mmol) were suspended in DMF (2 mL) and stirred for 16 hours. After adding distilled water (2 mL) to the reaction mixture, the mixture was extracted with EtOAc (3 mL×2). The organic layer was washed with brine (2 mL) and distilled water (2 mL), dried over anhydrous magnesium sulfate, filtered, and concentrated under reduced pressure. The resulting residue was subjected to MPLC (10% MeOH/DCM) to give 135 mg (39%) of a dark gray solid.

Step 5: Synthesis of N-(5-(4-(2,7-diazaspiro[3.5]nonane-2-carbonyl)piperidin-1-yl)pyridin-2-yl)-1-(4-cyano-3-(trifluoromethyl)phenyl)piperidine-4-carboxamide hydrochloride After suspending tert-butyl 2-(1-(6-(1-(4-cyano-3-(trifluoromethyl)phenyl)piperidine-4-carboxamido)pyridin-3-yl)piperidine-4-carbonyl)-2,7-diazaspiro[3.5]nonane-7-carboxylate (135 mg, 0.19 mmol) in DCM (1 mL), 4N HCl in dioxane (0.2 mL) was added and stirred at room temperature for 16 hours. The reaction solution was concentrated under reduced pressure. 123 mg (100%) of a dark gray solid was obtained.

Step 6: Synthesis of 1-(4-cyano-3-(trifluoromethyl)phenyl)-N-(5-(4-(7-(2-(2,6-dioxopiperidin-3-yl)-1,3-dioxoisoindolin-5-yl)-2,7-diazaspiro[3.5]nonane-2-carbonyl)piperidin-1-yl)pyridin-2-yl)piperidine-4-carboxamide N-(5-(4-(2,7-diazaspiro[3.5]nonane-2-carbonyl)piperidin-1-yl)pyridin-2-yl)-1-(4-cyano-3-(trifluoromethyl)phenyl)piperidine-4-carboxamide hydrochloride (38 mg, 0.06 mmol), 2-(2,6-dioxopiperidin-3-yl)-5-fluoroisoindoline-1,3-dione (Intermediate 2-1, 19 mg, 0.07 mmol), and DIPEA (0.03 mL, 0.17 mmol) were suspended in DMSO (1 mL) and stirred in a microwave reactor at 100° C. for 1 hour. After adding distilled water (1 mL) to the reaction mixture, the mixture was extracted with EtOAc (1 mL×2). The organic layer was washed with brine (1 mL×2), dried over anhydrous magnesium sulfate, filtered, and concentrated under reduced pressure. The resulting residue was subjected to PTLC to give 5.1 mg (10%) of a yellow solid.

Example 155: 1-(4-cyano-3-(trifluoromethyl)phenyl)-N-(5-(4-((7-(2-(2,6-dioxopiperidin-3-yl)-1,3-dioxoisoindolin-5-yl)-2,7-diazaspiro[3.5]nonan-2-yl)methyl)piperidin-1-yl)pyrazin-2-yl)piperidine-4-carboxamide

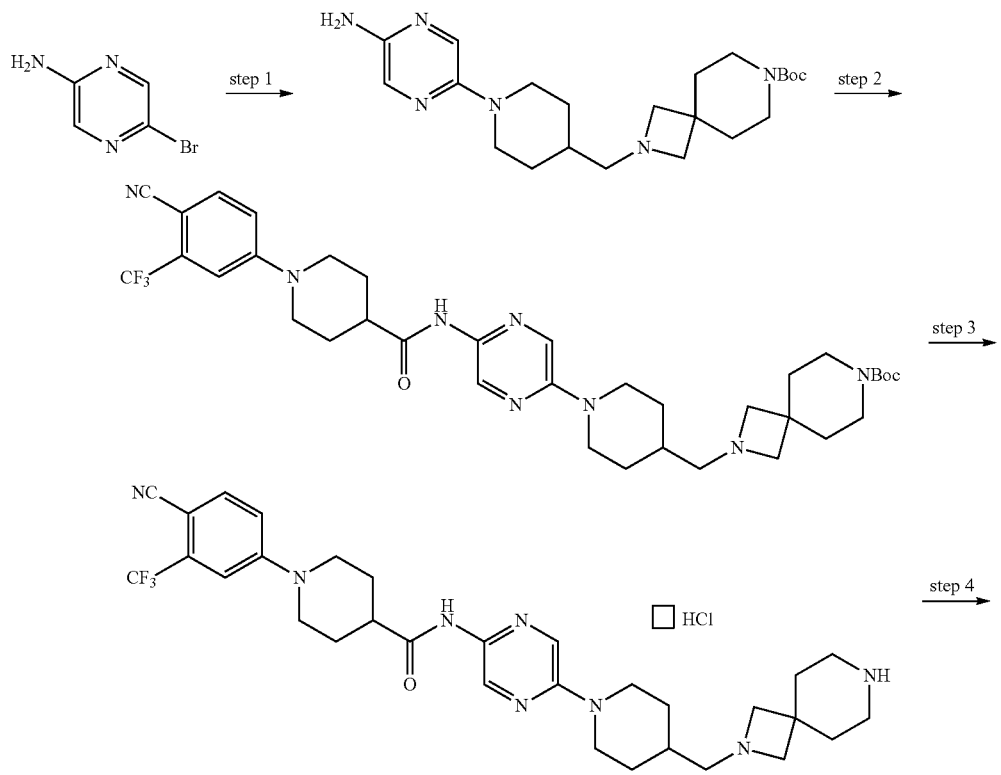

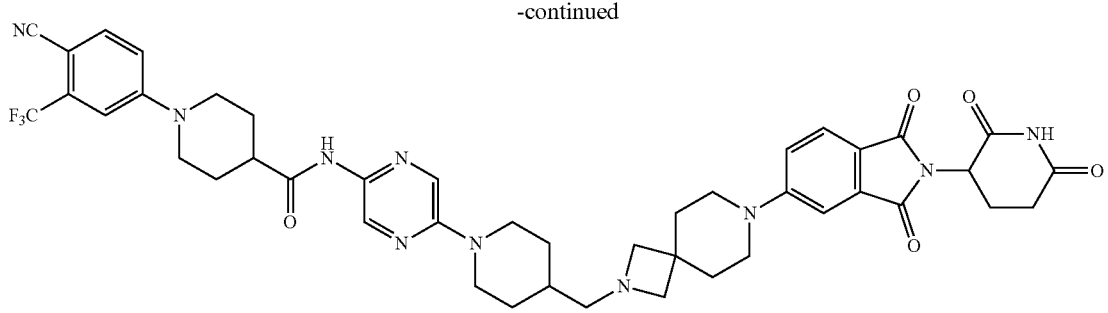

Step 1: Synthesis of tert-butyl 2-((1-(5-aminopyrazin-2-yl)piperidin-4-yl)methyl)-2,7-diazaspiro[3.5]nonane-7-carboxylate 5-bromopyrazin-2-amine (50 mg, 0.29 mmol), tert-butyl 2-(piperidin-4-ylmethyl)-2,7-diazaspiro[3.5]nonane-7-carboxylate (Intermediate 4-7, 140 mg, 0.44 mmol), CuI (11 mg, 0.058 mmol), 2-acetyl cyclohexanone (0.008 mL, 0.058 mmol), and $Cs_2CO_3$ (189 mg, 0.58 mmol) were suspended in DMF (1.0 mL) and stirred in a microwave reactor at 130° C. for 1 hour. After adding distilled water (10 ml) to the reaction solution, extraction was performed with EtOAc (25 ml×2), and the organic layer was dried over anhydrous sodium sulfate, filtered, and concentrated under reduced pressure. The resulting residue was subjected to MPLC (10% MeOH/DCM) to give 17 mg (14%) of a brown solid. m/z 417.33 [M+H]$^+$.

Step 2: Synthesis of tert-butyl 2-((1-(5-(1-(4-cyano-3-(trifluoromethyl)phenyl)piperidine-4-carboxamido)pyrazin-2-yl)piperidin-4-yl)methyl)-2,7-diazaspiro[3.5]nonane-7-carboxylate Tert-butyl 2-((1-(5-aminopyrazin-2-yl)piperidin-4-yl)methyl)-2,7-diazaspiro[3.5]nonane-7-carboxylate (45 mg, 0.11 mmol), 1-(4-cyano-3-(trifluoromethyl)phenyl)piperidine-4-carboxylic acid (Intermediate 1-1, 39 mg, 0.13 mmol), HATU (49 mg, 0.13 mmol), and DIPEA (0.04 mL, 0.22 mmol) were suspended in DMF (1.0 ml) and stirred at room temperature for 16 hours. After adding distilled water (15 ml) to the reaction solution, extraction was performed with EtOAc (20 ml×2), and the organic layer was dried over anhydrous sodium sulfate, filtered, and concentrated under reduced pressure. The resulting residue was subjected to MPLC (10% MeOH/DCM) to give 35 mg (45%) of a brown solid. m/z 697.40 [M+H]$^+$.

Step 3: Synthesis of N-(5-(4-((2,7-diazaspiro[3.5]nonan-2-yl)methyl)piperidin-1-yl)pyrazin-2-yl)-1-(4-cyano-3-(trifluoromethyl)phenyl)piperidine-4-carboxamide hydrochloride Tert-butyl 2-((1-(5-(1-(4-cyano-3-(trifluoromethyl)phenyl)piperidine-4-carboxamido)pyrazin-2-yl)piperidin-4-yl)methyl)-2,7-diazaspiro[3.5]nonane-7-carboxylate (35 mg, 0.050 mmol), and 4M HCl in dioxane (0.06 mL, 0.25 mmol) were suspended in DCM (0.5 mL) and stirred at room temperature for 2 hours. The reaction solution was concentrated under reduced pressure. 31 mg (98%) of an orange solid was obtained. m/z 597.33 [M+H]$^+$.

Step 4: Synthesis of 1-(4-cyano-3-(trifluoromethyl)phenyl)-N-(5-(4-((7-(2-(2,6-dioxopiperidin-3-yl)-1,3-dioxoisoindolin-5-yl)-2,7-diazaspiro[3.5]nonan-2-yl)methyl)piperidin-1-yl)pyrazin-2-yl)piperidine-4-carboxamide N-(5-(4-((2,7-diazaspiro[3.5]nonan-2-yl)methyl)piperidin-1-yl)pyrazin-2-yl)-1-(4-cyano-3-(trifluoromethyl)phenyl)piperidine-4-carboxamide hydrochloride (30 mg, 0.047 mmol), 2-(2,6-dioxopiperidin-3-yl)-5-fluoroisoindoline-1,3-dione (Intermediate 2-1, 19 mg, 0.071 mmol), and DIPEA (0.02 mL, 0.094 mmol) were suspended in DMSO (1.0 ml) and stirred at 90° C. for 16 hours. After adding distilled water (15 ml) to the reaction solution, extraction was performed with EtOAc (20 ml×2), and the organic layer was dried over anhydrous sodium sulfate, filtered, and concentrated under reduced pressure. The obtained residue was subjected to MPLC (10% MeOH/DCM) to give 6 mg (15%) of a yellow solid.

Example 156: 1-(4-cyano-3-(trifluoromethyl)phenyl)-N-(5-(4-(2-(4-(2-(2,6-dioxopiperidin-3-yl)-1,3-dioxoisoindolin-5-yl)piperazin-1-yl)ethyl)piperidin-1-yl)pyrazin-2-yl)piperidine-4-carboxamide

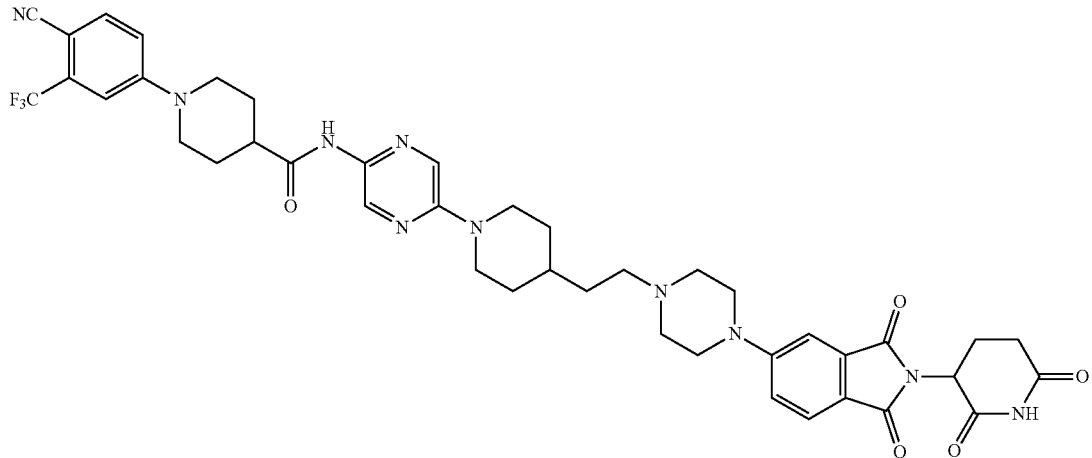

Example 156 was synthesized in a similar way to the synthesis method of Example 155, using tert-butyl 4-(2-(piperidin-4-yl)ethyl)piperazine-1-carboxylate (Intermediate 4-8) instead of tert-butyl 2-(piperidin-4-ylmethyl)-2,7-diazaspiro[3.5]nonane-7-carboxylate (Intermediate 4-7).

Example 157: 1-(4-cyano-3-(trifluoromethyl)phenyl)-N-(5-(4-((4-((1-(2-(2,6-dioxopiperidin-3-yl)-1,3-dioxoisoindolin-5-yl)piperidin-4-yl)methyl)piperazin-1-yl)methyl)piperidin-1-yl)pyrimidin-2-yl)piperidine-4-carboxamide

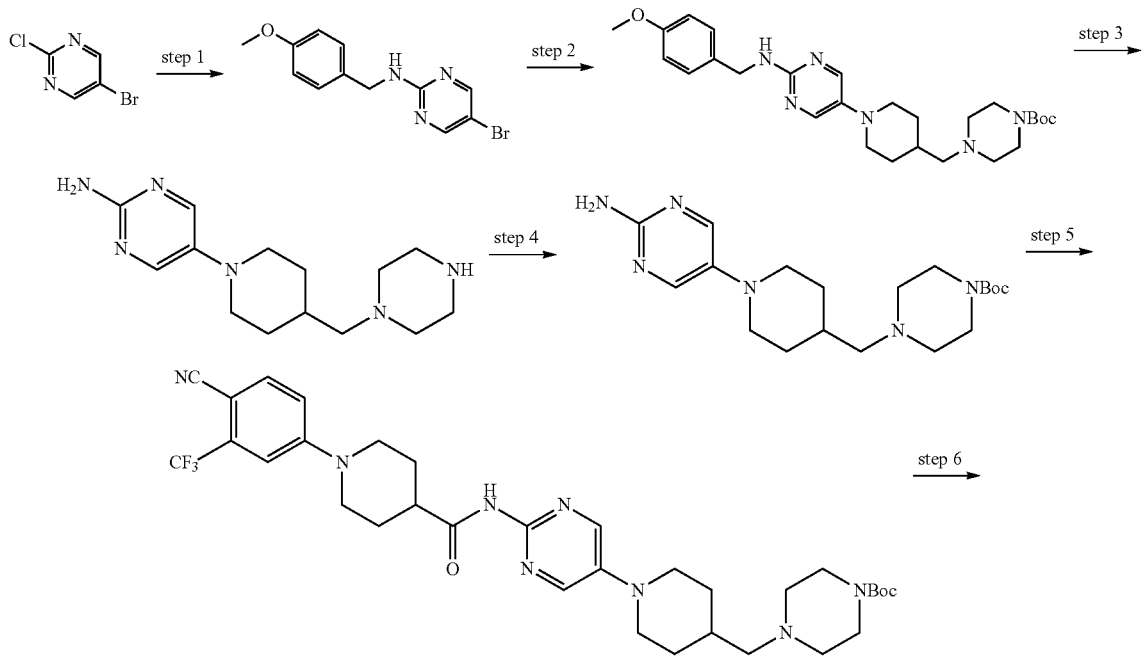

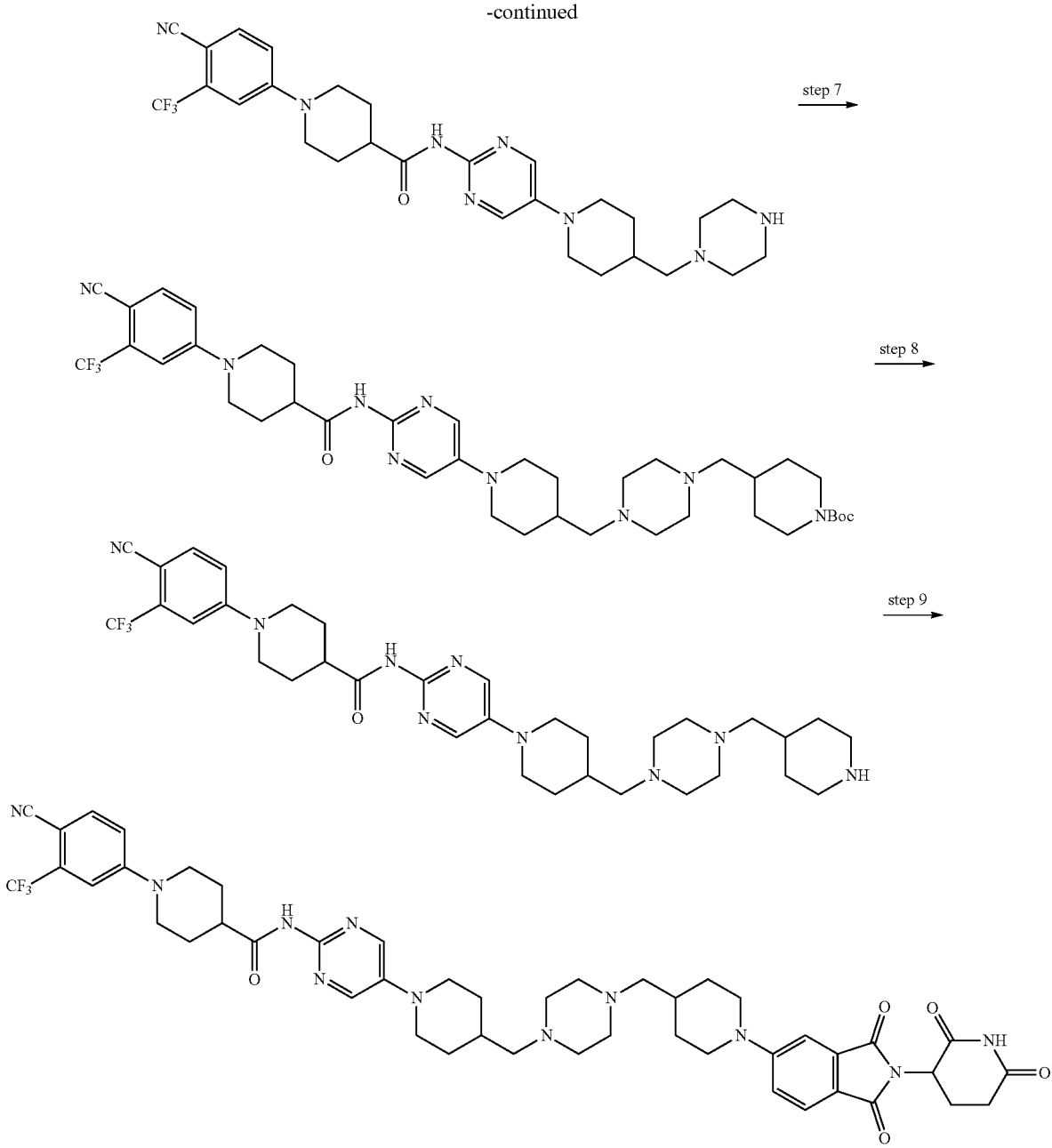

Step 1: Synthesis of 5-bromo-N-(4-methoxybenzyl)pyrimidin-2-amine 5-bromo-2-chloropyrimidine (1.00 g, 5.17 mmol), and 4-methoxybenzylamine (0.64 mL, 10.3 mmol) were suspended in ethanol (10.0 ml) and stirred at 80° C. for 16 hours. After concentrating the reaction solution under reduced pressure, distilled water (20 ml) was added, and the resulting solid was filtered and dried to give 772 mg (51%) of a white solid. m/z 294.97 [M+H]$^+$.

Step 2: Synthesis of tert-butyl 4-((1-(2-((4-methoxybenzyl)amino)pyrimidin-5-yl)piperidin-4-yl)methyl)piperazine-1-carboxylate 5-bromo-N-(4-methoxybenzyl)pyrimidin-2-amine (403 mg, 1.37 mmol), tert-butyl 4-(piperidin-4-ylmethyl)piperazine-1-carboxylate (Intermediate 4-3, 428 mg, 1.51 mmol), Pd(OAc)$_2$ (62 mg, 0.274 mmol), Xphos (158 mg, 0.274 mmol), and sodium t-butoxide (197 mg, 2.06 mmol) were suspended in toluene (15.0 mL) and stirred at 110° C. for 48 hours. After adding distilled water (10 ml) to the reaction solution, extraction was performed with EtOAc (25 ml×2), and the organic layer was dried over anhydrous sodium sulfate, filtered, and concentrated under reduced pressure. The resulting residue was subjected to MPLC (10% MeOH/DCM) to give 156 mg (23%) of a yellow solid. m/z 497.28 [M+H]$^+$.

Step 3: Synthesis of 5-(4-(piperazin-1-ylmethyl)piperidin-1-yl)pyrimidin-2-amine After suspending tert-butyl 4-((1-(2-((4-methoxybenzyl)amino)pyrimidin-5-yl)piperidin-4-yl)methyl)piperazine-1- carboxylate (156 mg, 0.314 mmol) in DCM (1.50 ml), TFA (1.50 mL) was added and stirred at 40° C. for 16 hours. After concentrating the reaction mixture, aqueous NaHCO$_3$ solution (15 ml) was added, followed by extraction with DCM (25 ml×2). The organic layer was dried over anhydrous sodium sulfate, filtered, and concentrated under reduced pressure. 475 mg of a brown liquid was obtained.

Step 4: Synthesis of tert-butyl 4-((1-(2-aminopyrimidin-5-yl)piperidin-4-yl)methyl)piperazine-1-carboxylate After suspending 5-(4-(piperazin-1-ylmethyl)piperidin-1-yl)pyrimidin-2-amine (475 mg) in DCM (10.0 ml), di-tert-butyl dicarbonate (102 mg, 0.471 mmol) and TEA (0.13 mL, 0.942 mmol) were added at 0° C. and stirred at room temperature for 1 hour. After adding distilled water (15 ml) to the reaction mixture, extraction was performed with DCM (20 ml×2), and the organic layer was dried over anhydrous sodium sulfate, filtered, and concentrated under reduced pressure. The resulting residue was subjected to MPLC (10% MeOH/DCM) to give 99 mg (2Step 84%) of a yellow solid. m/z 377.24 [M+H]$^+$.

Step 5: Synthesis of tert-butyl 4-((1-(2-(1-(4-cyano-3-(trifluoromethyl)phenyl)piperidine-4-carboxamido)pyrimidin-5-yl)piperidin-4-yl)methyl)piperazine-1-carboxylate After suspending oxalyl chloride (0.07 mL, 0.792 mmol), and DMF (0.01 mL) in DCM, 1-(4-cyano-3-(trifluoromethyl)phenyl)piperidine-4-carboxylic acid (Intermediate 1-1, 138 mg, 0.396 mmol) was added and stirred at room temperature for 3 hours. Tert-butyl 4-((1-(2-aminopyrimidin-5-yl)piperidin-4-yl)methyl)piperazine-1-carboxylate (99 mg, 0.264 mmol), and TEA (0.09 mL, 0.528 mmol) was added to the reaction solution and stirred at room temperature for 1 hour. After adding distilled water (15 ml) to the reaction solution, extraction was performed with EtOAc (20 ml×2), and the organic layer was dried over anhydrous sodium sulfate, filtered, and concentrated under reduced pressure. The obtained residue was subjected to MPLC (10% MeOH/DCM) to give 135 mg (78%) of an off-white solid. m/z 657.23 [M+H]$^+$.

Step 6: Synthesis of 1-(4-cyano-3-(trifluoromethyl)phenyl)-N-(5-(4-(piperazin-1-ylmethyl)piperidin-1-yl)pyrimidin-2-yl)piperidine-4-carboxamide After suspending tert-butyl 4-((1-(2-(1-(4-cyano-3-(trifluoromethyl)phenyl)piperidine-4-carboxamido)pyrimidin-5-yl)piperidin-4-yl)methyl)piperazine-1-carboxylate (135 mg, 0.206 mmol) in DCM (1.00 ml), 4 M HCl in dioxane (0.26 mL, 1.03 mmol) was added and stirred at room temperature for 1 hour. After concentrating the reaction mixture, aqueous NaHCO$_3$ solution (15 ml) was added, followed by extraction with DCM (25 ml×2). The organic layer was dried over anhydrous sodium sulfate, filtered, and concentrated under reduced pressure. 115 mg (98%) of a white solid was obtained. m/z 557.29 [M+H]$^+$.

Step 7: Synthesis of tert-butyl 4-((4-((1-(2-(1-(4-cyano-3-(trifluoromethyl)phenyl)piperidine-4-carboxamido)pyrimidin-5-yl)piperidin-4-yl)methyl)piperazin-1-yl)methyl)piperidine-1-carboxylate After suspending 1-(4-cyano-3-(trifluoromethyl)phenyl)-N-(5-(4-(piperazin-1-ylmethyl)piperidin-1-yl)pyrimidin-2-yl)piperidine-4-carboxamide (65 mg, 0.12 mmol), and tert-butyl 4-formylpiperidine-1-carboxylate (30 mg, 0.14 mmol) in ACN (2.0 ml), sodium triacetoxyborohydride (74 mg, 0.35 mmol) was added and stirred at room temperature for 16 hours. NaHCO$_3$ aqueous solution (15 ml) was added to the reaction mixture, followed by extraction with EtOAc (20 ml×2), and the organic layer was dried over anhydrous sodium sulfate, filtered, and concentrated under reduced pressure. The obtained residue was subjected to MPLC (10% MeOH/DCM) to give 48 mg (54%) of an off-white solid. m/z 754.34 [M+H]$^+$.

Step 8: Synthesis of 1-(4-cyano-3-(trifluoromethyl)phenyl)-N-(5-(4-((4-(piperidin-4-ylmethyl)piperazin-1-yl)methyl)piperidin-1-yl)pyrimidin-2-yl)piperidine-4-carboxamide After suspending tert-butyl 4-((4-((1-(2-(1-(4-cyano-3-(trifluoromethyl)phenyl)piperidine-4-carboxamido)pyrimidin-5-yl)piperidin-4-yl)methyl)piperazin-1-yl)methyl)piperidine-1-carboxylate (89 mg, 0.12 mmol) in DCM (1.00 ml), 4 M HCl in dioxane (0.15 mL, 0.59 mmol) was added and stirred at room temperature for 1 hour. After concentrating the reaction mixture, aqueous NaHCO$_3$ solution (15 ml) was added, followed by extraction with DCM (20 ml×2). The organic layer was dried over anhydrous sodium sulfate, filtered, and concentrated under reduced pressure. 76 mg (97%) of a white solid was obtained. m/z 654.44 [M+H]$^+$.

Step 9: Synthesis of 1-(4-cyano-3-(trifluoromethyl)phenyl)-N-(5-(4-((4-((1-(2-(2,6-dioxopiperidin-3-yl)-1,3-dioxoisoindolin-5-yl)piperidin-4-yl)methyl)piperazin-1-yl)methyl)piperidin-1-yl)pyrimidin-2-yl)piperidine-4-carboxamide 1-(4-cyano-3-(trifluoromethyl)phenyl)-N-(5-(4-((4-(piperidin-4-ylmethyl)piperazin-1-yl)methyl)piperidin-1-yl)pyrimidin-2-yl)piperidine-4-carboxamide (35 mg, 0.054 mmol), 2-(2,6-dioxopiperidin-3-yl)-5-fluoroisoindoline-1,3-dione (Intermediate 2-1, 22 mg, 0.081 mmol), and DIPEA (0.02 mL, 0.11 mmol) were suspended in DMSO (1.0 ml) and stirred at 90° C. for 16 hours. After adding distilled water (15 ml) to the reaction solution, extraction was performed with EtOAc (20 ml×2), and the organic layer was dried over anhydrous sodium sulfate, filtered, and concentrated under reduced pressure. The resulting residue was subjected to MPLC (10% MeOH/DCM) to give 40 mg (80%) of a yellow solid.

Example 158: 1-(4-cyano-3-(trifluoromethyl)phenyl)-N-(5-(4-((4-(((3R)-1-(2-(2,6-dioxopiperidin-3-yl)-1,3-dioxoisoindolin-5-yl)pyrrolidin-3-yl)methyl)piperazin-1-yl)methyl)piperidin-1-yl)pyrimidin-2-yl)piperidine-4-carboxamide

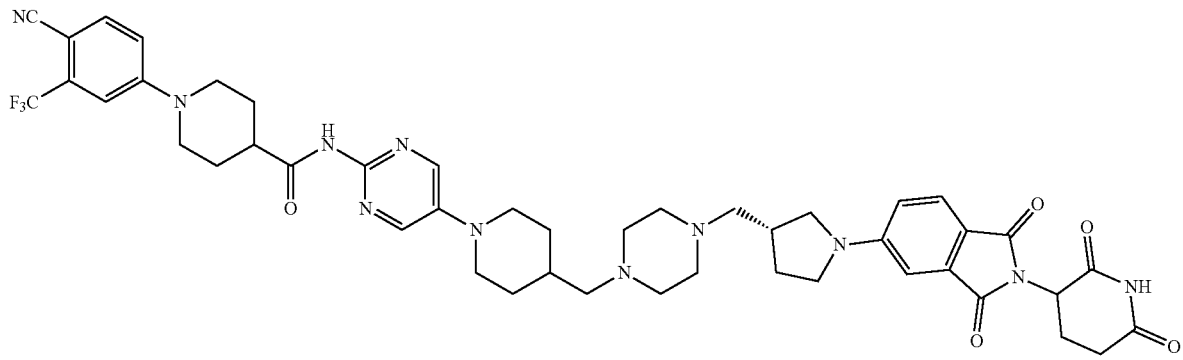 [SMILES: N#Cc1ccc(N2CCC(C(=O)Nc3ncc(N4CCC(CN5CCN(C[C@H]6CCN(c7ccc8c(c7)C(=O)N(C7CCC(=O)NC7=O)C8=O)C6)CC5)CC4)cn3)CC2)cc1C(F)(F)F]

Example 158 was synthesized in a similar way to the synthesis method of Example 157, using tert-butyl (S)-3-formylpyrrolidine-1-carboxylate instead of tert-butyl 4-formylpiperidine-1-carboxylate.

Example 159: 1-(4-cyano-3-(trifluoromethyl)phenyl)-N-(5-(4-((4-((1-(2-(2,6-dioxopiperidin-3-yl)-6-fluoro-1,3-dioxoisoindolin-5-yl)piperidin-4-yl)methyl)piperazin-1-yl)methyl)piperidin-1-yl)pyrimidin-2-yl)piperidine-4-carboxamide

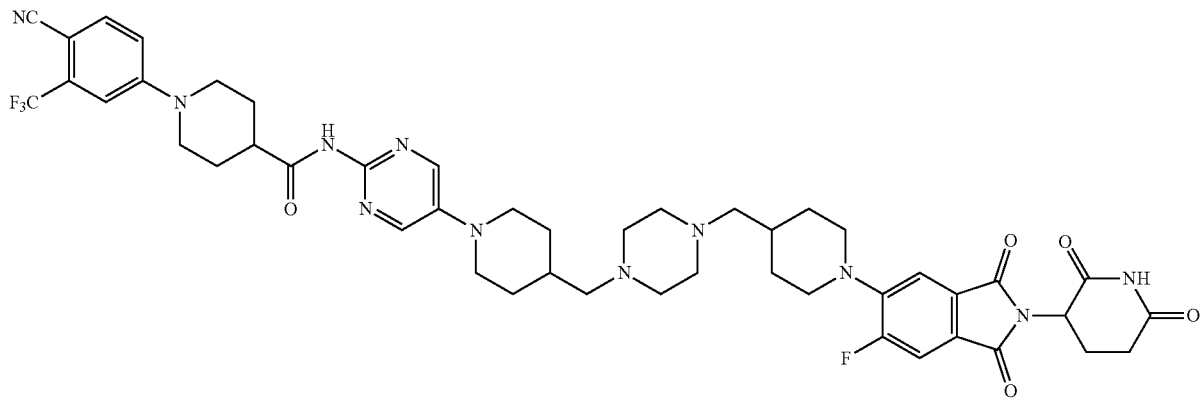

Example 159 was synthesized in a similar way to the synthesis method of Example 157, using 2-(2,6-dioxopiperidin-3-yl)-5,6-difluoroisoindoline-1,3-dione (Intermediate 2-3) instead of 2-(2,6-dioxopiperidin-3-yl)-5-fluoroisoindoline-1,3-dione (Intermediate 2-1).

Example 160: 1-(4-cyano-3-(trifluoromethyl)phenyl)-N-(5-(4-((4-(((3R)-1-(2-(2,6-dioxopiperidin-3-yl)-6-fluoro-1,3-dioxoisoindolin-5-yl)pyrrolidin-3-yl)methyl)piperazin-1-yl)methyl)piperidin-1-yl)pyrimidin-2-yl)piperidine-4-carboxamide

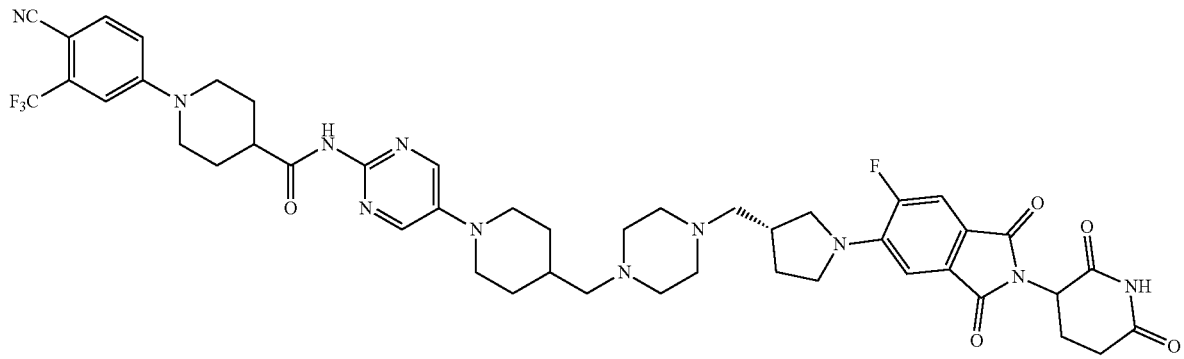 [SMILES: N#Cc1ccc(N2CCC(C(=O)Nc3ncc(N4CCC(CN5CCN(C[C@H]6CCN(c7cc8c(cc7F)C(=O)N(C7CCC(=O)NC7=O)C8=O)C6)CC5)CC4)cn3)CC2)cc1C(F)(F)F]

Example 160 was synthesized in a similar way to the synthesis method of Example 157, using tert-butyl (S)-3-formylpyrrolidine-1-carboxylate and 2-(2,6-dioxopiperidin-3-yl)-5,6-difluoroisoindoline-1,3-dione (Intermediate 2-3), respectively, instead of tert-butyl 4-formylpiperidine-1-carboxylate and 2-(2,6-dioxopiperidin-3-yl)-5-fluoroisoindoline-1,3-dione (Intermediate 2-1).

Example 161: 1-(4-cyano-3-(trifluoromethyl)phenyl)-N-(5-((4-((4-(2-(2,6-dioxopiperidin-3-yl)-1,3-dioxoisoindolin-5-yl)piperazin-1-yl)methyl)piperidin-1-yl)methyl)pyridin-2-yl)piperidine-4-carboxamide

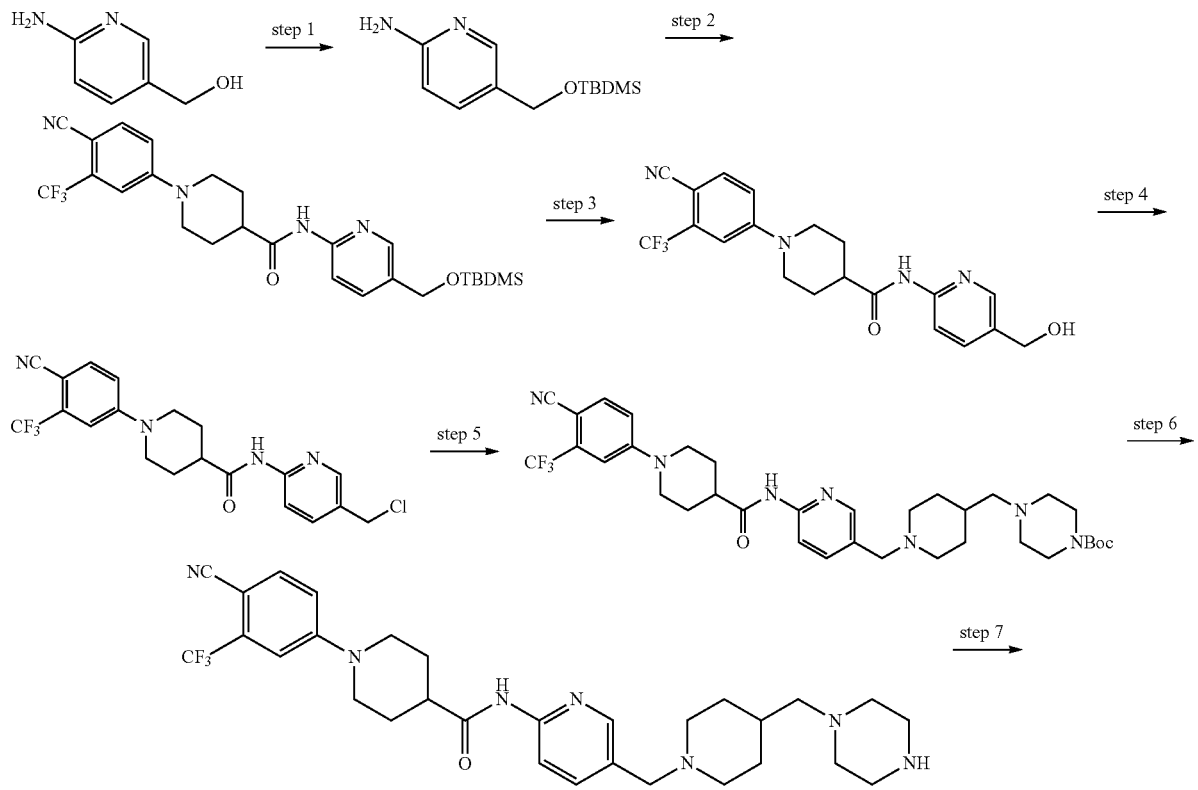

-continued

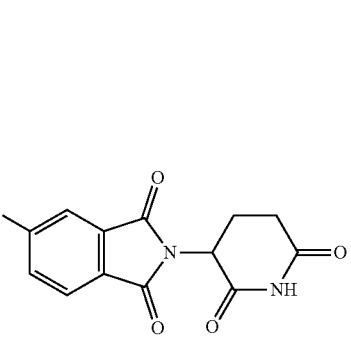

Step 1: Synthesis of 5-(((tert-butyldimethylsilyl)oxy)methyl)pyridin-2-amine After suspending (6-aminopyridin-3-yl)methanol (500 mg, 4.02 mmol) in DCM (20.0 ml) and DMF (5.0 mL), TBDMSCl (850 mg, 5.64 mmol), DIPEA (1.05 mL, 6.03 mmol), and DMAP (9.82 mg, 0.0804 mmol) were added at 0° C. and stirred at room temperature for 16 hours. After adding distilled water (15 ml) to the reaction mixture, extraction was performed with DCM (20 ml×2), and the organic layer was dried over anhydrous sodium sulfate, filtered, and concentrated under reduced pressure. The resulting residue was subjected to MPLC (10% MeOH/DCM) to give 816 mg (85%) of a yellow solid.

Step 2: Synthesis of N-(5-(((tert-butyldimethylsilyl)oxy)methyl)pyridin-2-yl)-1-(4-cyano-3-(trifluoromethyl)phenyl)piperidine-4-carboxamide 5-(((tert-butyldimethylsilyl)oxy)methyl)pyridin-2-amine (300 mg, 1.26 mmol), 1-(4-cyano-3-(trifluoromethyl)phenyl)piperidine-4-carboxylic acid (Intermediate 1-1, 450 mg, 1.51 mmol), HATU (574 mg, 1.51 mmol), and DIPEA (0.43 mL, 2.52 mmol) were suspended in DMF (2.0 ml) and stirred at room temperature for 16 hours. After adding distilled water (15 ml) to the reaction solution, extraction was performed with EtOAc (20 ml×2), and the organic layer was dried over anhydrous sodium sulfate, filtered, and concentrated under reduced pressure. The resulting residue was subjected to MPLC (10% MeOH/DCM) to give 457 mg (70%) of a white solid.

Step 3: Synthesis of 1-(4-cyano-3-(trifluoromethyl)phenyl)-N-(5-(hydroxymethyl)pyridin-2-yl)piperidine-4-carboxamide After suspending N-(5-(((tert-butyldimethylsilyl)oxy)methyl)pyridin-2-yl)-1-(4-cyano-3-(trifluoromethyl)phenyl)piperidine-4-carboxamide (457 mg, 0.881 mmol) in DCM (3.00 ml), 4 M HCl in dioxane (1.10 mL, 4.41 mmol) was added and stirred at room temperature for 1 hour. After concentrating the reaction mixture, aqueous NaHCO₃ solution (15 ml) was added, followed by extraction with DCM (20 ml×2). The organic layer was dried over anhydrous sodium sulfate, filtered, and concentrated under reduced pressure. 260 mg (73%) of a white solid was obtained. m/z 405.23 [M+H]$^+$.

Step 4: Synthesis of N-(5-(chloromethyl)pyridin-2-yl)-1-(4-cyano-3-(trifluoromethyl)phenyl)piperidine-4-carboxamide After suspending 1-(4-cyano-3-(trifluoromethyl)phenyl)-N-(5-(hydroxymethyl)pyridin-2-yl)piperidine-4-carboxamide (260 mg, 0.643 mmol) in DCM (10.0 ml), mesyl chloride (0.10 mL, 1.29 mmol) and DIPEA (0.45 mL, 2.57 mmol) were added and stirred at room temperature for 1 hour. After adding distilled water (15 ml) to the reaction mixture, extraction was performed with DCM (20 ml×2), and the organic layer was dried over anhydrous sodium sulfate, filtered, and concentrated under reduced pressure. 266 mg (98%) of a white solid was obtained. m/z 423.23 [M+H]$^+$.

Step 5: Synthesis of tert-butyl 4-((1-((6-(1-(4-cyano-3-(trifluoromethyl)phenyl)piperidine-4-carboxamido)pyridin-3-yl)methyl)piperidin-4-yl)methyl)piperazine-1-carboxylate N-(5-(chloromethyl)pyridin-2-yl)-1-(4-cyano-3-(trifluoromethyl)phenyl)piperidine-4-carboxamide (100 mg, 0.236 mmol), tert-butyl 4-(piperidin-4-ylmethyl)piperazine-1-carboxylate (Intermediate 4-3, 80 mg, 0.249 mmol), and NaHCO₃ (40 mg, 0.472 mmol) were suspended in DMF (2.0 ml) and stirred at 50° C. for 16 hours. After adding water (15 ml) to the reaction solution, extraction was performed with EtOAc (25 ml×2), and the organic layer was dried over anhydrous sodium sulfate, filtered, and concentrated under reduced pressure. The resulting residue was subjected to MPLC (50% EtOAc/DCM) to give 100 mg (63%) of a white solid. m/z 670.30 [M+H]$^+$.

Step 6: Synthesis of 1-(4-cyano-3-(trifluoromethyl)phenyl)-N-(5-((4-(piperazin-1-ylmethyl)piperidin-1-yl)methyl)pyridin-2-yl)piperidine-4-carboxamide After suspending tert-butyl 4-((1-((6-(1-(4-cyano-3-(trifluoromethyl)phenyl)piperidine-4-carboxamido)pyridin-3-yl)methyl)piperidin-4-yl)methyl)piperazine-1-carboxylate (100 mg, 0.149 mmol) in DCM (1.00 ml), 4 M HCl in dioxane (0.19 mL, 0.747 mmol) was added and stirred at room temperature for 1 hour. After concentrating the reaction mixture, aqueous NaHCO₃ solution (15 ml) was added, followed by extraction with DCM (20 ml×2). The organic layer was dried over anhydrous sodium sulfate, filtered, and concentrated under reduced pressure. 84 mg (99%) of a white solid was obtained. m/z 570.30 [M+H]$^+$.

Step 7: Synthesis of 1-(4-cyano-3-(trifluoromethyl)phenyl)-N-(5-((4-((4-(2-(2,6-dioxopiperidin-3-yl)-1,3-dioxoisoindolin-5-yl)piperazin-1-yl)methyl)piperidin-1-yl)methyl)pyridin-2-yl)piperidine-4-carboxamide 1-(4-cyano-3-(trifluoromethyl)phenyl)-N-(5-((4-(piperazin-1-ylmethyl)piperidin-1-yl)methyl)pyridin-2-yl)piperidine-4-carboxamide (40 mg, 0.070 mmol), 2-(2,6-dioxopiperidin-3-yl)-5-fluoroisoindoline-1,3-dione (Intermediate 2-1, 31 mg, 0.011 mmol), and DIPEA (0.03 mL, 0.15 mmol) were suspended in DMSO (1.0 ml) and stirred at 90° C. for 16 hours. After adding distilled water (15 ml) to the reaction solution, extraction was performed with EtOAc (20 ml×2), and the organic layer was dried over anhydrous sodium sulfate, filtered, and concentrated under reduced pressure.

The obtained residue was subjected to MPLC (10% MeOH/DCM) to give 20 mg (34%) of a yellow solid.

Example 162: 1-(4-cyano-3-(trifluoromethyl)phenyl)-N-(5-((4-((1-(2-(2,6-dioxopiperidin-3-yl)-1,3-dioxoisoindolin-5-yl)piperidin-4-yl)methyl)piperazin-1-yl)methyl)pyridin-2-yl)piperidine-4-carboxamide

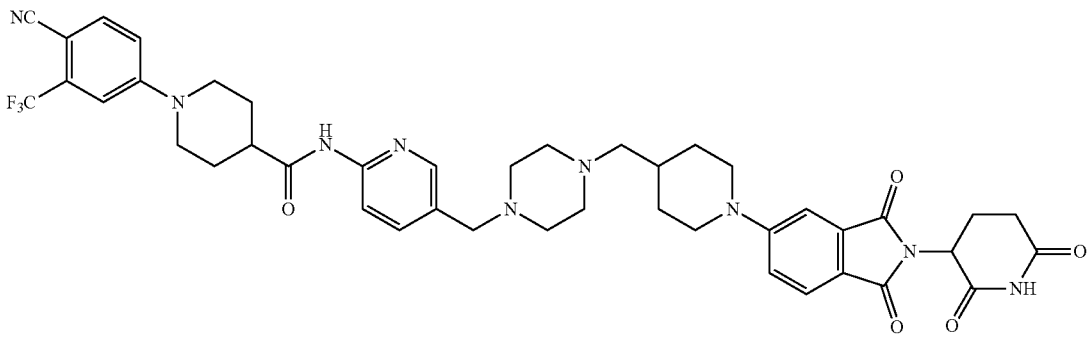 [SMILES: N#Cc1ccc(N2CCC(C(=O)Nc3ccc(CN4CCN(CC5CCN(c6ccc7c(c6)C(=O)N(C6CCC(=O)NC6=O)C7=O)CC5)CC4)cn3)CC2)cc1C(F)(F)F]

Example 162 was synthesized in a similar way to the synthesis method of Example 161, using tert-butyl 4-(piperazin-1-ylmethyl)piperidine-1-carboxylate (Intermediate 4-10) instead of tert-butyl 4-(piperidin-4-ylmethyl)piperazine-1-carboxylate (Intermediate 4-3).

Example 163: 1-(4-cyano-3-(trifluoromethyl)phenyl)-N-(5-((4-((4-((2-(2,6-dioxopiperidin-3-yl)-1,3-dioxoisoindolin-5-yl)oxy)piperidin-1-yl)methyl)piperidin-1-yl)methyl)pyridin-2-yl)piperidine-4-carboxamide

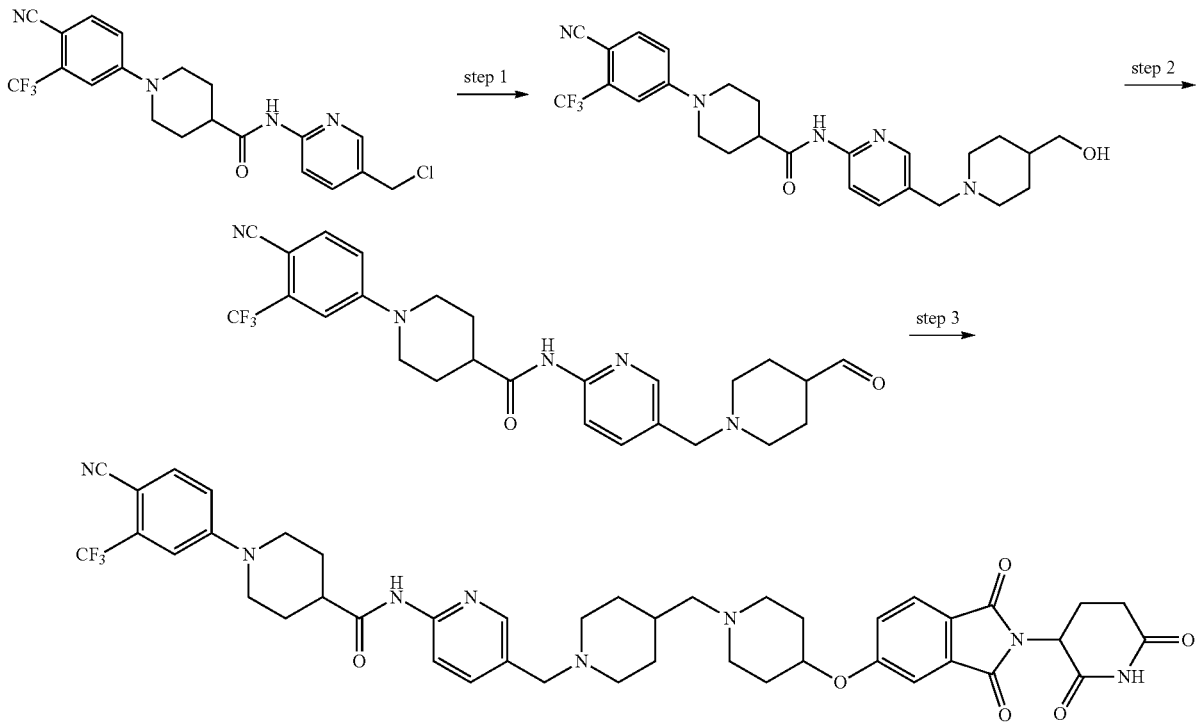

Step 1: Synthesis of 1-(4-cyano-3-(trifluoromethyl)phenyl)-N-(5-((4-(hydroxymethyl)piperidin-1-yl)methyl)pyridin-2-yl)piperidine-4-carboxamide N-(5-(chloromethyl)pyridin-2-yl)-1-(4-cyano-3-(trifluoromethyl)phenyl)piperidine-4-carboxamide (50 mg, 0.12 mmol), piperidin-4-ylmethanol (16 mg, 0.14 mmol), and NaHCO$_3$ (20 mg, 0.24 mmol) were suspended in DMF (1.0 ml) and stirred at 50° C. for 16 hours. After adding distilled water (1.0 ml) to the reaction solution, extraction was performed with EtOAc (1 ml×2), and the organic layer was dried over anhydrous sodium sulfate, filtered, and concentrated under reduced pressure. The obtained residue was subjected to MPLC (50% EtOAc/DCM) to give 37 mg (62%) of a white solid. m/z 502.26 [M+H]$^+$.

Step 2: Synthesis of 1-(4-cyano-3-(trifluoromethyl)phenyl)-N-(5-((4-formylpiperidin-1-yl)methyl)pyridin-2-yl)piperidine-4-carboxamide After suspending 1-(4-cyano-3-(trifluoromethyl)phenyl)-N-(5-((4-(hydroxymethyl)piperidin-1-yl)methyl)pyridin-2-yl)piperidine-4-carboxamide (37 mg, 0.074 mmol) in DCM (5.0 ml), DMP (38 mg, 0.089 mmol) was added and stirred at room temperature for 2 hours. After adding Na$_2$S$_2$O$_3$ aqueous solution (10 ml) to the reaction mixture, extraction was performed with DCM (20 ml×2), and the organic layer was dried over anhydrous sodium sulfate, filtered, and concentrated under reduced pressure. The resulting residue was subjected to MPLC (50% EtOAc/Hexane) to give 30 mg (81%) of a white solid. m/z 500.26 [M+H]$^+$.

Step 3: Synthesis of 1-(4-cyano-3-(trifluoromethyl)phenyl)-N-(5-((4-((4-((2-(2,6-dioxopiperidin-3-yl)-1,3-dioxoisoindolin-5-yl)oxy)piperidin-1-yl)methyl)piperidin-1-yl)methyl)pyridin-2-yl)piperidine-4-carboxamide After suspending 1-(4-cyano-3-(trifluoromethyl)phenyl)-N-(5-((4-formylpiperidin-1-yl)methyl)pyridin-2-yl)piperidine-4-carboxamide (30 mg, 0.060 mmol), and 2-(2,6-dioxopiperidin-3-yl)-5-(piperidin-4-yloxy)isoindoline-1,3-dione (24 mg, 0.066 mmol) in ACN (5.0 ml), sodium triacetoxyborohydride (38 mg, 0.18 mmol) was added and stirred at room temperature for 16 hours. NaHCO$_3$ aqueous solution (10 ml) was added to the reaction solution, followed by extraction with EtOAc (20 ml×2), and the organic layer was dried over anhydrous sodium sulfate, filtered, and concentrated under reduced pressure. The resulting residue was subjected to MPLC (10% MeOH/DCM) to give 28 mg (55%) of a white solid.

Example 164: 1-(4-cyano-3-(trifluoromethyl)phenyl)-N-(5-((1-((1-(2-(2,6-dioxopiperidin-3-yl)-1,3-dioxoisoindolin-5-yl)piperidin-4-yl)methyl)piperidin-4-yl)methyl)pyridin-2-yl)piperidine-4-carboxamide

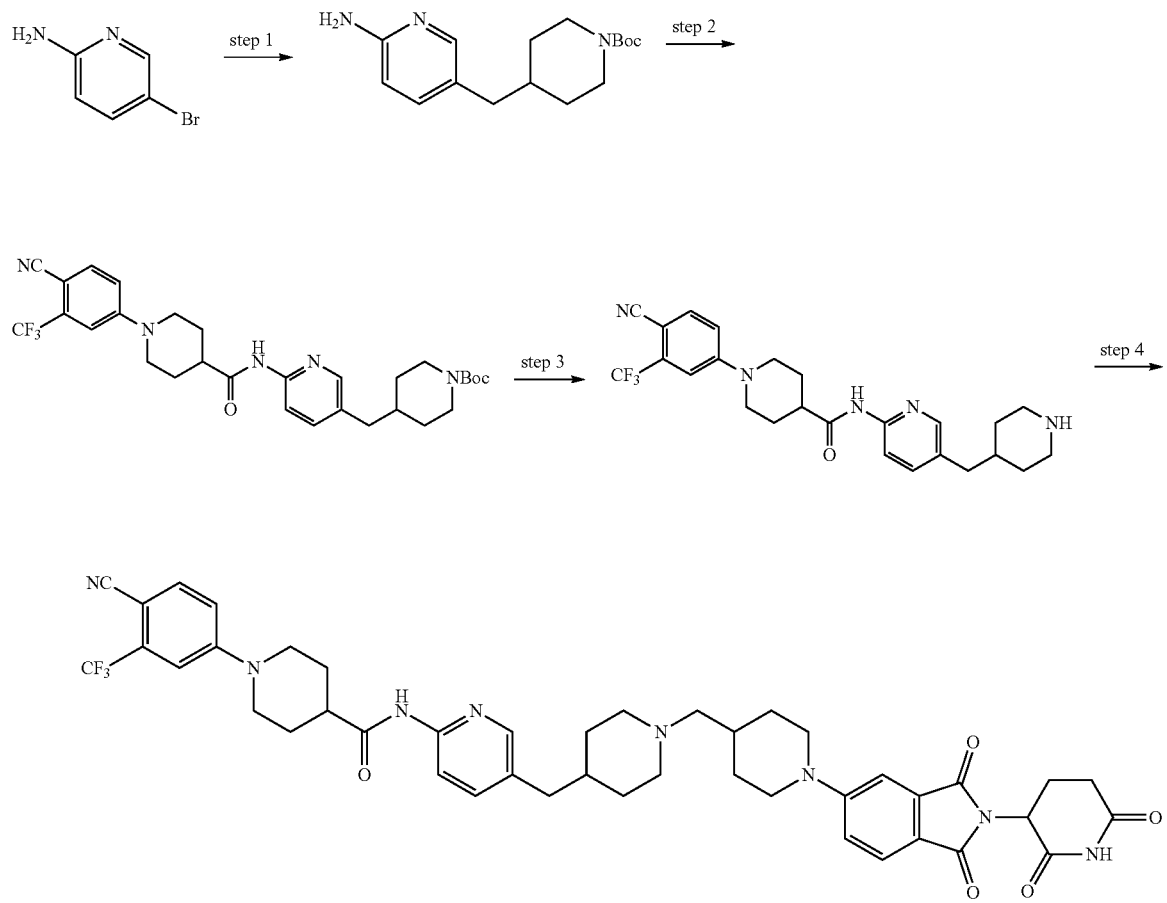

Step 1: Synthesis of tert-butyl 4-((6-aminopyridin-3-yl)methyl)piperidine-1-carboxylate 5-bromopyridin-2-amine (190 mg, 1.10 mmol), tert-butyl 4-methylenepiperidine-1-carboxylate (255 mg, 1.20 mmol), Pd(dppf)Cl$_2$·DCM (27 mg, 0.033 mmol), 0.5 M 9-BBN in THF (3.87 ml, 1.98 mmol), and K$_2$CO$_3$ (194 mg, 1.43 mmol) were suspended in DMF (2.4 ml) and stirred at room temperature for 2 hours. After adding distilled water (15 ml) to the reaction solution, extraction was performed with EtOAc (25 ml×2), and the organic layer was dried over anhydrous sodium sulfate, filtered, and concentrated under reduced pressure. The obtained residue was subjected to MPLC (10% MeOH/DCM) to give 179 mg (56%) of a yellow solid. m/z 292.25 [M+H]$^+$.

Step 2: Synthesis of tert-butyl 4-((6-(1-(4-cyano-3-(trifluoromethyl)phenyl)piperidine-4-carboxamido)pyridin-3-yl)methyl)piperidine-1-carboxylate Tert-butyl 4-((6-aminopyridin-3-yl)methyl)piperidine-1-carboxylate (179 mg, 0.614 mmol), 1-(4-cyano-3-(trifluoromethyl)phenyl)piperidine-4-carboxylic acid (Intermediate 1-1, 220 mg, 0.737 mmol), HATU (280 mg, 0.737 mmol), and DIPEA (0.21 ml, 1.23 mmol) were suspended in DMF (2.0 ml) and stirred at room temperature for 16 hours. After adding distilled water (15 ml) to the reaction solution, extraction was performed with EtOAc (20 ml×2), and the organic layer was dried over anhydrous sodium sulfate, filtered, and concentrated under reduced pressure. The resulting residue was subjected to MPLC (10% MeOH/DCM) to give 271 mg (77%) of a white solid. m/z 572.18 [M+H]$^+$.

Step 3: Synthesis of 1-(4-cyano-3-(trifluoromethyl)phenyl)-N-(5-(piperidin-4-ylmethyl)pyridin-2-yl)piperidine-4-carboxamide After suspending tert-butyl 4-((6-(1-(4-cyano-3-(trifluoromethyl)phenyl)piperidine-4-carboxamido)pyridin-3-yl)methyl)piperidine-1-carboxylate (271 mg, 0.398 mmol) in DCM (3.00 ml), 4 M HCl in dioxane (0.50 mL, 1.99 mmol) was added and stirred at room temperature for 1 hour. After concentrating the reaction mixture, aqueous NaHCO$_3$ solution (15 ml) was added, followed by extraction with DCM (25 ml×2). The organic layer was dried over anhydrous sodium sulfate, filtered, and concentrated under reduced pressure. 138 mg (62%) of a white solid was obtained. m/z 472.25 [M+H]$^+$.

Step 4: Synthesis of 1-(4-cyano-3-(trifluoromethyl)phenyl)-N-(5-((1-((1-(2-(2,6-dioxopiperidin-3-yl)-1,3-dioxoisoindolin-5-yl)piperidin-4-yl)methyl)piperidin-4-yl)methyl)pyridin-2-yl)piperidine-4-carboxamide After suspending 1-(4-cyano-3-(trifluoromethyl)phenyl)-N-(5-(piperidin-4-ylmethyl)pyridin-2-yl)piperidine-4-carboxamide (40 mg, 0.096 mmol), 1-(2-(2,6-dioxopiperidin-3-yl)-1,3-dioxoisoindolin-5-yl)piperidine-4-carbaldehyde (Intermediate 3-1, 39 mg, 0.11 mmol) in ACN (1.0 ml), sodium triacetoxyborohydride (61 mg, 0.29 mmol) was added and stirred at room temperature for 16 hours. NaHCO$_3$ aqueous solution (1.5 ml) was added to the reaction solution, followed by extraction with EtOAc (2.0 ml×2), and the organic layer was dried over anhydrous sodium sulfate, filtered, and concentrated under reduced pressure. The obtained residue was subjected to MPLC (10% MeOH/DCM) to give 45 mg (64%) of a yellow solid.

Example 165: 1-(4-cyano-3-(trifluoromethyl)phenyl)-N-(5-(2-(4-((4-(2-(2,6-dioxopiperidin-3-yl)-1,3-dioxoisoindolin-5-yl)piperazin-1-yl)methyl)piperidin-1-yl)ethyl)pyridin-2-yl)piperidine-4-carboxamide

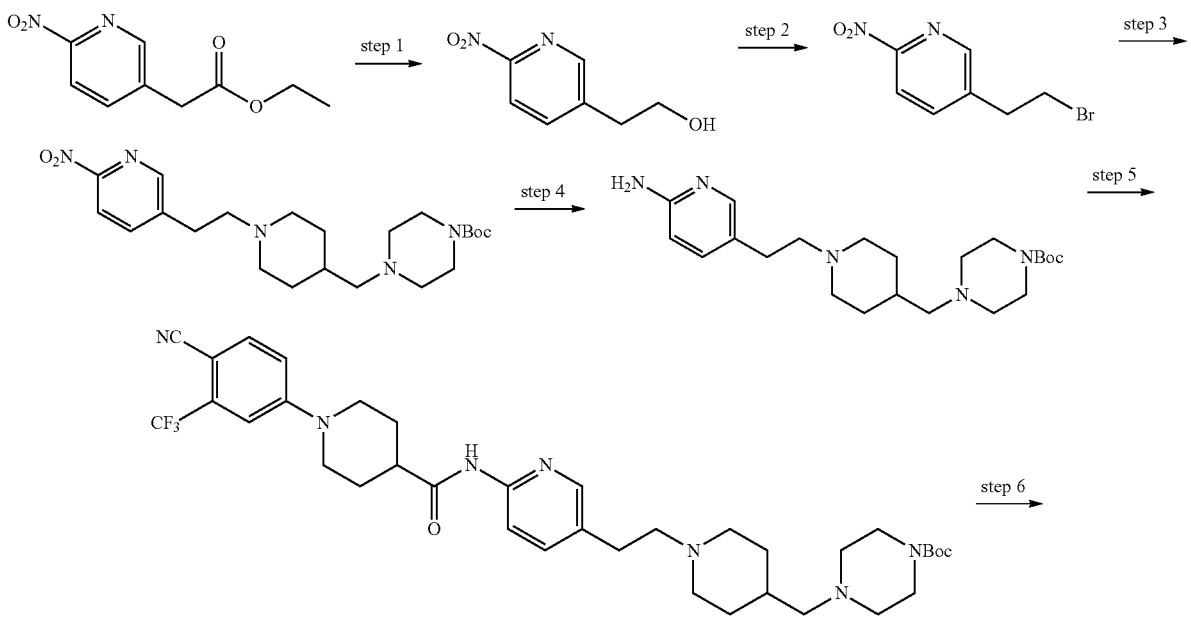

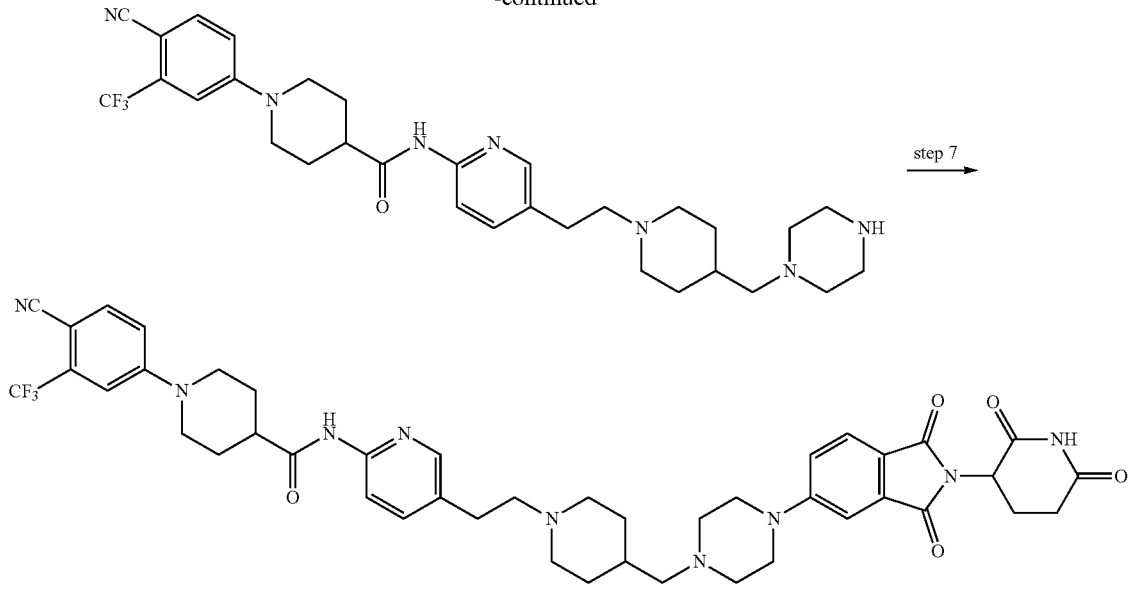

Step 1: Synthesis of 2-(6-nitropyridin-3-yl)ethan-1-ol

After suspending ethyl 2-(6-nitropyridin-3-yl)acetate (500 mg, 2.38 mmol) in anhydrous THF (10 ml), 1 M $BH_3 \cdot THF$ (7.14 ml, 7.14 mmol) was slowly added and stirred at 60° C. for 2 hours. After adding distilled water (10 ml) to the reaction solution, extraction was performed with EtOAc (15 ml×2), and the organic layer was dried over anhydrous magnesium sulfate, filtered, and concentrated under reduced pressure. The resulting residue was subjected to MPLC (50% EtOAc/Hexane) to give 300 mg (74%) of a white solid.

Step 2: Synthesis of 5-(2-bromoethyl)-2-nitropyridine

After suspending 2-(6-nitropyridin-3-yl)ethan-1-ol (358 mg, 2.13 mmol) in DCM (20.0 ml), triphenyl phosphine (614 mg, 2.34 mmol) and carbon tetrabromide (918 mg, 2.77 mmol) were added and stirred at room temperature for 16 hours. After adding distilled water (15 ml) to the reaction solution, extraction was performed with EtOAc (25 ml×2), and the organic layer was dried over anhydrous sodium sulfate, filtered, and concentrated under reduced pressure. The resulting residue was subjected to MPLC (50% EtOAc/Hexane) to give 490 mg (99%) of a white solid.

Step 3: Synthesis of tert-butyl 4-((1-(2-(6-nitropyridin-3-yl)ethyl)piperidin-4-yl)methyl)piperazine-1-carboxylate 5-(2-bromoethyl)-2-nitropyridine (100 mg, 0.430 mmol), tert-butyl 4-(piperidin-4-ylmethyl)piperazine-1-carboxylate (Intermediate 4-3, 147 mg, 0.520 mmol), and $K_2CO_3$ (119 mg, 0.600 mmol) were suspended in ACN (1.0 ml) and stirred at 70° C. for 16 hours. After adding distilled water (15 ml) to the reaction solution, extraction was performed with EtOAc (25 ml×2), and the organic layer was dried over anhydrous sodium sulfate, filtered, and concentrated under reduced pressure. The resulting residue was subjected to MPLC (10% MeOH/DCM) to give 161 mg (86%) of a white solid. m/z 434.11 $[M+H]^+$.

Step 4: Synthesis of tert-butyl 4-((1-(2-(6-aminopyridin-3-yl)ethyl)piperidin-4-yl)methyl)piperazine-1-carboxylate After suspending tert-butyl 4-((1-(2-(6-nitropyridin-3-yl)ethyl)piperidin-4-yl)methyl)piperazine-1-carboxylate (161 mg, 0.065 mmol) in a mixture of DCM (15 mL) and MeOH (5 mL), Pd/C (10 wt % Pd, 32 mg) was added and stirred under a hydrogen stream at room temperature for 4 hours. The reaction solution was filtered and concentrated. A black solid (133 mg, 89%) was obtained. m/z 404.27 $[M+H]^+$.

Step 5: Synthesis of tert-butyl 4-((1-(2-(6-(1-(4-cyano-3-(trifluoromethyl)phenyl)piperidine-4-carboxamido)pyridin-3-yl)ethyl)piperidin-4-yl)methyl)piperazine-1-carboxylate Tert-butyl 4-((1-(2-(6-aminopyridin-3-yl)ethyl)piperidin-4-yl)methyl)piperazine-1-carboxylate (133 mg, 0.330 mmol), 1-(4-cyano-3-(trifluoromethyl)phenyl)piperidine-4-carboxylic acid (Intermediate 1-1, 118 mg, 0.396 mmol), HATU (140 mg, 0.396 mmol), and DIPEA (0.11 mL, 0.660 mmol) were suspended in DMF (1.0 ml) and stirred at room temperature for 16 hours. After adding distilled water (15 ml) to the reaction solution, extraction was performed with EtOAc (20 ml×2), and the organic layer was dried over anhydrous sodium sulfate, filtered, and concentrated under reduced pressure. The obtained residue was subjected to MPLC (10% MeOH/DCM) to give 65 mg (29%) of a white solid. m/z 684.53 $[M+H]^+$.

Step 6: Synthesis of 1-(4-cyano-3-(trifluoromethyl)phenyl)-N-(5-(2-(4-(piperazin-1-ylmethyl)piperidin-1-yl)ethyl)pyridin-2-yl)piperidine-4-carboxamide After suspending tert-butyl 4-((1-(2-(6-(1-(4-cyano-3-(trifluoromethyl)phenyl)piperidine-4-carboxamido)pyridin-3-yl)ethyl)piperidin-4-yl)methyl)piperazine-1-carboxylate (65 mg, 0.095 mmol) in DCM (1.00 ml), 4 M HCl in dioxane (0.12 mL, 0.48 mmol) was added and stirred at room temperature for 1 hour. After concentrating the reaction mixture, aqueous NaHCO$_3$ solution (1.5 ml) was added, followed by extraction with DCM (2.0 ml×2). The organic layer was dried over anhydrous sodium sulfate, filtered, and concentrated under reduced pressure. 33 mg (60%) of a white solid was obtained. m/z 584.38 [M+H]$^+$.

Step 7: Synthesis of 1-(4-cyano-3-(trifluoromethyl) phenyl)-N-(5-(2-(4-((4-(2-(2,6-dioxopiperidin-3-yl)-1,3-dioxoisoindolin-5-yl)piperazin-1-yl)methyl)piperidin-1-yl)ethyl)pyridin-2-yl)piperidine-4-carboxamide 1-(4-cyano-3-(trifluoromethyl)phenyl)-N-(5-(2-(4-(piperazin-1-ylmethyl)piperidin-1-yl)ethyl)pyridin-2-yl)piperidine-4-carboxamide (33 mg, 0.057 mmol), 2-(2,6-dioxopiperidin-3-yl)-5-fluoroisoindoline-1,3-dione (Intermediate 2-1, 23 mg, 0.085 mmol), and DIPEA (0.02 mL, 0.11 mmol) were suspended in DMSO (1.0 ml) and stirred at 90° C. for 16 hours. After adding distilled water (10 ml) to the reaction solution, extraction was performed with EtOAc (2.0 ml×2), and the organic layer was dried over anhydrous sodium sulfate, filtered, and concentrated under reduced pressure. The resulting residue was subjected to MPLC (10% MeOH/DCM) to give 17 mg (36%) of a yellow solid.

Example 166: 1-(4-cyano-3-(trifluoromethyl)phenyl)-N-(5-(2-(4-((1-(2-(2,6-dioxopiperidin-3-yl)-1,3-dioxoisoindolin-5-yl)piperidin-4-yl)methyl)piperazin-1-yl)ethyl)pyridin-2-yl)piperidine-4-carboxamide

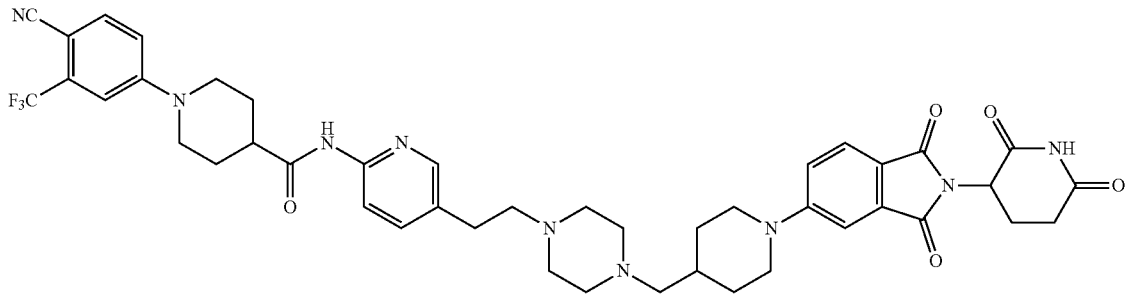 [SMILES: N#Cc1ccc(N2CCC(C(=O)Nc3ccc(CCN4CCN(CC5CCN(c6ccc7c(c6)C(=O)N(C6CCC(=O)NC6=O)C7=O)CC5)CC4)cn3)CC2)cc1C(F)(F)F]

Example 166 was synthesized in a similar way to the synthesis method of Example 165, using tert-butyl 4-(piperazin-1-ylmethyl)piperidine-1-carboxylate (Intermediate 4-10) instead of tert-butyl 4-(piperidin-4-ylmethyl)piperazine-1-carboxylate (Intermediate 4-3).

Example 167: 1-(4-cyano-3-(trifluoromethyl)phenyl)-N-(5-(2-(4-((2-(2,6-dioxopiperidin-3-yl)-1,3-dioxoisoindolin-5-yl)oxy)piperidin-1-yl)ethyl)pyridin-2-yl)piperidine-4-carboxamide

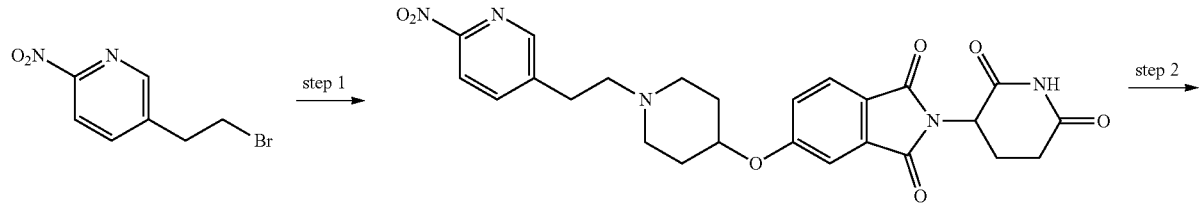

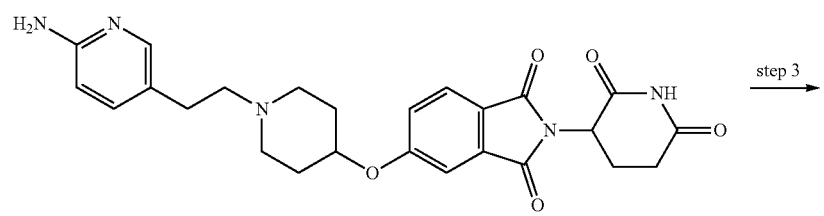

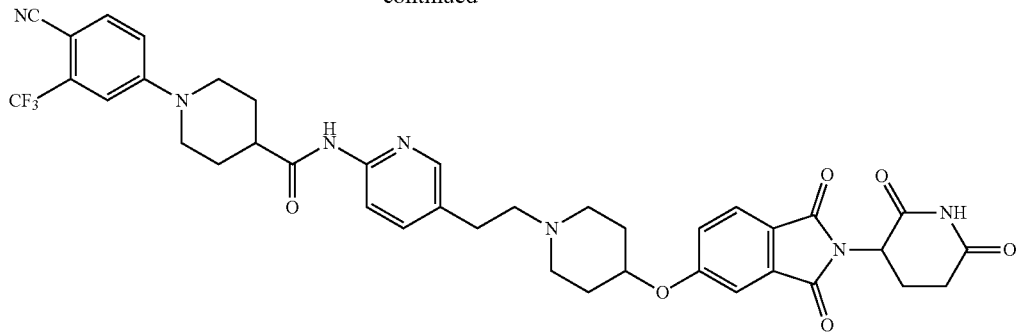

Step 1: Synthesis of 2-(2,6-dioxopiperidin-3-yl)-5-((1-(2-(6-nitropyridin-3-yl)ethyl)piperidin-4-yl)oxy)isoindoline-1,3-dione 5-(2-bromoethyl)-2-nitropyridine (50 mg, 0.22 mmol), 2-(2,6-dioxopiperidin-3-yl)-5-(piperidin-4-yloxy)isoindoline-1,3-dione (116 mg, 0.32 mmol), and $K_2CO_3$ (61 mg, 0.44 mmol) were suspended in ACN (1.0 ml) and stirred at 70° C. for 16 hours. After adding distilled water (15 ml) to the reaction solution, extraction was performed with EtOAc (25 ml×2), and the organic layer was dried over anhydrous sodium sulfate, filtered, and concentrated under reduced pressure. The obtained residue was subjected to MPLC (10% MeOH/DCM) to give 49 mg (44%) of a white solid. m/z 508.10 $[M+H]^+$.

Step 2: Synthesis of 5-((1-(2-(6-aminopyridin-3-yl)ethyl)piperidin-4-yl)oxy)-2-(2,6-dioxopiperidin-3-yl)isoindoline-1,3-dione After dissolving 2-(2,6-dioxopiperidin-3-yl)-5-((1-(2-(6-nitropyridin-3-yl)ethyl)piperidin-4-yl)oxy)isoindoline-1,3-dione (49 mg, 0.097 mmol) in a mixture of DCM (10 mL) and MeOH (5 mL), Pd/C (10 wt % Pd, 10 mg) was added and stirred under a hydrogen stream at room temperature for 4 hours. The reaction solution was filtered and concentrated. 41 mg (89%) of a purple solid was obtained. m/z 478.29 $[M+H]^+$.

Step 3: Synthesis of 1-(4-cyano-3-(trifluoromethyl)phenyl)-N-(5-(2-(4-((2-(2,6-dioxopiperidin-3-yl)-1,3-dioxoisoindolin-5-yl)oxy)piperidin-1-yl)ethyl)pyridin-2-yl)piperidine-4-carboxamide 5-((1-(2-(6-aminopyridin-3-yl)ethyl)piperidin-4-yl)oxy)-2-(2,6-dioxopiperidin-3-yl)isoindoline-1,3-dione (41 mg, 0.086 mmol), 1-(4-cyano-3-(trifluoromethyl)phenyl)piperidine-4-carboxylic acid (Intermediate 1-1, 30 mg, 0.10 mmol), HATU (38 mg, 0.10 mmol), and DIPEA (0.03 mL, 0.17 mmol) were suspended in DMF (1.0 ml) and stirred at room temperature for 16 hours. After adding distilled water (15 ml) to the reaction solution, extraction was performed with EtOAc (20 ml×2), and the organic layer was dried over anhydrous sodium sulfate, filtered, and concentrated under reduced pressure. The resulting residue was subjected to MPLC (10% MeOH/DCM) to give 10 mg (15%) of a white solid.

Example 168: 1-(4-cyano-3-(trifluoromethyl)phenyl)-N-(5-(2-(4-((1-(2-(2,6-dioxopiperidin-3-yl)-1,3-dioxoisoindolin-5-yl)piperidin-4-yl)methyl)piperazin-1-yl)ethoxy)pyridin-2-yl)piperidine-4-carboxamide

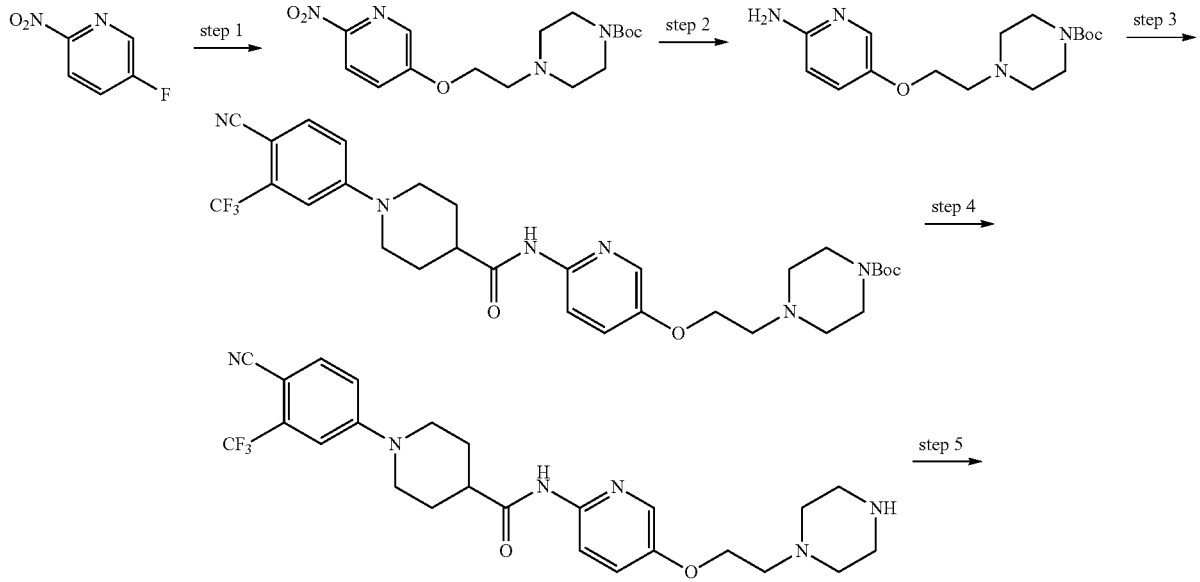

-continued

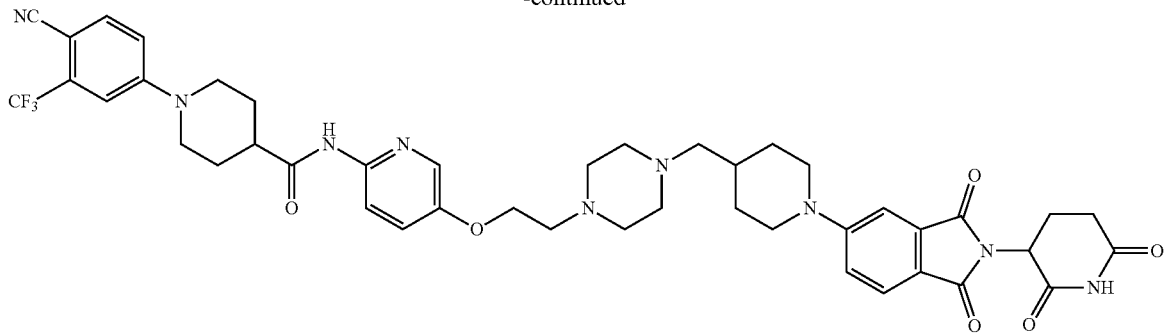

Step 1: Synthesis of tert-butyl 4-(2-((6-nitropyridin-3-yl)oxy)ethyl)piperazine-1-carboxylate After suspending tert-butyl 4-(2-hydroxyethyl)piperazine-1-carboxylate (Intermediate 4-11, 195 mg, 0.845 mmol) in THF, 60% NaH (33 mg, 0.845 mmol) was added at 0° C. and stirred at room temperature for 1 hour. After adding 5-fluoro-2-nitropyridine (100 mg, 0.704 mmol) to the reaction solution, the mixture was stirred at room temperature for 16 hours. After adding distilled water (15 ml) to the reaction solution, extraction was performed with EtOAc (25 ml×2), and the organic layer was dried over anhydrous sodium sulfate, filtered, and concentrated under reduced pressure. The resulting residue was subjected to MPLC (50% EtOAc/Hexane) to give 125 mg (52%) of a white solid.

Step 2: Synthesis of tert-butyl 4-(2-((6-aminopyridin-3-yl)oxy)ethyl)piperazine-1-carboxylate After dissolving tert-butyl 4-(2-((6-nitropyridin-3-yl)oxy)ethyl)piperazine-1-carboxylate (125 mg, 0.355 mmol) in a mixture of DCM (10 mL) and MeOH (5 mL), Pd/C (10 wt % Pd, 25 mg) was added and stirred under a hydrogen stream at room temperature for 2 hours. The reaction solution was filtered and concentrated. 111 mg (97%) of a purple solid was obtained. m/z 323.42 [M+H]$^+$.

Step 3: Synthesis of tert-butyl 4-(2-((6-(1-(4-cyano-3-(trifluoromethyl)phenyl)piperidine-4-carboxamido)pyridin-3-yl)oxy)ethyl)piperazine-1-carboxylate Tert-butyl 4-(2-((6-aminopyridin-3-yl)oxy)ethyl)piperazine-1-carboxylate (111 mg, 0.334 mmol), 1-(4-cyano-3-(trifluoromethyl)phenyl)piperidine-4-carboxylic acid (Intermediate 1-1, 112 mg, 0.378 mmol), HATU (143 mg, 0.378 mmol), and DIPEA (0.11 mL, 0.688 mmol) were suspended in DMF (2.0 ml) and stirred at room temperature for 16 hours. After adding distilled water (15 ml) to the reaction solution, extraction was performed with EtOAc (20 ml×2), and the organic layer was dried over anhydrous sodium sulfate, filtered, and concentrated under reduced pressure. The resulting residue was subjected to MPLC (10% MeOH/DCM) to give 179 mg (86%) of a white solid. m/z 603.31 [M+H]$^+$.

Step 4: Synthesis of 1-(4-cyano-3-(trifluoromethyl)phenyl)-N-(5-(2-(piperazin-1-yl)ethoxy)pyridin-2-yl)piperidine-4-carboxamide After suspending tert-butyl 4-(2-((6-(1-(4-cyano-3-(trifluoromethyl)phenyl)piperidine-4-carboxamido)pyridin-3-yl)oxy)ethyl)piperazine-1-carboxylate (179 mg, 0.297 mmol) in DCM (1.00 ml), 4 M HCl in dioxane (0.37 mL, 1.49 mmol) was added and stirred at room temperature for 1 hour. After concentrating the reaction mixture, aqueous NaHCO$_3$ solution (15 ml) was added, followed by extraction with DCM (20 ml×2). The organic layer was dried over anhydrous sodium sulfate, filtered, and concentrated under reduced pressure. 135 mg (91%) of a white solid was obtained. m/z 503.27 [M+H]$^+$.

Step 5: Synthesis of 1-(4-cyano-3-(trifluoromethyl)phenyl)-N-(5-(2-(4-((1-(2-(2,6-dioxopiperidin-3-yl)-1,3-dioxoisoindolin-5-yl)piperidin-4-yl)methyl)piperazin-1-yl)ethoxy)pyridin-2-yl)piperidine-4-carboxamide After suspending 1-(4-cyano-3-(trifluoromethyl)phenyl)-N-(5-(2-(piperazin-1-yl)ethoxy)pyridin-2-yl)piperidine-4-carboxamide (50 mg, 0.099 mmol), and 1-(2-(2,6-dioxopiperidin-3-yl)-1,3-dioxoisoindolin-5-yl)piperidine-4-carbaldehyde (Intermediate 3-1, 44 mg, 0.12 mmol) in ACN (10.0 ml), sodium triacetoxyborohydride (62 mg, 0.30 mmol) was added and stirred at room temperature for 16 hours. NaHCO$_3$ aqueous solution (10 ml) was added to the reaction solution, followed by extraction with EtOAc (20 ml×2), and the organic layer was dried over anhydrous sodium sulfate, filtered, and concentrated under reduced pressure. The resulting residue was subjected to MPLC (10% MeOH/DCM) to give 38 mg (45%) of a yellow solid.

Example 169: 1-(4-cyano-3-(trifluoromethyl)phe-
nyl)-N-(5-((1-((1-(2-(2,6-dioxopiperidin-3-yl)-1,3-
dioxoisoindolin-5-yl)piperidin-4-yl)methyl)piperi-
din-4-yl)oxy)pyridin-2-yl)piperidine-4-carboxamide

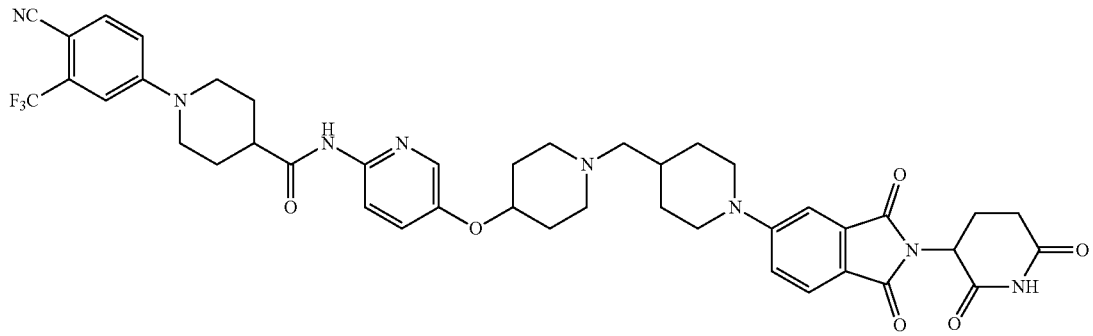

Example 169 was synthesized in a similar way to the synthesis method of Example 168, using tert-butyl 4-hydroxypiperidine-1-carboxylate instead of tert-butyl 4-(2-hydroxyethyl)piperazine-1-carboxylate (Intermediate 4-11).

Example 170: 1-(4-cyano-3-(trifluoromethyl)phe-
nyl)-N-(5-((1-((1-(2-(2,6-dioxopiperidin-3-yl)-6-
fluoro-1,3-dioxoisoindolin-5-yl)piperidin-4-yl)
methyl)piperidin-4-yl)oxy)pyridin-2-yl)piperidine-4-
carboxamide

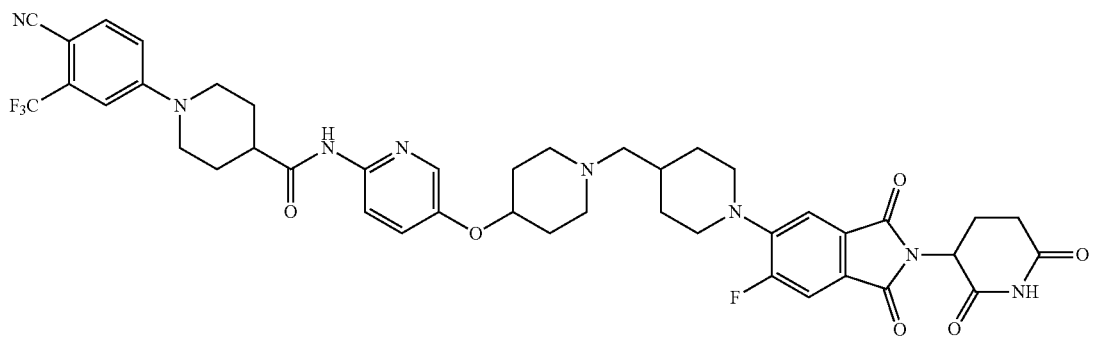 [SMILES: N#Cc1ccc(N2CCC(C(=O)Nc3ccc(OC4CCN(CC5CCN(c6cc7c(cc6F)C(=O)N(C6CCC(=O)NC6=O)C7=O)CC5)CC4)cn3)CC2)cc1C(F)(F)F]

Example 170 was synthesized in a similar way to the synthesis method of Example 168, using tert-butyl 4-hydroxypiperidine-1-carboxylate and 1-(2-(2,6-dioxopiperidin-3-yl)-6-fluoro-1,3-dioxoisoindolin-5-yl)piperidine-4-carbaldehyde (Intermediate 3-8), respectively, instead of tert-butyl 4-(2-hydroxyethyl)piperazine-1-carboxylate (Intermediate 4-11) and 1-(2-(2,6-dioxopiperidin-3-yl)-1,3-dioxoisoindolin-5-yl)piperidine-4-carbaldehyde (Intermediate 3-1).

Example 171: 1-(4-cyano-3-(trifluoromethyl)phe-
nyl)-N-(5-((1-((1-(2-(2,6-dioxopiperidin-3-yl)-1,3-
dioxoisoindolin-5-yl)azetidin-3-yl)methyl)piperidin-
4-yl)oxy)pyridin-2-yl)piperidine-4-carboxamide

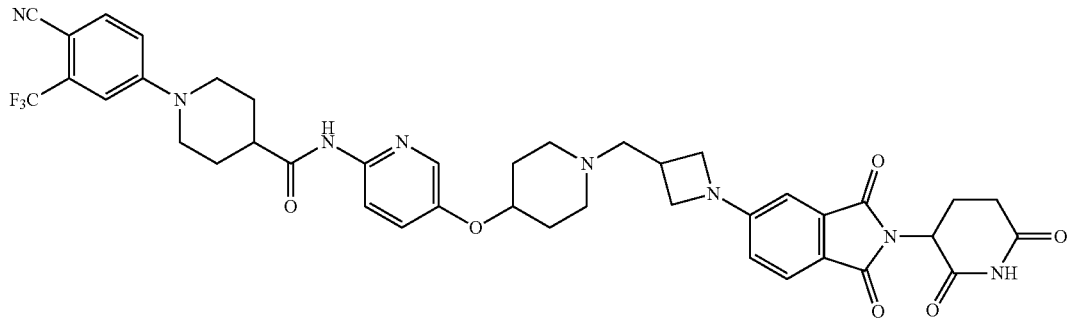 [SMILES: N#Cc1ccc(N2CCC(C(=O)Nc3ccc(OC4CCN(CC5CN(c6ccc7c(c6)C(=O)N(C6CCC(=O)NC6=O)C7=O)C5)CC4)cn3)CC2)cc1C(F)(F)F]

Example 171 was synthesized in a similar way to the synthesis method of Example 168, using tert-butyl 4-hydroxypiperidine-1-carboxylate and 1-(2-(2,6-dioxopiperidin-3-yl)-1,3-dioxoisoindolin-5-yl)azetidine-3-carbaldehyde (Intermediate 3-3), respectively, instead of tert-butyl 4-(2-hydroxyethyl)piperazine-1-carboxylate (Intermediate 4-11) and 1-(2-(2,6-dioxopiperidin-3-yl)-1,3-dioxoisoindolin-5-yl)piperidine-4-carbaldehyde (Intermediate 3-1).

Example 172: 1-(4-cyano-3-(trifluoromethyl)phe-
nyl)-N-(5-((1-((1-(2-(2,6-dioxopiperidin-3-yl)-1,3-
dioxoisoindolin-5-yl)-3-methylazetidin-3-yl)methyl)
piperidin-4-yl)oxy)pyridin-2-yl)piperidine-4-
carboxamide

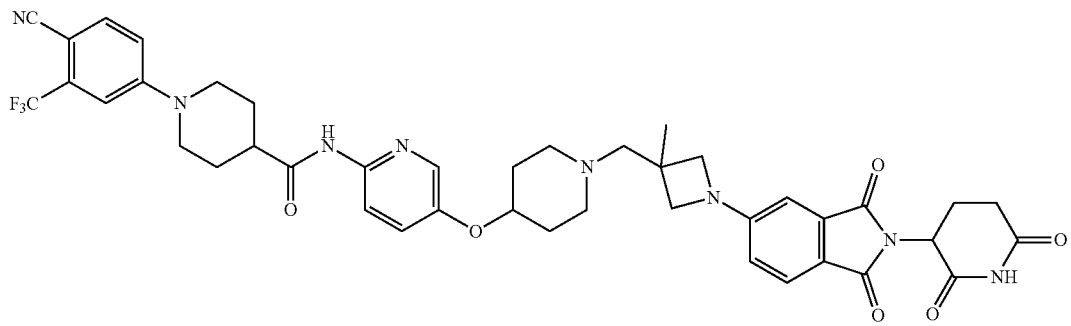

Example 172 was synthesized in a similar way to the synthesis method of Example 168, using tert-butyl 4-hydroxypiperidine-1-carboxylate and 1-(2-(2,6-dioxopiperidin-3-yl)-1,3-dioxoisoindolin-5-yl)-3-methylazetidine-3-carbaldehyde (Intermediate 3-12), respectively, instead of tert-butyl 4-(2-hydroxyethyl)piperazine-1-carboxylate (Intermediate 4-11) and 1-(2-(2,6-dioxopiperidin-3-yl)-1,3-dioxoisoindolin-5-yl)piperidine-4-carbaldehyde (Intermediate 3-1).

Example 173: 1-(4-cyano-3-(trifluoromethyl)phenyl)-N-(5-((1-((1-(2-(2,6-dioxopiperidin-3-yl)-1,3-dioxoisoindolin-5-yl)piperidin-4-yl)methyl)azetidin-3-yl)oxy)pyridin-2-yl)piperidine-4-carboxamide

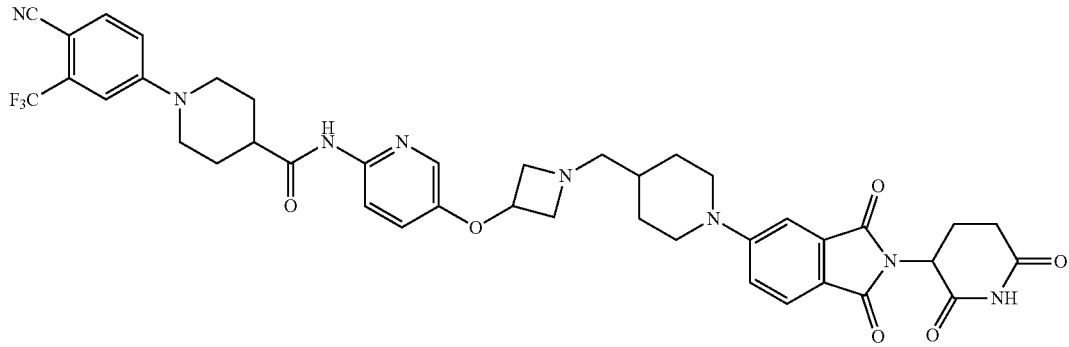 [SMILES: N#Cc1ccc(N2CCC(C(=O)Nc3ccc(OC4CN(CC5CCN(c6ccc7c(c6)C(=O)N(C6CCC(=O)NC6=O)C7=O)CC5)C4)cn3)CC2)cc1C(F)(F)F]

Example 173 was synthesized in a similar way to the synthesis method of Example 168, using tert-butyl 3-hydroxyazetidine-1-carboxylate instead of tert-butyl 4-(2-hydroxyethyl)piperazine-1-carboxylate (Intermediate 4-11).

Example 174: 1-(4-cyano-3-(trifluoromethyl)phenyl)-N-(5-((1-((1-(2-(2,6-dioxopiperidin-3-yl)-1,3-dioxoisoindolin-5-yl)piperidin-4-yl)methyl)piperidin-4-yl)methoxy)pyridin-2-yl)piperidine-4-carboxamide

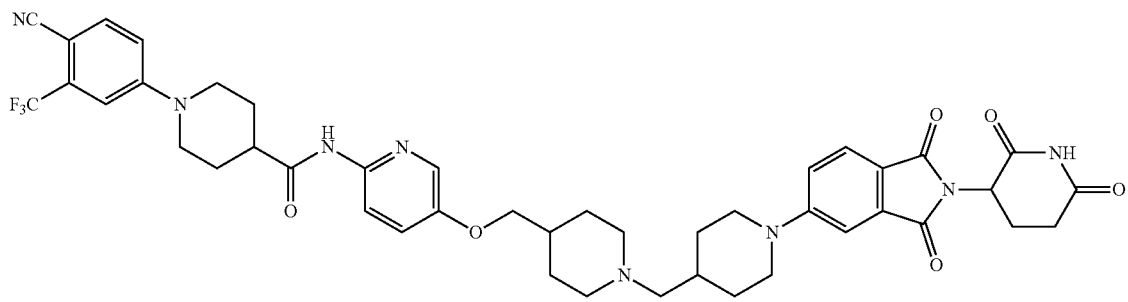 [SMILES: N#Cc1ccc(N2CCC(C(=O)Nc3ccc(OCC4CCN(CC5CCN(c6ccc7c(c6)C(=O)N(C6CCC(=O)NC6=O)C7=O)CC5)CC4)cn3)CC2)cc1C(F)(F)F]

Example 174 was synthesized in a similar way to the synthesis method of Example 168, using tert-butyl 4-(hydroxymethyl)piperidine-1-carboxylate instead of tert-butyl 4-(2-hydroxyethyl)piperazine-1-carboxylate (Intermediate 4-11).

Example 175: 1-(4-cyano-3-(trifluoromethyl)phenyl)-N-(5-(2-(1-((1-(2-(2,6-dioxopiperidin-3-yl)-1,3-dioxoisoindolin-5-yl)piperidin-4-yl)methyl)piperidin-4-yl)ethoxy)pyridin-2-yl)piperidine-4-carboxamide

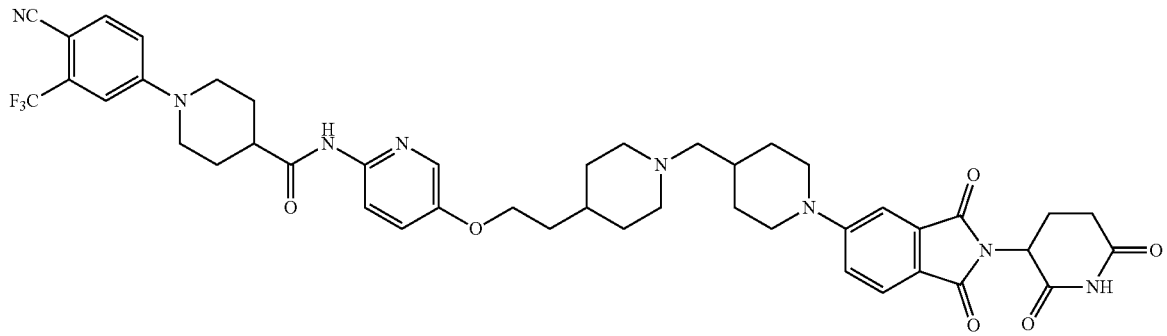 [SMILES: N#Cc1ccc(N2CCC(C(=O)Nc3ccc(OCCC4CCN(CC5CCN(c6ccc7c(c6)C(=O)N(C6CCC(=O)NC6=O)C7=O)CC5)CC4)cn3)CC2)cc1C(F)(F)F]

Example 175 was synthesized in a similar way to the synthesis method of Example 168, using tert-butyl 4-(2-hydroxyethyl)piperidine-1-carboxylate instead of tert-butyl 4-(2-hydroxyethyl)piperazine-1-carboxylate (Intermediate 4-11).

Example 176: 1-(4-cyano-3-(trifluoromethyl)phenyl)-N-(5-(2-(4-(2-((3-((2,6-dioxopiperidin-3-yl)amino)phenyl)amino)-2-oxoethyl)piperazin-1-yl)ethoxy)pyridin-2-yl)piperidine-4-carboxamide

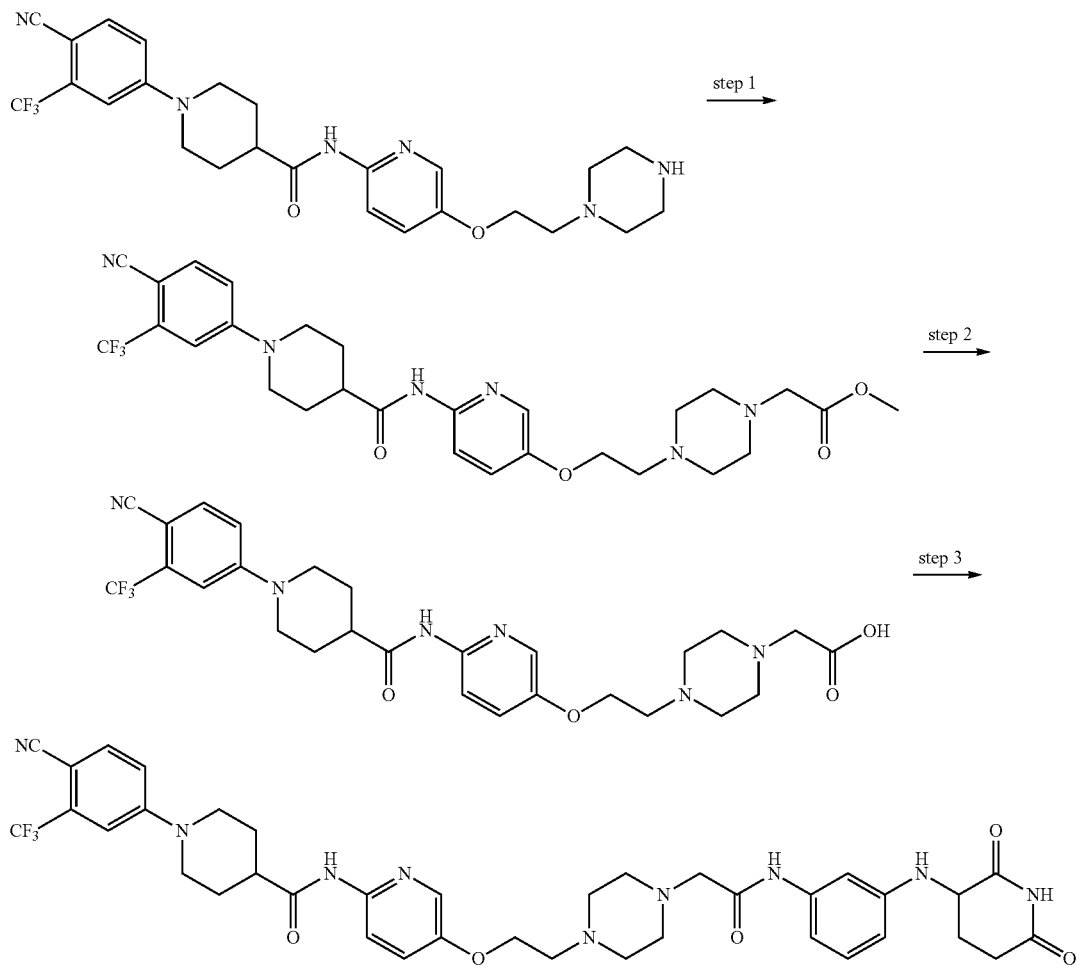

Step 1: Synthesis of methyl 2-(4-(2-((6-(1-(4-cyano-3-(trifluoromethyl)phenyl)piperidine-4-carboxamido)pyridin-3-yl)oxy)ethyl)piperazin-1-yl)acetate After suspending 1-(4-cyano-3-(trifluoromethyl)phenyl)-N-(5-(2-(piperazin-1-yl)ethoxy)pyridin-2-yl)piperidine-4-carboxamide (70 mg, 0.14 mmol) in THF (1.0 ml), methyl bromoacetate (0.013 mL, 0.14 mmol) and TEA (0.06 mL, 0.42 mmol) were added and stirred at room temperature for 2 hours. After adding distilled water (1.0 ml) to the reaction solution, extraction was performed with EtOAc (2.0 ml×2), and the organic layer was dried over anhydrous sodium sulfate, filtered, and concentrated under reduced pressure. The obtained residue was subjected to MPLC (50% EtOAc/Hexane) to give 50 mg (62%) of a white solid. m/z 575.26 [M+H]$^+$.

Step 2: Synthesis of 2-(4-(2-((6-(1-(4-cyano-3-(trifluoromethyl)phenyl)piperidine-4-carboxamido)pyridin-3-yl)oxy)ethyl)piperazin-1-yl)acetic acid After suspending methyl 2-(4-(2-((6-(1-(4-cyano-3-(trifluoromethyl)phenyl)piperidine-4-carboxamido)pyridin-3-yl)oxy)ethyl)piperazin-1-yl)acetate (50 mg, 0.087 mmol) in THF (2.0 mL) and distilled water (2.0 mL), LiOH·H$_2$O (14 mg, 0.35 mmol) was added and stirred at room temperature for 3 hours. After evaporation of the solvent and extraction with distilled water, 1 N HCl was added to the aqueous layer and extraction was performed with EtOAc (2.0 ml×2). The organic layer was dried over anhydrous sodium sulfate, filtered, and concentrated under reduced pressure. 20 mg (41%) of a white solid was obtained. m/z 561.28 [M+H]$^+$.

Step 3: Synthesis of 1-(4-cyano-3-(trifluoromethyl)phenyl)-N-(5-(2-(4-(2-((3-((2,6-dioxopiperidin-3-yl)amino)phenyl)amino)-2-oxoethyl)piperazin-1-yl)ethoxy)pyridin-2-yl)piperidine-4-carboxamide 2-(4-(2-((6-(1-(4-cyano-3-(trifluoromethyl)phenyl)piperidine-4-carboxamido)pyridin-3-yl)oxy)ethyl)piperazin-1-yl)acetic acid (20 mg, 0.036 mmol), 3-((3-aminophenyl)amino)piperidine-2,6-dione (Intermediate 2-7, 9.5 mg, 0.043 mmol), HATU (16 mg, 0.043 mmol), and DIPEA (0.01 mL, 0.072 mmol) were suspended in DMF (1.0 ml) and stirred at room temperature for 16 hours. After adding distilled water (10 ml) to the reaction solution, extraction was performed with EtOAc (20 ml×2), and the organic layer was dried over anhydrous sodium sulfate, filtered, and concentrated under reduced pressure. The obtained residue was subjected to MPLC (10% MeOH/DCM) to give 12 mg (44%) of a white solid.

Example 177: 1-(4-cyano-3-(trifluoromethyl)phenyl)-N-(5-(4-((4-(2-((3-((2,6-dioxopiperidin-3-yl)amino)phenyl)amino)-2-oxoethyl)piperazin-1-yl)methyl)piperidin-1-yl)pyridin-2-yl)piperidine-4-carboxamide

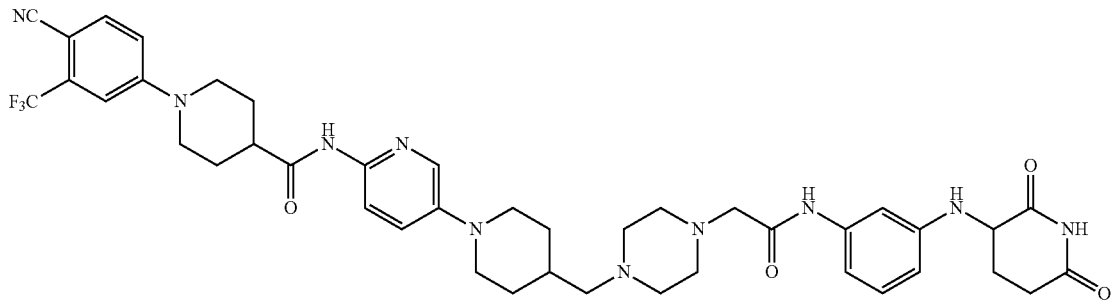 [SMILES: N#Cc1ccc(N2CCC(C(=O)Nc3ccc(N4CCC(CN5CCN(CC(=O)Nc6cccc(NC7CCC(=O)NC7=O)c6)CC5)CC4)cn3)CC2)cc1C(F)(F)F]

Example 177 was synthesized in a similar way to the synthesis method of Example 176, using 1-(4-cyano-3-(trifluoromethyl)phenyl)-N-(5-(4-(piperazin-1-ylmethyl)piperidin-1-yl)pyridin-2-yl)piperidine-4-carboxamide instead of 1-(4-cyano-3-(trifluoromethyl)phenyl)-N-(5-(2-(piperazin-1-yl)ethoxy)pyridin-2-yl)piperidine-4-carboxamide.

Example 178: 1-(4-cyano-3-(trifluoromethyl)phenyl)-N-(5-(2-(4-((2-(2,6-dioxopiperidin-3-yl)-1,3-dioxoisoindolin-5-yl)oxy)piperidin-1-yl)ethoxy)pyridin-2-yl)piperidine-4-carboxamide

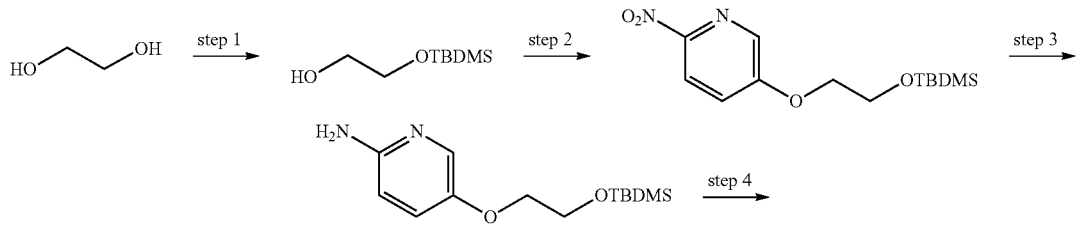

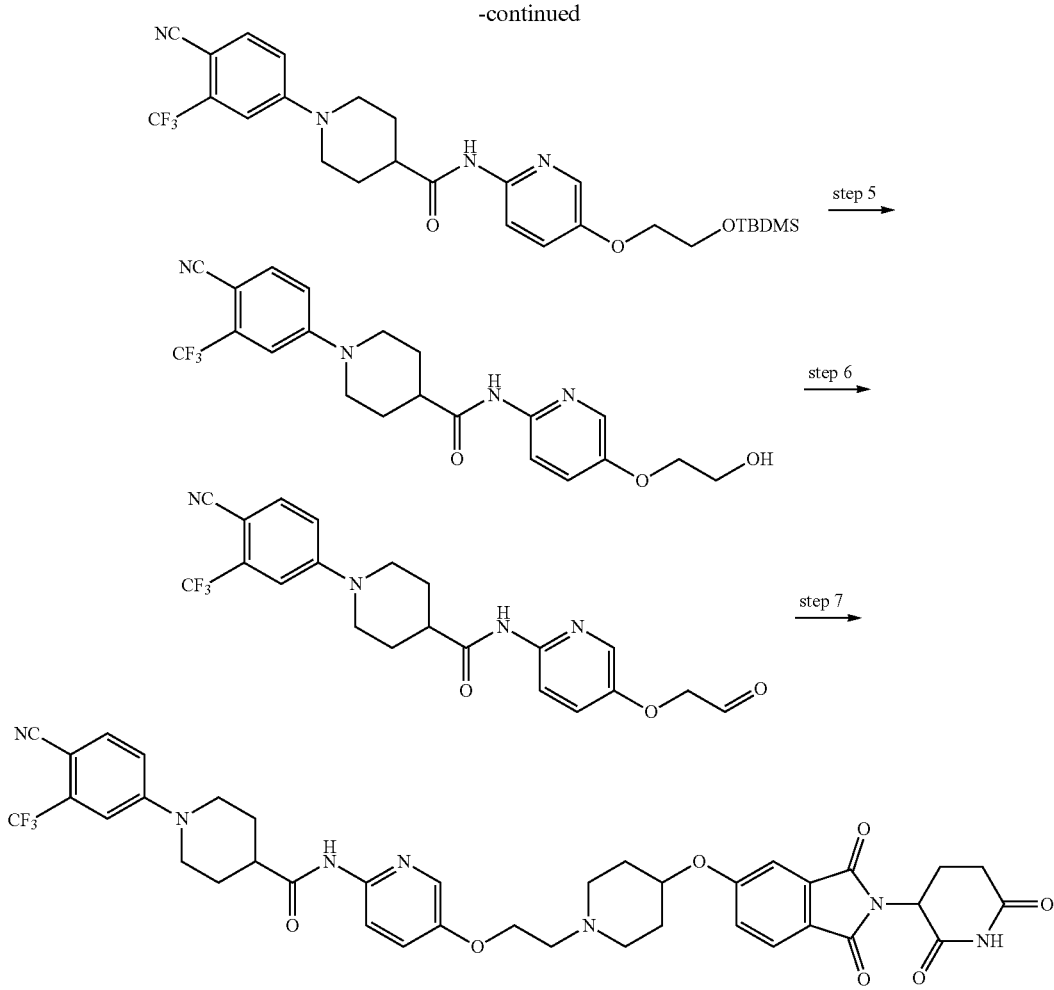

Step 1: Synthesis of 2-((tert-butyldimethylsilyl)oxy)ethan-1-ol

After suspending ethane-1,2-diol (500 mg, 8.06 mmol) in THF, 60% NaH (388 mg, 9.67 mmol) was added at 0° C. and stirred at room temperature for 1 hour. TBDMSCl (1.46 g, 9.67 mmol) was added to the reaction solution and stirred at room temperature for 16 hours. After adding distilled water (15 ml) to the reaction mixture, extraction was performed with EtOAc (20 ml×2), and the organic layer was dried over anhydrous sodium sulfate, filtered, and concentrated under reduced pressure. The resulting residue was subjected to MPLC (30% EtOAc/Hexane) to give 665 mg (46%) of a white solid.

Step 2: Synthesis of 5-(2-((tert-butyldimethylsilyl)oxy)ethoxy)-2-nitropyridine After suspending 2-((tert-butyldimethylsilyl)oxy)ethan-1-ol (629 mg, 3.57 mmol), 5-hydroxy-2-nitropyridine (500 mg, 3.57 mmol), and triphenyl phosphine (1.13 g, 4.28 mmol) in THF (15.0 ml), DEAD (0.67 mL, 4.28 mmol) was added and stirred at 40° C. for 4 hours. After adding distilled water (15 ml) to the reaction solution, extraction was performed with EtOAc (25 ml×2), and the organic layer was dried over anhydrous sodium sulfate, filtered, and concentrated under reduced pressure. The resulting residue was subjected to MPLC (30% EtOAc/Hexane) to give 650 mg (61%) of a colorless liquid. m/z 299.14 [M+H]+.

Step 3: Synthesis of 5-(2-((tert-butyldimethylsilyl)oxy)ethoxy)pyridin-2-amine After dissolving 5-(2-((tert-butyldimethylsilyl)oxy)ethoxy)-2-nitropyridine (320 mg, 1.07 mmol) in MeOH (10 mL), Pd/C (10 wt % Pd, 64 mg) was added and stirred under a hydrogen stream at room temperature for 2 hours. The reaction solution was filtered and concentrated. A purple solid (288 mg, 100%) was obtained. m/z 269.27 [M+H]+.

Step 4: Synthesis of N-(5-(2-((tert-butyldimethylsilyl)oxy)ethoxy)pyridin-2-yl)-1-(4-cyano-3-(trifluoromethyl)phenyl)piperidine-4-carboxamide 5-(2-((tert-butyldimethylsilyl)oxy)ethoxy)pyridin-2-amine (288 mg, 1.07 mmol), 1-(4-cyano-3-(trifluoromethyl)phenyl)piperidine-4-carboxylic acid (Intermediate 1-1, 384 mg, 1.29 mmol), HATU (490 mg, 1.29 mmol), and DIPEA (0.37 mL, 2.14 mmol) were suspended in DMF (2.0 ml) and stirred at room temperature for 16 hours. After adding distilled water (15 ml) to the reaction solution, extraction was performed with EtOAc (20 ml×2), and the organic layer was dried over anhydrous sodium sulfate, filtered, and concentrated under reduced pressure. The obtained residue was subjected to MPLC (10% MeOH/DCM) to give 356 mg (61%) of a white solid. m/z 549.23 [M+H]+.

Step 5: Synthesis of 1-(4-cyano-3-(trifluoromethyl) phenyl)-N-(5-(2-hydroxyethoxy)pyridin-2-yl)piperidine-4-carboxamide After suspending N-(5-(2-((tert-butyldimethylsilyl)oxy) ethoxy)pyridin-2-yl)-1-(4-cyano-3-(trifluoromethyl)phenyl) piperidine-4-carboxamide (156 mg, 0.284 mmol) in DCM (1.00 ml), 4 M HCl in dioxane (0.36 mL, 1.42 mmol) was added and stirred at room temperature for 1 hour. After concentrating the reaction solution, an aqueous NaHCO₃ solution (15 ml) was added, followed by extraction with DCM (20 ml×2). The organic layer was dried over anhydrous sodium sulfate, filtered, and concentrated under reduced pressure. 111 mg (90%) of a white solid was obtained. m/z 435.27 [M+H]+.

Step 6: Synthesis of 1-(4-cyano-3-(trifluoromethyl) phenyl)-N-(5-(2-oxoethoxy)pyridin-2-yl)piperidine-4-carboxamide After suspending 1-(4-cyano-3-(trifluoromethyl)phenyl)-N-(5-(2-hydroxyethoxy)pyridin-2-yl)piperidine-4-carboxamide (61 mg, 0.14 mmol) in DCM (5.0 ml), DMP (72 mg, 0.17 mmol) was added and stirred at room temperature for 2 hours. After adding Na₂S₂O₃ aqueous solution (10 ml) to the reaction mixture, extraction was performed with DCM (25 ml×2), and the organic layer was dried over anhydrous sodium sulfate, filtered, and concentrated under reduced pressure. The obtained residue was subjected to MPLC (50% EtOAc/DCM) to give 40 mg (66%) of a white solid. m/z 433.21 [M+H]+.

Step 7: Synthesis of 1-(4-cyano-3-(trifluoromethyl) phenyl)-N-(5-(2-(4-((2-(2,6-dioxopiperidin-3-yl)-1,3-dioxoisoindolin-5-yl)oxy)piperidin-1-yl)ethoxy) pyridin-2-yl)piperidine-4-carboxamide After suspending 1-(4-cyano-3-(trifluoromethyl)phenyl)-N-(5-(2-oxoethoxy)pyridin-2-yl)piperidine-4-carboxamide (40 mg, 0.093 mmol), and 2-(2,6-dioxopiperidin-3-yl)-5-(piperidin-4-yloxy)isoindoline-1,3-dione (33 mg, 0.093 mmol) in ACN (5.0 ml), sodium triacetoxyborohydride (59 mg, 0.28 mmol) was added and stirred at room temperature for 30 minutes. NaHCO₃ aqueous solution (10 ml) was added to the reaction solution, followed by extraction with EtOAc (10 ml×2), and the organic layer was dried over anhydrous sodium sulfate, filtered, and concentrated under reduced pressure. The resulting residue was subjected to MPLC (10% MeOH/DCM) to give 10 mg (14%) of a white solid.

The following Examples were synthesized similarly to the previous methods.

TABLE 4

| Example no. (Compound no.) | IUPAC name and Structure |
| --- | --- |
| 179 | 1-(4-cyano-3-(trifluoromethyl)phenyl)-N-(5-(3-((4-((1-(2-(2,6-dioxopiperidin-3-yl)-1,3-dioxoisoindolin-5-yl)piperidin-4-yl)methyl)piperazin-1-yl)methyl)-3-methylazetidin-1-yl)pyridin-2-yl)piperidine-4-carboxamide |
| 180 | 1-(4-cyano-3-(trifluoromethyl)phenyl)-N-(5-(3-((4-(((2-(2,6-dioxopiperidin-3-yl)-1,3-dioxoisoindolin-5-yl)oxy)methyl)piperidin-1-yl)methyl)-3-methylazetidin-1-yl)pyridin-2-yl)piperidine-4-carboxamide |

TABLE 4-continued

| Example no. (Compound no.) | IUPAC name and Structure |
|---|---|
| 181 | 1-(4-cyano-3-(trifluoromethyl)phenyl)-N-(5-((1-((1-(2-(2,6-dioxopiperidin-3-yl)-6-fluoro-1,3-dioxoisoindolin-5-yl)piperidin-4-yl)methyl)piperidin-4-yl)methoxy)pyridin-2-yl)piperidine-4-carboxamide |
| 182 | 1-(4-cyano-3-(trifluoromethyl)phenyl)-N-(5-((1-((1-(2-(2,6-dioxopiperidin-3-yl)-6-fluoro-1,3-dioxoisoindolin-5-yl)piperidin-4-yl) methyl)piperidin-4-yl)methyl)pyridin-2-yl)piperidine-4-carboxamide |
| 183 | 1-(4-cyano-3-(trifluoromethyl)phenyl)-N-(5-((1-((1-(2-(2,6-dioxopiperidin-3-yl)-1,3-dioxoisoindolin-5-yl)azetidin-3-yl)methyl)piperidin-4-yl)methoxy)pyridin-2-yl)piperidine-4-carboxamide |
| 184 | 1-(4-cyano-3-(trifluoromethyl)phenyl)-N-(5-((1-((1-(2-(2,6-dioxopiperidin-3-yl)-1,3-dioxoisoindolin-5-yl)-3-methylazetidin-3-yl)methyl)piperidin-4-yl)methoxy)pyridin-2-yl)piperidine-4-carboxamide |
| 185 | 1-(4-cyano-3-(trifluoromethyl)phenyl)-N-(5-((1-((1-(2-(2,6-dioxopiperidin-3-yl)-1,3-dioxoisoindolin-5-yl)piperidin-4-yl)methyl)azetidin-3-yl)methoxy)pyridin-2-yl)piperidine-4-carboxamide |

| Example no. (Compound no.) | IUPAC name and Structure |
|---|---|
| 186 | 1-(4-cyano-3-(trifluoromethyl)phenyl)-N-(5-((1-((1-(2-(2,6-dioxopiperidin-3-yl)-1,3-dioxoisoindolin-5-yl)piperidin-4-yl)methyl)-3-methylazetidin-3-yl)methoxy)pyridin-2-yl)piperidine-4-carboxamide |
| 187 | 1-(4-cyano-3-(trifluoromethyl)phenyl)-N-(6-((1-((1-(2-(2,6-dioxopiperidin-3-yl)-1,3-dioxoisoindolin-5-yl)piperidin-4-yl) methyl)piperidin-4-yl)oxy)pyridazin-3-yl)piperidine-4-carboxamide |
| 188 | 1-(4-cyano-3-(trifluoromethyl)phenyl)-N-(5-((4-((4-(2-(2,6-dioxopiperidin-3-yl)-6-fluoro-1,3-dioxoisoindolin-5-yl)piperazin-1-yl)methyl)piperidin-1-yl)methyl)pyridin-2-yl)piperidine-4-carboxamide |
| 189 | 1-(4-cyano-3-(trifluoromethyl)phenyl)-N-(5-(2-(4-((4-(2-(2,6-dioxopiperidin-3-yl)-6-fluoro-1,3-dioxoisoindolin-5-yl)piperazin-1-yl)methyl)piperidin-1-yl)ethyl)pyridin-2-yl)piperidine-4-carboxamide |
| 190 | 1-(4-cyano-3-(trifluoromethyl)phenyl)-N-(5-(3-((4-((4-(2-(2,6-dioxopiperidin-3-yl)-1,3-dioxoisoindolin-5-yl)piperazin-1-yl)methyl)piperidin-1-yl)methyl)azetidin-1-yl)pyridin-2-yl)piperidine-4-carboxamide |

| Example no. (Compound no.) | IUPAC name and Structure |
| --- | --- |
| 191 | 1-(4-cyano-3-(trifluoromethyl)phenyl)-N-(5-(3-((4-((4-(2-(2,6-dioxopiperidin-3-yl)-6-fluoro-1,3-dioxoisoindolin-5-yl)piperazin-1-yl)methyl)piperidin-1-yl) methyl)azetidin-1-yl)pyridin-2-yl)piperidine-4-carboxamide |
| 192 | 1-(4-cyano-3-(trifluoromethyl)phenyl)-N-(5-(4-(2-(4-(2-(2,6-dioxopiperidin-3-yl)-6-fluoro-1,3-dioxoisoindolin-5-yl)piperazin-1-yl)ethyl)piperidin-1-yl)pyridin-2-yl)piperidine-4-carboxamide |
| 193 | 1-(4-cyano-3-(trifluoromethyl)phenyl)-N-(5-((1-(2-(4-(2-(2,6-dioxopiperidin-3-yl)-1,3-dioxoisoindolin-5-yl)piperazin-1-yl)ethyl)piperidin-4-yl)methyl)pyridin-2-yl)piperidine-4-carboxamide |
| 194 | 1-(4-cyano-3-(trifluoromethyl)phenyl)-N-(5-((1-(2-(4-(2-(2,6-dioxopiperidin-3-yl)-6-fluoro-1,3-dioxoisoindolin-5-yl)piperazin-1-yl)ethyl)piperidin-4-yl)methyl)pyridin-2-yl)piperidine-4-carboxamide |

TABLE 4-continued

| Example no. (Compound no.) | IUPAC name and Structure |
| --- | --- |
| 195 | 1-(4-cyano-3-(trifluoromethyl)phenyl)-N-(5-((1-(2-(4-(2-(2,6-dioxopiperidin-3-yl)-1,3-dioxoisoindolin-5-yl)piperazin-1-yl)ethyl)piperidin-4-yl)oxy)pyridin-2-yl)piperidine-4-carboxamide |
| 196 | 1-(4-cyano-3-(trifluoromethyl)phenyl)-N-(5-((1-(2-(4-(2-(2,6-dioxopiperidin-3-yl)-6-fluoro-1,3-dioxoisoindolin-5-yl)piperazin-1-yl)ethyl)piperidin-4-yl)oxy)pyridin-2-yl)piperidine-4-carboxamide |
| 197 | 1-(4-cyano-3-(trifluoromethyl)phenyl)-N-(5-((1-(((1-(2-(2,6-dioxopiperidin-3-yl)-6-fluoro-1,3-dioxoisoindolin-5-yl)piperidin-4-yl)methyl)azetidin-3-yl)methoxy)pyridin-2-yl)piperidine-4-carboxamide |
| 198 | 1-(4-cyano-3-(trifluoromethyl)phenyl)-N-(5-((1-(2-(1-(2-(2,6-dioxopiperidin-3-yl)-1,3-dioxoisoindolin-5-yl)piperidin-4-yl)ethyl)piperidin-4-yl)oxy)pyridin-2-yl)piperidine-4-carboxamide |
| 199 | 1-(4-cyano-3-(trifluoromethyl)phenyl)-N-(6-((1-(((1-(2-(2,6-dioxopiperidin-3-yl)-1,3-dioxoisoindolin-5-yl)piperidin-4-yl)methyl)piperidin-4-yl) methyl)pyridazin-3-yl)piperidine-4-carboxamide |

TABLE 4-continued

| Example no. (Compound no.) | IUPAC name and Structure |
|---|---|
| 200 | 1-(4-cyano-3-(trifluoromethyl)phenyl)-N-(6-(2-(1-((1-(2-(2,6-dioxopiperidin-3-yl)-1,3-dioxoisoindolin-5-yl)piperidin-4-yl)methyl)piperidin-4-yl)ethyl)pyridazin-3-yl)piperidine-4-carboxamide |
| 201 | 1-(4-cyano-3-(trifluoromethyl)phenyl)-N-(6-((1-((1-(2-(2,6-dioxopiperidin-3-yl)-1,3-dioxoisoindolin-5-yl)piperidin-4-yl)methyl)azetidin-3-yl)oxy)pyridazin-3-yl)piperidine-4-carboxamide |
| 202 | 1-(4-cyano-3-(trifluoromethyl)phenyl)-N-(6-((1-((1-(2-(2,6-dioxopiperidin-3-yl)-1,3-dioxoisoindolin-5-yl)piperidin-4-yl)methyl)azetidin-3-yl)methoxy)pyridazin-3-yl)piperidine-4-carboxamide |
| 203 | 1-(4-cyano-3-(trifluoromethyl)phenyl)-N-(5-((1-((1-(2-(2,6-dioxopiperidin-3-yl)-1,3-dioxoisoindolin-5-yl)piperidin-4-yl)methyl)azetidin-3-yl)methyl)pyridin-2-yl)piperidine-4-carboxamide |
| 204 | 1-(4-cyano-3-(trifluoromethyl)phenyl)-N-(5-(2-(1-((1-(2-(2,6-dioxopiperidin-3-yl)-1,3-dioxoisoindolin-5-yl)piperidin-4-yl)methyl)azetidin-3-yl)ethyl)pyridin-2-yl)piperidine-4-carboxamide |

TABLE 4-continued

| Example no. (Compound no.) | IUPAC name and Structure |
|---|---|
| 205 | 1-(4-cyano-3-(trifluoromethyl)phenyl)-N-(6-(4-((4-((1-(2-(2,6-dioxopiperidin-3-yl)-1,3-dioxoisoindolin-5-yl)azetidin-3-yl)methyl)piperazin-1-yl)methyl)piperidin-1-yl)pyridazin-3-yl)piperidine-4-carboxamide |
| 206 | 1-(4-cyano-3-(trifluoromethyl)phenyl)-N-(6-(4-((4-((1-(2-(2,6-dioxopiperidin-3-yl)-1,3-dioxoisoindolin-5-yl)piperidin-4-yl)methyl)piperazin-1-yl)methyl)piperidin-1-yl)pyridazin-3-yl)piperidine-4-carboxamide |

The NMR and/or LC/MS results of the compounds synthesized above are summarized in Table 5 below.

TABLE 5

| Example | NMR and/or MS data |
|---|---|
| 1 | $^1$H NMR (600 MHz, DMSO-d6) δ 11.08 (s, 1H), 10.24 (s, 1H), 7.99 (d, J = 3.0 Hz, 1H), 7.90 (d, J = 9.1 Hz, 1H), 7.81 (d, J = 8.9 Hz, 1H), 7.68 (d, J = 8.5 Hz, 1H), 7.38 (dd, J = 9.2, 3.0 Hz, 1H), 7.33 (dd, J = 21.5, 2.1 Hz, 2H), 7.26 (ddd, J = 8.6, 5.9, 2.3 Hz, 2H), 5.07 (dd, J = 12.8, 5.5 Hz, 1H), 4.10 (d, J = 13.3 Hz, 2H), 3.65 (d, J = 12.2 Hz, 2H), 3.52-3.44 (m, J = 4.5 Hz, 4H), 3.05-2.97 (m, J = 11.5 Hz, 2H), 2.88 (ddd, J = 17.0, 13.9, 5.5 Hz, 1H), 2.79-2.72 (m, 1H), 2.69-2.63 (m, 2H), 2.61-2.53 (m, 4H), 2.22 (d, J = 7.2 Hz, 2H), 2.05-1.99 (m, 1H), 1.84 (dd, J = 28.6, 11.1 Hz, 4H), 1.75-1.69 (m, 1H), 1.67-1.60 (m, 2H), 1.29-1.20 (m, 2H). m/z 812.32 [M + H]$^+$. |
| 2 | $^1$H NMR (600 MHz, DMSO-d6) δ 11.08 (s, 1H), 10.23 (s, 1H), 7.99 (d, J = 3.0 Hz, 1H), 7.90 (d, J = 9.0 Hz, 1H), 7.68 (d, J = 8.5 Hz, 1H), 7.63 (d, J = 8.9 Hz, 1H), 7.37 (dd, J = 9.2, 2.9 Hz, 1H), 7.34 (s, 1H), 7.26 (d, J = 8.6 Hz, 1H), 7.16 (d, J = 2.5 Hz, 1H), 6.99 (dd, J = 9.1, 2.4 Hz, 1H), 5.07 (dd, J = 12.9, 5.5 Hz, 1H), 4.03 (d, J = 13.5 Hz, 2H), 3.65 (d, J = 12.3 Hz, 2H), 3.44 (s, 4H), 3.00-2.92 (m, 2H), 2.87 (dd, J = 21.2, 9.7 Hz, 1H), 2.78-2.71 (m, 1H), 2.70-2.63 (m, 2H), 2.62-2.53 (m, 4H), 2.22 (d, J = 7.2 Hz, 2H), 2.05-1.99 (m, 1H), 1.86-1.78 (m, 2H), 1.74-1.67 (m, 1H), 1.67-1.58 (m, J = 21.1, 12.0 Hz, 2H), 1.28-1.19 (m, 2H). m/z 778.43 [M + H]$^+$. |
| 3 | $^1$H NMR (600 MHz, CDCl3) δ 9.03 (s, 1H), 8.27 (s, 1H), 8.08 (d, J = 9.1 Hz, 1H), 7.96 (d, J = 2.9 Hz, 1H), 7.79 (d, J = 8.3 Hz, 1H), 7.62 (m, J = 8.8 Hz, 1H), 7.37 (d, J = 2.2 Hz, 1H), 7.32-7.28 (m, 1H), 7.21 (dd, J = 8.3, 2.3 Hz, 1H), 7.13 (d, J = 2.5 Hz, 1H), 6.97 (dd, J = 8.8, 2.6 Hz, 1H), 4.96 (dd, J = 12.6, 5.4 Hz, 1H), 4.28-4.18 (m, 2H), 3.99-3.91 (m, J = 9.9, 3.3 Hz, 2H), 3.60 (d, J = 12.2 Hz, 2H), 3.06 (m, 2H), 2.99-2.80 (m, 4H), 2.78-2.65 (m, 3H), 2.62 (s, 1H), 2.58-2.52 (m, 1H), 2.48 (s, 2H), 2.23 (d, J = 6.3 Hz, 2H), 2.19-2.13 (m, 1H), 2.08-2.05 (m, 1H), 1.98-1.91 (m, 2H), 1.87 (d, J = 12.3 Hz, 1H), 1.68-1.50 (m, 4H), 1.39-1.29 (m, 2H), 0.86 (m, 2H). m/z 856.21 [M + H]$^+$. |
| 4 | $^1$H NMR (400 MHz, CDCl$_3$) δ 9.60-9.37 (m, 1H), 8.39-8.30 (m, 1H), 8.08 (d, J = 8.9 Hz, 1H), 7.98 (d, J = 2.7 Hz, 1H), 7.91 (s, 1H), 7.83 (d, J = 7.3 Hz, 1H), 7.72 (d, J = 7.8 Hz, 1H), 7.62 (d, J = 8.9 Hz, 1H), 7.35-7.29 (m, 1H), 7.13 (s, 1H), 6.97 (d, J = 8.7 Hz, 1H), 5.00 (dd, J = 12.4, 5.3 Hz, 1H), 3.96 (d, J = 13.0 Hz, 2H), 3.73-3.54 (m, 4H), 3.12-3.00 (m, 2H), 2.98-2.74 (m, 3H), 2.75-2.64 (m, 2H), 2.62-2.55 (m, 1H), 2.55-2.31 (m, 8H), 2.28-2.21 (m, 2H), 2.21-2.13 (m, 1H), 2.12-2.02 (m, 2H), 2.00-1.91 (m, 2H), 1.87 (d, J = 12.4 Hz, 2H), 1.39-1.23 (m, 3H). m/z 826.40 [M + H]$^+$. |
| 5 | $^1$H NMR (600 MHz, DMSO-d6) δ 11.05 (s, 1H), 10.23 (s, 1H), 7.97 (d, J = 3.0 Hz, 1H), 7.89 (d, J = 9.0 Hz, 1H), 7.80 (d, J = 8.9 Hz, 1H), 7.56 (d, J = 8.4 Hz, 1H), 7.36 (dd, J = 9.2, 3.0 Hz, 1H), 7.29 (d, J = 2.3 Hz, 1H), 7.24 (dd, J = 8.9, 2.5 Hz, 1H), 7.10 (s, 1H), 7.09-7.05 (m, 1H), 7.00 (d, J = 7.7 Hz, 1H), 5.02 (dd, J = 12.8, 5.5 Hz, 1H), 4.10 (dd, J = 17.0, 9.2 Hz, 4H), 3.62 (d, J = 12.2 Hz, 2H), 3.49 (s, 4H), 3.03-2.95 (m, 2H), 2.90-2.81 (m, 2H), 2.73 (d, J = 16.4 Hz, 1H), 2.66-2.60 (m, 2H), 2.57 (d, J = 2.7 Hz, 1H), 2.42-2.36 (m, 2H), 2.32 (s, 2H), 2.18 (d, J = 7.1 Hz, 2H), 2.02-1.96 (m, 1H), 1.85 (d, J = 10.9 Hz, 2H), 1.79 (d, J = 11.1 Hz, 2H), 1.63 (dd, J = 21.0, 11.7 Hz, 2H), 1.21 (dd, J = 21.1, 11.7 Hz, 2H). m/z 869.24 [M + H]$^+$. |

TABLE 5-continued

| Example | NMR and/or MS data |
|---|---|
| 6 | $^1$H NMR (600 MHz, CDCl$_3$) δ 8.93 (s, 1H), 8.43 (s, 1H), 8.09 (d, J = 9.1 Hz, 1H), 7.94 (d, J = 2.9 Hz, 1H), 7.67 (d, J = 8.5 Hz, 1H), 7.62 (d, J = 8.8 Hz, 1H), 7.31 (dd, J = 9.1, 3.0 Hz, 1H), 7.28-7.27 (m, 1H), 7.13 (d, J = 2.5 Hz, 1H), 7.03 (dd, J = 8.7, 2.3 Hz, 1H), 6.97 (dd, J = 8.7, 2.6 Hz, 1H), 4.95 (dd, J = 12.5, 5.4 Hz, 1H), 4.01-3.89 (m, 4H), 3.60 (d, J = 12.2 Hz, 2H), 3.07-3.01 (m, 2H), 2.95 (s, 2H), 2.90-2.82 (m, 2H), 2.79-2.74 (m, 1H), 2.70 (dd, J = 11.9, 9.6 Hz, 2H), 2.56 (dd, J = 13.1, 9.1 Hz, 1H), 2.47 (s, 4H), 2.23 (dd, J = 12.2, 7.1 Hz, 41H), 2.17-2.11 (m, 1H), 2.08-2.02 (m, 2H), 1.99-1.93 (m, 2H), 1.88 (d, J = 6.8 Hz, 4H), 1.79 (d, J = 7.3 Hz, 1H), 1.69 (s, 4H), 1.38-1.30 (m, 2H), 1.27 (d, J = 12.9 Hz, 2H). m/z 909.40 [M + H]$^+$. |
| 7 | $^1$H NMR (600 MHz, CDCl$_3$) δ 9.06 (s, 1H), 8.23 (s, 1H), 8.07 (d, J = 9.0 Hz, 1H), 7.97 (d, J = 2.9 Hz, 1H), 7.67 (d, J = 8.6 Hz, 1H), 7.45 (d, J = 8.9 Hz, 1H), 7.30 (dd, J = 9.1, 3.0 Hz, 1H), 7.27 (d, J = 2.3 Hz, 1H), 7.03 (dd, J = 8.7, 2.3 Hz, 1H), 6.88 (d, J = 2.5 Hz, 1H), 6.74 (dd, J = 8.9, 2.5 Hz, 1H), 4.95 (dd, J = 12.6, 5.4 Hz, 1H), 3.93 (d, J = 13.1 Hz, 2H), 3.88 (d, J = 13.2 Hz, 2H), 3.60 (d, J = 12.2 Hz, 2H), 2.97 (dt, J = 13.0, 6.8 Hz, 4H), 2.91-2.79 (m, 2H), 2.76-2.73 (m, 1H), 2.70 (dd, J = 12.8, 10.6 Hz, 2H), 2.52 (dd, J = 13.1, 9.3 Hz, 1H), 2.45 (s, 4H), 2.22 (d, J = 11.4, 7.2 Hz, 4H), 2.18-2.12 (m, 1H), 2.03 (d, J = 10.8 Hz, 2H), 1.94 (d, J = 4.0 Hz, 1H), 1.92-1.85 (m, 4H), 1.79 (s, 1H), 1.59 (s, 4H), 1.34 (dd, J = 16.5, 7.5 Hz, 2H), 1.28 (dt, J = 20.8, 7.1 Hz, 2H). m/z 875.34 [M + H]$^+$. |
| 8 | $^1$H NMR (600 MHz, CDCl$_3$) δ 8.62 (d, J = 6.5 Hz, 1H), 8.04 (d, J = 9.0 Hz, 2H), 7.99 (d, J = 2.8 Hz, 1H), 7.67 (d, J = 8.6 Hz, 1H), 7.65 (d, J = 8.8 Hz, 1H), 7.31-7.29 (m, 1H), 7.29-7.27 (m, 1H), 7.27 (s, 1H), 7.17 (d, J = 2.5 Hz, 1H), 7.04 (dd, J = 8.6, 2.3 Hz, 1H), 7.01 (dd, J = 8.8, 2.6 Hz, 1H), 4.94 (dd, J = 12.6, 5.4 Hz, 1H), 3.95 (d, J = 12.8 Hz, 2H), 3.89 (d, J = 13.6 Hz, 2H), 3.63 (d, J = 12.2 Hz, 2H), 3.37 (td, J = 13.1, 2.6 Hz, 2H), 3.01-2.93 (m, 2H), 2.92-2.87 (m, 2H), 2.85-2.79 (m, 1H), 2.77-2.74 (m, 1H), 2.74-2.69 (m, 2H), 2.57-2.45 (m, 4H), 2.43-2.38 (m, J = 13.4, 4.4 Hz, 2H), 2.38-2.32 (m, 2H), 2.29-2.19 (m, 4H), 2.15-2.11 (m, 1H), 2.08-2.02 (m, 2H), 1.89 (d, J = 12.9 Hz, 4H), 1.84-1.75 (m, 2H), 1.67 (s, 2H), 1.38-1.31 (m, 2H), 1.31-1.26 (m, 2H). m/z 927.50 [M + H]$^+$. |
| 9 | $^1$H NMR (600 MHz, CDCl3) δ 8.64 (d, J = 6.3 Hz, 1H), 8.45 (d, J = 2.8 Hz, 1H), 8.14 (s, 1H), 8.04 (d, J = 9.1 Hz, 1H), 7.99 (d, J = 2.9 Hz, 1H), 7.68 (d, J = 8.5 Hz, 1H), 7.33 (d, J = 2.8 Hz, 1H), 7.31-7.28 (m, 2H), 7.06 (dd, J = 8.6, 2.3 Hz, 1H), 4.94 (dd, J = 12.6, 5.4 Hz, 1H), 3.99 (d, J = 13.0 Hz, 2H), 3.94 (d, J = 13.5 Hz, 2H), 3.64 (d, J = 12.2 Hz, 2H), 3.44 (td, J = 13.2, 2.7 Hz, 2H), 3.00 (t, J = 11.5 Hz, 2H), 2.92-2.87 (m, 1H), 2.85-2.78 (m, 1H), 2.77-2.73 (m, 1H), 2.73-2.69 (m, 2H), 2.63 (s, 4H), 2.54-2.48 (m, 2H), 2.48-2.35 (m, 4H), 2.24 (d, J = 6.8 Hz, 2H), 2.17-2.07 (m, 3H), 1.98 (d, J = 12.5 Hz, 2H), 1.88 (d, J = 12.4 Hz, 2H), 1.72-1.61 (m, 4H), 1.39-1.31 (m, 2H). m/z 910.55 [M + H]$^+$. |
| 10 | $^1$H NMR (600 MHz, CDCl$_3$) δ 8.63 (d, J = 6.4 Hz, 1H), 8.45 (d, J = 2.8 Hz, 1H), 8.09 (s, 1H), 8.04 (d, J = 9.1 Hz, 1H), 7.99 (d, J = 2.9 Hz, 1H), 7.67 (d, J = 8.6 Hz, 1H), 7.33 (d, J = 2.8 Hz, 1H), 7.30 (dd, J = 9.1, 3.0 Hz, 1H), 7.28 (d, J = 2.3 Hz, 1H), 7.04 (dd, J = 8.6, 2.3 Hz, 1H), 4.94 (dd, J = 12.5, 5.4 Hz, 1H), 4.04-3.90 (m, 4H), 3.64 (d, J = 12.2 Hz, 2H), 3.44 (td, J = 13.2, 2.8 Hz, 2H), 3.01-2.93 (m, 2H), 2.92-2.87 (m, 1H), 2.85-2.80 (m, 1H), 2.78-2.68 (m, 3H), 2.60-2.42 (m, 6H), 2.41-2.34 (m, 2H), 2.28-2.17 (m, 4H), 2.16-2.07 (m, 3H), 1.89 (d, J = 13.2 Hz, 4H), 1.82-1.75 (m, 1H), 1.70-1.63 (m, 1H), 1.38-1.31 (m, 2H), 1.32-1.23 (m, 2H). m/z 928.52 [M + H]$^+$. |
| 11 | $^1$H NMR (600 MHz, CDCl$_3$) δ 8.99 (s, 1H), 8.67 (s, 1H), 8.10 (d, J = 9.1 Hz, 1H), 7.92 (d, J = 2.9 Hz, 1H), 7.63 (dd, J = 12.6, 8.6 Hz, 2H), 7.31 (dd, J = 9.1, 3.0 Hz, 1H), 7.13 (d, J = 2.3 Hz, 1H), 6.97 (dd, J = 8.8, 2.5 Hz, 1H), 6.77 (d, J = 2.1 Hz, 1H), 6.48 (dd, J = 8.3, 2.1 Hz, 1H), 4.93 (dd, J = 12.5, 5.4 Hz, 1H), 4.14 (t, J = 7.9 Hz, 2H), 3.95 (d, J = 13.1 Hz, 2H), 3.72-3.68 (m, 2H), 3.60 (d, J = 12.0 Hz, 2H), 3.10-3.02 (m, 3H), 2.92-2.79 (m, 3H), 2.79-2.65 (m, 6H), 2.21 (s, 3H), 2.17-2.12 (m, 1H), 2.06 (d, J = 14.0 Hz, 3H), 1.92 (m, 6H), 0.87 (m, 2H). m/z 881.38 [M + H]$^+$. |
| 12 | $^1$H NMR (600 MHz, CDCl$_3$) δ 8.94 (d, J = 0.8 Hz, 1H), 8.33 (s, 1H), 8.08 (d, J = 8.7 Hz, 1H), 7.94 (d, J = 2.9 Hz, 1H), 7.64 (d, J = 8.1 Hz, 1H), 7.45 (d, J = 8.9 Hz, 1H), 7.30 (d, J = 7.0 Hz, 2H), 6.88 (s, 1H), 6.78-6.73 (m, 3H), 6.48 (d, J = 8.3 Hz, 1H), 4.93 (dd, J = 12.4, 5.4 Hz, 1H), 4.14 (t, J = 7.8 Hz, 2H), 3.89 (d, J = 12.5 Hz, 2H), 3.73-3.68 (m, 2H), 3.60 (d, J = 11.9 Hz, 2H), 3.00 (t, J = 12.4 Hz, 4H), 2.94-2.79 (m, 3H), 2.76-2.64 (m, 8H), 2.49 (s, 12H), 2.23 (s, 4H), 2.04 (d, J = 13.4 Hz, 4H), 1.93-1.88 (m, 6H), 0.91-0.86 (m, 2H). m/z 847.29 [M + H]$^+$. |
| 13 | $^1$H NMR (600 MHz, CDCl$_3$) δ 8.86 (s, 1H), 8.20 (s, 1H), 8.09 (d, J = 9.1 Hz, 1H), 7.98 (d, J = 2.9 Hz, 1H), 7.64 (d, J = 8.8 Hz, 1H), 7.59-7.55 (m, J = 8.4, 7.2 Hz, 1H), 7.38 (d, J = 7.1 Hz, 1H), 7.32 (dd, J = 9.1, 3.0 Hz, 1H), 7.18 (d, J = 8.4 Hz, 1H), 7.14 (d, J = 2.5 Hz, 1H), 6.98 (dd, J = 8.8, 2.6 Hz, 1H), 4.99 (dd, J = 12.5, 5.4 Hz, 1H), 3.96 (d, J = 13.1 Hz, 2H), 3.80-3.72 (m, 4H), 3.63 (d, J = 12.0 Hz, 2H), 3.09-3.01 (m, 2H), 2.89-2.82 (m, 2H), 2.80-2.75 (m, 1H), 2.75-2.70 (m, 2H), 2.60-2.54 (m, 1H), 2.54-2.40 (m, 6H), 2.32-2.21 (m, 4H), 2.17-2.11 (m, 1H), 2.10-2.04 (m, 2H), 2.00-1.86 (m, 5H), 1.78-1.65 (m, 4H), 1.52-1.44 (m, 2H), 1.40-1.31 (m, 2H). m/z 909.58 [M + H]$^+$. |
| 14 | $^1$H NMR (600 MHz, CDCl$_3$) δ 9.34 (s, 1H), 8.35 (s, 1H), 8.09 (d, J = 9.0 Hz, 1H), 8.00 (d, J = 2.8 Hz, 1H), 7.67 (d, J = 8.4 Hz, 1H), 7.63 (d, J = 8.8 Hz, 1H), 7.32 (dd, J = 9.1, 2.8 Hz, 1H), 7.14 (d, J = 2.1 Hz, 1H), 6.99-6.95 (m, 1H), 6.69 (d, J = 8.5 Hz, 1H), 4.96 (dd, J = 12.5, 5.4 Hz, 1H), 3.96 (d, J = 13.2 Hz, 2H), 3.62 (d, J = 12.1 Hz, 2H), 3.59-3.53 (m, 1H), 3.50-3.46 (m, 1H), 3.42 (s, 1H), 3.21-3.16 (m, 1H), 3.07-3.00 (m, 2H), 2.95-2.88 (m, 1H), 2.88-2.82 (m, 1H), 2.76 (s, 1H), 2.75-2.68 (m, 2H), 2.66-2.61 (m, 1H), 2.60-2.53 (m, 2H), 2.53-2.44 (m, 4H), 2.43-2.37 (m, 2H), 2.25 (d, J = 7.0 Hz, 2H), 2.23-2.19 (m, 1H), 2.15 (d, J = 5.4 Hz, 1H), 2.08 (m, 2H), 2.01-1.93 (m, 2H), 1.89 (d, J = 12.5 Hz, 2H), 1.86-1.80 (m, 1H), 1.73-1.61 (m, 4H), 1.41-1.32 (m, 2H). m/z 895.55 [M + H]$^+$. |
| 15 | $^1$H NMR (600 MHz, CDCl$_3$) δ 9.30 (s, 1H), 8.42 (s, 1H), 8.09 (d, J = 9.0 Hz, 1H), 8.00 (d, J = 2.8 Hz, 1H), 7.67 (d, J = 8.4 Hz, 1H), 7.63 (d, J = 8.8 Hz, 1H), 7.32 (dd, J = 9.1, 2.8 Hz, 1H), 7.14 (d, J = 2.1 Hz, 1H), 6.99-6.95 (m, 1H), 6.69 (d, J = 8.5 Hz, 1H), 4.96 (dd, J = 12.5, 5.4 Hz, 1H), 3.96 (d, J = 13.2 Hz, 2H), 3.62 (d, J = 12.1 Hz, 2H), 3.59-3.53 (m, 1H), 3.50-3.46 (m, 1H), 3.42 (s, 1H), 3.21-3.16 (m, 1H), 3.07-3.00 (m, 2H), 2.95-2.88 (m, 1H), 2.88-2.82 (m, 1H), 2.76 (s, 1H), 2.75-2.68 (m, 2H), 2.66-2.61 (m, 1H), 2.60-2.53 (m, 2H), 2.53-2.44 (m, 4H), 2.43-2.37 (m, 2H), 2.25 (d, J = 7.0 Hz, 2H), 2.23-2.19 (m, 1H), 2.15 (d, J = 5.4 Hz, 1H), 2.08 (m, 2H), 2.01-1.93 (m, 2H), 1.89 (d, J = 12.5 Hz, 2H), 1.86-1.80 (m, 1H), 1.73-1.61 (m, 4H), 1.41-1.32 (m, 2H). m/z 895.56 [M + H]$^+$. |
| 16 | $^1$H NMR (600 MHz, CDCl$_3$) δ 9.77 (s, 1H), 8.48 (s, 1H), 8.09 (d, J = 9.1 Hz, 1H), 8.00 (d, J = 2.9 Hz, 1H), 7.65 (d, J = 8.5 Hz, 1H), 7.61 (d, J = 8.8 Hz, 1H), 7.34-7.27 (m, 2H), 7.12 (d, J = 2.4 Hz, 1H), 7.05-7.01 (m, 1H), 6.95 (dd, J = 8.8, 2.5 Hz, 1H), 4.95 (dd, J = 12.5, 5.4 Hz, 1H), 3.98-3.91 (m, 2H), 3.91-3.83 (m, 1H), 3.77-3.69 (m, 1H), 3.61 (d, J = 12.1 Hz, 2H), 3.17-3.08 (m, 1H), 3.02 (t, J = 11.2 Hz, 2H), 2.97-2.92 (m, 1H), 2.92-2.86 (m, 2H), 2.86-2.80 (m, 1H), 2.78-2.68 (m, 3H), 2.61-2.54 (m, 1H), 2.54-2.41 (m, 4H), 2.39-2.31 (m, 2H), 2.31-2.21 (m, 3H), 2.20-2.11 (m, 2H), 2.09-2.01 (m, 2H), 1.98-1.91 (m, 2H), 1.91-1.80 (m, 4H), 1.79-1.74 (m, 1H), 1.73-1.64 (m, 2H), 1.64-1.55 (m, 3H), 1.40-1.29 (m, 2H). m/z 909.61 [M + H]$^+$. |
| 17 | $^1$H NMR (600 MHz, CDCl3) δ 9.91 (s, 1H), 8.55 (s, 1H), 8.08 (d, J = 9.1 Hz, 1H), 8.00 (d, J = 2.9 Hz, 1H), 7.65 (d, J = 8.5 Hz, 1H), 7.61 (d, J = 8.8 Hz, 1H), 7.34-7.27 (m, 2H), 7.12 (d, J = 2.4 Hz, 1H), 7.05-7.01 (m, 1H), 6.95 (dd, J = 8.8, 2.5 Hz, 1H), 4.95 (dd, J = 12.5, 5.4 Hz, 1H), 3.98-3.91 (m, 2H), 3.91-3.83 (m, 1H), 3.77-3.69 (m, 1H), 3.61 (d, J = 12.1 Hz, 2H), 3.17-3.08 (m, 1H), 3.02 (t, J = 11.2 Hz, 2H), 2.97-2.92 (m, 1H), 2.92-2.86 (m, 2H), 2.86-2.80 (m, 1H), 2.78-2.68 (m, 3H), 2.61-2.54 (m, 1H), 2.54-2.41 (m, 4H), 2.39-2.31 (m, 2H), 2.31-2.21 (m, 3H), 2.20-2.11 (m, 2H), 2.09-2.01 (m, 2H), 1.98-1.91 (m, 2H), 1.91-1.80 (m, 4H), 1.79-1.74 (m, 1H), 1.73-1.64 (m, 2H), 1.64-1.55 (m, 3H), 1.40-1.29 (m, 2H). m/z 909.48 [M + H]$^+$. |

TABLE 5-continued

| Example | NMR and/or MS data |
|---|---|
| 18 | ¹H NMR (600 MHz, CDCl₃) δ 9.25 (s, 1H), 8.24 (s, 1H), 8.00 (d, J = 9.1 Hz, 1H), 7.90 (d, J = 2.8 Hz, 1H), 7.54 (d, J = 8.8 Hz, 1H), 7.37 (t, J = 7.5 Hz, 1H), 7.30 (d, J = 7.3 Hz, 1H), 7.22 (dd, J = 9.1, 2.9 Hz, 1H), 7.06 (d, J = 2.5 Hz, 1H), 6.89 (dd, J = 8.8, 2.5 Hz, 1H), 4.86 (dd, J = 12.7, 5.4 Hz, 1H), 3.91-3.85 (m, 2H), 3.57 (d, J = 12.2 Hz, 2H), 3.52 (d, J = 12.2 Hz, 2H), 3.01-2.93 (m, 2H), 2.85-2.79 (m, 1H), 2.79-2.72 (m, 3H), 2.71-2.66 (m, 1H), 2.66-2.58 (m, 2H), 2.51-2.46 (m, 1H), 2.44-2.27 (m, 6H), 2.15 (t, J = 7.7 Hz, 4H), 2.09-2.04 (m, 1H), 2.01-1.96 (m, 2H), 1.91-1.84 (m, 2H), 1.84-1.76 (m, 4H), 1.67-1.61 (m, 1H), 1.60-1.54 (m, 1H), 1.53-1.46 (m, 2H), 1.34-1.22 (m, 4H). m/z 927.41 [M + H]⁺. |
| 19 | ¹H NMR (400 MHz, CDCl₃) δ 9.28 (s, 1H), 8.30 (s, 1H), 8.08 (d, J = 9.1 Hz, 1H), 7.98 (d, J = 2.9 Hz, 1H), 7.62 (d, J = 8.8 Hz, 1H), 7.38 (d, J = 12.3 Hz, 1H), 7.30 (dd, J = 9.2, 3.0 Hz, 1H), 7.13 (d, J = 2.5 Hz, 1H), 7.03 (d, J = 7.5 Hz, 1H), 6.97 (dd, J = 8.8, 2.5 Hz, 1H), 4.92 (dd, J = 12.4, 5.4 Hz, 1H), 3.99-3.91 (m, 2H), 3.71-3.55 (m, 15H), 3.36-3.28 (m, 1H), 3.10-2.99 (m, 2H), 2.95-2.85 (m, 1H), 2.85-2.76 (m, 1H), 2.75-2.65 (m, 3H), 2.61-2.50 (m, 4H), 2.50-2.43 (m, 5H), 2.43-2.34 (m, 3H), 2.23 (d, J = 7.1 Hz, 2H), 2.18-2.11 (m, 2H), 2.09-2.01 (m, 2H), 2.00-1.92 (m, 2H), 1.92-1.84 (m, 2H), 1.82-1.71 (m, 1H), 1.69-1.62 (m, 2H), 1.41-1.29 (m, 2H). m/z 913.35 [M + H]⁺. |
| 20 | ¹H NMR (400 MHz, CDCl₃) δ 9.65-9.51 (m, 1H), 8.40-8.31 (m, 1H), 8.08 (d, J = 9.0 Hz, 1H), 7.98 (d, J = 2.6 Hz, 1H), 7.62 (d, J = 8.8 Hz, 1H), 7.35 (d, J = 10.8 Hz, 1H), 7.30 (dd, J = 9.2, 2.9 Hz, 1H), 7.13 (d, J = 2.4 Hz, 1H), 6.97 (dd, J = 8.9, 2.5 Hz, 1H), 6.81 (d, J = 7.5 Hz, 1H), 4.92 (dd, J = 12.3, 5.3 Hz, 1H), 4.33-4.23 (m, 2H), 3.96 (d, J = 13.2 Hz, 2H), 3.88-3.80 (m, 2H), 3.60 (d, J = 2H), 3.11-2.96 (m, 3H), 2.94-2.72 (m, 3H), 2.72-2.64 (m, 4H), 2.61-2.55 (m, 1H), 2.55-2.33 (m, 8H), 2.22 (d, J = 7.0 Hz, 2H), 2.17-2.08 (m, 1H), 2.08-2.02 (m, 2H), 2.00-1.92 (m, 2H), 1.87 (d, J = 14.4 Hz, 1H), 1.56-1.45 (m, 1H), 1.40-1.29 (m, 2H). m/z 899.42 [M + H]⁺. |
| 21 | ¹H NMR (400 MHz, CDCl3) δ 8.09 (s, 1H), 7.65 (d, J = 8.6 Hz, 1H), 7.60 (d, J = 8.8 Hz, 1H), 7.39-7.33 (m, 2H), 7.26 (d, J = 2.3 Hz, 1H), 7.12 (d, J = 2.4 Hz, 1H), 7.10 (s, 1H), 7.02 (dd, J = 8.7, 2.3 Hz, 1H), 6.96 (dd, J = 8.9, 2.6 Hz, 1H), 6.91-6.86 (m, 2H), 4.91 (dd, J = 8.0, 4.5 Hz, 1H), 4.00-3.88 (m, 4H), 3.60 (d, J = 12.2 Hz, 2H), 3.08-2.99 (m, 2H), 2.99-2.89 (m, 2H), 2.87-2.76 (m, 2H), 2.75-2.69 (m, 1H), 2.67-2.58 (m, 2H), 2.54-2.28 (m, 9H), 2.23-2.16 (m, 4H), 2.14-2.08 (m, 1H), 2.07-2.01 (m, 2H), 1.99-1.91 (m, 2H), 1.91-1.80 (m, 4H), 1.80-1.72 (m, 1H), 1.61-1.56 (m, 1H), 1.37-1.29 (m, 2H), 1.29-1.18 (m, 2H). m/z 908.40 [M + H]⁺. |
| 22 | ¹H NMR (400 MHz, CDCl₃) δ 8.00 (s, 1H), 7.65 (d, J = 8.5 Hz, 1H), 7.62 (d, J = 8.9 Hz, 1H), 7.39-7.35 (m, 2H), 7.14 (d, J = 2.4 Hz, 1H), 7.09 (s, 1H), 6.98 (d, J = 8.9, 2.6 Hz, 1H), 6.95 (d, J = 2.2 Hz, 1H), 6.94-6.88 (m, 2H), 6.68 (dd, J = 8.6, 2.3 Hz, 1H), 4.94 (dd, J = 12.3, 5.3 Hz, 1H), 4.03-3.92 (m, 2H), 3.62 (d, J = 12.3 Hz, 2H), 3.60-3.54 (m, 1H), 3.54-3.46 (m, 1H), 3.46-3.38 (m, 1H), 3.22-3.15 (m, 1H), 3.11-3.01 (m, 2H), 2.93-2.86 (m, 1H), 2.86-2.79 (m, 1H), 2.79-2.72 (m, 1H), 2.71-2.63 (m, 2H), 2.63-2.58 (m, 1H), 2.55-2.45 (m, 5H), 2.45-2.35 (m, 4H), 2.23 (d, J = 7.0 Hz, 2H), 2.21-2.17 (m, 1H), 2.17-2.09 (m, 2H), 2.09-2.02 (m, 2H), 2.00-1.92 (m, 2H), 1.89-1.83 (m, 2H), 1.83-1.76 (m, 1H), 1.68-1.61 (m, 2H), 1.40-1.29 (m, 2H). m/z 894.50 [M + H]⁺. |
| 23 | ¹H NMR (400 MHz, CDCl₃) 9.47 (d, J = 15.3 Hz, 1H), 8.42 (d, J = 5.6 Hz, 1H), 8.08 (d, J = 9.1 Hz, 1H), 7.98 (d, J = 2.9 Hz, 1H), 7.66 (d, J = 8.6 Hz, 1H), 7.61 (d, J = 8.8 Hz, 1H), 7.30 (dd, J = 9.1, 3.0 Hz, 1H), 7.28-7.27 (m, 1H), 7.12 (d, J = 2.3 Hz, 1H), 7.02 (dd, J = 8.7, 2.2 Hz, 1H), 6.96 (dd, J = 8.8, 2.4 Hz, 1H), 4.95 (dd, J = 12.3, 5.3 Hz, 1H), 3.99-3.89 (m, 4H), 3.65-3.55 (m, 2H), 3.02 (t, J = 12.6 Hz, 2H), 2.91 (dd, J = 20.1, 9.6 Hz, 2H), 2.88-2.76 (m, 3H), 2.75-2.66 (m, 2H), 2.66-2.60 (m, 2H), 2.60-2.51 (m, 2H), 2.43-2.34 (m, 1H), 2.29-2.20 (m, 1H), 2.19-2.11 (m, 4H), 2.10-1.99 (m, 4H), 1.98-1.85 (m, 6H), 1.82-1.73 (m, 2H), 1.65-1.54 (m, 2H), 1.39-1.28 (m, 2H), 1.27-1.19 (m, 2H), 1.01 (d, J = 6.1 Hz, 3H). m/z 923.56 [M + H]⁺. |
| 24 | ¹H NMR (400 MHz, CDCl₃) δ 9.69-9.63 (m, 1H), 8.39 (s, 1H), 8.08 (d, J = 9.1 Hz, 1H), 7.99 (d, J = 2.9 Hz, 1H), 7.66-7.60 (m, 2H), 7.30 (dd, J = 9.2, 3.0 Hz, 1H), 7.13 (d, J = 2.5 Hz, 1H), 6.96 (dd, J = 8.8, 2.5 Hz, 1H), 6.77 (d, J = 0.5 Hz, 1H), 6.48 (dd, J = 8.4, 2.1 Hz, 1H), 4.94 (dd, J = 12.2, 5.3 Hz, 1H), 4.16-4.09 (m, 2H), 3.99-3.90 (m, 2H), 3.73-3.66 (m, 2H), 3.63-3.56 (m, 2H), 3.08-2.97 (m, 3H), 2.92-2.78 (m, 3H), 2.74-2.55 (m, 8H), 2.42-2.32 (m, 1H), 2.27-2.19 (m, 2H), 2.18-2.09 (m, 3H), 2.01-1.87 (m, 5H), 1.82-1.73 (m, 1H), 1.65-1.59 (m, 1H), 1.38-1.26 (m, 2H), 1.01 (d, J = 6.0 Hz, 3H). m/z 895.50 [M + H]⁺. |
| 25 | ¹H NMR (400 MHz, CDCl₃) δ 9.54 (s, 1H), 8.39 (s, 1H), 8.08 (d, J = 9.1 Hz, 1H), 7.99 (d, J = 2.9 Hz, 1H), 7.66 (d, J = 8.5 Hz, 1H), 7.61 (d, J = 8.8 Hz, 1H), 7.34-7.28 (m, 1H), 7.12 (d, J = 2.1 Hz, 1H), 7.02 (dd, J = 8.7, 1.9 Hz, 1H), 6.99-6.94 (m, 1H), 4.95 (dd, J = 12.2, 5.3 Hz, 1H), 4.00-3.88 (m, 4H), 3.60 (d, J = 12.1 Hz, 2H), 3.08-2.97 (m, 3H), 2.97-2.85 (m, 3H), 2.85-2.77 (m, 2H), 2.76-2.63 (m, 4H), 2.63-2.49 (m, 3H), 2.41-2.33 (m, 1H), 2.28-2.21 (m, 1H), 2.19-2.11 (m, 4H), 2.09-2.02 (m, 3H), 2.00-1.93 (m, 3H), 1.92-1.84 (m, 4H), 1.81-1.70 (m, 2H), 1.69-1.61 (m, 1H), 1.38-1.28 (m, 2H), 1.26-1.14 (m, 2H), 0.99 (d, J = 6.1 Hz, 3H). m/z 923.53 [M + H]⁺. |
| 26 | ¹H NMR (400 MHz, CDCl₃) δ 10.63 (s, 1H), 8.82 (s, 1H), 8.09 (d, J = 9.1 Hz, 1H), 8.02 (d, J = 2.9 Hz, 1H), 7.65-7.58 (m, 2H), 7.31 (dd, J = 9.1, 2.9 Hz, 1H), 7.11 (s, 1H), 6.95 (d, J = 8.9 Hz, 1H), 6.77 (s, 1H), 6.48 (s, 1H), 4.95 (dd, J = 12.1, 5.2 Hz, 1H), 4.17-4.06 (m, 2H), 3.93 (d, J = 13.0 Hz, 2H), 3.73-3.67 (m, 1H), 3.66-3.55 (m, 3H), 3.09-2.96 (m, 4H), 2.93-2.82 (m, 2H), 2.81-2.74 (m, 2H), 2.72-2.63 (m, 4H), 2.62-2.55 (m, 1H), 2.52-2.39 (m, 2H), 2.35-2.27 (m, 1H), 2.18 (d, J = 7.2 Hz, 3H), 2.16-2.11 (m, 1H), 2.08-2.01 (m, 3H), 1.98-1.91 (m, 2H), 1.89-1.83 (m, 2H), 1.70-1.62 (m, 1H), 1.38-1.28 (m, 2H), 1.06 (d, J = 6.1 Hz, 3H). m/z 895.51 [M + H]⁺. |
| 27 | ¹H NMR (400 MHz, CDCl₃) δ 9.31 (s, 1H), 8.23 (s, 1H), 8.03 (d, J = 8.9 Hz, 1H), 7.65 (d, J = 8.6 Hz, 1H), 7.60 (d, J = 8.8 Hz, 1H), 7.51 (t, J = 2.8 Hz, 1H), 7.26 (s, 1H), 7.11 (d, J = 2.4 Hz, 1H), 7.01 (dd, J = 8.7, 2.3 Hz, 1H), 6.94 (dd, J = 8.8, 2.5 Hz, 1H), 6.79 (dd, J = 8.9, 2.9 Hz, 1H), 4.93 (dd, J = 12.2, 5.3 Hz, 1H), 4.01 (t, J = 7.4 Hz, 2H), 3.98-3.87 (m, 4H), 3.53 (t, J = 6.4 Hz, 2H), 3.07-2.98 (m, 2H), 2.98-2.88 (m, 3H), 2.88-2.70 (m, 3H), 2.64 (d, J = 7.2 Hz, 2H), 2.58-2.51 (m, 1H), 2.51-2.33 (m, 8H), 2.19 (d, J = 7.0 Hz, 2H), 2.16-2.09 (m, 1H), 2.08-2.00 (m, 2H), 1.98-1.89 (m, 2H), 1.89-1.82 (m, 2H), 1.80-1.70 (m, 1H), 1.31-1.18 (m, 2H). m/z 881.47 [M + H]⁺. |
| 28 | ¹H NMR (400 MHz, CDCl₃) δ 9.48 (d, J = 43.1 Hz, 1H), 8.36 (d, J = 14.7 Hz, 1H), 8.04 (d, J = 8.9 Hz, 1H), 7.62 (dd, J = 15.8, 8.6 Hz, 1H), 7.53 (t, J = 3.0 Hz, 1H), 7.11 (d, J = 2.4 Hz, 1H), 6.96-6.91 (m, 1H), 6.80 (dd, J = 8.9, 2.9 Hz, 1H), 6.66 (d, J = 8.5, 2.0 Hz, 1H), 4.94 (dd, J = 12.2, 5.3 Hz, 1H), 4.07-3.98 (m, 2H), 3.98-3.88 (m, 2H), 3.60-3.51 (m, 3H), 3.51-3.42 (m, 1H), 3.42-3.34 (m, 1H), 3.23-3.12 (m, 1H), 3.07-2.94 (m, 3H), 2.93-2.70 (m, 3H), 2.66 (d, J = 7.1 Hz, 2H), 2.62-2.28 (m, 12H), 2.25-2.09 (m, 2H), 2.09-2.00 (m, 2H), 2.00-1.86 (m, 2H), 1.86-1.75 (m, 1H). m/z 867.41 [M + H]⁺. |
| 29 | ¹H NMR (400 MHz, CDCl₃) δ 9.56 (d, J = 42.2 Hz, 1H), 8.41 (d, J = 14.2 Hz, 1H), 8.05 (d, J = 8.9 Hz, 1H), 7.65 (d, J = 8.4 Hz, 1H), 7.61 (d, J = 8.8 Hz, 1H), 7.54 (dd, J = 7.3, 4.3 Hz, 1H), 7.12 (d, J = 2.4 Hz, 1H), 6.98-6.93 (m, 2H), 6.81 (dd, J = 8.9, 2.9 Hz, 1H), 6.66 (dd, J = 8.5, 1.9 Hz, 1H), 4.95 (dd, J = 12.2, 5.3 Hz, 1H), 4.03 (td, J = 7.5, 1.5 Hz, 2H), 3.94 (d, J = 13.2 Hz, 2H), 3.59-3.51 (m, 3H), 3.51-3.44 (m, 1H), 3.44-3.35 (m, 1H), 3.24-3.13 (m, 1H), 3.10-2.95 (m, 3H), 2.95-2.83 (m, 2H), 2.82-2.69 (m, 1H), 2.69-2.64 (m, 2H), 2.64-2.30 (m, 12H), 2.25-2.11 (m, 2H), 2.11-2.01 (m, 2H), 2.00-1.88 (m, 2H), 1.88-1.77 (m, 1H). m/z 867.49 [M + H]⁺. |
| 30 | ¹H NMR (400 MHz, CDCl₃) δ 9.47-9.32 (m, 1H), 8.30-8.23 (m, 1H), 8.05 (d, J = 8.9 Hz, 1H), 7.68-7.60 (m, 2H), 7.53 (d, J = 2.7 Hz, 1H), 7.13 (d, J = 2.4 Hz, 1H), 6.97 (dd, J = 8.9, 2.4 Hz, 1H), 6.81 (dd, J = 8.9, 2.7 Hz, 1H), 6.77 (d, J = 2.1 Hz, 1H), 6.49 (dd, J = 8.3, 2.1 Hz, 1H), 4.94 (dd, J = 12.2, 5.3 Hz, 1H), 4.15-4.09 (m, 2H), 4.06-4.00 (m, 2H), |

TABLE 5-continued

| Example | NMR and/or MS data |
|---|---|
| | 3.95 (d, J = 13.1 Hz, 2H), 3.72-3.66 (m, 2H), 3.60-3.52 (m, 2H), 3.11-2.95 (m, 4H), 2.93-2.72 (m, 3H), 2.71-2.64 (m, 4H), 2.60-2.54 (m, 1H), 2.54-2.38 (m, 8H), 2.17-2.10 (m, 1H), 2.10-2.01 (m, 3H), 2.01-1.87 (m, 2H). m/z 853.45 [M + H]$^+$. |
| 31 | $^1$H NMR (400 MHz, CDCl$_3$) δ 9.76 (s, 1H), 8.42 (s, 1H), 8.05 (d, J = 8.9 Hz, 1H), 7.66-7.58 (m, 2H), 7.55 (d, J = 2.8 Hz, 1H), 7.13 (d, J = 2.5 Hz, 1H), 6.96 (dd, J = 8.8, 2.5 Hz, 1H), 6.81 (dd, J = 8.9, 2.8 Hz, 1H), 6.77 (d, J = 2.0 Hz, 1H), 6.48 (d, J = 8.3, 2.0 Hz, 1H), 4.94 (dd, J = 12.2, 5.2 Hz, 1H), 4.12 (t, J = 8.0 Hz, 1H), 4.07-3.99 (m, 2H), 3.99-3.90 (m, 2H), 3.73-3.66 (m, 2H), 3.59-3.54 (m, 1H), 3.54-3.48 (m, 1H), 3.10-2.93 (m, 5H), 2.93-2.81 (m, 2H), 2.81-2.67 (m, 3H), 2.64 (d, J = 7.4 Hz, 3H), 2.61-2.52 (m, 1H), 2.51-2.36 (m, 2H), 2.31-2.21 (m, 2H), 2.17-2.09 (m, 1H), 2.08-2.01 (m, 2H), 2.00-1.88 (m, 3H), 1.06 (d, J = 6.2 Hz, 3H). m/z 867.45 [M + H]$^+$. |
| 32 | $^1$H NMR (400 MHz, CDCl$_3$) δ 9.60 (s, 1H), 8.37 (s, 1H), 8.05 (d, J = 8.9 Hz, 1H), 7.67-7.60 (m, 2H), 7.54 (d, J = 2.8 Hz, 1H), 7.13 (d, J = 2.3 Hz, 1H), 6.97 (dd, J = 8.9, 2.3 Hz, 1H), 6.81 (dd, J = 8.9, 2.9 Hz, 1H), 6.78-6.74 (m, 1H), 6.49 (dd, J = 8.3, 2.0 Hz, 1H), 4.94 (dd, J = 12.2, 5.3 Hz, 1H), 4.17-4.08 (m, 2H), 4.01 (t, J = 7.3 Hz, 2H), 3.98-3.91 (m, 2H), 3.76-3.68 (m, 1H), 3.68-3.61 (m, 1H), 3.55 (t, J = 6.4 Hz, 2H), 3.11-3.00 (m, 4H), 2.99-2.94 (m, 1H), 2.93-2.73 (m, 4H), 2.71-2.59 (m, 4H), 2.59-2.52 (m, 1H), 2.52-2.36 (m, 2H), 2.35-2.18 (m, 2H), 2.17-2.10 (m, 1H), 2.10-2.01 (m, 2H), 2.01-1.87 (m, 3H), 1.06 (d, J = 6.1 Hz, 3H). m/z 867.52 [M + H]$^+$. |
| 33 | $^1$H NMR (600 MHz, DMSO-d6) δ 10.95 (s, 1H), 10.24 (s, 1H), 7.98 (d, J = 2.9 Hz, 1H), 7.90 (d, J = 9.0 Hz, 1H), 7.82 (d, J = 8.9 Hz, 1H), 7.76 (d, J = 8.6 Hz, 1H), 7.37 (dd, J = 9.2, 3.0 Hz, 1H), 7.31 (d, J = 2.3 Hz, 1H), 7.25 (dd, J = 9.0, 2.5 Hz, 1H), 6.40 (d, J = 8.6 Hz, 1H), 5.07 (dd, J = 13.3, 5.1 Hz, 1H), 4.26 (d, J = 17.5 Hz, 1H), 4.15-4.07 (m, 3H), 3.89-3.85 (m, 1H), 3.63 (d, J = 12.0 Hz, 2H), 3.53-3.46 (m, 4H), 3.32-3.25 (m, 2H), 3.05-2.97 (m, 2H), 2.95-2.87 (m, 1H), 2.79-2.73 (m, 1H), 2.65-2.60 (m, 4H), 2.58-2.56 (m, 2H), 2.48-2.45 (m, 1H), 2.43-2.38 (m, 2H), 2.37-2.31 (m, 2H), 2.16 (d, J = 7.2 Hz, 2H), 2.00-1.93 (m, 1H), 1.86 (d, J = 10.8 Hz, H), 1.78 (d, J = 11.4 Hz, 20H), 1.65 (dd, J = 20.9, 11.7 Hz, 2H), 1.23-1.16 (m, 2H). m/z 854.58 [M + H]$^+$. |
| 34 | $^1$H NMR (600 MHz, CDCl3) δ 8.81 (s, 1H), 8.25 (s, 1H), 8.08 (d, J = 9.1 Hz, 1H), 7.96 (d, J = 2.9 Hz, 1H), 7.81 (d, J = 8.9 Hz, 1H), 7.62 (d, J = 8.8 Hz, 1H), 7.30 (dd, J = 9.1, 3.0 Hz, 1H), 7.13 (d, J = 2.5 Hz, 1H), 6.97 (dd, J = 8.8, 2.6 Hz, 1H), 6.65 (d, J = 9.0 Hz, 1H), 5.20 (dd, J = 13.3, 5.1 Hz, 1H), 4.48-4.40 (m, 2H), 4.30 (d, J = 16.2 Hz, 1H), 4.17 (d, J = 16.2 Hz, 1H), 3.96 (d, J = 13.3 Hz, 2H), 3.60 (d, J = 12.1 Hz, 2H), 3.09-3.01 (m, 2H), 2.97-2.88 (m, 3H), 2.85-2.79 (m, 2H), 2.70 (m, 2H), 2.57 (m, 2H), 2.45 (s, 5H), 2.37-2.30 (m, 2H), 2.24-2.19 (m, 4H), 2.06 (m, 2H), 1.98-1.93 (m, 2H), 1.88 (d, J = 12.6 Hz, 3H), 1.82 (m, 1H), 1.36-1.30 (m, 2H), 1.26 (s, 1H), 1.19 (d, J = 11.6 Hz, 2H), 0.87 (m, 2H). m/z 896.57 [M + H]$^+$. |
| 35 | $^1$H NMR (600 MHz, CDCl$_3$) δ 9.84 (s, 1H), 8.55 (s, 1H), 8.08 (d, J = 9.0 Hz, 1H), 7.99 (d, J = 2.3 Hz, 1H), 7.63 (t, J = 9.2 Hz, 2H), 7.30 (dd, J = 9.1, 2.5 Hz, 1H), 7.12 (s, 1H), 6.96 (dd, J = 8.8 Hz, 1H), 6.78 (s, 1H), 6.50 (d, J = 8.2 Hz, 1H), 4.95-4.90 (m, 1H), 4.11-4.05 (m, 2H), 3.93 (d, J = 13.1 Hz, 2H), 3.90-3.85 (m, 2H), 3.61 (d, J = 11.6 Hz, 2H), 3.40-3.35 (m, 1H), 3.01 (t, J = 12.2 Hz, 2H), 2.92-2.87 (m, 1H), 2.87-2.80 (m, 1H), 2.78-2.73 (m, 1H), 2.73-2.66 (m, 2H), 2.60-2.53 (m, 2H), 2.53-2.39 (m, 5H), 2.24 (d, J = 6.8 Hz, 2H), 2.19-2.12 (m, 1H), 2.08-2.00 (m, 3H), 1.98-1.91 (m, 2H), 1.87 (d, J = 12.2 Hz, 2H), 1.38-1.28 (m, 2H). m/z 867.49 [M + H]$^+$. |
| 36 | $^1$H NMR (400 MHz, CDCl$_3$) δ 9.46 (s, 1H), 8.30 (s, 1H), 8.04 (d, J = 8.9 Hz, 1H), 7.63 (t, J = 8.2 Hz, 1H), 7.54 (d, J = 2.8 Hz, 1H), 7.12 (d, J = 2.4 Hz, 1H), 6.96 (dd, J = 8.8, 2.5 Hz, 1H), 6.84-6.79 (m, 1H), 6.79-6.75 (m, 1H), 6.51 (dd, J = 8.3, 2.1 Hz, 1H), 4.94 (dd, J = 12.2, 5.4 Hz, 1H), 4.08 (t, J = 7.2 Hz, 2H), 4.02 (t, J = 7.4 Hz, 2H), 3.98-3.91 (m, 2H), 3.90-3.83 (m, 2H), 3.56 (t, J = 6.3 Hz, 2H), 3.42-3.34 (m, 1H), 3.07-2.95 (m, 3H), 2.94-2.80 (m, 2H), 2.80-2.72 (m, 1H), 2.68 (d, J = 7.2 Hz, 2H), 2.63-2.33 (m, 9H), 2.18-2.10 (m, 1H), 2.08-2.01 (m, 2H), 1.99-1.86 (m, 2H). m/z 839.46 [M + H]$^+$. |
| 37 | $^1$H NMR (600 MHz, CDCl$_3$) δ 9.35 (d, J = 19.4 Hz, 1H), 8.35 (d, J = 5.3 Hz, 1H), 8.10 (d, J = 9.1 Hz, 1H), 8.00 (d, J = 2.9 Hz, 1H), 7.83 (d, J = 8.7 Hz, 1H), 7.64 (d, J = 8.8 Hz, 1H), 7.32 (dd, J = 9.2, 2.7 Hz, 1H), 7.15 (d, J = 2.5 Hz, 1H), 6.98 (dd, J = 8.8, 2.5 Hz, 1H), 6.40 (d, J = 8.7 Hz, 1H), 5.22 (dd, J = 13.3, 5.1 Hz, 1H), 4.34 (dd, J = 16.2, 7.1 Hz, 1H), 4.22 (dd, J = 16.2, 6.2 Hz, 1H), 3.96 (d, J = 13.2 Hz, 2H), 3.78-3.74 (m, 1H), 3.72-3.69 (m, 1H), 3.66-3.60 (m, 2H), 3.53-3.46 (m, 1H), 3.30-3.22 (m, 1H), 3.09-3.02 (m, 2H), 2.96-2.91 (m, 1H), 2.88-2.82 (m, 1H), 2.72 (t, J = 11.2 Hz, 2H), 2.63-2.55 (m, 2H), 2.54-2.45 (m, 4H), 2.45-2.39 (m, 2H), 2.39-2.31 (m, 2H), 2.25 (d, J = 5.5 Hz, 4H), 2.22-2.15 (m, 1H), 2.11-2.04 (m, 2H), 2.00-1.93 (m, 2H), 1.93-1.86 (m, 2H), 1.85-1.75 (m, 2H), 1.71-1.64 (m, 2H), 1.41-1.31 (m, 2H). m/z 882.46 [M + H]$^+$. |
| 38 | $^1$H NMR (600 MHz, CDCl$_3$) δ 9.34 (s, 1H), 8.27 (s, 1H), 8.00 (d, J = 9.1 Hz, 1H), 7.90 (d, J = 2.9 Hz, 1H), 7.54 (d, J = 8.8 Hz, 1H), 7.30 (d, J = 12.3 Hz, 1H), 7.22 (dd, J = 9.2, 2.9 Hz, 1H), 7.05 (d, J = 2.5 Hz, 1H), 6.95 (d, J = 7.5 Hz, 1H), 6.89 (dd, J = 8.8, 2.5 Hz, 1H), 4.85 (dd, J = 12.6, 5.4 Hz, 1H), 3.87 (d, J = 13.2 Hz, 2H), 3.62-3.56 (m, 1H), 3.56-3.48 (m, J = 12.8, 8.9 Hz, 2H), 3.27-3.20 (m, 1H), 3.00-2.92 (m, 2H), 2.85-2.78 (m, 1H), 2.78-2.71 (m, 1H), 2.71-2.65 (m, 1H), 2.65-2.57 (m, 2H), 2.53-2.42 (m, 3H), 2.42-2.23 (m, 6H), 2.15 (d, J = 7.1 Hz, 2H), 2.11-2.03 (m, 2H), 2.01-1.95 (m, 2H), 1.90-1.83 (m, 2H), 1.84-1.77 (m, 2H), 1.72-1.63 (m, 1H), 1.62-1.55 (m, 1H), 1.53-1.44 (m, 3H), 1.30-1.22 (m, 2H). m/z 913.48 [M + H]$^+$. |
| 39 | $^1$H NMR (400 MHz, CDCl$_3$) δ 9.35 (d, J = 19.4 Hz, 1H), 8.35 (d, J = 5.3 Hz, 1H), 8.10 (d, J = 9.1 Hz, 1H), 8.00 (d, J = 2.9 Hz, 1H), 7.83 (d, J = 8.7 Hz, 1H), 7.64 (d, J = 8.8 Hz, 1H), 7.32 (dd, J = 9.2, 2.7 Hz, 1H), 7.15 (d, J = 2.5 Hz, 1H), 6.98 (dd, J = 8.8, 2.5 Hz, 1H), 6.40 (d, J = 8.7 Hz, 1H), 5.22 (dd, J = 13.3, 5.1 Hz, 1H), 4.34 (dd, J = 16.2, 7.1 Hz, 1H), 4.22 (dd, J = 16.2, 6.2 Hz, 1H), 3.96 (d, J = 13.2 Hz, 2H), 3.78-3.74 (m, 1H), 3.72-3.69 (m, 1H), 3.66-3.60 (m, 2H), 3.53-3.46 (m, 1H), 3.30-3.22 (m, 1H), 3.09-3.02 (m, 2H), 2.96-2.91 (m, 1H), 2.88-2.82 (m, 1H), 2.72 (t, J = 11.2 Hz, 2H), 2.63-2.55 (m, 2H), 2.54-2.45 (m, 4H), 2.45-2.39 (m, 2H), 2.39-2.31 (m, 2H), 2.25 (d, J = 5.5 Hz, 4H), 2.22-2.15 (m, 1H), 2.11-2.04 (m, 2H), 2.00-1.93 (m, 2H), 1.93-1.86 (m, 2H), 1.85-1.75 (m, 2H), 1.71-1.64 (m, 2H), 1.41-1.31 (m, 2H). m/z 882.37 [M + H]$^+$. |
| 40 | $^1$H NMR (400 MHz, CDCl$_3$) δ 9.48 (d, J = 28.0 Hz, 1H), 8.35 (d, J = 8.0 Hz, 1H), 8.07 (d, J = 9.1 Hz, 1H), 7.99 (d, J = 2.8 Hz, 1H), 7.63 (dd, J = 8.4, 6.8 Hz, 1H), 7.30 (dd, J = 9.2, 2.9 Hz, 1H), 7.13 (d, J = 2.3 Hz, 1H), 6.96 (dd, J = 8.9, 2.5 Hz, 1H), 6.78 (d, J = 1.9 Hz, 1H), 6.50 (dd, J = 8.3, 2.0 Hz, 1H), 4.94 (dd, J = 12.2, 5.3 Hz, 1H), 4.08 (t, J = 7.4 Hz, 1H), 3.94 (d, J = 13.2 Hz, 2H), 3.91-3.84 (m, 2H), 3.64-3.55 (m, 2H), 3.37-3.28 (m, 1H), 3.08-2.97 (m, 2H), 2.94-2.87 (m, 2H), 2.87-2.72 (m, 3H), 2.72-2.67 (m, 2H), 2.65-2.51 (m, 3H), 2.45-2.35 (m, 1H), 2.30-2.10 (m, 3H), 2.09-2.00 (m, 4H), 1.99-1.86 (m, 4H), 1.78 (d, J = 12.7 Hz, 1H), 1.67-1.59 (m, 1H), 1.38-1.26 (m, 2H), 1.04 (d, J = 6.1 Hz, 3H). m/z 881.46 [M + H]$^+$. |
| 41 | $^1$H NMR (400 MHz, CDCl$_3$) δ 9.48 (d, J = 28.0 Hz, 1H), 8.35 (d, J = 8.0 Hz, 1H), 8.07 (d, J = 9.1 Hz, 1H), 7.99 (d, J = 2.8 Hz, 1H), 7.63 (dd, J = 8.4, 6.8 Hz, 1H), 7.30 (dd, J = 9.2, 2.9 Hz, 1H), 7.13 (d, J = 2.3 Hz, 1H), 6.96 (dd, J = 8.9, 2.5 Hz, 1H), 6.78 (d, J = 1.9 Hz, 1H), 6.50 (dd, J = 8.3, 2.0 Hz, 1H), 4.94 (dd, J = 12.2, 5.3 Hz, 1H), 4.08 (t, J = 7.4 Hz, 1H), 3.94 (d, J = 13.2 Hz, 2H), 3.91-3.84 (m, 2H), 3.64-3.55 (m, 2H), 3.37-3.28 (m, 1H), 3.08-2.97 (m, 2H), 2.94-2.87 (m, 2H), 2.87-2.72 (m, 3H), 2.72-2.67 (m, 2H), 2.65-2.51 (m, 3H), 2.45-2.35 (m, 1H), 2.30-2.10 (m, 3H), 2.09-2.00 (m, 4H), 1.99-1.86 (m, 4H), 1.78 (d, J = 12.7 Hz, 1H), 1.67-1.59 (m, 1H), 1.38-1.26 (m, 2H), 1.04 (d, J = 6.1 Hz, 3H). m/z 881.47 [M + H]$^+$. |

TABLE 5-continued

| Example | NMR and/or MS data |
|---|---|
| 42 | $^1$H NMR (400 MHz, CDCl$_3$) δ 9.67 (s, 1H), 8.43 (s, 1H), 8.08 (d, J = 9.1 Hz, 1H), 7.99 (d, J = 2.7 Hz, 1H), 7.67 (d, J = 8.5 Hz, 1H), 7.62 (d, J = 8.8 Hz, 1H), 7.32-7.27 (m, 2H), 7.13 (d, J = 2.5 Hz, 1H), 7.04 (dd, J = 8.7, 2.3 Hz, 1H), 6.96 (dd, J = 8.8, 2.6 Hz, 1H), 4.95 (dd, J = 12.3, 5.3 Hz, 1H), 4.02-3.89 (m, 4H), 3.64-3.56 (m, 2H), 3.08-2.94 (m, 4H), 2.94-2.82 (m, 3H), 2.82-2.63 (m, 5H), 2.62-2.52 (m, 2H), 2.48-2.39 (m, 1H), 2.38-2.29 (m, 2H), 2.25-2.19 (m, 1H), 2.19-2.11 (m, 1H), 2.10-2.00 (m, 4H), 2.00-1.88 (m, 6H), 1.77 (d, J = 12.8 Hz, 1H), 1.67-1.60 (m, 2H), 1.40-1.20 (m, 2H), 1.01 (d, J = 6.1 Hz, 3H). m/z 909.55 [M + H]$^+$. |
| 43 | $^1$H NMR (600 MHz, CDCl$_3$) δ 8.99 (s, 1H), 8.42 (s, 1H), 8.12 (d, J = 9.1 Hz, 1H), 7.86 (d, J = 2.9 Hz, 1H), 7.83 (d, J = 8.9 Hz, 1H), 7.61 (d, J = 8.7 Hz, 1H), 7.32 (dd, J = 9.2, 3.0 Hz, 1H), 7.13 (d, J = 2.5 Hz, 1H), 6.97 (dd, J = 8.8, 2.6 Hz, 1H), 6.67 (d, J = 8.9 Hz, 1H), 5.20 (dd, J = 13.3, 5.1 Hz, 1H), 4.53-4.44 (m, 2H), 4.30 (d, J = 16.2 Hz, 1H), 4.17 (d, J = 16.2 Hz, 1H), 3.95 (d, J = 13.2 Hz, 2H), 3.63-3.55 (m, 2H), 3.11-3.04 (m, 2H), 2.99-2.91 (m, 2H), 2.91-2.86 (m, 1H), 2.86-2.79 (m, 2H), 2.77-2.72 (m, 1H), 2.72-2.64 (m, 2H), 2.62-2.55 (m, 2H), 2.43-2.35 (m, 2H), 2.35-2.29 (m, 1H), 2.28-2.19 (m, 2H), 2.07-2.02 (m, 2H), 1.98-1.91 (m, 4H), 1.79-1.74 (m, 2H), 1.67-1.58 (m, 2H), 1.57-1.49 (m, 2H), 1.37-1.30 (m, 2H), 1.30-1.23 (m, 2H), 1.02 (d, J = 6.1 Hz, 3H). m/z 896.60 [M + H]$^+$. |
| 44 | $^1$H NMR (600 MHz, CDCl$_3$) δ 8.88 (s, 1H), 8.46 (s, 1H), 8.08 (d, J = 9.1 Hz, 1H), 7.94 (d, J = 2.9 Hz, 1H), 7.81 (d, J = 8.9 Hz, 1H), 7.62 (d, J = 8.8 Hz, 1H), 7.30 (dd, J = 9.1, 3.0 Hz, 1H), 7.13 (d, J = 2.5 Hz, 1H), 6.97 (dd, J = 8.8, 2.5 Hz, 1H), 6.64 (d, J = 9.0 Hz, 1H), 5.20 (dd, J = 13.4, 5.1 Hz, 1H), 4.48-4.40 (m, 2H), 4.30 (d, J = 16.2 Hz, 1H), 4.17 (d, J = 16.2 Hz, 1H), 3.95 (d, J = 13.3 Hz, 2H), 3.63-3.56 (m, 2H), 3.09-3.02 (m, 2H), 2.98-2.88 (m, 3H), 2.86-2.79 (m, 2H), 2.75-2.63 (m, 3H), 2.63-2.58 (m, 1H), 2.58-2.53 (m, 1H), 2.42-2.36 (m, 1H), 2.35-2.29 (m, 1H), 2.27-2.19 (m, 2H), 2.16 (d, 2H), 2.08-2.03 (m, 2H), 2.04-2.00 (m, 1H), 1.99-1.90 (m, 3H), 1.86 (d, J = 12.6 Hz, 2H), 1.79 (d, J = 11.8 Hz, 2H), 1.37-1.27 (m, 2H), 1.22-1.14 (m, 2H), 1.01 (d, J = 6.1 Hz, 3H). m/z 910.68 [M + H]$^+$. |
| 45 | $^1$H NMR (600 MHz, CDCl$_3$) δ 9.36 (s, 1H), 8.45 (s, 1H), 8.07 (d, J = 9.1 Hz, 1H), 7.96 (d, J = 2.9 Hz, 1H), 7.83 (d, J = 8.9 Hz, 1H), 7.61 (d, J = 8.7 Hz, 1H), 7.32 (dd, J = 9.2, 3.0 Hz, 1H), 7.13 (d, J = 2.5 Hz, 1H), 6.97 (dd, J = 8.8, 2.6 Hz, 1H), 6.67 (d, J = 8.9 Hz, 1H), 5.20 (dd, J = 13.3, 5.1 Hz, 1H), 4.53-4.44 (m, 2H), 4.30 (d, J = 16.2 Hz, 1H), 4.17 (d, J = 16.2 Hz, 1H), 3.95 (d, J = 13.2 Hz, 2H), 3.63-3.55 (m, 2H), 3.11-3.04 (m, 2H), 2.99-2.91 (m, 2H), 2.91-2.86 (m, 1H), 2.86-2.79 (m, 2H), 2.77-2.72 (m, 1H), 2.72-2.64 (m, 2H), 2.62-2.55 (m, 2H), 2.55-2.50 (m, 1H), 2.43-2.35 (m, 2H), 2.35-2.29 (m, 1H), 2.28-2.19 (m, 2H), 2.07-2.02 (m, 2H), 1.98-1.91 (m, 4H), 1.79-1.74 (m, 2H), 1.67-1.58 (m, 2H), 1.57-1.49 (m, 2H), 1.37-1.30 (m, 2H), 1.30-1.23 (m, 2H), 1.02 (d, J = 6.1 Hz, 3H). m/z 896.57 [M + H]$^+$. |
| 46 | $^1$H NMR (600 MHz, CDCl$_3$) δ 9.07 (s, 1H), 8.25 (s, 1H), 8.07 (d, J = 9.1 Hz, 1H), 7.947 (d, J = 2.9 Hz, 1H), 7.81 (d, J = 8.9 Hz, 1H), 7.62 (d, J = 8.8 Hz, 1H), 7.30 (dd, J = 9.1, 3.0 Hz, 1H), 7.13 (d, J = 2.5 Hz, 1H), 6.97 (dd, J = 8.8, 2.5 Hz, 1H), 6.64 (d, J = 9.0 Hz, 1H), 5.20 (dd, J = 13.4, 5.1 Hz, 1H), 4.48-4.40 (m, 2H), 4.30 (d, J = 16.2 Hz, 1H), 4.17 (d, J = 16.2 Hz, 1H), 3.95 (d, J = 13.3 Hz, 2H), 3.63-3.56 (m, 2H), 3.09-3.02 (m, 2H), 2.98-2.88 (m, 3H), 2.86-2.79 (m, 2H), 2.75-2.63 (m, 3H), 2.63-2.58 (m, 1H), 2.58-2.53 (m, 1H), 2.42-2.36 (m, 1H), 2.35-2.29 (m, 1H), 2.27-2.19 (m, 2H), 2.16 (d, 2H), 2.08-2.03 (m, 2H), 2.04-2.00 (m, 1H), 1.99-1.90 (m, 3H), 1.86 (d, J = 12.6 Hz, 2H), 1.79 (d, J = 11.8 Hz, 2H), 1.37-1.27 (m, 2H), 1.22-1.14 (m, 2H), 1.01 (d, J = 6.1 Hz, 3H). m/z 910.63 [M + H]$^+$. |
| 47 | $^1$H NMR (600 MHz, CDCl$_3$) δ 8.62 (d, J = 19.0 Hz, 1H), 8.12-8.04 (m, 2H), 7.95 (s, 1H), 7.81 (d, J = 8.9 Hz, 1H), 7.62 (d, J = 8.8 Hz, 1H), 7.29 (d, J = 9.3 Hz, 1H), 7.13 (s, 1H), 6.97 (d, J = 9.0 Hz, 1H), 6.65 (d, J = 8.8 Hz, 1H), 5.20 (dd, J = 13.4, 5.0 Hz, 1H), 4.53-4.38 (m, 3H), 4.30 (d, J = 16.3 Hz, 1H), 4.17 (d, J = 16.3 Hz, 1H), 3.96 (d, J = 13.1 Hz, 2H), 3.60 (d, J = 12.1 Hz, 2H), 3.10-3.02 (m, 2H), 3.00-2.88 (m, 3H), 2.87-2.78 (m, 2H), 2.73-2.66 (m, 2H), 2.66-2.58 (m, 1H), 2.57-2.51 (m, 2H), 2.45-2.38 (m, 1H), 2.38-2.25 (m, 3H), 2.25-2.13 (m, 3H), 2.10-2.01 (m, 3H), 2.01-1.90 (m, 3H), 1.88 (d, J = 13.5 Hz, 2H), 1.82-1.76 (m, 2H), 1.70-1.62 (m, 2H), 1.38-1.29 (m, 2H), 1.22-1.11 (m, 2H), 1.06-0.93 (m, 3H). m/z 910.46 [M + H]$^+$. |
| 48 | $^1$H NMR (600 MHz, CDCl$_3$) δ 8.62 (d, J = 19.0 Hz, 1H), 8.12-8.04 (m, 2H), 7.95 (s, 1H), 7.81 (d, J = 8.9 Hz, 1H), 7.62 (d, J = 8.8 Hz, 1H), 7.29 (d, J = 9.3 Hz, 1H), 7.13 (s, 1H), 6.97 (d, J = 9.0 Hz, 1H), 6.65 (d, J = 8.8 Hz, 1H), 5.20 (dd, J = 13.4, 5.0 Hz, 1H), 4.53-4.38 (m, 3H), 4.30 (d, J = 16.3 Hz, 1H), 4.17 (d, J = 16.3 Hz, 1H), 3.96 (d, J = 13.1 Hz, 2H), 3.60 (d, J = 12.1 Hz, 2H), 3.10-3.02 (m, 2H), 3.00-2.88 (m, 3H), 2.87-2.78 (m, 2H), 2.73-2.66 (m, 2H), 2.66-2.58 (m, 1H), 2.57-2.51 (m, 2H), 2.45-2.38 (m, 1H), 2.38-2.25 (m, 3H), 2.25-2.13 (m, 3H), 2.10-2.01 (m, 3H), 2.01-1.90 (m, 3H), 1.88 (d, J = 13.5 Hz, 2H), 1.82-1.76 (m, 2H), 1.70-1.62 (m, 2H), 1.38-1.29 (m, 2H), 1.22-1.11 (m, 2H), 1.06-0.93 (m, 3H). m/z 910.61 [M + H]$^+$. |
| 49 | $^1$H NMR (600 MHz, CDCl$_3$) δ 9.20 (s, 1H), 8.28 (s, 1H), 8.07 (d, J = 9.1 Hz, 1H), 7.97 (d, J = 2.9 Hz, 1H), 7.67 (d, J = 8.5 Hz, 1H), 7.62 (d, J = 8.8 Hz, 1H), 7.30 (dd, J = 9.2, 3.0 Hz, 1H), 7.27 (d, J = 2.4 Hz, 1H), 7.13 (d, J = 2.4 Hz, 1H), 7.04 (dd, J = 8.6, 2.3 Hz, 1H), 6.97 (dd, J = 8.8, 2.5 Hz, 1H), 4.94 (dd, J = 12.5, 5.4 Hz, 1H), 3.95 (d, J = 13.2 Hz, 2H), 3.59 (d, J = 12.1 Hz, 2H), 3.45-3.35 (m, 4H), 3.07 (s, 4H), 3.06-3.01 (m, 2H), 2.89 (dd, J = 9.9, 6.1 Hz, 2H), 2.86-2.80 (m, 1H), 2.77-2.71 (m, 2H), 2.69 (dd, J = 19.6, 9.6 Hz, 2H), 2.59-2.52 (m, 2H), 2.41 (d, J = 6.7 Hz, 2H), 2.17-2.11 (m, 1H), 2.10-2.04 (m, 2H), 1.95 (dd, J = 18.2, 6.7 Hz, 3H), 1.89-1.83 (m, 4H), 1.82 (s, 1H), 1.35 (dd, J = 12.1, 3.4 Hz, 2H). m/z 852.40 [M + H]$^+$. |
| 50 | $^1$H NMR (600 MHz, CDCl$_3$) δ 9.49 (s, 1H), 8.45 (s, 1H), 8.08 (d, J = 9.1 Hz, 1H), 7.96 (d, J = 2.9 Hz, 1H), 7.67 (d, J = 8.5 Hz, 1H), 7.44 (t, J = 6.4 Hz, 1H), 7.29 (dd, J = 9.2, 2.9 Hz, 1H), 7.27 (d, J = 2.6 Hz, 1H), 7.03 (dd, J = 8.6, 2.3 Hz, 1H), 6.87 (d, J = 2.5 Hz, 1H), 6.74 (dd, J = 8.9, 2.5 Hz, 1H), 4.94 (dd, J = 12.6, 5.4 Hz, 1H), 3.90-3.84 (m, J = 13.2 Hz, 2H), 3.59 (d, J = 12.2 Hz, 2H), 3.43-3.33 (m, 4H), 3.09 (s, 4H), 2.97 (td, J = 13.1, 2.7 Hz, 2H), 2.92-2.86 (m, 4H), 2.86-2.79 (m, 1H), 2.78-2.71 (m, 1H), 2.71-2.64 (m, 2H), 2.57-2.50 (m, 1H), 2.43 (d, J = 5.5 Hz, 2H), 2.18-2.11 (m, 1H), 2.06-2.00 (m, 2H), 1.95-1.89 (m, 2H), 1.89-1.84 (m, 4H), 1.83 (d, J = 13.4 Hz, 2H), 1.52-1.44 (m, 1H), 1.35 (ddd, J = 15.7, 12.5, 3.7 Hz, 2H). m/z 818.36 [M + H]$^+$. |
| 51 | $^1$H NMR (600 MHz, CDCl$_3$) δ 8.49 (s, 1H), 8.09 (d, J = 9.1 Hz, 1H), 7.97 (s, 1H), 7.95 (d, J = 2.9 Hz, 1H), 7.67 (d, J = 8.5 Hz, 1H), 7.60 (d, J = 8.8 Hz, 1H), 7.29 (dd, J = 9.2, 3.0 Hz, 1H), 7.28 (d, J = 2.3 Hz, 1H), 7.11 (d, J = 2.5 Hz, 1H), 7.05 (d, J = 8.6, 2.3 Hz, 1H), 6.95 (dd, J = 8.8, 2.6 Hz, 1H), 4.94 (dd, J = 12.6, 5.4 Hz, 1H), 3.60 (d, J = 13.9, 8.9 Hz, 4H), 3.43-3.36 (m, 4H), 3.37-3.31 (m, 2H), 3.08 (s, 4H), 2.92-2.86 (m, 1H), 2.86-2.78 (m, 1H), 2.78-2.72 (m, 1H), 2.72-2.65 (m, 2H), 2.42 (s, 2H), 2.29 (d, J = 14.2 Hz, 2H), 2.13 (s, 1H), 1.85 (d, J = 24.1 Hz, 4H), 1.73-1.66 (m, 2H), 1.61 (s, 2H), 1.47 (d, J = 17.4 Hz, 1H), 1.37 (d, J = 14.2 Hz, 5H). m/z 866.40 [M + H]$^+$. |
| 52 | $^1$H NMR (600 MHz, CDCl$_3$) δ 9.58 (s, 1H), 8.43 (s, 1H), 8.12 (d, J = 9.0 Hz, 1H), 8.08 (d, J = 9.1 Hz, 1H), 7.98 (d, J = 2.9 Hz, 1H), 7.61 (d, J = 8.8 Hz, 1H), 7.36 (d, J = 2.5 Hz, 1H), 7.31-7.28 (m, 1H), 7.12 (d, J = 2.4 Hz, 1H), 6.96 (dd, J = 8.8, 2.5 Hz, 1H), 5.80 (dd, J = 11.8, 5.4 Hz, 1H), 3.99-3.90 (m, 2H), 3.59 (d, J = 12.2 Hz, 2H), 3.50-3.39 (m, 4H), 3.10 (s, 4H), 3.03 (dd, J = 17.6, 7.3 Hz, 2H), 2.95 (dd, J = 20.4, 8.9 Hz, 2H), 2.85 (d, J = 15.9 Hz, 1H), 2.72-2.65 (m, 2H), 2.57 (s, 1H), 2.43 (s, 1H), 2.39 (dd, J = 9.8, 5.4 Hz, 2H), 1.97-1.92 (m, 2H), 1.90 (s, 4H), 1.84 (d, J = 12.5 Hz, 2H), 1.46 (s, 2H), 1.40-1.31 (m, 2H). m/z 852.44 [M + H]$^+$. |
| 53 | $^1$H NMR (600 MHz, CDCl$_3$) δ 9.56 (s, 1H), 8.45 (s, 1H), 8.08 (d, J = 9.1 Hz, 1H), 7.97 (dd, J = 6.0, 3.1 Hz, 2H), 7.61 (d, J = 8.8 Hz, 1H), 7.51 (d, J = 2.8 Hz, 1H), 7.42 (dd, J = 9.2, 2.9 Hz, 1H), 7.30 (dd, J = 9.1, 3.0 Hz, 1H), 7.12 (d, J = 2.4 Hz, 1H), 6.95 (dd, J = 8.8, 2.5 Hz, 1H), 5.78 (dd, J = 11.9, 5.5 Hz, 1H), 3.93 (d, J = 13.2 Hz, 2H), 3.59 (d, J = 12.2 Hz, 2H), 3.50-3.40 (m, 4H), 3.09 (s, 4H), 3.02 (dd, J = 17.6, 7.3 Hz, 2H), 2.99-2.91 (m, 2H), 2.85 (d, J = 14.1 |

TABLE 5-continued

| Example | NMR and/or MS data |
|---|---|
| | Hz, 1H), 2.68 (dd, J = 12.0, 9.9 Hz, 2H), 2.56 (s, 1H), 2.40 (dd, J = 13.1, 7.7 Hz, 3H), 2.08-2.02 (m, 2H), 1.94 (dd, J = 16.1, 6.8 Hz, 2H), 1.89 (d, J = 15.9 Hz, 4H), 1.83 (d, J = 11.3 Hz, 2H), 1.48 (s, 1H), 1.35 (dd, J = 12.1, 3.2 Hz, 2H). m/z 852.38 [M + H]⁺. |
| 54 | ¹H NMR (600 MHz, CDCl₃) δ 8.63 (d, J = 6.4 Hz, 1H), 8.26 (s, 1H), 8.04 (d, J = 9.1 Hz, 1H), 7.98 (d, J = 2.7 Hz, 1H), 7.67 (d, J = 8.5 Hz, 1H), 7.65 (d, J = 8.8 Hz, 1H), 7.31-7.27 (m, 2H), 7.16 (s, 1H), 7.05 (dd, J = 8.6, 1.7 Hz, 1H), 7.01 (d, J = 8.8, 2.1 Hz, 1H), 4.94 (dd, J = 12.5, 5.4 Hz, 1H), 3.88 (d, J = 13.4 Hz, 2H), 3.62 (d, J = 12.1 Hz, 2H), 3.43-3.30 (m, 5H), 3.08 (s, 4H), 2.92-2.85 (m, 1H), 2.80 (ddd, J = 25.2, 17.4, 4.6 Hz, 2H), 2.71 (d, J = 17.3, 7.4 Hz, 2H), 2.42 (d, J = 7.9 Hz, 2H), 2.38-2.32 (m, 1H), 2.15-2.09 (m, 1H), 2.05 (dd, J = 14.4, 9.8 Hz, 2H), 1.85 (d, J = 18.9 Hz, 4H), 1.61 (s, 4H), 1.49 (s, 1H), 1.36 (dd, J = 22.2, 11.4 Hz, 2H). m/z 870.44 [M + H]⁺. |
| 55 | ¹H NMR (600 MHz, CDCl₃) δ 9.27 (s, 1H), 8.42 (s, 1H), 8.12 (d, J = 9.1 Hz, 1H), 7.84 (s, 1H), 7.66 (dd, J = 13.9, 8.7 Hz, 2H), 7.30 (d, J = 9.2 Hz, 1H), 7.27 (s, 1H), 7.18 (s, 1H), 7.04 (dd, J = 14.3, 8.8 Hz, 1H), 4.94 (dd, J = 12.5, 5.4 Hz, 1H), 3.87 (d, J = 12.9 Hz, 2H), 3.52 (d, J = 11.9 Hz, 2H), 3.44-3.34 (m, 6H), 3.09 (s, 4H), 2.89-2.85 (m, 1H), 2.85-2.79 (m, 1H), 2.75-2.68 (m, 1H), 2.66-2.59 (m, 2H), 2.43 (s, 1H), 2.40-2.33 (m, 2H), 2.15-2.10 (m, 1H), 1.88 (s, 4H), 1.84 (d, J = 12.6 Hz, 4H), 1.66-1.55 (m, 2H), 1.38-1.29 (m, 2H). m/z 868.38 [M + H]⁺. |
| 56 | ¹H NMR (600 MHz, CDCl₃) δ 9.86 (s, 1H), 8.56 (s, 1H), 8.08 (d, J = 9.1 Hz, 1H), 7.97 (d, J = 2.9 Hz, 1H), 7.65 (s, 1H), 7.56 (d, J = 8.7 Hz, 1H), 7.30 (dd, J = 9.1, 2.9 Hz, 1H), 7.04-7.00 (m, 1H), 6.77 (d, J = 2.3 Hz, 1H), 6.60 (dd, J = 8.7, 2.4 Hz, 1H), 4.94 (dd, J = 12.6, 5.4 Hz, 1H), 3.70-3.66 (m, 1H), 3.59 (d, J = 12.0 Hz, 2H), 3.51-3.46 (m, 1H), 3.42-3.32 (m, 5H), 3.15-3.03 (m, 4H), 2.92-2.88 (m, 2H), 2.88-2.80 (m, 2H), 2.77-2.72 (m, 1H), 2.68 (t, J = 11.4 Hz, 2H), 2.61-2.54 (m, 2H), 2.43 (s, 2H), 2.34-2.30 (m, 1H), 2.15-2.10 (m, 1H), 1.92-1.79 (m, 6H), 1.46 (s, 2H), 1.40-1.31 (m, 2H). m/z 852.40 [M + H]⁺. |
| 57 | ¹H NMR (600 MHz, CDCl₃) δ 9.86 (s, 1H), 8.53 (s, 1H), 8.37 (d, J = 2.6 Hz, 1H), 8.07 (d, J = 9.1 Hz, 1H), 7.99 (d, J = 2.7 Hz, 1H), 7.67 (d, J = 8.5 Hz, 1H), 7.30 (dd, J = 9.1, 2.8 Hz, 1H), 7.03 (dd, J = 8.6, 2.1 Hz, 1H), 4.95 (dd, J = 12.6, 5.4 Hz, 1H), 3.97 (d, J = 13.2 Hz, 2H), 3.59 (d, J = 12.0 Hz, 2H), 3.43-3.34 (m, 4H), 3.14-3.09 (m, 2H), 3.09-3.02 (m, 4H), 2.92-2.87 (m, 1H), 2.87-2.81 (m, 1H), 2.79-2.72 (m, 1H), 2.68 (t, J = 11.3 Hz, 2H), 2.63-2.57 (m, 1H), 2.41 (d, J = 6.3 Hz, 2H), 2.17-2.13 (m, J = 9.0, 4.0 Hz, 1H), 2.12-2.06 (m, 2H), 2.01-1.93 (m, 2H), 1.89-1.84 (m, 4H), 1.84-1.79 (m, 2H), 1.50-1.42 (m, 1H), 1.39-1.31 (m, 2H). m/z 853.37 [M + H]⁺. |
| 58 | ¹H NMR (600 MHz, CDCl₃) δ 8.64 (d, J = 6.3 Hz, 1H), 8.45 (d, J = 2.8 Hz, 1H), 8.22 (s, 1H), 8.04 (d, J = 9.1 Hz, 1H), 7.99 (d, J = 2.8 Hz, 1H), 7.68 (d, J = 8.5 Hz, 1H), 7.33 (d, J = 2.8 Hz, 1H), 7.31-7.29 (m, 1H), 7.28 (d, J = 2.2 Hz, 1H), 7.05 (dd, J = 8.6, 2.3 Hz, 1H), 4.94 (dd, J = 12.6, 5.4 Hz, 1H), 3.94 (d, J = 13.4 Hz, 2H), 3.63 (d, J = 12.2 Hz, 2H), 3.47-3.41 (m, 2H), 3.41-3.36 (m, 4H), 3.08 (s, 4H), 2.92-2.85 (m, 1H), 2.84-2.78 (m, 1H), 2.76-2.73 (m, 1H), 2.73-2.69 (m, 2H), 2.48-2.40 (m, 3H), 2.40-2.35 (m, 1H), 2.17-2.08 (m, 3H), 1.96-1.81 (m, 6H), 1.49 (s, 1H), 1.42-1.32 (m, 2H). m/z 871.43 [M + H]⁺. |
| 59 | ¹H NMR (600 MHz, CDCl₃) δ 8.08 (d, J = 2.7 Hz, 1H), 8.03 (s, 1H), 7.82 (dd, J = 9.1, 2.7 Hz, 1H), 7.67 (d, J = 8.5 Hz, 1H), 7.62 (d, J = 8.8 Hz, 1H), 7.27 (d, J = 2.3 Hz, 1H), 7.14 (d, J = 2.4 Hz, 1H), 7.05 (dd, J = 8.6, 2.3 Hz, 1H), 7.01 (s, 1H), 6.98 (dd, J = 8.8, 2.5 Hz, 1H), 6.65 (d, J = 9.2 Hz, 1H), 4.93 (dd, J = 12.6, 5.4 Hz, 1H), 4.21 (d, J = 12.9 Hz, 2H), 3.98 (d, J = 13.2 Hz, 2H), 3.44-3.36 (m, 2H), 3.08 (d, J = 2.3 Hz, 4H), 3.06-3.03 (m, 2H), 2.92-2.85 (m, 2H), 2.82-2.71 (m, 15.0, 8.0 Hz, 5H), 2.54-2.48 (m, 1H), 2.44-2.36 (m, 2H), 2.16-2.11 (m, 1H), 2.09-2.03 (m, 2H), 1.99-1.92 (m, 2H), 1.87 (s, 4H), 1.79 (d, J = 11.8 Hz, 2H). m/z 852.40 [M + H]⁺. |
| 60 | ¹H NMR (600 MHz, CDCl₃) δ 8.07 (d, J = 2.7 Hz, 1H), 8.01 (s, 1H), 7.82 (dd, J = 9.1, 2.7 Hz, 1H), 7.67 (d, J = 8.5 Hz, 1H), 7.46 (d, J = 8.9 Hz, 1H), 7.05 (dd, J = 8.6, 2.3 Hz, 1H), 7.00 (s, 1H), 6.89 (d, J = 2.5 Hz, 1H), 6.76 (dd, J = 8.9, 2.5 Hz, 1H), 6.64 (d, J = 9.2 Hz, 1H), 4.93 (dd, J = 12.6, 5.4 Hz, 1H), 4.21 (d, J = 13.1 Hz, 2H), 3.92 (d, J = 13.1 Hz, 2H), 3.46-3.35 (m, 4H), 3.08 (s, 4H), 3.03-2.97 (m, 2H), 2.91-2.86 (m, 2H), 2.84-2.70 (m, 5H), 2.52-2.46 (m, 1H), 2.39 (s, 2H), 2.15-2.10 (m, 1H), 2.05-2.01 (m, 2H), 1.98-1.91 (m, 2H), 1.87 (s, 4H), 1.79 (d, J = 12.1 Hz, 2H). m/z 818.36 [M + H]⁺. |
| 61 | ¹H NMR (600 MHz, CDCl₃) δ 9.31 (s, 1H), 8.31 (s, 1H), 8.04 (d, J = 9.0 Hz, 1H), 7.67 (d, J = 8.5 Hz, 1H), 7.62 (t, J = 6.0 Hz, 2H), 7.28 (d, J = 2.3 Hz, 1H), 7.13 (d, J = 2.4 Hz, 1H), 7.04 (dd, J = 8.6, 2.3 Hz, 1H), 6.96 (dd, J = 8.8, 2.5 Hz, 1H), 6.90 (dd, J = 9.1, 3.0 Hz, 1H), 4.95 (dd, J = 12.5, 5.4 Hz, 1H), 3.95 (d, J = 13.2 Hz, 2H), 3.44-3.36 (m, 5H), 3.36-3.32 (m, 1H), 3.27 (dd, J = 16.2, 8.0 Hz, 1H), 3.10 (s, 4H), 3.06-2.99 (m, 2H), 2.88 (s, 3H), 2.87-2.81 (m, 1H), 2.80-2.71 (m, 2H), 2.56 (d, J = 9.3, 5.2 Hz, 3H), 2.35 (d, J = 14.3, 7.2 Hz, 2H), 2.17-2.11 (m, 2H), 2.09-2.04 (m, 2H), 1.94 (dd, J = 16.2, 6.9 Hz, 2H), 1.90-1.80 (m, 4H), 1.73 (dd, J = 12.2, 8.4 Hz, 1H). m/z 838.40 [M + H]⁺. |
| 62 | ¹H NMR (600 MHz, CDCl₃) δ 8.86 (s, 1H), 8.11 (s, 1H), 8.03 (d, J = 8.9 Hz, 1H), 7.67 (d, J = 8.6 Hz, 1H), 7.62 (d, J = 7.7 Hz, 2H), 7.29 (d, J = 11.2 Hz, 2H), 7.13 (s, 1H), 7.05 (d, J = 8.7 Hz, 1H), 6.97 (d, J = 8.7 Hz, 1H), 6.90 (d, J = 9.2 Hz, 1H), 4.94 (dd, J = 12.3, 5.1 Hz, 1H), 3.95 (d, J = 13.2 Hz, 2H), 3.53-3.36 (m, 6H), 3.34 (m, 1H), 3.27 (dd, J = 16.3, 8.1 Hz, 1H), 3.10 (s, 4H), 3.07-2.96 (m, 4H), 2.94-2.69 (m, 4H), 2.68-2.42 (m, 4H), 2.35 (m, 1H), 2.14 (m, 3H), 2.06 (d, J = 11.3 Hz, 3H), 1.94 (dd, J = 23.1, 12.2 Hz, 3H), 1.87 (s, 5H), 1.79-1.69 (m, 2H). m/z 838.34 [M + H]⁺. |
| 63 | ¹H NMR (600 MHz, CDCl₃) δ 9.43 (s, 1H), 8.34 (s, 1H), 8.08 (d, J = 9.1 Hz, 1H), 7.98 (d, J = 2.9 Hz, 1H), 7.63 (d, J = 12.9, 8.6 Hz, 2H), 7.31 (d, J = 9.2, 2.9 Hz, 1H), 7.13 (d, J = 2.3 Hz, 1H), 6.96 (dd, J = 8.8, 2.5 Hz, 1H), 6.77 (d, J = 2.1 Hz, 1H), 6.49 (dd, J = 8.4, 2.1 Hz, 1H), 4.94 (dd, J = 12.6, 5.4 Hz, 1H), 3.94 (dd, J = 10.3, 3.0 Hz, 2H), 3.72 (s, 2H), 3.60 (d, J = 8.0 Hz, 2H), 3.08-2.99 (m, 2H), 2.93-2.87 (m, 1H), 2.84 (d, J = 13.2, 4.2 Hz, 1H), 2.78-2.72 (m, 1H), 2.72-2.66 (m, 2H), 2.56 (m, 1H), 2.37 (s, 2H), 2.20 (d, J = 7.0 Hz, 1H), 2.17-2.12 (m, 1H), 2.06 (d, J = 11.3 Hz, 2H), 1.98-1.91 (m, 3H), 1.90-1.82 (m, 3H), 1.61 (s, 2H), 1.33 (dd, J = 22.1, 11.2 Hz, 2H). m/z 852.35 [M + H]⁺. |
| 64 | ¹H NMR (600 MHz, CDCl₃) δ 9.32 (s, 1H), 8.35 (s, 1H), 8.08 (d, J = 9.1 Hz, 1H), 7.98 (d, J = 2.7 Hz, 1H), 7.64 (d, J = 8.3 Hz, 1H), 7.45 (d, J = 7.4 Hz, 1H), 7.31 (dd, J = 9.2, 2.8 Hz, 1H), 6.87 (d, J = 2.3 Hz, 1H), 6.77 (d, J = 1.8 Hz, 1H), 6.74 (dd, J = 8.9, 2.3 Hz, 1H), 6.49 (dd, J = 8.3, 1.8 Hz, 1H), 4.94 (dd, J = 12.5, 5.4 Hz, 1H), 3.88 (d, J = 13.2 Hz, 2H), 3.72 (s, 4H), 3.60 (d, J = 11.7 Hz, 2H), 2.97 (t, J = 11.2 Hz, 2H), 2.89 (d, J = 18.6 Hz, 1H), 2.84 (dd, J = 13.1, 4.2 Hz, 1H), 2.75 (m, 1H), 2.71 (t, J = 10.9 Hz, 2H), 2.54 (s, 1H), 2.38 (s, 4H), 2.20 (d, J = 6.6 Hz, 2H), 2.14 (m, 1H), 2.03 (d, J = 11.0 Hz, 2H), 1.95-1.88 (m, 2H), 1.85 (s, 4H), 1.62 (s, 2H), 1.34 (dd, J = 22.7, 11.3 Hz, 2H). m/z 818.37 [M + H]⁺. |
| 65 | ¹H NMR (600 MHz, DMSO-d6) δ 10.34 (s, 1H), 10.24 (s, 1H), 7.98 (d, J = 2.9 Hz, 1H), 7.89 (d, J = 9.0 Hz, 1H), 7.81 (d, J = 8.8 Hz, 1H), 7.64 (dd, J = 8.6, 2.2 Hz, 1H), 7.58 (d, J = 2.2 Hz, 1H), 7.36 (dd, J = 9.2, 3.0 Hz, 1H), 7.30 (s, 1H), 7.26-7.24 (m, 1H), 7.15 (d, J = 8.8 Hz, 1H), 4.10 (dd, J = 10.5, 5.2 Hz, 2H), 4.02 (s, 2H), 3.86 (d, J = 7.3 Hz, 3H), 3.71 (s, 2H), 3.62 (d, J = 12.4 Hz, 2H), 3.61-3.56 (m, 2H), 3.17 (d, J = 5.3 Hz, 1H), 3.03-2.97 (m, 2H), 2.69 (s, 2H), 2.65-2.60 (m, 2H), 2.40-2.38 (m, 1H), 2.11 (d, J = 7.3 Hz, 2H), 1.86 (d, J = 11.1 Hz, 2H), 1.79-1.73 (m, 2H), 1.71 (s, 2H), 1.68-1.60 (m, 4H), 1.18 (d, J = 7.2 Hz, 2H). m/z 842.47 [M + H]⁺. |
| 66 | ¹H NMR (600 MHz, CDCl₃) δ 8.28 (s, 1H), 8.08 (d, J = 9.1 Hz, 1H), 7.96 (d, J = 2.9 Hz, 1H), 7.64 (d, J = 8.3 Hz, 1H), 7.62 (d, J = 8.8 Hz, 1H), 7.29 (dd, J = 9.1, 3.0 Hz, 1H), 7.13 (d, J = 2.4 Hz, 1H), 6.97 (dd, J = 8.8, 2.6 Hz, 1H), 6.91 (s, 1H), 6.49 (dd, J = 8.4, 2.1 Hz, 1H), 4.95 (dd, J = 12.6, 5.4 Hz, 1H), 4.09 (s, 2H), 3.98-3.92 (m, 2H), 3.59 (d, J = 11.6 Hz, 2H), 3.43 (d, J = 10.2 Hz, 4H), 3.08-3.02 (m, 2H), 2.93-2.80 (m, 3H), 2.77-2.72 (m, 1H), 2.69 (ddd, J = |

TABLE 5-continued

| Example | NMR and/or MS data |
|---|---|
| | 12.7, 10.2, 5.4 Hz, 2H), 2.60-2.53 (m, 1H), 2.44 (d, J = 7.2 Hz, 1H), 2.39-2.34 (m, 1H), 2.16-2.10 (m, 1H), 2.06 (d, J = 14.0 Hz, 2H), 1.94 (td, J = 15.5, 4.0 Hz, 2H), 1.86-1.78 (m, 2H), 1.52-1.45 (m, 2H), 1.40-1.31 (m, 2H). m/z 824.33 [M + H]$^+$. |
| 67 | $^1$H NMR (600 MHz, CDCl$_3$) δ 8.15 (s, 1H), 8.07 (d, J = 9.0 Hz, 1H), 7.96 (d, J = 2.8 Hz, 1H), 7.65 (d, J = 8.3 Hz, 1H), 7.46 (d, J = 8.9 Hz, 1H), 7.29 (dd, J = 9.2, 3.1 Hz, 1H), 6.88 (d, J = 2.5 Hz, 1H), 6.75 (dd, J = 8.9, 2.5 Hz, 1H), 6.49 (dd, J = 8.3, 2.1 Hz, 1H), 4.94 (dd, J = 12.6, 5.4 Hz, 1H), 4.09 (s, 4H), 3.89 (d, J = 13.3 Hz, 2H), 3.59 (d, J = 12.1 Hz, 2H), 3.42 (s, 4H), 3.04-2.96 (m, 2H), 2.92-2.79 (m, 3H), 2.77-2.71 (m, 1H), 2.71-2.65 (m, 2H), 2.52 (d, J = 11.0 Hz, 1H), 2.43 (s, 1H), 2.38 (d, J = 6.5 Hz, 1H), 2.15-2.10 (m, 1H), 2.04 (d, J = 11.2 Hz, 2H), 1.92 (d, J = 9.2 Hz, 2H), 1.87-1.78 (m, 2H), 1.51-1.44 (m, 2H), 1.41-1.31 (m, 2H). m/z 790.37 [M + H]$^+$. |
| 68 | $^1$H NMR (600 MHz, CDCl$_3$) δ 8.64 (s, 1H), 8.35 (s, 1H), 8.08 (d, J = 9.2 Hz, 1H), 7.93 (d, J = 2.8 Hz, 1H), 7.67 (d, J = 8.5 Hz, 1H), 7.62 (d, J = 8.8 Hz, 1H), 7.31 (dd, J = 9.2, 2.9 Hz, 1H), 7.13 (d, J = 2.5 Hz, 1H), 7.02 (dd, J = 8.7, 2.2 Hz, 1H), 6.97 (dd, J = 8.8, 2.5 Hz, 1H), 4.94 (dd, J = 12.5, 5.4 Hz, 2H), 3.95 (d, J = 13.3 Hz, 2H), 3.86 (d, J = 13.0 Hz, 1H), 3.60 (d, J = 12.1 Hz, 2H), 3.48-3.36 (m, 4H), 3.09-3.02 (m, 2H), 2.92-2.87 (m, 1H), 2.84-2.79 (m, 1H), 2.75 (dd, J = 15.1, 3.5 Hz, 1H), 2.71 (dd, J = 16.1, 10.4 Hz, 2H), 2.55 (d, J = 11.2 Hz, 1H), 2.41 (s, 4H), 2.24 (d, J = 6.9 Hz, 2H), 2.15-2.11 (m, 1H), 2.06 (d, J = 13.9 Hz, 2H), 1.97-1.90 (m, 2H), 1.87 (d, J = 12.1 Hz, 2H), 1.62 (s, 4H), 1.58 (d, J = 5.2 Hz, 4H), 1.37-1.31 (m, 2H). m/z 880.34 [M + H]$^+$. |
| 69 | $^1$H NMR (600 MHz, CDCl$_3$) δ 8.81 (s, 1H), 8.18 (s, 1H), 8.07 (d, J = 9.1 Hz, 1H), 7.96 (d, J = 2.9 Hz, 1H), 7.67 (d, J = 8.6 Hz, 1H), 7.46 (d, J = 8.9 Hz, 1H), 7.30 (dd, J = 9.2, 2.9 Hz, 1H), 7.02 (dd, J = 8.6, 2.2 Hz, 1H), 6.88 (d, J = 2.5 Hz, 1H), 6.75 (dd, J = 8.9, 2.5 Hz, 1H), 4.95 (dd, J = 12.5, 5.4 Hz, 1H), 3.89 (d, J = 13.2 Hz, 2H), 3.60 (d, J = 12.3 Hz, 2H), 3.47-3.35 (m, 4H), 3.02-2.95 (m, 2H), 2.90 (d, J = 17.3 Hz, 1H), 2.87-2.80 (m, 1H), 2.78-2.73 (m, 1H), 2.73-2.66 (m, 2H), 2.55-2.50 (m, 1H), 2.47-2.35 (m, 4H), 2.24 (d, J = 7.1 Hz, 2H), 2.17-2.12 (m, 1H), 2.04 (d, J = 13.4 Hz, 2H), 1.96-1.89 (m, 2H), 1.87 (d, J = 12.0 Hz, 2H), 1.66-1.60 (m, 4H), 1.38-1.31 (m, 2H). m/z 846.32 [M + H]$^+$. |
| 70 | $^1$H NMR (600 MHz, CDCl$_3$) δ 8.63 (s, 1H), 8.37 (s, 1H), 8.09 (d, J = 9.0 Hz, 1H), 7.93 (d, J = 2.7 Hz, 1H), 7.68 (d, J = 8.5 Hz, 1H), 7.62 (d, J = 8.8 Hz, 1H), 7.34-7.30 (m, 1H), 7.30-7.28 (m, 1H), 7.14 (d, J = 2.3 Hz, 1H), 7.05 (dd, J = 8.6, 2.3 Hz, 1H), 6.97 (dd, J = 8.8, 2.5 Hz, 1H), 4.94 (dd, J = 12.5, 5.4 Hz, 1H), 4.02-3.94 (m, 2H), 3.60 (d, J = 12.1 Hz, 2H), 3.10-3.03 (m, 2H), 3.03-2.96 (m, 2H), 2.94-2.87 (m, 1H), 2.87-2.79 (m, 1H), 2.78-2.73 (m, 1H), 2.73-2.67 (m, 2H), 2.62 (s, 1H), 2.56 (s, 2H), 2.51 (s, 2H), 2.24 (d, J = 6.7 Hz, 2H), 2.17-2.11 (m, 1H), 2.06 (d, J = 13.8 Hz, 2H), 1.98 (d, J = 14.0 Hz, 2H), 1.93 (td, J = 18.1, 6.6 Hz, 1H), 1.87 (d, J = 10.9 Hz, 2H), 1.75-1.59 (m, 8H), 1.36-1.28 (m, 2H). m/z 895.36 [M + H]$^+$. |
| 71 | $^1$H NMR (600 MHz, CDCl$_3$) δ 8.57 (s, 1H), 8.26 (s, 1H), 8.08 (d, J = 9.1 Hz, 1H), 7.93 (d, J = 2.9 Hz, 1H), 7.68 (d, J = 8.5 Hz, 1H), 7.46 (d, J = 8.9 Hz, 1H), 7.31 (dd, J = 3.0 Hz, 1H), 7.29 (dd, J = 5.7, 2.5 Hz, 1H), 7.05 (dd, J = 8.6, 2.3 Hz, 1H), 6.89 (d, J = 2.5 Hz, 1H), 6.75 (dd, J = 8.9, 2.5 Hz, 1H), 4.94 (dd, J = 12.5, 5.4 Hz, 2H), 3.98 (d, J = 13.0 Hz, 2H), 3.90 (d, J = 13.1 Hz, 2H), 3.60 (d, J = 12.0 Hz, 2H), 3.01 (dd, J = 17.4, 7.2 Hz, 2H), 2.94-2.87 (m, 1H), 2.87-2.80 (m, 1H), 2.79-2.73 (m, 1H), 2.73-2.67 (m, 2H), 2.61 (d, J = 15.1 Hz, 3H), 2.51 (d, J = 18.6 Hz, 3H), 2.23 (d, J = 7.1 Hz, 2H), 2.17-2.12 (m, 1H), 2.07-2.01 (m, 2H), 2.00-1.95 (m, 2H), 1.92 (d, J = 9.3 Hz, 1H), 1.88 (d, J = 14.1 Hz, 2H), 1.63 (s, 8H), 1.33 (d, J = 11.8 Hz, 2H). m/z 861.34 [M + H]$^+$. |
| 72 | $^1$H NMR (600 MHz, CDCl$_3$) δ 8.62 (d, J = 6.5 Hz, 1H), 8.05 (s, 1H), 8.04 (d, J = 9.2 Hz, 1H), 7.99 (d, J = 2.8 Hz, 1H), 7.68 (d, J = 8.5 Hz, 1H), 7.65 (d, J = 8.8 Hz, 1H), 7.30 (d, J = 3.0 Hz, 1H), 7.28 (d, J = 2.4 Hz, 1H), 7.17 (d, J = 2.4 Hz, 1H), 7.05 (dd, J = 8.6, 2.3 Hz, 1H), 7.01 (dd, J = 8.8, 2.6 Hz, 1H), 4.94 (dd, J = 12.6, 5.4 Hz, 1H), 3.99 (d, J = 12.8 Hz, 2H), 3.89 (d, J = 13.4 Hz, 2H), 3.63 (d, J = 12.2 Hz, 2H), 3.37 (d, J = 13.1, 2.6 Hz, 2H), 3.00 (t, J = 11.6 Hz, 2H), 2.90 (dd, J = 16.9, 3.3 Hz, 1H), 2.84-2.79 (m, 1H), 2.76 (d, J = 5.1 Hz, 1H), 2.73-2.69 (m, 2H), 2.67-2.56 (m, 4H), 2.52-2.46 (m, 2H), 2.44-2.39 (m, 2H), 2.39-2.32 (m, 2H), 2.23 (d, J = 7.0 Hz, 2H), 2.16-2.11 (m, 1H), 2.09-2.02 (m, 2H), 1.98 (d, J = 11.5 Hz, 2H), 1.88 (d, J = 12.9 Hz, 2H), 1.69-1.59 (m, 4H), 1.39-1.30 (m, 2H). m/z 913.45 [M + H]$^+$. |
| 73 | $^1$H NMR (600 MHz, CDCl$_3$) δ 9.71 (s, 1H), 8.45 (s, 1H), 8.38 (d, J = 2.7 Hz, 1H), 8.07 (d, J = 9.0 Hz, 1H), 7.99 (d, J = 2.7 Hz, 1H), 7.67 (d, J = 8.5 Hz, 1H), 7.31-7.29 (m, 1H), 7.29 (d, J = 4.7 Hz, 1H), 7.05 (dd, J = 8.6, 2.1 Hz, 1H), 4.95 (dd, J = 12.6, 5.4 Hz, 1H), 3.97 (d, J = 13.2 Hz, 4H), 3.61 (d, J = 12.1 Hz, 2H), 3.11 (dd, J = 18.1, 6.6 Hz, 2H), 2.98 (t, J = 12.7 Hz, 2H), 2.92-2.87 (m, 1H), 2.87-2.81 (m, 1H), 2.79-2.74 (m, 1H), 2.73-2.66 (m, 2H), 2.64-2.54 (m, 4H), 2.52-2.40 (m, 4H), 2.22 (d, J = 7.0 Hz, 2H), 2.17-2.13 (m, J = 9.0, 3.9 Hz, 1H), 2.12-2.07 (m, 2H), 2.02-1.93 (m, 4H), 1.87 (d, J = 12.4 Hz, 2H), 1.69-1.58 (m, 3H), 1.38-1.29 (m, 2H). m/z 896.47 [M + H]$^+$. |
| 74 | $^1$H NMR (600 MHz, CDCl$_3$) δ 8.64 (d, J = 6.3 Hz, 1H), 8.45 (d, J = 2.8 Hz, 1H), 8.14 (s, 1H), 8.04 (d, J = 9.1 Hz, 1H), 7.99 (d, J = 2.9 Hz, 1H), 7.68 (d, J = 8.5 Hz, 1H), 7.33 (d, J = 2.8 Hz, 1H), 7.31-7.28 (m, 1H), 7.06 (dd, J = 8.6, 2.3 Hz, 1H), 4.94 (dd, J = 12.6, 5.4 Hz, 1H), 3.99 (d, J = 13.0 Hz, 2H), 3.94 (d, J = 13.5 Hz, 2H), 3.64 (d, J = 12.2 Hz, 2H), 3.44 (td, J = 13.2, 2.7 Hz, 2H), 3.00 (t, J = 11.5 Hz, 2H), 2.92-2.87 (m, 1H), 2.85-2.78 (m, 1H), 2.77-2.73 (m, 1H), 2.73-2.69 (m, 2H), 2.63 (s, 4H), 2.54-2.48 (m, 2H), 2.48-2.35 (m, 4H), 2.24 (d, J = 6.8 Hz, 2H), 2.17-2.07 (m, 3H), 1.98 (d, J = 12.5 Hz, 2H), 1.88 (d, J = 12.4 Hz, 2H), 1.72-1.61 (m, 4H), 1.39-1.31 (m, 2H). m/z 914.52 [M + H]$^+$. |
| 75 | $^1$H NMR (600 MHz, CDCl$_3$) δ 8.45 (s, 1H), 8.06 (d, J = 8.5 Hz, 1H), 7.94 (d, J = 2.8 Hz, 1H), 7.83 (d, J = 8.7 Hz, 1H), 7.62 (d, J = 8.8 Hz, 1H), 7.29 (d, J = 8.9 Hz, 1H), 7.13 (s, 1H), 6.97 (d, J = 8.7 Hz, 1H), 6.67 (d, J = 8.8 Hz, 1H), 5.20 (dd, J = 13.2, 5.3 Hz, 1H), 4.50 (m, 2H), 4.30 (d, J = 16.2 Hz, 1H), 4.17 (d, J = 16.4 Hz, 1H), 3.96 (d, J = 13.1 Hz, 2H), 3.60 (d, J = 12.0 Hz, 2H), 3.12-3.01 (m, 2H), 3.00-2.92 (m, 1H), 2.91-2.89 (m, 1H), 2.85-2.76 (m, 2H), 2.75-2.67 (m, 2H), 2.62 (m, 2H), 2.54 (m, 4H), 2.37-2.29 (m, 2H), 2.23 (s, 3H), 2.06 (d, J = 10.8 Hz, 2H), 1.99-1.91 (m, 2H), 1.86 (m, 2H), 1.54-1.52 (m, 2H), 1.45 (s, 2H), 1.34 (d, J = 9.3 Hz, 1H), 1.25 (s, 2H), 0.84 (s, 2H). m/z 882.56 [M + H]$^+$. |
| 76 | $^1$H NMR (600 MHz, CDCl$_3$) δ 9.10 (s, 1H), 8.22 (s, 1H), 8.07 (d, J = 9.1 Hz, 1H), 7.97 (d, J = 2.9 Hz, 1H), 7.62 (d, J = 8.8 Hz, 1H), 7.58-7.53 (m, 1H), 7.37 (d, J = 7.1 Hz, 1H), 7.30 (dd, J = 9.1, 2.9 Hz, 1H), 7.16 (d, J = 8.5 Hz, 1H), 7.12 (d, J = 2.4 Hz, 1H), 6.96 (dd, J = 8.8, 2.5 Hz, 1H), 4.97 (dd, J = 12.6, 5.4 Hz, 1H), 3.94 (d, J = 13.1 Hz, 2H), 3.86-3.76 (m, 2H), 3.61 (d, J = 12.2 Hz, 2H), 3.07-2.98 (m, 2H), 2.97-2.87 (m, 3H), 2.87-2.80 (m, 1H), 2.76-2.72 (m, 1H), 2.72-2.67 (m, 2H), 2.67-2.61 (m, 2H), 2.57-2.52 (m, 1H), 2.52-2.36 (m, 4H), 2.23 (d, J = 7.1 Hz, 2H), 2.15-2.10 (m, 1H), 2.08-2.02 (m, 2H), 2.01-1.91 (m, 3H), 1.91-1.84 (m, 2H), 1.83-1.75 (m, 2H), 1.69-1.62 (m, 2H), 1.38-1.29 (m, 2H). m/z 895.56 [M + H]$^+$. |
| 77 | $^1$H NMR (600 MHz, DMSO-d6) δ 11.09 (s, 1H), 10.25 (s, 1H), 7.99 (d, J = 2.6 Hz, 1H), 7.90 (d, J = 9.0 Hz, 1H), 7.82 (d, J = 8.9 Hz, 1H), 7.69 (d, J = 8.5 Hz, 1H), 7.38 (d, J = 6.4 Hz, 2H), 7.31 (d, J = 2.3 Hz, 1H), 7.28 (d, J = 7.5 Hz, 1H), 7.25 (dd, J = 9.0, 2.5 Hz, 1H), 5.08 (dd, J = 12.9, 5.4 Hz, 1H), 4.10 (d, J = 13.4 Hz, 2H), 3.64 (d, J = 11.6 Hz, 2H), 3.46 (s, 4H), 3.00 (t, J = 11.6 Hz, 3H), 2.89 (ddd, J = 17.0, 14.1, 5.5 Hz, 2H), 2.75 (d, J = 15.9 Hz, 1H), 2.59 (dt, J = 11.2, 8.2 Hz, 4H), 2.55-2.51 (m, 2H), 2.47-2.35 (m, 5H), 2.01 (dd, J = 13.2, 8.2 Hz, 1H), 1.91 (s, 1H), 1.86 (d, J = 10.6 Hz, 2H), 1.74 (d, J = 11.2 Hz, 2H), 1.70-1.59 (m, 3H), 1.26 (s, 4H). m/z 867.50 [M + H]$^+$. |

TABLE 5-continued

| Example | NMR and/or MS data |
|---|---|
| 78 | $^1$H NMR (600 MHz, CDCl$_3$) δ 8.79 (s, 1H), 8.09 (s, 1H), 8.07 (d, J = 9.1 Hz, 1H), 7.96 (d, J = 2.9 Hz, 1H), 7.85 (d, J = 8.8 Hz, 1H), 7.62 (d, J = 8.8 Hz, 1H), 7.31-7.28 (m, 1H), 7.13 (d, J = 2.4 Hz, 1H), 6.97 (dd, J = 8.9, 2.6 Hz, 1H), 6.65 (d, J = 8.9 Hz, 1H), 5.20 (dd, J = 13.4, 5.0 Hz, 1H), 4.32 (d, J = 16.3 Hz, 1H), 4.18 (d, J = 16.3 Hz, 1H), 3.96 (d, J = 13.2 Hz, 2H), 3.76-3.66 (m, 4H), 3.59 (d, J = 12.0 Hz, 2H), 3.57-3.51 (m, J = 7.0 Hz, 1H), 3.09-2.99 (m, 3H), 2.97-2.89 (m, 2H), 2.86-2.79 (m, 1H), 2.73-2.66 (m, 2H), 2.58-2.51 (m, 1H), 2.49-2.38 (m, 4H), 2.37-2.28 (m, 2H), 2.24-2.19 (m, 1H), 2.10-2.03 (m, 2H), 1.99-1.91 (m, 2H), 1.86-1.79 (m, 2H), 1.66-1.58 (m, 2H), 1.52-1.44 (m, 2H), 1.41-1.31 (m, 2H). m/z 854.50 [M + H]$^+$. |
| 79 | $^1$H NMR (600 MHz, DMSO) δ 11.08 (s, 1H), 10.24 (s, 1H), 7.97 (d, J = 2.8 Hz, 1H), 7.90 (d, J = 9.0 Hz, 1H), 7.81 (d, J = 8.9 Hz, 1H), 7.68 (d, J = 8.5 Hz, 1H), 7.36 (dd, J = 9.1, 2.9 Hz, 1H), 7.34-7.30 (m, 2H), 7.25 (d, J = 8.2 Hz, 2H), 5.07 (dd, J = 12.8, 5.4 Hz, 1H), 4.11-4.08 (m, 2H), 3.61 (d, J = 11.9 Hz, 2H), 3.42 (s, 6H), 3.17 (d, J = 5.2 Hz, 2H), 3.00 (t, J = 11.5 Hz, 2H), 2.88-2.86 (m, 1H), 2.77-2.75 (m, 2H), 2.68-2.55 (m, 6H), 2.46 (s, 7H), 2.27 (s, 2H), 2.07-1.96 (m, 1H), 1.94-1.82 (m, 2H), 1.73 (d, J = 12.1 Hz, 2H), 1.64 (dd, J = 20.9, 11.6 Hz, 2H), 1.40 (s, 1H), 1.28-1.07 (m, 3H). m/z 881.52 [M + H]$^+$. |
| 80 | $^1$H NMR (600 MHz, CDCl$_3$) δ 9.20 (s, 1H), 8.25 (s, 1H), 8.09 (d, J = 9.1 Hz, 1H), 7.99 (d, J = 2.9 Hz, 1H), 7.86 (d, J = 8.8 Hz, 1H), 7.64 (d, J = 8.8 Hz, 1H), 7.31 (dd, J = 9.1, 2.9 Hz, 1H), 7.15 (d, J = 2.4 Hz, 1H), 6.99 (dd, J = 8.8, 2.5 Hz, 1H), 6.65 (d, J = 8.9 Hz, 1H), 5.23 (dd, J = 13.4, 5.1 Hz, 1H), 4.33 (d, J = 16.3 Hz, 1H), 4.20 (d, J = 16.3 Hz, 1H), 3.97 (d, J = 13.3 Hz, 2H), 3.76-3.64 (m, 4H), 3.61 (d, J = 12H), 3.56-3.49 (m, 2H), 3.09-3.03 (m, 2H), 2.97-2.90 (m, 1H), 2.90-2.85 (m, 1H), 2.85-2.80 (m, 2H), 2.80-2.75 (m, 1H), 2.72-2.66 (m, 2H), 2.61 (d, J = 6.7 Hz, 2H), 2.59-2.55 (m, 1H), 2.50 (t, J = 5.1 Hz, 4H), 2.42-2.31 (m, 3H), 2.29-2.22 (m, 1H), 2.11-2.06 (m, 2H), 2.01-1.93 (m, 2H), 1.84 (d, J = 12.0 Hz, 2H), 1.51-1.45 (m, 1H), 1.42-1.33 (m, J = 12.0, 8.8 Hz, 2H). m/z 868.51 [M + H]$^+$. |
| 81 | $^1$H NMR (600 MHz, CDCl$_3$) δ 9.50 (s, 1H), 8.40 (s, 1H), 8.07 (d, J = 9.1 Hz, 1H), 7.98 (d, J = 2.9 Hz, 1H), 7.68 (d, J = 8.5 Hz, 1H), 7.61 (d, J = 8.8 Hz, 1H), 7.32-7.27 (m, 2H), 7.03 (dd, J = 8.6, 2.2 Hz, 1H), 6.96 (dd, J = 8.9, 2.5 Hz, 1H), 4.95 (dd, J = 12.6, 5.4 Hz, 1H), 3.94 (d, J = 13.2 Hz, 2H), 3.60 (d, J = 12.1 Hz, 2H), 3.47-3.35 (m, 4H), 3.06-2.97 (m, 2H), 2.95-2.81 (m, 4H), 2.77-2.66 (m, 3H), 2.62-2.50 (m, 4H), 2.23 (d, J = 7.0 Hz, 2H), 2.22-2.17 (m, 1H), 2.17-2.12 (m, 1H), 2.09-2.02 (m, 2H), 1.98-1.92 (m, 2H), 1.92-1.84 (m, 2H), 1.74 (d, J = 12.2 Hz, 2H), 1.57-1.47 (m, 2H), 1.39-1.30 (m, 2H), 1.30-1.20 (m, 4H). m/z 909.51 [M + H]$^+$. |
| 82 | $^1$H NMR (600 MHz, CDCl$_3$) δ 9.75 (d, J = 45.7 Hz, 1H), 8.44 (d, J = 13.9 Hz, 1H), 8.08 (d, J = 9.1 Hz, 1H), 7.99 (d, J = 2.9 Hz, 1H), 7.69 (d, J = 8.5 Hz, 1H), 7.61 (d, J = 8.8 Hz, 1H), 7.30 (d, J = 9.2 Hz, 1H), 7.27 (d, J = 2.2 Hz, 1H), 7.12 (d, J = 2.3 Hz, 1H), 7.04 (dd, J = 8.6, 1.9 Hz, 1H), 6.96 (dd, J = 8.8, 2.5 Hz, 1H), 4.95 (dd, J = 12.6, 5.4 Hz, 1H), 3.94 (d, J = 13.2 Hz, 2H), 3.60 (d, J = 11.3 Hz, 2H), 3.41 (d, J = 4.2 Hz, 4H), 3.03 (t, J = 11.4 Hz, 2H), 2.92-2.87 (m, 1H), 2.87-2.81 (m, 1H), 2.79-2.72 (m, 2H), 2.72-2.66 (m, 2H), 2.65-2.57 (m, 3H), 2.57-2.52 (m, 3H), 2.50-2.41 (m, 2H), 2.41-2.33 (m, 3H), 2.33-2.27 (m, 1H), 2.25-2.21 (m, 1H), 2.21-2.17 (m, 1H), 2.16-2.12 (m, 1H), 2.09-2.03 (m, 2H), 2.02-1.97 (m, 1H), 1.97-1.91 (m, 2H), 1.91-1.83 (m, 2H), 1.52-1.46 (m, 1H), 1.40-1.31 (m, 2H). m/z 895.42 [M + H]$^+$. |
| 83 | $^1$H NMR (600 MHz, CDCl$_3$) δ 9.77 (s, 1H), 8.08 (d, J = 9.1 Hz, 1H), 7.98 (d, J = 2.9 Hz, 1H), 7.69 (d, J = 8.5 Hz, 1H), 7.61 (d, J = 8.8 Hz, 1H), 7.30 (dd, J = 9.1, 2.1 Hz, 1H), 7.27 (s, 1H), 7.12 (d, J = 2.4 Hz, 1H), 7.03 (dd, J = 8.6, 2.2 Hz, 1H), 6.95 (dd, J = 8.8, 2.5 Hz, 1H), 4.95 (dd, J = 12.6, 5.4 Hz, 1H), 3.97-3.90 (m, 2H), 3.61 (d, J = 11.8 Hz, 2H), 3.44-3.36 (m, 4H), 3.05-2.99 (m, 2H), 2.92-2.87 (m, 1H), 2.87-2.81 (m, 1H), 2.78-2.73 (m, 2H), 2.73-2.68 (m, 2H), 2.64-2.58 (m, 3H), 2.58-2.52 (m, 3H), 2.44-2.36 (m, 3H), 2.18-2.12 (m, 1H), 2.08-2.02 (m, 2H), 1.99-1.86 (m, 5H), 1.85-1.75 (m, 3H), 1.73-1.64 (m, 2H), 1.58-1.53 (m, 1H), 1.41-1.19 (m, 4H). m/z 895.24 [M + H]$^+$. |
| 84 | $^1$H NMR (600 MHz, CDCl$_3$) δ 9.28 (s, 1H), 8.27 (s, 1H), 8.07 (d, J = 9.1 Hz, 1H), 7.99 (d, J = 2.9 Hz, 1H), 7.67 (d, J = 8.5 Hz, 1H), 7.61 (d, J = 8.8 Hz, 1H), 7.30 (dd, J = 9.1, 2.9 Hz, 1H), 7.13 (d, J = 2.4 Hz, 1H), 7.03 (dd, J = 8.6, 2.3 Hz, 1H), 6.96 (dd, J = 8.8, 2.6 Hz, 1H), 4.94 (dd, J = 12.6, 5.4 Hz, 1H), 3.95 (d, J = 13.1 Hz, 4H), 3.60 (d, J = 11.5 Hz, 2H), 3.07-3.01 (m, 2H), 3.01-2.94 (m, 2H), 2.92-2.87 (m, 1H), 2.86-2.80 (m, 1H), 2.78-2.73 (m, 1H), 2.73-2.67 (m, 2H), 2.59-2.53 (m, 1H), 2.23-2.18 (m, 3H), 2.18-2.15 (m, 2H), 2.14 (s, 1H), 2.08-2.05 (m, 1H), 1.97-1.92 (m, 2H), 1.91-1.84 (m, 2H), 1.75 (s, 2H), 1.64-1.57 (m, 4H), 1.33-1.19 (m, 4H). m/z 854.50 [M + H]$^+$. |
| 85 | $^1$H NMR (600 MHz, CDCl$_3$) δ 9.49 (s, 1H), 8.37 (s, 1H), 8.06 (d, J = 9.1 Hz, 1H), 7.97 (d, J = 2.9 Hz, 1H), 7.66 (d, J = 8.4 Hz, 1H), 7.61 (d, J = 8.8 Hz, 1H), 7.28 (dd, J = 9.2, 3.0 Hz, 1H), 7.12 (d, J = 2.4 Hz, 1H), 6.98 (d, J = 2.1 Hz, 1H), 6.95 (dd, J = 8.8, 2.6 Hz, 1H), 6.70 (dd, J = 8.5, 2.2 Hz, 1H), 4.95 (dd, J = 12.6, 5.4 Hz, 1H), 3.97-3.90 (m, 2H), 3.70-3.63 (m, 2H), 3.59 (d, J = 12.2 Hz, 2H), 3.29 (dd, J = 10.0, 2.6 Hz, 2H), 3.06-2.98 (m, 4H), 2.93-2.87 (m, 1H), 2.86-2.80 (m, 1H), 2.78-2.71 (m, 1H), 2.71-2.66 (m, 2H), 2.66-2.61 (m, 2H), 2.57 (d, J = 9.3 Hz, 2H), 2.56-2.51 (m, 1H), 2.33 (d, J = 7.2 Hz, 2H), 2.17-2.11 (m, 1H), 2.09-2.02 (m, 2H), 1.97-1.89 (m, 2H), 1.85 (d, J = 11.7 Hz, 2H), 1.37-1.28 (m, 2H). m/z 838.38 [M + H]$^+$. |
| 86 | $^1$H NMR (600 MHz, CDCl$_3$) δ 9.33 (s, 1H), 8.43 (s, 1H), 8.08 (d, J = 9.1 Hz, 1H), 7.97 (d, J = 2.9 Hz, 1H), 7.69 (d, J = 8.5 Hz, 1H), 7.62 (d, J = 8.8 Hz, 1H), 7.30 (dd, J = 9.2, 3.0 Hz, 1H), 7.28 (d, J = 2.3 Hz, 1H), 7.13 (d, J = 2.5 Hz, 1H), 7.05 (dd, J = 8.6, 2.3 Hz, 1H), 6.96 (dd, J = 8.8, 2.6 Hz, 1H), 4.95 (dd, J = 12.6, 5.4 Hz, 1H), 3.94 (d, J = 9.9, 3.3 Hz, 2H), 3.60 (d, J = 12.2 Hz, 2H), 3.48-3.39 (m, 4H), 3.04 (td, J = 13.1, 2.8 Hz, 2H), 2.90 (d, J = 19.1 Hz, 1H), 2.83 (d, J = 4.2 Hz, 1H), 2.77-2.72 (m, 1H), 2.72-2.67 (m, 2H), 2.64-2.57 (m, 4H), 2.57 (d, J = 4.2 Hz, 1H), 2.48-2.43 (m, 2H), 2.17-2.12 (m, 1H), 2.08-2.02 (m, 2H), 1.98-1.90 (m, 2H), 1.83 (d, J = 11.9 Hz, 2H), 1.53 (dd, J = 14.5, 6.8 Hz, 2H), 1.48 (s, 1H), 1.43-1.35 (m, 2H). m/z 826.32 [M + H]$^+$. |
| 87 | $^1$H NMR (600 MHz, DMSO-d6) δ 11.07 (s, 1H), 10.22 (s, 1H), 7.97 (d, J = 3.0 Hz, 1H), 7.88 (d, J = 9.1 Hz, 1H), 7.67 (d, J = 8.5 Hz, 1H), 7.62 (d, J = 8.9 Hz, 1H), 7.36 (dd, J = 9.2, 3.0 Hz, 1H), 7.32 (s, 1H), 7.24 (dd, J = 8.7, 2.1 Hz, 1H), 7.15 (d, J = 2.5 Hz, 1H), 6.98 (dd, J = 9.1, 2.5 Hz, 1H), 5.06 (dd, J = 12.9, 5.4 Hz, 1H), 4.01 (d, J = 13.4 Hz, 2H), 3.61 (d, J = 12.3 Hz, 2H), 3.42 (s, 4H), 3.37 (s, 2H), 2.98-2.91 (m, 2H), 2.90-2.83 (m, 1H), 2.73 (s, 1H), 2.63-2.57 (m, 2H), 2.55 (d, J = 3.8 Hz, 1H), 2.54-2.50 (m, 2H), 2.39-2.32 (m, 2H), 2.02-1.97 (m, 1H), 1.81 (d, J = 10.2 Hz, 2H), 1.76 (d, J = 12.0 Hz, 2H), 1.61 (dd, J = 16.6, 7.4 Hz, 2H), 1.43 (s, 3H), 1.30-1.21 (m, 2H). m/z 792.33 [M + H]$^+$. |
| 88 | $^1$H NMR (600 MHz, CDCl3) δ 8.63 (d, J = 6.5 Hz, 1H), 8.10 (s, 1H), 8.04 (d, J = 9.1 Hz, 1H), 7.99 (d, J = 2.9 Hz, 1H), 7.70 (d, J = 8.5 Hz, 1H), 7.64 (d, J = 8.8 Hz, 1H), 7.31-7.29 (m, 2H), 7.16 (d, J = 2.5 Hz, 1H), 7.06 (dd, J = 8.6, 2.3 Hz, 1H), 7.01 (dd, J = 8.8, 2.6 Hz, 1H), 4.94 (dd, J = 12.6, 5.4 Hz, 1H), 3.88 (d, J = 13.5 Hz, 2H), 3.63 (d, J = 12.3 Hz, 2H), 3.53-3.42 (m, 4H), 3.37 (td, J = 13.2, 2.7 Hz, 2H), 2.93-2.79 (m, 3H), 2.73 (ddd, J = 13.5, 11.8, 5.0 Hz, 4H), 2.62-2.57 (m, 3H), 2.50-2.44 (m, 2H), 2.39 (ddd, J = 20.5, 13.7, 9.2 Hz, 2H), 2.15-2.11 (m, 1H), 2.08-2.01 (m, 2H), 1.84 (d, J = 11.9 Hz, 2H), 1.55-1.47 (m, 3H), 1.41 (dt, J = 19.8, 10.0 Hz, 2H). m/z 844.40 [M + H]$^+$. |
| 89 | $^1$H NMR (600 MHz, CDCl3) δ 9.23 (s, 1H), 8.39 (d, J = 2.8 Hz, 1H), 8.29 (s, 1H), 8.07 (d, J = 9.1 Hz, 1H), 7.98 (d, J = 2.9 Hz, 1H), 7.69 (d, J = 8.5 Hz, 1H), 7.33-7.27 (m, 3H), 7.05 (dd, J = 8.6, 2.3 Hz, 1H), 4.95 (dd, J = 12.6, 5.4 Hz, 1H), 3.98 (d, J = 13.3 Hz, 2H), 3.60 (d, J = 12.3 Hz, 2H), 3.51-3.40 (m, 4H), 3.16-3.09 (m, 2H), 2.85 (ddd, J = 23.0, 16.8, 11.5 Hz, 3H), 2.77-2.68 (m, 3H), 2.64-2.55 (m, 4H), 2.49-2.42 (m, 2H), 2.13 (ddd, J = 24.8, 10.8, 6.3 Hz, 3H), 2.01-1.94 (m, 2H), 1.83 (d, J = 12.2 Hz, 2H), 1.54-1.46 (m, 3H), 1.43-1.37 (m, 2H). m/z 827.38 [M + H]$^+$. |

TABLE 5-continued

| Example | NMR and/or MS data |
|---|---|
| 90 | $^1$H NMR (600 MHz, CDCl3) δ 8.64 (d, J = 6.4 Hz, 1H), 8.45 (d, J = 2.8 Hz, 1H), 8.13 (s, 1H), 8.04 (d, J = 9.1 Hz, 1H), 7.99 (d, J = 2.9 Hz, 1H), 7.70 (d, J = 8.5 Hz, 1H), 7.33 (d, J = 2.8 Hz, 1H), 7.30 (dd, J = 7.6, 2.5 Hz, 2H), 7.06 (dd, J = 8.6, 2.3 Hz, 1H), 4.96-4.93 (m, 1H), 3.93 (d, J = 13.4 Hz, 2H), 3.63 (d, J = 12.3 Hz, 2H), 3.48-3.39 (m, 6H), 2.91-2.80 (m, 3H), 2.74 (dd, J = 9.7, 7.3 Hz, 2H), 2.64-2.57 (m, 4H), 2.48-2.45 (m, 2H), 2.39 (ddd, J = 26.9, 12.4, 4.9 Hz, 2H), 2.14-2.08 (m, 3H), 1.84 (d, J = 12.2 Hz, 2H), 1.55-1.50 (m, 3H), 1.45-1.39 (m, 2H). m/z 845.35 [M + H]$^+$. |
| 91 | $^1$H NMR (600 MHz, CDCl3) δ 9.01 (s, 1H), 8.21 (s, 1H), 8.06 (d, J = 9.1 Hz, 1H), 7.96 (d, J = 2.9 Hz, 1H), 7.67 (d, J = 8.5 Hz, 1H), 7.61 (s, 1H), 7.28 (dd, J = 10.3, 2.5 Hz, 2H), 7.13 (d, J = 2.4 Hz, 1H), 7.03 (dd, J = 8.6, 2.3 Hz, 1H), 6.96 (dd, J = 8.8, 2.6 Hz, 1H), 4.94 (dd, J = 12.5, 5.4 Hz, 1H), 3.96 (d, J = 4.3 Hz, 2H), 3.58 (d, J = 12.2 Hz, 2H), 3.08-3.01 (m, 2H), 3.01-2.95 (m, 2H), 2.91-2.79 (m, 3H), 2.78-2.71 (m, 2H), 2.68 (d, J = 11.8 Hz, 2H), 2.64-2.48 (m, 6H), 2.40 (s, 2H), 2.24-2.19 (m, 1H), 2.13 (d, J = 2.4 Hz, 1H), 2.06 (dd, J = 17.9, 7.4 Hz, 2H), 2.01 (d, J = 6.3 Hz, 1H), 1.98-1.93 (m, 2H), 1.80 (d, J = 10.5 Hz, 2H), 1.62-1.60 (m, 2H), 1.49-1.45 (m, 2H), 1.39 (dd, J = 12.0, 8.5 Hz, 3H), 1.34-1.25 (m, 4H). m/z 909.55 [M + H]$^+$. |
| 92 | $^1$H NMR (600 MHz, CDCl3) δ 8.55 (s, 1H), 8.07 (d, J = 9.0 Hz, 1H), 7.96 (d, J = 2.9 Hz, 1H), 7.85 (d, J = 8.8 Hz, 1H), 7.62 (d, J = 8.8 Hz, 1H), 7.30 (dd, J = 9.3, 3.0 Hz, 2H), 7.14 (d, J = 2.6 Hz, 1H), 6.98 (dd, J = 8.9, 2.6 Hz, 1H), 6.66 (d, J = 8.9 Hz, 1H), 5.21 (dd, J = 13.3, 5.2 Hz, 1H), 4.32 (d, J = 16.3 Hz, 1H), 4.18 (d, J = 16.3 Hz, 1H), 3.96 (d, J = 13.3 Hz, 2H), 3.75-3.69 (m, 2H), 3.60 (d, J = 12.0 Hz, 2H), 3.11-3.01 (m, 2H), 2.92 (d, J = 15.6 Hz, 2H), 2.86-2.81 (m, 1H), 2.75-2.67 (m, 2H), 2.61-2.48 (m, 4H), 2.51-2.42 (m, 2H), 2.38-2.28 (m, 1H), 2.25-2.20 (m, 1H), 2.10-2.03 (m, 2H), 1.97-1.93 (m, 2H), 1.84 (d, J = 11.9 Hz, 2H), 1.52-1.46 (m, 2H), 1.41 (d, J = 8.7 Hz, 1H), 1.26 (s, 2H), 0.91-0.82 (m, 2H). m/z 813.43 [M + H]$^+$. |
| 93 | $^1$H NMR (600 MHz, CDCl$_3$) δ 9.14 (s, 1H), 8.24 (s, 1H), 8.09 (d, J = 9.0 Hz, 1H), 8.01-7.97 (m, 1H), 7.65-7.63 (m, 1H), 7.61 (dd, J = 8.3, 7.2 Hz, H), 7.43 (d, J = 7.2 Hz, 1H), 7.32 (dd, J = 9.1, 2.9 Hz, 2H), 7.19 (d, J = 8.3 Hz, 1H), 7.14 (d, J = 2.4 Hz, 1H), 6.99 (dd, J = 8.8, 2.5 Hz, 1H), 4.99 (dd, J = 12.5, 5.5 Hz, 1H), 3.96 (d, J = 13.2 Hz, 2H), 3.62 (d, J = 12.2 Hz, 2H), 3.47-3.35 (m, 4H), 3.10-3.02 (m, 2H), 2.94-2.89 (m, 1H), 2.88-2.82 (m, 1H), 2.79-2.75 (m, 1H), 2.75-2.67 (m, 4H), 2.59-2.54 (m, 1H), 2.54-2.49 (m, 2H), 2.18-2.12 (m, 1H), 2.11-2.07 (m, 2H), 2.00-1.92 (m, 2H), 1.85 (d, J = 11.2 Hz, 2H), 1.57-1.52 (m, 2H), 1.52-1.47 (m, 1H), 1.37-1.45 (m, 2H). m/z 826.23 [M + H]$^+$. |
| 94 | $^1$H NMR (600 MHz, CDCl3) δ 8.48 (s, 1H), 8.39 (s, 1H), 8.07 (d, J = 9.1 Hz, 1H), 7.97 (dd, J = 5.4, 3.0 Hz, 1H), 7.65 (dd, J = 8.4, 7.1 Hz, 1H), 7.61 (d, J = 8.8, 3.9 Hz, 1H), 7.30 (dd, J = 9.4, 6.8 Hz, 1H), 7.12 (dd, J = 5.2, 2.5 Hz, 1H), 6.97-6.91 (m, 2H), 6.66-6.63 (m, 1H), 4.95-4.91 (m, 1H), 3.97-3.90 (m, 2H), 3.61-3.54 (m, 2H), 3.51-3.36 (m, 4H), 3.28 (dd, J = 16.0, 9.7 Hz, 2H), 3.09-3.01 (m, 2H), 2.89-2.78 (m, 3H), 2.75 (ddd, J = 15.2, 9.3, 4.3 Hz, 2H), 2.71-2.64 (m, 2H), 2.61-2.55 (m, 2H), 2.49-2.47 (m, 2H), 2.42 (d, J = 9.2 Hz, 1H), 2.14-2.10 (m, 1H), 2.07 (dd, J = 8.5, 5.3 Hz, 2H), 1.91 (dd, J = 20.3, 8.6 Hz, 2H), 1.87 (d, J = 7.2 Hz, 2H), 1.79 (t, J = 13.1 Hz, 2H), 1.46 (d, J = 8.1 Hz, 3H). m/z 866.46 [M + H]$^+$. |
| 95 | $^1$H NMR (600 MHz, CDCl$_3$) δ 9.08 (s, 1H), 8.24 (s, 1H), 8.07 (d, J = 7.5 Hz, 1H), 7.97 (s, 1H), 7.67-7.59 (m, 2H), 7.29 (d, J = 9.1 Hz, 1H), 7.13 (s, 1H), 6.97 (d, J = 8.6 Hz, 1H), 6.78 (s, 1H), 6.50 (d, J = 8.3 Hz, 1H), 4.98-4.91 (m, 1H), 3.95 (d, J = 11.3 Hz, 2H), 3.73 (s, 4H), 3.59 (d, J = 11.5 Hz, 2H), 3.08-2.99 (m, 2H), 2.89 (d, J = 16.8 Hz, 1H), 2.86-2.79 (m, 1H), 2.75 (d, J = 16.9 Hz, 1H), 2.73-2.65 (m, 2H), 2.60-2.52 (m, 1H), 2.50-2.21 (m, 6H), 2.17-2.10 (m, 1H), 2.10-1.99 (m, 3H), 1.99-1.90 (m, 2H), 1.90-1.84 (m, 4H), 1.84-1.76 (m, 2H), 1.53-1.47 (m, 2H), 1.41 (dd, J = 25.5, 14.0 Hz, 2H). m/z 866.53 [M + H]$^+$. |
| 96 | $^1$H NMR (600 MHz, CDCl$_3$) δ 8.93 (s, 1H), 8.18 (s, 1H), 8.07 (d, J = 9.0 Hz, 1H), 7.81 (d, J = 8.5 Hz, 1H), 7.62 (d, J = 8.6 Hz, 1H), 7.29 (d, J = 9.2 Hz, 1H), 7.13 (s, 1H), 6.97 (d, J = 8.6 Hz, 1H), 6.23 (d, J = 8.5 Hz, 1H), 5.22-5.16 (m, 1H), 4.32 (d, J = 16.2 Hz, 1H), 4.19 (d, J = 16.4 Hz, 1H), 3.95 (d, J = 12.7 Hz, 2H), 3.92-3.77 (m, 4H), 3.60 (d, J = 12.7 Hz, 2H), 3.11-3.01 (m, 2H), 2.94-2.89 (m, 1H), 2.87-2.78 (m, 2H), 2.73-2.65 (m, 2H), 2.59-2.51 (m, 1H), 2.50-2.40 (m, 2H), 2.40-2.28 (m, 4H), 2.24-2.18 (m, 1H), 2.10-2.03 (m, 2H), 1.99-1.91 (m, 2H), 1.91-1.83 (m, 4H), 1.81 (d, J = 12.2 Hz, 1H), 1.53-1.47 (m, 2H), 1.47-1.43 (m, 1H), 1.43-1.34 (m, 2H). m/z 853.50 [M + H]$^+$. |
| 97 | $^1$H NMR (600 MHz, CDCl$_3$) δ 11.09 (s, 1H), 10.24 (s, 1H), 7.98 (d, J = 3.0 Hz, 1H), 7.90 (d, J = 9.0 Hz, 1H), 7.82 (d, J = 8.9 Hz, 1H), 7.69 (d, J = 8.5 Hz, 1H), 7.40-7.33 (m, 2H), 7.31 (s, 1H), 7.26 (dd, J = 14.8, 5.8 Hz, 2H), 5.08 (dd, J = 12.9, 5.4 Hz, 1H), 4.10 (d, J = 13.0 Hz, 2H), 3.62 (d, J = 12.3 Hz, 2H), 3.45 (s, 7H), 3.17 (d, J = 5.1 Hz, 1H), 3.00 (t, J = 11.6 Hz, 4H), 2.95-2.83 (m, 2H), 2.75 (d, J = 14.7 Hz, 2H), 2.68-2.55 (m, 7H), 2.39 (d, J = 1.8 Hz, 5H), 2.08-1.97 (m, 1H), 1.86 (d, J = 10.8 Hz, 2H), 1.72 (d, J = 11.0 Hz, 2H), 1.65 (dd, J = 21.1, 12.0 Hz, 3H), 1.43 (s, 1H), 1.24 (t, J = 11.6 Hz, 5H). m/z 881.52 [M + H]$^+$. |
| 98 | $^1$H NMR (600 MHz, CDCl$_3$) δ 8.79 (s, 1H), 8.10 (s, 1H), 8.06 (d, J = 9.0 Hz, 1H), 7.95 (d, J = 2.9 Hz, 1H), 7.86 (d, J = 8.8 Hz, 1H), 7.62 (d, J = 8.8 Hz, 1H), 7.28 (dd, J = 9.2, 3.0 Hz, 1H), 7.13 (d, J = 2.4 Hz, 1H), 6.97 (dd, J = 8.8, 2.5 Hz, 1H), 6.65 (d, J = 8.9 Hz, 1H), 5.21 (dd, J = 13.3, 5.1 Hz, 1H), 4.31 (d, J = 16.3 Hz, 1H), 4.18 (d, J = 16.3 Hz, 1H), 3.96 (d, J = 13.2 Hz, 2H), 3.78-3.68 (m, 4H), 3.62-3.55 (m, 2H), 3.09-3.02 (m, 2H), 2.94-2.89 (m, 1H), 2.87-2.79 (m, 2H), 2.74-2.66 (m, 2H), 2.58-2.52 (m, 1H), 2.46-2.38 (m, 4H), 2.37-2.29 (m, 2H), 2.25-2.19 (m, 1H), 2.09-2.02 (m, 2H), 1.99-1.90 (m, 2H), 1.83-1.78 (m, 2H), 1.69-1.61 (m, 2H), 1.50-1.44 (m, 2H), 1.42-1.32 (m, 2H), 1.32-1.26 (m, 2H). m/z 868.49 [M + H]$^+$. |
| 99 | $^1$H NMR (600 MHz, CDCl$_3$) δ 8.96 (s, 1H), 8.20 (s, 1H), 8.07 (d, J = 9.1 Hz, 1H), 7.96 (d, J = 2.9 Hz, 1H), 7.64 (d, J = 8.3 Hz, 1H), 7.62 (d, J = 8.8 Hz, 1H), 7.29 (dd, J = 9.3, 2.8 Hz, 1H), 7.13 (d, J = 2.3 Hz, 1H), 6.97 (dd, J = 8.9, 2.4 Hz, 1H), 6.78 (d, J = 2.0 Hz, 1H), 6.52 (dd, J = 8.2, 2.0 Hz, 1H), 4.93 (dd, J = 12.5, 5.4 Hz, 1H), 4.12-4.07 (m, 2H), 3.95 (d, J = 13.3 Hz, 2H), 3.91-3.86 (m, 2H), 3.58 (d, J = 12.1 Hz, 2H), 3.42-3.37 (m, 1H), 3.09-3.01 (m, 2H), 2.92-2.86 (m, 1H), 2.84-2.79 (m, 1H), 2.77-2.72 (m, 1H), 2.72-2.65 (m, 2H), 2.59-2.51 (m, 3H), 2.51-2.45 (m, 2H), 2.45-2.38 (m, 2H), 2.16-2.11 (m, 1H), 2.10-2.02 (m, 3H), 1.98-1.90 (m, 2H), 1.84-1.79 (m, 1H), 1.61 (s, 4H), 1.52-1.46 (m, 2H), 1.43-1.36 (m, 2H). m/z 881.54 [M + H]$^+$. |
| 100 | $^1$H NMR (600 MHz, CDCl$_3$) δ 8.39 (s, 1H), 8.06 (d, J = 9.1 Hz, 1H), 7.95 (d, J = 2.9 Hz, 1H), 7.81 (d, J = 8.5 Hz, 1H), 7.62 (d, J = 8.9 Hz, 1H), 7.29 (d, J = 3.0 Hz, 1H), 7.13 (d, J = 2.5 Hz, 1H), 6.98 (d, J = 8.9 Hz, 1H), 6.25 (d, J = 8.6 Hz, 1H), 5.18 (dd, J = 13.2, 5.1 Hz, 1H), 4.31 (d, J = 16.3 Hz, 1H), 4.23-4.14 (m, 2H), 4.04-3.93 (m, 4H), 3.58 (d, J = 12.0 Hz, 2H), 3.39-3.35 (m, 1H), 3.10-3.03 (m, 2H), 2.94-2.89 (m, 1H), 2.85-2.87 (m, 1H), 2.72-2.67 (m, 2H), 2.57-2.50 (m, 2H), 2.50-2.45 (m, 2H), 2.45-2.38 (m, 2H), 2.34-2.29 (m, 1H), 2.24-2.19 (m, 1H), 2.09-2.04 (m, 2H), 1.98-1.91 (m, 2H), 1.81 (d, J = 10.7 Hz, 2H), 1.73-1.59 (m, 4H), 1.53-1.46 (m, 2H), 1.43-1.36 (m, 2H). m/z 868.51 [M + H]$^+$. |
| 101 | $^1$H NMR (600 MHz, CDCl$_3$) δ 10.12 (s, 1H), 8.64 (s, 1H), 8.00 (d, J = 9.1 Hz, 1H), 7.88 (d, J = 2.9 Hz, 1H), 7.57 (d, J = 8.4 Hz, 1H), 7.53 (d, J = 8.8 Hz, 1H), 7.20 (d, J = 3.0 Hz, 1H), 7.05 (d, J = 2.5 Hz, 1H), 6.89 (d, J = 2.1 Hz, 1H), 6.87 (dd, J = 9.0, 2.7 Hz, 1H), 6.61 (dd, J = 8.5, 2.1 Hz, 1H), 4.88 (dd, J = 12.5, 5.4 Hz, 1H), 3.84 (d, J = 13.2 Hz, 2H), 3.58-3.50 (m, 2H), 3.44 (d, J = 9.7 Hz, 2H), 3.30-3.21 (m, 2H), 3.01-2.94 (m, 2H), 2.93-2.87 (m, 2H), 2.84-2.78 (m, 1H), 2.78-2.72 (m, 1H), 2.71-2.63 (m, 1H), 2.61-2.50 (m, 4H), 2.47-2.36 (m, 2H), 2.09-2.03 (m, 1H), 1.99-1.91 (m, 2H), 1.88-1.79 (m, 2H), 1.71 (d, J = 12.0 Hz, 2H), 1.66-1.53 (m, 2H), 1.45-1.38 (m, 2H), 1.35-1.30 (m, 1H), 1.30-1.22 (m, 2H). m/z 852.49 [M + H]$^+$. |

TABLE 5-continued

| Example | NMR and/or MS data |
|---|---|
| 102 | ¹H NMR (600 MHz, CDCl₃) δ 9.25 (s, 1H), 8.29 (s, 1H), 8.07 (d, J = 8.8 Hz, 1H), 7.97 (s, 1H), 7.68 (d, J = 8.5 Hz, 1H), 7.62 (d, J = 8.9 Hz, 1H), 7.31-7.28 (m, 2H), 7.13 (s, 1H), 7.05 (d, J = 8.6 Hz, 1H), 6.97 (d, J = 8.8 Hz, 1H), 4.95 (dd, J = 11.9, 4.8 Hz, 1H), 3.99 (d, J = 12.6 Hz, 2H), 3.95 (d, J = 12.9 Hz, 2H), 3.59 (d, J = 11.6 Hz, 2H), 3.09-3.01 (m, 2H), 3.01-2.94 (m, 2H), 2.94-2.86 (m, 1H), 2.86-2.80 (m, 1H), 2.78-2.73 (m, 1H), 2.73-2.67 (m, 2H), 2.67-2.61 (m, 1H), 2.58-2.53 (m, 1H), 2.54-2.46 (m, 2H), 2.27 (s, 3H), 2.18-2.12 (m, 1H), 2.10-2.04 (m, 2H), 1.99-1.92 (m, 2H), 1.88 (d, J = 12.6 Hz, 2H), 1.80 (d, J = 12.4 Hz, 2H), 1.49-1.42 (m, 3H), 1.41-1.33 (m, 2H), 1.30-1.25 (m, 2H). m/z 854.51 [M + H]⁺. |
| 103 | ¹H NMR (600 MHz, CDCl₃) δ 8.10 (s, 1H), 8.01 (d, J = 2.7 Hz, 1H), 7.67 (dd, J = 8.7, 1.8 Hz, 2H), 7.63 (dd, J = 9.1, 2.8 Hz, 1H), 7.27 (d, J = 2.3 Hz, 1H), 7.12 (d, J = 2.5 Hz, 1H), 7.05 (dd, J = 8.6, 2.3 Hz, 1H), 6.96 (dd, J = 8.8, 2.6 Hz, 1H), 6.66 (d, J = 9.1 Hz, 1H), 6.17 (s, 1H), 4.93 (dd, J = 12.6, 5.4 Hz, 1H), 4.20 (d, J = 13.0 Hz, 2H), 3.72 (dd, J = 6.3, 4.4 Hz, 4H), 3.53 (dd, J = 6.3, 4.4 Hz, 4H), 3.39 (d, J = 5.5 Hz, 4H), 3.12 (s, 4H), 2.92-2.82 (m, 2H), 2.76 (m, 3H), 2.42 (s, 2H), 2.16-2.10 (m, 1H), 1.88 (s, 4H), 1.79 (d, J = 11.5 Hz, 2H), 1.62-1.54 (m, 2H). m/z 853.38 [M + H]⁺. |
| 104 | ¹H NMR (600 MHz, CDCl₃) δ 8.11 (s, 1H), 8.01 (d, J = 2.3 Hz, 1H), 7.67 (d, J = 8.5 Hz, 1H), 7.63 (dd, J = 9.0, 2.4 Hz, 1H), 7.50 (d, J = 8.8 Hz, 1H), 7.27 (s, 1H), 7.05 (d, J = 8.4 Hz, 1H), 6.87 (d, J = 2.3 Hz, 1H), 6.74 (d, J = 8.9 Hz, 1H), 6.65 (d, J = 9.1 Hz, 1H), 6.19 (s, 1H), 4.93 (dd, J = 12.5, 5.3 Hz, 1H), 4.20 (d, J = 12.9 Hz, 2H), 3.75-3.66 (m, 4H), 3.51-3.42 (m, 4H), 3.42-3.35 (m, 4H), 3.18 (s, 4H), 2.91-2.82 (m, 2H), 2.79-2.70 (m, 3H), 2.47 (d, J = 6.1 Hz, 2H), 2.16-2.11 (m, 1H), 1.89 (s, 4H), 1.65-1.57 (m, 2H). m/z 819.34 [M + H]⁺. |
| 105 | ¹H NMR (600 MHz, DMSO-d6) δ 10.85 (s, 1H), 10.24 (s, 1H), 8.71 (d, J = 8.3 Hz, 1H), 8.31 (d, J = 2.7 Hz, 1H), 7.98 (d, J = 2.9 Hz, 1H), 7.90 (d, J = 9.4 Hz, 1H), 7.84 (d, J = 8.8 Hz, 1H), 7.82 (d, J = 8.8 Hz, 1H), 7.41 (dd, J = 8.8, 2.8 Hz, 1H), 7.36 (dd, J = 9.2, 2.9 Hz, 1H), 7.31 (s, 1H), 7.25 (d, J = 8.9 Hz, 1H), 4.77-4.71 (m, 1H), 4.12-4.07 (m, , 2H), 3.95 (d, J = 12.3 Hz, 2H), 3.62 (d, J = 11.9 Hz, 2H), 3.04-2.96 (m, 2H), 2.91-2.83 (m, 2H), 2.77 (d, J = 17.9 Hz, 2H), 2.70-2.56 (m, 9H), 2.42-2.31 (m, 3H), 2.22-2.16 (m, 1H), 2.13 (d, J = 7.3 Hz, 2H), 2.03-2.00 (m, 1H), 1.86 (d, J = 13.0 Hz, 2H), 1.77 (d, J = 10.8 Hz, 2H), 1.69-1.60 (m, 2H), 1.53-1.44 (m, 2H), 1.26-1.19 (m, 2H). m/z 870.57 [M + H]⁺. |
| 106 | ¹H NMR (600 MHz, DMSO-d6) δ 10.85 (s, 1H), 10.24 (s, 1H), 8.70 (d, J = 8.2 Hz, 1H), 8.30 (d, J = 2.8 Hz, 1H), 7.98 (d, J = 3.0 Hz, 1H), 7.90 (d, J = 8.9 Hz, 1H), 7.84 (d, J = 8.8 Hz, 1H), 7.82 (d, J = 8.9 Hz, 1H), 7.39 (dd, J = 9.0, 2.7 Hz, 1H), 7.36 (dd, J = 9.3, 3.0 Hz, 1H), 7.31 (d, J = 2.4 Hz, 1H), 7.25 (d, J = 8.9 Hz, 1H), 4.77-4.71 (m, 1H), 4.10 (d, J = 13.6 Hz, 2H), 3.93 (d, J = 12.7 Hz, 2H), 3.63 (d, J = 12.4 Hz, 2H), 3.05-2.97 (m, 2H), 2.89-2.82 (m, 2H), 2.81-2.72 (m, 2H), 2.68-2.55 (m, 7H), 2.41-2.26 (m, 6H), 2.20-2.16 (m, 1H), 2.14 (d, J = 5.8 Hz, 4H), 2.03-1.99 (m, 1H), 1.86 (d, J = 11.7 Hz, 2H), 1.81-1.72 (m, 4H), 1.69-1.60 (m, 2H), 1.24-1.12 (m, 4H). m/z 884.57 [M + H]⁺. |
| 107 | ¹H NMR (600 MHz, DMSO-d6) δ 10.85 (s, 1H), 10.24 (s, 1H), 8.73 (d, J = 8.3 Hz, 1H), 8.32 (d, J = 2.8 Hz, 1H), 7.99 (d, J = 3.0 Hz, 1H), 7.90 (d, J = 9.0 Hz, 1H), 7.86 (d, J = 8.8 Hz, 1H), 7.82 (d, J = 8.9 Hz, 1H), 7.42 (dd, J = 8.9, 2.8 Hz, 1H), 7.37 (dd, J = 9.2, 3.0 Hz, 1H), 7.31 (d, J = 2.3 Hz, 1H), 7.25 (d, J = 8.9, 2.5 Hz, 1H), 4.78-4.71 (m, 1H), 4.13-4.07 (m, 2H), 3.63 (d, J = 12.0 Hz, 2H), 3.38-3.34 (m, 4H), 3.04-2.96 (m, 2H), 2.81-2.73 (m, 2H), 2.66-2.60 (m, 3H), 2.54-2.52 (m, 4H), 2.42-2.35 (m, 2H), 2.21-2.13 (m, 2H), 2.00 (m, 1H), 1.86 (d, J = 10.6 Hz, 2H), 1.77 (d, J = 11.8 Hz, 2H), 1.69-1.60 (m, 2H), 1.49-1.41 (m, 2H), 1.32-1.26 (m, 2H). m/z 823.51 [M + Na]⁺. |
| 108 | ¹H NMR (600 MHz, CDCl₃) δ 8.74 (s, 1H), 8.46 (d, J = 6.8 Hz, 1H), 8.21 (d, J = 2.7 Hz, 1H), 8.14 (s, 1H), 8.09 (d, J = 9.1 Hz, 1H), 8.02 (d, J = 8.8 Hz, 1H), 7.99 (s, 1H), 7.64 (d, J = 8.8 Hz, 1H), 7.32 (dd, J = 9.0, 2.6 Hz, 1H), 7.22 (dd, J = 8.7, 2.6 Hz, 1H), 7.16 (s, 1H), 7.00 (dd, J = 8.8, 2.4 Hz, 1H), 4.84-4.78 (m, 1H), 3.98 (d, J = 13.0 Hz, 2H), 3.87 (d, J = 11.7 Hz, 2H), 3.66-3.60 (m, 2H), 3.14-3.05 (m, 2H), 2.95-2.88 (m, 2H), 2.88-2.85 (m, 1H), 2.85-2.81 (m, 1H), 2.79-2.70 (m, 3H), 2.70-2.62 (m, 2H), 2.61-2.55 (m, 1H), 2.45-2.39 (m, 1H), 2.30-2.24 (m, 2H), 2.20 (d, J = 7.1 Hz, 2H), 2.13-2.08 (m, 2H), 2.08-2.02 (m, 2H), 2.02-1.98 (m, 2H), 1.98-1.94 (m, 2H), 1.94-1.88 (m, 1H), 1.77-1.73 (m, 1H), 1.79-1.72 (m, 2H), 1.40-1.29 (m, 4H), 1.04 (d, J = 6.1 Hz, 3H). m/z 898.57 [M + H]⁺. |
| 109 | ¹H NMR (600 MHz, CDCl₃) δ 8.74 (s, 1H), 8.46 (d, J = 6.8 Hz, 1H), 8.21 (d, J = 2.7 Hz, 1H), 8.14 (s, 1H), 8.09 (d, J = 9.1 Hz, 1H), 8.02 (d, J = 8.8 Hz, 1H), 7.99 (s, 1H), 7.64 (d, J = 8.8 Hz, 1H), 7.32 (dd, J = 9.0, 2.6 Hz, 1H), 7.22 (dd, J = 8.7, 2.6 Hz, 1H), 7.16 (s, 1H), 7.00 (dd, J = 8.8, 2.4 Hz, 1H), 4.84-4.78 (m, 1H), 3.98 (d, J = 13.0 Hz, 2H), 3.87 (d, J = 11.7 Hz, 2H), 3.66-3.60 (m, 2H), 3.14-3.05 (m, 2H), 2.95-2.88 (m, 2H), 2.88-2.85 (m, 1H), 2.85-2.81 (m, 1H), 2.79-2.70 (m, 3H), 2.70-2.62 (m, 2H), 2.61-2.55 (m, 1H), 2.45-2.39 (m, 1H), 2.30-2.24 (m, 2H), 2.20 (d, J = 7.1 Hz, 2H), 2.13-2.08 (m, 2H), 2.08-2.02 (m, 2H), 2.02-1.98 (m, 2H), 1.98-1.94 (m, 2H), 1.94-1.88 (m, 1H), 1.77-1.73 (m, 1H), 1.79-1.72 (m, 2H), 1.40-1.29 (m, 4H), 1.04 (d, J = 6.1 Hz, 3H). m/z 898.59 [M + H]⁺. |
| 110 | ¹H NMR (600 MHz, CDCl₃) δ 9.42 (s, 1H), 8.37 (s, 1H), 8.10 (d, J = 9.1 Hz, 1H), 8.00 (d, J = 2.9 Hz, 1H), 7.71 (d, J = 8.5 Hz, 1H), 7.64 (d, J = 8.8 Hz, 1H), 7.32 (dd, J = 9.1, 2.9 Hz, 1H), 7.18 (d, J = 2.3 Hz, 1H), 7.15 (d, J = 2.5 Hz, 1H), 7.07 (dd, J = 8.6, 2.3 Hz, 1H), 6.98 (dd, J = 8.8, 2.6 Hz, 1H), 4.97 (dd, J = 12.6, 5.4 Hz, 1H), 3.96 (d, J = 13.2 Hz, 2H), 3.63 (d, J = 12.1 Hz, 2H), 3.52-3.41 (m, 4H), 3.10-3.02 (m, 2H), 2.95-2.89 (m, 1H), 2.89-2.82 (m, 1H), 2.81-2.75 (m, 1H), 2.75-2.70 (m, 2H), 2.70-2.63 (m, 4H), 2.61-2.57 (m, 1H), 2.56 (s, 3H), 2.30-2.24 (m, 4H), 2.18-2.14 (m, 1H), 2.11-2.05 (m, 2H), 2.01-1.92 (m, 2H), 1.92-1.86 (m, 3H), 1.71-1.65 (m, 2H), 1.38-1.30 (m, 2H). m/z 869.47 [M + H]⁺. |
| 111 | ¹H NMR (600 MHz, CDCl₃) δ 10.52 (s, 1H), 8.82 (s, 1H), 8.14 (d, J = 9.1 Hz, 1H), 8.01 (d, J = 2.9 Hz, 1H), 7.82 (d, J = 17.5 Hz, 1H), 7.60 (d, J = 8.6 Hz, 1H), 7.31 (dt, J = 13.1, 6.6 Hz, 1H), 7.12 (d, J = 2.5 Hz, 1H), 6.98-6.91 (m, 2H), 6.72 (dd, J = 8.4, 2.2 Hz, 1H), 4.94 (dd, J = 12.5, 5.4 Hz, 1H), 4.88 (t, J = 5.3 Hz, 1H), 3.93 (dd, J = 9.9, 3.3 Hz, 2H), 3.86-3.71 (m, 2H), 3.62 (m, 2H), 3.24 (dd, J = 15.1, 9.3 Hz, 2H), 3.15-3.10 (m, 3H), 3.01 (td, J = 13.0, 2.7 Hz, 2H), 2.93-2.70 (m, 3H), 2.64-2.56 (m, 1H), 2.45-2.34 (m, 2H), 2.18-2.09 (m, 1H), 2.09-1.99 (m, 2H), 1.93 (td, J = 15.4, 4.0 Hz, 2H), 1.77-1.64 (m, 4H), 1.51-1.41 (m, 2H). m/z 828.32 [M + H]⁺. |
| 112 | ¹H NMR (600 MHz, CDCl₃) δ 10.05 (s, 1H), 8.92 (s, 1H), 8.11 (d, J = 8.8 Hz, 1H), 7.97 (d, J = 12.4 Hz, 1H), 7.57 (dd, J = 8.3, 3.6 Hz, 1H), 7.52-7.41 (m, 1H), 7.03-6.94 (m, 1H), 8.26-6.65 (m, 1H), 5.40-5.30 (m, 1H), 4.92 (dd, J = 12.5, 5.4 Hz, 1H), 3.90 (m, 1H), 3.79 (m, 1H), 3.64 (m, 1H), 3.25 (m, 1H), 3.14 (m, 2H), 3.03 (d, J = 12.0 Hz, 1H), 2.91-2.68 (m, 2H), 2.66-2.52 (m, 1H), 2.46-2.25 (m, 7H), 2.25-2.09 (m, 7H), 2.03 (s, 1H), 1.92 (d, J = 11.2 Hz, 1H), 1.77-1.61 (m, 2H), 1.53-1.47 (m, 2H), 1.26 (d, J = 10.7 Hz, 2H), 0.91-0.80 (m, 2H). m/z 794.35 [M + H]⁺. |
| 113 | ¹H NMR (600 MHz, CDCl3) δ 8.94 (s, 1H), 8.14 (s, 1H), 8.09 (d, J = 9.1 Hz, 1H), 7.96 (d, J = 2.9 Hz, 1H), 7.78 (d, J = 8.3 Hz, 1H), 7.62 (d, J = 8.8 Hz, 1H), 7.33 (d, J = 2.2 Hz, 1H), 7.30-7.27 (m, 1H), 7.18 (dd, J = 8.3, 2.3 Hz, 1H), 7.13 (d, J = 2.4 Hz, 1H), 6.97 (dd, J = 8.8, 2.6 Hz, 1H), 4.96 (dd, J = 12.6, 5.4 Hz, 1H), 4.09 (t, J = 6.6 Hz, 2H), 3.95 (dd, J = 9.9, 3.3 Hz, 2H), 3.25-3.14 (m, 4H), 3.09-3.01 (m, 2H), 2.93-2.71 (m, 4H), 2.63-2.56 (m, 4H), 2.46-2.40 (m, 2H), 2.18-2.13 (m, 1H), 2.09-2.05 (m, 2H), 1.94 (m, 2H), 1.90-1.84 (m, 2H), 1.61 (d, J = 14.9, 7.5 Hz, 2H), 1.51 (dd, J = 16.6, 12.8 Hz, 2H). m/z 801.40 [M + H]⁺. |
| 114 | ¹H NMR (600 MHz, CDCl3) δ 9.26 (s, 1H), 8.24 (s, 1H), 8.09 (d, J = 9.1 Hz, 1H), 7.97 (d, J = 2.8 Hz, 1H), 7.78 (d, J = 8.3 Hz, 1H), 7.45 (d, J = 8.9 Hz, 1H), 7.33 (d, J = 2.2 Hz, 1H), 7.28 (dd, J = 5.0, 1.7 Hz, 1H), 7.18 (dd, J = 8.3, 2.3 Hz, 1H), 6.88 (d, J = 2.5 Hz, 1H), 6.74 (dd, J = 8.9, 2.5 Hz, 1H), 4.96 (dd, J = 12.6, 5.4 Hz, 1H), 4.09 (t, J = 6.4 |

TABLE 5-continued

| Example | NMR and/or MS data |
|---|---|
| | Hz, 2H), 3.92-3.83 (m, 2H), 3.23-3.13 (m, 4H), 2.98 (m, 2H), 2.90-2.77 (m, 3H), 2.63-2.57 (m, 4H), 2.55-2.50 (m, 1H), 2.45-2.39 (m, 2H), 2.19-2.13 (m, 1H), 2.06-2.00 (m, 2H), 1.95-1.83 (m, 4H), 1.61 (m, 2H), 1.52 (m, 2H). m/z 767.43 [M + H]⁺. |
| 115 | ¹H NMR (600 MHz, CDCl3) δ 10.07 (s, 1H), 8.58 (s, 1H), 8.11 (d, J = 9.1 Hz, 1H), 7.99 (d, J = 2.9 Hz, 1H), 7.77 (d, J = 8.3 Hz, 1H), 7.62 (d, J = 8.8 Hz, 1H), 7.35 (d, J = 2.2 Hz, 1H), 7.32-7.27 (m, 1H), 7.18 (dd, J = 8.3, 2.3 Hz, 1H), 7.13 (d, J = 2.5 Hz, 1H), 6.96 (dd, J = 8.8, 2.5 Hz, 1H), 4.96 (dd, J = 12.6, 5.4 Hz, 1H), 4.12 (t, J = 6.4 Hz, 2H), 3.95 (dd, J = 9.9, 3.3 Hz, 2H), 3.24-3.13 (m, 4H), 3.05 (m, 2H), 2.93-2.71 (m, 4H), 2.60 (m, 2H), 2.60 (m, J = 13.9, 9.3 Hz, 4H), 2.51-2.39 (m, 2H), 2.19-2.11 (m, 1H), 2.06 (dd, J = 13.7, 3.7 Hz, 2H), 1.99-1.81 (m, 4H), 1.71 (m, 2H). m/z 787.41 [M + H]⁺. |
| 116 | ¹H NMR (600 MHz, CDCl3) δ 10.15 (s, 1H), 8.68 (s, 1H), 8.11 (d, J = 9.1 Hz, 1H), 7.99 (d, J = 2.9 Hz, 1H), 7.77 (d, J = 8.3 Hz, 1H), 7.45 (dd, J = 8.8, 4.8 Hz, 1H), 7.34 (d, J = 2.2 Hz, 1H), 7.31-7.28 (m, 1H), 7.18 (dd, J = 8.3, 2.2 Hz, 1H), 6.87 (d, J = 2.4 Hz, 1H), 6.74 (dd, J = 8.9, 2.4 Hz, 1H), 4.96 (dd, J = 12.5, 5.4 Hz, 1H), 4.12 (t, J = 6.4 Hz, 2H), 3.92-3.81 (m, 2H), 3.22-3.14 (m, 4H), 2.99 (dd, J = 17.4, 5.5 Hz, 2H), 2.87-2.72 (m, 3H), 2.67-2.59 (m, 4H), 2.56 (dd, J = 11.1, 3.8 Hz, 1H), 2.51-2.44 (m, 2H), 2.16 (m, 1H), 2.05-1.99 (m, 2H), 1.95-1.85 (m, 4H), 1.71 (m, 2H). m/z 753.37 [M + H]⁺. |
| 117 | ¹H NMR (600 MHz, CDCl3) δ 9.38 (s, 1H), 8.36 (s, 1H), 8.10 (d, J = 9.1 Hz, 1H), 7.97 (d, J = 2.9 Hz, 1H), 7.68 (d, J = 8.5 Hz, 1H), 7.62 (d, J = 8.8 Hz, 1H), 7.29-7.27 (m, 2H), 7.13 (d, J = 2.5 Hz, 1H), 7.05 (dd, J = 8.6, 2.3 Hz, 1H), 6.97 (dd, J = 8.8, 2.5 Hz, 1H), 4.95 (dd, J = 12.6, 5.4 Hz, 1H), 3.95 (dd, J = 9.9, 3.3 Hz, 2H), 3.73-3.69 (m, 2H), 3.60 (m, 1H), 3.30-3.24 (m, 2H), 3.20-3.15 (m, 4H), 3.05 (m, 2H), 2.92-2.80 (m, 4H), 2.75 (m, 2H), 2.72-2.67 (m, 4H), 2.60-2.52 (m, 2H), 2.17-2.11 (m, 1H), 2.07-2.00 (m, 2H), 1.99-1.89 (m, 4H), 1.73 (m, 3H). m/z 842.35 [M + H]⁺. |
| 118 | ¹H NMR (600 MHz, CDCl3) δ 8.68 (s, 1H), 8.09 (d, J = 9.0 Hz, 1H), 8.05 (s, 1H), 7.95 (d, J = 2.8 Hz, 1H), 7.68 (d, J = 8.5 Hz, 1H), 7.46 (d, J = 8.9 Hz, 1H), 7.30-7.27 (m, 2H), 7.07-7.03 (m, 1H), 6.89 (d, J = 2.5 Hz, 1H), 6.75 (dd, J = 8.9, 2.5 Hz, 1H), 4.94 (dd, J = 12.5, 5.4 Hz, 1H), 3.90 (d, J = 13.1 Hz, 2H), 3.70 (m, 2H), 3.60 (m, 2H), 3.36-3.25 (m, 2H), 3.21-3.12 (m, 4H), 3.05-2.95 (m, 2H), 2.93-2.80 (m, 2H), 2.72-2.63 (m, 4H), 2.57-2.48 (m, 2H), 2.19-2.11 (m, 1H), 2.07-2.01 (m, 2H), 2.00-1.86 (m, 4H), 1.77-1.69 (m, 2H). m/z 808.38 [M + H]⁺. |
| 119 | ¹H NMR (600 MHz, CDCl3) δ 9.40 (s, 1H), 8.45 (s, 1H), 8.10 (d, J = 9.1 Hz, 1H), 7.97 (d, J = 2.9 Hz, 1H), 7.66 (d, J = 8.5 Hz, 1H), 7.62 (d, J = 8.8 Hz, 1H), 7.34-7.28 (m, 2H), 7.13 (d, J = 2.4 Hz, 1H), 7.02 (dd, J = 8.6, 2.3 Hz, 1H), 6.96 (dd, J = 8.8, 2.5 Hz, 1H), 4.94 (dd, J = 12.6, 5.4 Hz, 1H), 3.99-3.86 (m, 4H), 3.18 (s, 4H), 3.07-3.00 (m, 2H), 2.96 (m, 2H), 2.89 (m, 2H), 2.86-2.79 (m, 1H), 2.74 (m, 2H), 2.65-2.52 (m, 4H), 2.45 (s, 2H), 2.16-2.11 (m, 1H), 2.08-2.01 (m, 2H), 1.94 (m, 2H), 1.83 (d, J = 11.7 Hz, 2H), 1.52 (s, 2H), 1.32 (m, 2H). m/z 826.24 [M + H]⁺. |
| 120 | ¹H NMR (600 MHz, CDCl3) δ 9.07 (s, 1H), 8.43 (s, 1H), 8.11 (d, J = 9.1 Hz, 1H), 7.95 (d, J = 2.9 Hz, 1H), 7.67 (d, J = 8.5 Hz, 1H), 7.45 (d, J = 8.9 Hz, 1H), 7.30 (dd, J = 9.2, 8.5 Hz, 1H), 7.02 (dd, J = 8.7, 2.3 Hz, 1H), 6.88 (d, J = 2.5 Hz, 1H), 6.74 (dd, J = 8.9, 2.5 Hz, 1H), 4.94 (dd, J = 12.6, 5.4 Hz, 1H), 4.00-3.84 (m, 4H), 3.28-3.12 (m, 4H), 3.02-2.93 (m, 3H), 2.92-2.80 (m, 2H), 2.74 (m, 2H), 2.64-2.58 (m, 4H), 2.57-2.50 (m, 1H), 2.48-2.41 (m, 2H), 2.16-2.10 (m, 1H), 2.06-2.00 (m, 2H), 1.91 (m, 2H), 1.84 (d, J = 11.2 Hz, 2H), 1.51 (dd, J = 14.8, 7.0 Hz, 2H), 1.36-1.28 (m, 2H). m/z 792.37 [M + H]⁺. |
| 121 | ¹H NMR (600 MHz, CDCl₃) δ 9.41 (s, 1H), 8.30 (s, 1H), 8.06-8.00 (m, 1H), 7.80 (d, J = 2.9 Hz, 1H), 7.67 (d, J = 8.5 Hz, 1H), 7.62 (d, J = 8.8 Hz, 1H), 7.13 (d, J = 2.5 Hz, 1H), 7.07 (dd, J = 9.0, 2.9 Hz, 1H), 7.03 (dd, J = 8.6, 2.3 Hz, 1H), 6.96 (dd, J = 8.8, 2.5 Hz, 1H), 4.95 (dd, J = 12.6, 5.4 Hz, 1H), 3.94 (dd, J = 17.0, 7.7 Hz, 4H), 3.61 (d, J = 4.6 Hz, 4H), 3.19 (d, J = 6.5 Hz, 2H), 3.07-3.00 (m, 2H), 2.99-2.91 (m, 2H), 2.90-2.80 (m, 2H), 2.78-2.71 (m, 1H), 2.56 (s, 1H), 2.47 (s, 2H), 2.31 (s, 2H), 2.25-2.17 (m, 1H), 2.06 (d, J = 10.1 Hz, 1H), 1.98-1.89 (m, 2H), 1.89-1.81 (m, 2H), 1.77 (s, 1H), 1.66 (dd, J = 12.9, 8.9 Hz, 2H), 1.30-1.21 (m, 2H). m/z 852.46 [M + H]⁺. |
| 122 | ¹H NMR (600 MHz, CDCl₃) δ 8.03 (d, J = 2.6 Hz, 1H), 7.97 (s, 1H), 7.81 (dd, J = 8.9, 2.6 Hz, 1H), 7.67 (d, J = 8.6 Hz, 1H), 7.46 (d, J = 8.9 Hz, 1H), 7.27 (d, J = 2.3 Hz, 1H), 7.04 (dd, J = 8.6, 2.3 Hz, 1H), 6.99 (s, 1H), 6.89 (d, J = 2.5 Hz, 1H), 6.76 (dd, J = 8.9, 2.5 Hz, 1H), 6.27 (d, J = 8.9 Hz, 1H), 4.94 (dd, J = 12.5, 5.4 Hz, 1H), 3.93 (dd, J = 17.1, 13.6 Hz, 4H), 3.71 (s, 4H), 3.05-2.92 (m, 5H), 2.92-2.68 (m, 4H), 2.49 (tt, J = 11.1, 3.8 Hz, 1H), 2.41-2.28 (m, 4H), 2.22-2.16 (m, 2H), 2.16-2.09 (m, 2H), 2.04 (dt, J = 14.2, 6.9 Hz, 2H), 1.98-1.85 (m, 5H), 1.82 (t, J = 5.3 Hz, 5H), 0.92-0.86 (m, 2H). m/z 818.37 [M + H]⁺. |
| 123 | ¹H NMR (600 MHz, CDCl₃) δ 9.62 (s, 1H), 8.49 (s, 1H), 8.04 (d, J = 8.9 Hz, 1H), 7.79 (d, J = 2.8 Hz, 1H), 7.63 (dd, J = 12.9, 8.5 Hz, 2H), 7.12 (d, J = 2.4 Hz, 1H), 7.07 (dd, J = 9.0, 2.9 Hz, 1H), 6.96 (dd, J = 8.8, 2.5 Hz, 1H), 6.76 (d, J = 2.0 Hz, 1H), 6.48 (dd, J = 8.3, 2.1 Hz, 1H), 4.94 (dd, J = 12.5, 5.4 Hz, 1H), 4.09 (t, J = 8.0 Hz, 2H), 3.94 (d, J = 13.3 Hz, 2H), 3.70-3.64 (m, 2H), 3.60 (s, 2H), 3.20 (s, 2H), 3.07-3.00 (m, 2H), 2.98 (d, J = 7.4 Hz, 1H), 2.88 (d, J = 18.4 Hz, 1H), 2.83-2.78 (m, 1H), 2.78-2.71 (m, 2H), 2.66 (d, J = 7.4 Hz, 2H), 2.59-2.48 (m, 3H), 2.38 (d, J = 9.2 Hz, 2H), 2.16-2.10 (m, 1H), 2.06 (s, 2H), 1.99-1.90 (m, 2H), 1.72-1.60 (m, 4H). m/z 824.29 [M + H]⁺. |
| 124 | ¹H NMR (600 MHz, CDCl₃) δ 10.43 (s, 1H), 8.81 (s, 1H), 8.06 (d, J = 9.0 Hz, 1H), 7.83 (d, J = 2.8 Hz, 1H), 7.65 (d, J = 8.3 Hz, 1H), 7.47 (d, J = 8.9 Hz, 1H), 7.09 (dd, J = 9.0, 2.9 Hz, 1H), 6.87 (d, J = 2.5 Hz, 1H), 6.78 (d, J = 2.0 Hz, 1H), 6.75 (dd, J = 8.9, 2.5 Hz, 1H), 6.48 (dd, J = 8.3, 2.1 Hz, 1H), 4.97 (dd, J = 12.6, 5.4 Hz, 1H), 4.10 (td, J = 7.9, 2.4 Hz, 2H), 3.87 (d, J = 9.9, 3.2 Hz, 2H), 3.68 (dd, J = 7.9, 5.4 Hz, 3H), 3.61 (s, 2H), 3.21 (s, 2H), 3.07-2.98 (m, 1H), 2.98-2.90 (m, 3H), 2.90-2.81 (m, 2H), 2.81-2.72 (m, 1H), 2.68 (d, J = 7.3 Hz, 2H), 2.56 (m, 3H), 2.40 (m, 2H), 2.19-2.13 (m, 1H), 2.03 (dd, J = 13.1, 2.2 Hz, 2H), 1.97-1.83 (m, 3H), 1.76-1.58 (m, 2H). m/z 790.37 [M + H]⁺. |
| 125 | ¹H NMR (600 MHz, CDCl₃) δ 8.84 (s, 1H), 8.60 (s, 1H), 8.05 (d, J = 8.9 Hz, 1H), 7.75 (d, J = 2.8 Hz, 1H), 7.65 (d, J = 8.4 Hz, 1H), 7.61 (d, J = 8.7 Hz, 1H), 7.13 (s, 1H), 7.10 (d, J = 9.4, 3.2 Hz, 1H), 6.98-6.93 (m, 2H), 6.67 (d, J = 6.5 Hz, 1H), 4.94 (dd, J = 12.5, 5.4 Hz, 1H), 3.95 (d, J = 13.1 Hz, 2H), 3.87-3.83 (m, 1H), 3.67-3.59 (m, 1H), 3.56-3.51 (m, 1H), 3.47 (s, 1H), 3.41-3.37 (m, 1H), 3.20 (s, 2H), 3.17-3.13 (m, 1H), 3.13-3.09 (m, 1H), 3.08-3.02 (m, 2H), 2.89 (d, J = 19.5 Hz, 1H), 2.85-2.80 (m, 1H), 2.77-2.72 (m, 1H), 2.61-2.53 (m, 2H), 2.53-2.48 (m, 1H), 2.46-2.37 (m, 2H), 2.34-2.29 (m, 1H), 2.21-2.17 (m, 1H), 2.14-2.08 (m, 2H), 2.07-2.01 (m, 2H), 1.98-1.91 (m, 2H), 1.91-1.83 (m, 2H), 1.81-1.77 (m, 2H), 1.73-1.63 (m, 4H). m/z 838.38 [M + H]⁺. |
| 126 | ¹H NMR (600 MHz, CDCl₃) δ 9.29 (s, 1H), 8.32 (d, J = 10.4 Hz, 1H), 8.03 (d, J = 8.9 Hz, 1H), 7.80 (d, J = 2.8 Hz, 1H), 7.65 (d, J = 8.4 Hz, 1H), 7.61 (d, J = 8.8 Hz, 1H), 7.12 (d, J = 2.4 Hz, 1H), 7.08 (dd, J = 9.2, 2.7 Hz, 1H), 6.98-6.95 (m, 1H), 6.94 (d, J = 2.1 Hz, 1H), 6.66 (d, J = 8.6 Hz, 1H), 4.95 (dd, J = 12.5, 5.4 Hz, 1H), 3.94 (d, J = 13.2 Hz, 2H), 3.62 (d, J = 6.1 Hz, 4H), 3.53 (d, J = 8.1 Hz, 1H), 3.46 (s, 1H), 3.42-3.36 (m, 1H), 3.19 (d, J = 15.2 Hz, 1H), 3.16-3.11 (m, 1H), 3.08-3.01 (m, 2H), 2.89 (d, J = 18.2 Hz, 1H), 2.87-2.80 (m, 1H), 2.75 (dd, J = 16.7, 5.0 Hz, 1H), 2.56 (d, J = 12.4 Hz, 2H), 2.48 (s, 1H), 2.39 (dd, J = 24.6, 9.1 Hz, 2H), 2.32 (s, 1H), 2.17 (s, 1H), 2.16-2.11 (m, 1H), 2.09-2.04 (m, 2H), 1.97-1.90 (m, 2H), 1.85 (m, 1H), 1.77 (m, J = 12.0 Hz, 1H), 1.66 (m, 4H). m/z 838.29 [M + H]⁺. |
| 127 | ¹H NMR (600 MHz, CDCl₃) δ 8.08 (d, J = 2.6 Hz, 1H), 8.05 (s, 1H), 7.83 (dd, J = 9.1, 2.7 Hz, 1H), 7.66 (d, J = 8.6 Hz, 1H), 7.62 (d, J = 8.8 Hz, 1H), 7.14 (d, J = 2.4 Hz, 1H), 7.05-7.02 (m, 1H), 7.02 (s, 1H), 6.98 (dd, J = 8.8, 2.5 Hz, 1H), 6.66 (d, J = 9.2 Hz, 1H), 4.93 (dd, J = 12.5, 5.4 Hz, H), 3.98 (d, J = 13.4 Hz, 2H), 3.94 (d, J = 12.2 Hz, 2H), 3.53-3.42 (m, 4H), 3.12-3.02 (m, 4H), 2.98-2.92 (m, 2H), 2.88 (ddd, J = 15.5, 9.5, 4.0 Hz, 1H), 2.84-2.79 (m, 1H), 2.73 (ddd, J = 16.9, 13.6, 5.1 Hz, 1H), 2.51 (ddd, J = 10.9, 9.5, 3.9 Hz, 1H), 2.39 (s, 2H), 2.16-2.10 (m, 1H), 2.07 |

TABLE 5-continued

| Example | NMR and/or MS data |
|---|---|
| | (d, J = 9.4 Hz, 2H), 1.97 (d, J = 4.0 Hz, 2H), 1.85 (d, J = 13.1 Hz, 2H), 1.81 (s, 4H), 1.29 (d, J = 10.9 Hz, 2H). m/z 852.35 [M + H]+. |
| 128 | $^1$H NMR (600 MHz, CDCl$_3$) δ 8.08 (s, 1H), 7.84 (d, J = 7.1 Hz, 1H), 7.65-7.61 (m, 2H), 7.14 (s, 1H), 7.01 (s, 1H), 6.98 (d, J = 8.7 Hz, 1H), 6.79 (s, 1H), 6.66 (d, J = 9.0 Hz, 1H), 6.48 (d, J = 8.3 Hz, 1H), 4.93 (dd, J = 12.4, 5.1 Hz, 1H), 4.13-4.07 (m, 2H), 3.98 (d, J = 13.2 Hz, 2H), 3.74-3.68 (m, 4H), 3.51-3.41 (m, 4H), 3.10 (s, 2H), 3.09-3.04 (m, 2H), 2.91-2.86 (m, J = 16.7 Hz, 1H), 2.84-2.78 (m, 4H), 2.73 (d, J = 13.0 Hz, 1H), 2.54-2.49 (m, 1H), 2.16-2.11 (m, J = 6.3 Hz, 1H), 2.08-2.03 (m, 2H), 1.99-1.92 (m, 2H), 1.86-1.77 (m, 4H). m/z 824.30 [M + H]+. |
| 129 | $^1$H NMR (600 MHz, CDCl$_3$) δ 8.11 (d, J = 2.7 Hz, 1H), 7.93 (s, 1H), 7.86 (d, J = 2.7 Hz, 1H), 7.68 (d, J = 8.5 Hz, 1H), 7.63 (d, J = 8.8 Hz, 1H), 7.28 (d, J = 2.3 Hz, 1H), 7.14 (d, J = 2.5 Hz, 1H), 7.07-7.02 (m, 2H), 6.98 (dd, J = 8.8, 2.5 Hz, 1H), 6.68 (d, J = 9.2 Hz, 1H), 4.94 (dd, J = 12.6, 5.4 Hz, 1H), 3.98 (d, J = 13.1 Hz, 4H), 3.93 (s, 2H), 3.78 (s, 2H), 3.58-3.52 (m, 2H), 3.49-3.43 (m, 2H), 3.12-3.01 (m, 2H), 2.90 (d, J = 16.9 Hz, 1H), 2.85-2.80 (m, 1H), 2.77-2.71 (m, 1H), 2.55-2.50 (m, 1H), 2.50-2.44 (m, 1H), 2.17-2.11 (m, 1H), 2.10-2.04 (m, 2H), 2.01-1.95 (m, 2H), 1.94-1.89 (m, 2H), 1.85 (ddd, J = 17.3, 14.1, 6.2 Hz, 6H). m/z 866.34 [M + H]+. |
| 130 | $^1$H NMR (600 MHz, DMSO-d6) δ 11.05 (s, 1H), 10.25 (s, 1H), 7.98 (d, J = 2.9 Hz, 1H), 7.90 (d, J = 9.0 Hz, 1H), 7.80 (d, J = 8.9 Hz, 1H), 7.56 (d, J = 8.4 Hz, 1H), 7.37 (dd, J = 9.2, 2.9 Hz, 1H), 7.28 (d, J = 2.3 Hz, 1H), 7.24 (dd, J = 9.0, 2.5 Hz, 1H), 7.10 (s, 3H), 7.08-7.03 (m, 1H), 7.00 (d, J = 7.6 Hz, 1H), 5.02 (dd, J = 12.8, 5.5 Hz, 1H), 4.36 (d, J = 12.8 Hz, 1H), 4.18-4.04 (m, 4H), 3.92 (d, J = 13.0 Hz, 1H), 3.10 (s, 4H), 2.99 (dd, J = 23.1, 11.0 Hz, 2H), 2.90-2.81 (m, 1H), 2.75 (s, 1H), 2.67-2.61 (m, 1H), 2.59-2.50 (m, 4H), 2.18 (d, J = 6.7 Hz, 2H), 1.98 (dd, J = 13.4, 7.7 Hz, 1H), 1.90-1.80 (m, 3H), 1.78-1.71 (m, 2H), 1.68-1.58 (m, 2H), 1.17-1.06 (m, 2H), 0.94 (d, J = 12.1 Hz, 2H). m/z 869.40 [M + H]+. |
| 131 | $^1$H NMR (600 MHz, CDCl3) δ 8.92 (s, 1H), 8.35 (s, 1H), 8.32 (d, J = 1.6 Hz, 1H), 8.16 (d, J = 8.6 Hz, 1H), 7.70 (dd, J = 8.6, 2.2 Hz, 1H), 7.67 (d, J = 8.5 Hz, 1H), 7.62 (d, J = 8.8 Hz, 1H), 7.27 (d, J = 2.3 Hz, 1H), 7.14 (d, J = 2.5 Hz, 1H), 7.03 (dd, J = 8.6, 2.3 Hz, 1H), 6.97 (dd, J = 8.8, 2.6 Hz, 1H), 4.95 (dd, J = 12.6, 5.4 Hz, 1H), 3.95 (t, J = 12.6 Hz, 4H), 3.08-3.02 (m, 2H), 3.00-2.93 (m, 2H), 2.90 (d, J = 18.5 Hz, 1H), 2.87-2.81 (m, 1H), 2.78-2.67 (m, 3H), 2.59 (s, 1H), 2.22-2.16 (m, 2H), 2.16-2.12 (m, 1H), 2.08 (d, J = 9.6 Hz, 2H), 2.00-1.94 (m, 2H), 1.92 (dd, J = 12.5, 3.0 Hz, 4H), 1.75 (s, 4H). m/z 835.27 [M + H]+. |
| 132 | $^1$H NMR (600 MHz, CDCl$_3$) δ 8.88 (s, 1H), 8.33 (d, J = 2.0 Hz, 1H), 8.27 (s, 1H), 8.16 (d, J = 8.7 Hz, 1H), 7.71 (dd, J = 8.6, 2.2 Hz, 1H), 7.66-7.61 (m, 1H), 7.14 (d, J = 2.5 Hz, 1H), 6.98 (dd, J = 8.8, 2.6 Hz, 1H), 6.78 (d, J = 2.1 Hz, 1H), 6.49 (dd, J = 8.3, 2.0 Hz, 1H), 4.94 (dd, J = 12.5, 5.4 Hz, 1H), 4.18-4.11 (m, 2H), 3.96 (d, J = 13.2 Hz, 2H), 3.73-3.67 (m, 2H), 3.09-3.01 (m, 2H), 2.90 (d, J = 17.7 Hz, 1H), 2.86-2.80 (m, 1H), 2.79-2.70 (m, 3H), 2.67 (d, J = 7.3 Hz, 2H), 2.65-2.62 (m, 1H), 2.62-2.52 (m, 2H), 2.25 (s, 2H), 2.17-2.11 (m, 1H), 2.08 (d, J = 10.1 Hz, 2H), 1.97-1.91 (m, 2H), 1.76 (d, J = 9.1 Hz, 2H). m/z 807.23 [M + H]+. |
| 133 | $^1$H NMR (400 MHz, CDCl$_3$) δ 9.52 (s, 1H), 8.51 (s, 1H), 8.14-8.08 (m, 1H), 7.65 (d, J = 8.5 Hz, 1H), 7.60 (d, J = 8.8 Hz, 1H), 7.52 (dd, J = 8.7, 2.1 Hz, 1H), 7.25 (s, 1H), 7.12 (d, J = 2.1 Hz, 1H), 7.01 (dd, J = 8.6, 2.0 Hz, 1H), 6.95 (dd, J = 8.8, 2.2 Hz, 1H), 4.93 (dd, J = 12.3, 5.2 Hz, 1H), 3.99-3.86 (m, 4H), 3.03 (t, J = 11.3 Hz, 2H), 2.98-2.89 (m, 2H), 2.88-2.78 (m, 4H), 2.78-2.66 (m, 1H), 2.63-2.53 (m, 3H), 2.20-2.10 (m, 3H), 2.09-2.00 (m, 3H), 1.99-1.90 (m, 2H), 1.86 (d, J = 10.8 Hz, 4H), 1.79-1.72 (m, 1H), 1.70-1.64 (m, 2H), 1.55-1.48 (m, 2H), 1.24-1.18 (m, 2H). m/z 839.38 [M + H]+. |
| 134 | $^1$H NMR (600 MHz, CDCl$_3$) δ 9.93 (s, 1H), 9.04 (s, 1H), 8.42 (s, 1H), 8.23 (d, J = 8.7 Hz, 1H), 7.77 (dd, J = 8.7, 2.1 Hz, 1H), 7.63 (t, J = 9.2 Hz, 2H), 7.22 (d, J = 2.2 Hz, 1H), 7.13 (d, J = 2.4 Hz, 1H), 7.02-6.92 (m, 2H), 4.96 (dd, J = 12.5, 5.4 Hz, 1H), 3.96 (d, J = 13.2 Hz, 2H), 3.54 (s, 2H), 3.44-3.32 (m, 2H), 3.27 (s, 4H), 3.13-3.04 (m, 2H), 2.94-2.86 (m, 2H), 2.86-2.79 (m, 1H), 2.75 (ddd, J = 16.5, 13.4, 4.9 Hz, 2H), 2.66 (tt, J = 10.9, 3.9 Hz, 1H), 2.28-2.11 (m, 1H), 2.08 (dd, J = 14.9, 4.3 Hz, 3H), 2.03-1.91 (m, 4H), 1.91-1.83 (m, 4H), 0.92-0.83 (m, 2H). m/z 793.21 [M + H]+. |
| 135 | $^1$H NMR (400 MHz, DMSO-d6) δ 10.91 (s, 1H), 10.21 (s, 1H), 8.28 (s, 1H), 7.93 (d, J = 2.7 Hz, 1H), 7.86 (d, J = 9.1 Hz, 1H), 7.77 (d, J = 8.9 Hz, 1H), 7.45 (d, J = 8.5 Hz, 1H), 7.35-7.29 (m, 1H), 7.27 (s, 1H), 7.23-7.19 (m, 1H), 7.00 (d, J = 9.2 Hz, 2H), 5.00 (dd, J = 13.3, 5.2 Hz, 1H), 4.27 (d, J = 16.9 Hz, 1H), 4.14 (d, J = 16.7 Hz, 1H), 4.06 (d, J = 13.7 Hz, 2H), 3.57 (d, J = 12.1 Hz, 2H), 3.24 (s, 4H), 2.97 (d, J = 12.3 Hz, 2H), 2.92 (s, 4H), 2.84 (d, J = 13.4 Hz, 1H), 2.71 (s, 2H), 2.61 (d, J = 19.5 Hz, 2H), 2.54 (d, J = 12.3 Hz, 2H), 2.33 (s, 1H), 2.29 (s, 2H), 1.91 (s, 1H), 1.82 (d, J = 11.1 Hz, 2H), 1.70 (s, 5H), 1.65-1.54 (m, 2H), 1.34 (s, 2H), 1.18 (d, J = 12.6 Hz, 2H). m/z 838.41 [M + H]+. |
| 136 | $^1$H NMR (600 MHz, DMSO-d6) δ 10.93 (s, 1H), 9.85 (s, 1H), 8.02 (d, J = 2.6 Hz, 1H), 7.84 (d, J = 8.8 Hz, 1H), 7.77 (d, J = 9.0 Hz, 1H), 7.48 (d, J = 8.5 Hz, 1H), 7.40 (d, J = 2.7 Hz, 1H), 7.37 (d, J = 2.0 Hz, 1H), 7.32-7.28 (m, 1H), 7.05 (s, 1H), 7.03 (d, J = 9.1 Hz, 1H), 5.02 (dd, J = 13.2, 5.1 Hz, 1H), 4.29 (d, J = 16.8 Hz, 1H), 4.17 (d, J = 16.8 Hz, 1H), 4.06 (d, J = 14.4 Hz, 2H), 3.65 (d, J = 12.0 Hz, 2H), 3.25 (d, J = 12.2 Hz, 6H), 2.96 (s, 2H), 2.92-2.84 (m, 2H), 2.66-2.60 (m, 2H), 2.60-2.53 (m, 2H), 2.40-2.26 (m, 3H), 2.20-2.12 (m, 1H), 2.12-2.06 (m, 1H), 2.01 (d, J = 12.5 Hz, 2H), 1.96-1.91 (m, 1H), 1.80-1.69 (m, 5H), 1.43 (s, 2H), 1.22-1.14 (m, 2H). m/z 856.41 [M + H]+. |
| 137 | $^1$H NMR (600 MHz, DMSO-d6) δ 10.93 (s, 1H), 10.23 (s, 1H), 8.62 (d, J = 2.5 Hz, 1H), 7.96 (s, 1H), 7.89 (d, J = 9.0 Hz, 1H), 7.61 (d, J = 2.5 Hz, 1H), 7.48 (d, J = 8.4 Hz, 1H), 7.35 (d, J = 6.8 Hz, 1H), 7.07-7.01 (m, 2H), 5.03 (dd, J = 13.3, 5.0 Hz, 1H), 4.30 (d, J = 16.8 Hz, 1H), 4.23-4.11 (m, J = 14.9, 8.8 Hz, 3H), 3.60 (d, J = 11.5 Hz, 2H), 3.26 (s, 4H), 3.09-3.01 (m, 2H), 2.94 (s, 4H), 2.91-2.84 (m, 1H), 2.79-2.73 (m, 1H), 2.62-2.54 (m, 3H), 2.38-2.27 (m, 3H), 1.97-1.92 (m, 1H), 1.91-1.83 (m, 2H), 1.78-1.69 (m, 4H), 1.69-1.62 (m, 2H), 1.42-1.34 (m, 2H), 1.26-1.18 (m, 2H). m/z 839.48 [M + H]+. |
| 138 | $^1$H NMR (600 MHz, DMSO-d6) δ 10.93 (s, 1H), 10.23 (s, 1H), 7.97 (d, J = 2.8 Hz, 1H), 7.88 (d, J = 9.1 Hz, 1H), 7.80 (d, J = 8.9 Hz, 1H), 7.49 (d, J = 8.5 Hz, 1H), 7.37-7.33 (m, 1H), 7.29 (s, 1H), 7.24 (dd, J = 8.9, 2.6 Hz, 1H), 7.04 (d, J = 13.2 Hz, 1H), 5.03 (dd, J = 13.3, 5.1 Hz, 1H), 4.30 (d, J = 17.0 Hz, 1H), 4.18 (d, J = 17.0 Hz, 1H), 4.09 (d, J = 13.0 Hz, 2H), 3.61 (d, J = 11.3 Hz, 2H), 3.46-3.40 (m, 4H), 3.29-3.24 (m, 4H), 3.01-2.96 (m, 2H), 2.90-2.84 (m, 2H), 2.76-2.72 (m, 1H), 2.64-2.55 (m, 4H), 2.39-2.30 (m, 2H), 1.96-1.92 (m, 1H), 1.87-1.82 (m, 2H), 1.79-1.75 (m, 2H), 1.75-1.69 (m, 2H), 1.66-1.58 (m, 2H), 1.45-1.38 (m, 2H), 1.26-1.20 (m, 2H). m/z 852.42 [M + H]+. |
| 139 | $^1$H NMR (600 MHz, CDCl$_3$) δ 8.40 (s, 1H), 8.35 (s, 1H), 8.09 (d, J = 9.2 Hz, 1H), 7.92 (d, J = 2.9 Hz, 1H), 7.74 (d, J = 8.6 Hz, 1H), 7.62 (d, J = 8.8 Hz, 1H), 7.31 (dd, J = 9.2, 2.8 Hz, 1H), 7.02-6.96 (m, 2H), 6.88 (s, 2H), 5.20 (s, 1H), 4.41 (d, J = 15.7 Hz, 1H), 4.27 (d, J = 15.6 Hz, 1H), 3.96 (d, J = 13.3 Hz, 2H), 3.60 (d, J = 12.2 Hz, 2H), 3.37-3.30 (m, 4H), 3.10-3.04 (m, 2H), 2.94-2.89 (m, 1H), 2.86-2.80 (m, 2H), 2.74-2.68 (m, 2H), 2.65-2.59 (m, 4H), 2.55 (d, J = 10.8 Hz, 1H), 2.49-2.43 (m, 2H), 2.36-2.31 (m, 1H), 2.24-2.19 (m, 1H), 2.08-2.03 (m, 2H), 1.97-1.91 (m, 2H), 1.84 (d, J = 12.9 Hz, 2H), 1.56-1.50 (m, 4H), 1.42-1.37 (m, 2H). m/z 812.40 [M + H]+. |
| 140 | $^1$H NMR (600 MHz, DMSO-d6) δ 10.95 (s, 1H), 10.24 (s, 1H), 7.98 (d, J = 3.0 Hz, 1H), 7.90 (d, J = 9.0 Hz, 1H), 7.82 (d, J = 8.9 Hz, 1H), 7.50 (d, J = 8.5 Hz, 1H), 7.36 (dd, J = 9.2, 3.0 Hz, 1H), 7.31 (d, J = 2.4 Hz, 1H), 7.25 (dd, J = 8.9, 2.5 Hz, 1H), 7.05 (dd, J = 11.2, 2.5 Hz, 2H), 5.04 (dd, J = 13.3, 5.1 Hz, 1H), 4.32 (d, J = 16.9 Hz, 1H), 4.20 (d, J = 16.9 Hz, 1H), 4.10 (d, J = 13.4 Hz, 2H), 3.89 (d, J = 12.4 Hz, 2H), 3.62 (d, J = 12.3 Hz, 2H), 3.00 (t, J = 11.6 Hz, |

TABLE 5-continued

| Example | NMR and/or MS data |
|---|---|
| | 2H), 2.95-2.70 (m, 4H), 2.61 (dd, J = 27.1, 15.7 Hz, 6H), 2.37 (ddd, J = 21.5, 8.5, 5.1 Hz, 6H), 2.13 (d, J = 7.2 Hz, 2H), 1.99-1.92 (m, 2H), 1.85 (t, J = 13.1 Hz, 4H), 1.77 (d, J = 11.4 Hz, 2H), 1.71-1.58 (m, 4H), 1.54-1.41 (m, 3H), 1.23 (d, J = 12.0 Hz, 2H). m/z 881.46 [M + H]$^+$. |
| 141 | $^1$H NMR (600 MHz, DMSO-d6) δ 10.95 (s, 1H), 9.86 (d, J = 3.1 Hz, 1H), 8.03 (d, J = 2.9 Hz, 1H), 7.86 (d, J = 8.8 Hz, 1H), 7.79 (d, J = 9.0 Hz, 1H), 7.50 (d, J = 8.4 Hz, 1H), 7.43-7.37 (m, 2H), 7.32 (dd, J = 8.9, 2.4 Hz, 1H), 7.08-7.01 (m, 2H), 5.04 (dd, J = 13.3, 5.1 Hz, 1H), 4.32 (d, J = 16.8 Hz, 1H), 4.20 (d, J = 16.8 Hz, 1H), 4.08 (d, J = 13.6 Hz, 2H), 3.89 (d, J = 12.4 Hz, 2H), 3.67 (d, J = 12.2 Hz, 2H), 3.28 (t, J = 13.2 Hz, 3H), 2.98-2.86 (m, 2H), 2.82 (t, J = 11.6 Hz, 2H), 2.70-2.61 (m, 4H), 2.45-2.23 (m, 5H), 2.19 (dd, J = 26.3, 16.5 Hz, 1H), 2.16-2.06 (m, 3H), 2.02 (t, J = 12.6 Hz, 2H), 1.98-1.93 (m, 1H), 1.86 (t, J = 24.5 Hz, 2H), 1.77 (d, J = 11.5 Hz, 2H), 1.65 (s, 1H), 1.47 (dd, J = 20.5, 11.3 Hz, 2H), 1.26-1.14 (m, 2H). m/z 899.52 [M + H]$^+$. |
| 142 | $^1$H NMR (600 MHz, DMSO-d6) δ 10.93 (s, 1H), 10.23 (s, 1H), 8.61 (d, J = 2.7 Hz, 1H), 7.96 (d, J = 2.9 Hz, 1H), 7.88 (d, J = 9.1 Hz, 1H), 7.61 (d, J = 2.6 Hz, 1H), 7.48 (d, J = 8.4 Hz, 1H), 7.35 (dd, J = 9.2, 2.9 Hz, 1H), 7.08-6.99 (m, 2H), 5.02 (dd, J = 13.2, 5.1 Hz, 1H), 4.30 (d, J = 16.8 Hz, 1H), 4.23-4.13 (m, 3H), 3.88 (d, J = 12.1 Hz, 2H), 3.61 (d, J = 11.9 Hz, 2H), 3.05 (t, J = 11.6 Hz, 2H), 2.94-2.85 (m, 2H), 2.80 (t, J = 12.1 Hz, 2H), 2.76 (s, 1H), 2.67-2.57 (m, 4H), 2.43-2.25 (m, 6H), 2.10 (d, J = 14.2 Hz, 2H), 1.99-1.91 (m, 1H), 1.90-1.85 (m, 2H), 1.82 (d, J = 11.3 Hz, 2H), 1.75 (d, J = 12.0 Hz, 2H), 1.70-1.58 (m, 2H), 1.54-1.39 (m, 2H), 1.27-1.12 (m, 2H). m/z 882.47 [M + H]$^+$. |
| 143 | $^1$H NMR (600 MHz, DMSO-d6) δ 10.93 (s, 1H), 10.22 (s, 1H), 7.96 (s, 1H), 7.88 (d, J = 8.9 Hz, 1H), 7.80 (d, J = 8.9 Hz, 1H), 7.48 (d, J = 8.4 Hz, 1H), 7.35 (d, J = 9.2 Hz, 1H), 7.29 (s, 1H), 7.23 (d, J = 8.9 Hz, 1H), 7.02 (d, J = 9.5 Hz, 2H), 5.02 (dd, J = 13.2, 5.0 Hz, 1H), 4.29 (d, J = 16.7 Hz, 1H), 4.19 (s, 1H), 4.08 (d, J = 13.3 Hz, 2H), 3.84 (d, J = 12.2 Hz, 2H), 3.61 (d, J = 12.0 Hz, 2H), 3.00-2.95 (m, 2H), 2.92-2.85 (m, 2H), 2.83-2.77 (m, 2H), 2.77-2.72 (m, 1H), 2.65-2.56 (m, 3H), 2.56-2.51 (m, 2H), 2.40-2.24 (m, 6H), 2.17-2.08 (m, 4H), 1.98-1.92 (m, 1H), 1.84 (d, J = 11.4 Hz, 2H), 1.78-1.69 (m, 4H), 1.67-1.59 (m, 2H), 1.22-1.09 (m, 4H). m/z 895.42 [M + H]$^+$. |
| 144 | $^1$H NMR (600 MHz, DMSO-d6) δ 10.94 (s, 1H), 9.86 (d, J = 3.2 Hz, 1H), 8.03 (d, J = 3.0 Hz, 1H), 7.85 (d, J = 8.9 Hz, 1H), 7.79 (d, J = 9.0 Hz, 1H), 7.49 (d, J = 8.5 Hz, 1H), 7.42-7.38 (m, 2H), 7.32 (d, J = 8.9, 2.5 Hz, 1H), 7.03 (d, J = 9.0 Hz, 2H), 5.06-5.03 (m, 1H), 4.30 (s, 1H), 4.20 (s, 1H), 4.08 (d, J = 14.0 Hz, 2H), 3.86 (d, J = 12.4 Hz, 2H), 3.67 (d, J = 12.2 Hz, 2H), 3.26 (d, J = 11.2 Hz, 2H), 2.93-2.87 (m, 2H), 2.83-2.79 (m, 2H), 2.69-2.58 (m, 5H), 2.42-2.32 (m, 6H), 2.22-2.07 (m, 8H), 2.04-1.92 (m, 5H), 1.76 (d, J = 13.4 Hz, 4H), 1.65-1.62 (m, 3H). m/z 913.52 [M + H]$^+$. |
| 145 | $^1$H NMR (600 MHz, DMSO-d6) δ 10.94 (s, 1H), 10.24 (s, 1H), 8.63 (d, J = 2.7 Hz, 1H), 7.98 (d, J = 2.8 Hz, 1H), 7.90 (d, J = 9.1 Hz, 1H), 7.62 (d, J = 2.6 Hz, 1H), 7.49 (d, J = 8.4 Hz, 1H), 7.36 (dd, J = 9.3, 2.8 Hz, 1H), 7.03 (d, J = 9.0 Hz, 2H), 5.04 (dd, J = 13.2, 5.1 Hz, 1H), 4.31 (d, J = 16.9 Hz, 1H), 4.19 (dd, J = 15.1, 7.7 Hz, 3H), 3.86 (d, J = 12.5 Hz, 2H), 3.63 (d, J = 11.6 Hz, 2H), 3.09-3.04 (m, 2H), 2.89-2.85 (m, 2H), 2.80 (d, J = 22.5, 11.2 Hz, 3H), 2.61 (dd, J = 28.1, 18.5 Hz, 7H), 2.40-2.32 (m, 4H), 2.14 (s, 4H), 1.99-1.93 (m, 2H), 1.92-1.84 (m, 3H), 1.77 (d, J = 12.2 Hz, 4H), 1.67 (dd, J = 22.3, 10.6 Hz, 4H), 1.26-1.23 (m, 4H). m/z 896.55 [M + H]$^+$. |
| 146 | $^1$H NMR (400 MHz, CDCl$_3$) δ 9.53 (s, 1H), 8.82 (d, J = 5.2 Hz, 1H), 8.09 (d, J = 9.1 Hz, 1H), 7.93 (d, J = 2.9 Hz, 1H), 7.76 (d, J = 8.3 Hz, 1H), 7.60 (d, J = 8.8 Hz, 1H), 7.34-7.28 (m, 2H), 7.17 (dd, J = 8.4, 2.2 Hz, 2H), 7.12 (d, J = 2.5 Hz, 1H), 6.95 (dd, J = 8.9, 2.6 Hz, 1H), 4.95 (dd, J = 12.4, 5.4 Hz, 1H), 4.45 (d, J = 2.3 Hz, 1H), 3.98-3.88 (m, 2H), 3.59 (d, J = 12.1 Hz, 2H), 3.09-2.97 (m, 2H), 2.95-2.77 (m, 2H), 2.75-2.72 (m, 1H), 2.72-2.64 (m, 2H), 2.63-2.54 (m, 12H), 2.23 (d, J = 6.6 Hz, 2H), 2.18-2.11 (m, 1H), 2.07-1.98 (m, 4H), 1.98-1.90 (m, 2H), 1.89-1.78 (m, 4H), 1.66-1.56 (m, 1H), 1.38-1.28 (m, 2H), 1.28-1.20 (m, 2H). m/z 827.40 [M + H]$^+$. |
| 147 | $^1$H NMR (400 MHz, CDCl$_3$) δ 9.48 (s, 1H), 8.67 (s, 1H), 8.10 (d, J = 9.1 Hz, 1H), 7.96 (d, J = 2.7 Hz, 1H), 7.78 (d, J = 8.3 Hz, 1H), 7.62 (d, J = 8.8 Hz, 1H), 7.35-7.29 (m, 2H), 7.18 (dd, J = 8.3, 2.2 Hz, 1H), 7.13 (s, 1H), 6.97 (dd, J = 8.8, 2.2 Hz, 1H), 4.96 (dd, J = 12.3, 5.1 Hz, 1H), 4.00-3.88 (m, 4H), 3.61 (d, J = 12.1 Hz, 2H), 3.11-3.01 (m, 2H), 2.99-2.86 (m, 2H), 2.84-2.77 (m, 4H), 2.76-2.65 (m, 1H), 2.64-2.54 (m, 2H), 2.30-2.21 (m, 1H), 2.20-2.11 (m, 2H), 2.10-2.00 (m, 1H), 1.96 (m, 4H), 1.91-1.79 (m, 5H), 1.72-1.61 (m, 1H), 1.51-1.39 (m, 2H), 1.38-1.27 (m, 2H). m/z 841.31 [M + H]$^+$. |
| 148 | $^1$H NMR (400 MHz, DMSO-d$_6$) δ 11.08 (s, 1H), 10.15 (s, 1H), 7.82 (d, J = 8.8 Hz, 1H), 7.80-7.76 (m, 2H), 7.50 (d, J = 2.9 Hz, 1H), 7.42 (d, J = 2.1 Hz, 1H), 7.33 (dd, J = 8.4, 2.1 Hz, 1H), 7.27 (d, J = 2.2 Hz, 1H), 7.21 (dd, J = 9.0, 2.2 H, 1H z), 6.83 (dd, J = 8.8, 2.9 Hz, 1H), 5.08 (dd, J = 12.9, 5.4 Hz, 1H), 4.70-4.63 (m, 1H), 4.06 (d, J = 13.3 Hz, 2H), 3.90 (t, J = 7.4 Hz, 2H), 3.45-3.40 (m, 2H), 2.99-2.91 (m, 2H), 2.90-2.79 (m, 2H), 2.74-2.65 (m, 1H), 2.61-2.60 (m, 1H), 2.60-2.51 (m, 4H), 2.40-2.37 (m, 1H), 2.24 (d, J = 8.9 Hz, 2H), 2.04-1.98 (m, 1H), 1.95-1.88 (m, 2H), 1.85-1.77 (m, 2H), 1.68-1.54 (m, 4H). m/z 799.40 [M + H]$^+$. |
| 149 | $^1$H NMR (400 MHz, DMSO-d$_6$) δ 11.08 (s, 1H), 10.15 (s, 1H), 7.83 (d, J = 8.8 Hz, 1H), 7.80-7.76 (m, 2H), 7.50 (d, J = 2.9 Hz, 1H), 7.40 (d, J = 2.2 Hz, 1H), 7.32 (dd, J = 8.3, 2.2 Hz, 1H), 7.27 (d, J = 2.3 Hz, 1H), 7.21 (dd, J = 8.9, 2.3 Hz, 1H), 6.83 (dd, J = 8.8, 2.9 Hz, 1H), 5.08 (dd, J = 12.9, 5.4 Hz, 1H), 4.06 (d, J = 13.4 Hz, 2H), 4.01 (d, J = 6.2 Hz, 2H), 3.89 (t, J = 7.4 Hz, 2H), 3.42 (t, J = 6.4 Hz, 2H), 2.96 (t, J = 11.6 Hz, 2H), 2.92-2.77 (m, 4H), 2.75-2.65 (m, 1H), 2.55-2.53 (m, 1H), 2.44-2.42 (m, 3H), 2.06-1.97 (m, 1H), 1.96-1.87 (m, 2H), 1.85-1.77 (m, 2H), 1.76-1.67 (m, 3H), 1.66-1.53 (m, 2H), 1.34-1.23 (m, 2H). m/z 813.35 [M + H]$^+$. |
| 150 | $^1$H NMR (600 MHz, CDCl3) δ 9.49 (s, 1H), 8.39 (s, 1H), 8.08 (d, J = 9.1 Hz, 1H), 7.99 (d, J = 2.8 Hz, 1H), 7.69 (d, J = 8.5 Hz, 1H), 7.62 (d, J = 8.8 Hz, 1H), 7.30 (dd, J = 9.1, 2.9 Hz, 1H), 7.28 (d, J = 2.1 Hz, 1H), 7.13 (d, J = 2.2 Hz, 1H), 7.04 (d, J = 8.6, 2.2 Hz, 1H), 6.96 (dd, J = 8.8, 2.4 Hz, 1H), 4.95 (dd, J = 12.6, 5.4 Hz, 1H), 3.94 (d, J = 13.2 Hz, 2H), 3.67 (t, J = 5.7 Hz, 2H), 3.52-3.47 (m, 1H), 3.43 (dd, J = 13.1, 8.2 Hz, 4H), 3.07-3.00 (m, 2H), 2.99-2.93 (m, 2H), 2.92-2.80 (m, 3H), 2.79-2.72 (m, 2H), 2.71-2.63 (m, 4H), 2.60-2.53 (m, 1H), 2.18-2.10 (m, 1H), 2.06 (d, J = 12.4 Hz, 2H), 1.98 (dd, J = 19.3, 8.1 Hz, 2H), 1.95-1.89 (m, 2H), 1.80-1.70 (m, 2H), 1.50-1.39 (m, 2H). m/z 842.46 [M + H]$^+$. |
| 151 | $^1$H NMR (600 MHz, CDCl3) δ 8.93 (s, 1H), 8.13 (s, 1H), 8.07 (d, J = 9.1 Hz, 1H), 7.97 (d, J = 2.8 Hz, 1H), 7.69 (d, J = 8.5 Hz, 1H), 7.45 (d, J = 8.9 Hz, 1H), 7.31-7.27 (m, 2H), 7.05 (dd, J = 8.6, 2.3 Hz, 1H), 6.88 (d, J = 2.5 Hz, 1H), 6.75 (dd, J = 8.9, 2.5 Hz, 1H), 4.95 (dd, J = 12.5, 5.4 Hz, 1H), 3.89 (d, J = 13.2 Hz, 2H), 3.67 (t, J = 5.7 Hz, 2H), 3.49 (m, 1H), 3.44-3.37 (m, 4H), 3.03-2.93 (m, 3H), 2.89 (dd, J = 19.6, 3.1 Hz, 2H), 2.86-2.80 (m, 2H), 2.78-2.73 (m, 2H), 2.69 (m, 4H), 2.56-2.50 (m, 1H), 2.14 (m, 1H), 2.08-1.97 (m, 4H), 1.92 (m, 2H), 1.81-1.71 (m, 2H), 1.49 (d, J = 6.6 Hz, 2H). m/z 808.44 [M + H]$^+$. |
| 152 | $^1$H NMR (600 MHz, CDCl3) δ 9.78 (s, 1H), 8.52 (s, 1H), 8.11 (d, J = 9.0 Hz, 1H), 8.00 (d, J = 2.9 Hz, 1H), 7.64 (d, J = 8.8 Hz, 1H), 7.61 (dd, J = 8.4, 7.2 Hz, 1H), 7.42 (d, J = 7.1 Hz, 1H), 7.35 (dd, J = 9.1, 2.9 Hz, 1H), 7.18 (d, J = 8.4 Hz, 1H), 7.15 (d, J = 2.5 Hz, 1H), 6.99 (dd, J = 8.9, 2.6 Hz, 1H), 4.98 (dd, J = 12.4, 5.4 Hz, 1H), 3.97 (d, J = 13.0 Hz, 2H), 3.74-3.66 (m, 2H), 3.56-3.50 (m, 1H), 3.46-3.29 (m, 6H), 3.12-3.05 (m, 2H), 3.05-2.97 (m, 2H), 2.92-2.87 (m, 1H), 2.87-2.77 (m, 4H), 2.77-2.71 (m, 2H), 2.64-2.58 (m, 1H), 2.19-2.14 (m, 1H), 2.08 (dd, J = 8.3, 5.7 Hz, 2H), 2.02-1.92 (m, 4H), 1.86-1.76 (m, 2H), 1.61-1.58 (m, 2H). m/z 842.49 [M + H]$^+$. |

TABLE 5-continued

| Example | NMR and/or MS data |
|---|---|
| 153 | $^1$H NMR (600 MHz, CDCl$_3$) δ 8.99 (s, 1H), 8.21 (s, 1H), 8.08 (d, J = 9.1 Hz, 1H), 8.00 (d, J = 2.9 Hz, 1H), 7.70 (d, J = 8.5 Hz, 1H), 7.62 (d, J = 8.8 Hz, 1H), 7.33 (dd, J = 9.1, 2.9 Hz, 1H), 7.28 (d, J = 2.2 Hz, 1H), 7.13 (d, J = 2.4 Hz, 1H), 7.04 (dd, J = 8.6, 2.3 Hz, 1H), 6.97 (dd, J = 8.8, 2.6 Hz, 1H), 4.94 (dd, J = 12.6, 5.4 Hz, 1H), 3.95 (d, J = 13.2 Hz, 2H), 3.42 (dd, J = 53.2, 21.7 Hz, 6H), 3.21-3.15 (m, 2H), 3.07-3.01 (m, 2H), 2.92-2.81 (m, 3H), 2.78-2.65 (m, 6H), 2.57-2.53 (m, 1H), 2.16-2.12 (m, 1H), 2.08-2.03 (m, 2H), 1.98-1.90 (m, 2H), 1.80 (d, J = 12.2 Hz, 2H), 1.70 (dd, J = 17.1, 11.0 Hz, 4H). |
| 154 | $^1$H NMR (600 MHz, CDCl$_3$) δ 10.26 (s, 1H), 8.79 (s, 1H), 8.10 (d, J = 9.1 Hz, 1H), 7.99 (d, J = 2.9 Hz, 1H), 7.69 (d, J = 8.5 Hz, 1H), 7.61 (d, J = 8.8 Hz, 1H), 7.31 (dd, J = 9.2, 2.9 Hz, 1H), 7.29 (d, J = 2.2 Hz, 1H), 7.11 (d, J = 2.4 Hz, 1H), 7.05 (dd, J = 8.6, 2.3 Hz, 1H), 6.95 (dd, J = 8.8, 2.5 Hz, 1H), 4.96 (dd, J = 12.6, 5.4 Hz, 1H), 4.00-3.89 (m, 4H), 3.79 (s, 2H), 3.65 (d, J = 12.2 Hz, 2H), 3.43 (d, J = 13.3 Hz, 2H), 3.40-3.33 (m, 2H), 3.09-2.95 (m, 2H), 2.95-2.81 (m, 2H), 2.76 (dt, J = 22.0, 8.4 Hz, 2H), 2.64-2.54 (m, 2H), 2.32 (m, 1H), 2.20-2.11 (m, 1H), 2.09-2.01 (m, 2H), 1.93 (m, 9H), 1.81 (d, J = 11.0 Hz, 2H). m/z 866.38 [M + H]$^+$. |
| 155 | $^1$H NMR (600 MHz, CDCl$_3$) δ 8.99 (s, 1H), 8.37 (s, 1H), 7.84 (s, 1H), 7.79 (s, 1H), 7.67 (d, J = 8.5 Hz, 1H), 7.62 (d, J = 8.7 Hz, 1H), 7.27 (d, J = 2.3 Hz, 1H), 7.13 (s, 1H), 7.04 (dd, J = 8.6, 2.1 Hz, 1H), 6.97 (dd, J = 8.8, 2.5 Hz, 1H), 4.94 (dd, J = 12.6, 5.4 Hz, 1H), 4.23 (d, J = 13.0 Hz, 2H), 3.96 (d, J = 12.9 Hz, 2H), 3.45-3.33 (m, 4H), 3.11 (s, 4H), 3.09-3.02 (m, 2H), 2.91-2.86 (m, 1H), 2.86-2.80 (m, 2H), 2.76-2.70 (m, 2H), 2.59-2.53 (m, 1H), 2.46-2.37 (m, 2H), 2.16-2.11 (m, 1H), 2.05 (d, J = 8.0 Hz, 2H), 1.98-1.91 (m, 2H), 1.87 (s, 2H), 1.83 (d, J = 13.2 Hz, 2H), 1.64-1.54 (m, 4H). m/z 853.42 [M + H]$^+$. |
| 156 | $^1$H NMR (600 MHz, CDCl$_3$) δ 8.99 (s, 1H), 8.60 (s, 1H), 7.89 (s, 1H), 7.81 (s, 1H), 7.70 (dd, J = 8.4, 3.0 Hz, 1H), 7.64-7.59 (m, 1H), 7.31-7.28 (m, 1H), 7.15-7.11 (m, 1H), 7.08-7.03 (m, 1H), 6.99-6.95 (m, 1H), 4.95 (dd, J = 8.3, 4.2 Hz, 1H), 4.23 (d, J = 12.7 Hz, 2H), 3.96 (d, J = 12.9 Hz, 2H), 3.43 (s, 4H), 3.04 (t, J = 12.5 Hz, 2H), 2.95-2.80 (m, 4H), 2.78-2.70 (m, 1H), 2.61-2.57 (m, 4H), 2.57-2.53 (m, 1H), 2.49-2.43 (m, 2H), 2.18-2.12 (m, 1H), 2.10-2.04 (m, 2H), 1.82 (d, J = 12.6 Hz, 2H), 1.65-1.59 (m, 1H), 1.54-1.48 (m, J = 5.1 Hz, 2H), 1.33-1.24 (m, 2H). m/z 827.38 [M + H]$^+$. |
| 157 | $^1$H NMR (400 MHz, CDCl$_3$) δ 8.87 (s, 1H), 8.30-8.20 (m, 3H), 7.65 (d, J = 8.6 Hz, 1H), 7.59 (d, J = 8.8 Hz, 1H), 7.26 (s, 1H), 7.10 (d, J = 2.5 Hz, 1H), 7.01 (dd, J = 8.7, 2.3 Hz, 1H), 6.94 (dd, J = 8.9, 2.6 Hz, 1H), 4.93 (dd, J = 12.4, 5.4 Hz, 1H), 3.96-3.86 (m, 4H), 3.59 (d, J = 12.1 Hz, 2H), 3.07-3.00 (m, 2H), 2.99-2.89 (m, 3H), 2.89-2.76 (m, 2H), 2.76-2.66 (m, 3H), 2.42 (s, 8H), 2.23-2.17 (m, 4H), 2.16-2.10 (m, 1H), 2.10-2.02 (m, 2H), 2.00-1.91 (m, 1H), 1.91-1.82 (m, 4H), 1.84-1.72 (m, 1H), 1.69-1.63 (m, 1H), 1.37-1.19 (m, 4H). m/z 910.56 [M + H]$^+$. |
| 158 | $^1$H NMR (600 MHz, CDCl$_3$) δ 8.72 (s, 1H), 8.28 (s, 2H), 8.20 (s, 1H), 7.65 (d, J = 8.4 Hz, 1H), 7.61 (d, J = 8.8 Hz, 1H), 7.12 (d, J = 2.5 Hz, 1H), 6.97-6.93 (m, 2H), 6.67 (d, J = 8.5, 2.2 Hz, 1H), 4.95 (dd, J = 12.5, 5.4 Hz, 1H), 3.97-3.90 (m, 2H), 3.61 (d, J = 12.2 Hz, 2H), 3.58-3.53 (m, 1H), 3.50-3.45 (m, 1H), 3.43-3.37 (m, 1H), 3.20-3.15 (m, 1H), 3.10-3.02 (m, 2H), 2.91-2.87 (m, 1H), 2.86-2.79 (m, 1H), 2.78-2.70 (m, 3H), 2.64-2.59 (m, 1H), 2.58-2.51 (m, 2H), 2.50-2.42 (m, 4H), 2.42-2.35 (m, 2H), 2.24 (d, J = 7.2 Hz, 2H), 2.23-2.18 (m, 1H), 2.16-2.11 (m, 1H), 2.10-2.05 (m, 2H), 2.00-1.93 (m, 2H), 1.90 (d, J = 11.9 Hz, 2H), 1.86-1.78 (m, 1H), 1.72-1.63 (m, 2H), 1.59-1.54 (m, 2H), 1.37-1.30 (m, 2H). m/z 896.49 [M + H]$^+$. |
| 159 | $^1$H NMR (400 MHz, CDCl$_3$) δ 8.70 (s, 1H), 8.26 (s, 2H), 8.16 (s, 1H), 7.60 (d, J = 8.8 Hz, 1H), 7.43 (d, J = 11.0 Hz, 1H), 7.36 (d, J = 7.3 Hz, 1H), 7.11 (d, J = 2.5 Hz, 1H), 6.94 (dd, J = 8.8, 2.6 Hz, 1H), 4.92 (dd, J = 12.5, 5.3 Hz, 1H), 3.92 (dt, J = 12.8, 3.4 Hz, 2H), 3.67-3.55 (m, 4H), 3.10-3.00 (m, 2H), 2.94-2.86 (m, 1H), 2.86-2.78 (m, 3H), 2.77-2.67 (m, 3H), 2.57-2.32 (m, 7H), 2.26-2.18 (m, 4H), 2.17-2.09 (m, 1H), 2.09-2.02 (m, 2H), 2.00-1.92 (m, 2H), 1.92-1.83 (m, 4H), 1.78-1.61 (m, 4H), 1.43-1.25 (m, 4H). m/z 928.56 [M + H]$^+$. |
| 160 | $^1$H NMR (400 MHz, CDCl$_3$) δ 8.88 (s, 1H), 8.28 (s, 3H), 7.62 (dd, J = 8.8, 0.5 Hz, 1H), 7.39 (d, J = 12.3 Hz, 1H), 7.13 (d, J = 2.5 Hz, 1H), 7.03 (d, J = 7.5 Hz, 1H), 6.96 (dd, J = 8.9, 2.6 Hz, 1H), 4.93 (dd, J = 12.4, 5.4 Hz, 1H), 3.94 (dt, J = 12.8, 3.4 Hz, 2H), 3.71-3.55 (m, 5H), 3.35-3.28 (m, 1H), 3.12-3.02 (m, 2H), 2.94-2.80 (m, 2H), 2.79-2.68 (m, 3H), 2.60-2.49 (m, 5H), 2.49-2.41 (m, 2H), 2.41-2.33 (m, 2H), 2.24 (d, J = 7.2 Hz, 2H), 2.19-2.09 (m, 2H), 2.09-2.04 (m, 2H), 2.03-1.95 (m, 2H), 1.95-1.86 (m, 2H), 1.80-1.72 (m, 1H), 1.72-1.66 (m, 1H), 1.40-1.27 (m, 2H). m/z 914.52 [M + H]$^+$. |
| 161 | $^1$H NMR (400 MHz, CDCl$_3$) δ 9.11 (s, 1H), 8.36 (s, 1H), 8.21 (d, J = 1.8 Hz, 1H), 8.16 (d, J = 8.4 Hz, 1H), 7.72-7.65 (m, 2H), 7.62 (d, J = 8.8 Hz, 1H), 7.28-7.27 (m, 1H), 7.13 (d, J = 2.5 Hz, 1H), 7.03 (dd, J = 8.6, 2.3 Hz, 1H), 6.97 (dd, J = 8.8, 2.6 Hz, 1H), 4.95 (dd, J = 12.4, 5.3 Hz, 1H), 3.95 (d, J = 13.2 Hz, 2H), 3.47 (s, 2H), 3.44-3.35 (m, 4H), 3.10-3.00 (m, 2H), 2.95-2.69 (m, 5H), 2.64-2.56 (m, 1H), 2.57-2.48 (m, 4H), 2.22 (d, J = 7.1 Hz, 2H), 2.18-2.11 (m, 1H), 2.10-2.01 (m, 2H), 2.01-1.89 (m, 4H), 1.74 (d, J = 12.3 Hz, 2H), 1.54-1.48 (m, 1H), 1.28-1.18 (m, 2H). m/z 826.41 [M + H]$^+$. |
| 162 | $^1$H NMR (400 MHz, CDCl$_3$) δ 9.68-9.08 (m, 1H), 8.54 (s, 1H), 8.22 (s, 1H), 8.17 (d, J = 8.5 Hz, 1H), 7.71 (dd, J = 8.5, 2.1 Hz, 1H), 7.66 (d, J = 8.6 Hz, 1H), 7.62 (d, J = 8.8 Hz, 1H), 7.13 (s, 1H), 7.05-6.99 (m, 1H), 6.96 (d, J = 8.8 Hz, 1H), 4.95 (dd, J = 12.3, 5.4 Hz, 1H), 4.00-3.86 (m, 4H), 3.48 (s, 2H), 3.09-2.99 (m, 2H), 2.99-2.90 (m, 2H), 2.90-2.70 (m, 3H), 2.63-2.54 (m, 1H), 2.53-2.25 (m, 8H), 2.19 (d, J = 7.1 Hz, 2H), 2.18-2.10 (m, 1H), 2.10-2.01 (m, 2H), 2.01-1.91 (m, 2H), 1.87 (d, J = 13.2 Hz, 2H), 1.81-1.71 (m, 1H), 1.32-1.18 (m, 2H). m/z 826.41 [M + H]$^+$. |
| 163 | $^1$H NMR (400 MHz, CDCl$_3$) δ 9.16-9.07 (m, 1H), 8.40-8.34 (m, 1H), 8.20 (d, J = 2.0 Hz, 1H), 8.16 (d, J = 8.5 Hz, 1H), 7.77 (d, J = 8.3 Hz, 1H), 7.70 (dd, J = 8.5, 2.0 Hz, 1H), 7.63 (d, J = 8.8 Hz, 1H), 7.32 (d, J = 2.2 Hz, 1H), 7.18 (dd, J = 8.5, 2.2 Hz, 1H), 7.14 (d, J = 2.4 Hz, 1H), 6.98 (dd, J = 8.8, 2.4 Hz, 1H), 4.96 (dd, J = 12.4, 5.3 Hz, 1H), 4.50-4.39 (m, 1H), 4.04-3.92 (m, 2H), 3.45 (s, 2H), 3.10-3.01 (m, 2H), 2.95-2.88 (m, 1H), 2.88-2.72 (m, 4H), 2.71-2.63 (m, 2H), 2.62-2.55 (m, 1H), 2.29-2.21 (m, 1H), 2.18 (d, J = 6.9 Hz, 2H), 2.16-2.12 (m, 1H), 2.11-2.03 (m, 2H), 2.03-1.88 (m, 6H), 1.87-1.77 (m, 2H), 1.71 (d, J = 11.6 Hz, 2H), 1.50-1.42 (m, 1H), 1.24-1.14 (m, 2H). m/z 841.46 [M + H]$^+$. |
| 164 | $^1$H NMR (400 MHz, CDCl$_3$) δ 9.61 (s, 1H), 8.55 (s, 1H), 8.13 (d, J = 8.5 Hz, 1H), 8.10 (d, J = 1.7 Hz, 1H), 7.66 (d, J = 8.6 Hz, 1H), 7.62 (d, J = 8.8 Hz, 1H), 7.51 (dd, J = 8.5, 1.7 Hz, 1H), 7.26-7.26 (m, 1H), 7.13 (d, J = 2.3 Hz, 1H), 7.02 (dd, J = 8.6, 2.2 Hz, 1H), 6.96 (dd, J = 8.8, 2.3 Hz, 1H), 4.95 (dd, J = 12.2, 5.3 Hz, 1H), 4.00-3.86 (m, 4H), 3.08-2.98 (m, 2H), 2.98-2.92 (m, 2H), 2.92-2.86 (m, 2H), 2.85-2.80 (m, 2H), 2.80-2.69 (m, 1H), 2.65-2.54 (m, 1H), 2.50 (d, J = 6.8 Hz, 2H), 2.18-2.10 (m, 3H), 2.06 (d, J = 11.5 Hz, 2H), 2.00-1.91 (m, 2H), 1.90-1.80 (m, 4H), 1.78-1.69 (m, 1H), 1.63-1.58 (m, 2H), 1.51-1.41 (m, 2H), 1.34-1.16 (m, 4H). m/z 825.29 [M + H]$^+$. |
| 165 | $^1$H NMR (400 MHz, CDCl$_3$) δ 8.98 (s, 1H), 8.29 (s, 1H), 8.16-8.07 (m, 2H), 7.68 (d, J = 8.5 Hz, 1H), 7.61 (d, J = 8.8 Hz, 1H), 7.58-7.53 (m, 1H), 7.29-7.26 (m, 1H), 7.12 (d, J = 2.4 Hz, 1H), 7.04 (dd, J = 8.5, 2.3 Hz, 1H), 6.96 (dd, J = 8.8, 2.4 Hz, 1H), 4.93 (dd, J = 12.3, 5.3 Hz, 1H), 3.99-3.90 (m, 2H), 3.45-3.33 (m, 4H), 3.09-3.00 (m, 2H), 3.00-2.94 (m, 2H), 2.93-2.81 (m, 2H), 2.81-2.67 (m, 3H), 2.64-2.47 (m, 7H), 2.23 (d, J = 6.9 Hz, 2H), 2.18-2.11 (m, 1H), 2.09-2.03 (m, 2H), 2.01-1.86 (m, 4H), 1.83-1.72 (m, 2H), 1.62-1.58 (m, 1H), 1.32-1.25 (m, 2H). m/z 840.44 [M + H]$^+$. |
| 166 | $^1$H NMR (400 MHz, CDCl$_3$) δ 9.22 (s, 1H), 8.37 (s, 1H), 8.16 (d, J = 1.9 Hz, 1H), 8.13 (d, J = 8.5 Hz, 1H), 7.67 (d, J = 8.6 Hz, 1H), 7.62 (d, J = 8.8 Hz, 1H), 7.57 (dd, J = 8.5, 1.9 Hz, 1H), 7.27 (d, J = 2.4 Hz, 1H), 7.14 (d, J = 2.4 Hz, |

TABLE 5-continued

| Example | NMR and/or MS data |
|---|---|
| | 1H), 7.03 (dd, J = 8.8, 2.4 Hz, 1H), 6.97 (dd, J = 8.6, 2.4 Hz, 1H), 4.95 (dd, J = 12.3, 5.3 Hz, 1H), 4.01-3.90 (m, 4H), 3.10-3.01 (m, 2H), 3.01-2.91 (m, 2H), 2.91-2.80 (m, 2H), 2.79-2.73 (m, 3H), 2.65-2.50 (m, 7H), 2.50-2.38 (m, 4H), 2.21 (d, J = 7.1 Hz, 2H), 2.17-2.12 (m, 2H), 2.11-2.03 (m, 2H), 2.01-1.92 (m, 2H), 1.92-1.85 (m, 2H), 1.83-1.73 (m, 1H), 1.34-1.20 (m, 2H). m/z 840.43 [M + H]+. |
| 167 | $^1$H NMR (400 MHz, CDCl$_3$) δ 9.83 (s, 1H), 8.62 (s, 1H), 8.18 (d, J = 2.1 Hz, 1H), 8.16 (d, J = 8.5 Hz, 1H), 7.78 (d, J = 8.3 Hz, 1H), 7.63 (d, J = 8.8 Hz, 1H), 7.58 (dd, J = 8.5, 2.1 Hz, 1H), 7.33 (d, J = 12.4, 5.2 Hz, 1H), 7.19 (d, J = 8.3, 2.2 Hz, 1H), 7.14 (d, J = 2.5 Hz, 1H), 6.98 (dd, J = 8.8, 2.5 Hz, 1H), 4.97 (dd, J = 12.4, 5.2 Hz, 1H), 4.56-4.45 (m, 1H), 4.02-3.92 (m, 2H), 3.14-3.02 (m, 2H), 2.97-2.82 (m, 2H), 2.82-2.69 (m, 5H), 2.68-2.54 (m, 3H), 2.48-2.36 (m, 2H), 2.22-2.13 (m, 1H), 2.11-2.00 (m, 4H), 2.00-1.93 (m, 2H), 1.93-1.81 (m, 2H). m/z 758.39 [M + H]+. |
| 168 | $^1$H NMR (400 MHz, CDCl$_3$) δ 9.16 (s, 1H), 8.31 (s, 1H), 8.14 (d, J = 9.1 Hz, 1H), 8.00 (d, J = 3.0 Hz, 1H), 7.66 (d, J = 8.6 Hz, 1H), 7.62 (d, J = 8.8 Hz, 1H), 7.31-7.27 (m, 2H), 7.13 (d, J = 2.5 Hz, 1H), 7.03 (dd, J = 8.6, 2.3 Hz, 1H), 6.97 (dd, J = 8.8, 2.5 Hz, 1H), 4.95 (dd, J = 12.2, 5.3 Hz, 1H), 4.12 (t, J = 5.6 Hz, 2H), 4.03-3.88 (m, 4H), 3.10-2.98 (m, 2H), 2.98-2.91 (m, 2H), 2.90-2.72 (m, 5H), 2.71-2.54 (m, 5H), 2.54-5.38 (m, 5H), 2.21 (d, J = 7.0 Hz, 2H), 2.18-2.11 (m, 2H), 2.11-2.02 (m, 2H), 2.00-1.91 (m, 2H), 1.91-1.84 (m, 2H), 1.83-1.73 (s, 1H), 1.33-1.21 (m, 2H). m/z 856.36 [M + H]+. |
| 169 | $^1$H NMR (400 MHz, CDCl$_3$) δ 8.84 (s, 1H), 8.18 (s, 1H), 8.13 (d, J = 9.0 Hz, 1H), 7.99 (d, J = 2.9 Hz, 1H), 7.67 (d, J = 8.5 Hz, 1H), 7.62 (d, J = 8.8 Hz, 1H), 7.31-7.27 (m, 2H), 7.13 (d, J = 2.5 Hz, 1H), 7.03 (dd, J = 8.5, 2.3 Hz, 1H), 6.97 (dd, J = 8.8, 2.5 Hz, 1H), 4.95 (dd, J = 12.3, 5.3 Hz, 1H), 4.32-4.23 (m, 1H), 4.00-3.89 (m, 4H), 3.09-2.99 (m, 2H), 2.99-2.89 (m, 2H), 2.89-2.73 (m, 3H), 2.73-2.66 (m, 2H), 2.60-2.51 (m, 1H), 2.33-2.23 (m, 2H), 2.21 (d, J = 7.1 Hz, 2H), 2.18-2.12 (m, 1H), 2.12-2.03 (m, 2H), 2.03-1.95 (m, 3H), 1.95-1.87 (m, 3H), 1.83-1.71 (m, 3H), 1.33-1.21 (m, 2H). m/z 827.26 [M + H]+. |
| 170 | $^1$H NMR (400 MHz, CDCl$_3$) δ 9.08-8.75 (m, 1H), 8.25 (s, 1H), 8.14 (d, J = 9.0 Hz, 1H), 7.99 (d, J = 2.8 Hz, 1H), 7.63 (d, J = 8.8 Hz, 1H), 7.46 (d, J = 11.0 Hz, 1H), 7.39 (d, J = 7.3 Hz, 1H), 7.29 (d, J = 9.0, 2.8 Hz, 1H), 7.15-7.12 (m, 1H), 6.99-6.94 (m, J = 8.8 Hz, 1H), 4.94 (dd, J = 12.4, 5.3 Hz, 1H), 4.32-4.23 (m, 1H), 3.96 (d, J = 13.1 Hz, 2H), 3.65 (d, J = 11.8 Hz, 2H), 3.05 (t, J = 12.5 Hz, 2H), 2.95-2.77 (m, 5H), 2.77-2.65 (m, 2H), 2.60-2.50 (m, 1H), 2.32-2.20 (m, 4H), 2.18-2.11 (m, 1H), 2.11-2.03 (m, 2H), 2.03-1.94 (m, 3H), 1.94-1.86 (m, 3H), 1.85-1.77 (m, 2H), 1.73-1.64 (m, 1H), 1.44-1.32 (m, 2H). m/z 845.33 [M + H]+. |
| 171 | $^1$H NMR (400 MHz, CDCl$_3$) δ 9.43 (s, 1H), 8.38 (s, 1H), 8.15 (d, J = 9.1 Hz, 1H), 8.00 (d, J = 2.9 Hz, 1H), 7.66-7.60 (m, 2H), 7.31-7.27 (m, 1H), 7.13 (d, J = 2.3 Hz, 1H), 6.97 (dd, J = 8.8, 2.3 Hz, 1H), 6.78 (d, J = 2.0 Hz, 1H), 6.49 (dd, J = 8.3, 2.0 Hz, 1H), 4.94 (dd, J = 12.2, 5.4 Hz, 1H), 4.31 (s, 1H), 4.14 (t, J = 8.0 Hz, 2H), 3.95 (d, J = 13.1 Hz, 2H), 3.73-3.66 (m, 2H), 3.10-2.96 (m, 3H), 2.93-2.74 (m, 3H), 2.75-2.65 (m, 4H), 2.61-2.53 (m, 2H), 2.39-2.27 (m, 2H), 2.18-2.11 (m, 1H), 2.11-2.03 (m, 2H), 2.03-1.88 (m, 4H), 1.86-1.76 (m, 2H). m/z 799.32 [M + H]+. |
| 172 | $^1$H NMR (400 MHz, CDCl$_3$) δ 9.44 (s, 1H), 8.45 (s, 1H), 8.15 (d, J = 9.1 Hz, 1H), 8.00 (d, J = 2.9 Hz, 1H), 7.67-7.59 (m, 2H), 7.30-7.27 (m, 1H), 7.13 (d, J = 2.5 Hz, 1H), 6.97 (dd, J = 8.8, 2.5 Hz, 1H), 6.76 (d, J = 2.1 Hz, 1H), 6.48 (dd, J = 8.3, 2.1 Hz, 1H), 4.94 (dd, J = 12.3, 5.3 Hz, 1H), 4.35-4.25 (m, 1H), 3.96 (d, J = 13.2 Hz, 2H), 3.78-3.72 (m, 2H), 3.72-3.67 (m, 2H), 3.11-3.02 (m, 2H), 2.93-2.71 (m, 3H), 2.71-2.64 (m, 3H), 2.63-2.57 (m, 1H), 2.55 (s, 23H), 2.37-2.27 (m, 2H), 2.19-2.10 (m, 1H), 2.10-2.03 (m, 2H), 2.02-1.88 (m, 4H), 1.85-1.74 (m, 2H), 1.43 (s, 3H). m/z 813.32 [M + H]+. |
| 173 | $^1$H NMR (400 MHz, CDCl$_3$) δ 9.61 (s, 1H), 8.47 (s, 1H), 8.15 (d, J = 9.1 Hz, 1H), 7.87 (d, J = 2.9 Hz, 1H), 7.67 (d, J = 8.6 Hz, 1H), 7.62 (d, J = 8.8 Hz, 1H), 7.27-7.26 (m, 1H), 7.17 (d, J = 9.1, 3.0 Hz, 1H), 7.13 (d, J = 2.4 Hz, 1H), 7.02 (dd, J = 8.6, 2.3 Hz, 1H), 6.96 (dd, J = 8.8, 2.5 Hz, 1H), 4.95 (dd, J = 12.2, 5.3 Hz, 1H), 4.82-4.73 (m, 1H), 3.99-3.88 (m, 4H), 3.85-3.78 (m, 2H), 3.16-3.09 (m, 2H), 3.09-3.00 (m, 2H), 2.99-2.90 (m, 2H), 2.90-2.68 (m, 3H), 2.62-2.52 (m, 1H), 2.44 (d, J = 6.9 Hz, 2H), 2.19-2.11 (m, 1H), 2.11-2.01 (m, 2H), 1.99-1.89 (m, 2H), 1.89-1.80 (m, 2H), 1.66-1.60 (m, 1H), 1.34-1.20 (m, 2H). m/z 799.32 [M + H]+. |
| 174 | $^1$H NMR (400 MHz, CDCl$_3$) δ 9.22 (s, 1H), 8.30 (s, 1H), 8.14 (d, J = 9.1 Hz, 1H), 7.98 (d, J = 2.9 Hz, 1H), 7.67 (d, J = 8.6 Hz, 1H), 7.62 (d, J = 8.8 Hz, 1H), 7.27 (d, J = 2.3 Hz, 1H), 7.24 (d, J = 3.0 Hz, 1H), 7.13 (d, J = 2.6 Hz, 1H), 7.03 (dd, J = 8.6, 2.3 Hz, 1H), 6.97 (dd, J = 8.8, 2.6 Hz, 1H), 4.95 (dd, J = 12.3, 5.3 Hz, 1H), 4.01-3.89 (m, 4H), 3.82 (d, J = 5.9 Hz, 2H), 3.11-3.00 (m, 2H), 3.00-2.92 (m, 2H), 2.92-2.86 (m, 3H), 2.86-2.69 (m, 2H), 2.62-2.53 (m, 1H), 2.19 (d, J = 7.1 Hz, 2H), 2.17-2.11 (m, 2H), 2.11-2.01 (m, 3H), 2.00-1.92 (m, 4H), 1.91-1.86 (m, 2H), 1.85-1.70 (m, 5H), 1.45-1.33 (m, 2H), 1.33-1.20 (m, 2H). m/z 841.38 [M + H]+. |
| 175 | $^1$H NMR (400 MHz, CDCl$_3$) δ 9.16 (s, 1H), 8.32 (s, 1H), 8.14 (d, J = 9.1 Hz, 1H), 7.98 (d, J = 3.0 Hz, 1H), 7.66 (d, J = 8.6 Hz, 1H), 7.62 (d, J = 8.8 Hz, 1H), 7.28-7.27 (m, 1H), 7.26-7.24 (m, 1H), 7.13 (d, J = 2.5 Hz, 1H), 7.03 (dd, J = 8.8, 2.3 Hz, 1H), 6.97 (dd, J = 8.6, 2.5 Hz, 1H), 4.95 (dd, J = 12.3, 5.3 Hz, 1H), 4.02 (t, J = 6.4 Hz, 2H), 3.99-3.88 (m, 4H), 3.09-3.00 (m, 2H), 2.99-2.91 (m, 2H), 2.91-2.81 (m, 3H), 2.81-2.68 (m, 2H), 2.62-2.51 (m, 1H), 2.17 (d, J = 6.5 Hz, 2H), 2.15-2.11 (m, 1H), 2.10-2.00 (m, 3H), 2.00-1.84 (m, 6H), 1.82-1.77 (m, 1H), 1.76-1.68 (m, 4H), 1.57-1.46 (m, 2H), 1.37-1.30 (m, 2H). m/z 855.46 [M + H]+. |
| 176 | $^1$H NMR (400 MHz, CDCl$_3$) δ 9.05 (s, 1H), 8.80-8.74 (m, 1H), 8.22-8.19 (m, 1H), 8.16 (d, J = 9.1 Hz, 1H), 8.03 (d, J = 3.0 Hz, 1H), 7.63 (d, J = 8.8 Hz, 1H), 7.32-7.28 (m, 3H), 7.18-7.12 (m, 2H), 6.98 (dd, J = 8.8, 2.5 Hz, 1H), 6.83-6.79 (m, 1H), 6.45 (dd, J = 7.8, 2.0 Hz, 1H), 4.68 (d, J = 4.0 Hz, 1H), 4.16 (t, J = 5.5 Hz, 2H), 4.14-4.09 (m, 1H), 4.02-3.93 (m, 2H), 3.16-3.03 (m, 4H), 2.92-2.86 (m, 3H), 2.85-2.74 (m, 2H), 2.73-2.62 (m, 8H), 2.61-2.53 (m, 2H), 2.12-2.01 (m, 2H), 2.01-1.89 (m, 2H). m/z 762.38 [M + H]+. |
| 177 | $^1$H NMR (400 MHz, DMSO-d$_6$) δ 10.73 (s, 1H), 10.19 (s, 1H), 9.33 (s, 1H), 7.94 (d, J = 3.0 Hz, 1H), 7.85 (d, J = 9.1 Hz, 1H), 7.77 (d, J = 8.9 Hz, 1H), 7.32 (dd, J = 9.1, 3.0 Hz, 1H), 7.27 (d, J = 2.3 Hz, 1H), 7.21 (dd, J = 9.0, 2.3 Hz, 1H), 6.99-6.93 (m, 2H), 6.77 (d, J = 8.9 Hz, 1H), 6.35 (dd, J = 8.2, 1.6 Hz, 1H), 5.83 (d, J = 7.8 Hz, 1H), 4.26-4.18 (m, 1H), 4.06 (d, J = 13.3 Hz, 2H), 3.59 (d, J = 12.0 Hz, 2H), 3.04 (d, J = 11.5 Hz, 2H), 2.96 (t, J = 11.5 Hz, 2H), 2.75-2.65 (m, 1H), 2.65-2.61 (m, 2H), 2.61-2.56 (m, 2H), 2.41-2.33 (m, 6H), 2.13 (d, J = 7.2 Hz, 2H), 2.10-2.01 (m, 1H), 1.96-1.86 (m, 2H), 1.86-1.78 (m, 2H), 1.78-1.68 (m, 2H), 1.66-1.54 (m, 2H), 1.19-1.09 (m, 2H). m/z 815.38 [M + H]+. |
| 178 | $^1$H NMR (400 MHz, DMSO-d$_6$) δ 11.08 (s, 1H), 10.35 (s, 1H), 8.00 (d, J = 3.0 Hz, 1H), 7.95 (d, J = 9.1 Hz, 1H), 7.80-7.76 (m, 2H), 7.42 (d, J = 2.2 Hz, 1H), 7.39 (dd, J = 9.1, 3.0 Hz, 1H), 7.33 (d, J = 8.4, 2.2 Hz, 1H), 7.27 (d, J = 2.3 Hz, 1H), 7.23-7.29 (m, 1H), 5.07 (dd, J = 12.9, 5.4 Hz, 1H), 4.68 (d, J = 3.8 Hz, 1H), 4.12-4.03 (m, 4H), 2.96 (t, J = 11.5 Hz, 2H), 2.91-2.79 (m, 1H), 2.79-2.71 (m, 3H), 2.71-2.66 (m, 2H), 2.40-2.32 (m, 3H), 2.04-1.97 (m, 1H), 1.97-1.90 (m, 2H), 1.87-1.79 (m, 2H), 1.67-1.57 (m, 4H). m/z 774.33 [M + H]+. |
| 179 | $^1$H NMR (400 MHz, CDCl$_3$) δ 9.89 (s, 1H), 8.49 (s, 1H), 8.04 (d, J = 8.9 Hz, 1H), 7.66 (d, J = 8.6 Hz, 1H), 7.61 (d, J = 8.8 Hz, 1H), 7.53 (d, J = 2.8 Hz, 1H), 7.27-7.26 (m, 1H), 7.12 (d, J = 2.5 Hz, 1H), 7.02 (dd, J = 8.6, 2.3 Hz, 1H), 6.95 (dd, J = 8.8, 2.5 Hz, 1H), 6.79 (dd, J = 8.9, 2.8 Hz, 1H), 4.95 (dd, J = 12.3, 5.3 Hz, 1H), 3.98-3.87 (m, 4H), 3.64-3.55 (m, 4H), 3.06-2.97 (m, 2H), 2.97-2.89 (m, 2H), 2.89-2.67 (m, 3H), 2.61-2.51 (m, 1H), 2.50 (s, 2H), 2.42 (s, 8H), 2.19 (d, J = 7.0 Hz, 2H), 2.16-2.10 (m, 1H), 2.09-2.01 (m, 2H), 2.00-1.91 (m, 2H), 1.91-1.82 (m, 2H), 1.81-1.70 (m, 1H), 1.42 (s, 3H), 1.33-1.24 (m, 2H). m/z 895.56 [M + H]+. |

TABLE 5-continued

| Example | NMR and/or MS data |
|---|---|
| 180 | ¹H NMR (400 MHz, CDCl₃) δ 9.57 (s, 1H), 8.37 (s, 1H), 8.06 (d, J = 8.9 Hz, 1H), 7.79 (d, J = 8.3 Hz, 1H), 7.63 (d, J = 8.8 Hz, 1H), 7.54 (d, J = 2.8 Hz, 1H), 7.34 (d, J = 2.1 Hz, 1H), 7.19 (dd, J = 8.3, 2.1 Hz), 7.14 (d, J = 2.2 Hz, 1H), 6.98 (dd, J = 8.8, 2.2 Hz, 1H), 6.81 (dd, J = 8.9, 2.8 Hz, 1H), 4.98 (dd, J = 12.4, 5.2 Hz, 1H), 3.97 (d, J = 13.2 Hz, 2H), 3.91 (d, J = 5.9 Hz, 2H), 3.66-3.56 (m, 4H), 3.10-3.00 (m, 2H), 2.97-2.83 (m, 2H), 2.83-2.70 (m, 3H), 2.62-2.53 (m, 1H), 2.51 (s, 2H), 2.21-2.13 (m, 1H), 2.13-2.02 (m, 4H), 2.02-1.89 (m, 2H), 1.87-1.75 (m, 3H), 1.48-1.35 (m, 5H). m/z 827.40 [M + H]⁺. |
| 181 | ¹H NMR (400 MHz, DMSO-d₆) δ 11.08 (s, 1H), 10.34 (s, 1H), 8.28 (s, 1H), 7.98 (d, J = 3.1 Hz, 1H), 7.95 (d, J = 9.1 Hz, 1H), 7.78 (d, J = 8.9 Hz, 1H), 7.66 (d, J = 11.5 Hz, 1H), 7.39 (d, J = 7.6 Hz, 1H), 7.38-7.34 (m, 1H), 7.27 (d, J = 2.4 Hz, 1H), 7.21 (dd, J = 8.9, 2.4 Hz, 1H), 5.06 (dd, J = 12.8, 5.4 Hz, 1H), 4.06 (d, J = 13.4 Hz, 2H), 3.83 (d, J = 5.7 Hz, 2H), 3.61-3.52 (m, 2H), 3.04-2.92 (m, 2H), 2.90-2.79 (m, 6H), 2.77-2.68 (m, 1H), 2.12 (d, J = 6.8 Hz, 2H), 2.04-1.94 (m, 1H), 1.87-1.75 (m, 7H), 1.75-1.66 (m, 5H), 1.66-1.53 (m, 3H), 1.32-1.16 (m, 5H). m/z 859.40 [M + H]⁺. |
| 182 | ¹H NMR (400 MHz, CDCl₃) δ 10.00 (s, 1H), 8.67 (s, 1H), 8.13 (d, J = 8.5 Hz, 1H), 8.08 (d, J = 1.9 Hz, 1H), 7.61 (d, J = 8.8 Hz, 1H), 7.50 (dd, J = 8.5, 1.9 Hz, 1H), 7.43 (d, J = 11.0 Hz, 1H), 7.36 (d, J = 7.3 Hz, 1H), 7.12 (d, J = 2.4 Hz, 1H), 6.95 (dd, J = 8.8, 2.4 Hz, 1H), 4.93 (dd, J = 12.4, 5.3 Hz, 1H), 3.98-3.89 (m, 2H), 3.61 (d, J = 10.3 Hz, 2H), 3.09-2.97 (m, 2H), 2.93-2.70 (m, 7H), 2.65-2.54 (m, 1H), 2.48 (d, J = 6.9 Hz, 2H), 2.21-2.10 (m, 3H), 2.08-2.00 (m, 2H), 1.98-1.89 (m, 2H), 1.89-1.76 (m, 4H), 1.74-1.64 (m, 1H), 1.57-1.52 (m, 2H), 1.50-1.41 (m, 1H), 1.37-1.20 (m, 4H). m/z 843.37 [M + H]⁺. |
| 183 | ¹H NMR (400 MHz, CDCl₃) δ 9.52 (s, 1H), 8.39 (s, 1H), 8.14 (d, J = 9.1 Hz, 1H), 7.99 (d, J = 3.0 Hz, 1H), 7.66-7.58 (m, 2H), 7.27-7.23 (m, 1H), 7.13 (d, J = 2.5 Hz, 1H), 6.97 (dd, J = 8.8, 2.5 Hz, 1H), 6.78 (d, J = 2.1 Hz, 1H), 6.48 (dd, J = 8.3, 2.1 Hz, 1H), 4.94 (dd, J = 12.3, 5.3 Hz, 1H), 4.14 (t, J = 7.8 Hz, 2H), 3.99-3.91 (m, 2H), 3.82 (d, J = 5.8 Hz, 2H), 3.72-3.64 (m, 2H), 3.09-2.96 (m, 3H), 2.95-2.88 (m, 2H), 2.88-2.72 (m, 3H), 2.67 (d, J = 7.3 Hz, 2H), 2.62-2.53 (m, 1H), 2.19-2.11 (m, 1H), 2.11-2.01 (m, 4H), 2.00-1.88 (m, 2H), 1.87-1.78 (m, 3H), 1.45-1.35 (m, 2H). m/z 813.36 [M + H]⁺. |
| 184 | ¹H NMR (400 MHz, CDCl₃) δ 8.88 (s, 1H), 8.20 (s, 1H), 8.13 (d, J = 9.0 Hz, 1H), 7.97 (d, J = 2.9 Hz, 1H), 7.63 (dd, J = 8.5, 5.3 Hz, 2H), 7.24-7.22 (m, 1H), 7.13 (d, J = 2.4 Hz, 1H), 6.98-6.94 (m, 1H), 6.76 (d, J = 2.0 Hz, 1H), 6.49 (dd, J = 8.3, 2.0 Hz, 1H), 4.97-4.90 (m, 1H), 4.02-3.91 (m, 2H), 3.81 (d, J = 5.8 Hz, 2H), 3.76 (d, J = 7.7 Hz, 2H), 3.70 (d, J = 7.7 Hz, 2H), 3.09-3.00 (m, 2H), 2.96-2.68 (m, 5H), 2.52 (s, 2H), 2.15-2.02 (m, 5H), 2.02-1.88 (m, 2H), 1.83-1.73 (m, 3H), 1.44-1.35 (m, 5H). m/z 827.42 [M + H]⁺. |
| 185 | ¹H NMR (400 MHz, CDCl₃) δ 9.74 (s, 1H), 8.56 (s, 1H), 8.16 (d, J = 9.1 Hz, 1H), 8.01 (d, J = 3.0 Hz, 1H), 7.66 (d, J = 8.6 Hz, 1H), 7.62 (d, J = 8.8 Hz, 1H), 7.28 (dd, J = 9.1, 3.0 Hz, 1H), 7.26-7.25 (m, 1H), 7.13 (d, J = 2.5 Hz, 1H), 7.02 (dd, J = 8.6, 2.3 Hz, 1H), 6.97 (dd, J = 8.8, 2.5 Hz, 1H), 4.95 (dd, J = 12.4, 5.2 Hz, 1H), 4.11 (d, J = 6.6 Hz, 2H), 3.98-3.86 (m, 4H), 3.42 (t, J = 7.1 Hz, 2H), 3.14-2.99 (m, 4H), 2.97-2.90 (m, 3H), 2.89-2.68 (m, 3H), 2.64-2.54 (m, 1H), 2.37 (d, J = 6.8 Hz, 2H), 2.19-2.12 (m, 1H), 2.10-2.01 (m, 2H), 2.00-1.89 (m, 2H), 1.87-1.79 (m, 2H), 1.58-1.52 (m, 1H), 1.34-1.21 (m, 2H). m/z 813.39 [M + H]⁺. |
| 186 | ¹H NMR (400 MHz, CDCl₃) δ 9.96 (s, 1H), 8.62 (s, 1H), 8.16 (d, J = 9.1 Hz, 1H), 8.03 (d, J = 2.9 Hz, 1H), 7.66 (d, J = 8.6 Hz, 1H), 7.62 (d, J = 8.8 Hz, 1H), 7.29 (dd, J = 9.1, 2.9 Hz, 1H), 7.26-7.25 (m, 1H), 7.13 (d, J = 2.4 Hz, 1H), 7.02 (dd, J = 8.6, 2.3 Hz, 1H), 6.96 (dd, J = 8.8, 2.4 Hz, 1H), 4.95 (dd, J = 12.3, 5.3 Hz, 1H), 4.00 (s, 2H), 3.98-3.87 (m, 4H), 3.27 (d, J = 7.2 Hz, 2H), 3.09-2.99 (m, 2H), 2.97-2.90 (m, 4H), 2.89-2.68 (m, 3H), 2.63-2.54 (m, 1H), 2.37 (d, J = 6.8 Hz, 2H), 2.19-2.11 (m, 1H), 2.12-2.02 (m, 2H), 2.00-1.89 (m, 2H), 1.83 (d, J = 11.6 Hz, 2H), 1.57-1.52 (m, 1H), 1.33 (s, 3H), 1.31-1.20 (m, 2H). m/z 827.42 [M + H]⁺. |
| 187 | ¹H NMR (400 MHz, CDCl₃) δ 8.65 (s, 1H), 8.38 (d, J = 9.5 Hz, 1H), 8.18 (s, 1H), 7.67 (d, J = 8.6 Hz, 1H), 7.63 (d, J = 8.8 Hz, 1H), 7.30-7.27 (m, 1H), 7.14 (d, J = 2.4 Hz, 1H), 7.04 (dd, J = 8.7, 2.3 Hz, 1H), 7.02-6.96 (m, 2H), 5.28-5.19 (m, 1H), 4.95 (dd, J = 12.3, 5.3 Hz, 1H), 4.04-3.90 (m, 4H), 3.13-3.03 (m, 2H), 3.03-2.93 (m, 2H), 2.92-2.75 (m, 3H), 2.74-2.63 (m, 3H), 2.32-2.23 (m, 2H), 2.22 (d, J = 7.1 Hz, 2H), 2.16-2.12 (m, 1H), 2.12-2.05 (m, 2H), 2.03-1.94 (m, 2H), 1.93-1.88 (m, 2H), 1.86-1.72 (m, 2H), 1.33-1.21 (m, 2H). m/z 828.40 [M + H]⁺. |
| 188 | ¹H NMR (400 MHz, CDCl₃) δ 8.97 (s, 1H), 8.32 (s, 1H), 8.21 (d, J = 1.9 Hz, 1H), 8.16 (d, J = 8.5 Hz, 1H), 7.70 (dd, J = 8.5, 1.9 Hz, 1H), 7.63 (d, J = 8.8 Hz, 1H), 7.46 (d, J = 11.1 Hz, 1H), 7.37 (d, J = 7.3 Hz, 1H), 7.14 (d, J = 2.5 Hz, 1H), 6.97 (dd, J = 8.8, 2.5 Hz, 1H), 4.94 (dd, J = 12.4, 5.3 Hz, 1H), 4.01-3.91 (m, 2H), 3.46 (s, 2H), 3.32-3.18 (m, 4H), 3.11-3.00 (m, 2H), 2.97-2.68 (m, 5H), 2.63-2.50 (m, 5H), 2.24 (d, J = 7.1 Hz, 2H), 2.18-2.11 (m, 1H), 2.10-2.04 (m, 2H), 2.03-1.86 (m, 4H), 1.79-1.68 (m, 2H), 1.54-1.46 (m, 1H), 1.26-1.16 (m, 2H). m/z 844.42 [M + H]⁺. |
| 189 | ¹H NMR (400 MHz, CDCl₃) δ 9.64 (s, 1H), 8.53 (s, 1H), 8.18-8.12 (m, 2H), 7.63 (d, J = 8.8 Hz, 1H), 7.58 (dd, J = 8.5, 2.3 Hz, 1H), 7.47 (d, J = 11.0 Hz, 1H), 7.38 (d, J = 7.3 Hz, 1H), 7.14 (d, J = 2.4 Hz, 1H), 6.98 (dd, J = 8.8, 2.4 Hz, 1H), 4.95 (dd, J = 12.4, 5.4 Hz, 1H), 4.00-3.93 (m, 2H), 3.31-3.22 (m, 4H), 3.10-3.03 (m, 2H), 3.03-2.96 (m, 2H), 2.96-2.81 (m, 2H), 2.81-2.71 (m, 3H), 2.64-2.51 (m, 7H), 2.25 (d, J = 7.1 Hz, 2H), 2.19-2.1 (m, 1H), 2.10-2.04 (m, 3H), 2.02-1.9 (m, 4H), 1.82-1.75 (m, 2H), 1.55-1.50 (m, 1H), 1.30-1.26 (m, 2H). m/z 858.48 [M + H]⁺. |
| 190 | ¹H NMR (400 MHz, CDCl₃) δ 8.12 (s, 1H), 8.01 (d, J = 8.8 Hz, 1H), 7.82 (s, 1H), 7.68 (d, J = 8.6 Hz, 1H), 7.61 (d, J = 8.8 Hz, 1H), 7.47 (d, J = 2.9 Hz, 1H), 7.27-7.27 (m, 1H), 7.12 (d, J = 2.8 Hz, 1H), 7.04 (dd, J = 8.6, 2.4 Hz, 1H), 6.96 (dd, J = 8.6, 2.8 Hz, 1H), 6.79 (dd, J = 8.8, 2.9 Hz, 1H), 4.95-4.91 (m, 1H), 4.05-3.99 (m, 2H), 3.93-3.91 (m, 2H), 3.58-3.52 (m, 2H), 3.42-3.35 (m, 4H), 3.10-2.99 (m, 3H), 2.92-2.82 (m, 3H), 2.81-2.70 (m, 2H), 2.66-2.60 (m, 2H), 2.57-2.48 (m, 5H), 2.23 (d, J = 6.8 Hz, 2H), 2.15-2.08 (m, 1H), 2.06-2.01 (m, 4H), 1.97-1.90 (m, 2H), 1.79-1.72 (m, 2H), 1.45-1.42 (m, 2H), 0.95-0.89 (m, 2H). m/z 881.53 [M + H]⁺. |
| 191 | ¹H NMR (400 MHz, CDCl₃) δ 8.93 (s, 1H), 8.11 (s, 1H), 8.03 (d, J = 8.8 Hz, 1H), 7.62 (d, J = 8.8 Hz, 1H), 7.51 (d, J = 2.8 Hz, 1H), 7.47 (d, J = 11.1 Hz, 1H), 7.37 (d, J = 7.3 Hz, 1H), 7.13 (d, J = 2.4 Hz, 1H), 6.97 (dd, J = 8.8, 2.4 Hz, 1H), 6.81 (dd, J = 8.8, 2.8 Hz, 1H), 4.94 (dd, J = 12.3, 5.3 Hz, 1H), 4.03 (t, J = 7.4 Hz, 2H), 3.95 (d, J = 13.2 Hz, 2H), 3.54 (t, J = 6.4 Hz, 2H), 3.32-3.22 (m, 4H), 3.08-2.97 (m, 3H), 2.94-2.71 (m, 5H), 2.67-2.61 (m, 2H), 2.61-2.49 (m, 5H), 2.25 (d, J = 7.1 Hz, 2H), 2.18-2.11 (m, 1H), 2.10-2.02 (m, 2H), 2.02-1.86 (m, 4H), 1.81-1.72 (m, 2H), 1.54-1.46 (m, 1H), 1.28-1.19 (m, 3H). m/z 899.62 [M + H]⁺. |
| 192 | ¹H NMR (400 MHz, DMSO-d₆) δ 11.11 (s, 1H), 10.24 (s, 1H), 7.98 (d, J = 2.9 Hz, 1H), 7.90 (d, J = 9.0 Hz, 1H), 7.81 (d, J = 8.9 Hz, 1H), 7.73 (d, J = 11.5 Hz, 1H), 7.45 (d, J = 7.4 Hz, 1H), 7.37 (dd, J = 9.0, 2.9 Hz, 1H), 7.31 (d, J = 2.2 Hz, 1H), 7.25 (dd, J = 8.9, 2.2 Hz, 1H), 5.11 (dd, J = 12.8, 5.4 Hz, 1H), 4.10 (d, J = 13.4 Hz, 2H), 3.63 (d, J = 12.0 Hz, 2H), 3.27-3.21 (m, 4H), 3.05-2.95 (m, 2H), 2.93-2.82 (m, 1H), 2.79-2.71 (m, 1H), 2.63-2.61 (m, 2H), 2.56-2.53 (m, 5H), 2.42-2.37 (m, 1H), 2.09-1.98 (m, 1H), 1.90-1.81 (m, 2H), 1.80-1.73 (m, 2H), 1.71-1.58 (m, 2H), 1.49-1.41 (m, 4H), 1.32-1.20 (m, 2H). m/z 844.48 [M + H]⁺. |

Experimental Example 1: Androgen Receptor (AR) Protein Degradation Assay

After treating LNCaP cells with the synthesized Example compound, the amount of AR protein present in the cells was measured. The amount of AR protein was measured using western blotting detection method. The protocol of the experiment using LNCaP cells was as follows:

[Culture] LNCaP cells were resuspended in RPMI1640 MEDIUM (Hyclone, SH30027.01), 10% FBS (Hyclone, SV30207.02), and 1% Penicillin-streptomycin (Welgene, LS 202-02) media to be 3×10$^5$/mL. Then, 1 mL each was seeded in a 12-well plate. After that, they were cultured for 3 days.

[Compound treatment] 10 μl of 0.1, 1, 10, and 100 μM compound, which is the final compound treatment concentration and a 100× stock of 0.001, 0.01, 0.1, and 1 μM, was added in 1 ml media of each well, and 20 hours later, the cells were harvested.

[Cell Lysis] Cell pellets were suspended using 1% SDS lysis buffer (50 mM Tris, 1 mM EDTA, 1% SDS, pH 8.0, 0.5 mM PMSF, 1× Protease/Phosphatase inhibitor Cocktail (Cell Signaling Technology, 5872s)), and sonication (70% AMP, 5 cycles (30 sec ON/59 sec OFF)) was performed. Cell lysate was obtained after centrifugation at 4° C., 15000 g, for 20 minutes.

[Protein quantification] A BCA protein assay (SMART™ BCA Protein Assay Kit, iNtRON Biotechnology, 21071) was performed using a 96-well microplate. After adding 5 μl cell lysate and 5 μl 1% SDS lysis buffer to each well of the 96-well plate, 200 μl of BCA reagent (Reagent A:Reagent B=50:1) was additionally added. After incubation at 37° C. for 30 minutes, it was cooled at room temperature for 10 minutes. Then, absorbance was measured at a wavelength of 562 nm. The unknown protein concentration was measured using a BSA standard curve (0, 0.125, 0.25, 0.5, 1, 2 mg/ml). Western blotting samples were prepared by mixing cell lysate, 1% SDS lysis buffer, 4× Bolt™ LDS Sample buffer (Invitrogen, B0008), and 10× Bolt™ Sample Reducing Agent (Invitrogen, B0009) and boiling the mixture at 70° C. for 10 minutes.

[Electrophoresis] After loading 8 μg of protein sample into each well of Bolt™ 4 to 12%, Bis-Tris, 1.0 mm Mini Protein Gel, 17-well (Invitrogen, NW04127BOX), Bolt™ MES SDS Running Buffer (Invitrogen, B0002) was used for electrophoresis at 200V (constant V) for 50 minutes.

[Transfer] Using electrophoresis gel and Trans-Blot® Turbo™ Transfer Starter System (Bio-RAD, #17001918, Mini Nitrocellulose), transfer proceeded for 15 minutes under the condition of 1.3A (Constant A) and 25V (Limit V). To confirm protein transfer, 15 ml of Ponceau S solution (Sigma, P7170-1L) was used for staining for 1 minute, followed by washing to confirm the degree of transfer.

[Blocking] Membranes for AR detection were blocked for 45 minutes with 5% skim milk/0.2% TBST (Skim milk: BD, 232100/20× TBS: Biosesang, TR2008-100-00/10% Tween 20 Solution: Bio-RAD, #161-0781). Membranes for GAPDH and β-actin detection were blocked for 45 minutes with Odyssey blocking buffer: 0.1% TBST=1:1 (Odyssey blocking buffer: Li-COR Biosciences, 927-50000).

[Antibody and detection] The primary AR antibody (Androgen Receptor: CST, 5153s) was mixed with 5% skim milk/0.2% TBST at a ratio of 1:1000 and attached for 3 hours at room temperature. Primary β-actin antibody (GeneTex, 629630) was mixed with 5% BSA/0.2% TBST at a ratio of 1:2000 and attached for 3 hours at room temperature. Primary GAPDH antibody (GeneTex, 100118) was mixed with 5% BSA/0.2% TBST at a ratio of 1:2000 and attached for 3 hours at room temperature. After 3 hours, it was washed 3 times every 5 minutes using TBST (0.2% Tween 20). Anti-rabbit IgG, HRP-linked Antibody (CST, 7074s), secondary antibody for the AR antibody was mixed with 5% skim milk/0.2% TBST at a ratio of 1:5000 and attached for 45 minutes at room temperature. IRDye® 800CW Goat anti-Rabbit IgG Secondary Antibody and IRDye® 680RD Goat anti-Mouse IgG Secondary Antibody (LI-COR, 926-32211, 926-68070), secondary antibodies against β-actin antibody and GAPDH antibody were mixed with 5% BSA/0.2% TBST at a ratio of 1:10000 and attached at room temperature for 45 minutes. After 45 minutes, it was washed 5 times every 5 minutes using TBST (0.2% Tween 20). After reacting to the membrane using SuperSignal™ West Pico Plus Chemiluminescent Substrate (Thermo Scientific, 34580), detection was performed using Odyssey® Fc Imaging system (LI-COR, 2800).

These evaluation results are summarized and shown in Table 6 below.

TABLE 6

| Example no. | AR Degradation (%) | | | |
|---|---|---|---|---|
| | 0.01 μM | 0.1 μM | 1 μM | 10 μM |
| 1 | 55 | 98 | 99 | 99 |
| 2 | −9 | 68 | 97 | 96 |
| 3 | 45 | 98 | 96 | |
| 4 | 24 | 86 | 96 | |
| 5 | 82 | 97 | 97 | 97 |
| 6 | 83 | 99 | 99 | 97 |
| 7 | 87 | 99 | 99 | 94 |
| 8 | 37 | 87 | 95 | |
| 9 | 62 | 95 | 95 | |
| 10 | 9 | 52 | 74 | |
| 11 | 76 | 97 | 97 | 93 |
| 12 | 52 | 95 | 97 | 94 |
| 13 | 59 | 91 | 94 | |
| 14 | 72 | 98 | 97 | |
| 15 | 60 | 97 | 98 | |
| 16 | 50 | 94 | 97 | |
| 17 | 44 | 90 | 90 | |
| 18 | 36 | 93 | 95 | |
| 19 | 42 | 93 | 96 | |
| 20 | 67 | 97 | 97 | |
| 21 | 47 | 50 | 63 | |
| 22 | 1 | 24 | 49 | |
| 23 | 69 | 98 | 97 | |
| 24 | 53 | 96 | 95 | |
| 25 | 73 | 98 | 98 | |
| 26 | 75 | 98 | 98 | |
| 27 | 78 | 97 | 97 | |
| 28 | 82 | 96 | 95 | |
| 29 | 80 | 97 | 97 | |
| 30 | 78 | 99 | 97 | |
| 31 | 67 | 99 | 97 | |
| 32 | 62 | 99 | 99 | |
| 33 | 54 | 90 | 72 | |
| 34 | 88 | 99 | 96 | |
| 35 | 71 | 97 | 95 | |
| 36 | 66 | 94 | 94 | |
| 37 | 51 | 93 | 90 | |
| 38 | 44 | 93 | 97 | |
| 39 | 80 | 98 | 95 | |
| 40 | 43 | 94 | 94 | |
| 41 | 62 | 93 | 86 | |
| 42 | 65 | 96 | 94 | |
| 43 | 68 | 94 | 83 | |
| 44 | 80 | 98 | 93 | |
| 45 | 66 | 95 | 87 | |
| 46 | 70 | 97 | 91 | |
| 47 | 65 | 95 | 89 | |
| 48 | 59 | 94 | 87 | |
| 49 | 68 | 98 | 99 | 99 |
| 50 | 61 | 97 | 99 | 98 |
| 51 | 33 | 85 | 94 | |

TABLE 6-continued

| Example no. | AR Degradation (%) | | | |
|---|---|---|---|---|
| | 0.01 μM | 0.1 μM | 1 μM | 10 μM |
| 52 | 50 | 91 | 97 | |
| 53 | 27 | 89 | 93 | |
| 54 | 60 | 95 | 98 | |
| 55 | 34 | 69 | 95 | |
| 56 | -8 | 87 | 95 | |
| 57 | 43 | 85 | 96 | |
| 58 | 16 | 41 | 77 | |
| 59 | 9 | 32 | 47 | 68 |
| 60 | 16 | 32 | 32 | 66 |
| 61 | 57 | 94.5 | 97.5 | 96 |
| 62 | 69 | 95 | 96 | 87.5 |
| 63 | 45 | 94 | 98.5 | 94.5 |
| 64 | 71.5 | 97 | 98.5 | 98.5 |
| 65 | 55 | 80 | 82 | 63 |
| 66 | 75.5 | 95.5 | 97 | 94 |
| 67 | 46 | 90 | 88 | 86 |
| 68 | 66 | 91 | 90 | 85 |
| 69 | 40 | 83 | 85 | 82 |
| 70 | 85 | 99 | 99 | 97 |
| 71 | 75 | 97 | 98 | 98 |
| 72 | 59 | 94 | 97 | |
| 73 | 55 | 88 | 92 | |
| 74 | 20 | 66 | 83 | |
| 75 | 82 | 97 | 90 | |
| 76 | 36 | 85 | 88 | |
| 77 | 46 | 96 | 97 | |
| 78 | 49 | 88 | 71 | |
| 79 | 31 | 94 | 95 | |
| 80 | 34 | 90 | 57 | |
| 81 | 44 | 87 | 96 | |
| 82 | 33 | 87 | 95 | |
| 83 | 25 | 87 | 96 | |
| 84 | 59 | 89 | 88 | |
| 85 | 24 | 89 | 92 | |
| 86 | 65 | 94 | 96 | |
| 87 | 30 | 88 | 90 | |
| 88 | 35 | 87 | 96 | |
| 89 | 35 | 73 | 91 | |
| 90 | 23 | 57 | 82 | |
| 91 | 48 | 96 | 98 | |
| 92 | 53 | 67 | 96 | |
| 93 | -11 | 55 | 68 | |
| 94 | 75 | 98 | 98 | |
| 95 | 62 | 96 | 97 | |
| 96 | 71 | 93 | 91 | |
| 97 | 39 | 93 | 96 | |
| 98 | 48 | 89 | 76 | |
| 99 | 70 | 98 | 96 | |
| 100 | 31 | 84 | 89 | |
| 101 | 63 | 95 | 95 | |
| 102 | 35 | 90 | 92 | |
| 103 | -9 | 15 | 44 | 58 |
| 104 | -2 | -5 | 36 | 59 |
| 105 | 43 | 82 | 92 | |
| 106 | 32 | 86 | 96 | |
| 107 | 44 | 85 | 93 | |
| 108 | 51 | 85 | 89 | |
| 109 | 30 | 82 | 83 | |
| 110 | 56 | 89 | 88 | |
| 111 | 29 | 70 | 67 | 67 |
| 112 | 9 | 55 | 50 | 48 |
| 113 | 55 | 92 | 87 | |
| 114 | 41 | 89 | 91 | |
| 115 | 18 | 89 | 87 | |
| 116 | 24 | 43 | 53 | |
| 117 | 35 | 84 | 94 | |
| 118 | 34 | 62 | 88 | |
| 119 | 21 | 90 | 26 | |
| 120 | 0 | 88 | 96 | |
| 121 | 81 | 98 | 98 | |
| 122 | 71 | 76 | 74 | |
| 123 | 55 | 91 | 97 | |
| 124 | 52 | 88 | 96 | |
| 125 | 25 | 84 | 92 | |
| 126 | 51 | 89 | 96 | |
| 127 | 34 | 52 | 66 | |
| 128 | 28 | 43 | 61 | |
| 129 | 11 | 42 | 71 | |
| 130 | 78 | 95 | 95 | 93 |
| 131 | 28 | 66 | 82 | 87 |
| 132 | 31 | 67 | 72 | 77 |
| 133 | 60 | 93 | 98 | |
| 134 | 56 | 87 | 96 | 92 |
| 135 | 35 | 94 | 85 | |
| 136 | 38 | 92 | 91 | |
| 137 | 46 | 86 | 82 | |
| 138 | 52 | 95 | 90 | |
| 139 | 30 | 92 | 84 | |
| 140 | 87 | 98 | 95 | |
| 141 | 66 | 92 | 90 | |
| 142 | 55 | 87 | 83 | |
| 143 | 73 | 97 | 97 | |
| 144 | 43 | 84 | 95 | |
| 145 | 20 | 84 | 88 | |
| 146 | 67 | 97 | 98 | |
| 147 | 68 | 96 | 97 | |
| 148 | 27 | 87 | 93 | |
| 149 | 56 | 97 | 97 | |
| 150 | 55 | 97 | 99 | |
| 151 | -14 | 76 | 92 | |
| 152 | -46 | 28 | 29 | |
| 153 | 56 | 95 | 97 | |
| 154 | 26 | 86 | 91 | |
| 155 | 38 | 89 | 98 | |
| 156 | 35 | 76 | 96 | |
| 157 | 0 | 33 | 78 | |
| 158 | -7 | 27 | 65 | |
| 159 | -16 | -5 | 84 | |
| 160 | -19 | 4 | 71 | |
| 161 | 9 | 58 | 86 | |
| 162 | 62 | 95 | 97 | |
| 163 | -14 | 60 | 78 | |
| 164 | 79 | 96 | 97 | |
| 165 | 42 | 87 | 95 | |
| 166 | 69 | 96 | 97 | |
| 167 | 25 | 67 | 85 | |
| 168 | 73 | 97 | 99 | |
| 169 | 85 | 99 | 99 | |
| 170 | 52 | 90 | 97 | |
| 171 | 69 | 93 | 95 | |
| 172 | 56 | 91 | 91 | |
| 173 | 58 | 90 | 92 | |
| 174 | 73 | 91 | 95 | |
| 175 | 70 | 95 | 97 | |
| 176 | -2 | -22 | 16 | |
| 177 | 14 | 37 | 35 | |
| 178 | 23 | 64 | 87 | |
| 179 | 73 | 98 | 97 | |
| 180 | 36 | 97 | 98 | |
| 181 | 75 | 93 | 97 | |
| 182 | 72 | 96 | 98 | |
| 183 | 72 | 87 | 93 | |
| 184 | 72 | 91 | 97 | |
| 185 | 85 | 97 | 99 | |
| 186 | 66 | 94 | 96 | |
| 187 | 63 | 90 | | |
| 188 | 1 | 45 | | |
| 189 | 8 | 79 | | |
| 190 | -11 | 61 | | |
| 191 | 3 | 84 | | |
| 192 | -11 | 15 | 67 | |

As shown in Table 5, the compounds according to the present invention showed good activity in degrading the androgen receptor.

In particular, in various aspects such as androgen receptor degradation activity, the compounds of example 6, 11, 14, 15, 18, 19, 20, 34, 35, 38, 43, 44, 49, 66, 70, 75, 86, 121, 133, 140, 143, 146, 147, 164, 169, 170, 173, 174, 175, 181, 182, 185, 187, and 197 were preferred.

The invention claimed is:
1. A compound of Chemical Formula 1:

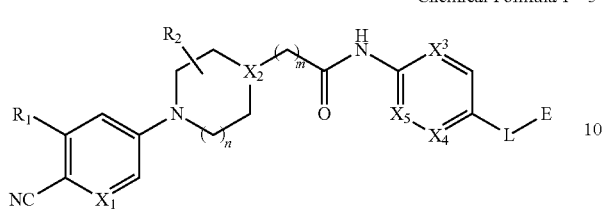

Chemical Formula 1 or a pharmaceutically acceptable salt or stereoisomer thereof,
wherein:
$X_1$ is CH;
$R_1$ is H, halogen, $C_{1-6}$ haloalkyl, or $OC_{1-6}$ alkyl;
each $R_2$ is independently H or $C_{1-4}$ alkyl;
$X_2$ is $CR_3$;
$R_3$ is H, halogen, $C_{1-6}$ alkyl, or OH;

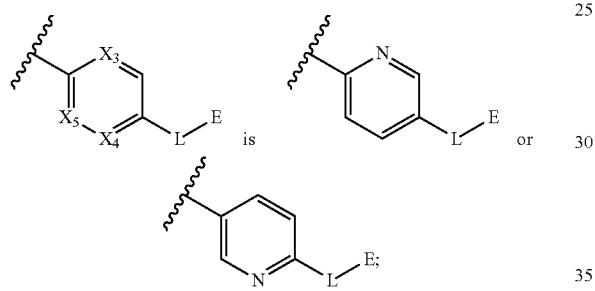

L is Chemical Formula 2:

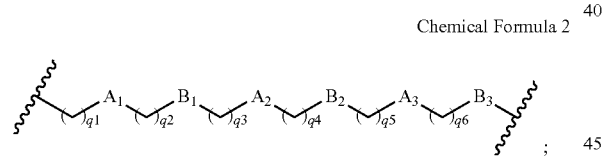

Chemical Formula 2 q1 is 0;
$A_1$ is a direct bond;
q2 is 0;
$B_1$ is a direct bond;
q3 is 0;
$A_2$ is —O—;
q4 is 0;
$B_2$ is a direct bond,

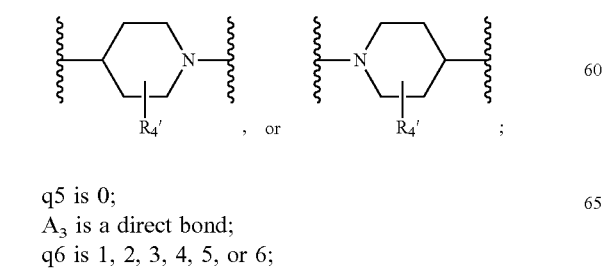

q5 is 0;
$A_3$ is a direct bond;
q6 is 1, 2, 3, 4, 5, or 6;

$B_3$ is

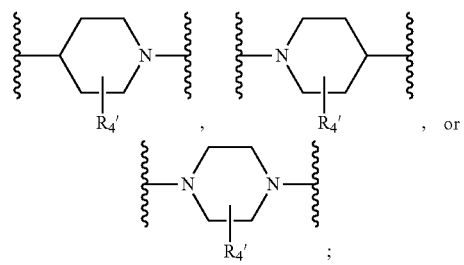

each $R_4'$ is independently H, halogen, $C_{1-6}$ alkyl, $C_{1-6}$ haloalkyl, or OH;
E is Chemical Formula 3:

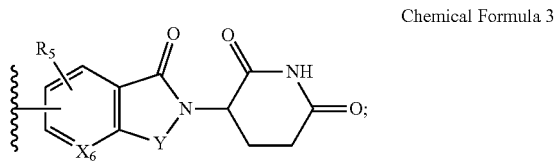

Chemical Formula 3 each $R_5$ is independently H, halogen, $C_{1-4}$ alkyl, $C_{1-4}$ haloalkyl, or $OC_{1-4}$ alkyl;
$X_6$ is CH;
Y is —$CR_6R_6$— or —C(O)—;
each $R_6$ is independently H, $C_{1-4}$ alkyl, or $C_{1-4}$ haloalkyl;
m is 0; and
n is 1.

2. The compound of claim 1, or a pharmaceutically acceptable salt or stereoisomer thereof, wherein:
$R_1$ is halogen or $C_{1-6}$ haloalkyl;
each $R_2$ is independently H;
$X_2$ is $CR_3$;
$R_3$ is H, F, or $CH_3$;

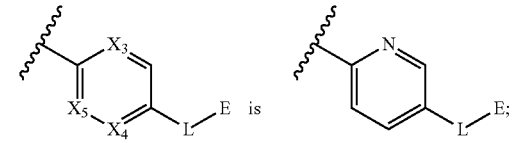

L is Chemical Formula 2:

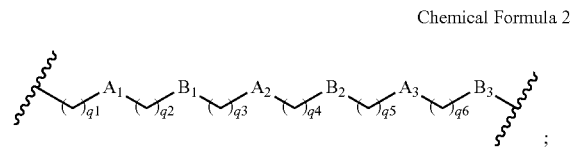

Chemical Formula 2 q1 is 0;
$A_1$ is a direct bond;
q2 is 0;
$B_1$ is a direct bond;
q3 is 0;
$A_2$ is —O—;
q4 is 0;

B₂ is a direct bond,
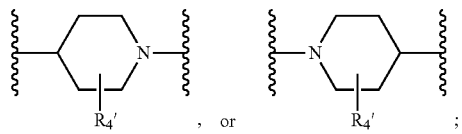
, or
q5 is 0;
A₃ is a direct bond;
q6 is 1, 2, 3, 4, 5, or 6;
B₃ is
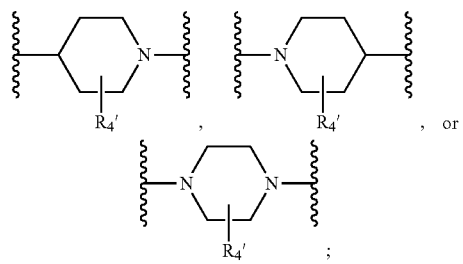
, or
;
each $R_4'$ is independently H or $C_{1-4}$ alkyl;
E is Chemical Formula 3:
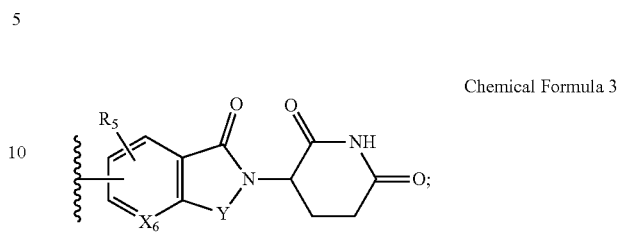
Chemical Formula 3
each $R_5$ is independently H or halogen;
$X_6$ is CH;
Y is —$CR_6R_6$— or —C(O)—;
each $R_6$ is independently H;
m is 0; and
n is 1.
3. The compound of claim 1, wherein the compound is selected from the group consisting of:
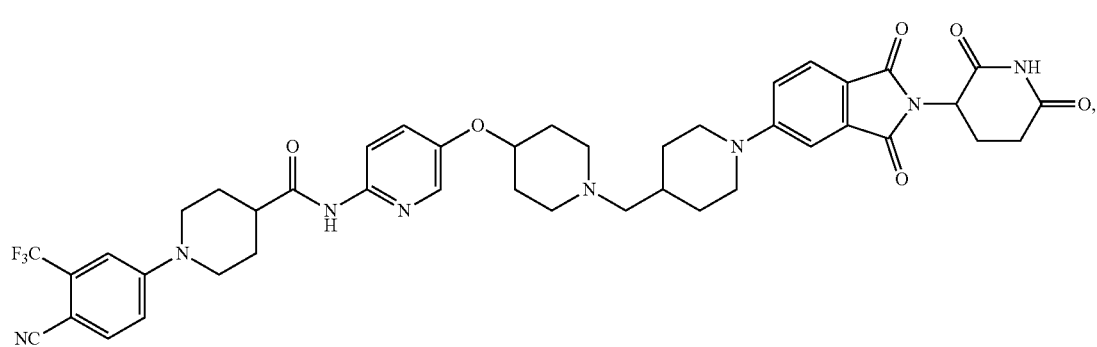
169
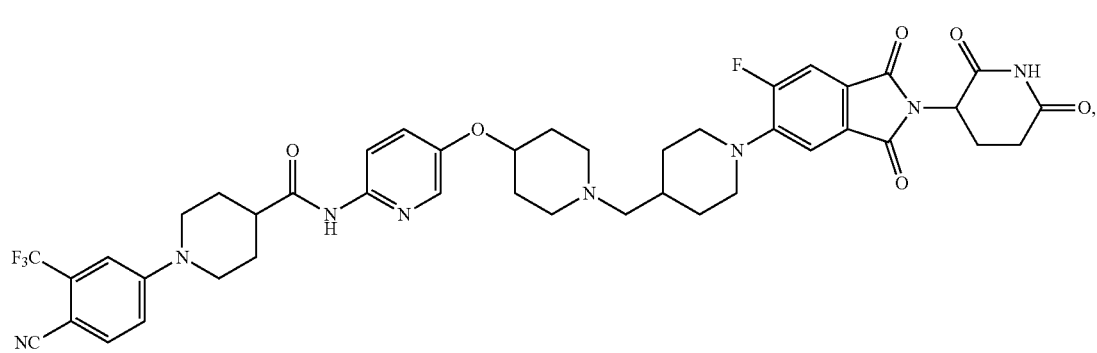
170
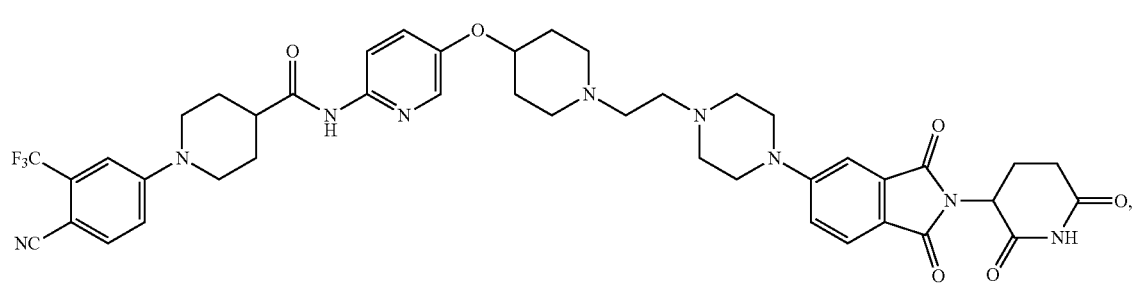
195

-continued

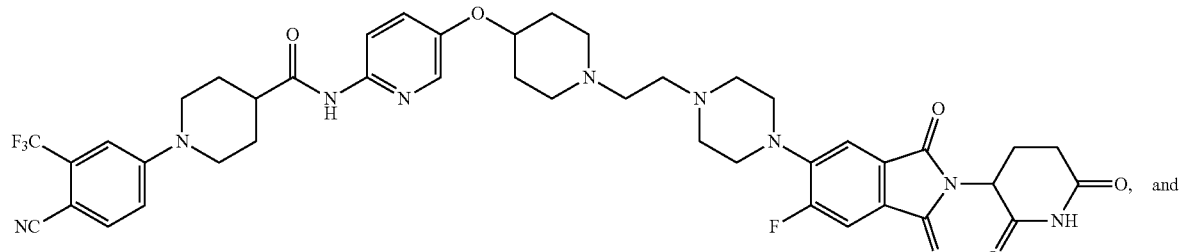

196

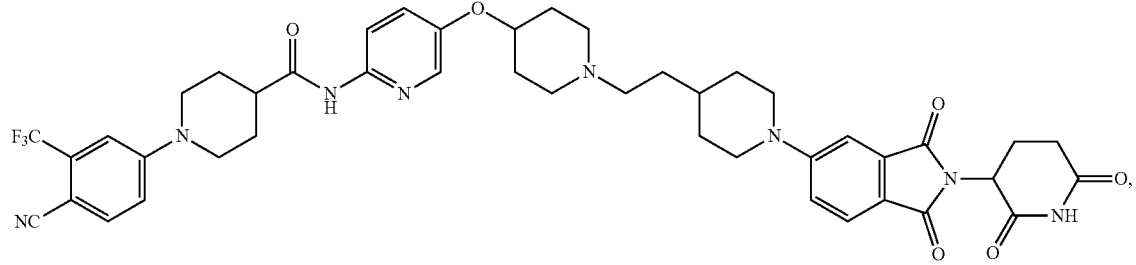

198 or a pharmaceutically acceptable salt or stereoisomer thereof.

4. The compound of claim 3, wherein the compound is selected from the group consisting of:

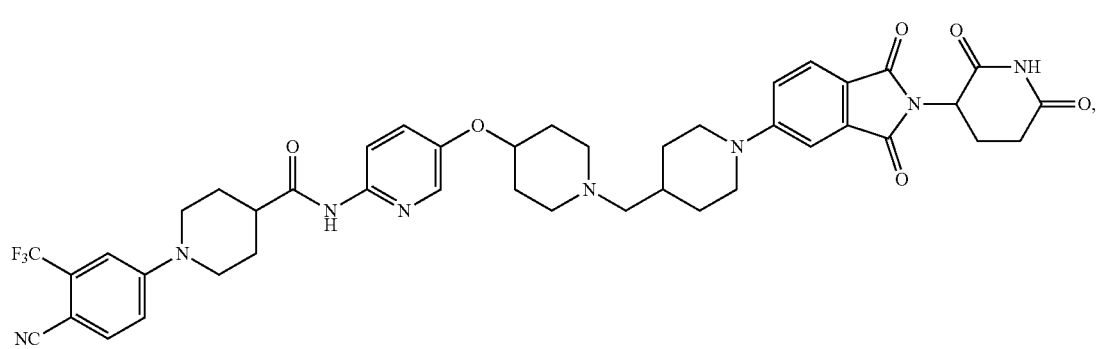

169 and

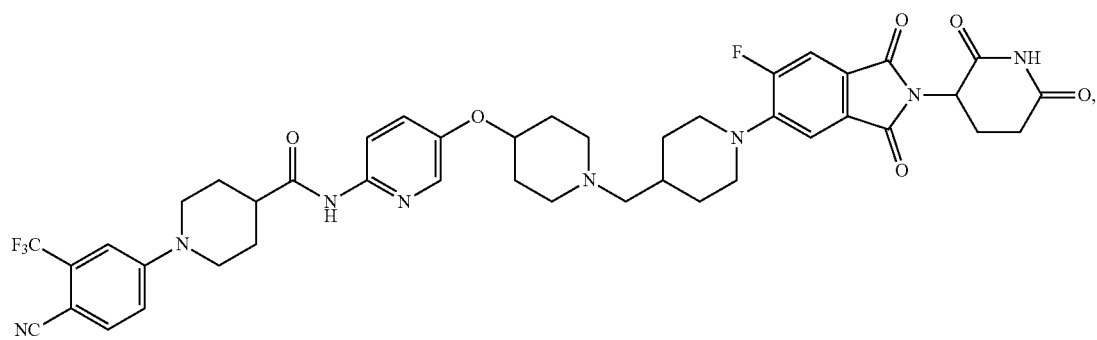

170 or a pharmaceutically acceptable salt or stereoisomer thereof.

5. A pharmaceutical composition comprising a pharmaceutically acceptable carrier and a compound of claim 1, or a pharmaceutically acceptable salt or stereoisomer thereof.

6. A method for degrading or inhibiting androgen receptor (AR) activity in a subject, wherein the method comprises administering to the subject in need thereof a therapeutically effective amount of the pharmaceutical composition of claim 5.

7. The method of claim 6, wherein the subject has a condition, disorder, or disease selected from the group consisting of acne, alopecia, cancer, a cutaneous wound, hirsutism, and Kennedy's disease.

8. The method of claim 7, wherein the cancer is prostate cancer.

* * * * *